United States Patent
Han et al.

(10) Patent No.: US 12,250,879 B2
(45) Date of Patent: Mar. 11, 2025

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Su Jin Han, Daejeon (KR); Dong Hoon Lee, Daejeon (KR); Boon Jae Jang, Daejeon (KR); Wanpyo Hong, Daejeon (KR); Min Woo Jung, Daejeon (KR); Jungha Lee, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1019 days.

(21) Appl. No.: 17/274,878

(22) PCT Filed: Sep. 20, 2019

(86) PCT No.: PCT/KR2019/012236
§ 371 (c)(1),
(2) Date: Mar. 10, 2021

(87) PCT Pub. No.: WO2020/060286
PCT Pub. Date: Mar. 26, 2020

(65) Prior Publication Data
US 2022/0059773 A1 Feb. 24, 2022

(30) Foreign Application Priority Data

Sep. 21, 2018 (KR) .................. 10-2018-0114411
Sep. 19, 2019 (KR) .................. 10-2019-0115650

(51) Int. Cl.
*C07D 405/14* (2006.01)
*C07D 409/14* (2006.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
CPC .. C07D 405/14; C07D 409/14; C07D 487/04; C07D 495/04; C07D 491/048;
(Continued)

(56) References Cited

U.S. PATENT DOCUMENTS 10,985,330 B2  4/2021 Parham et al.
2004/0251816 A1 12/2004 Leo et al.
(Continued)

FOREIGN PATENT DOCUMENTS

EP   3257850 A1   12/2017
JP   2016-149473   8/2016
(Continued)

OTHER PUBLICATIONS

A machine generated English translation of the WO 2019/093666 A1, Cho et al., May 2019. (Year: 2019).*
(Continued)

*Primary Examiner* — Laura L Stockton
(74) *Attorney, Agent, or Firm* — BRYAN CAVE LEIGHTON PAISNER LLP

(57) ABSTRACT

Provided is a heterocyclic compound of Chemical Formula 1:

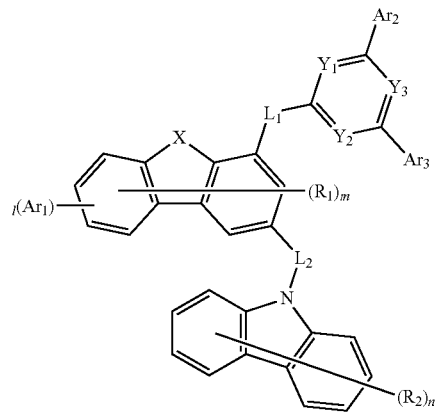

wherein:
X is O or S;
$Y_1$, $Y_2$ and $Y_3$ are each independently CH or N, provided that at least one is N;
$L_1$ and $L_2$ are each independently a direct bond, a substituted or unsubstituted $C_{6-60}$ arylene, or a substituted or unsubstituted $C_{5-60}$ heteroarylene containing at least one of N, O and S; and
Ar is a substituted or unsubstituted $C_{6-60}$ aryl, and $Ar_2$ and $Ar_3$ are each independently a substituted or unsubstituted $C_{6-60}$ aryl or a $C_{5-60}$ heteroaryl containing at least one of N, O and S, provided that when all of $Ar_1$, $Ar_2$ and $Ar_3$ are a substituted or unsubstituted $C_{6-60}$ aryl, any one of $Ar_1$, $Ar_2$ and $Ar_3$ is substituted with 4 or more deuteriums;
and an organic light emitting device including the same.

8 Claims, 1 Drawing Sheet

(51) Int. Cl.
  *C07D 487/04* (2006.01)
  *C07D 491/048* (2006.01)
  *C07D 495/04* (2006.01)
  *H10K 85/60* (2023.01)
  *H10K 50/11* (2023.01)
  *H10K 50/15* (2023.01)
  *H10K 50/16* (2023.01)
  *H10K 50/17* (2023.01)

(52) U.S. Cl.
  CPC ....... *C07D 487/04* (2013.01); *C07D 491/048* (2013.01); *C07D 495/04* (2013.01); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/17* (2023.02); *H10K 50/171* (2023.02)

(58) Field of Classification Search
  CPC ............. H10K 85/654; H10K 85/6572; H10K 85/6574; H10K 85/6576; H10K 50/11; H10K 50/15; H10K 50/16; H10K 50/17; H10K 50/171
  See application file for complete search history.

(56) References Cited

U.S. PATENT DOCUMENTS

| | | |
|---|---|---|
| 2014/0346483 A1 | 11/2014 | Yu et al. |
| 2016/0226001 A1 | 8/2016 | Parham et al. |
| 2017/0194574 A1 | 7/2017 | Ishidai et al. |
| 2017/0213988 A1 | 7/2017 | Park et al. |
| 2017/0331052 A1 | 11/2017 | Park et al. |
| 2018/0037546 A1 | 2/2018 | Sugino et al. |
| 2018/0166634 A1 | 6/2018 | Numata et al. |
| 2018/0287072 A1 | 10/2018 | Park et al. |
| 2019/0047991 A1 | 2/2019 | Jung et al. |
| 2019/0393422 A1 | 12/2019 | Sakamoto |

FOREIGN PATENT DOCUMENTS

| | | |
|---|---|---|
| JP | 2017-092276 | 5/2017 |
| JP | 2017-103437 | 6/2017 |
| JP | 2017-123460 | 7/2017 |
| JP | 2019-108315 | 7/2019 |
| KR | 10-2013-0073537 | 7/2013 |
| KR | 10-2016-0054582 | 5/2016 |
| KR | 10-2017-0013152 | 2/2017 |
| KR | 10-1693744 | 2/2017 |
| KR | 10-2017-0053590 | 5/2017 |
| KR | 10-2017-0057660 | 5/2017 |
| KR | 10-2017-0067671 | 6/2017 |
| KR | 10-1805686 | 12/2017 |
| KR | 10-2018-0051355 | 5/2018 |
| KR | 10-2018-0061076 | 6/2018 |
| KR | 10-2018-0068882 | 6/2018 |
| KR | 10-2020-0001641 | 1/2020 |
| WO | 2003-012890 | 2/2003 |
| WO | 2015-165563 | 11/2015 |
| WO | 2017-018795 | 2/2017 |
| WO | 2017-078494 | 5/2017 |
| WO | 2019-093666 | 5/2019 |

OTHER PUBLICATIONS

Tong et al., J. Phys. Chem. C, 2007, 111, 3490-3494. (Year: 2007).*
Tsuji et al., Chem. Commun., 2014, 50, 14870-14872. (Year: 2014).*

* cited by examiner

[FIG. 1]
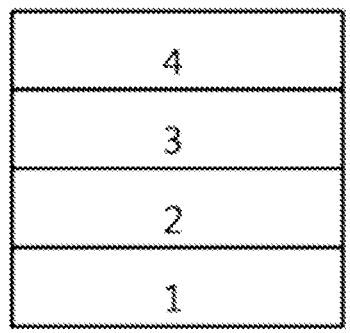
[FIG. 2]
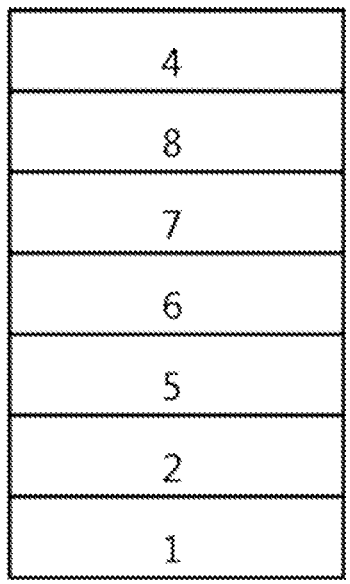

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/012236 filed on Sep. 20, 2019, which claims priority to and the benefit of Korean Patent Application No. 10-2018-0114411 filed on Sep. 21, 2018 and Korean Patent Application No. 10-2019-0115650 filed on Sep. 19, 2019 in the Korean Intellectual Property Office, each of which is incorporated herein by reference in its entirety.

FIELD OF THE INVENTION

The present disclosure relates to a novel heterocyclic compound and to an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Unexamined Patent Publication No. 10-2013-073537

SUMMARY OF THE INVENTION

Technical Problem

It is an object of the present disclosure to provide a novel heterocyclic compound and an organic light emitting device including the same.

Technical Solution

In one aspect of the invention, provided is a compound of Chemical Formula 1:

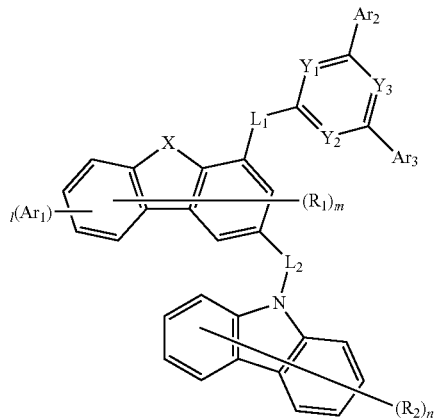

Chemical Formula 1 wherein, in Chemical Formula 1:

X is O or S;

$Y_1$, $Y_2$ and $Y_3$ are each independently CH or N, provided that at least one of $Y_1$, $Y_2$ and $Y_3$ is N;

$L_1$ and $L_2$ are each independently a direct bond, a substituted or unsubstituted $C_{6-60}$ arylene, or a substituted or unsubstituted $C_{5-60}$ heteroarylene containing at least one heteroatom selected from the group consisting of N, O and S;

$Ar_1$ is a substituted or unsubstituted $C_{6-60}$ aryl;

$Ar_2$ and $Ar_3$ are each independently a substituted or unsubstituted $C_{6-60}$ aryl or a substituted or unsubstituted $C_{5-60}$ heteroaryl containing at least one heteroatom selected from the group consisting of N, O and S;

provided that when all of $Ar_1$, $Ar_2$ and $Ar_3$ are a substituted or unsubstituted $C_{6-60}$ aryl, any one of $Ar_1$, $Ar_2$ and $Ar_3$ is substituted with 4 or more deuteriums;

each $R_1$ is independently hydrogen, deuterium, halogen, or a substituted or unsubstituted $C_{1-60}$ alkyl;

each $R_2$ is independently hydrogen, deuterium, halogen, cyano, a substituted or unsubstituted $C_{1-60}$ alkyl, a substituted or unsubstituted $C_{1-60}$ alkoxy, a substituted or unsubstituted $C_{3-60}$ cycloalkyl, a substituted or unsubstituted $C_{1-60}$ haloalkyl, a substituted or unsubstituted $C_{1-60}$ haloalkoxy, a substituted or unsubstituted $C_{6-60}$ arylamine, a substituted or unsubstituted $C_{1-60}$ alkylamine, a $C_{1-60}$ trifluoroalkyl, a $C_{1-60}$ trifluoroalkoxy, a substituted or unsubstituted $C_{6-60}$ aryl, or a substituted or unsubstituted $C_{5-60}$ heteroaryl containing at least one of N, O and S, which can bond with the carbon atom of carbazole to form a condensed ring;

m is an integer from 0 to 3;

n is an integer from 0 to 6; and l is 1 or 2.

In another aspect of the invention, provided is an organic light emitting device including: a first electrode; a second electrode that is provided opposite to the first electrode; and one or more organic material layers that are provided between the first electrode and the second electrode, wherein one or more layers of the organic material layers include the above-mentioned compound of the present disclosure.

Advantageous Effects

The above-mentioned compound of Chemical Formula 1 can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION

Hereinafter, embodiments of the present disclosure will be described in more detail to facilitate understanding of the invention.

One embodiment of the invention provides a compound of Chemical Formula 1:

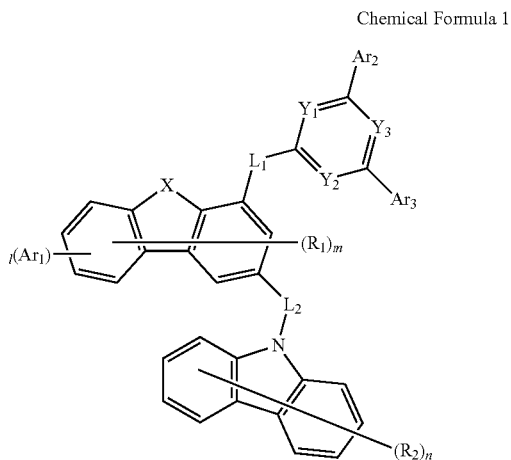

Chemical Formula 1 wherein, in Chemical Formula 1:
X is O or S;
$Y_1$, $Y_2$ and $Y_3$ are each independently CH or N, provided that at least one of $Y_1$, $Y_2$ and $Y_3$ is N;
$L_1$ and $L_2$ are each independently a direct bond, a substituted or unsubstituted $C_{6-60}$ arylene, or a substituted or unsubstituted $C_{5-60}$ heteroarylene containing at least one heteroatom selected from the group consisting of N, O and S;
$Ar_1$ is a substituted or unsubstituted $C_{6-60}$ aryl;
$Ar_2$ and $Ar_3$ are each independently a substituted or unsubstituted $C_{6-60}$ aryl or a substituted or unsubstituted $C_{5-60}$ heteroaryl containing at least one heteroatom selected from the group consisting of N, O and S;
provided that when all of $Ar_1$, $Ar_2$ and $Ar_3$ are a substituted or unsubstituted $C_{6-60}$ aryl, any one of $Ar_1$, $Ar_2$ and $Ar_3$ is substituted with 4 or more deuteriums,
wherein all of $Ar_1$, $Ar_2$ and $Ar_3$ are a substituted or unsubstituted $C_{6-60}$ aryl, it means a case where they are the same or different substituted or unsubstituted $C_{6-60}$ aryl;
each $R_1$ is independently hydrogen, deuterium, halogen, or a substituted or unsubstituted $C_{1-60}$ alkyl;
each $R_2$ is independently hydrogen, deuterium, halogen, cyano, a substituted or unsubstituted $C_{1-60}$ alkyl, a substituted or unsubstituted $C_{1-60}$ alkoxy, a substituted or unsubstituted $C_{3-60}$ cycloalkyl, a substituted or unsubstituted $C_{1-60}$ haloalkyl, a substituted or unsubstituted $C_{1-60}$ haloalkoxy, a substituted or unsubstituted $C_{6-60}$ arylamine, a substituted or unsubstituted $C_{1-60}$ alkylamine, a $C_{1-60}$ trifluoroalkyl, a $C_{1-60}$ trifluoroalkoxy, a substituted or unsubstituted $C_{6-60}$ aryl, or a substituted or unsubstituted $C_{5-60}$ heteroaryl containing at least one of N, O and S, which can bond with the carbon atom of carbazole to form a condensed ring;
m is an integer from 0 to 3;
n is an integer from 0 to 6; and
l is 1 or 2.

In the above, when $Ar_1$, $Ar_2$ and $Ar_3$ are a substituted or unsubstituted $C_{6-60}$ aryl, it means a case where $Ar_1$, $Ar_2$ and $Ar_3$ are simultaneously the same or different substituted or unsubstituted $C_{6-60}$ aryl.

As used herein, the notation and ⁕ and ⁞ mean a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto:

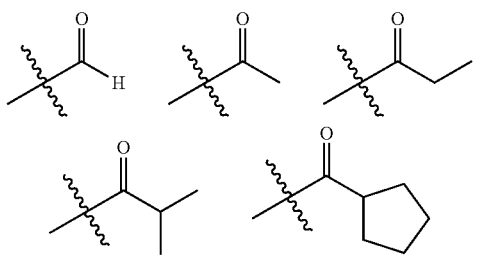

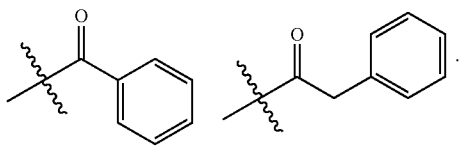
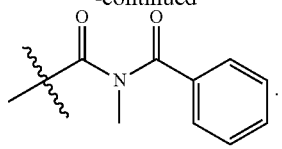

In the present specification, an ester group can have a structure in which oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

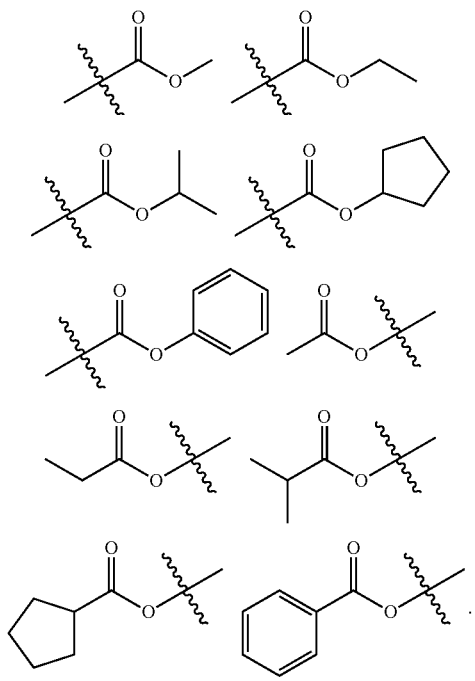

In the present specification, the number of carbon atoms of an imide group is not particularly limited, but is preferably 1 to 25. Specifically, the imide group can be a compound having the following structural formulae, but is not limited thereto:

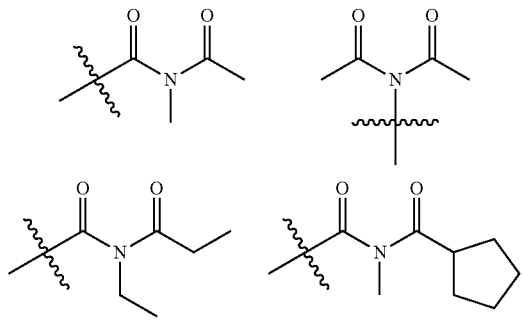

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

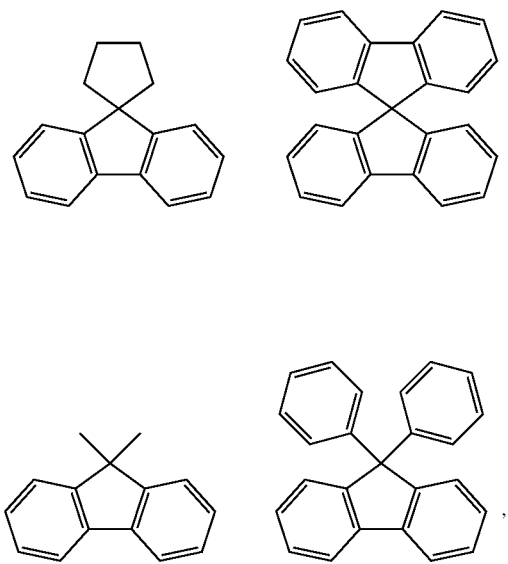

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, an thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heteroaryl can be applied, except that the heterocycle is not a monovalent group but formed by combining two substituent groups.

Preferably, the compound of Chemical Formula 1 can be any one compound selected from the group consisting of compounds of the following Chemical Formulae 2 to 8:

Chemical Formula 2

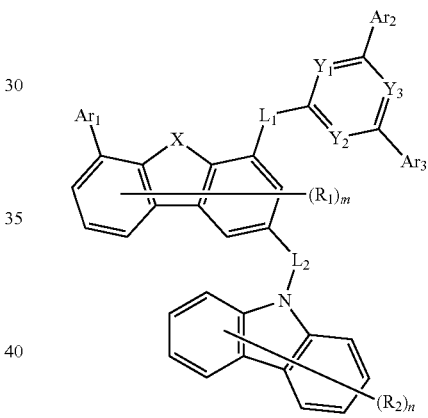

Chemical Formula 3

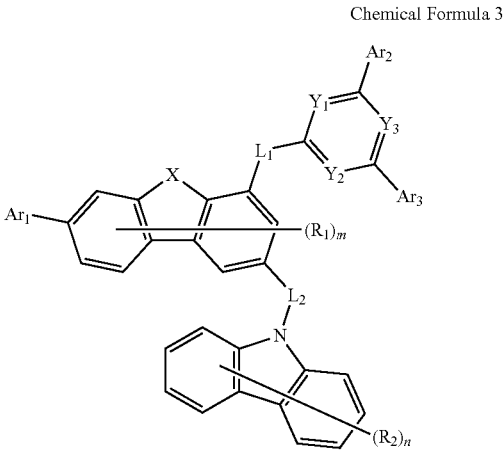

Chemical Formula 4
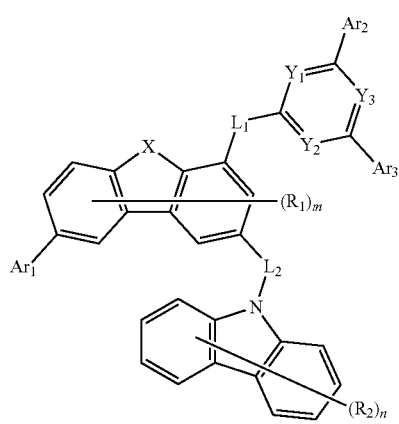
Chemical Formula 5
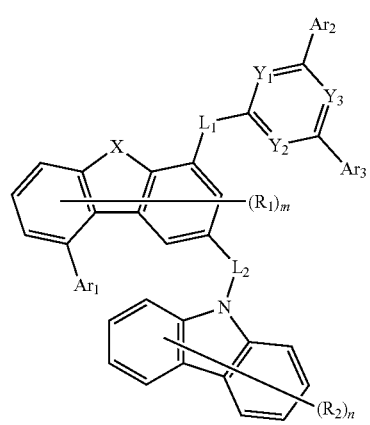
Chemical Formula 6
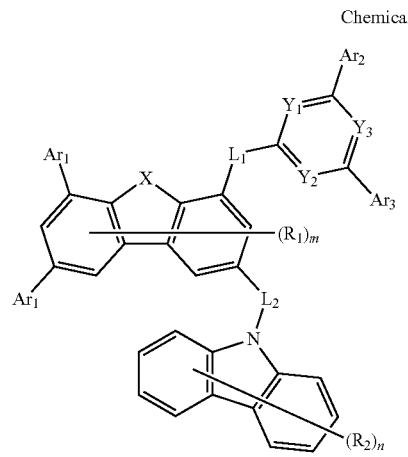
Chemical Formula 7
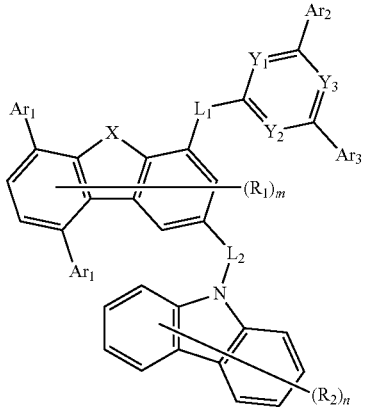
Chemical Formula 8
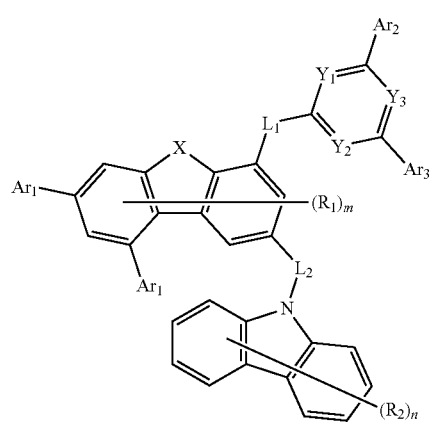
wherein, in Chemical Formulas 2 to 8:
$X$, $Y_1$, $Y_2$, $Y_3$, $L_1$, $L_2$, $Ar_1$, $Ar_2$, $Ar_3$, $R_1$, $R_2$, m and n are as previously defined for Chemical Formula 1.
Preferably, $L_1$ and $L_2$ can be each independently a direct bond or any one selected from the group consisting of the following:
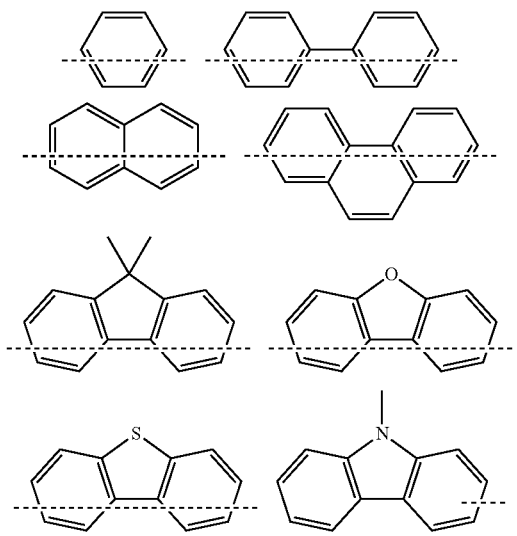

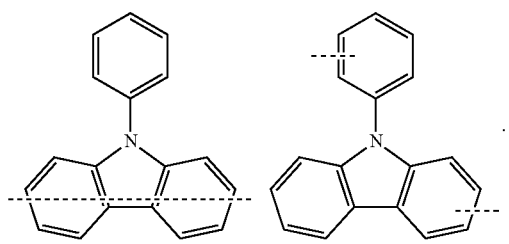

Preferably, Ar$_1$ can be any one selected from the group consisting of the following:

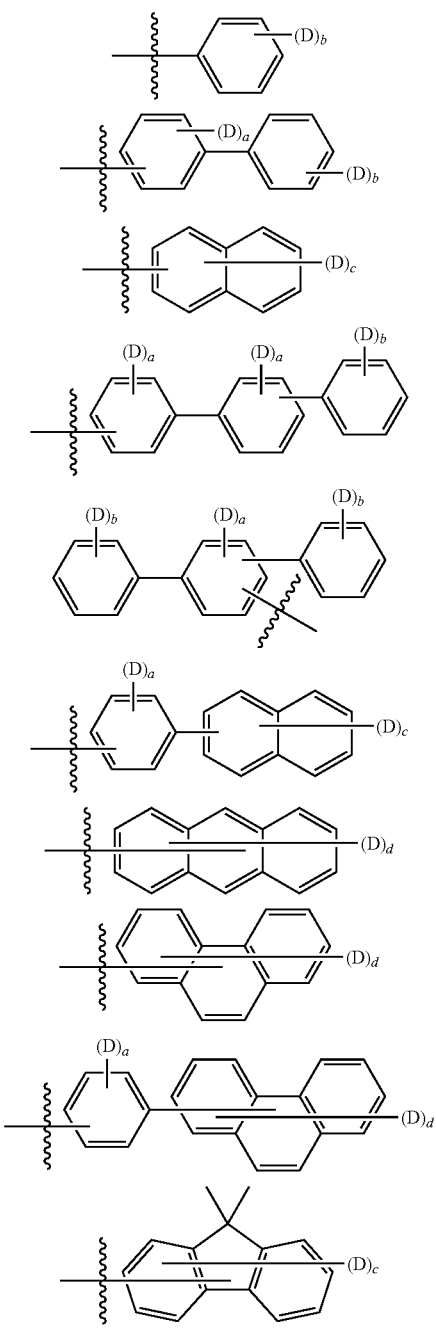

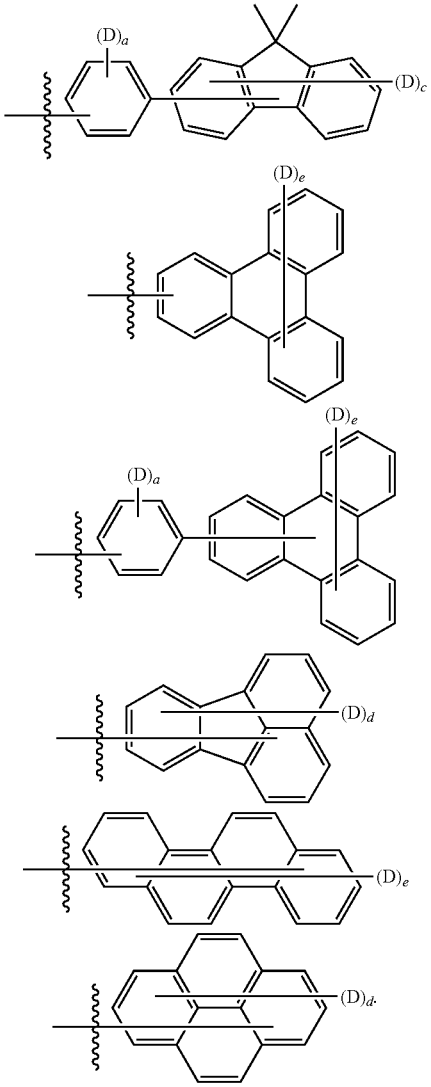

In the above formulas:
a is an integer from 0 to 4;
b is an integer from 0 to 5;
c is an integer from 0 to 7;
d is an integer from 0 to 9; and
e is an integer from 0 to 11.

Preferably, Ar$_1$ is each independently phenyl, biphenylyl, naphthyl, phenanthrenyl or triphenylenyl, which are unsubstituted or substituted with deuterium.

Preferably, Ar$_2$ and Ar$_3$ can be each independently any one selected from the group consisting of:

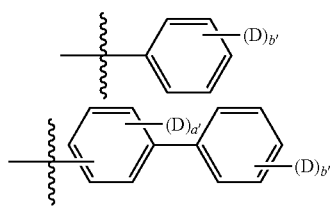

-continued

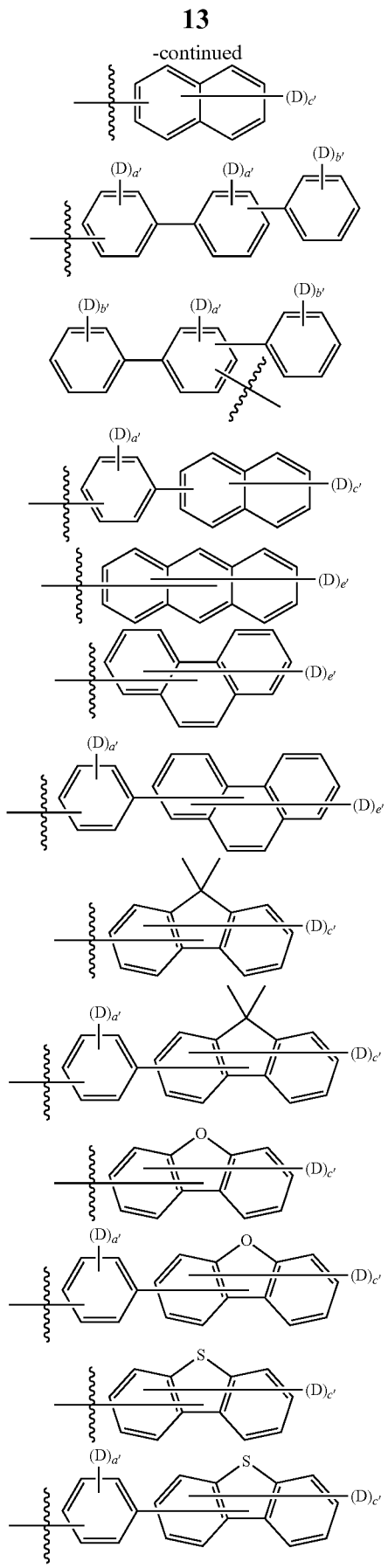

-continued

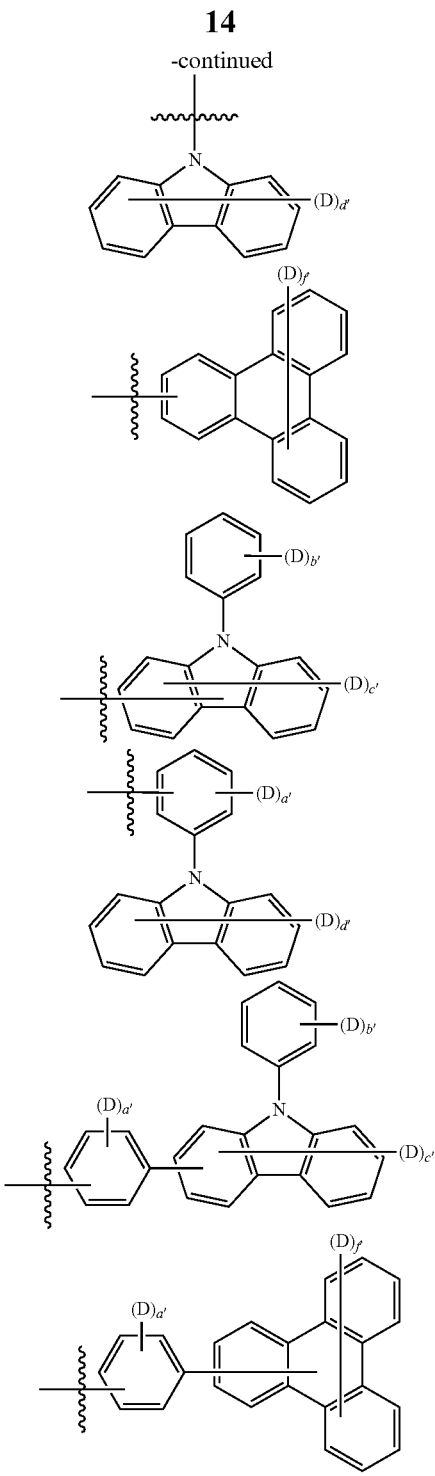

wherein in the above formulas:
a' is an integer from 0 to 4;
b' is an integer from 0 to 5;
c' is an integer from 0 to 7;
d' is an integer from 0 to 8;
e' is an integer from 0 to 9; and
f' is an integer from 0 to 11.

Preferably, each $R_1$ can independently be hydrogen or deuterium, more preferably hydrogen.

Preferably, each $R_2$ is independently hydrogen, deuterium, halogen, cyano, methoxy, trifluoromethyl, trifluoromethoxy, phenyl, pyridinyl, isoquinolinyl, or any one selected from the group consisting of the following:

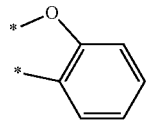 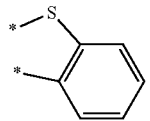

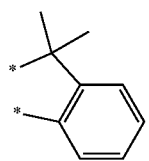 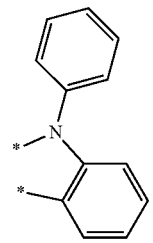

wherein in the above formulas, the two * are each connected to an adjacent carbon of the carbazole in Chemical Formula 1; and the phenyl can be substituted with any one selected from the group consisting of halogen, cyano, methoxy, trifluoromethyl and trifluoromethoxy.

Preferably, in the compound of Chemical Formula 1, at least one of $L_1$, $Ar_2$ and $Ar_3$ can contain at least one heteroatom selected from the group consisting of N, O, and S.

Preferably, the compound of Chemical Formula 1 can be any one selected from the group consisting of:

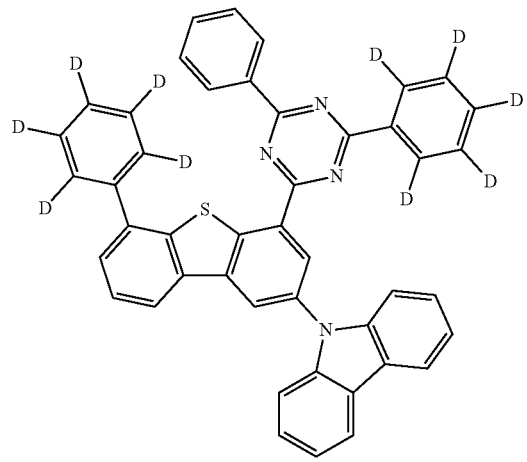

-continued

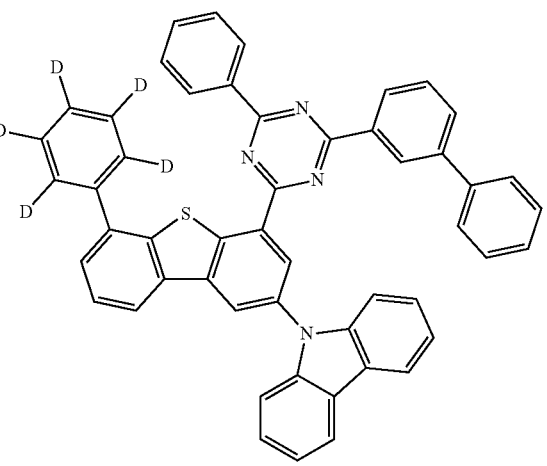

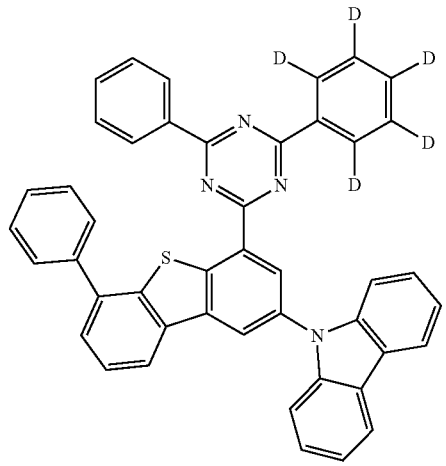

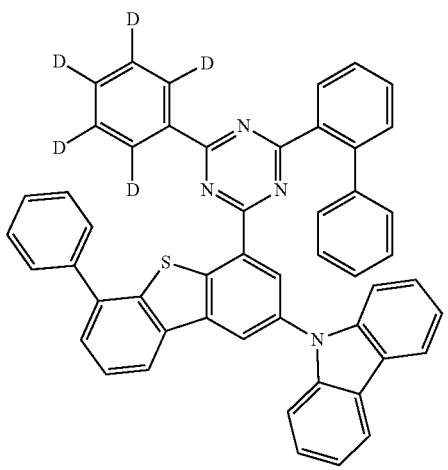

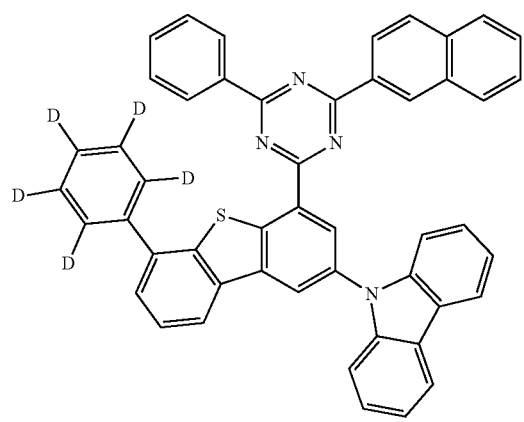
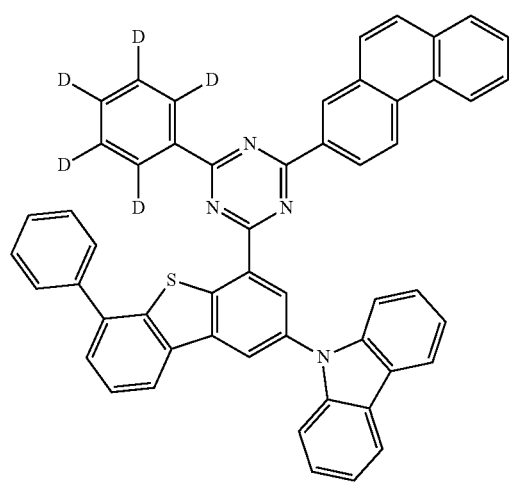
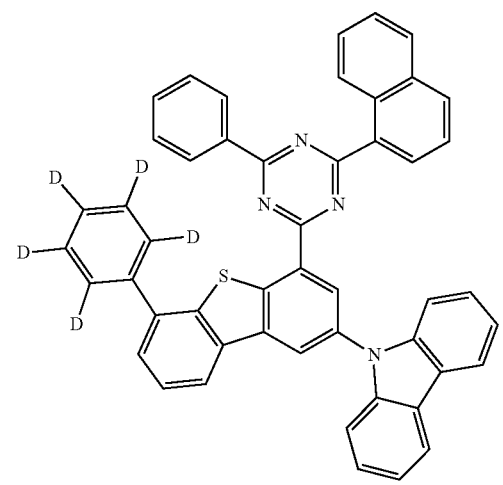
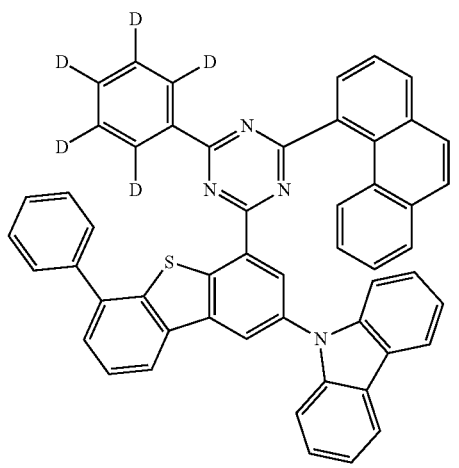
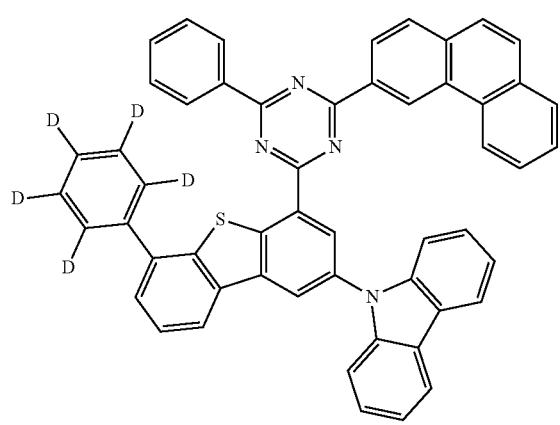
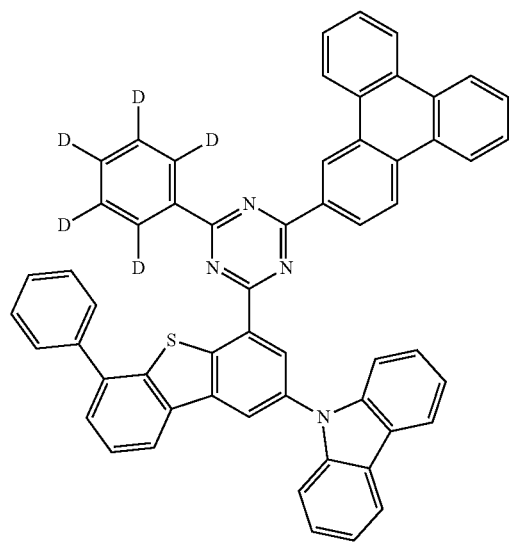

-continued
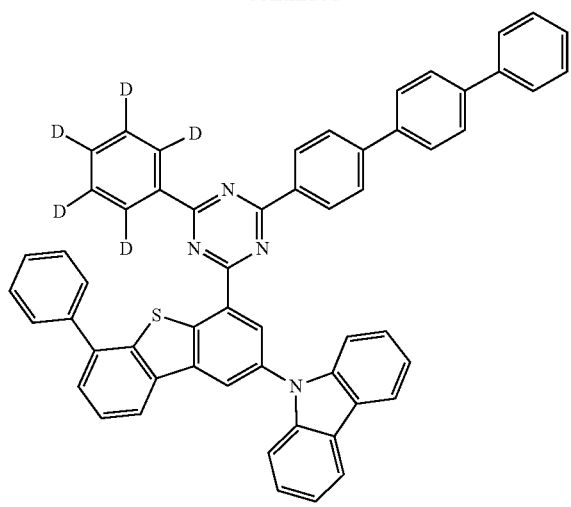
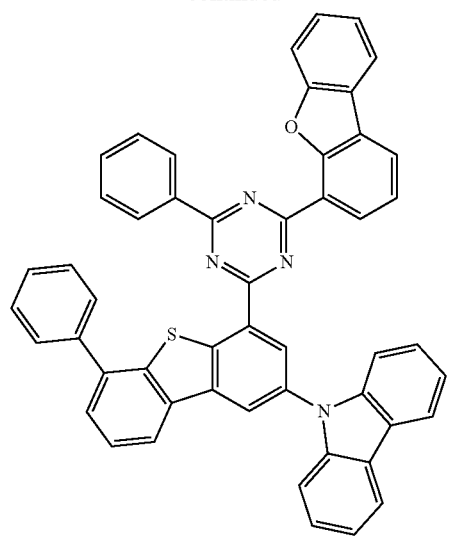
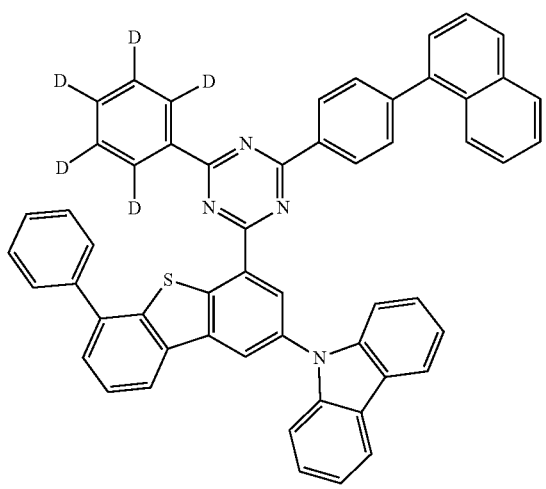
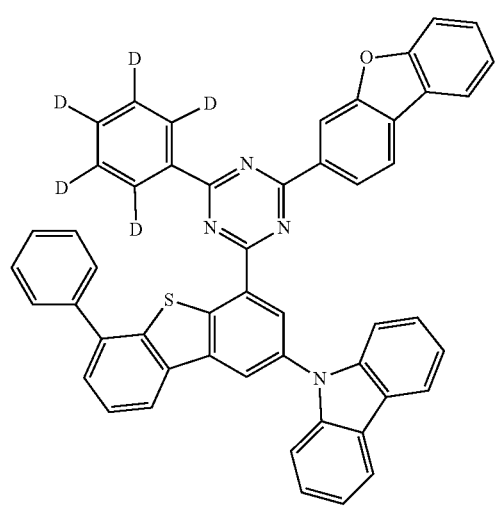
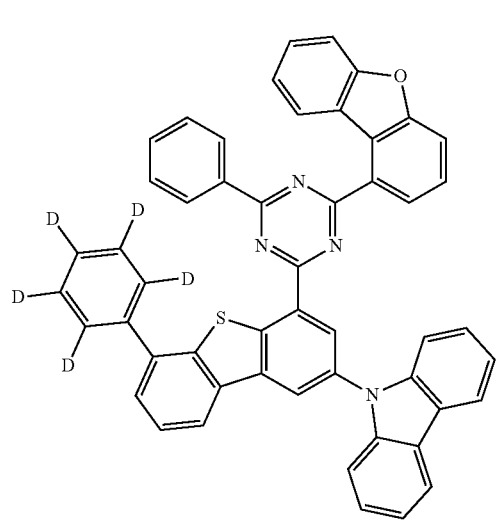
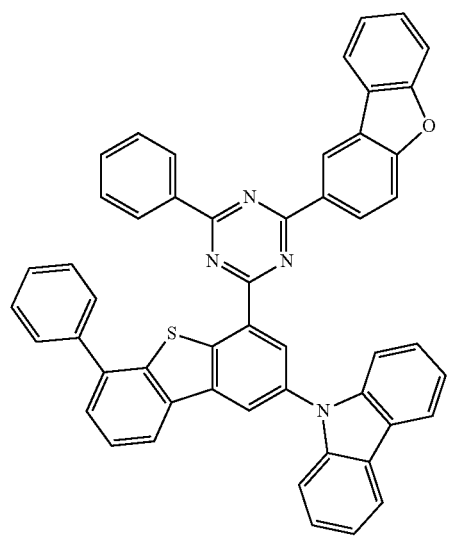

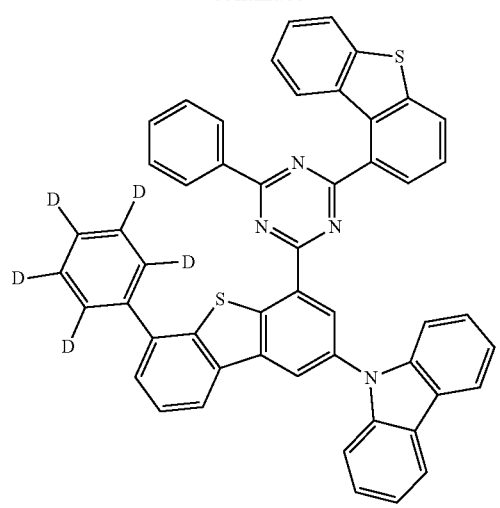
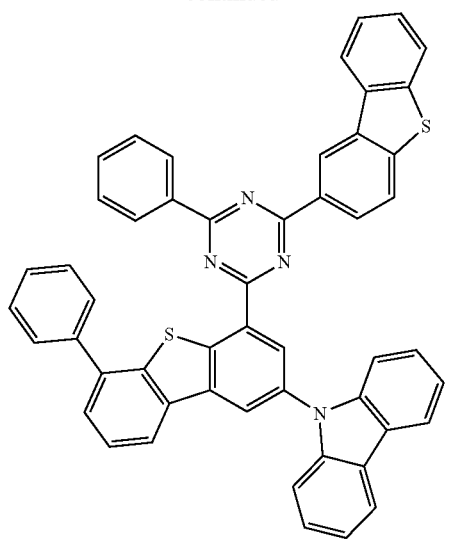
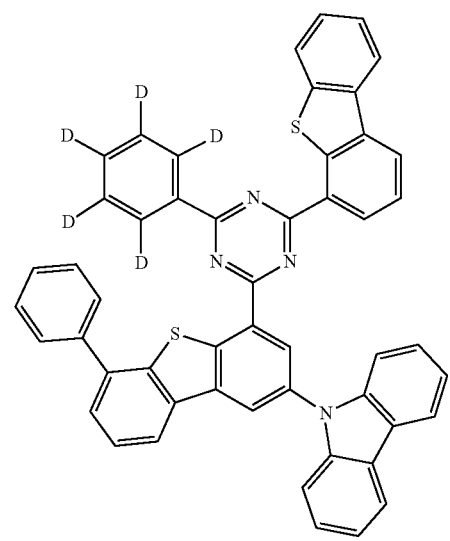
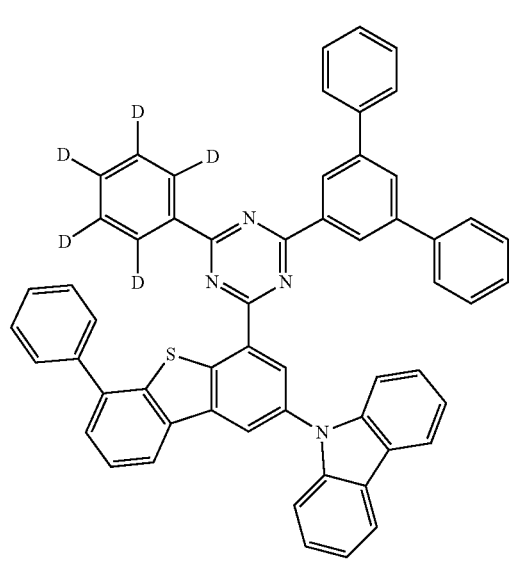
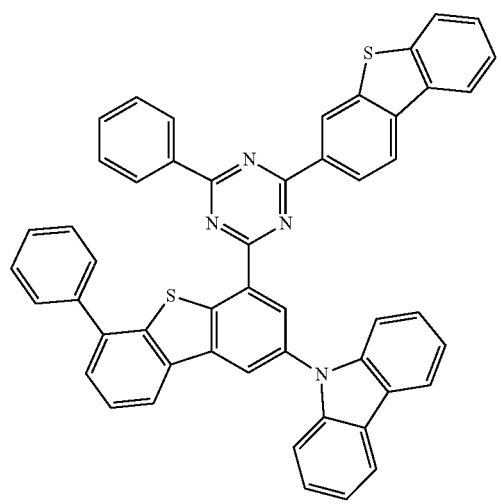
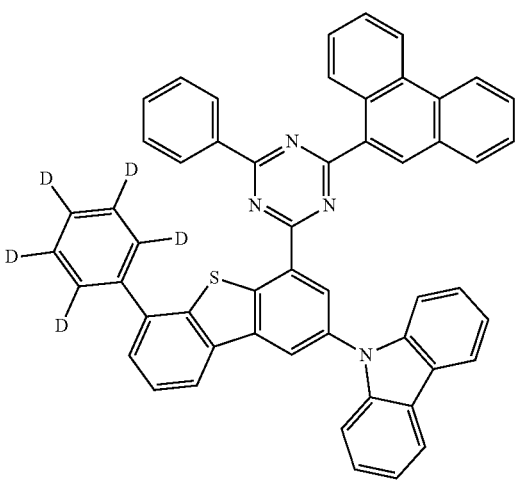

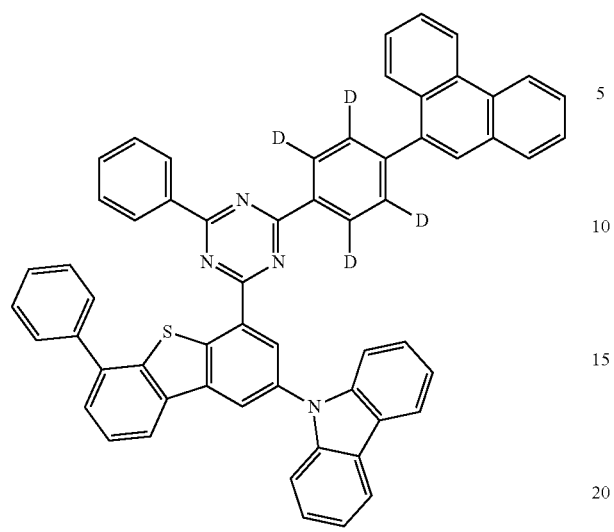
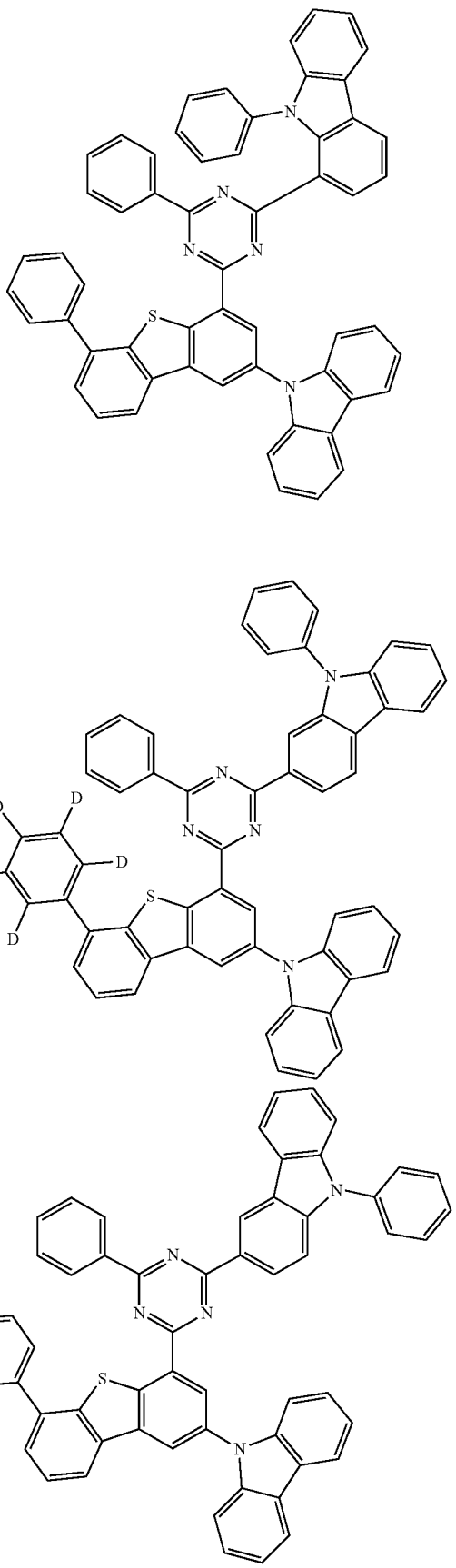

25
-continued
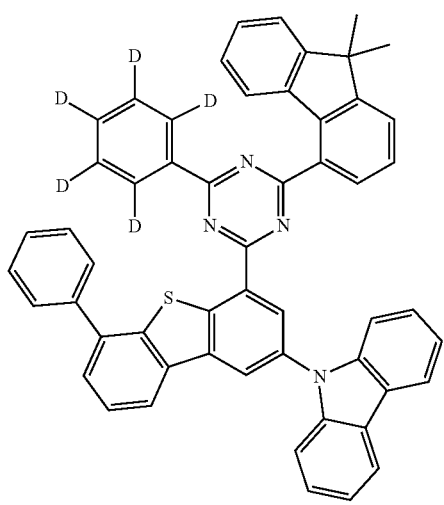
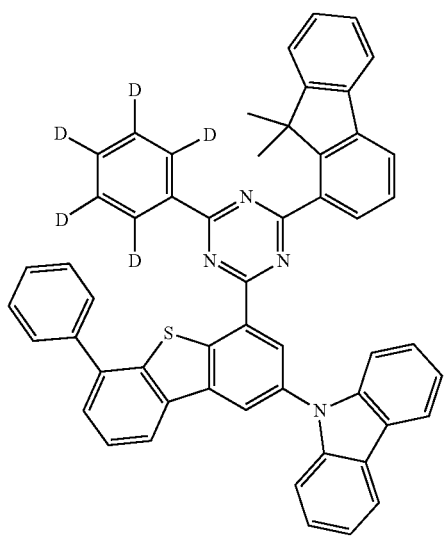
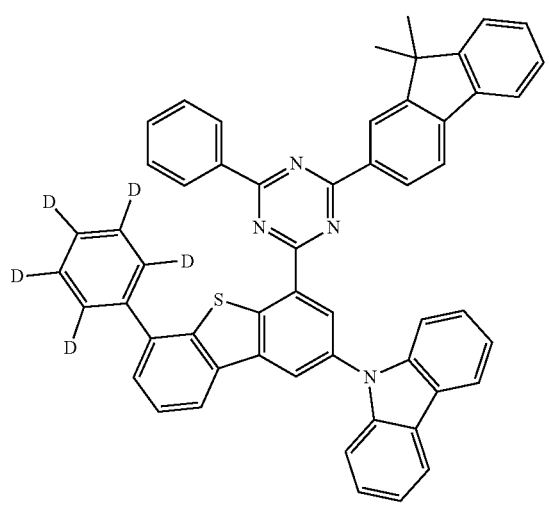
26
-continued
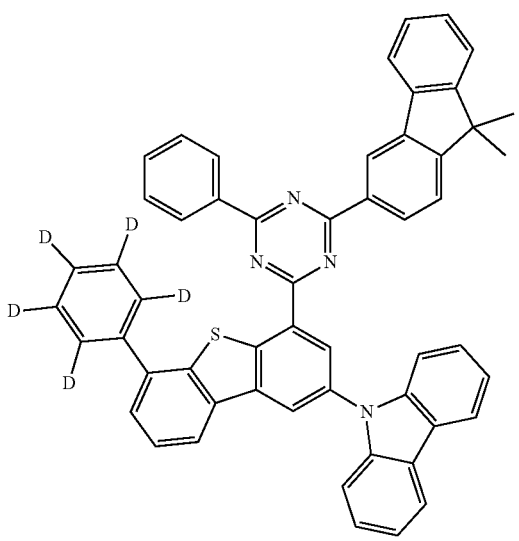
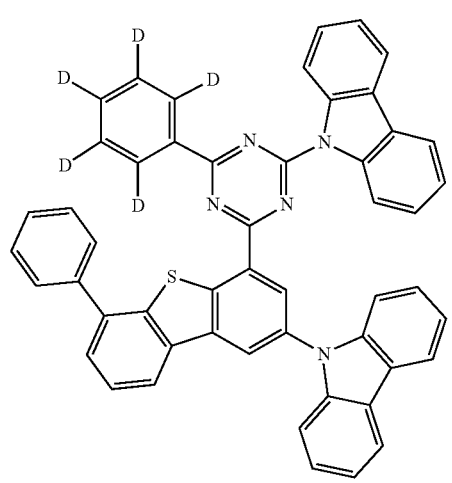
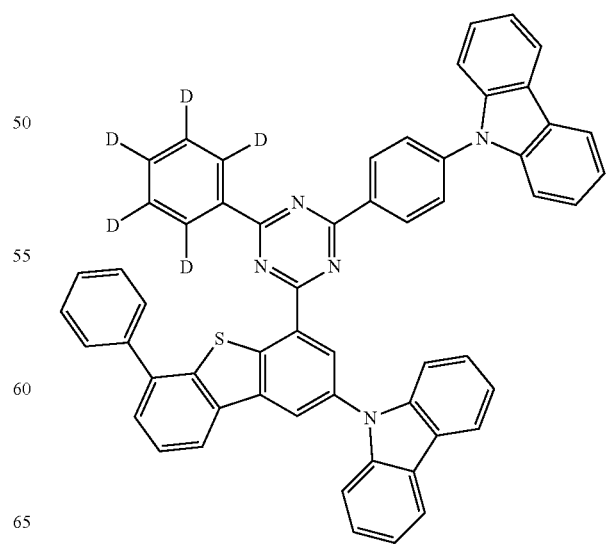

27
-continued
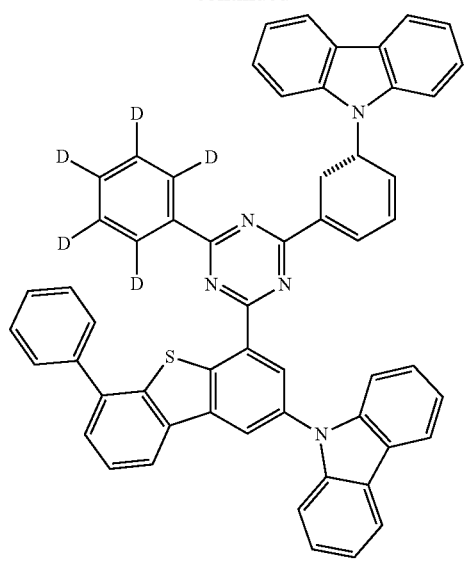
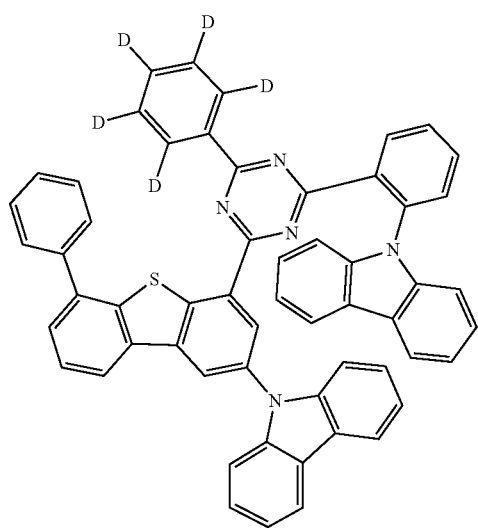
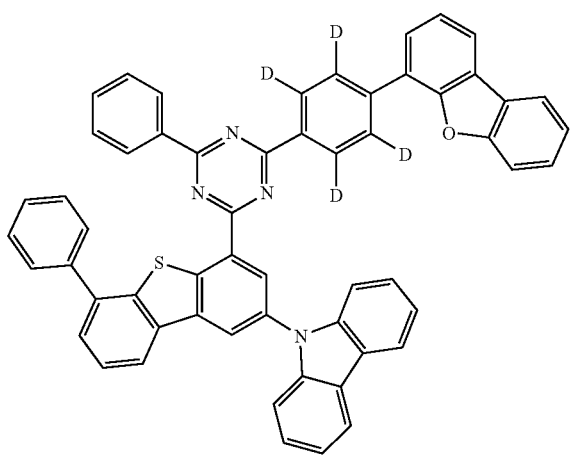
28
-continued
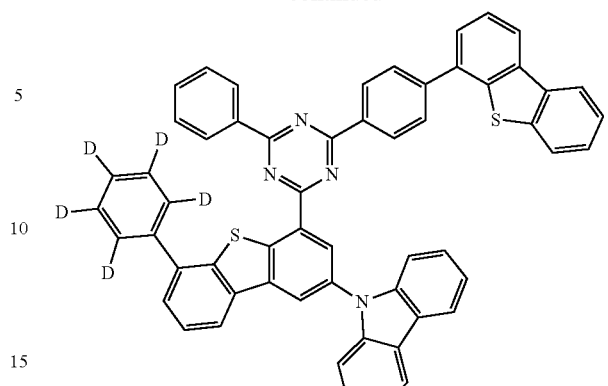
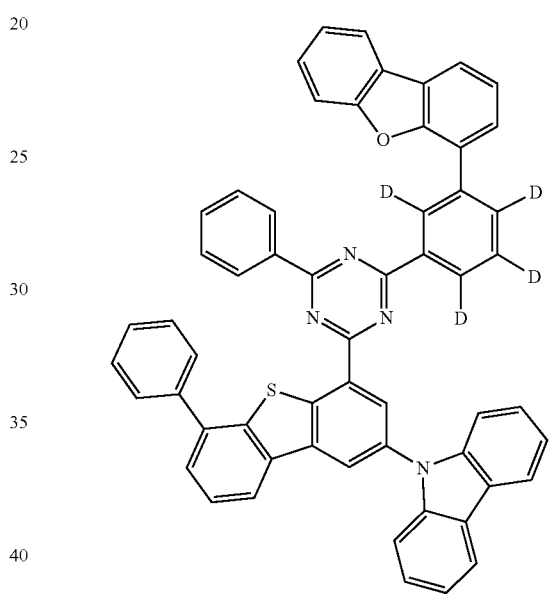
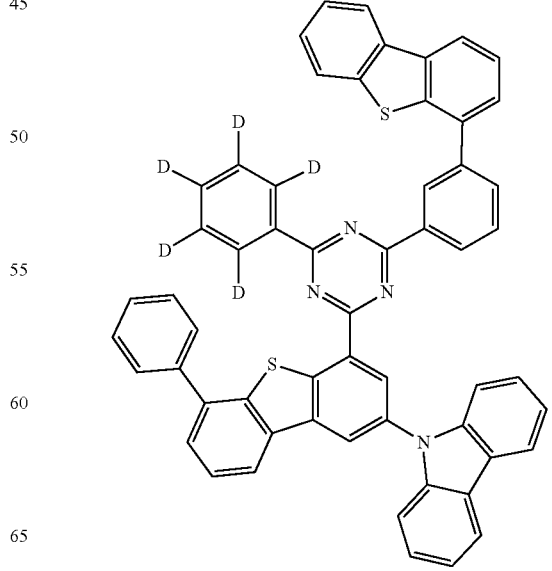

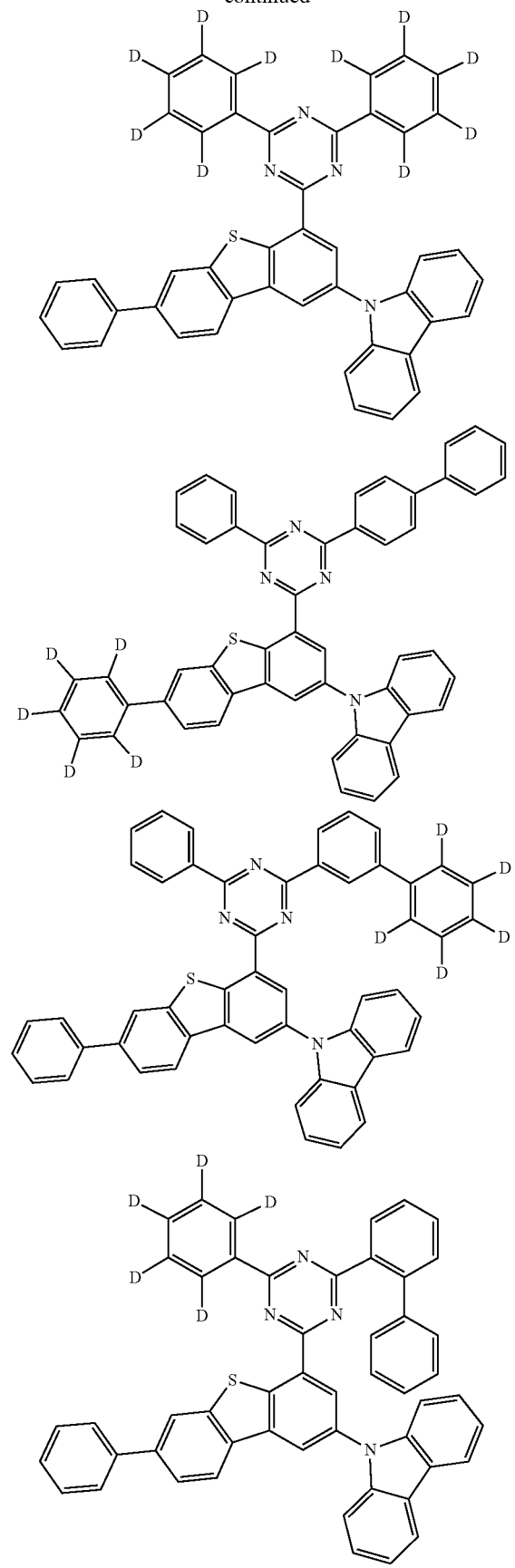

31
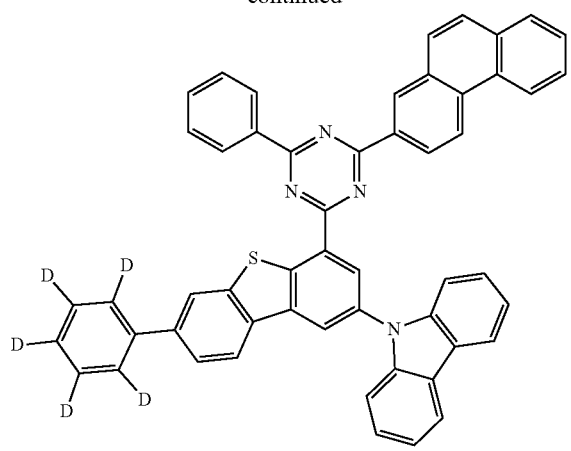
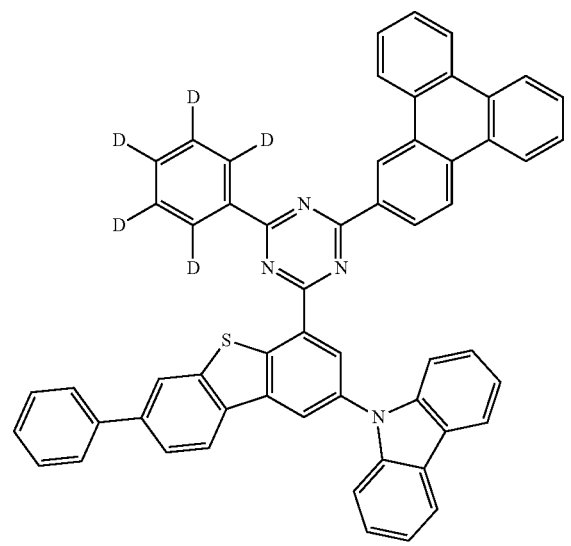
32
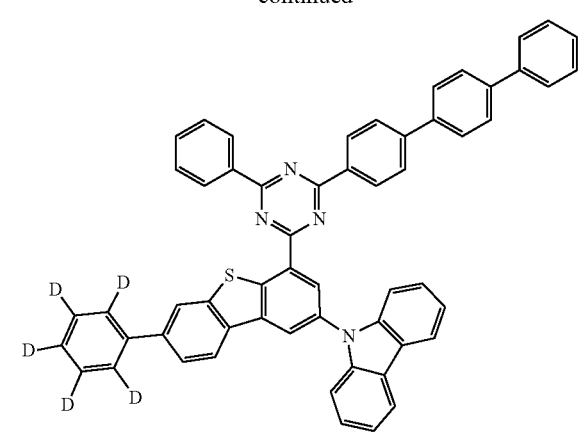
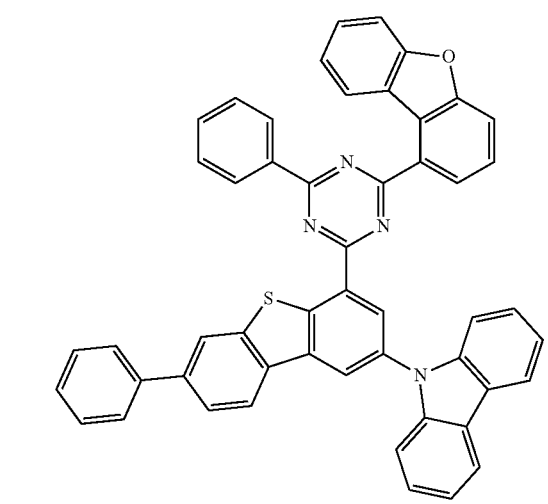

33
-continued
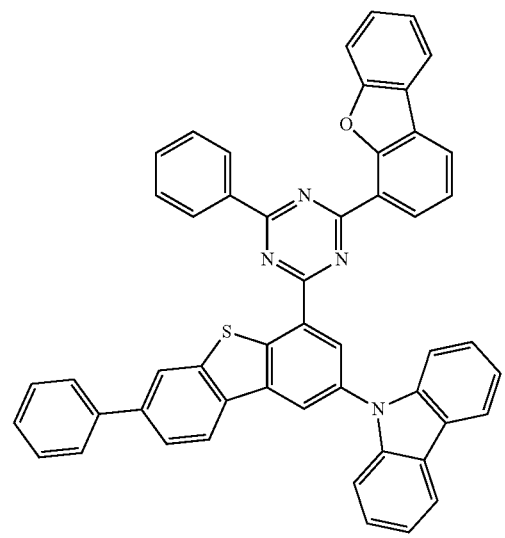
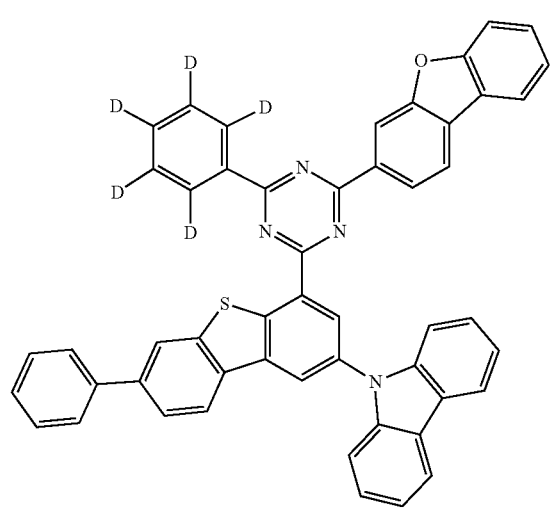
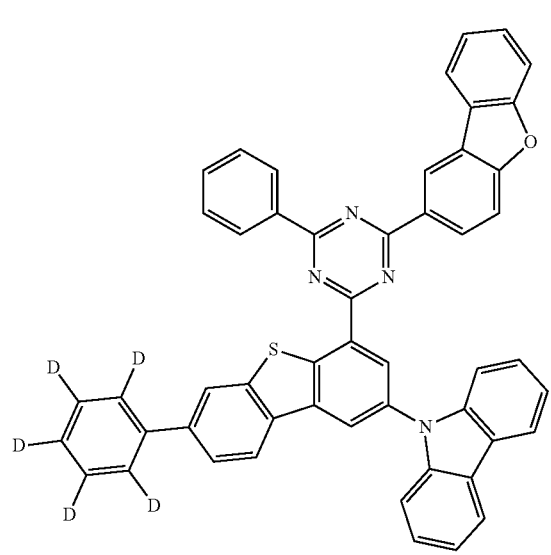
34
-continued
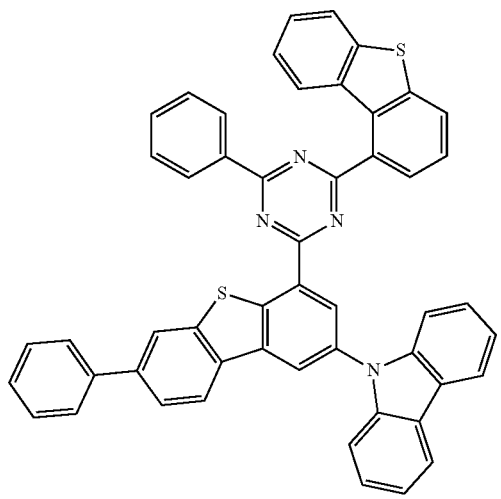
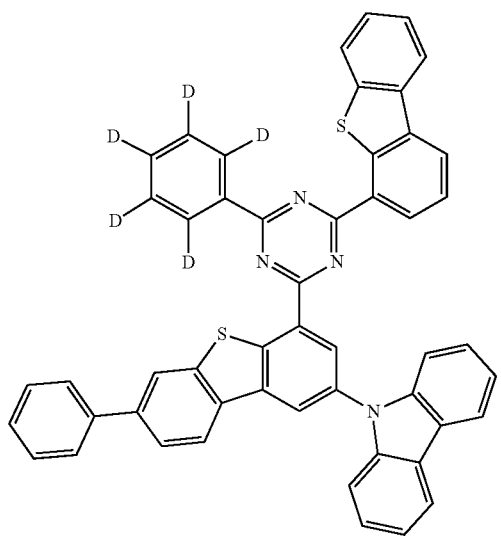
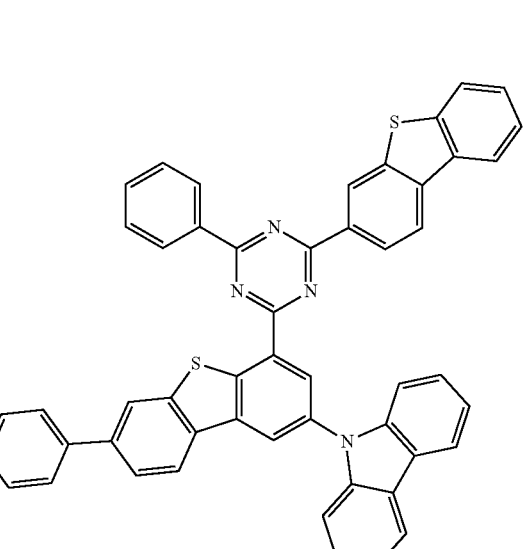

35
-continued
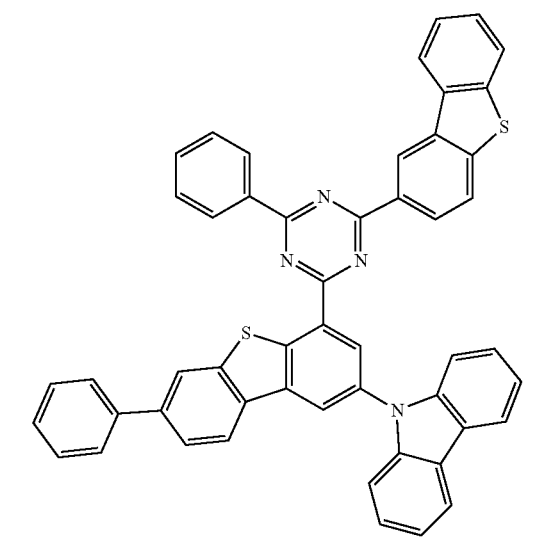
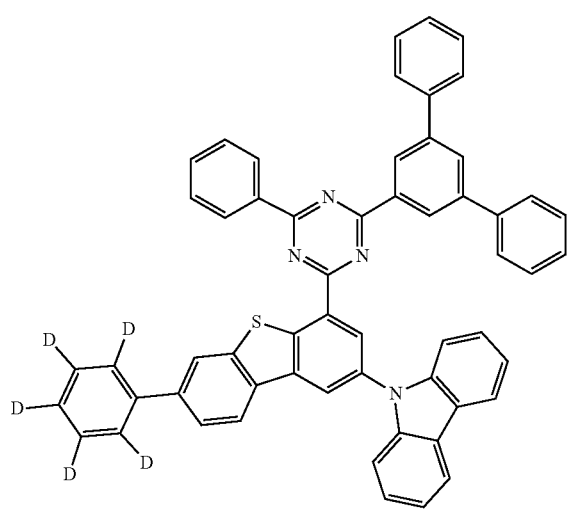
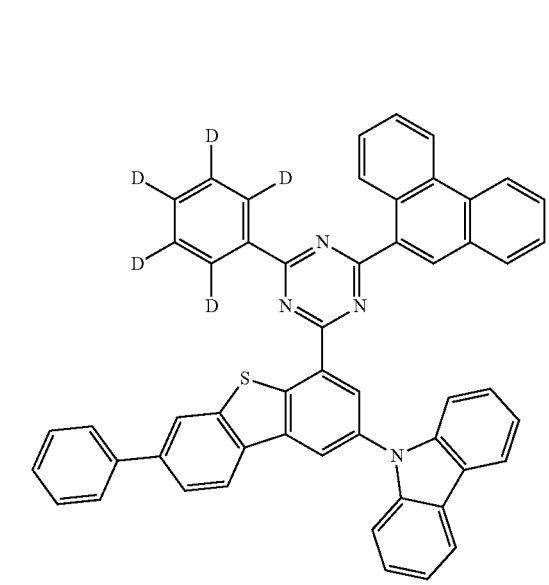
36
-continued
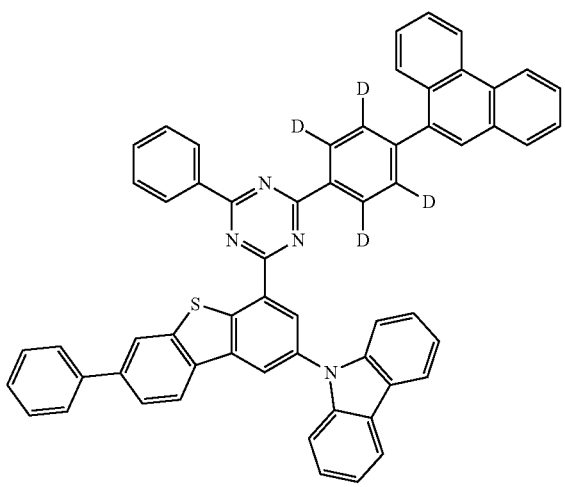
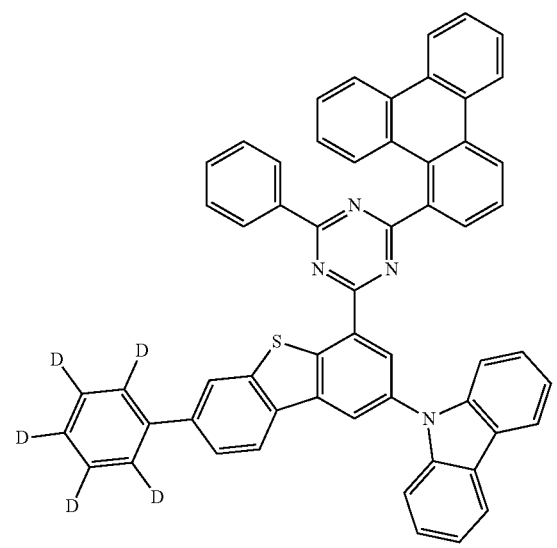
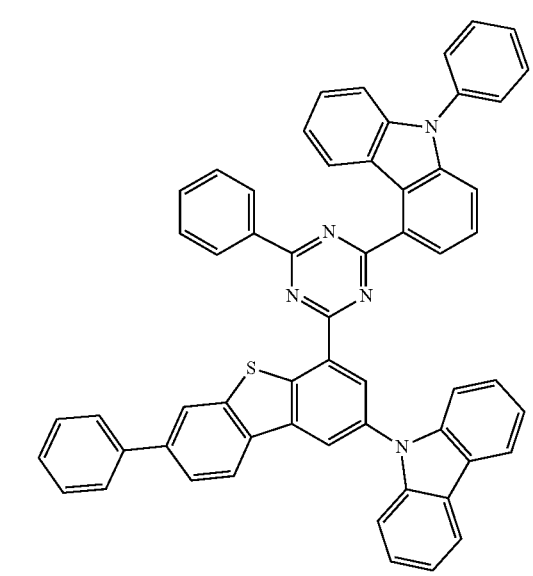

37
-continued
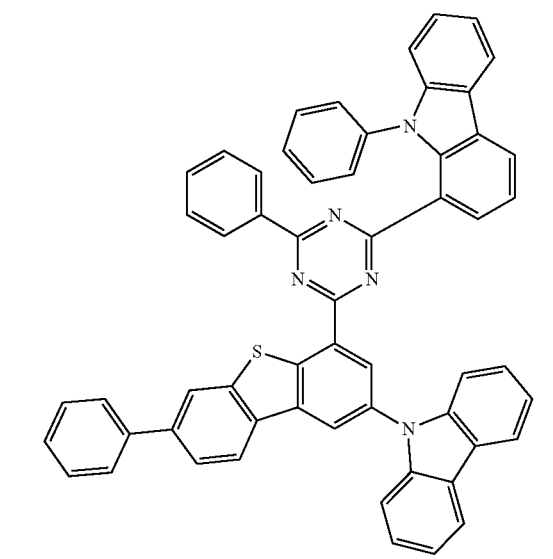
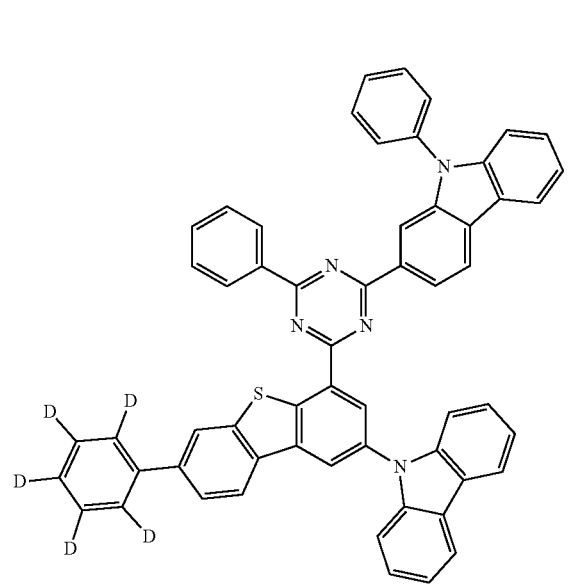
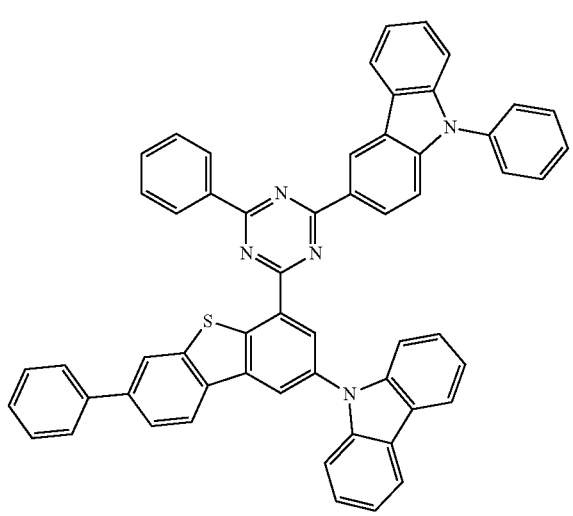
38
-continued
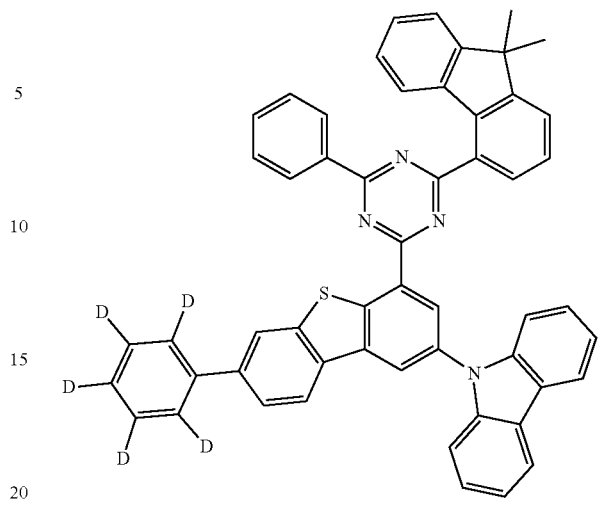
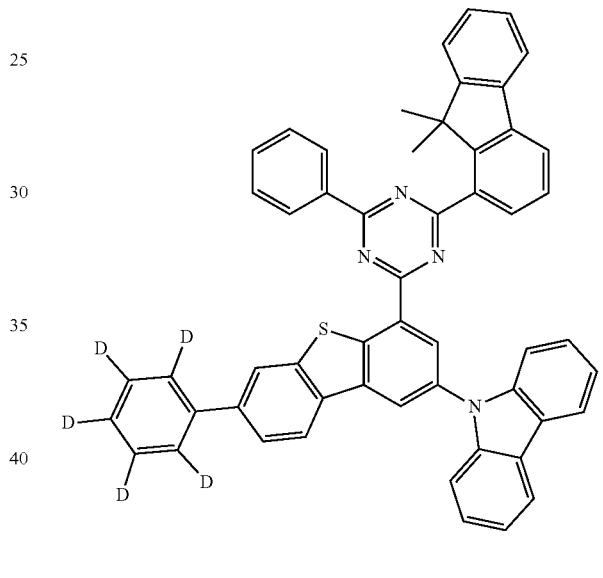
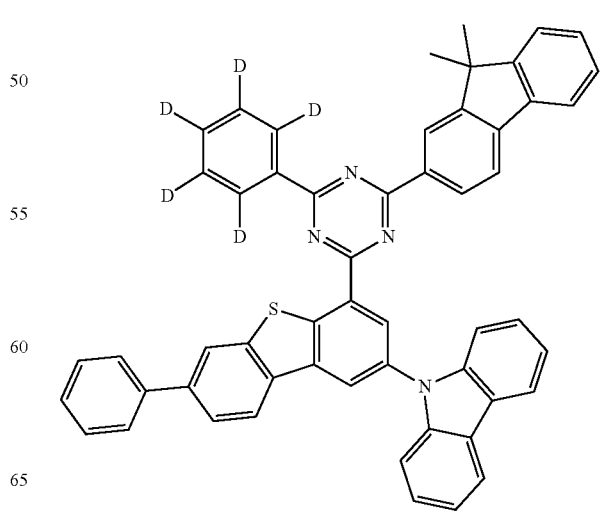

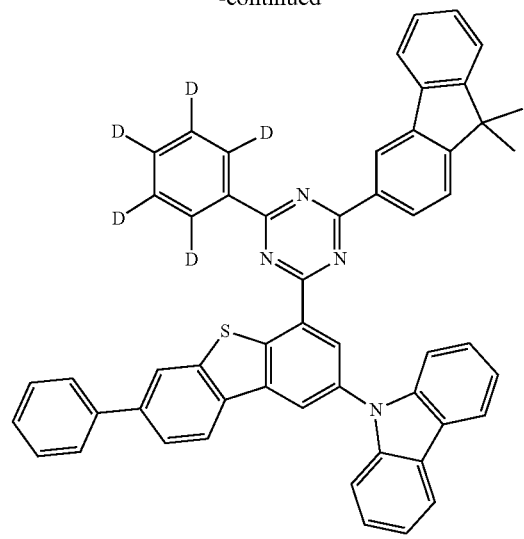

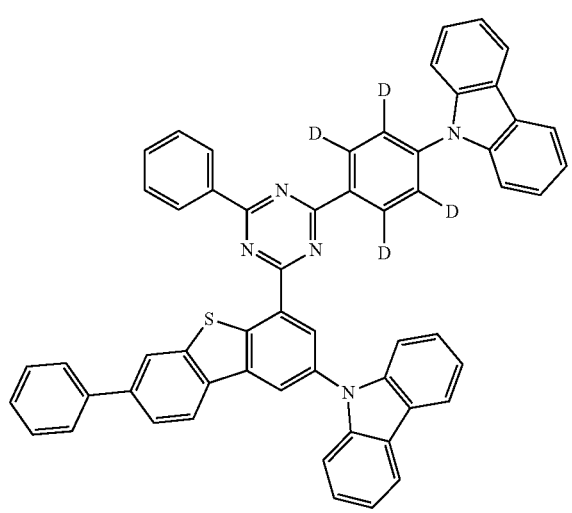
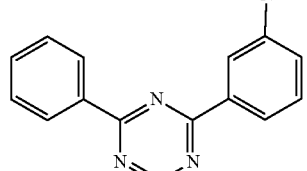
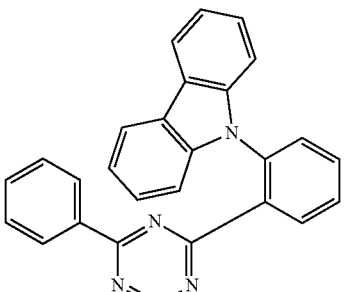
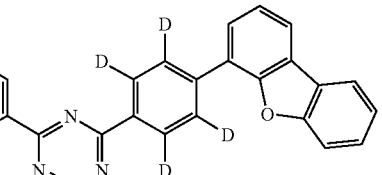

41
-continued
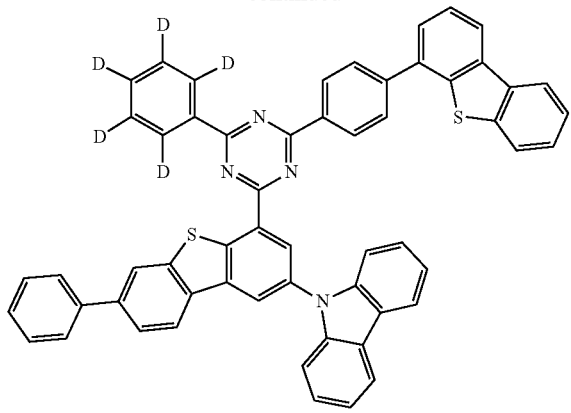
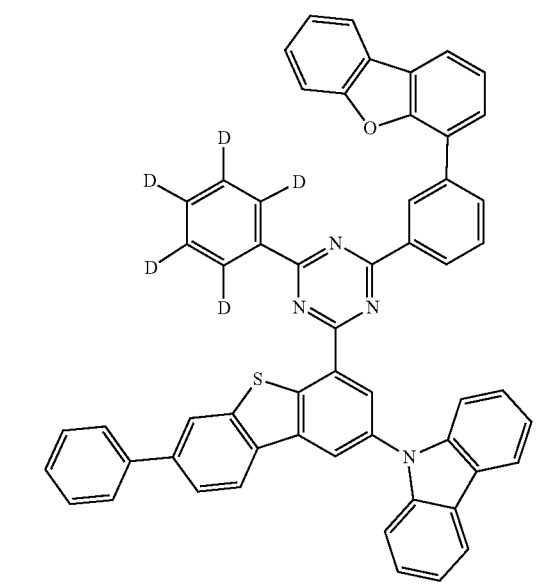
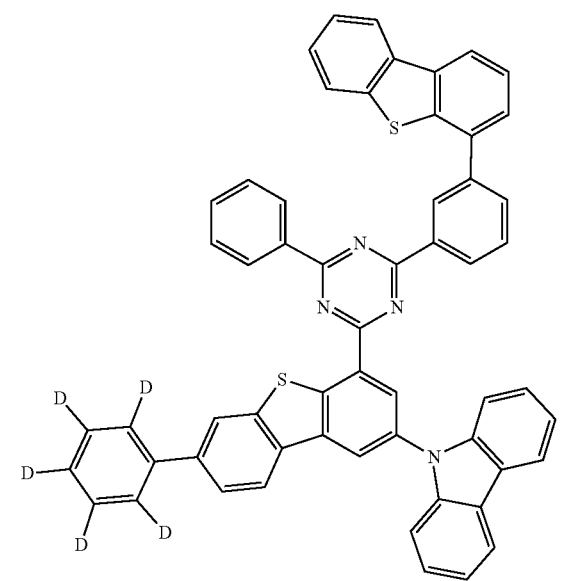
42
-continued
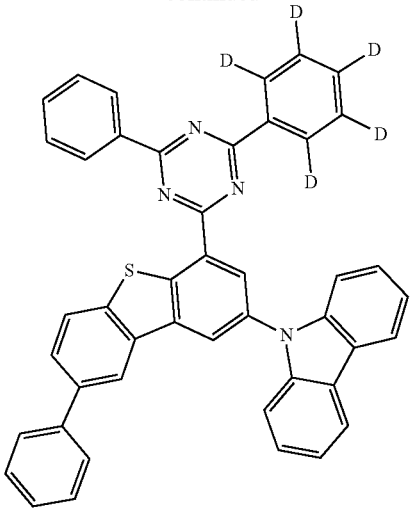
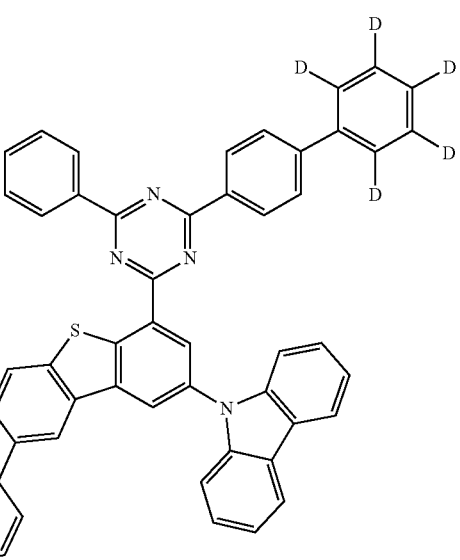
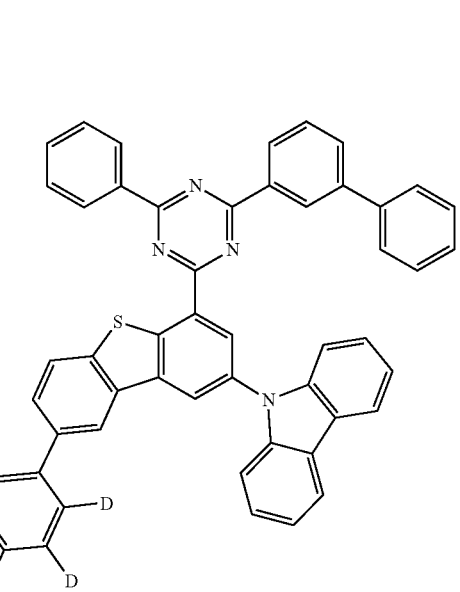

-continued
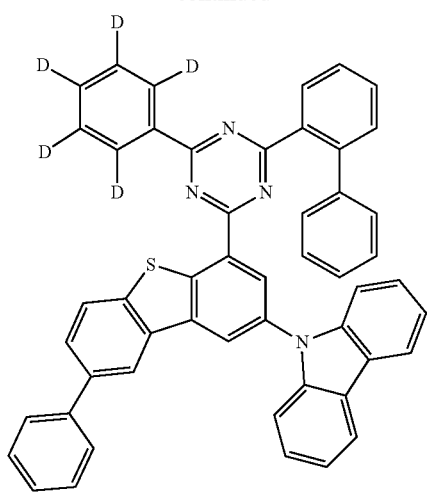
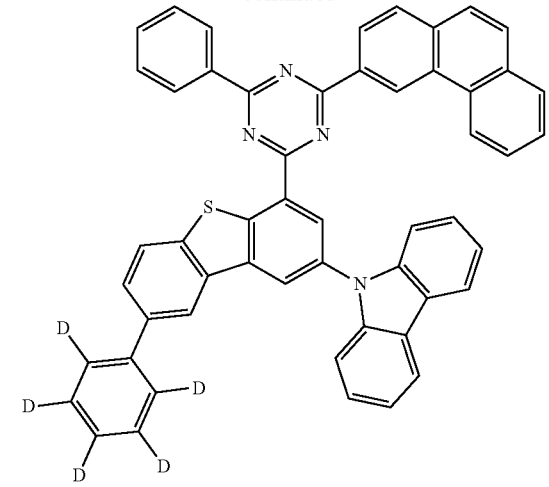
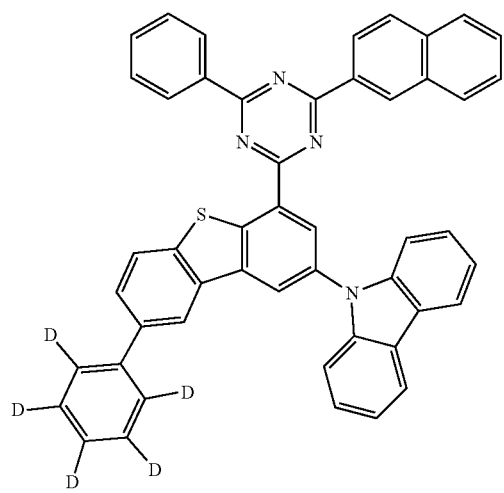
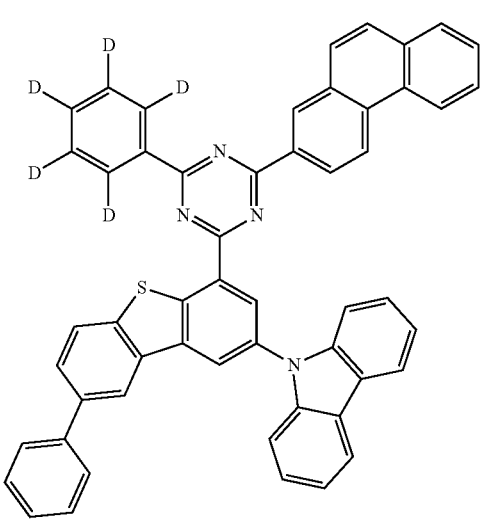
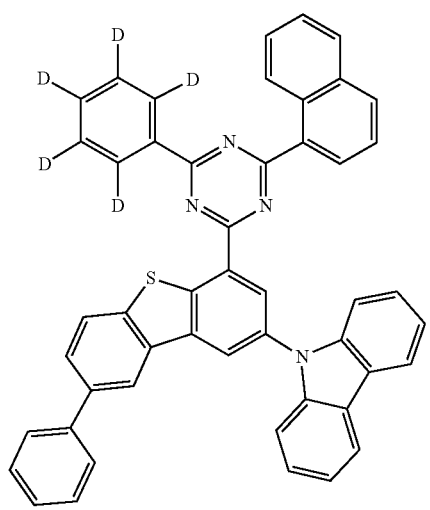
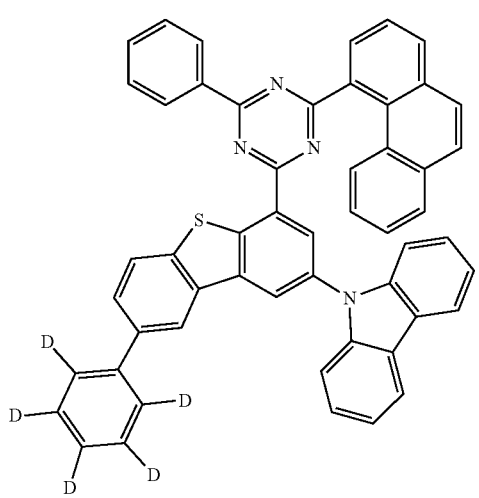

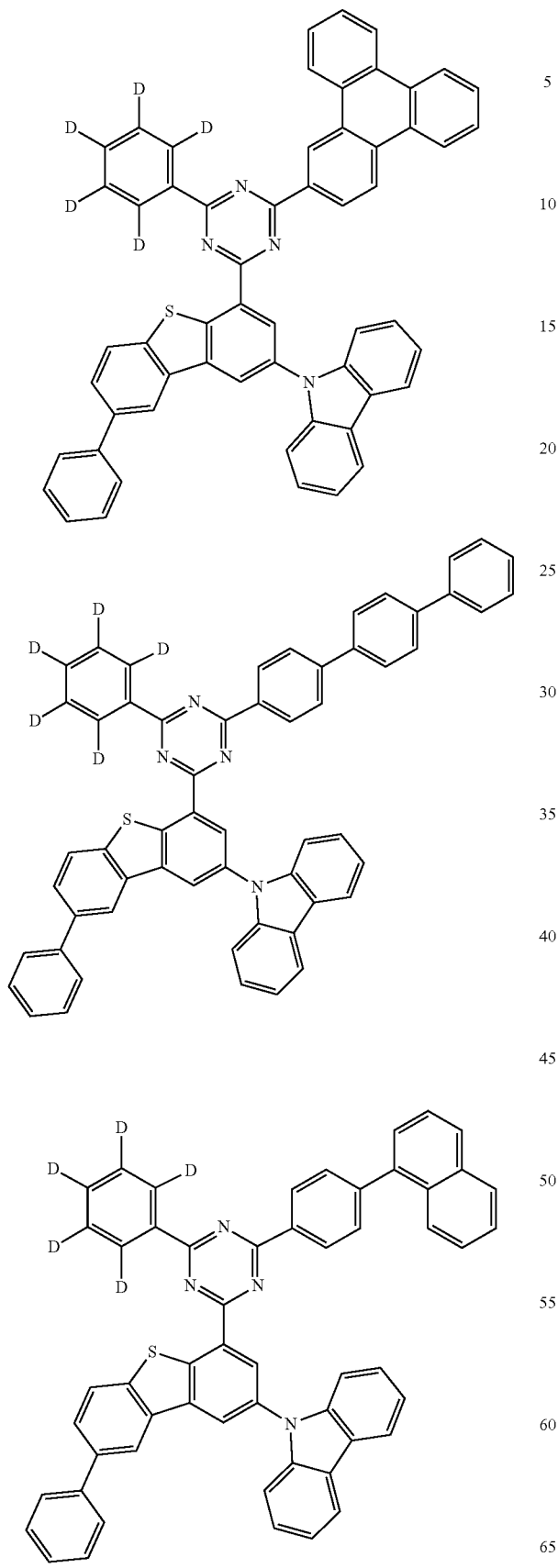

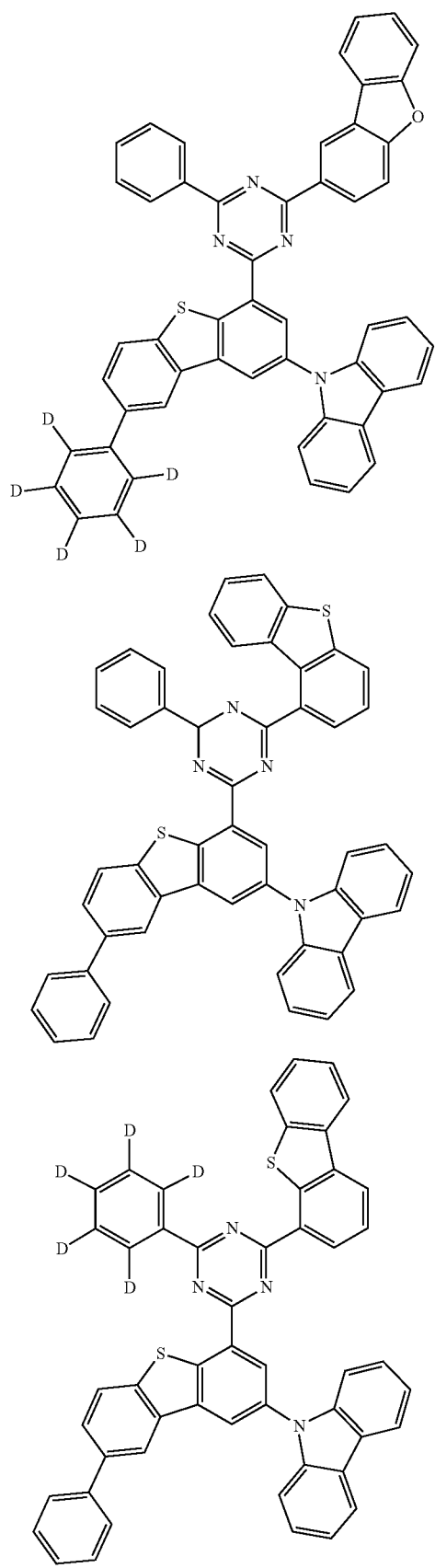
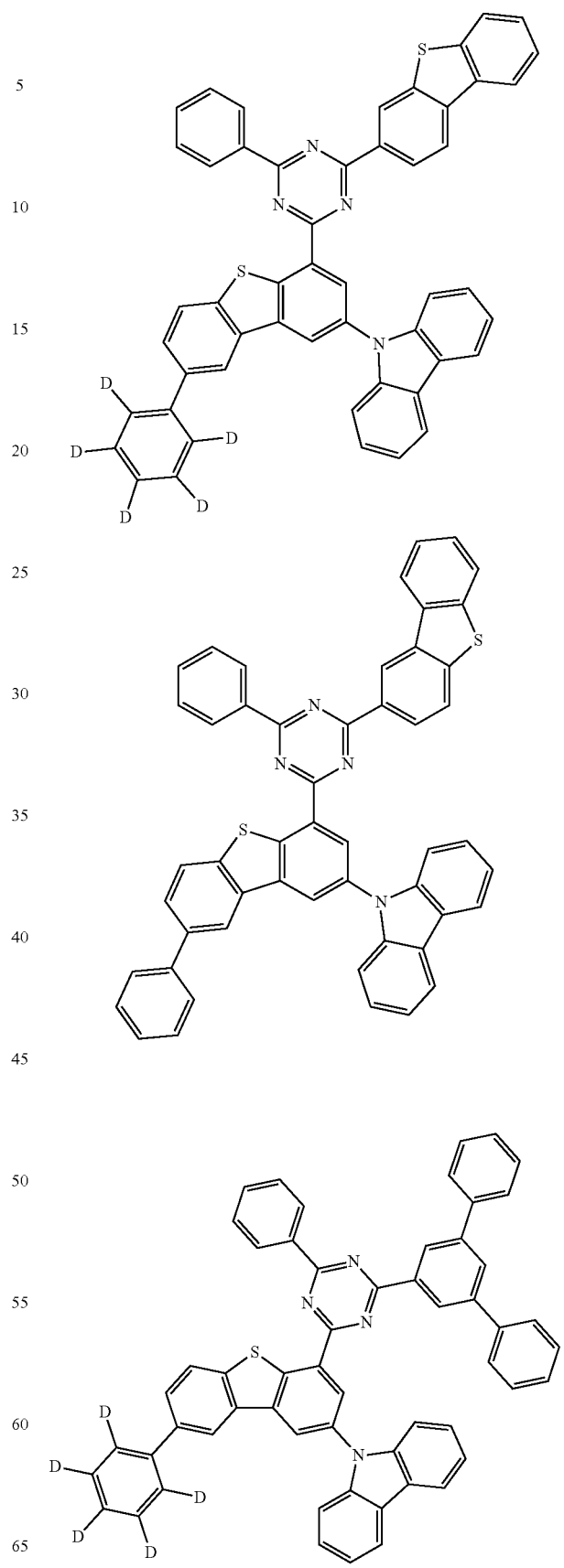

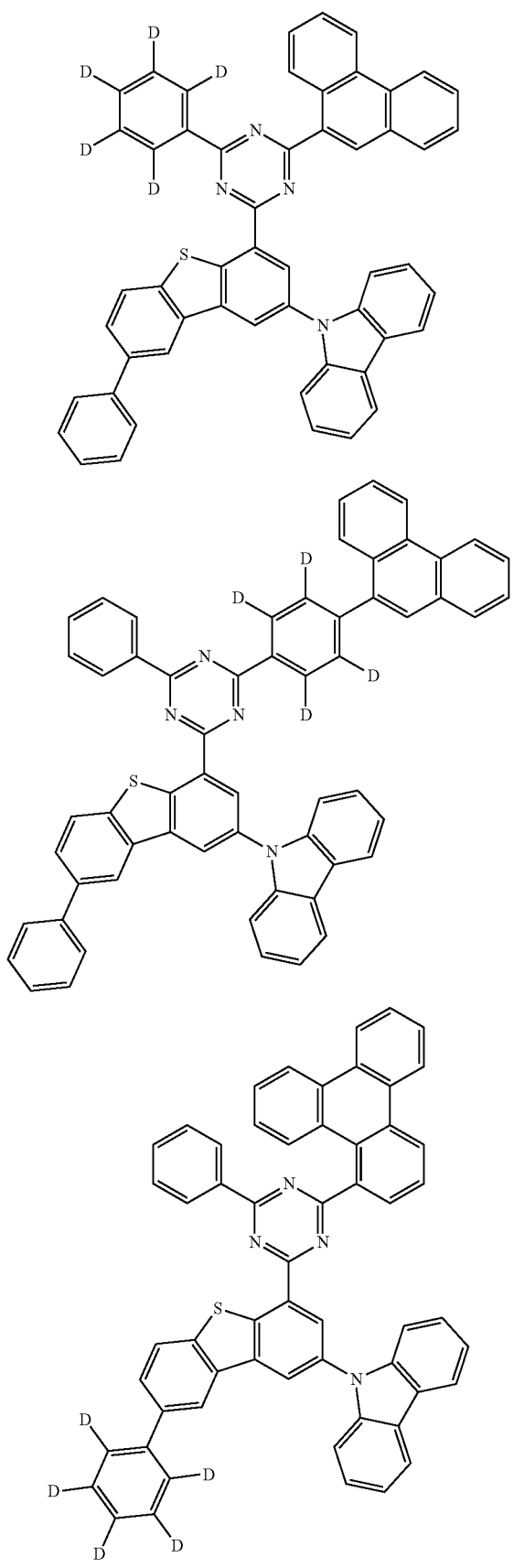
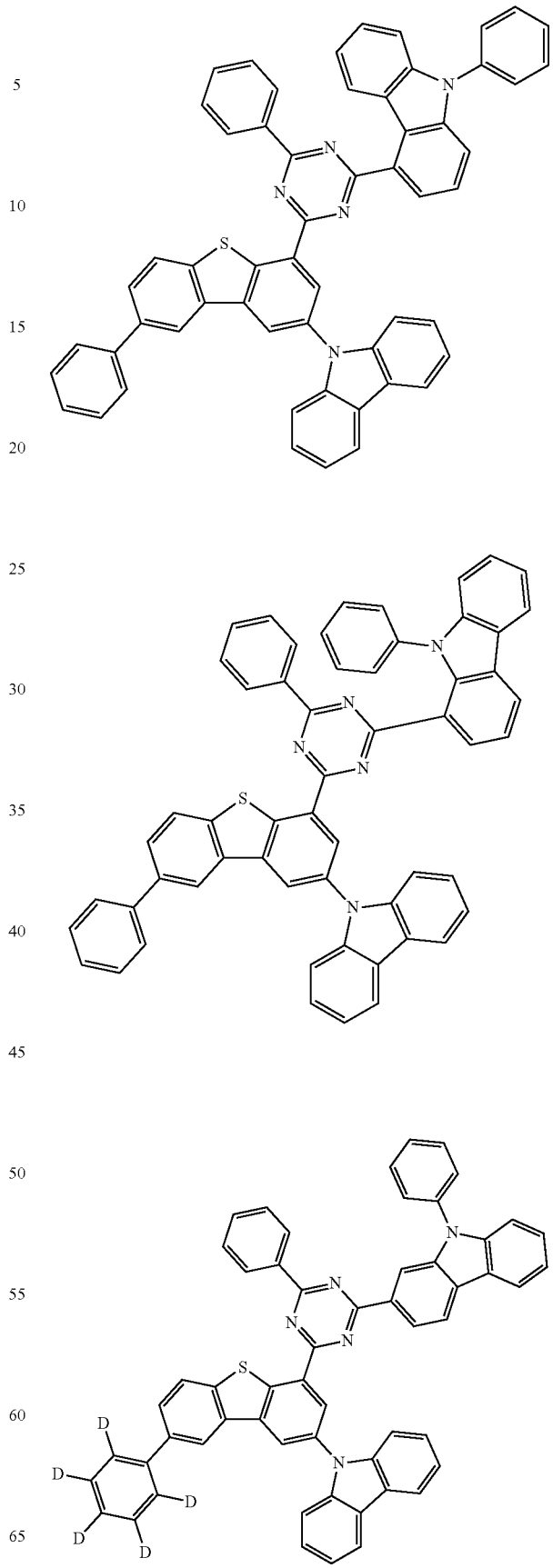

51
-continued
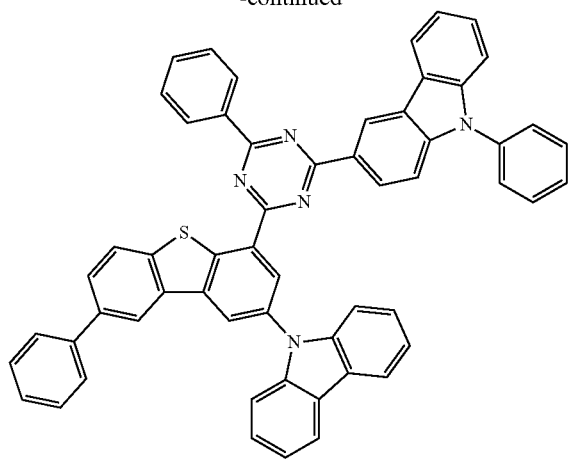
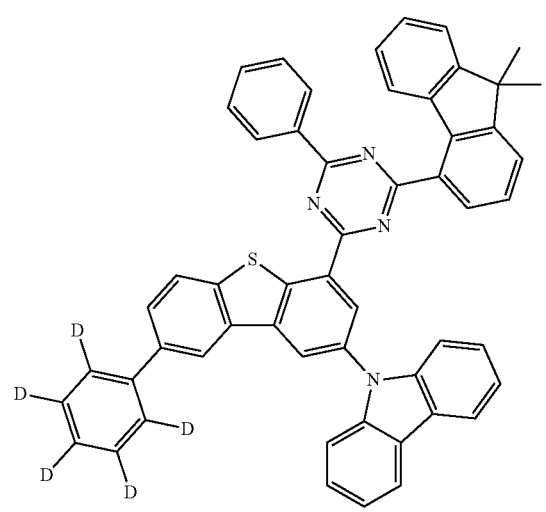
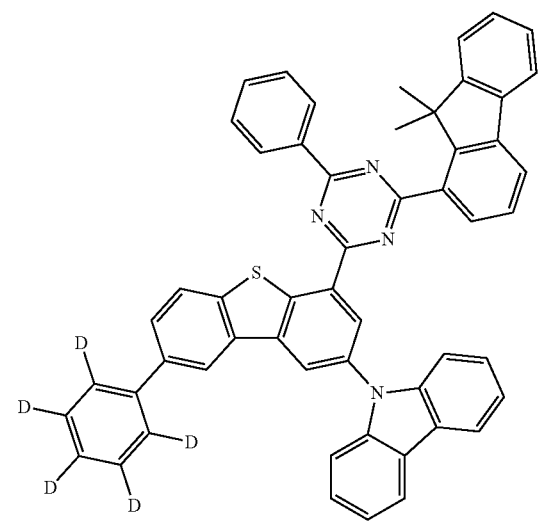
52
-continued
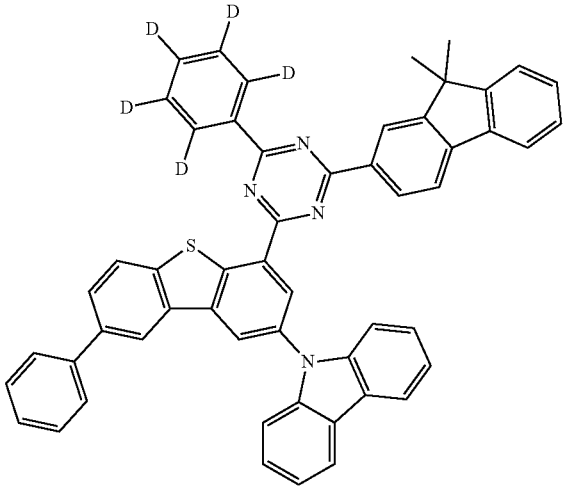
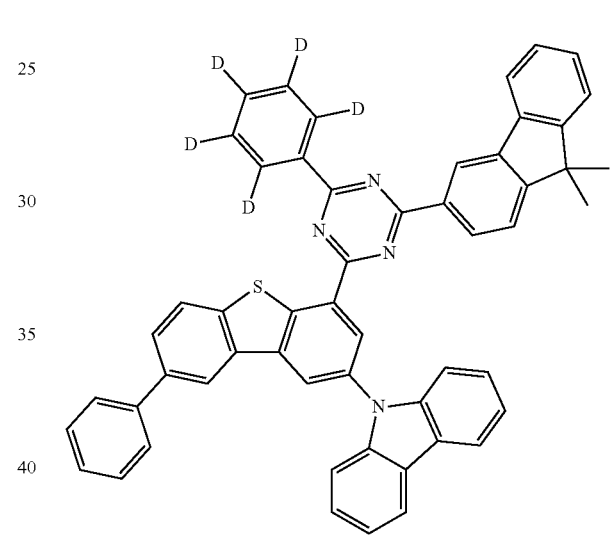
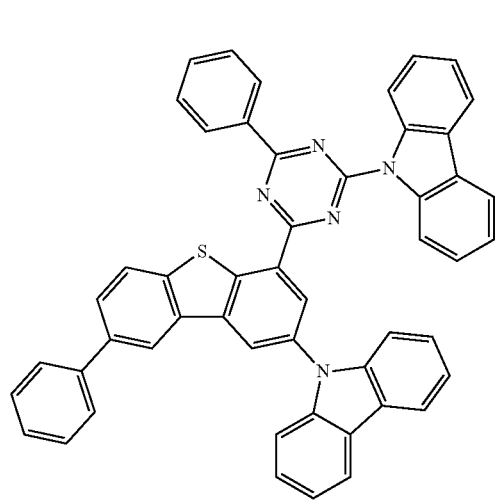

53
-continued
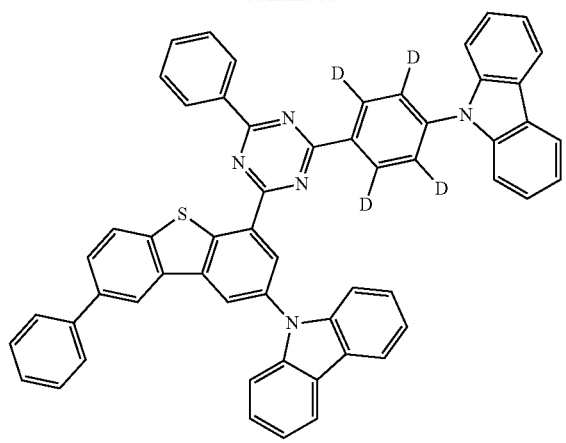
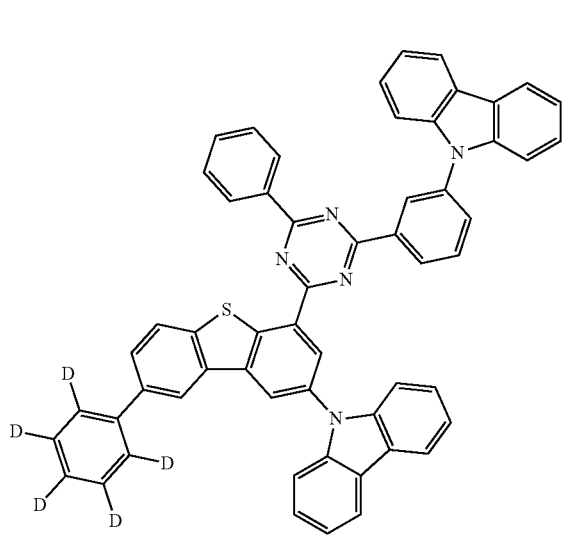
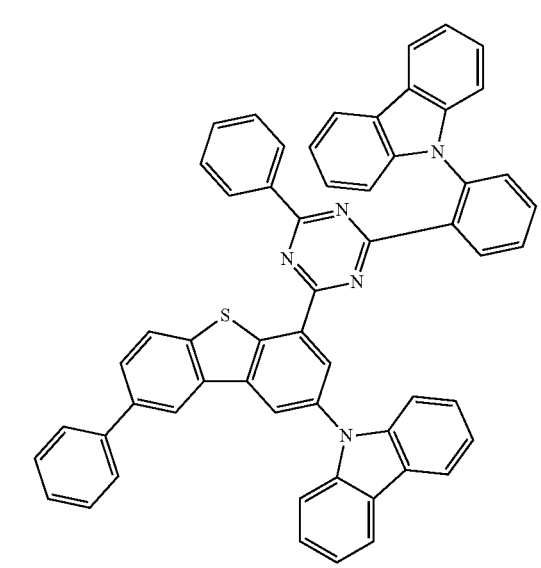
54
-continued
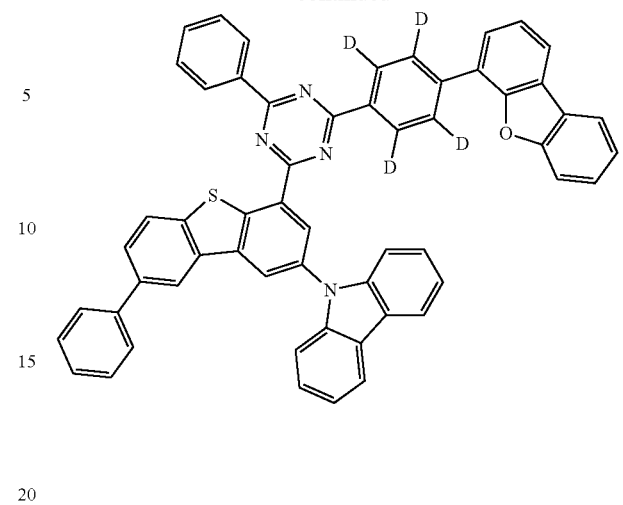
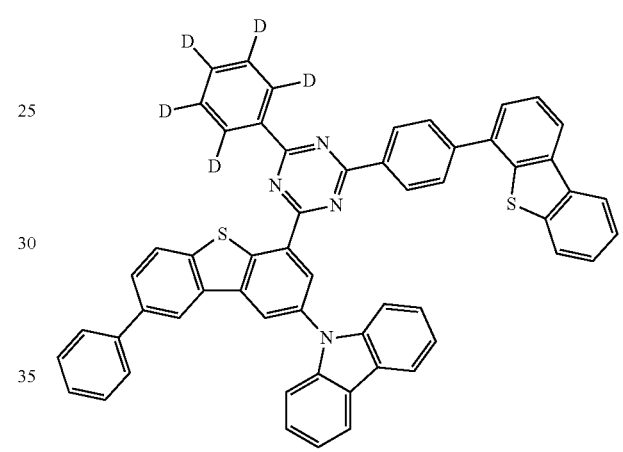
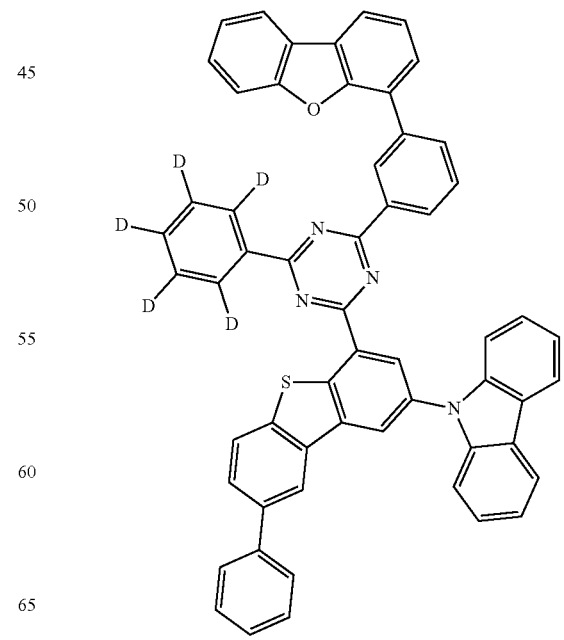

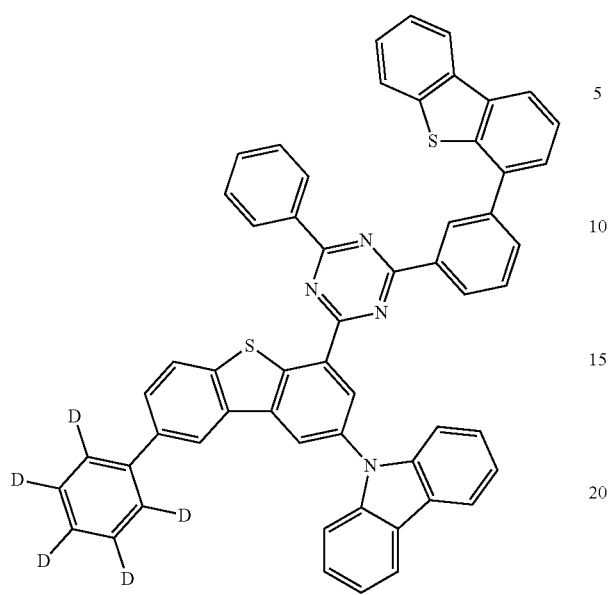
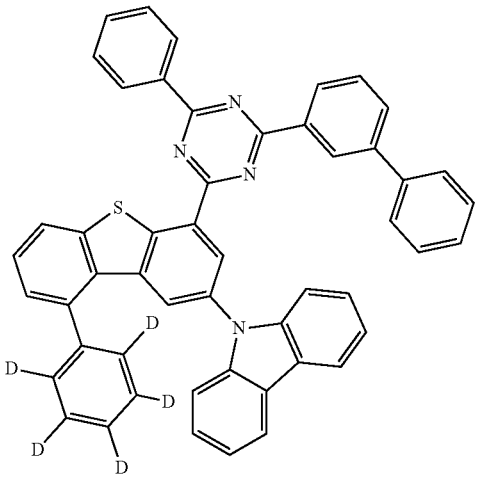
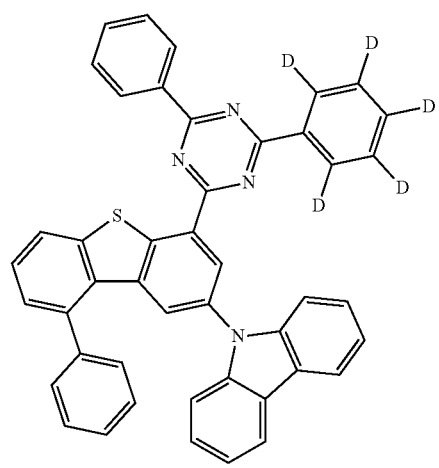
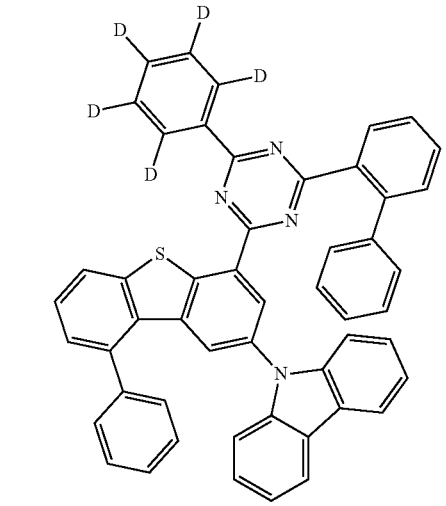
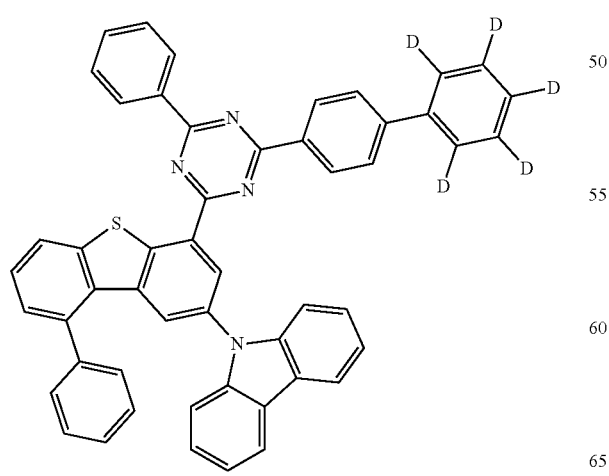
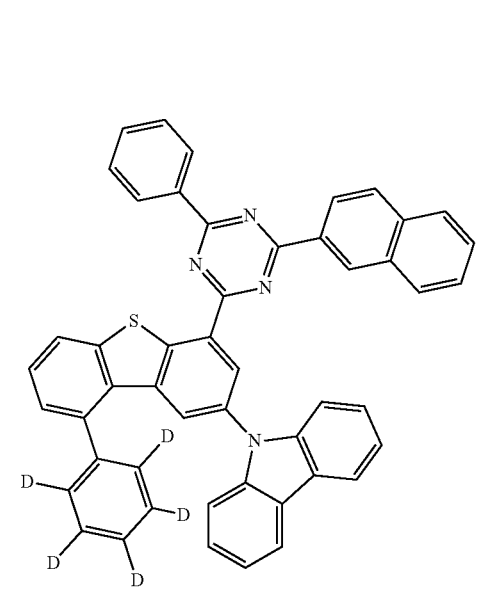

57
-continued
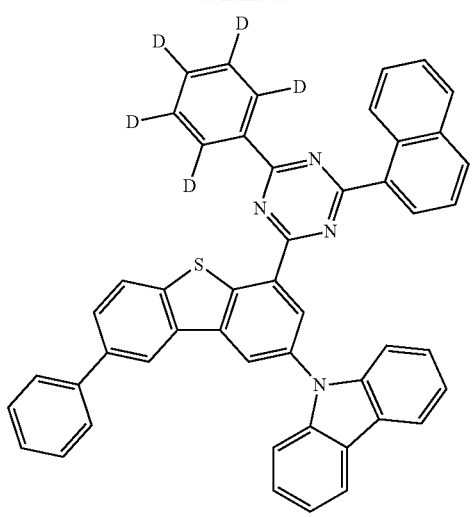
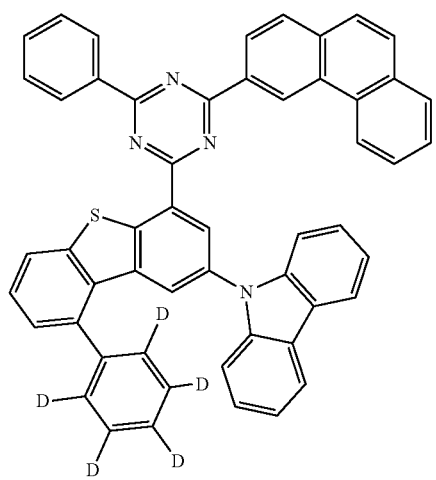
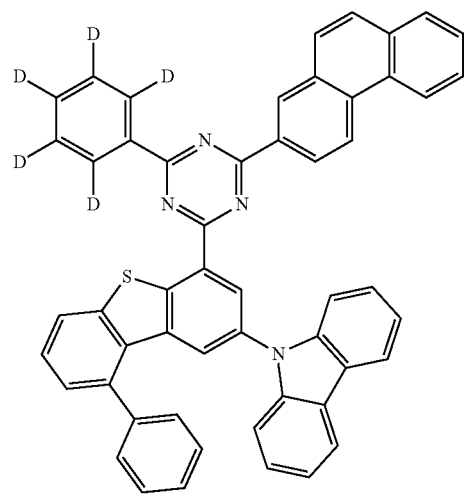
58
-continued
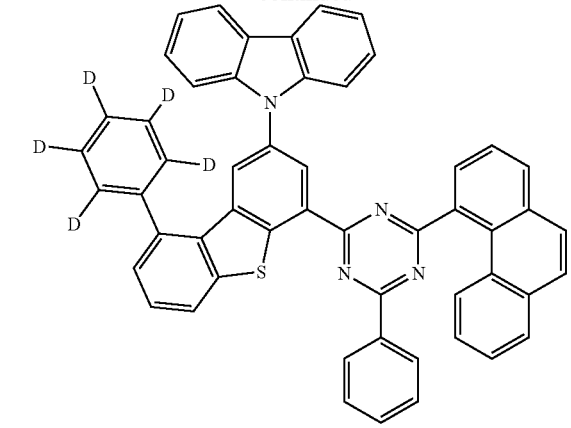
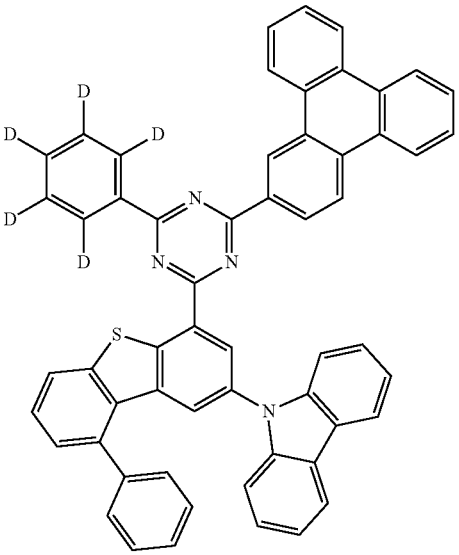
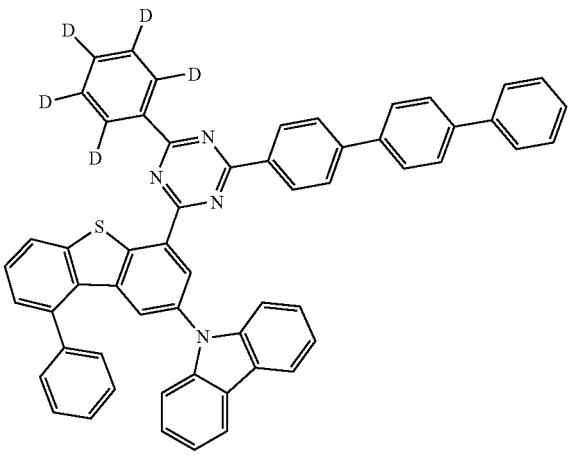

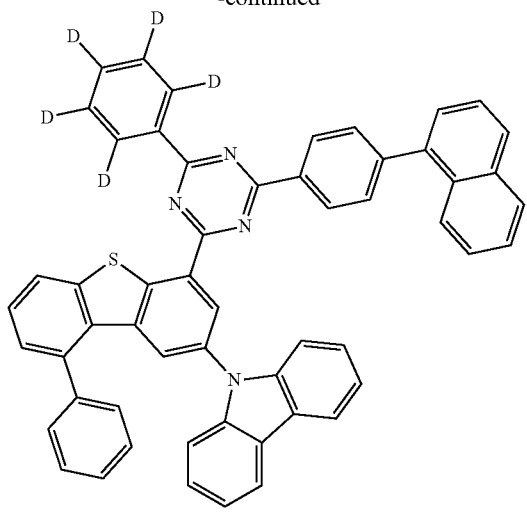
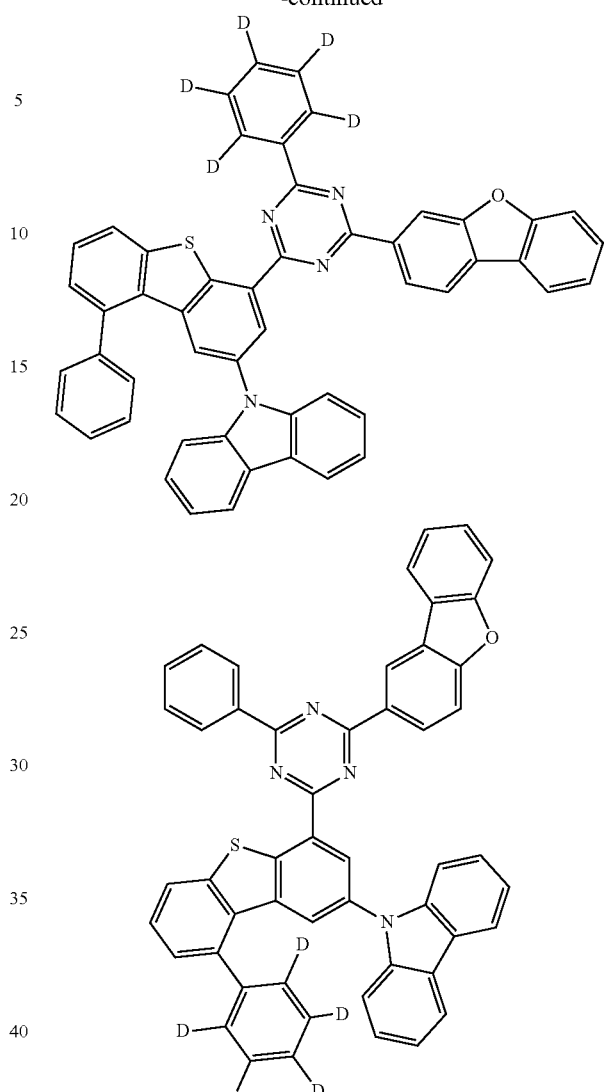
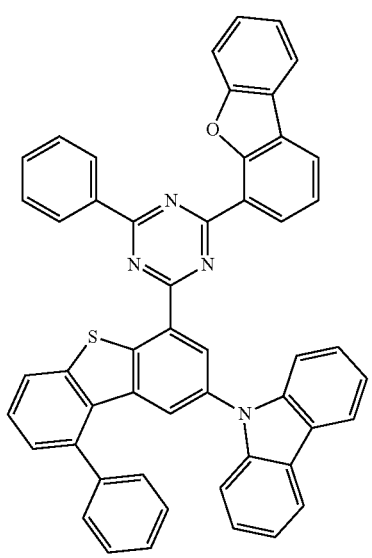
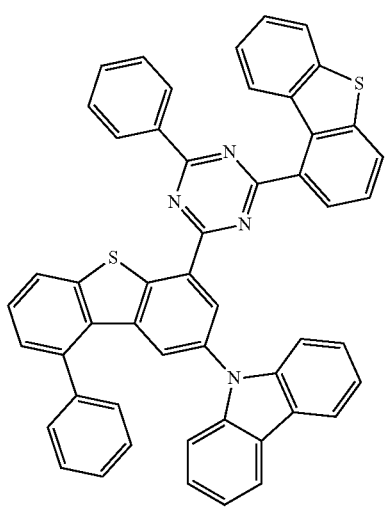

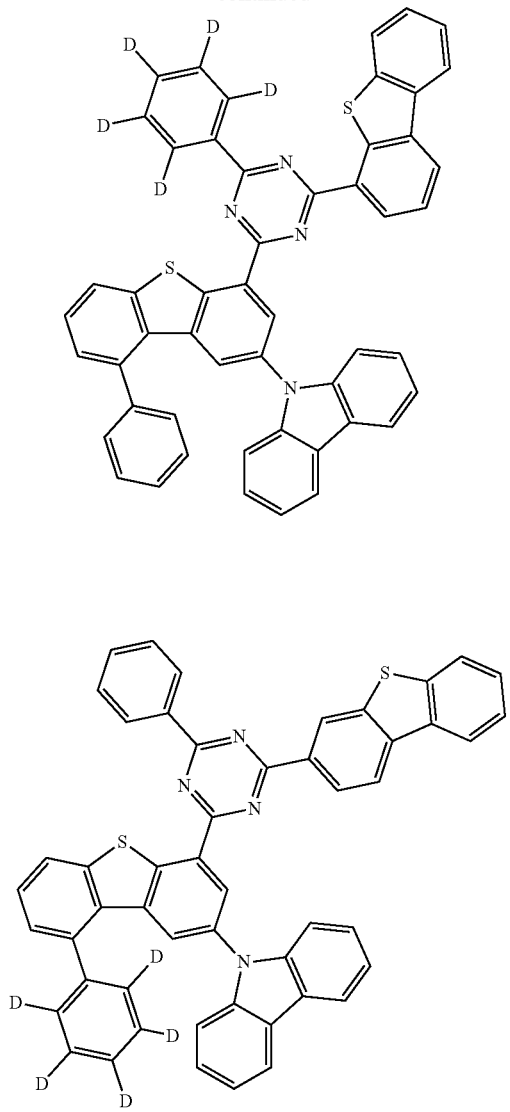
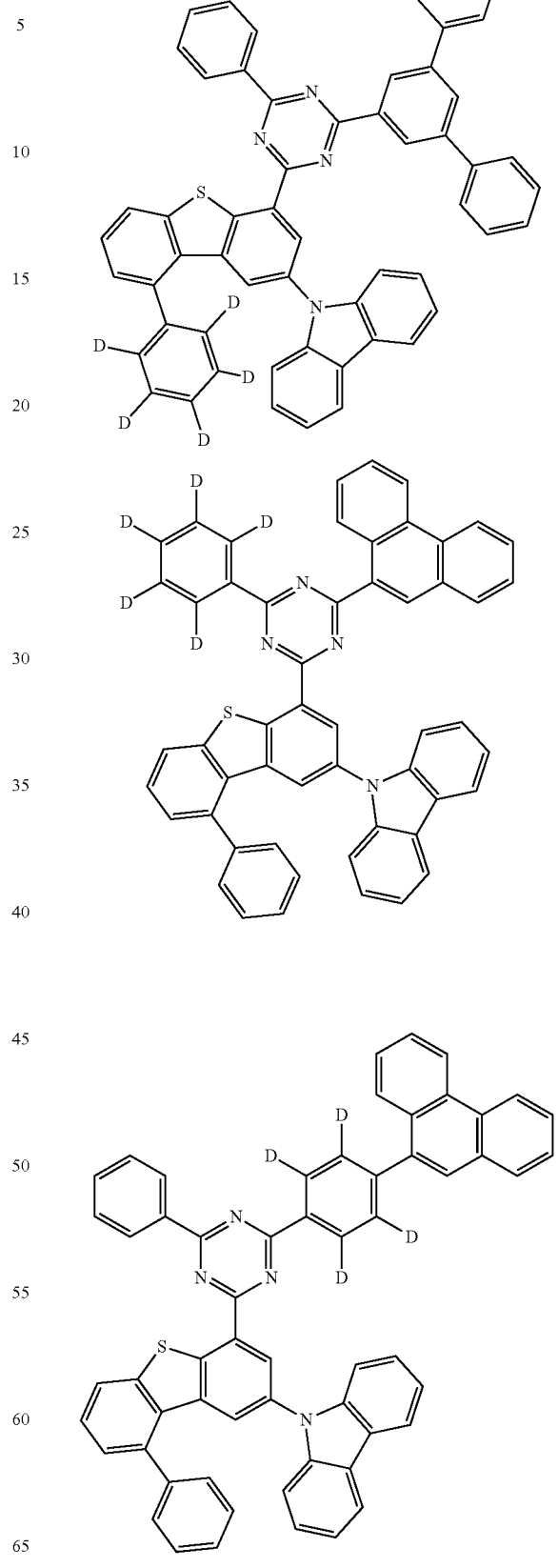

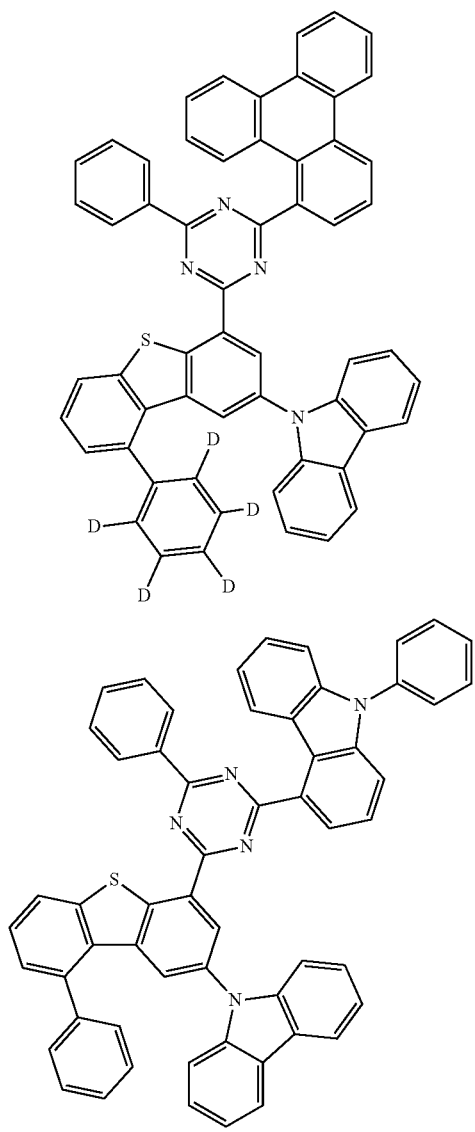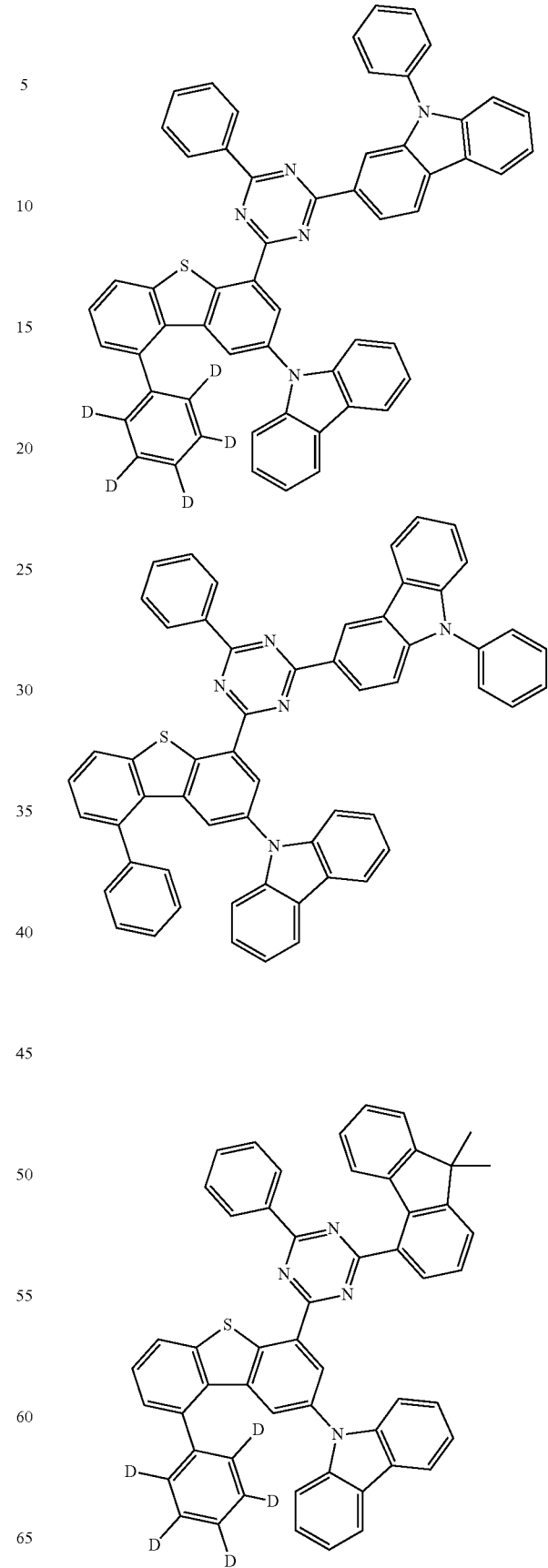

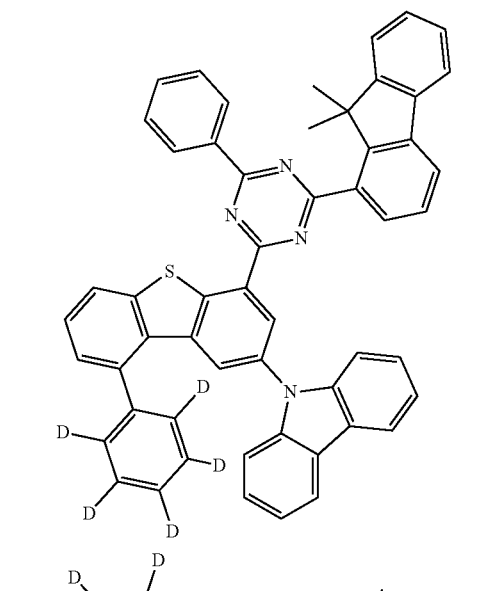
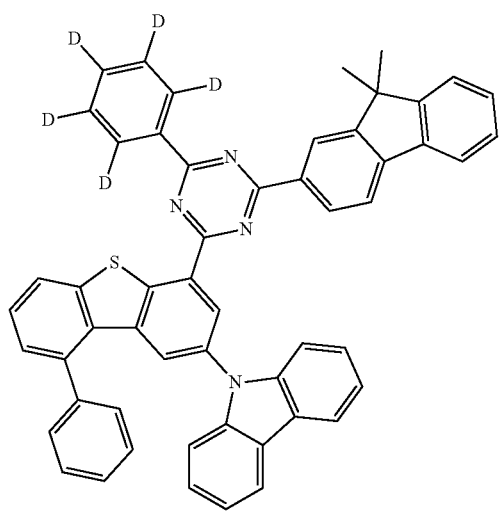
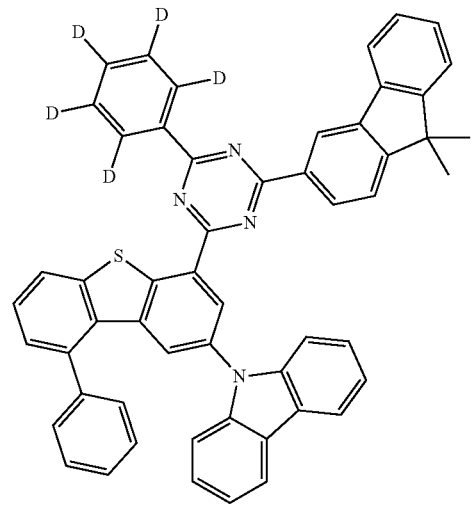
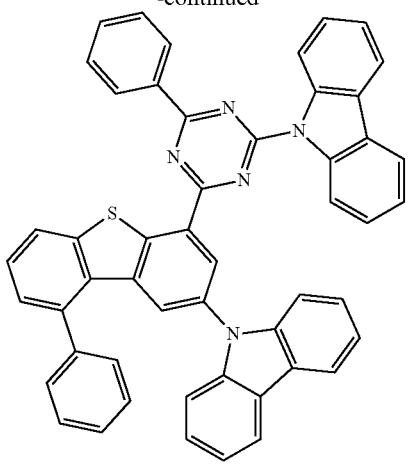
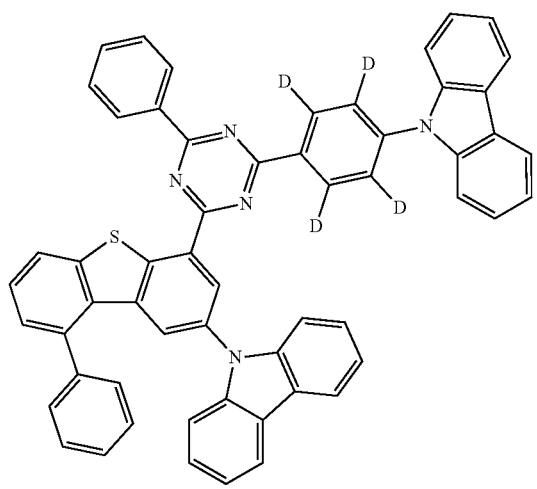
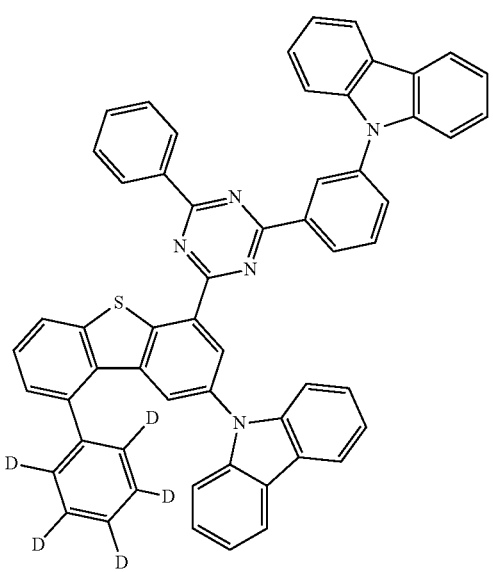

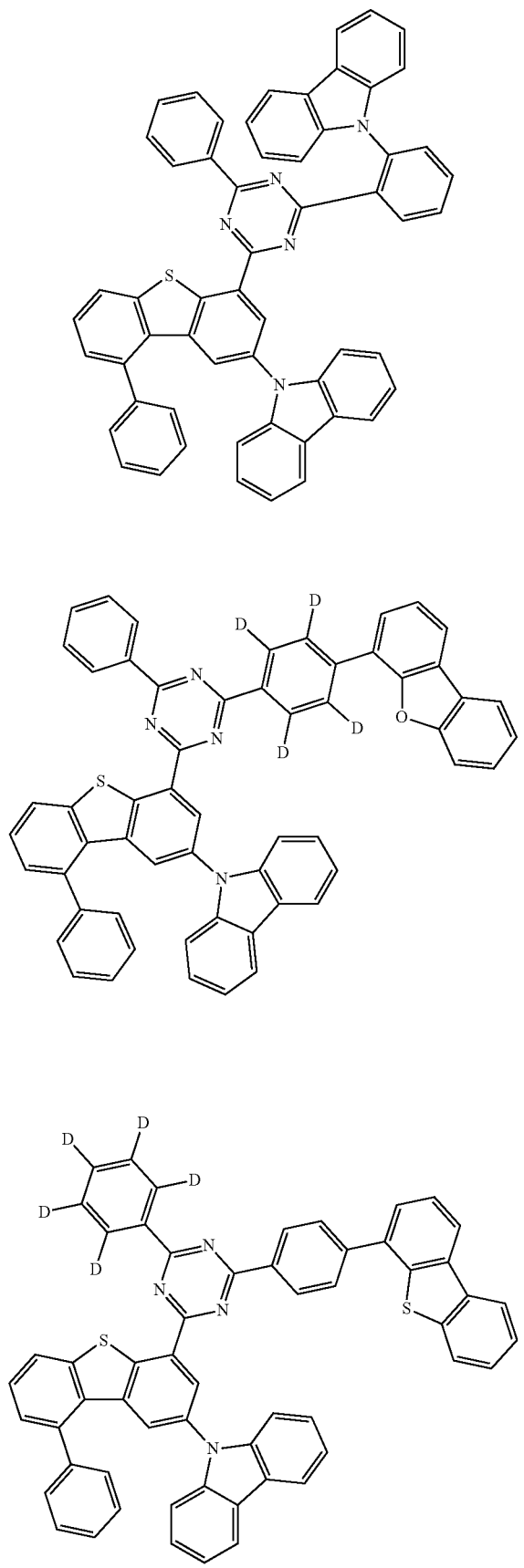
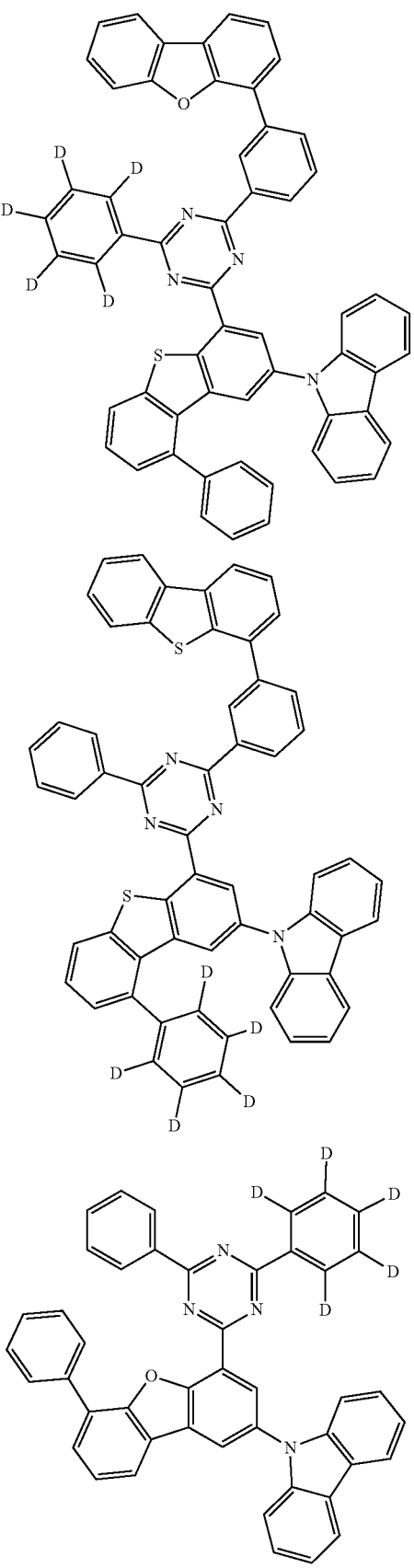

69
-continued
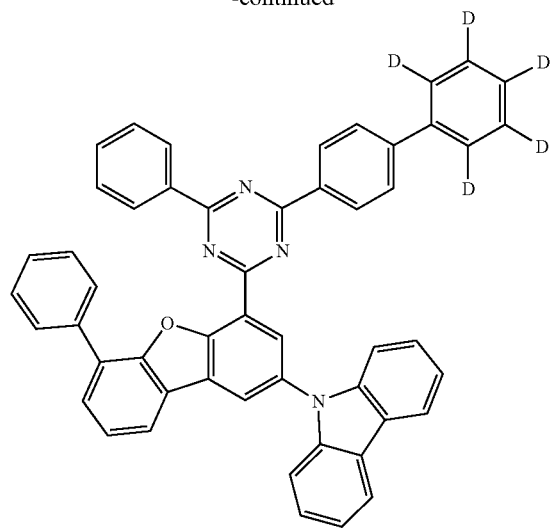
70
-continued
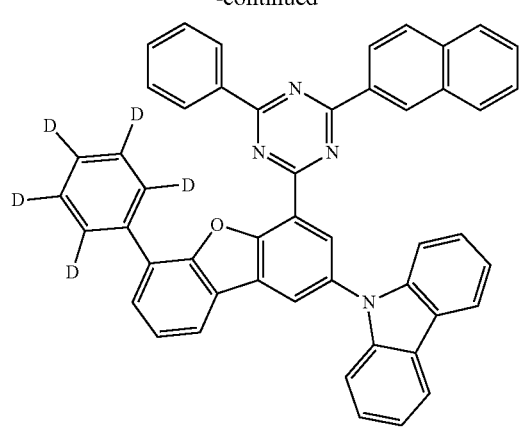
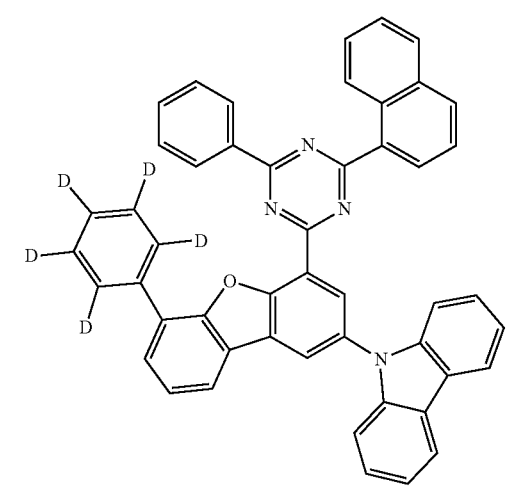
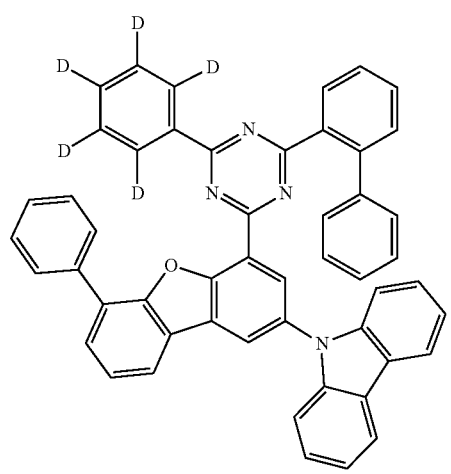
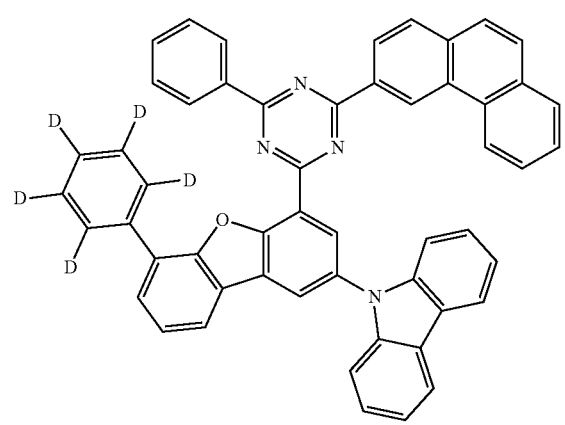

-continued
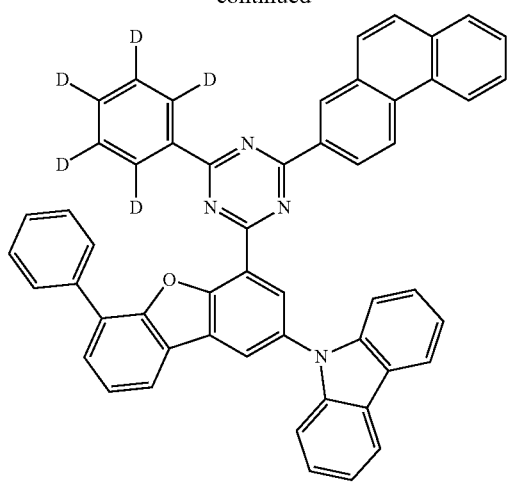
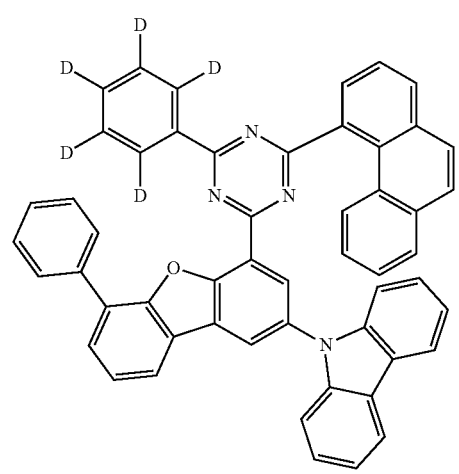
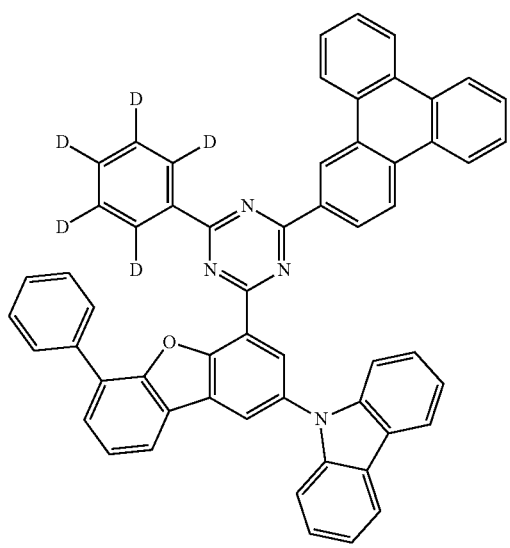
-continued
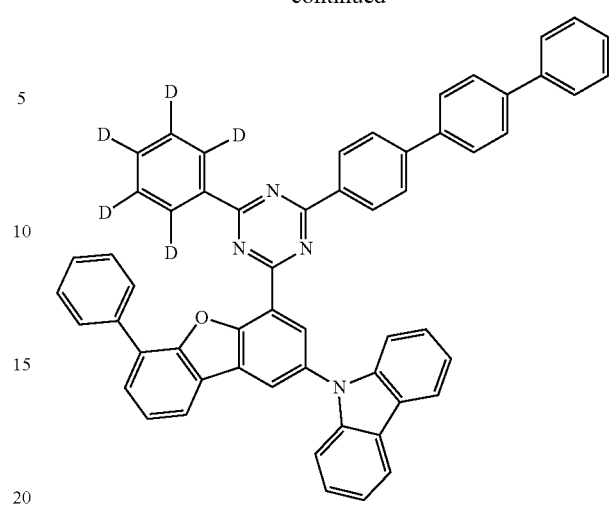
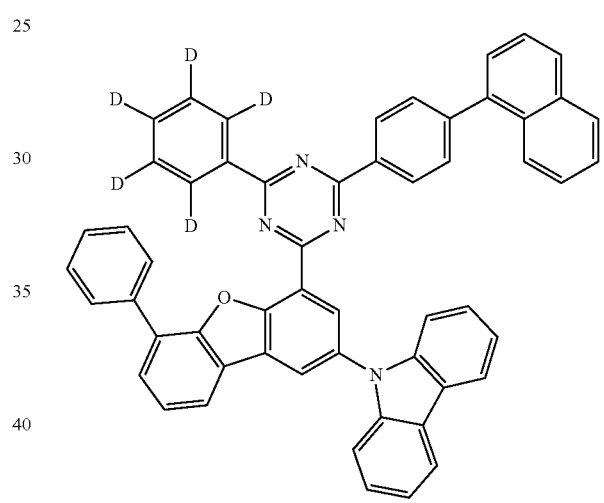
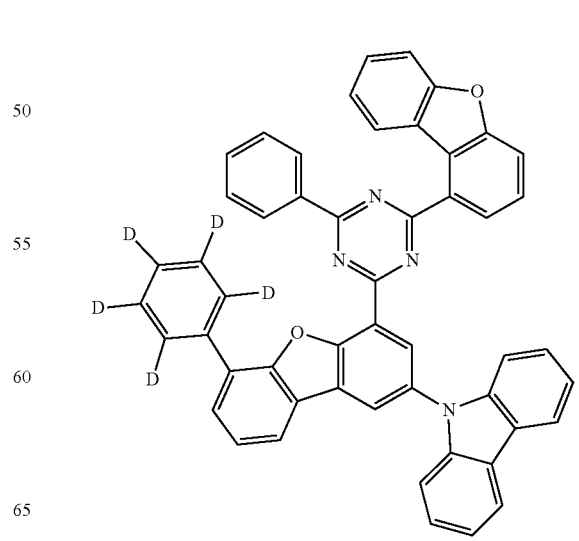

-continued
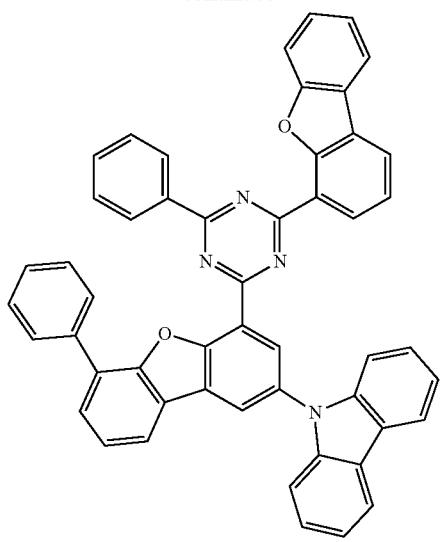
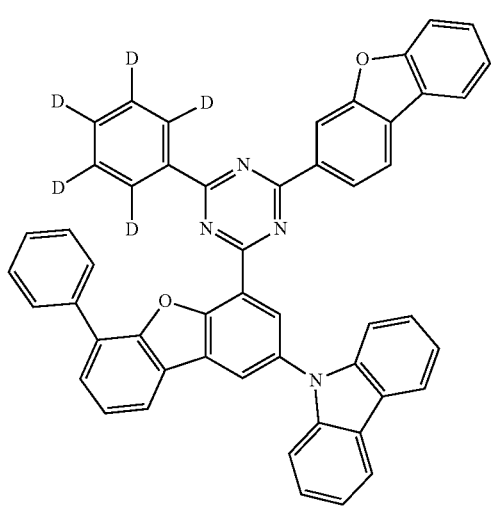
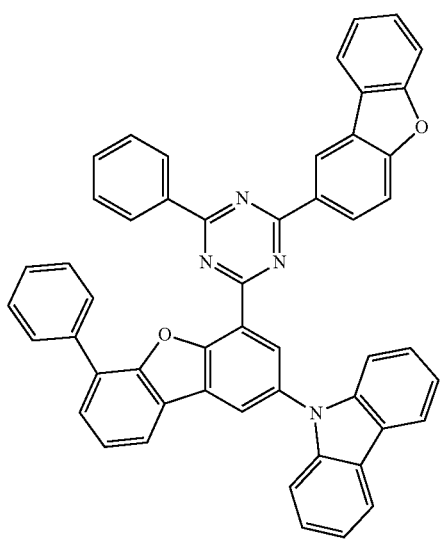
-continued
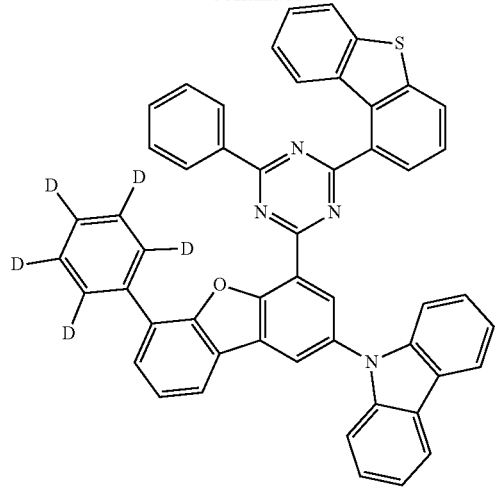
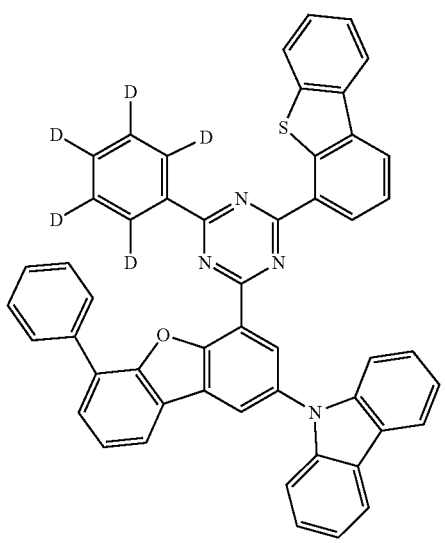
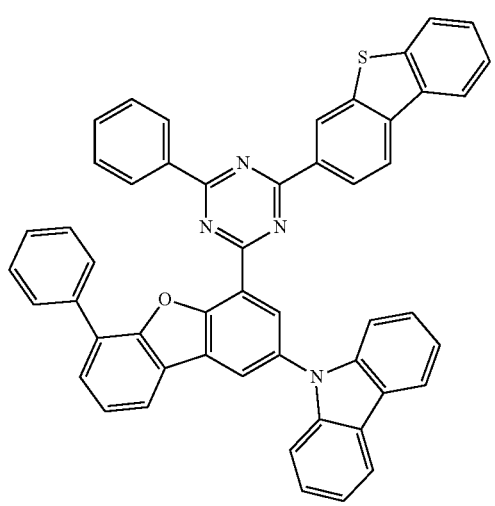

75
-continued
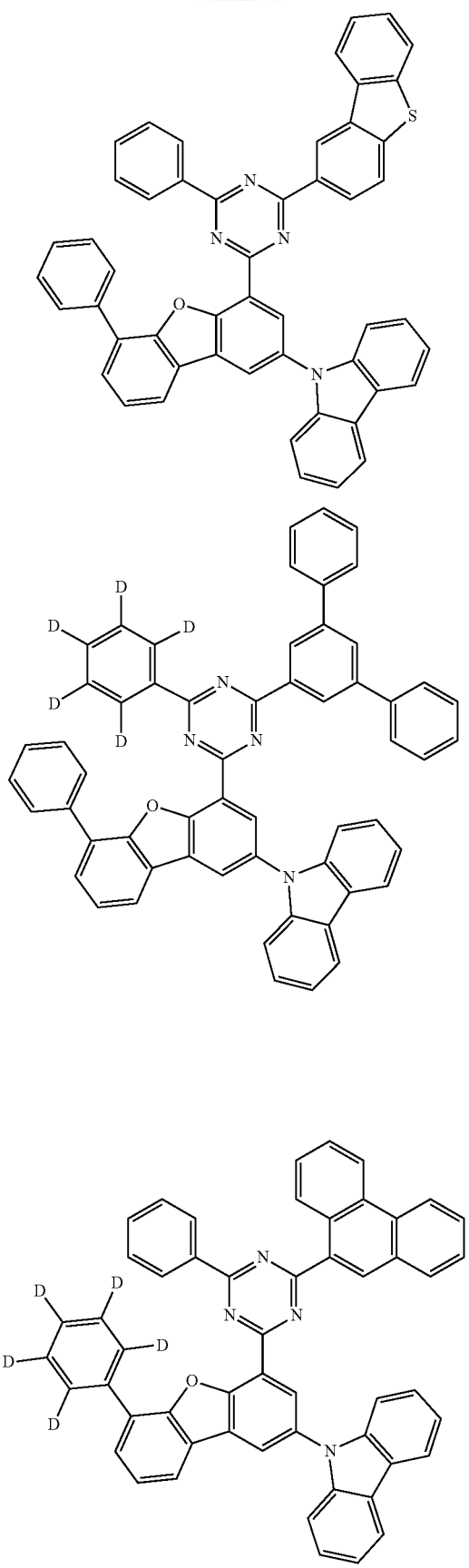
76
-continued
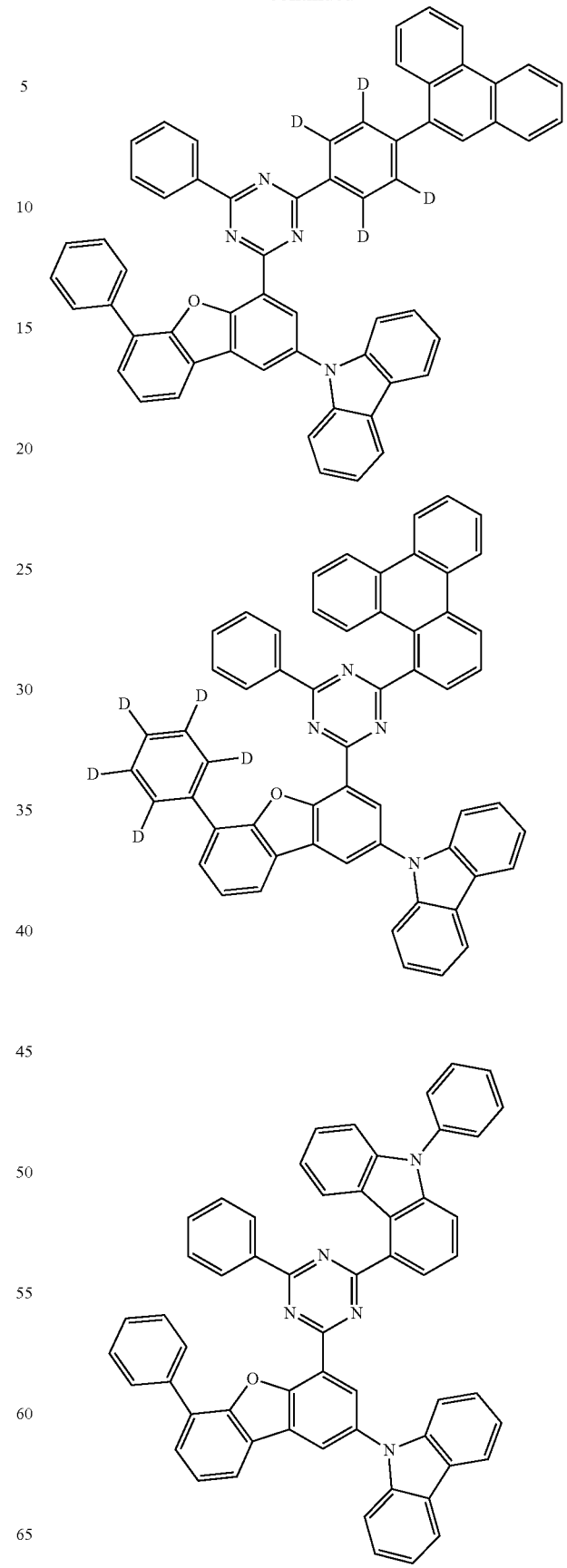

77
-continued
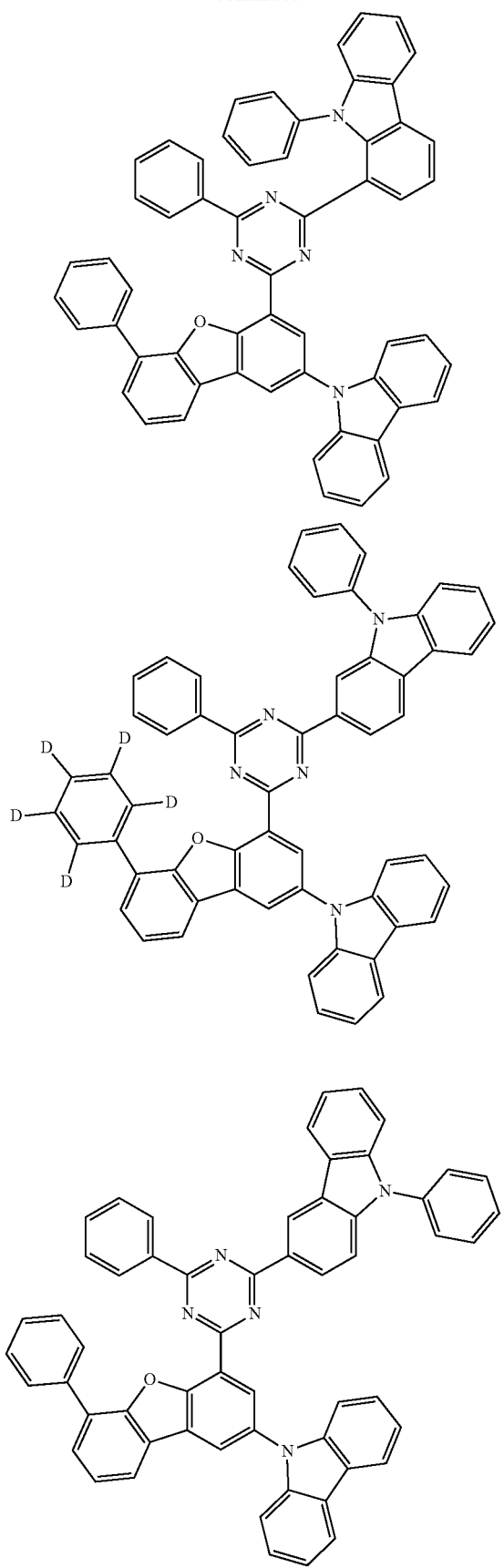
78
-continued
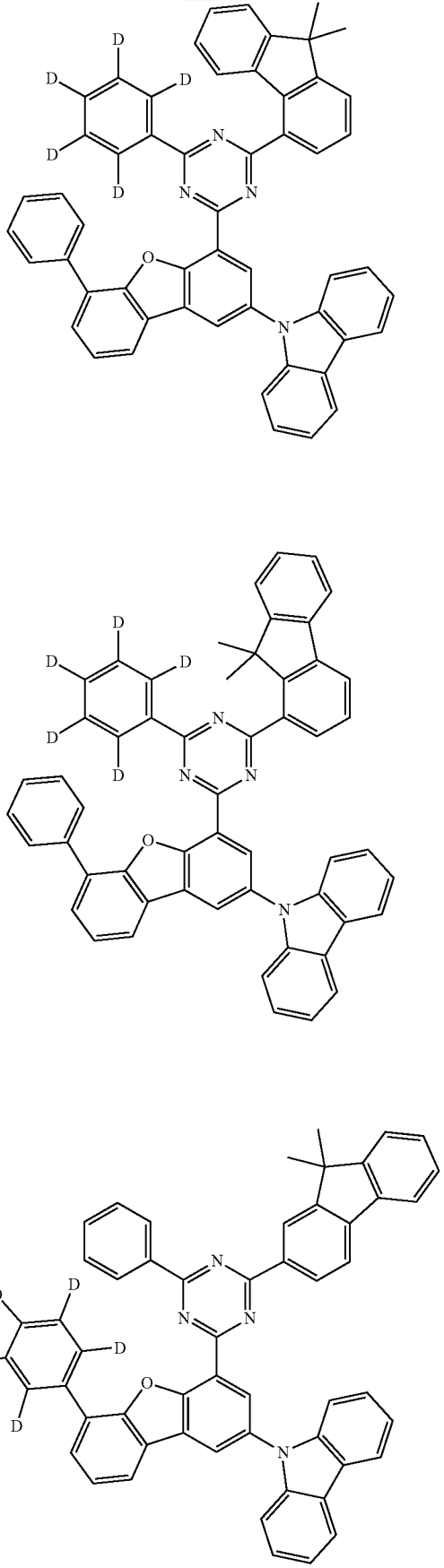

-continued
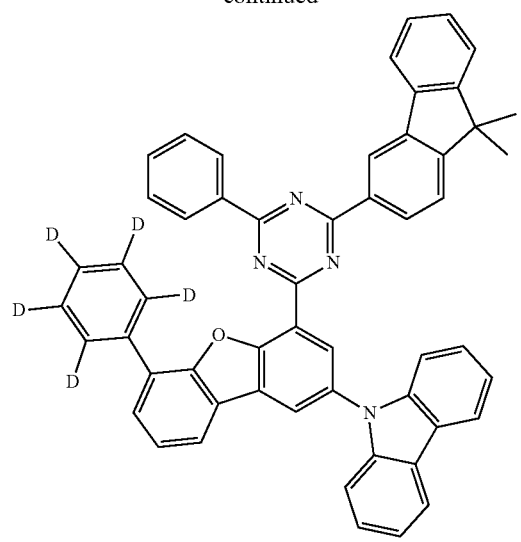
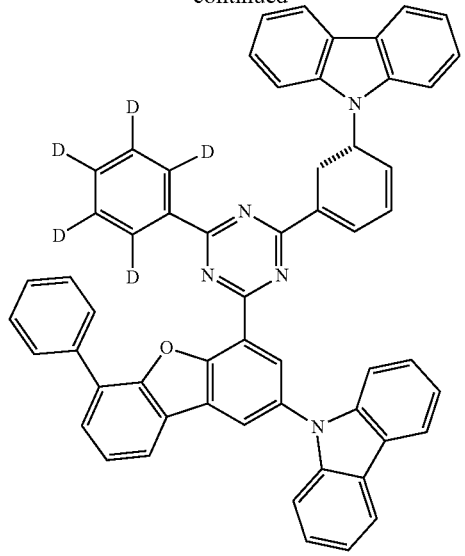
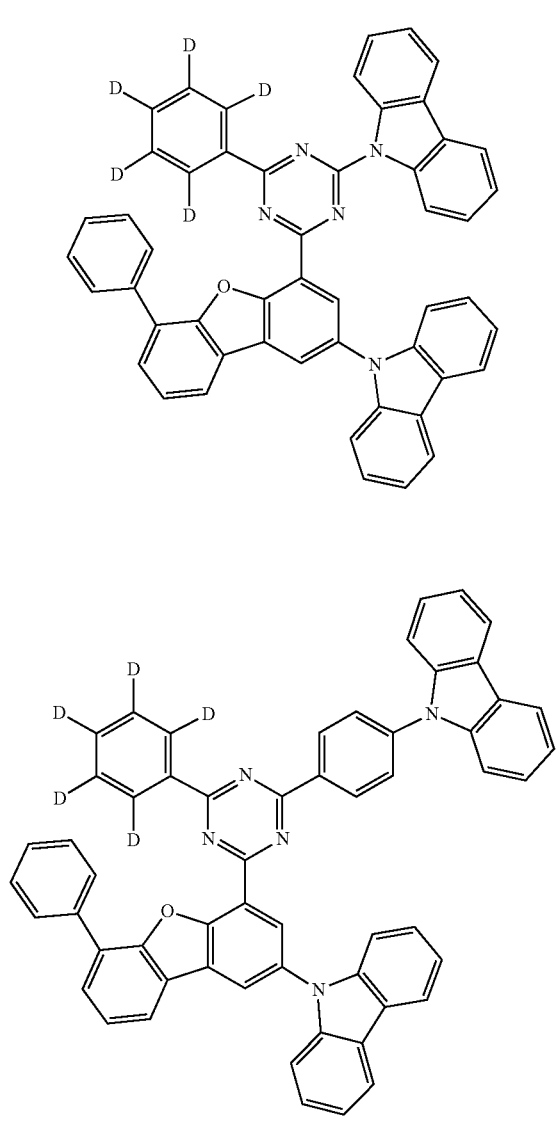
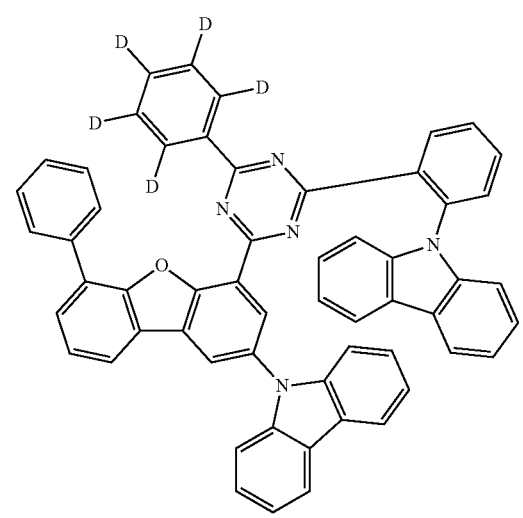
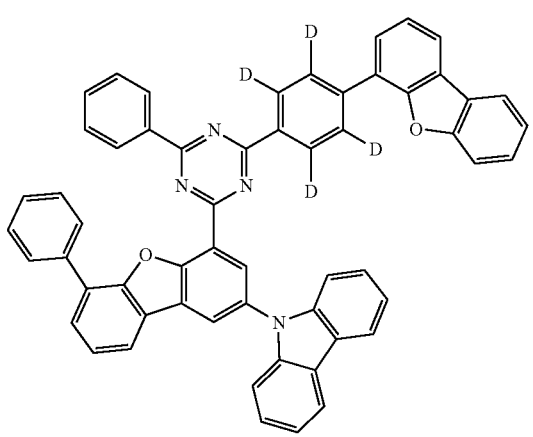

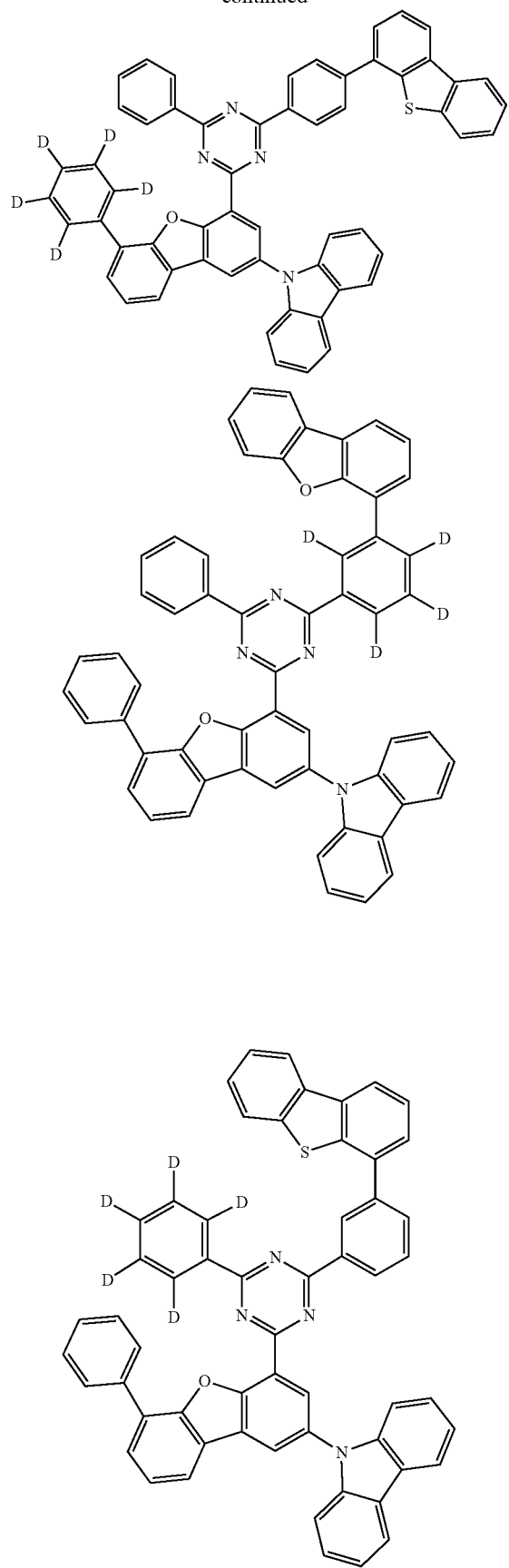
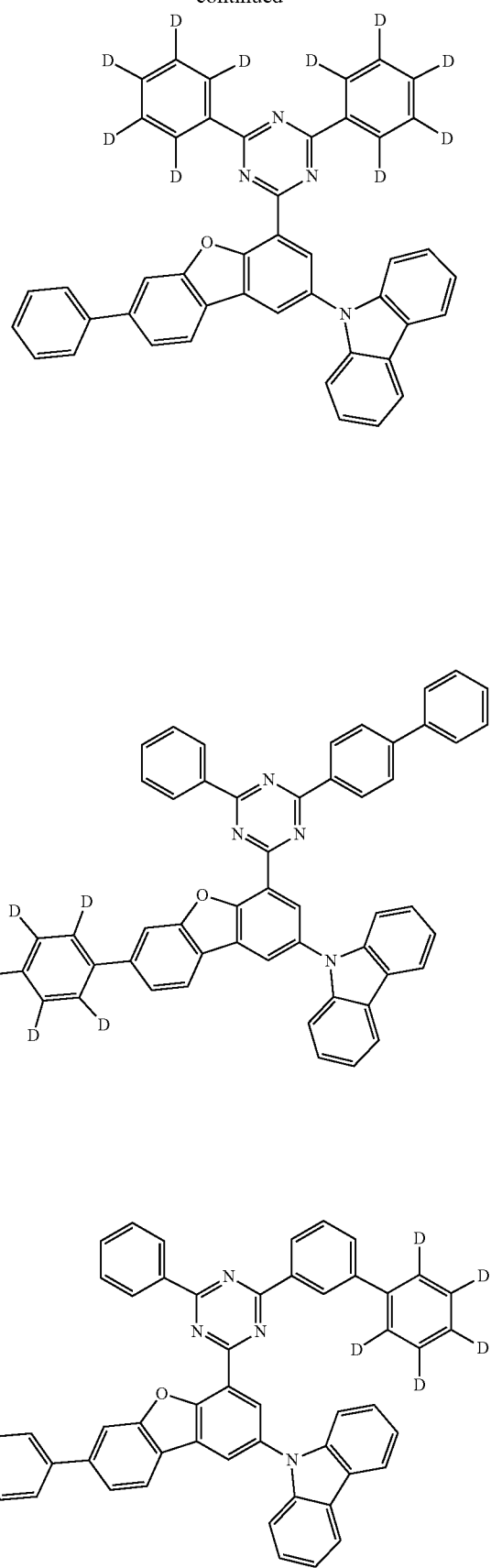

-continued
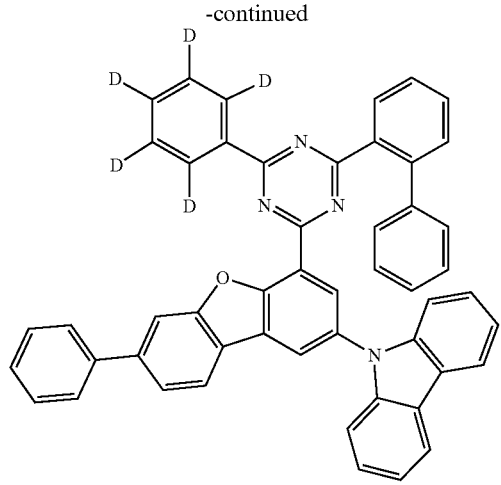
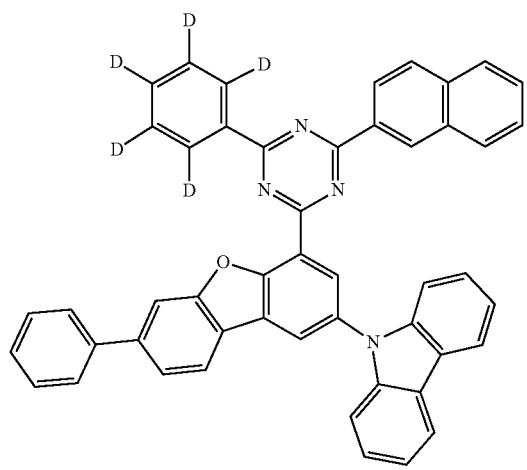
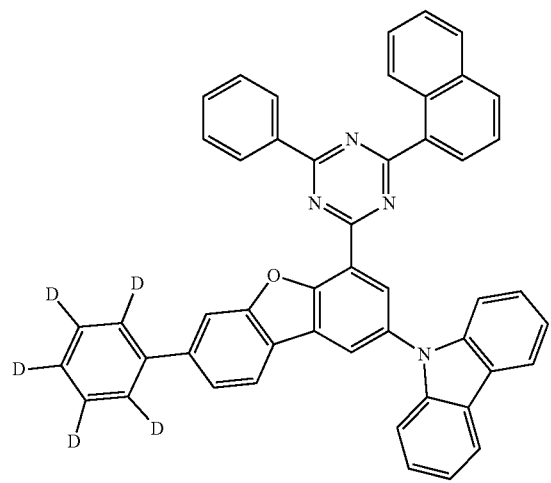
-continued
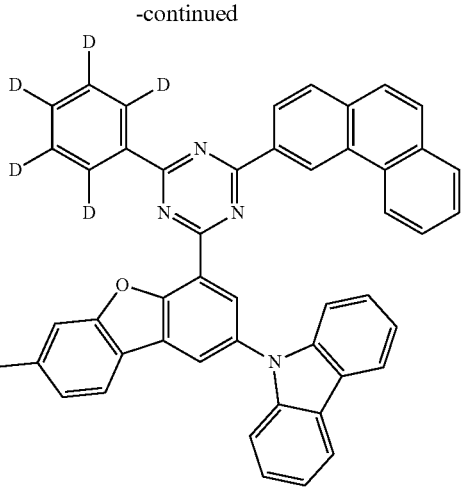
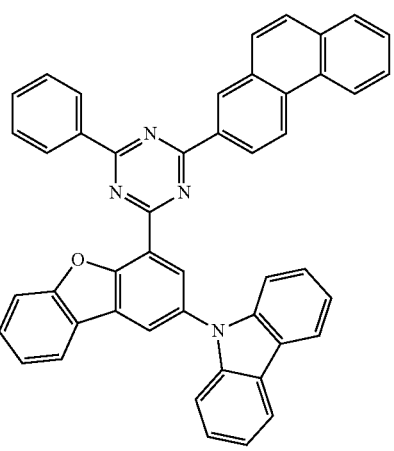
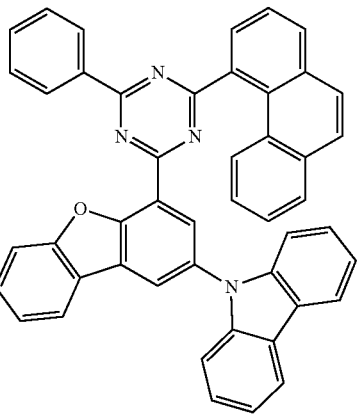

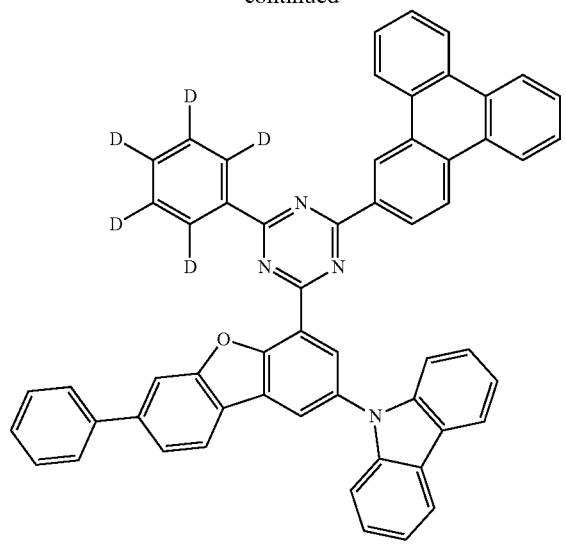
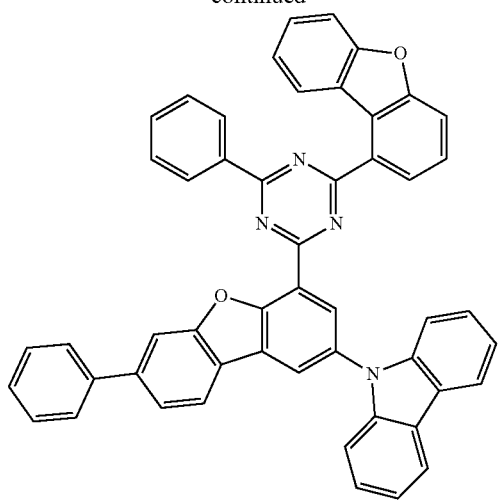
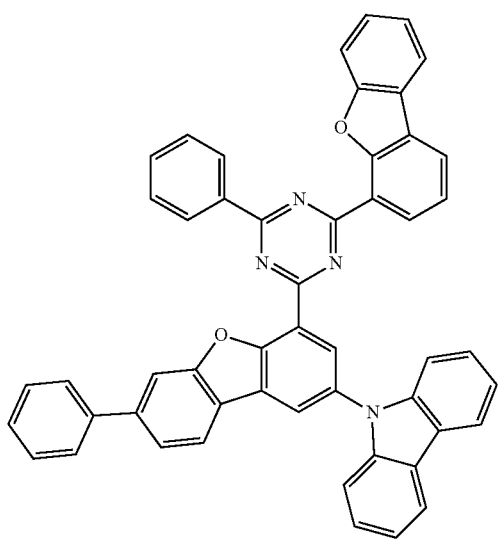
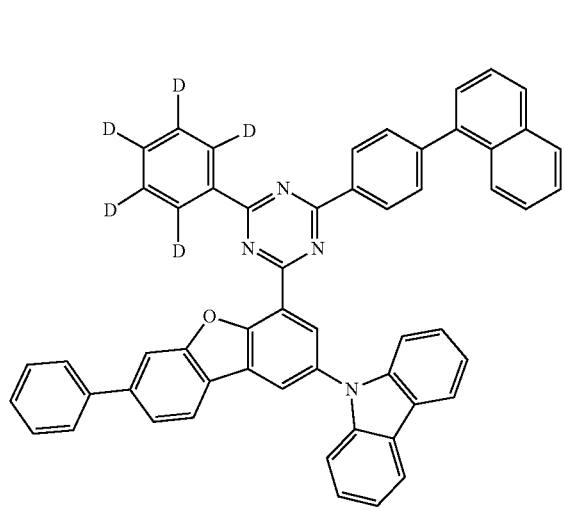
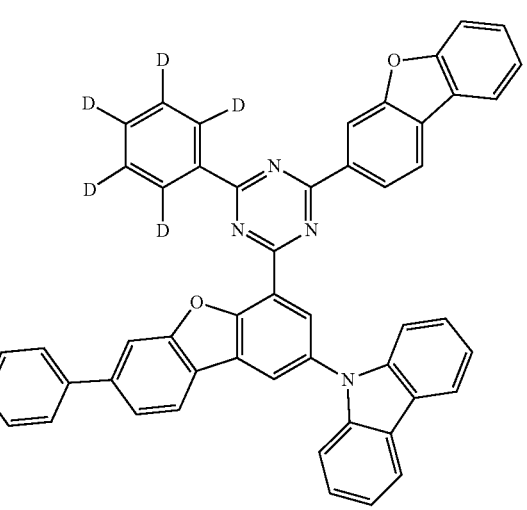

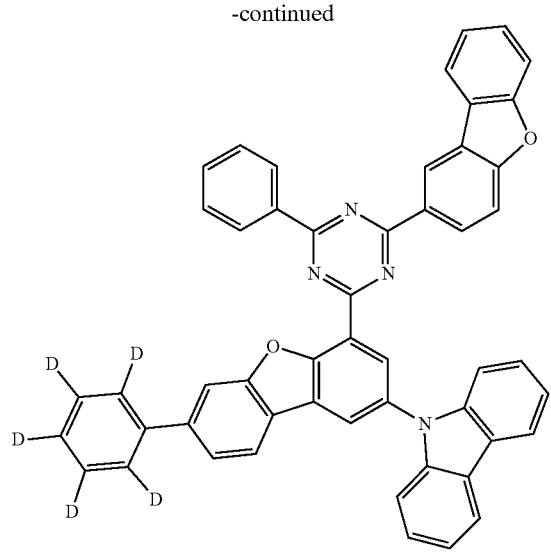
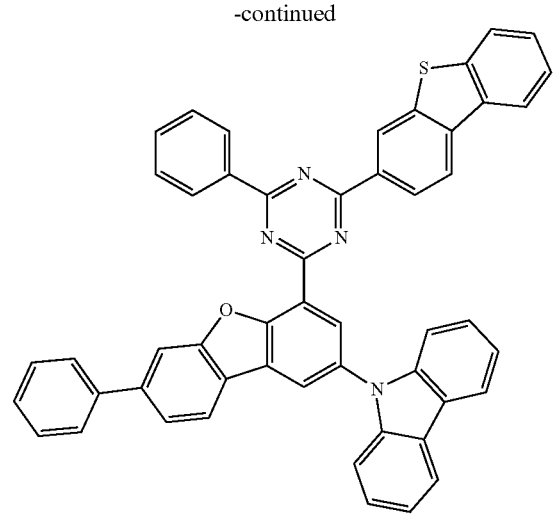
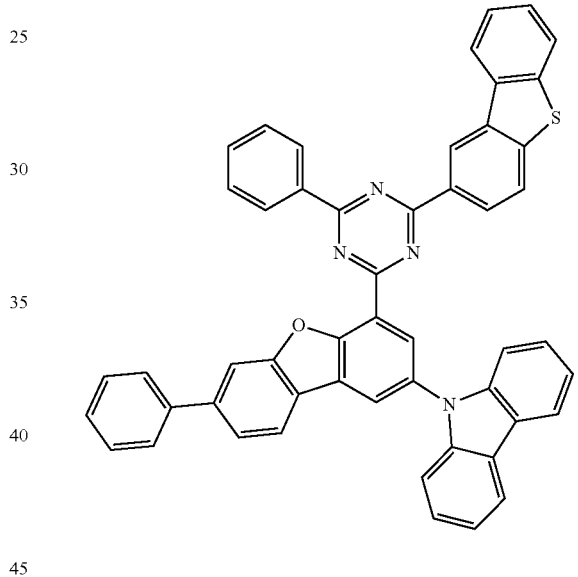
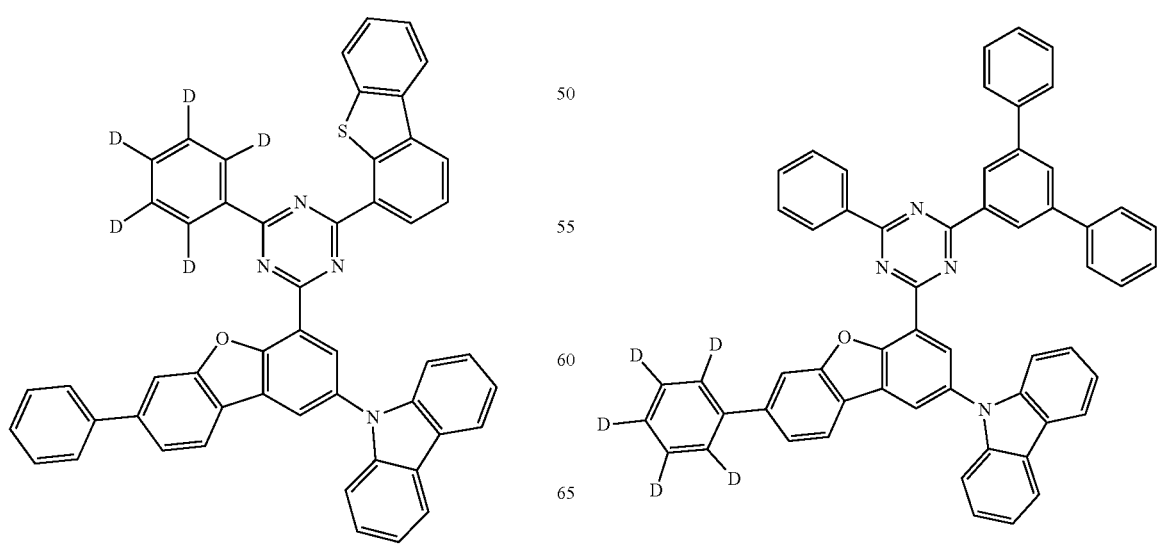

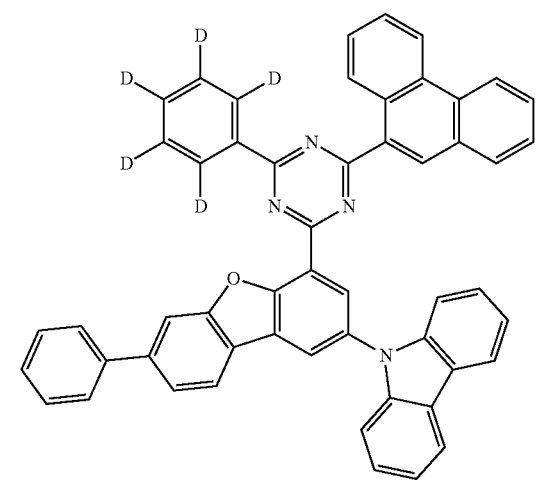
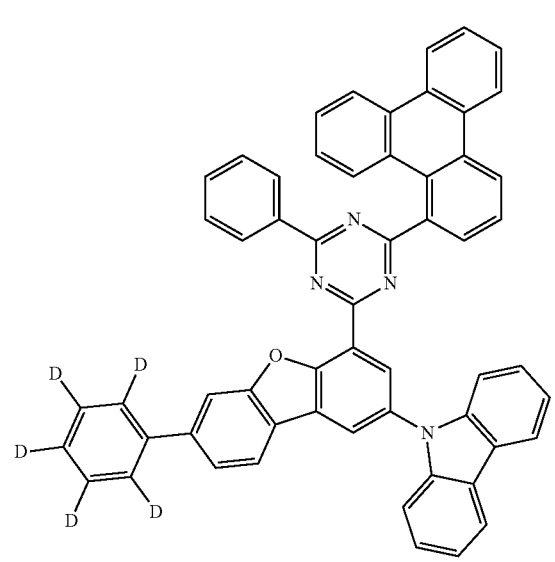
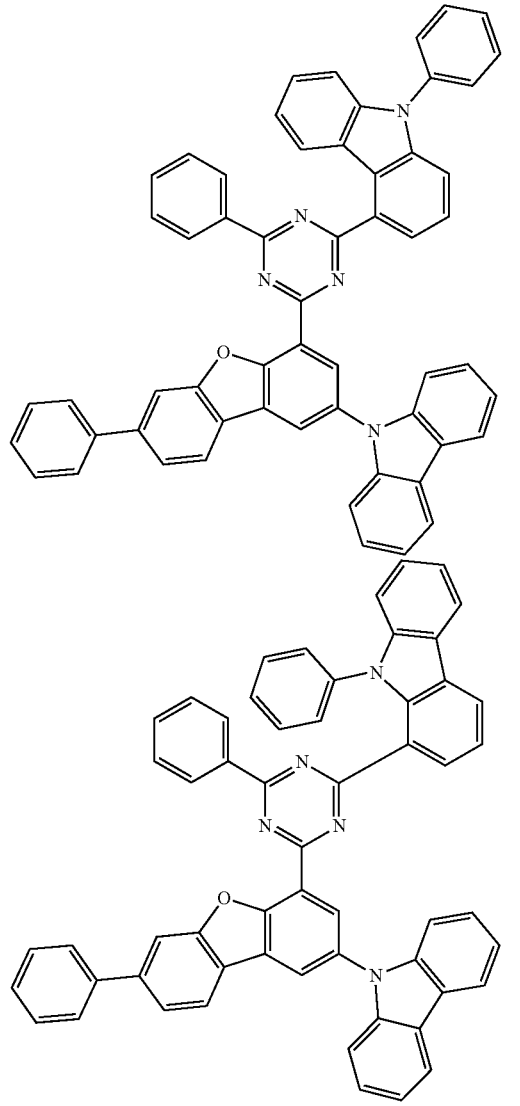
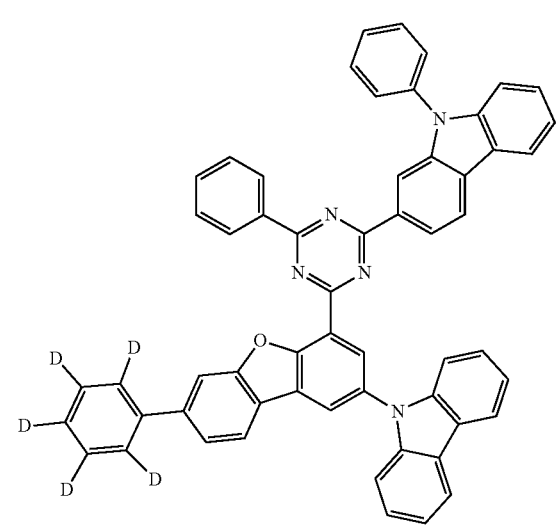

91
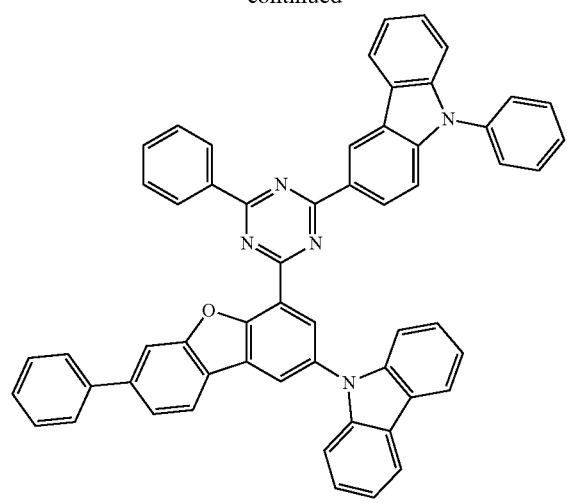
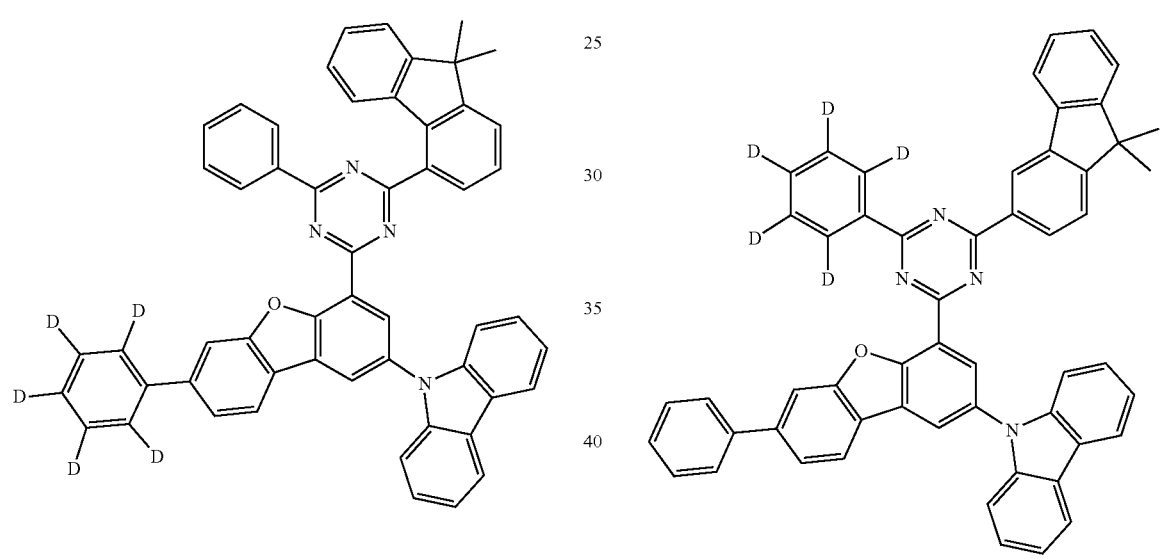
92
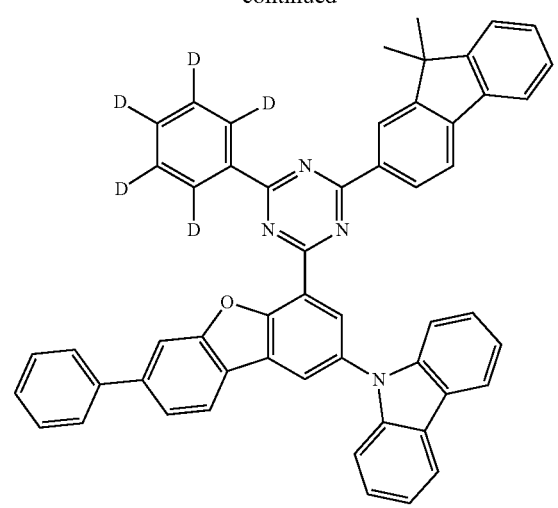
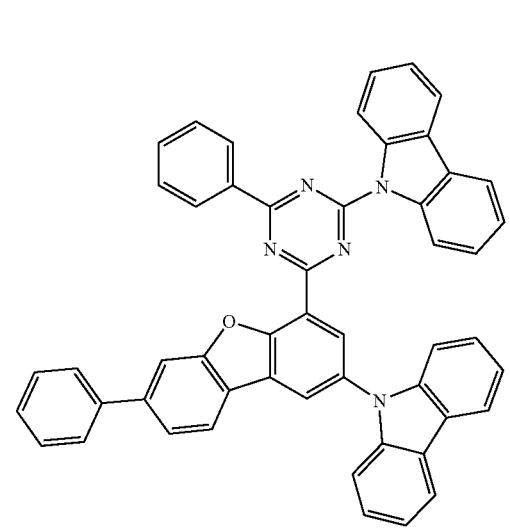

93
-continued
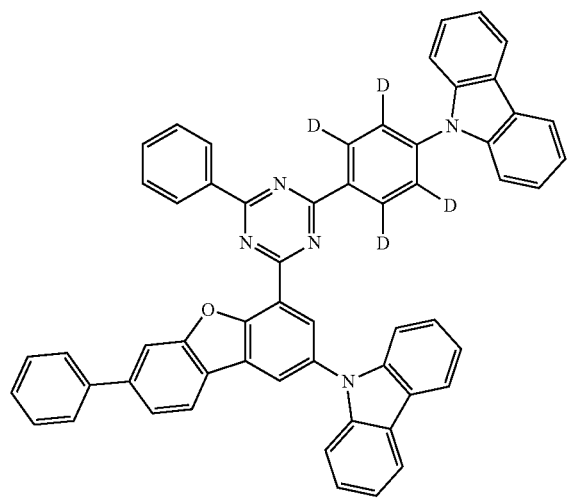
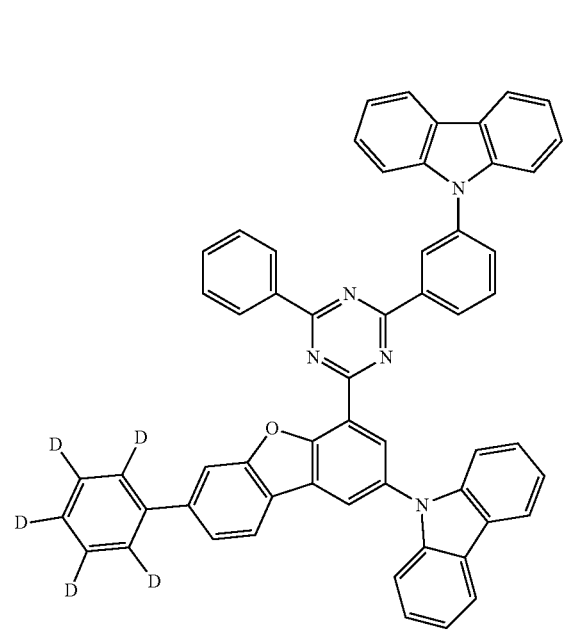
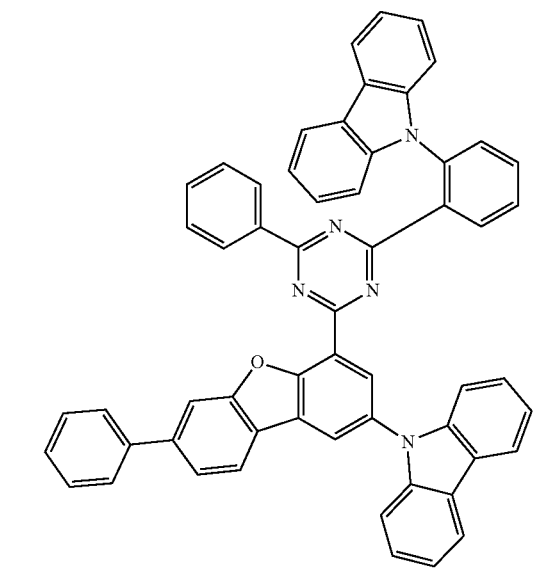
94
-continued
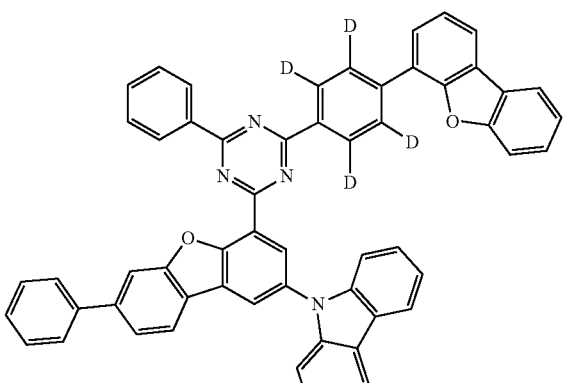
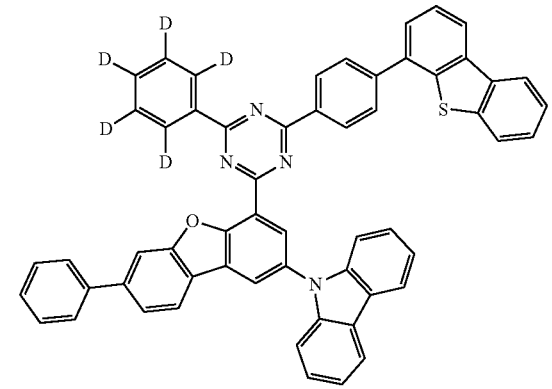
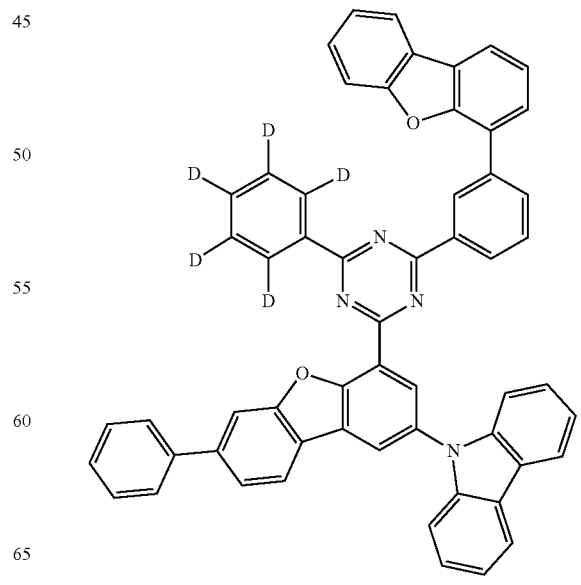

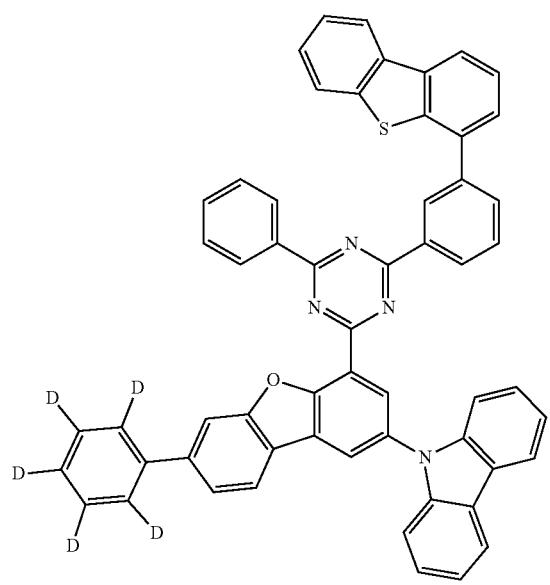 [SMILES: [2H]c1c([2H])c([2H])c(-c2ccc3c(c2)oc2c(-c4nc(-c5ccccc5)nc(-c5cccc(-c6cccc7c6sc6ccccc67)c5)n4)cc(-n4c5ccccc5c5ccccc54)cc23)c([2H])c1[2H]]
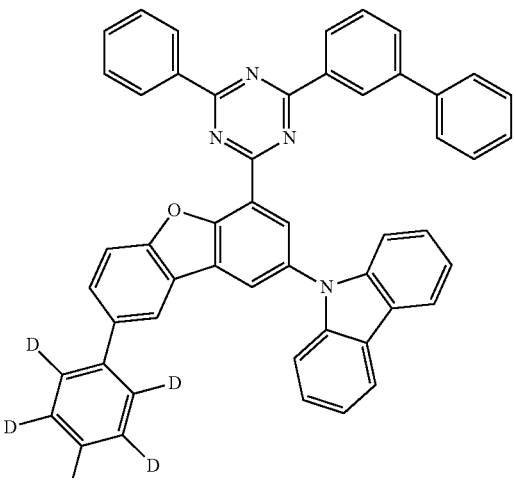

97
-continued

98
-continued

99
-continued
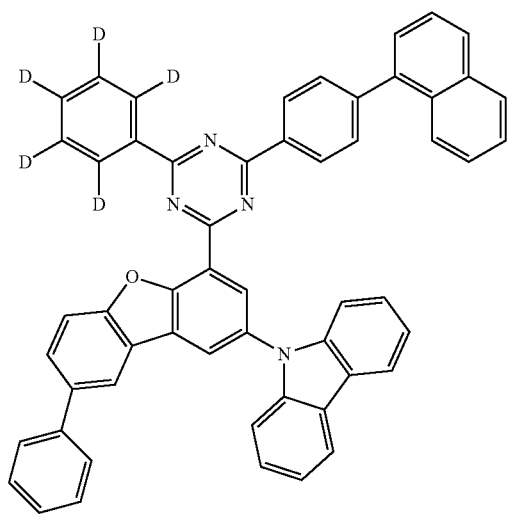
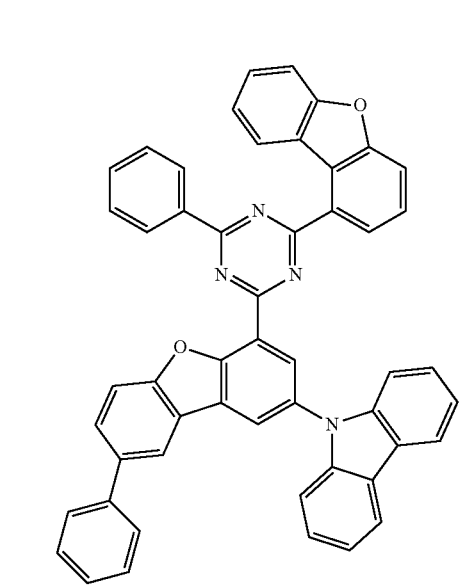
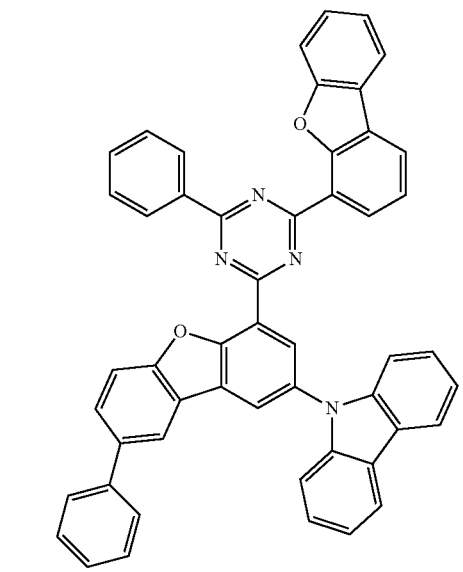
100
-continued
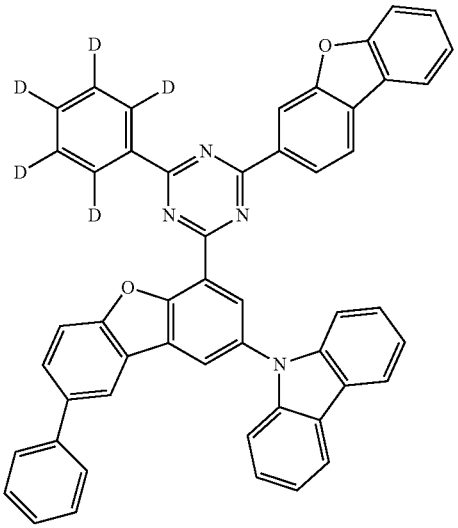
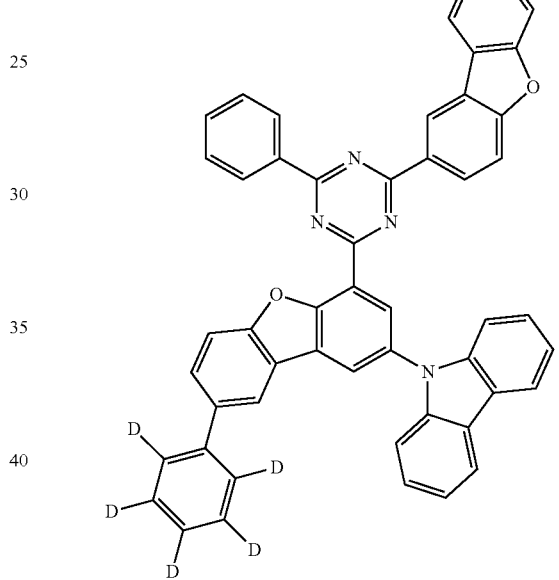
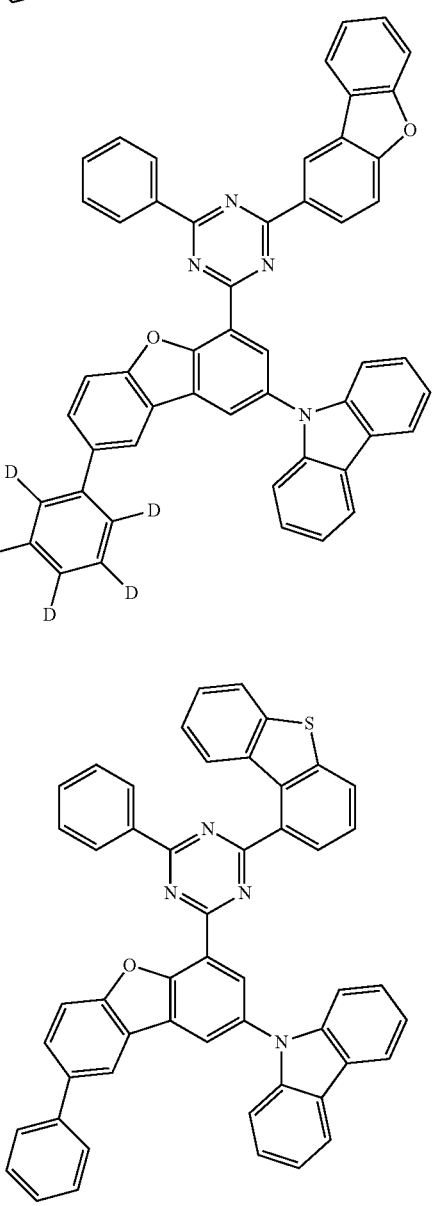

101
-continued
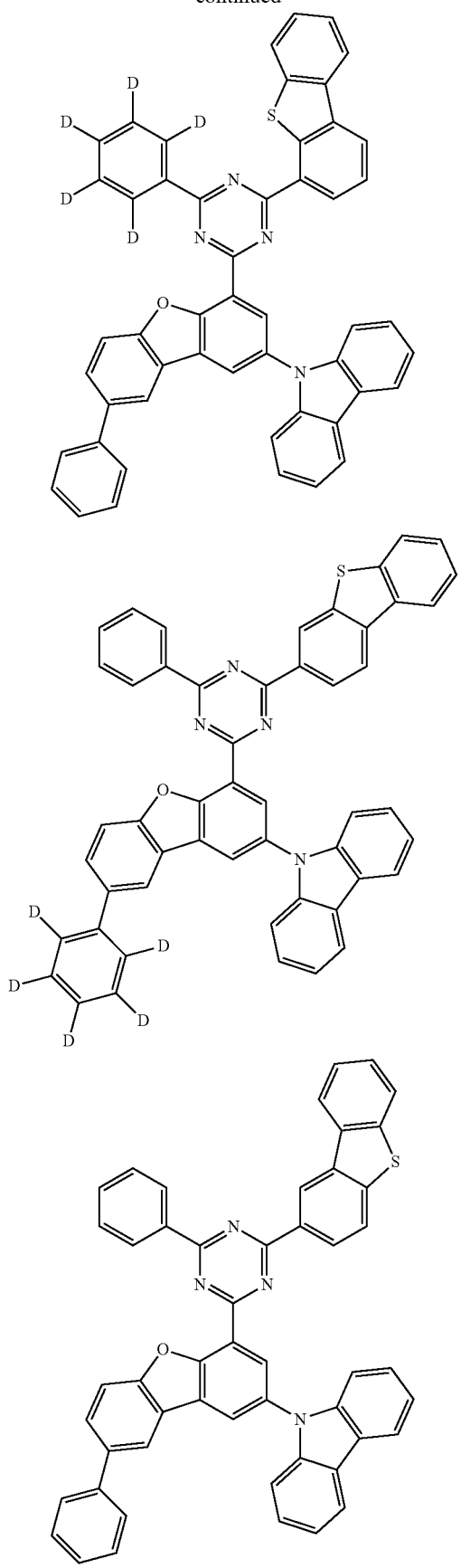
102
-continued
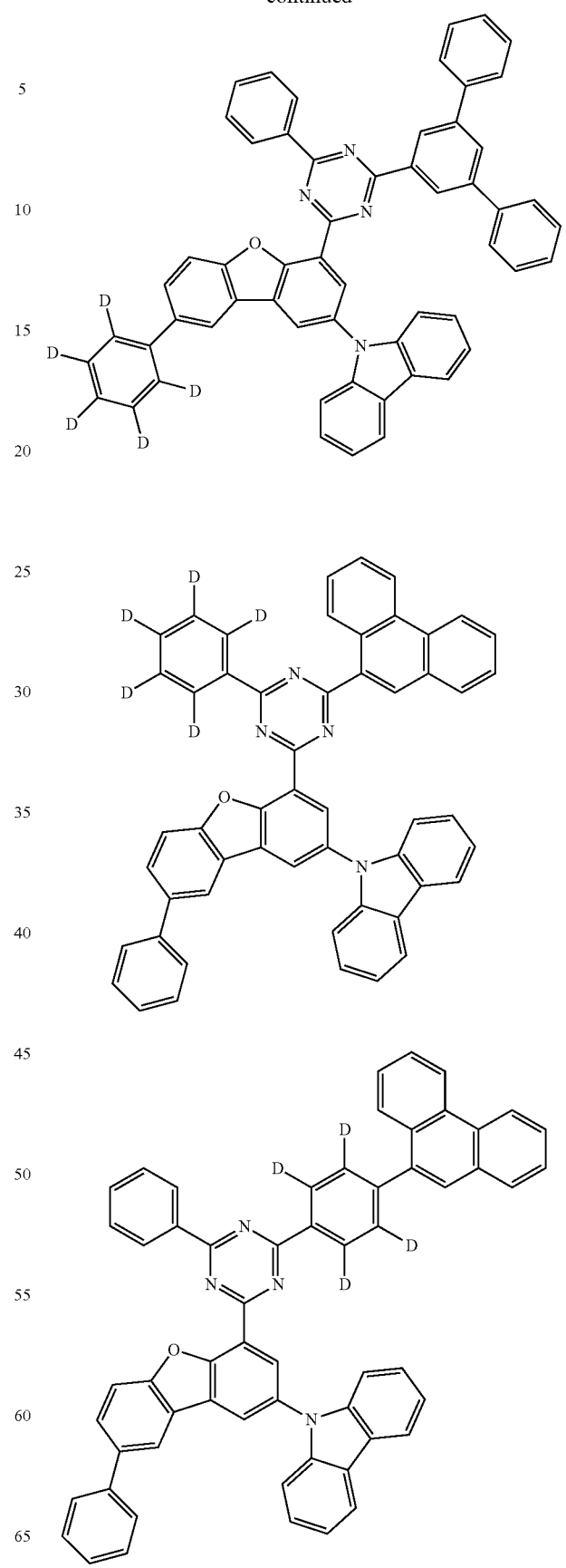

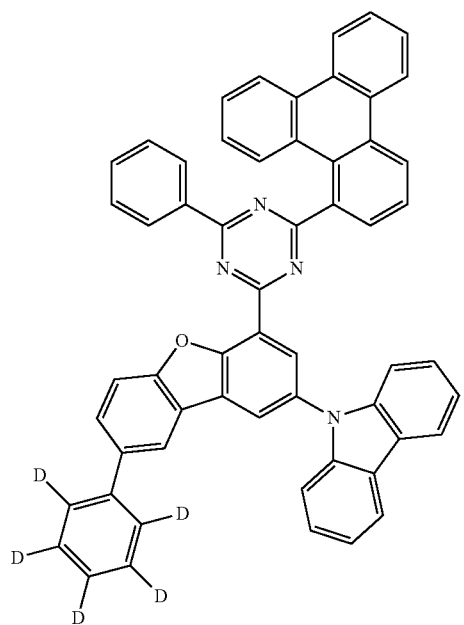
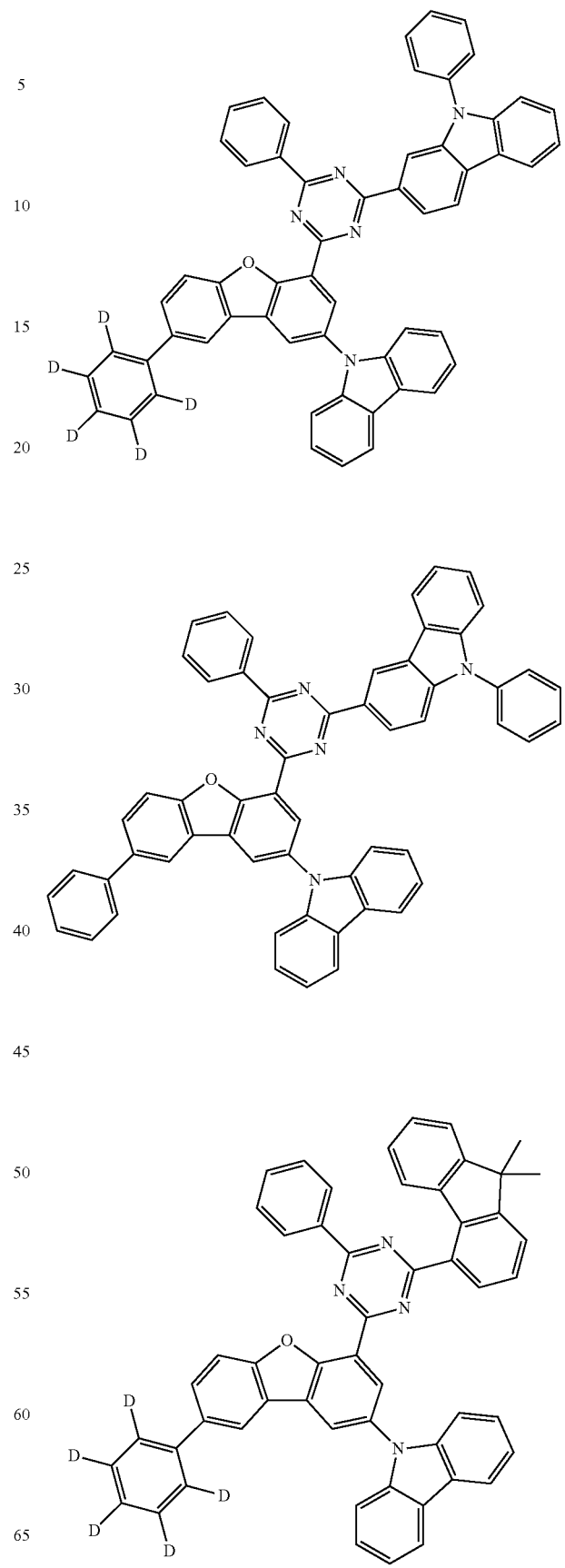

105
-continued
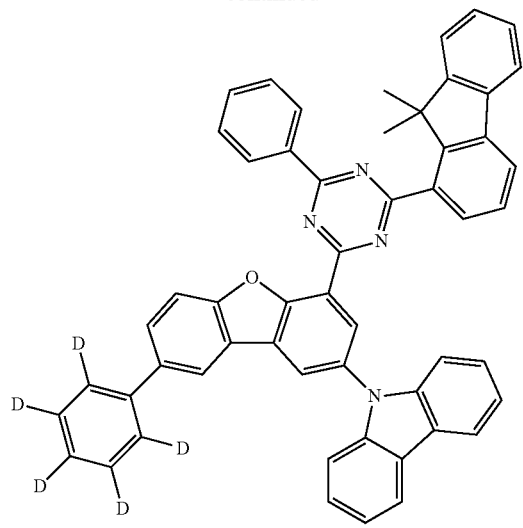
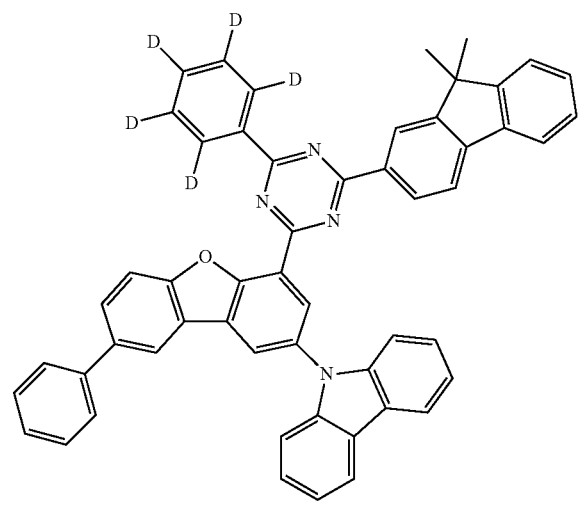
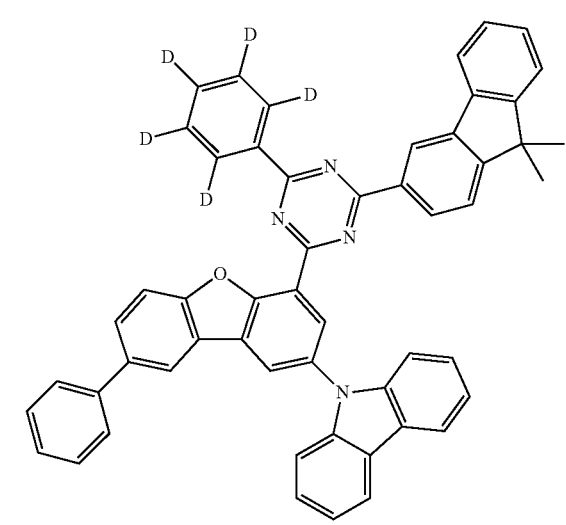
106
-continued
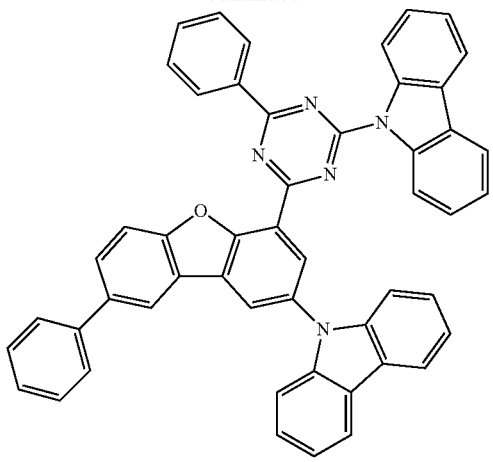
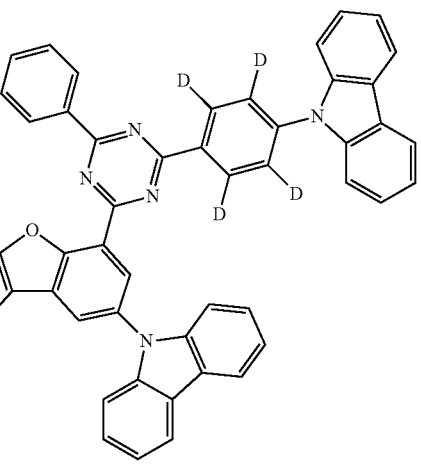
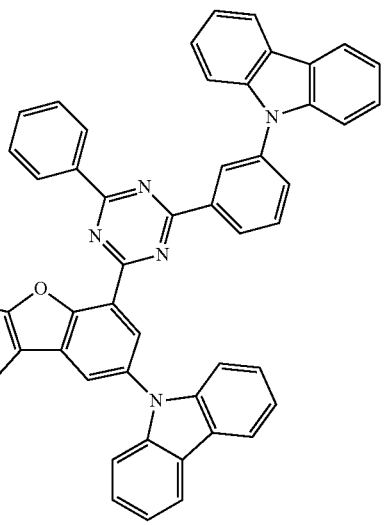

107
-continued
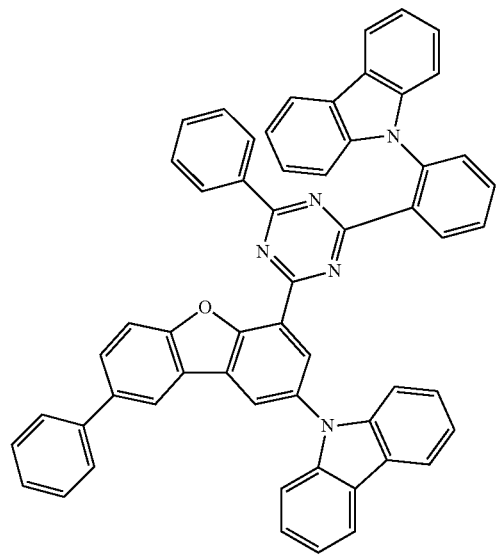
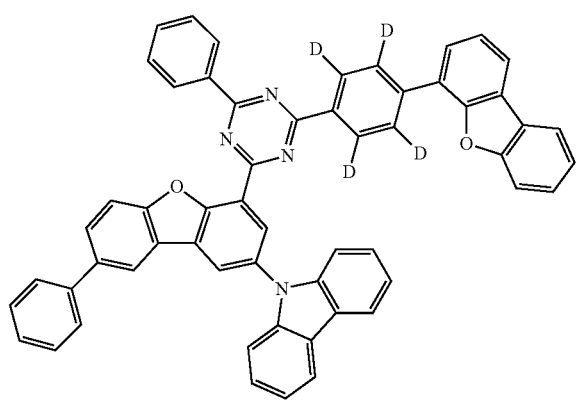
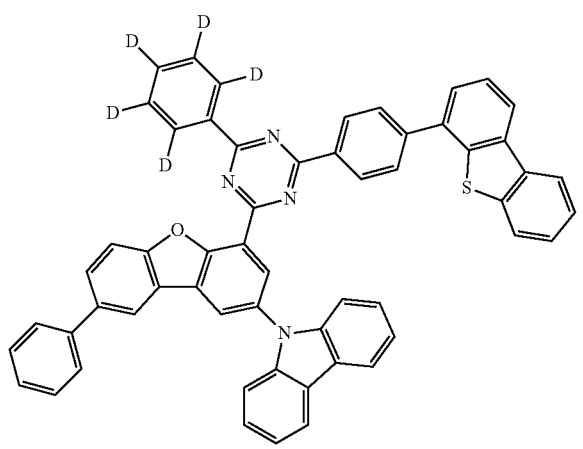
108
-continued
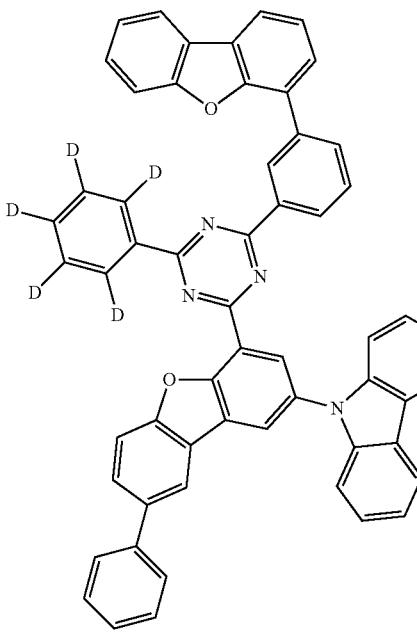
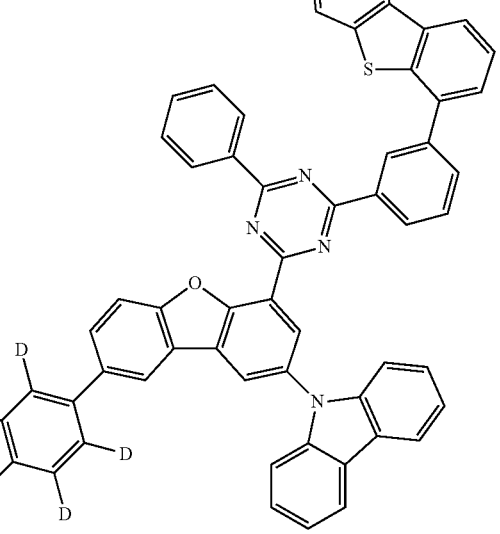
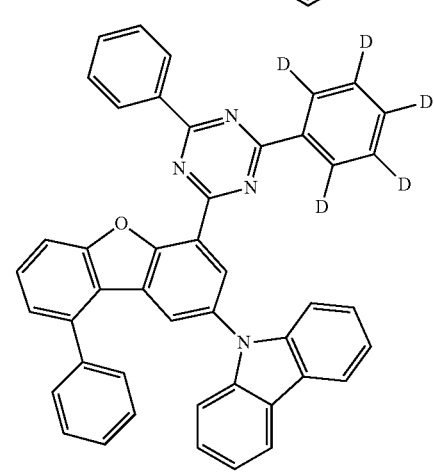

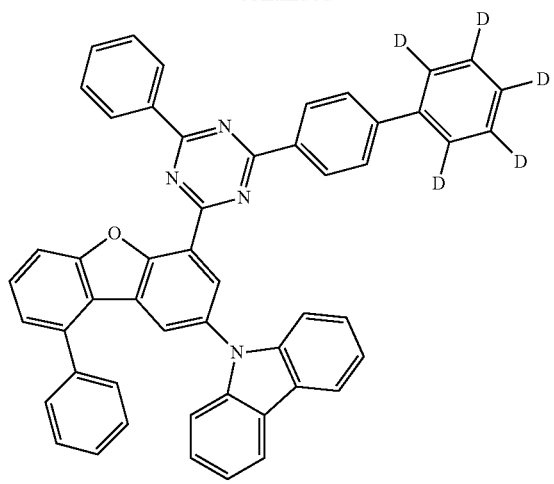
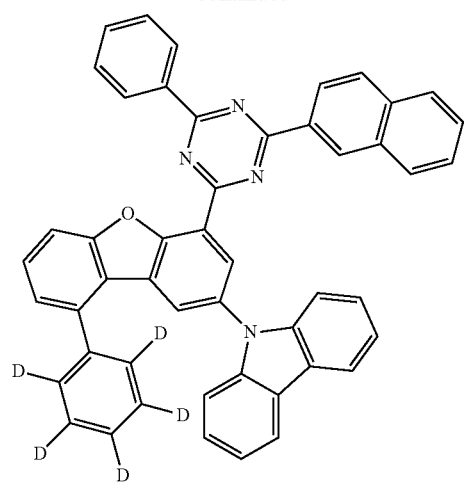
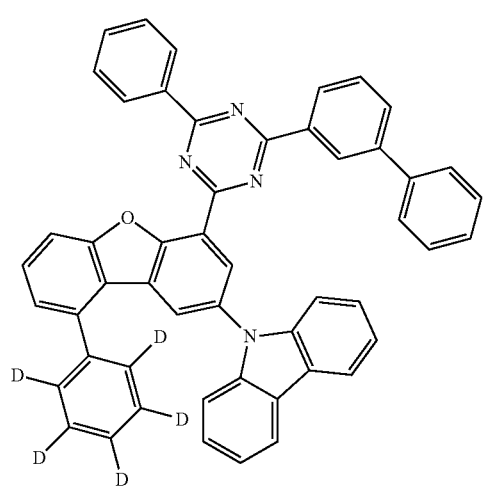
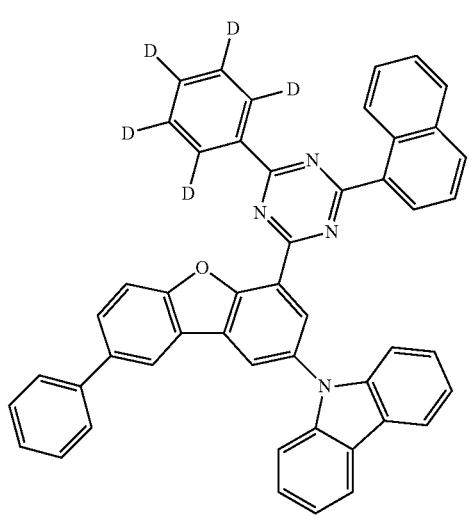
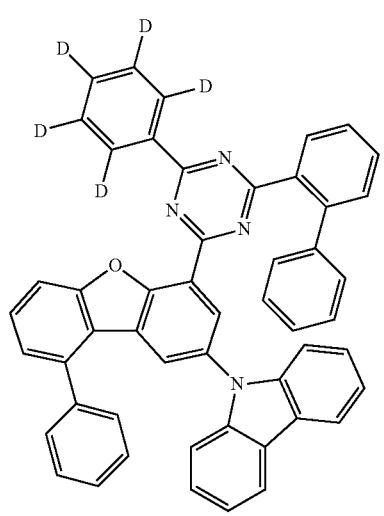
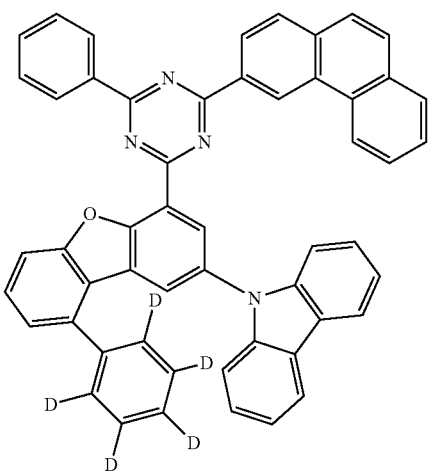

111
-continued
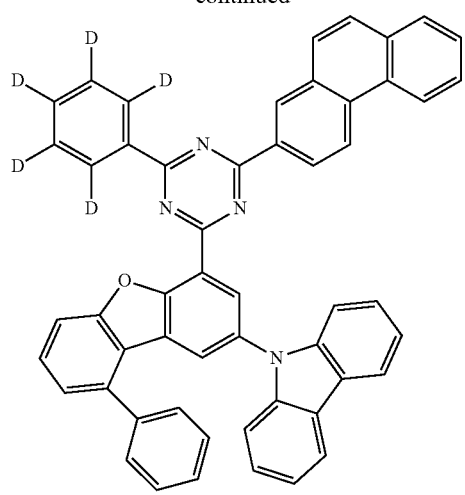
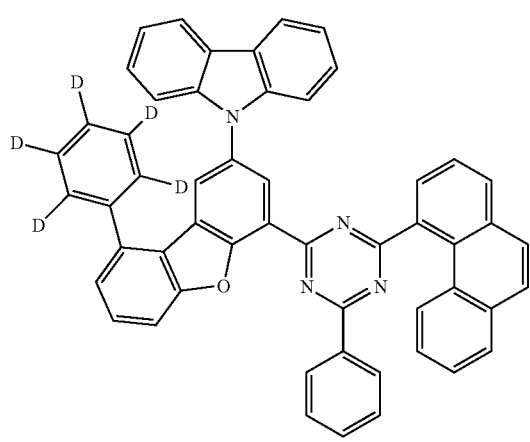
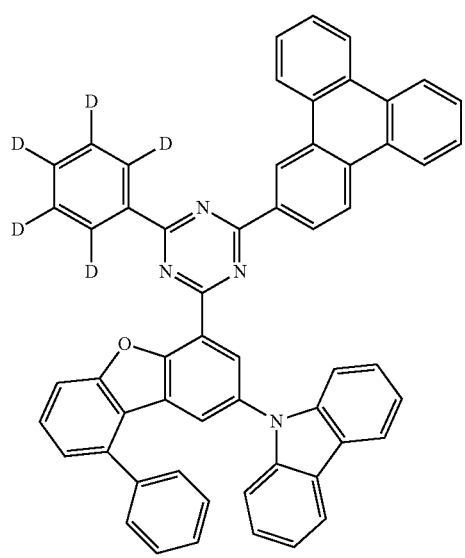
112
-continued
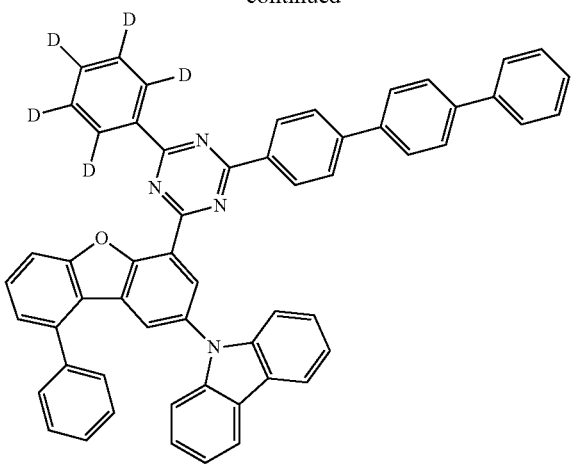
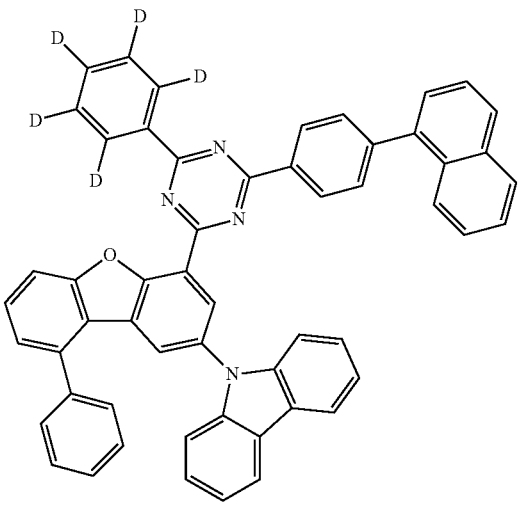
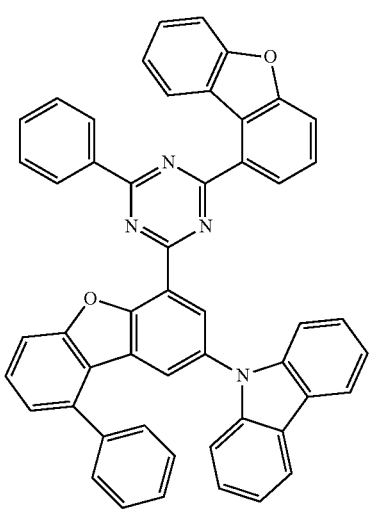

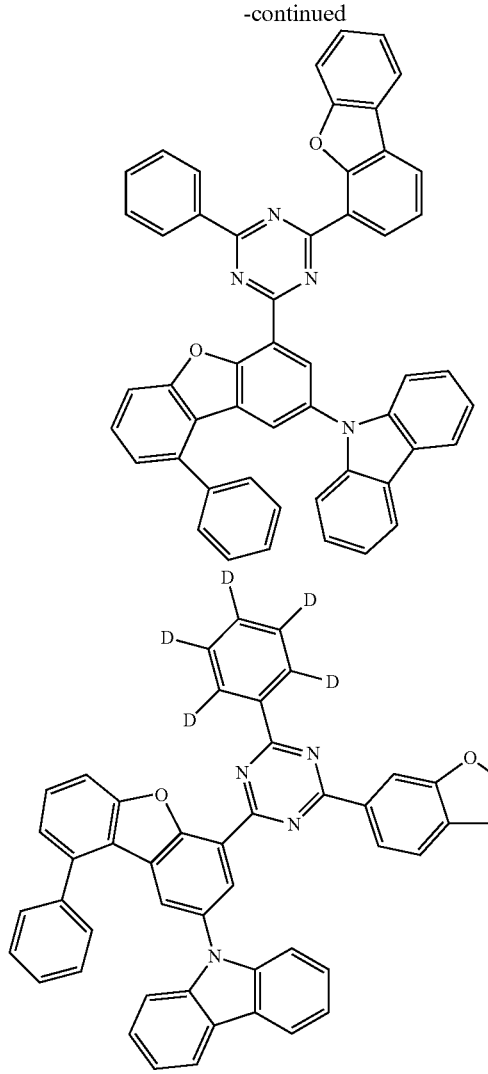
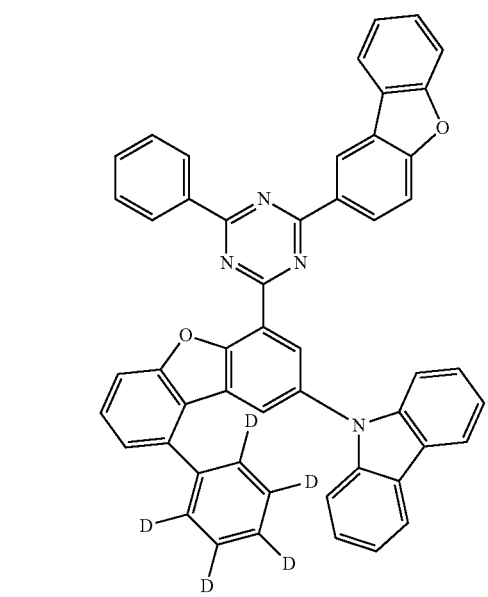
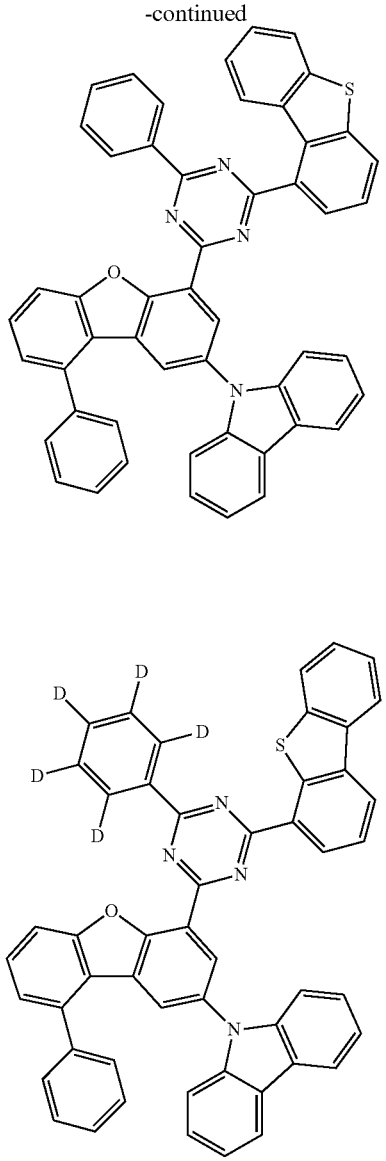
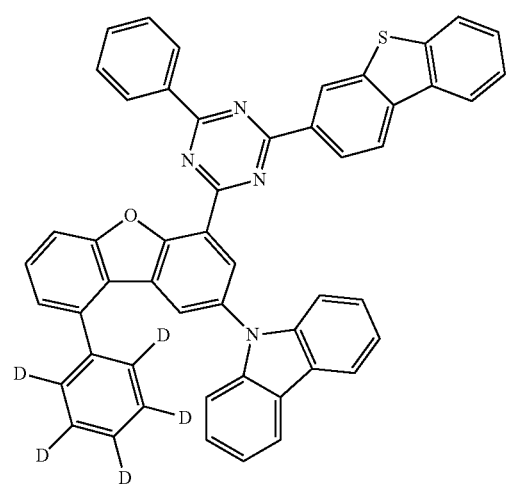

115
-continued
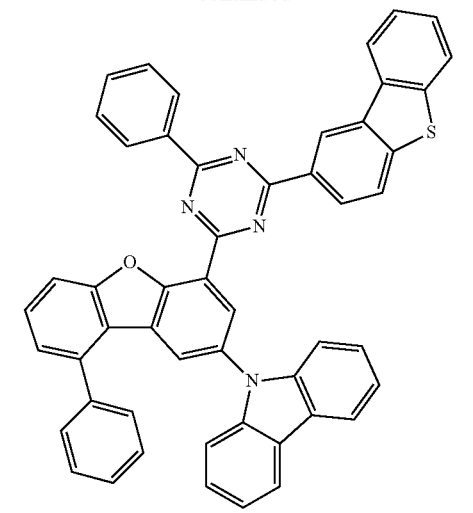
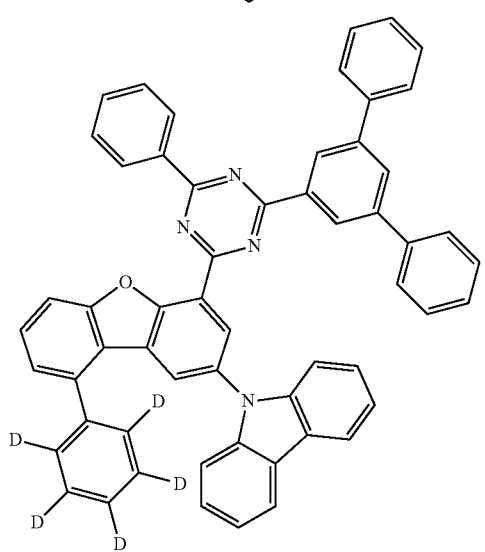
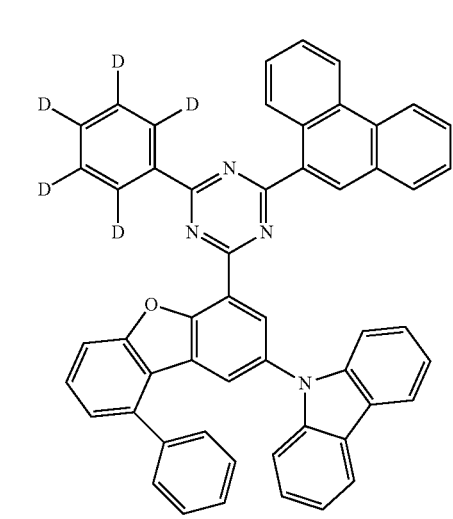
116
-continued
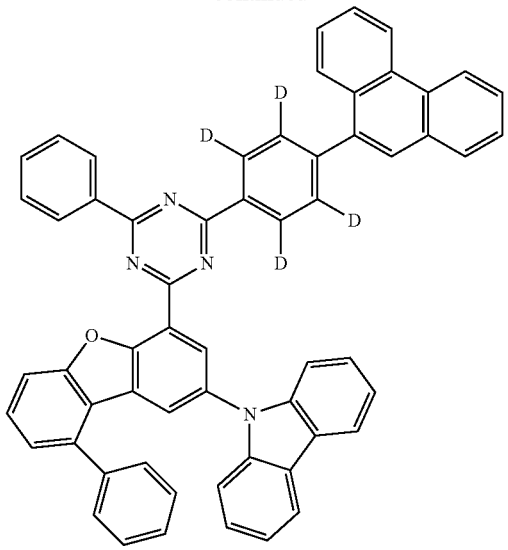
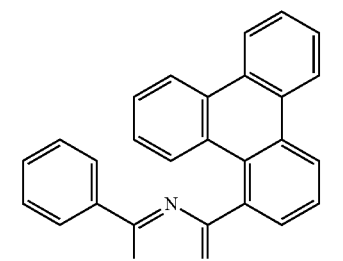
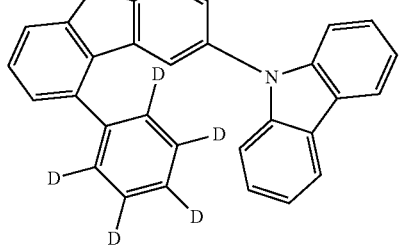
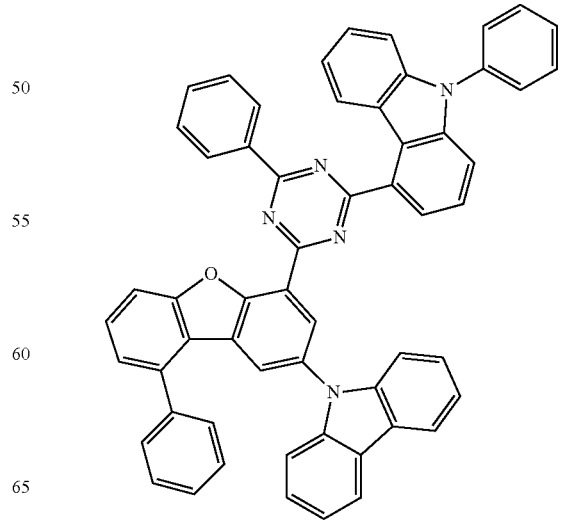

117
-continued
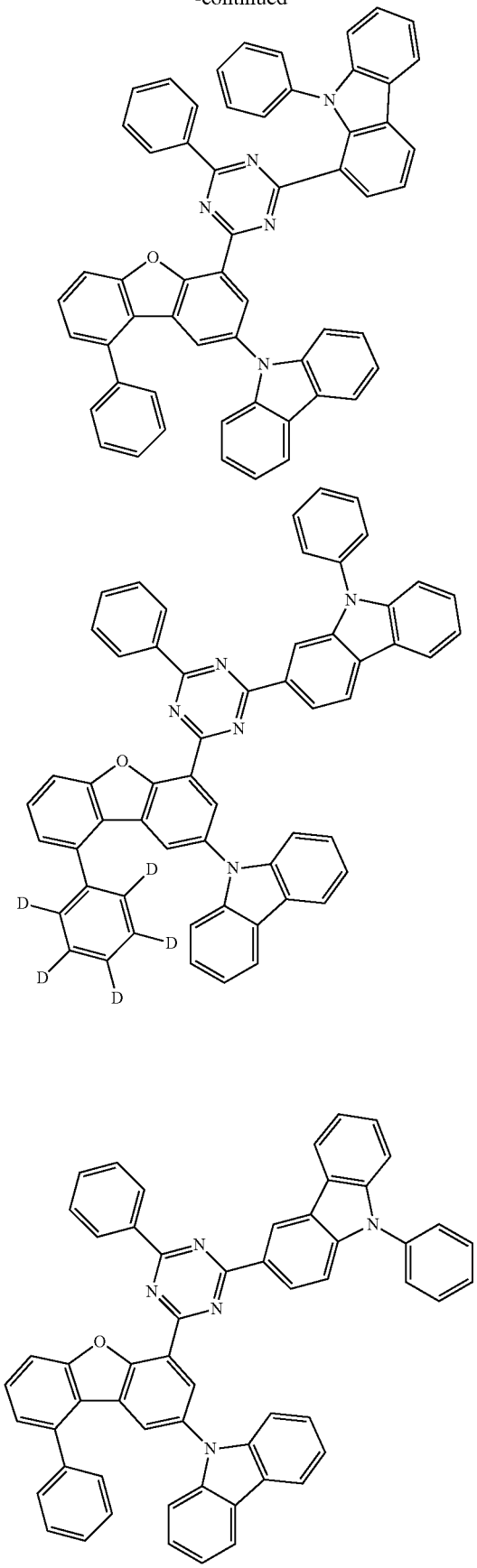
118
-continued
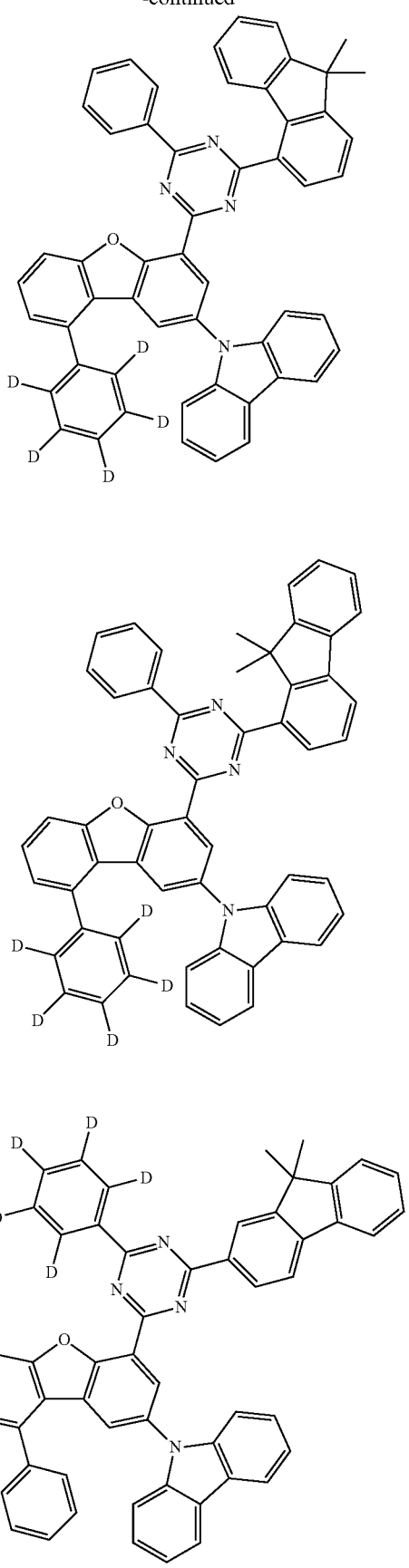

119
-continued
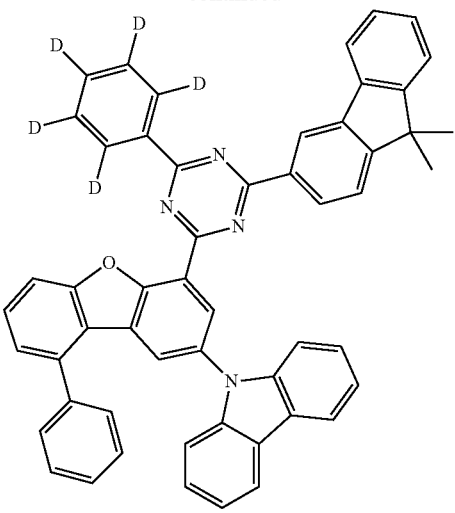
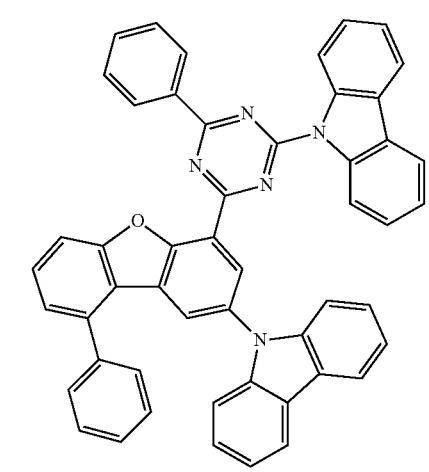
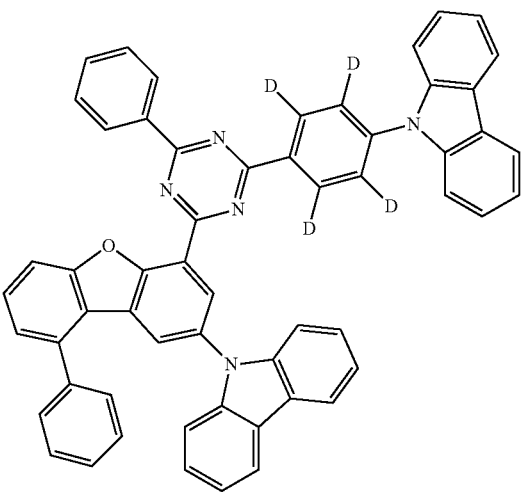
120
-continued
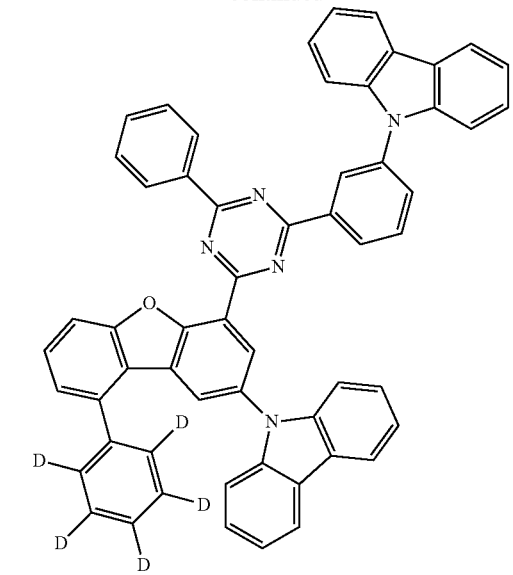
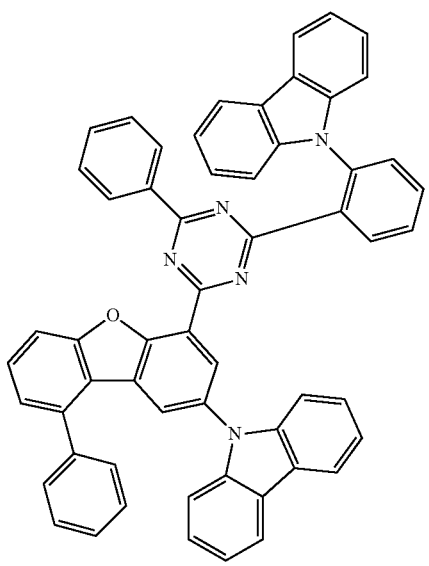
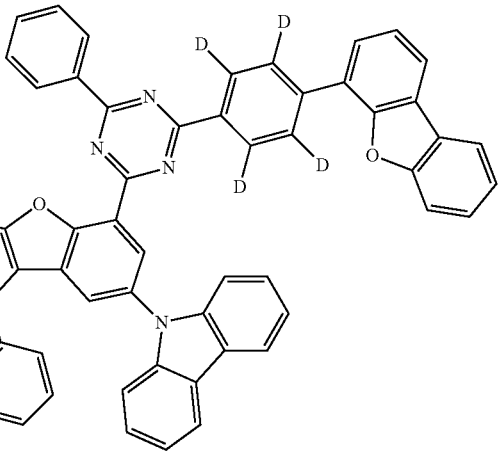

121
-continued
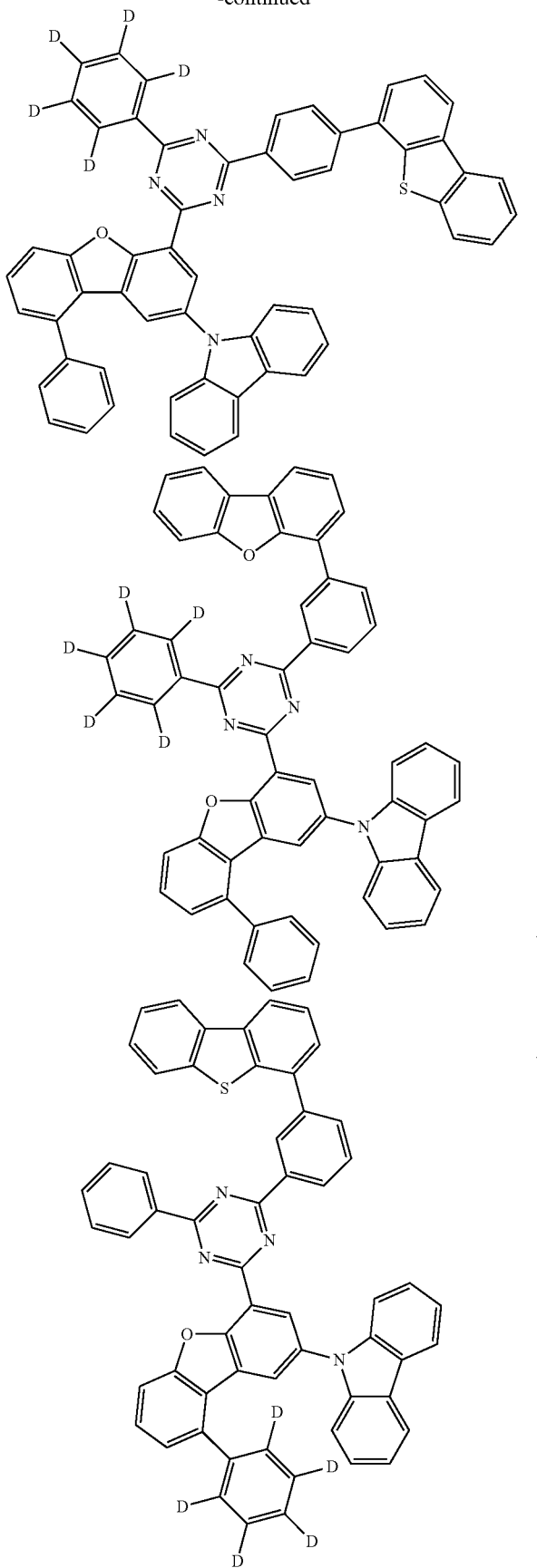
122
-continued
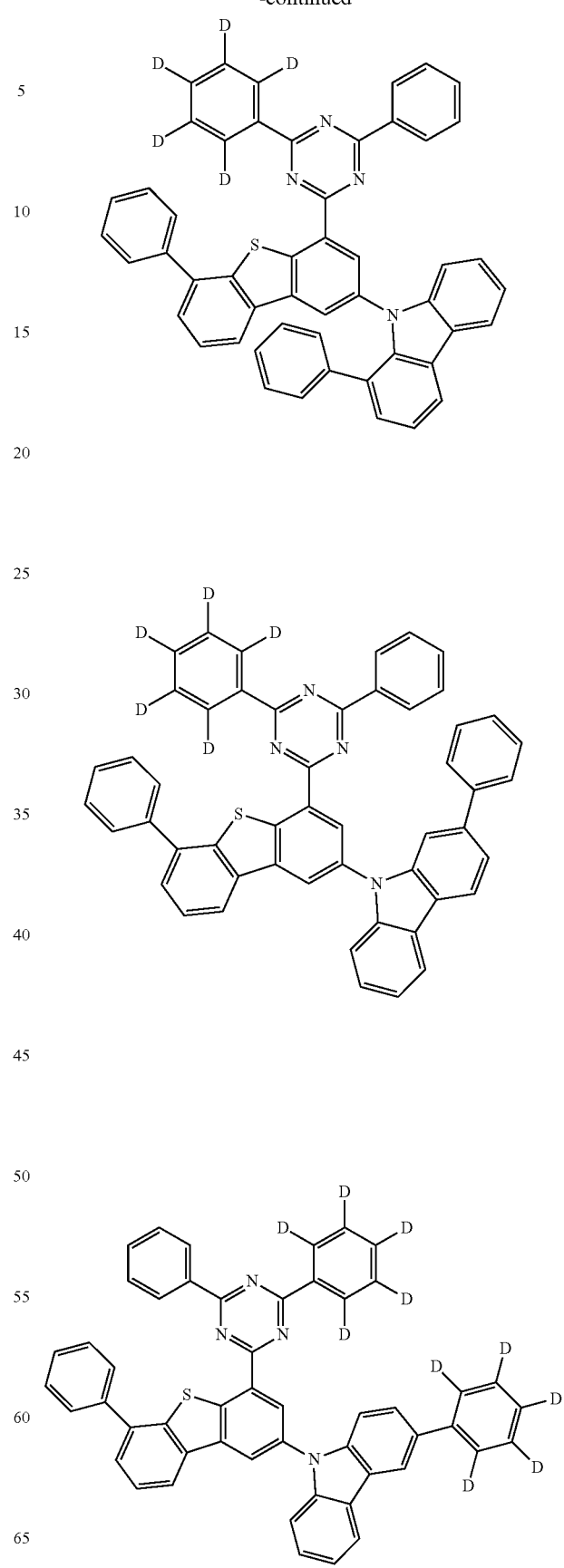

123
-continued
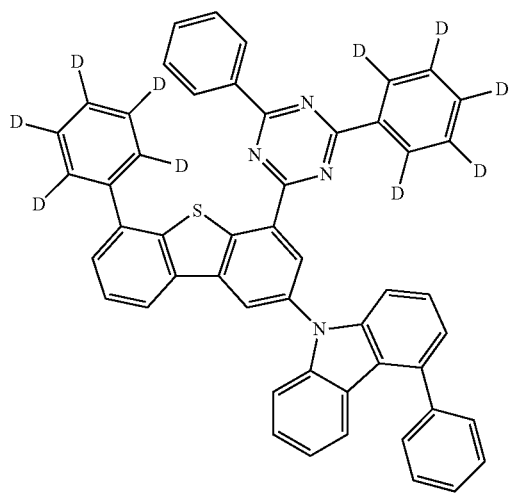
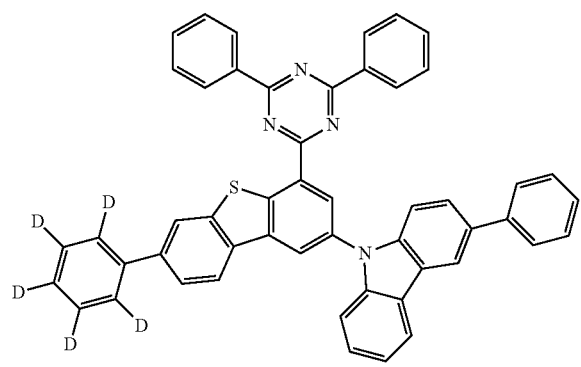
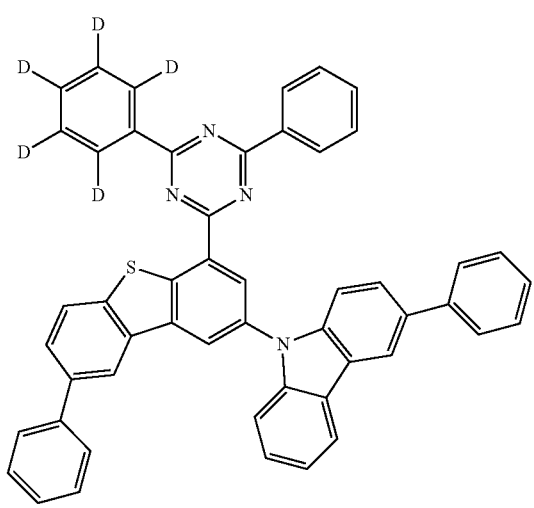
124
-continued
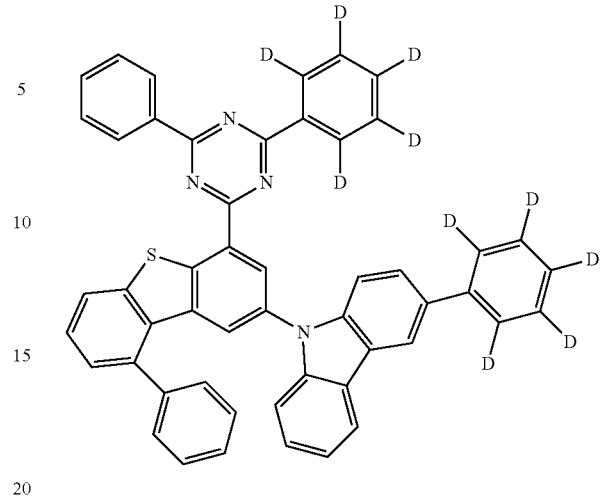
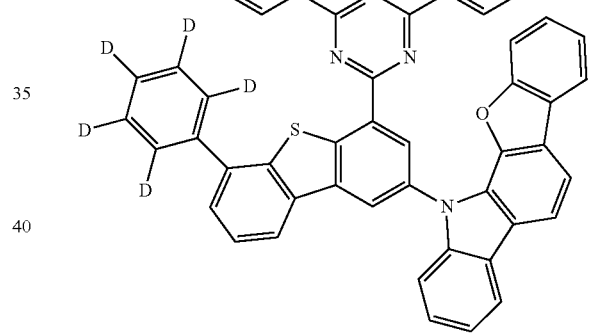
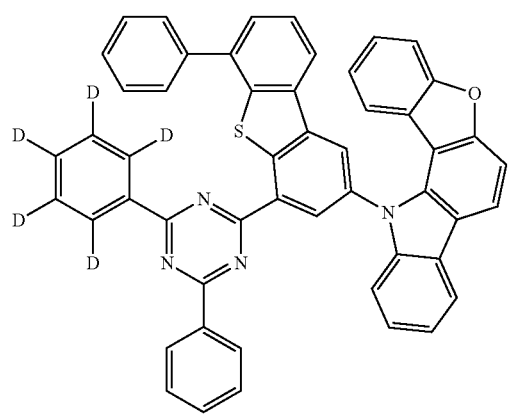

125
-continued
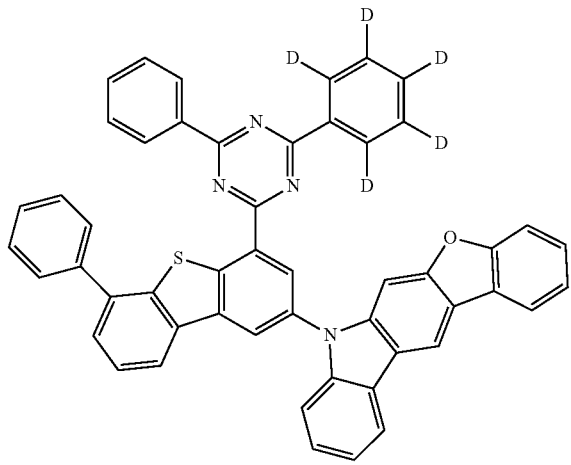
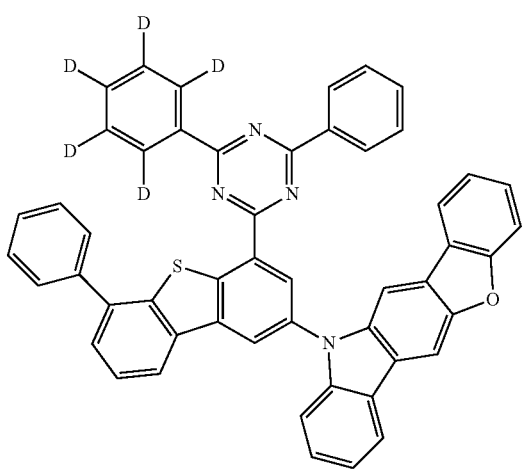
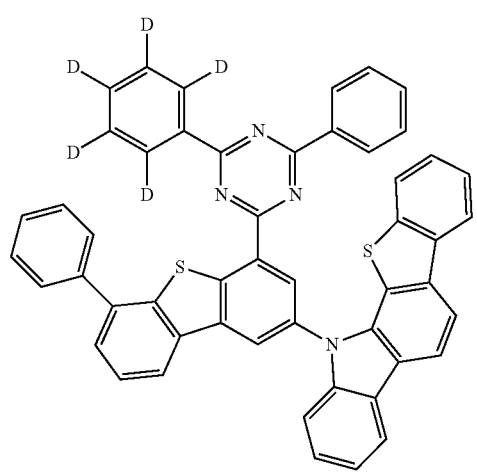
126
-continued
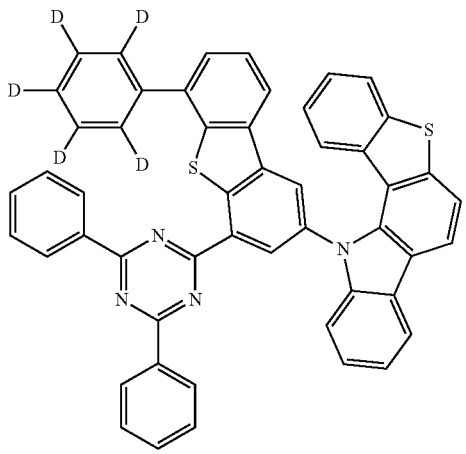
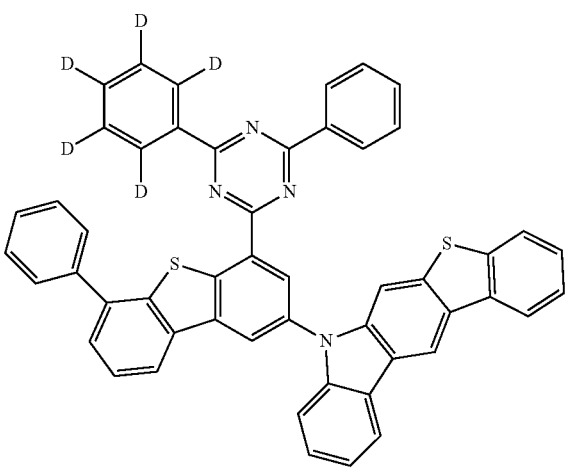
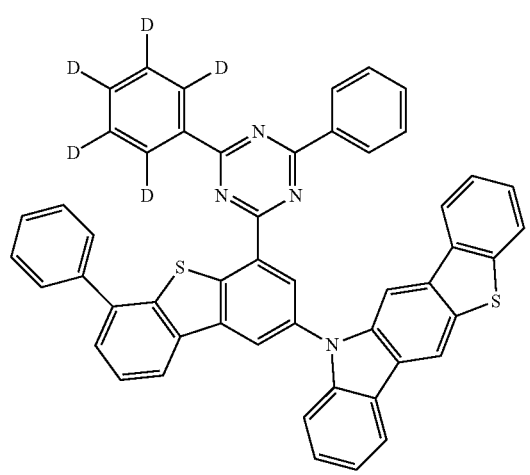

127
-continued
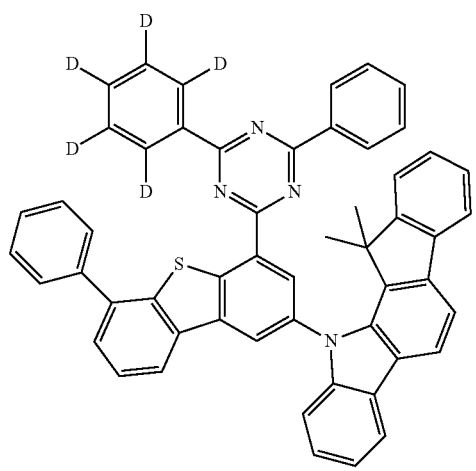
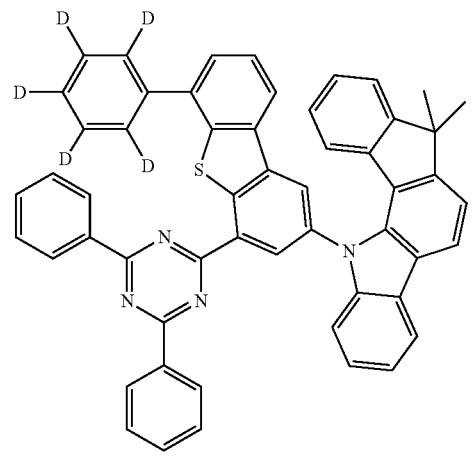
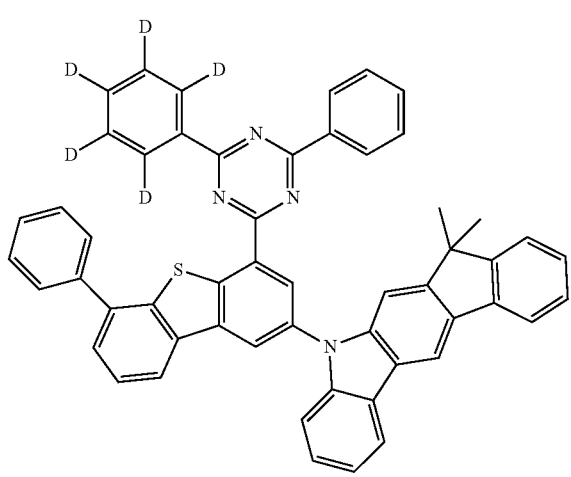
128
-continued
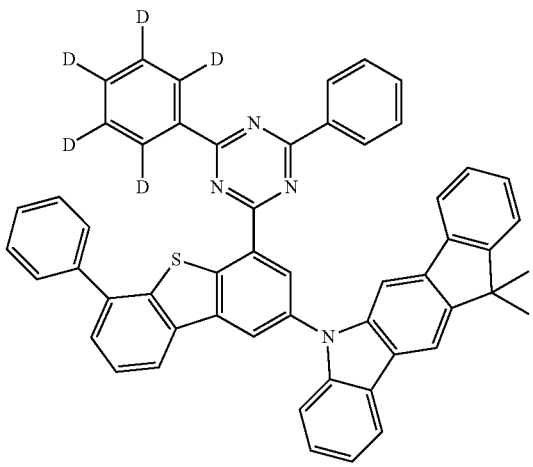
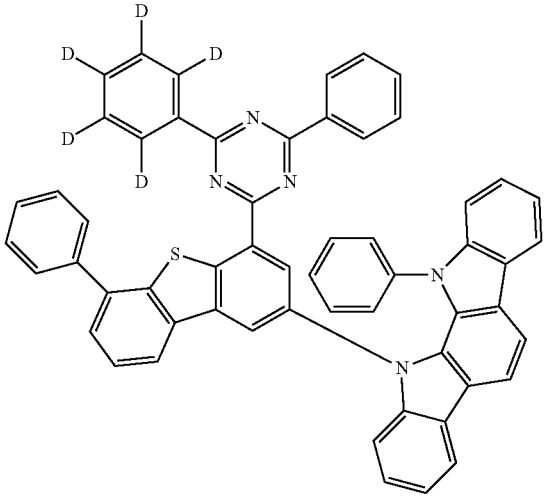
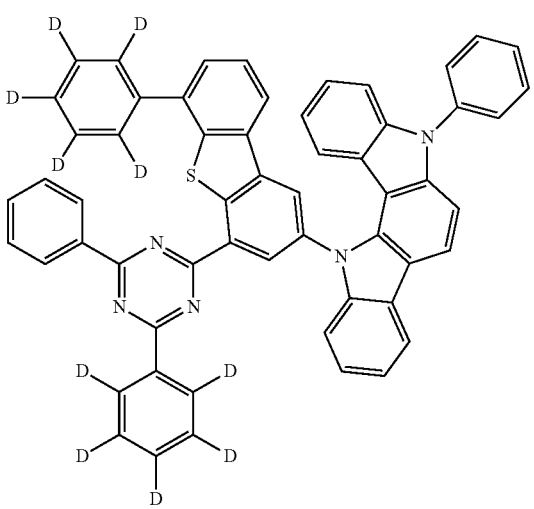

129
-continued
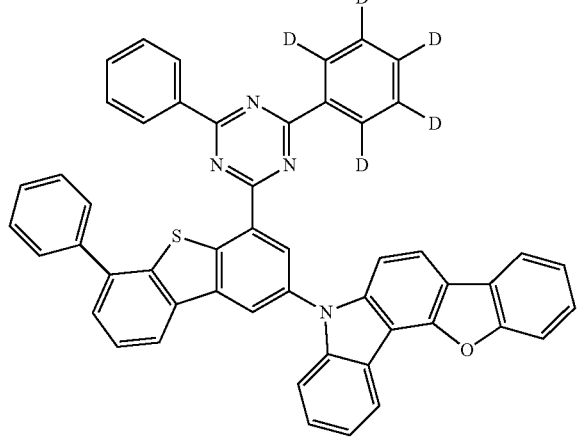
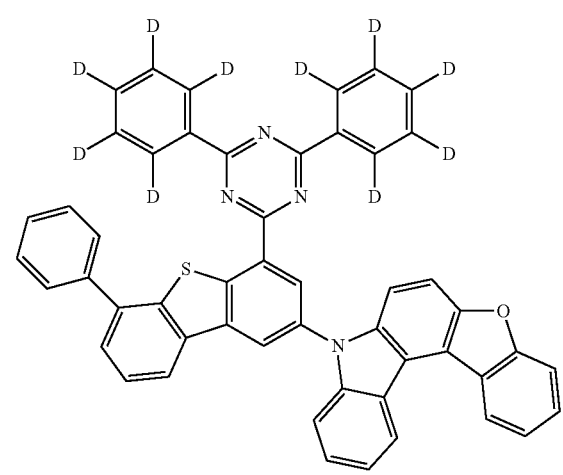
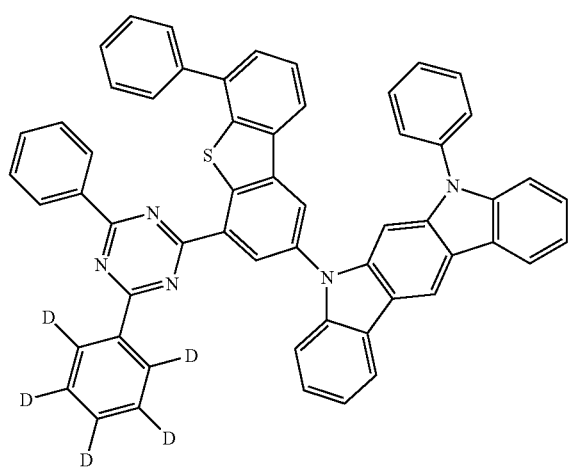
130
-continued
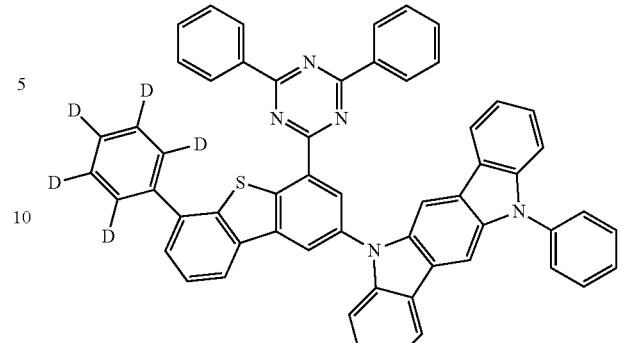
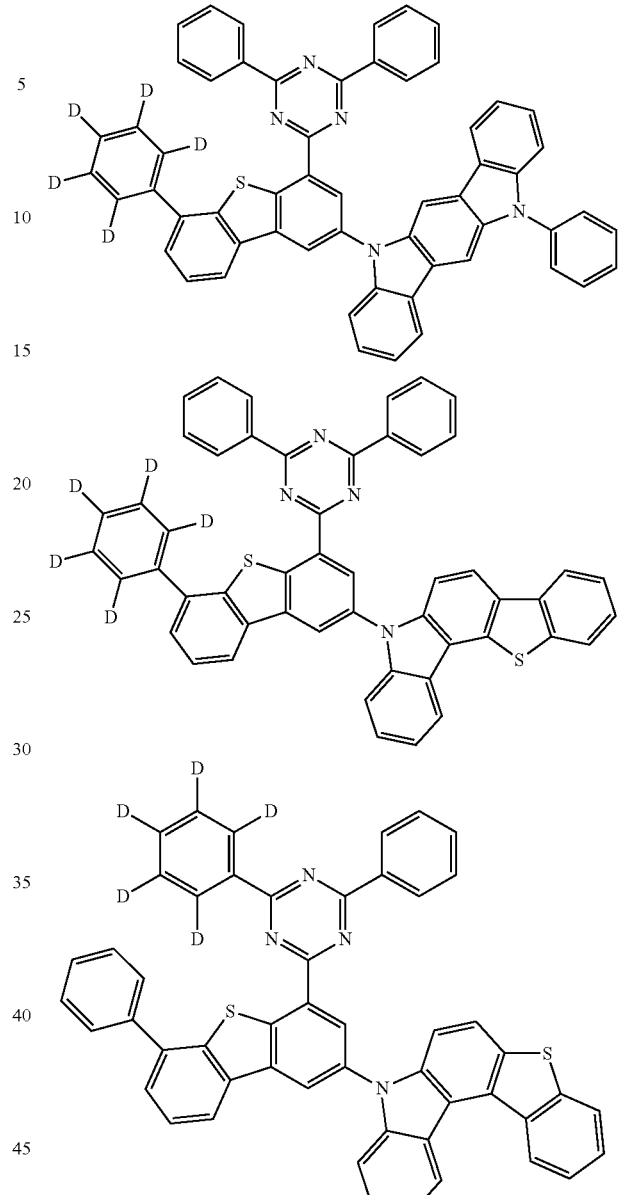
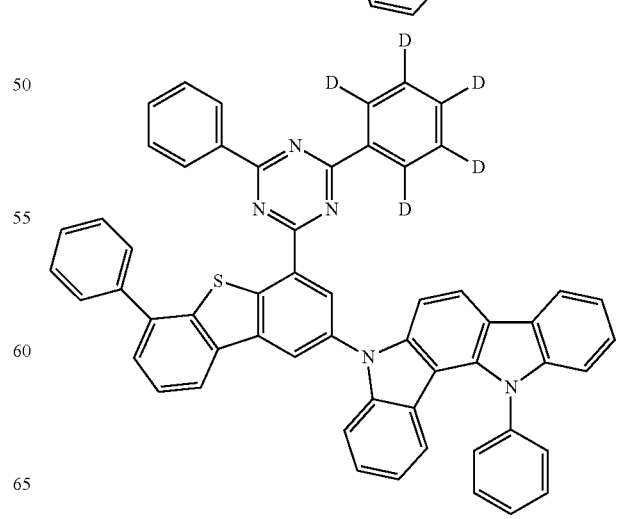

131
-continued
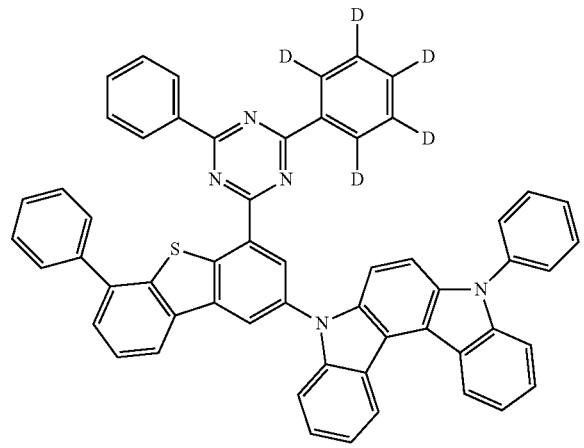
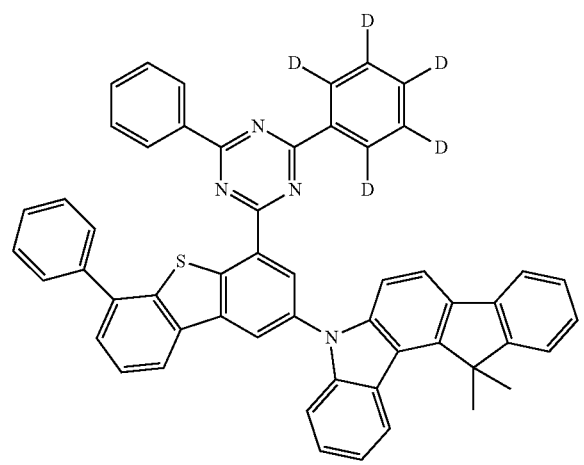
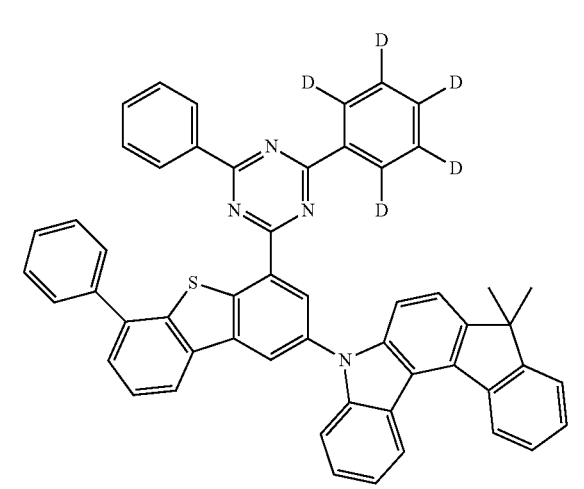
132
-continued
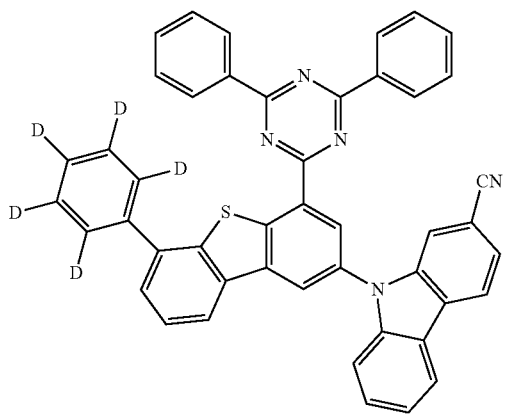
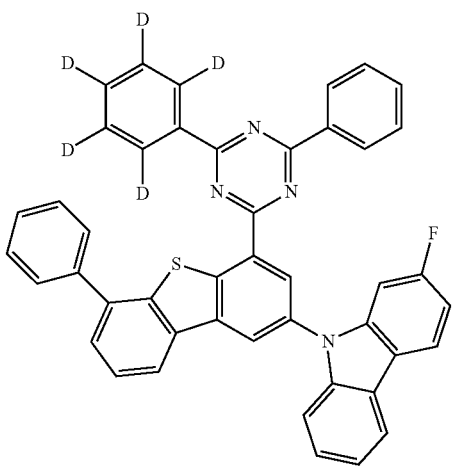
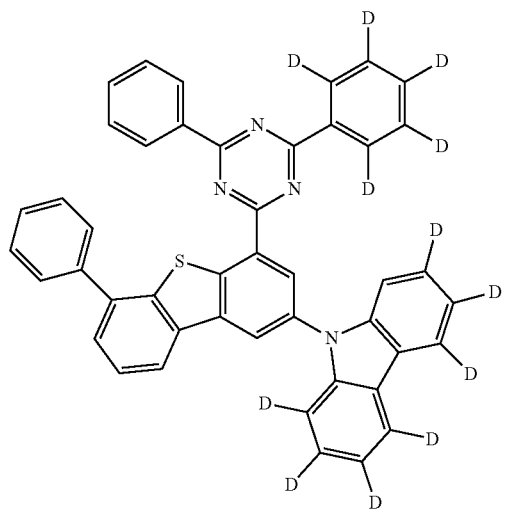

133
-continued
134
-continued
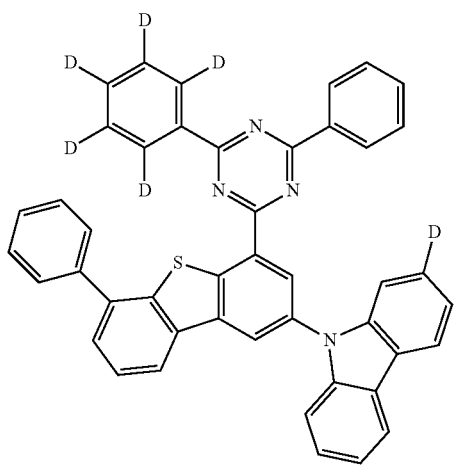
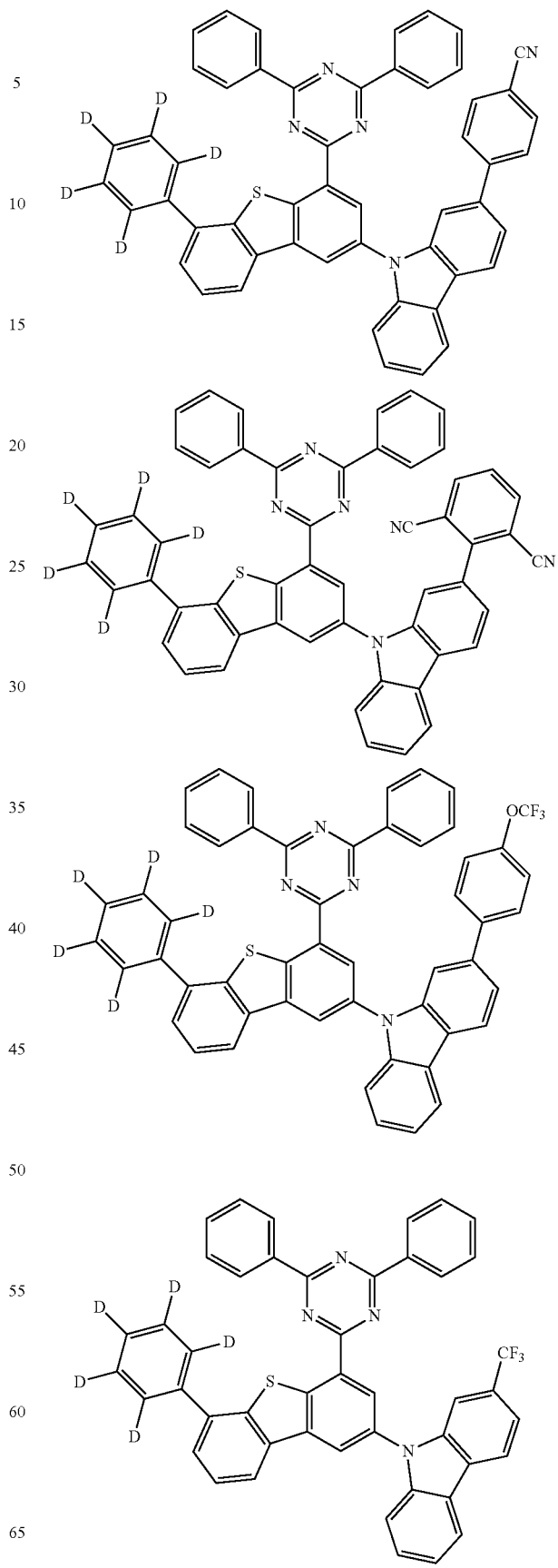

135
-continued
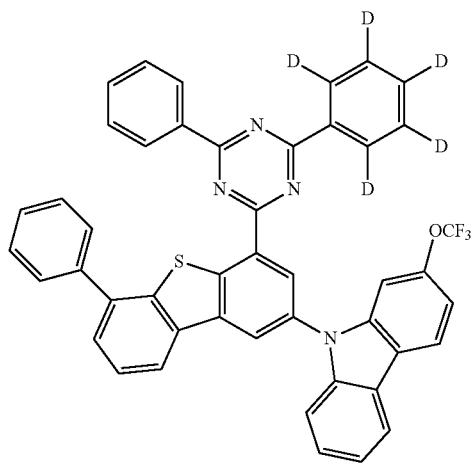
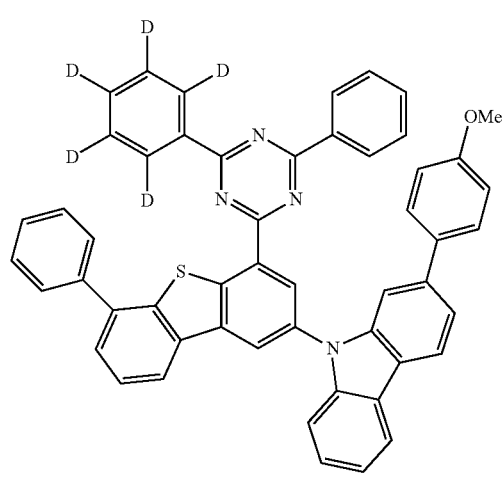
136
-continued
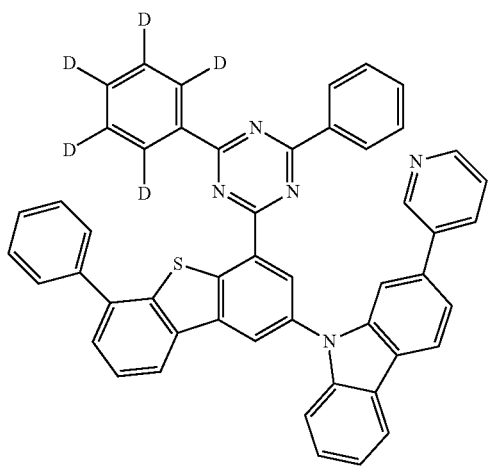
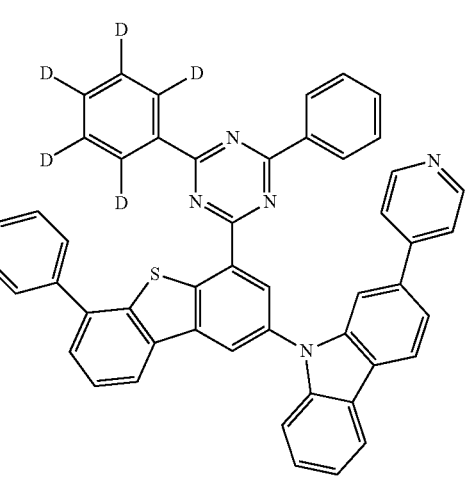
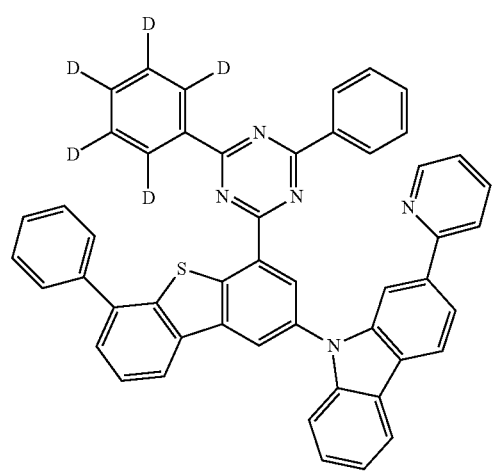
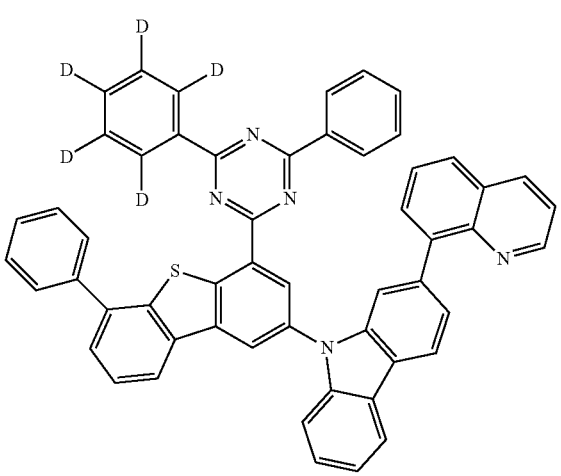

137
-continued
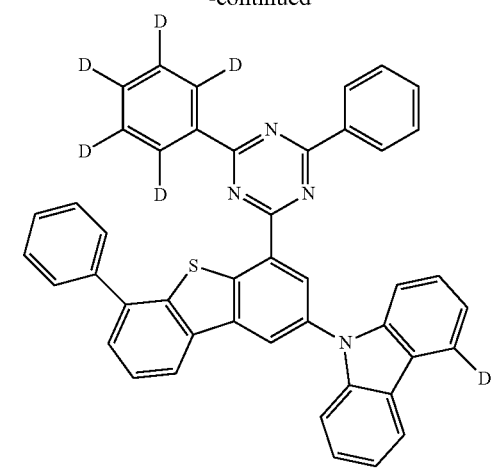
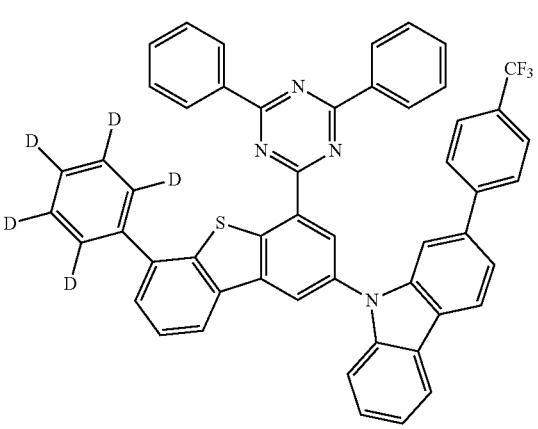
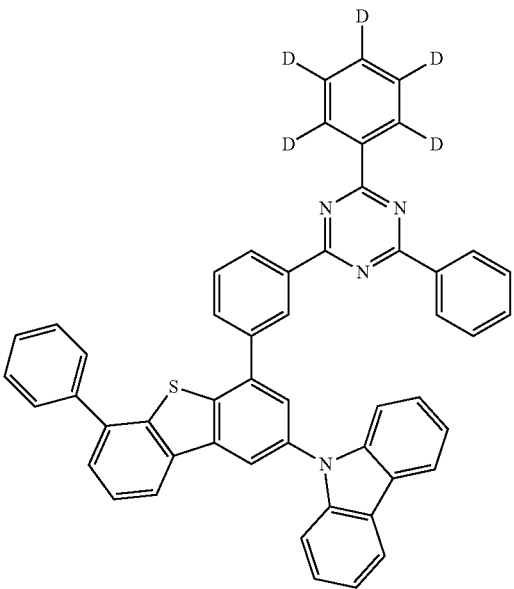
138
-continued
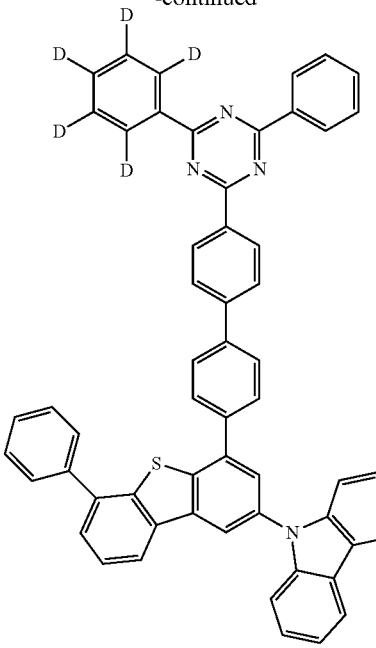
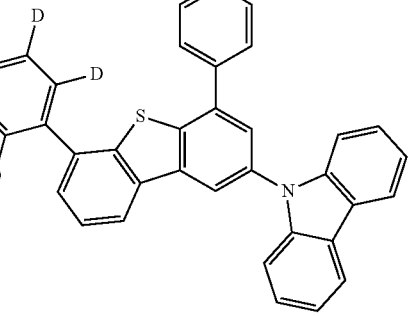

139
-continued
140
-continued
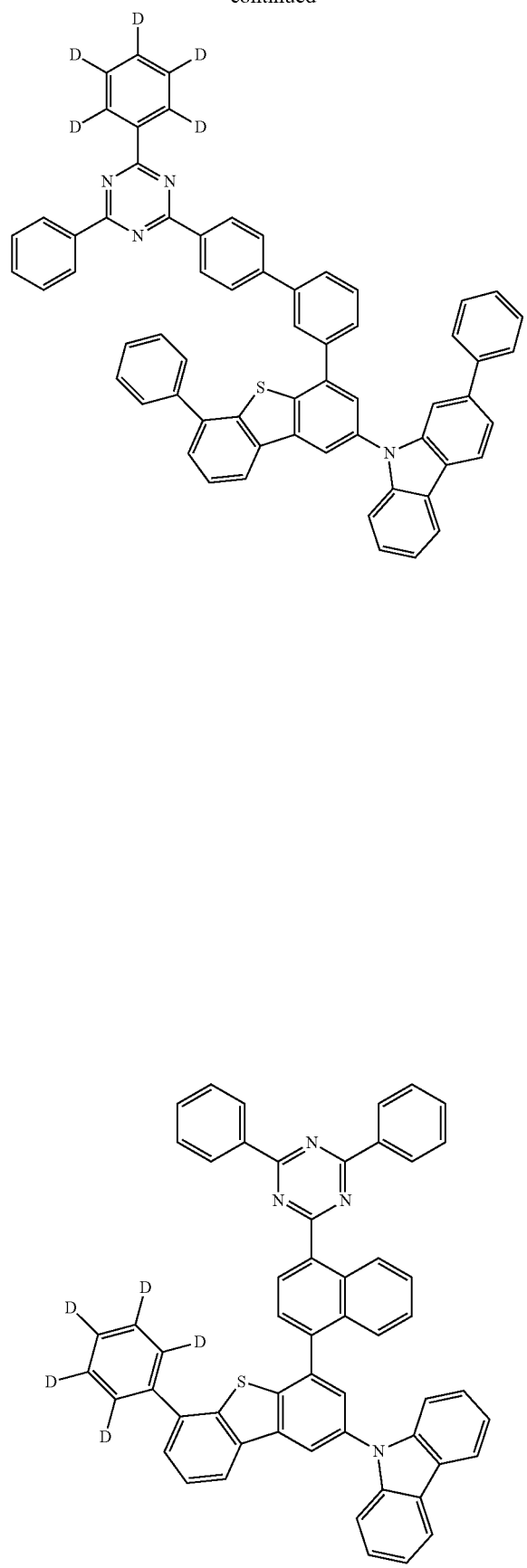
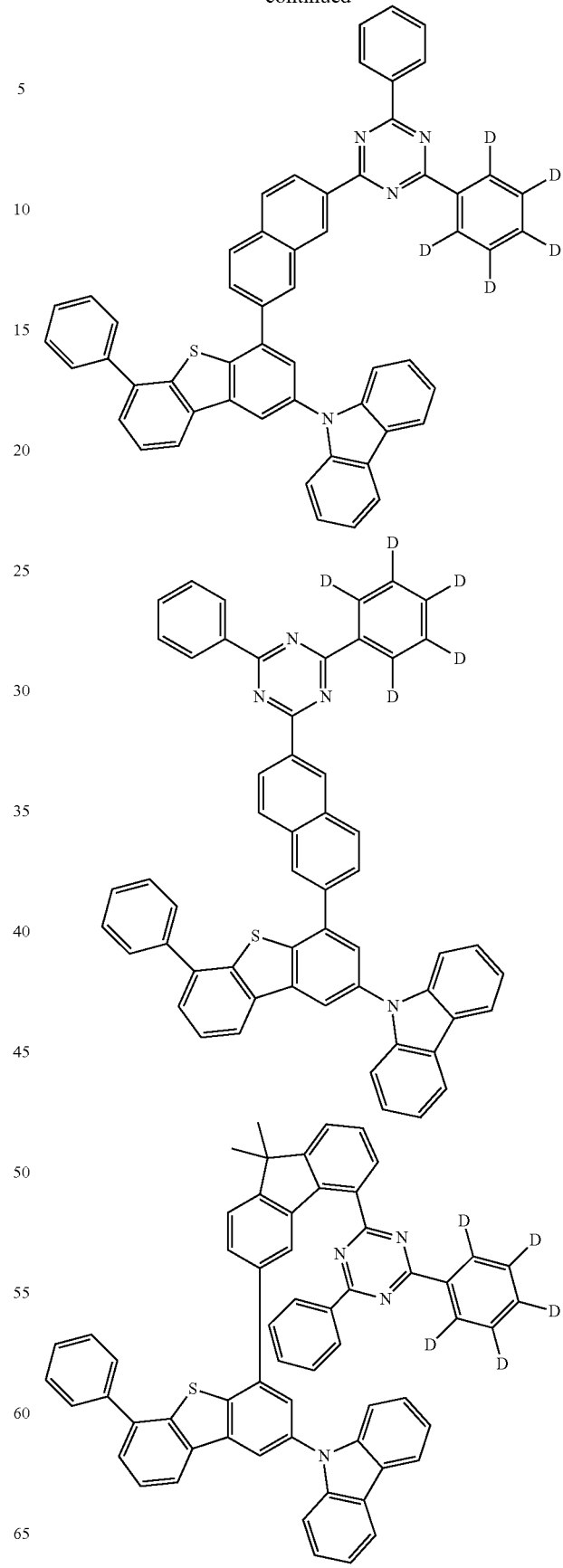

141
-continued
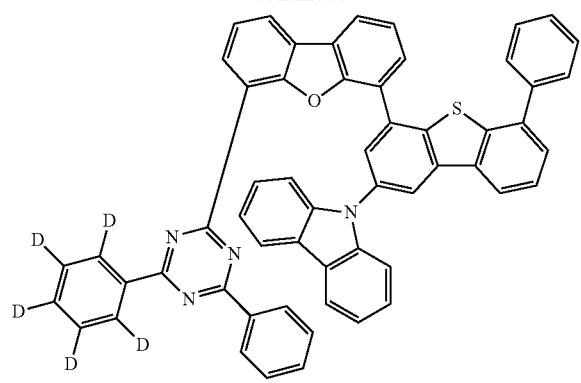
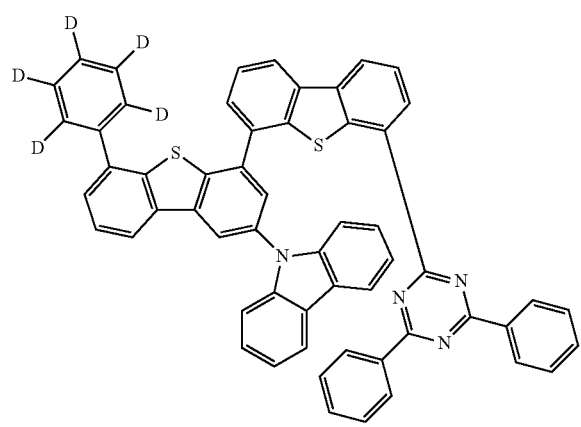
142
-continued
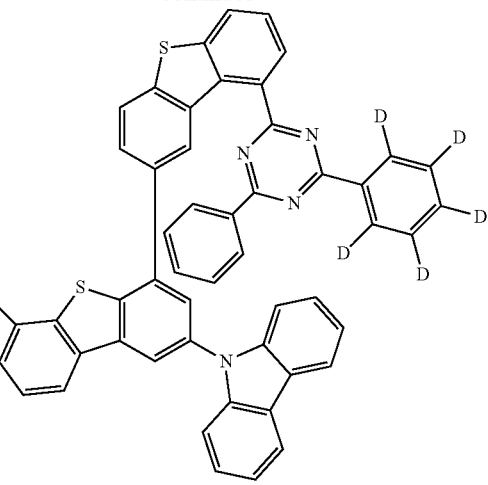
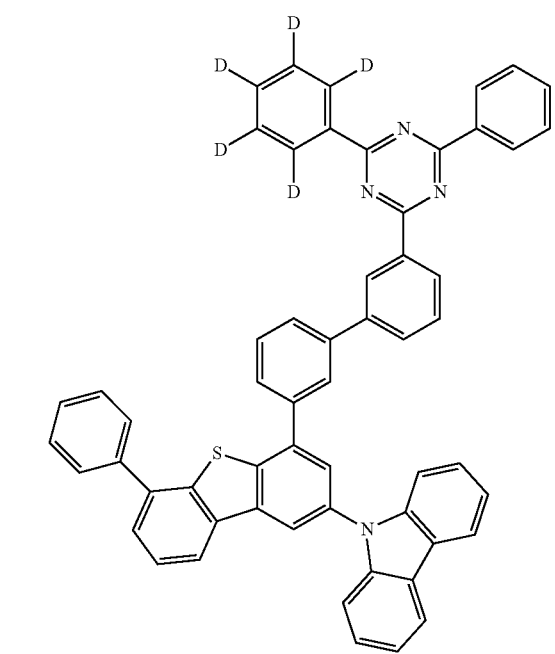

143
-continued
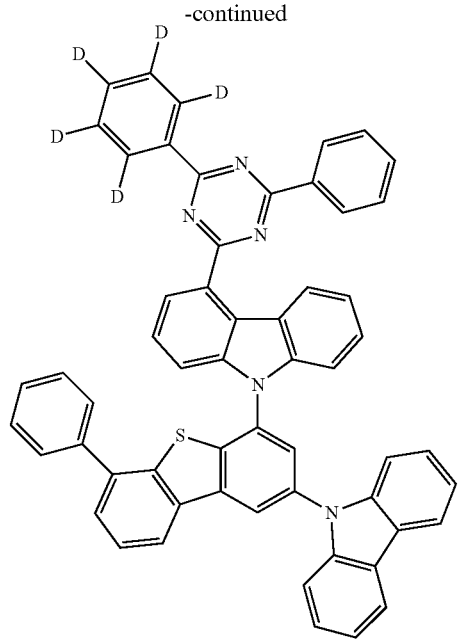
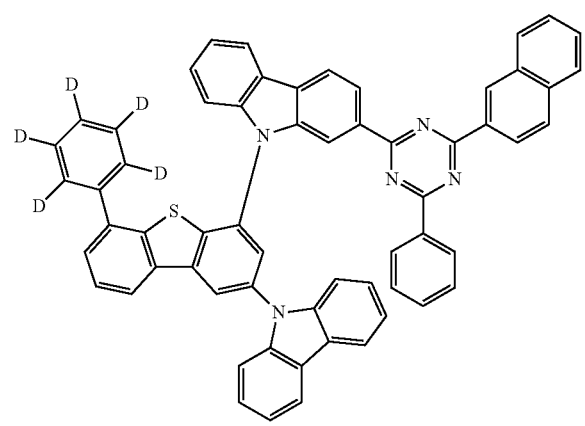
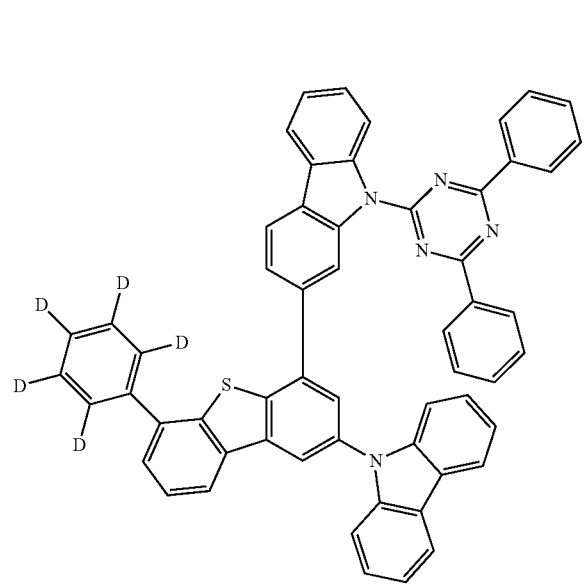
144
-continued
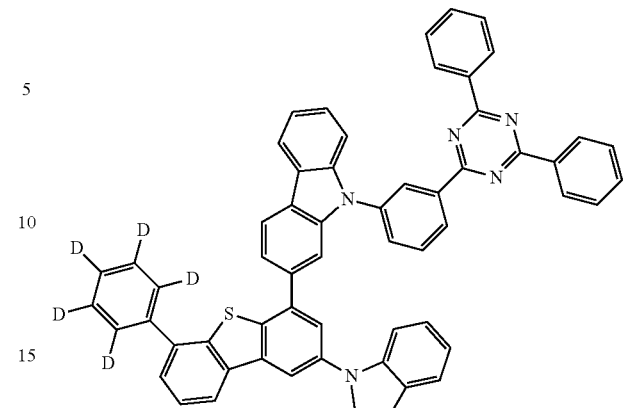
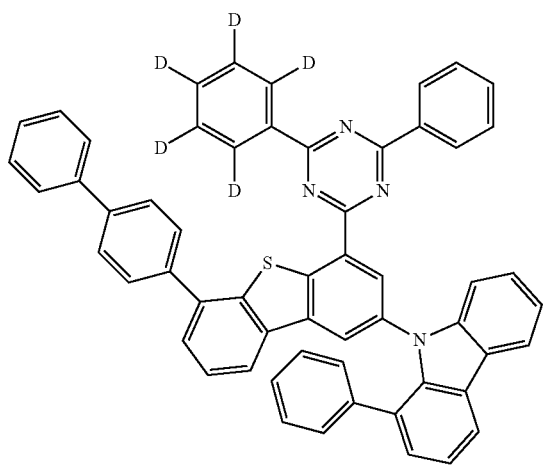

-continued

147
-continued
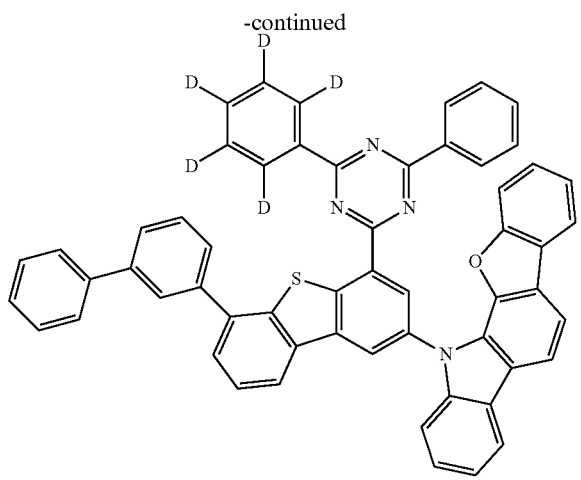
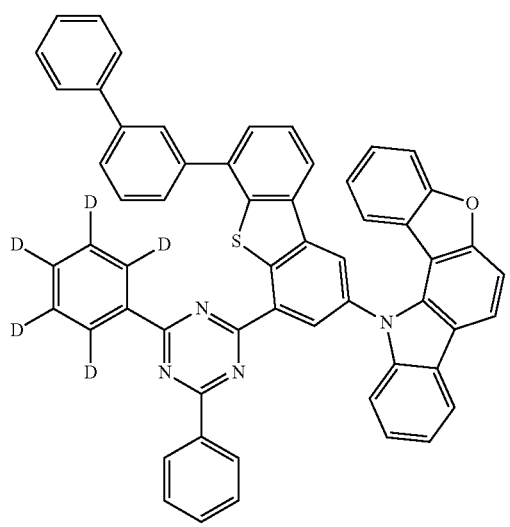
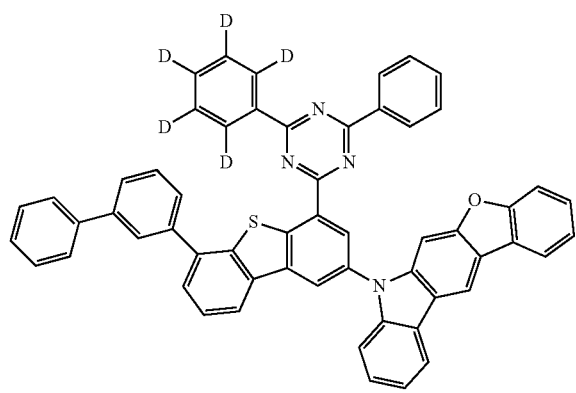
148
-continued
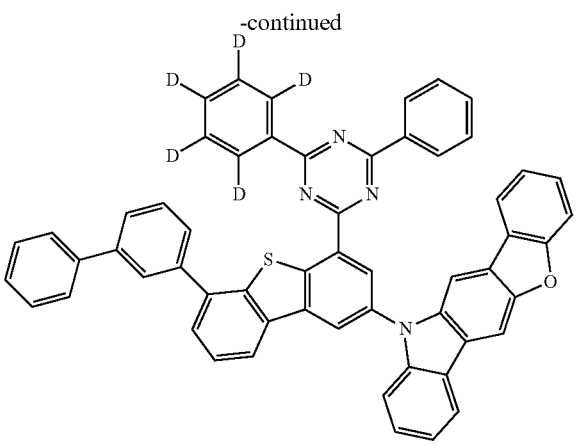
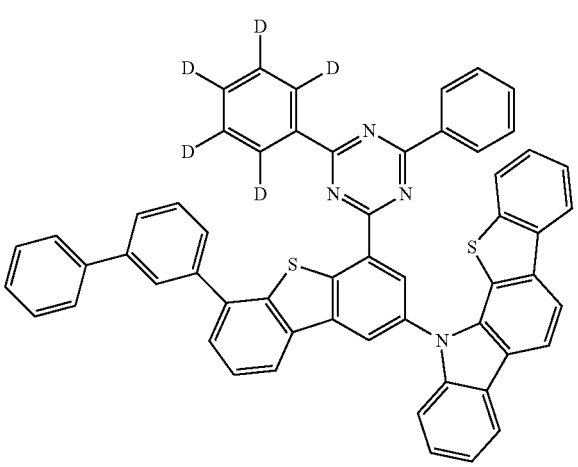
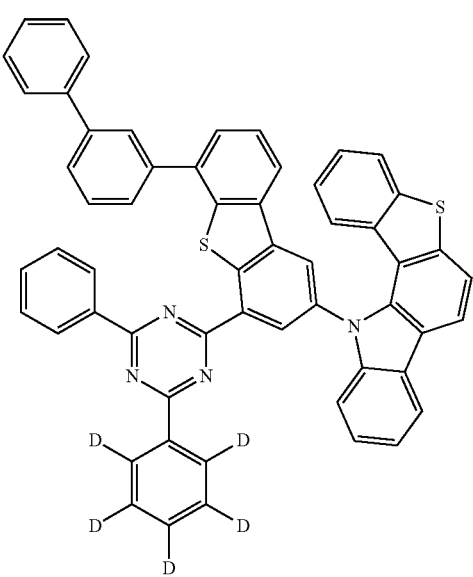

149
-continued
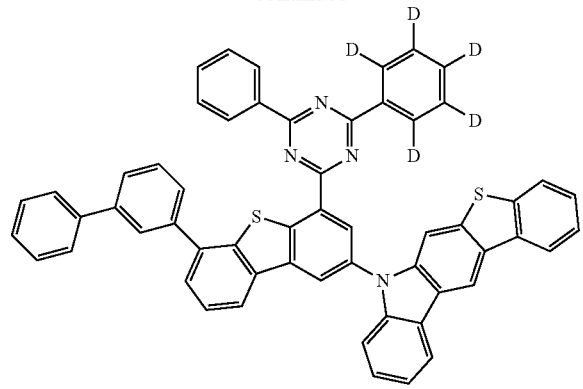
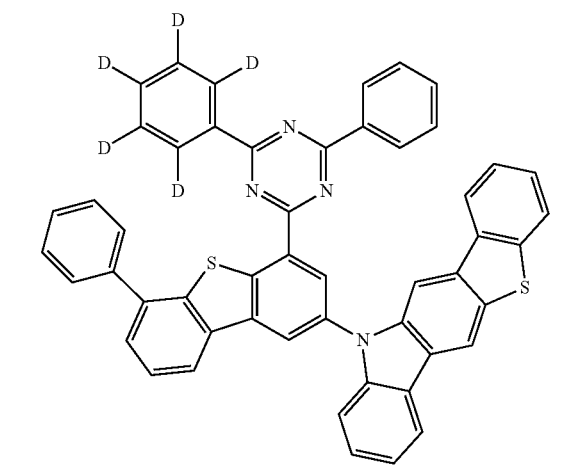
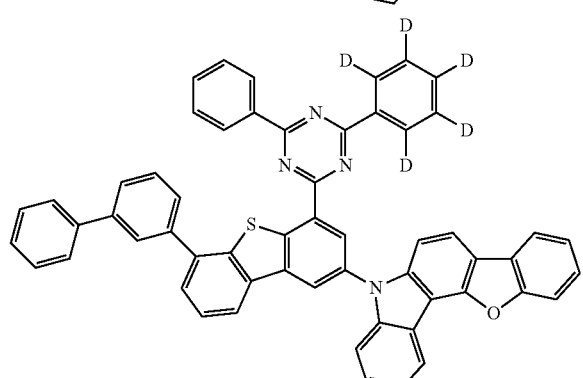
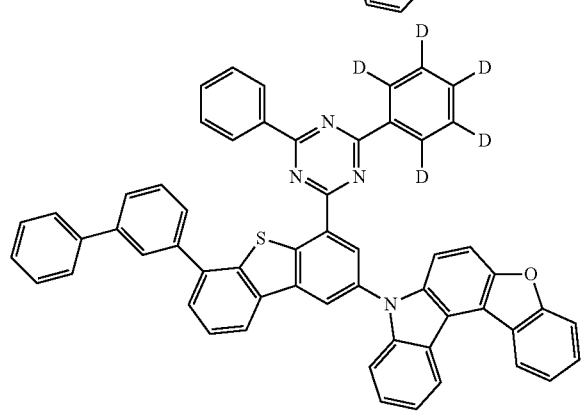
150
-continued
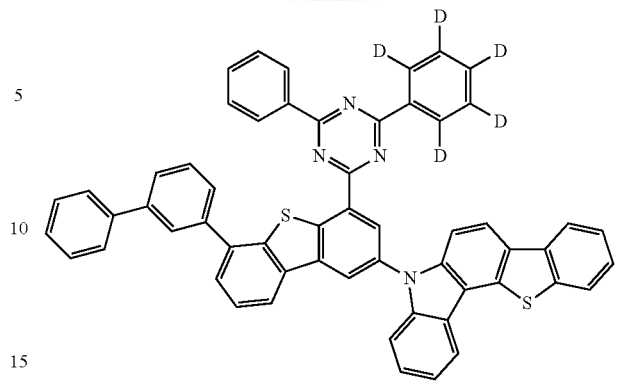
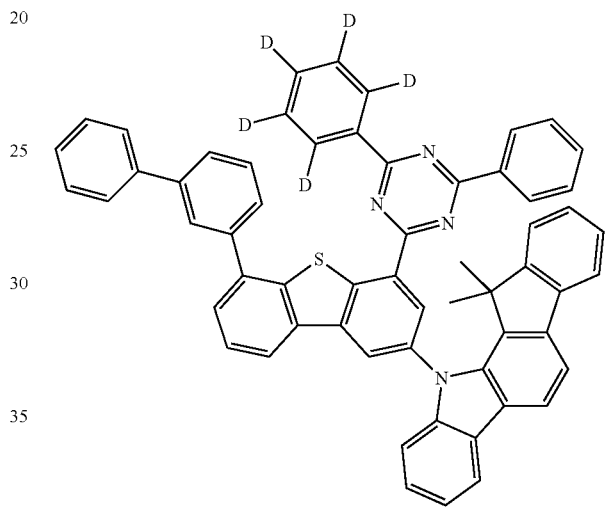
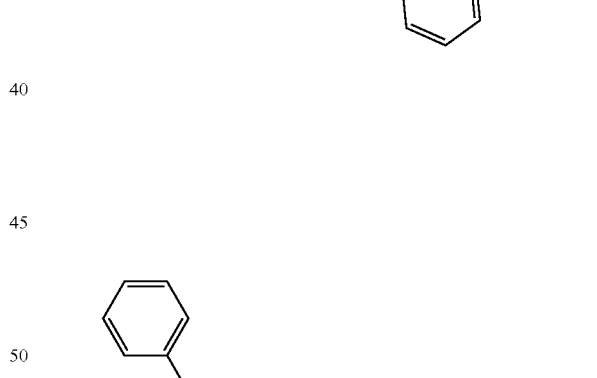
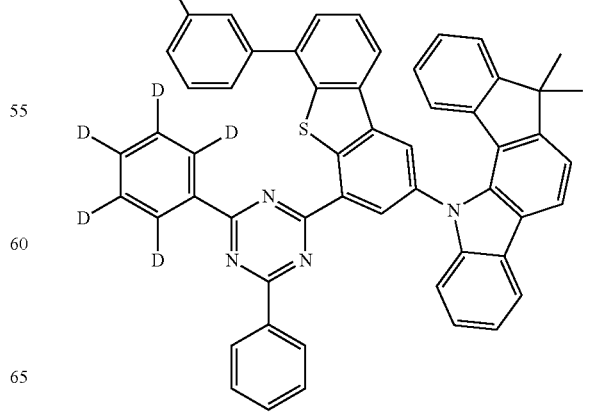

151
-continued
152
-continued
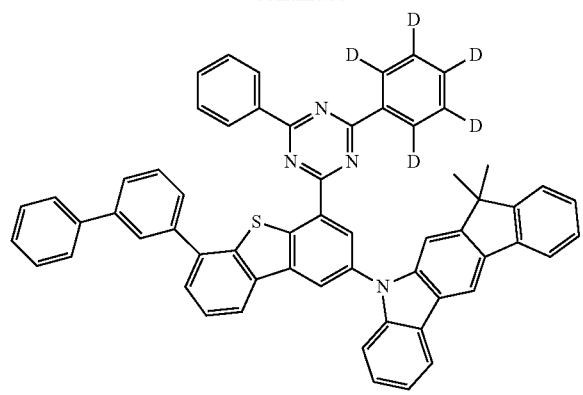
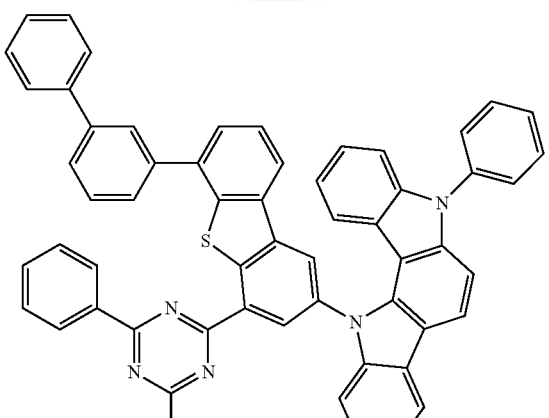
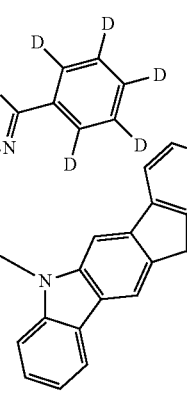
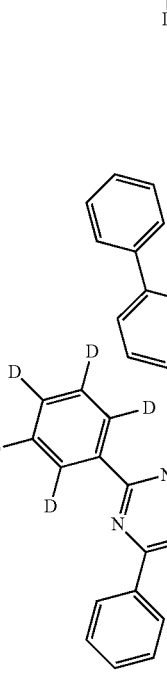
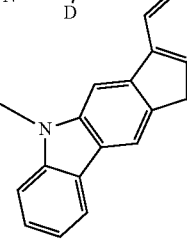
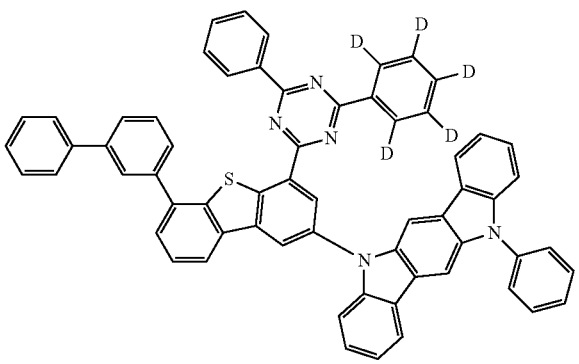

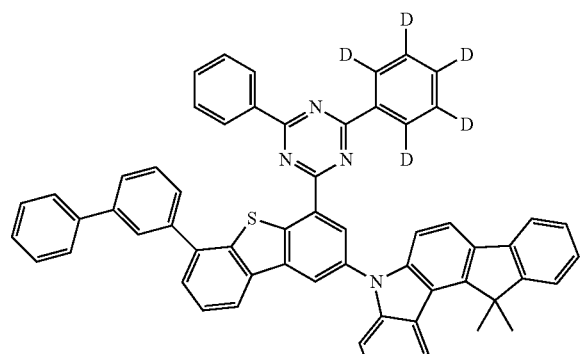
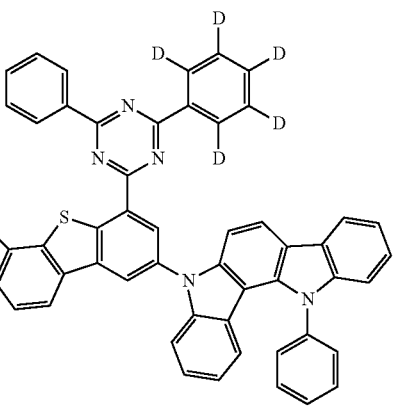
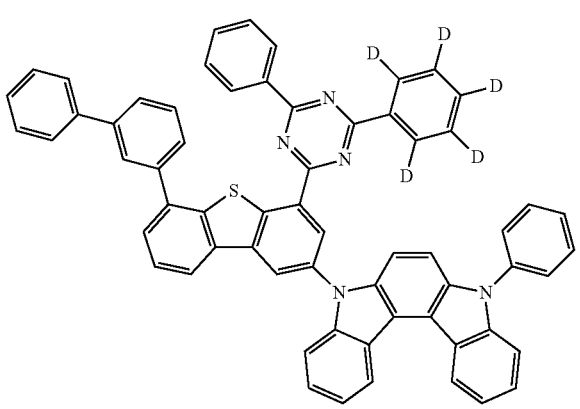
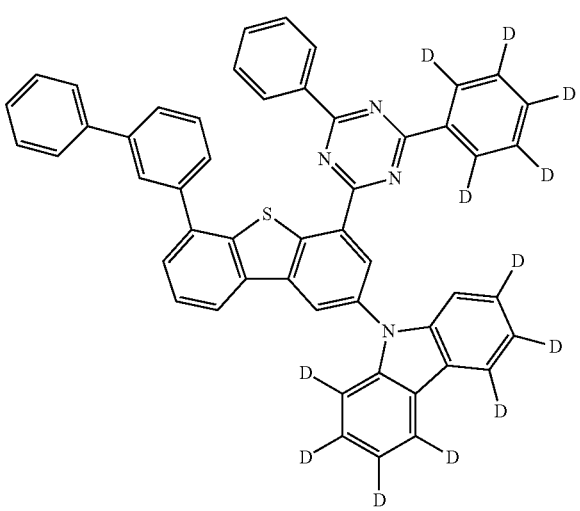

155
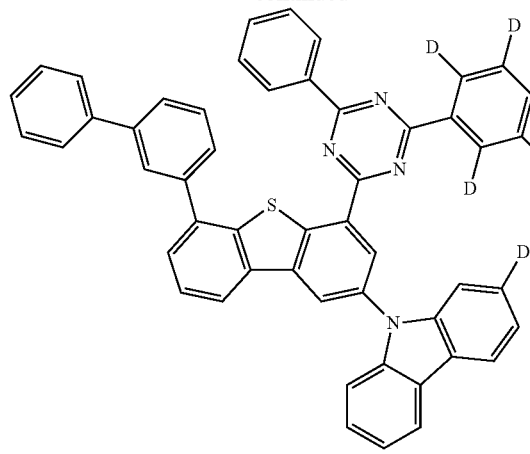
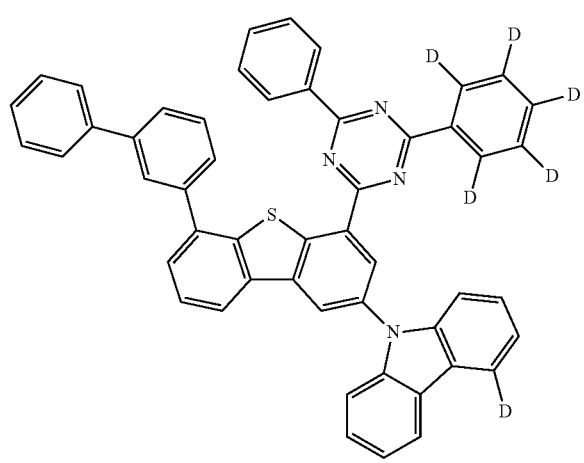
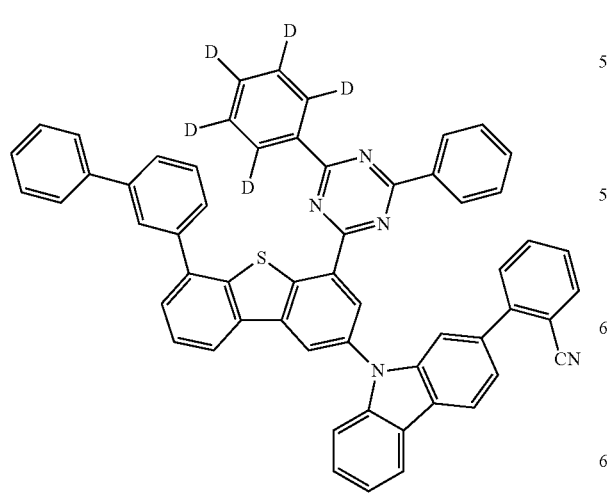
156
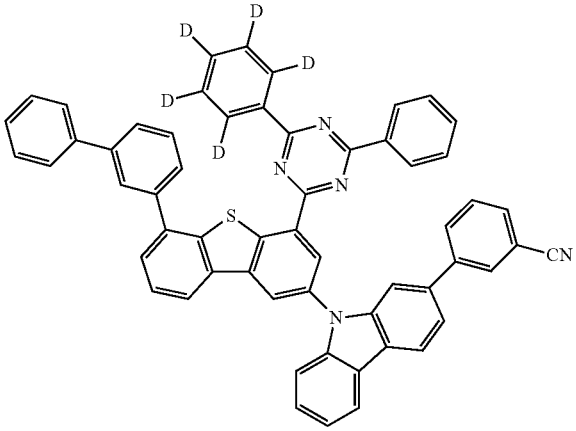
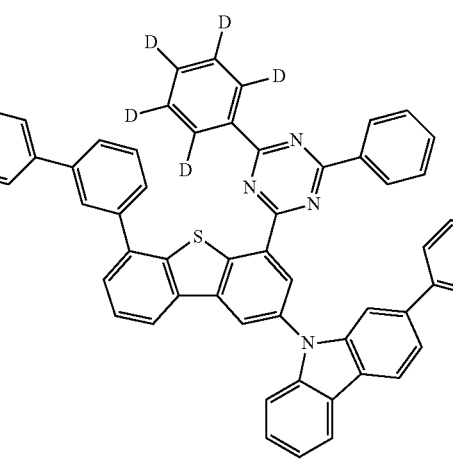
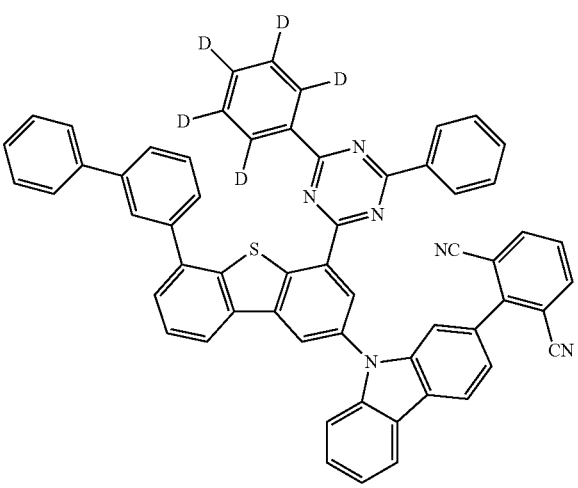

157
-continued
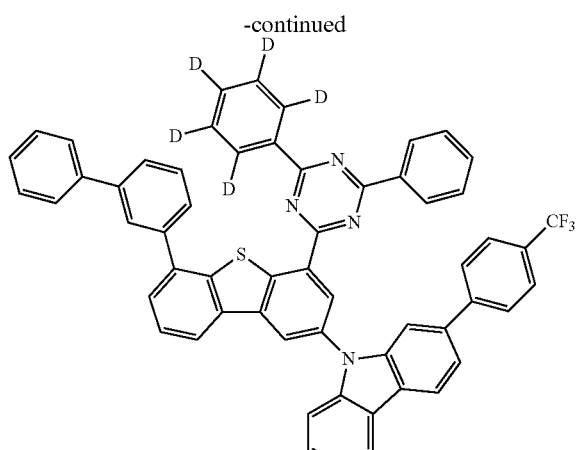
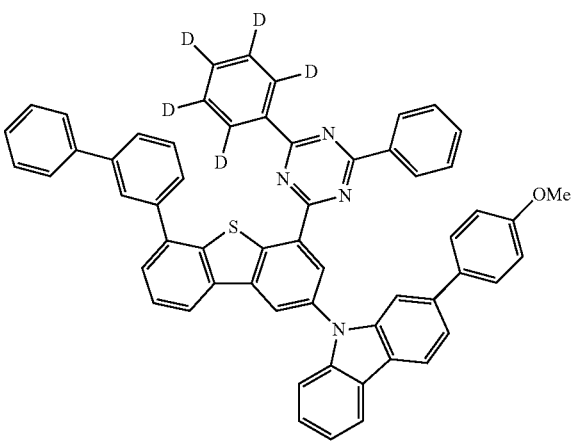
158
-continued
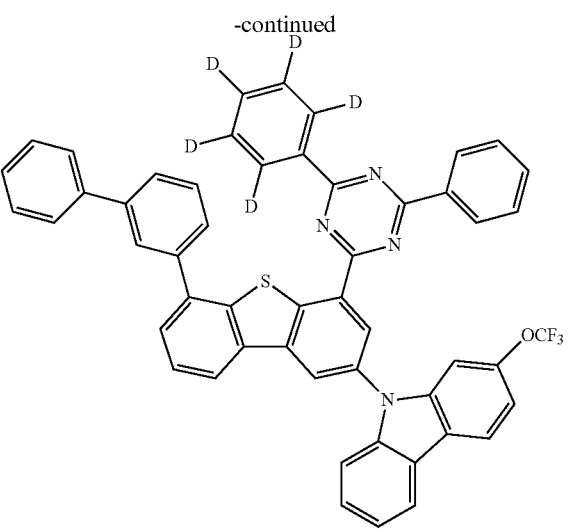
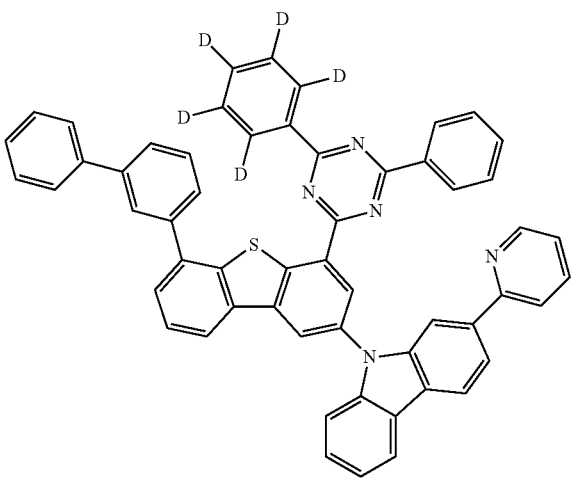

159
-continued
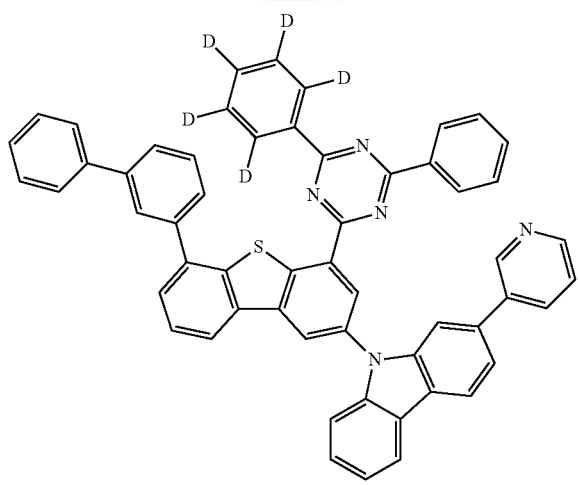
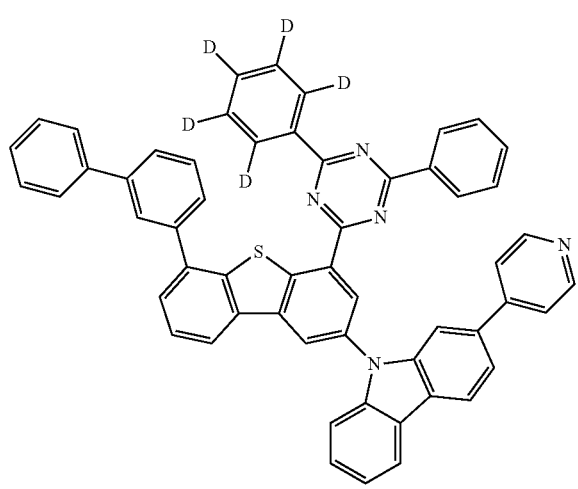
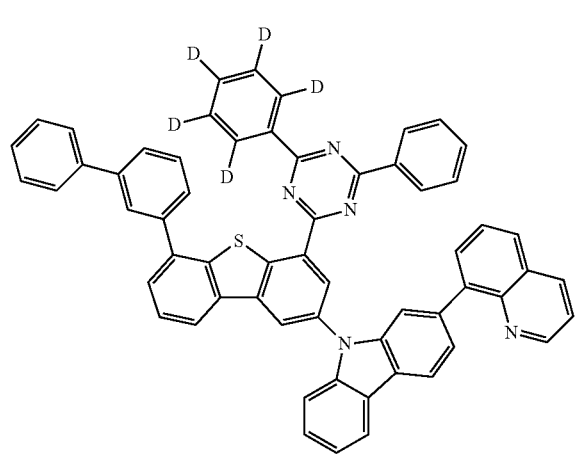
160
-continued
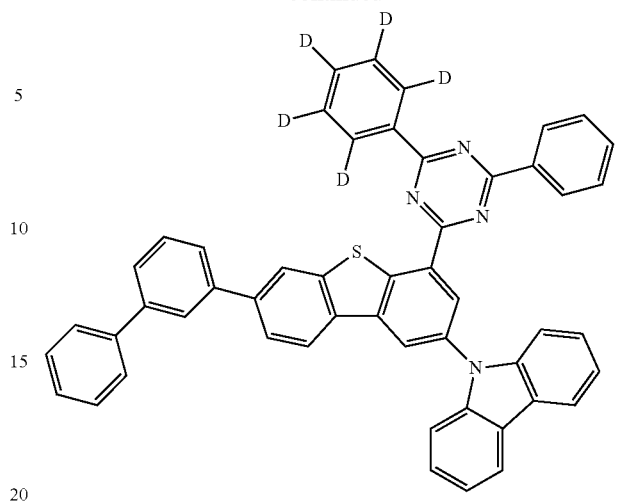
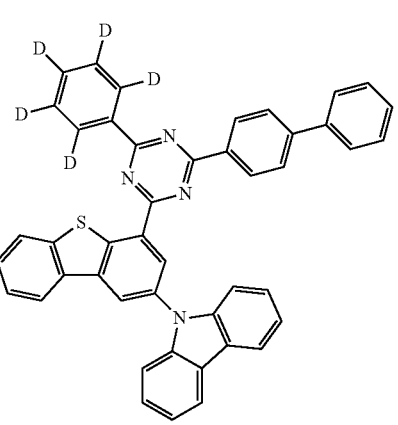
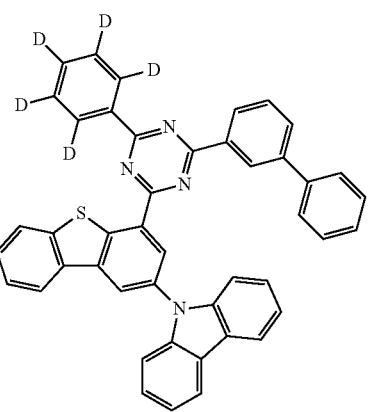

161
-continued
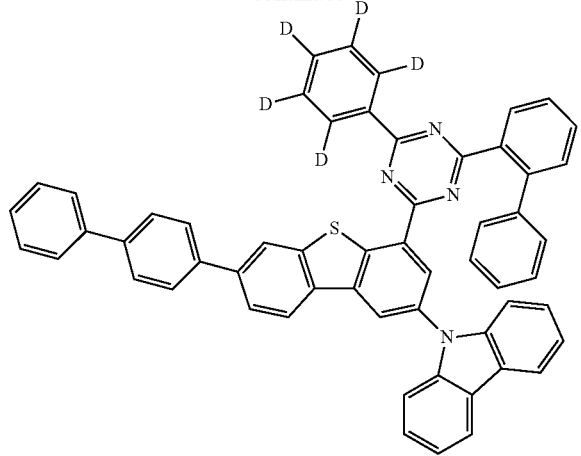
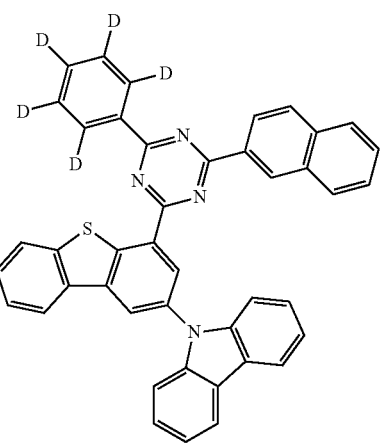
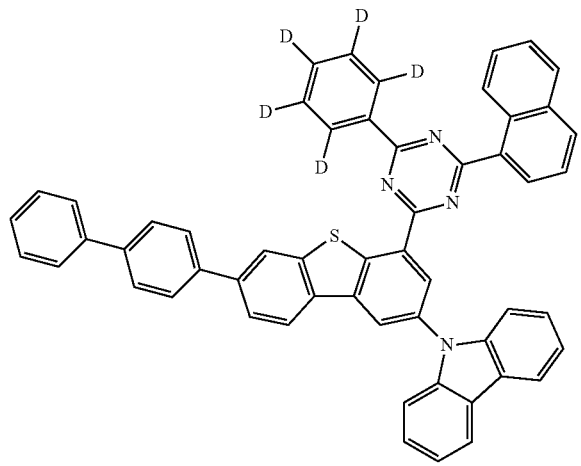
162
-continued
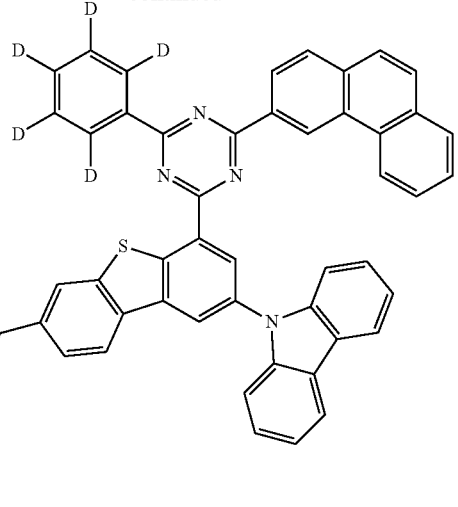
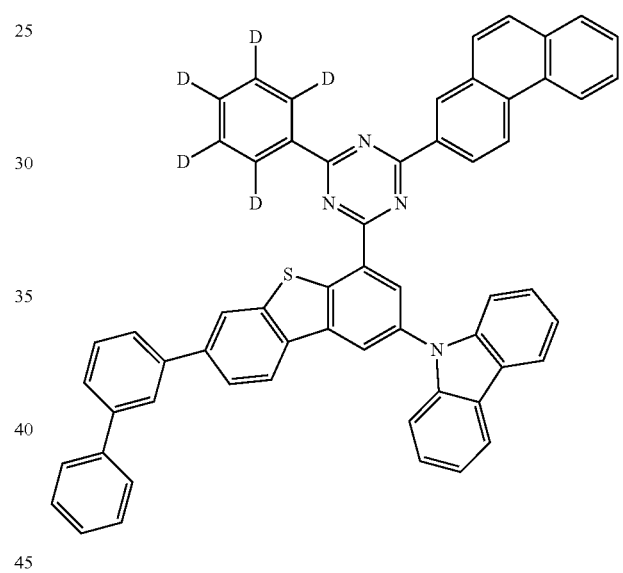
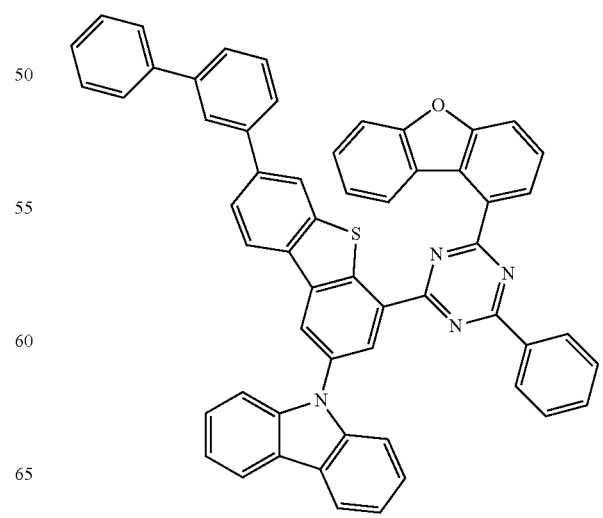

163
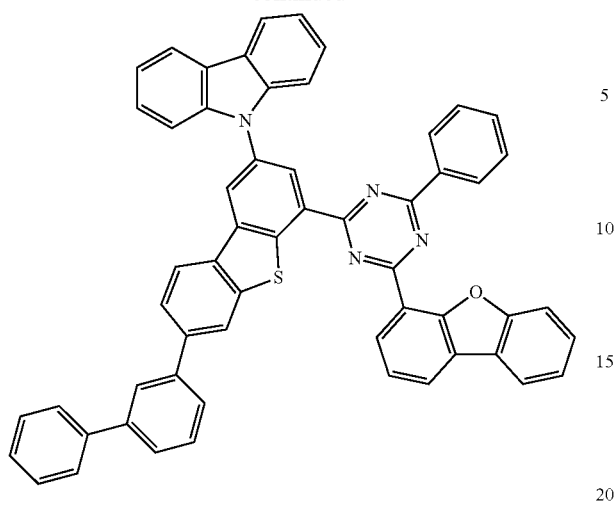
164
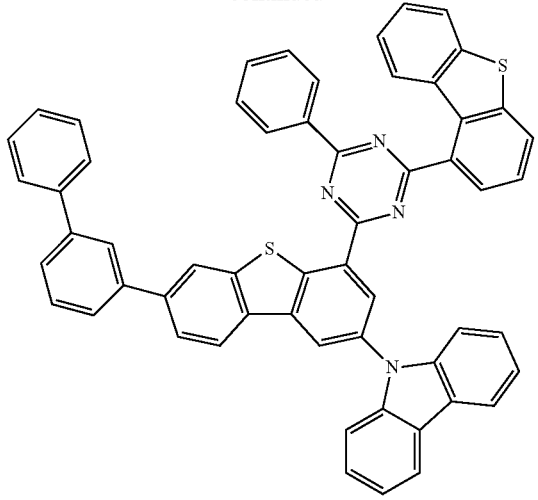
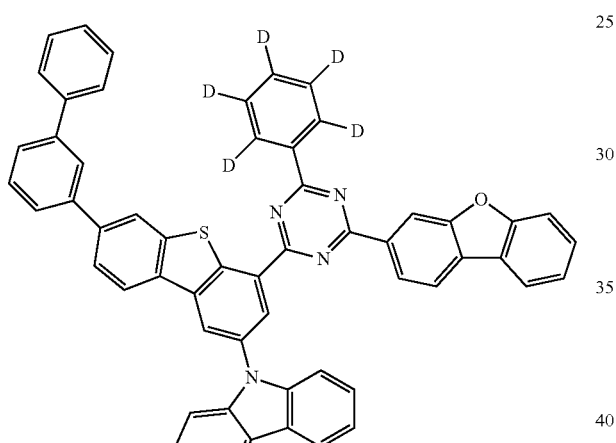
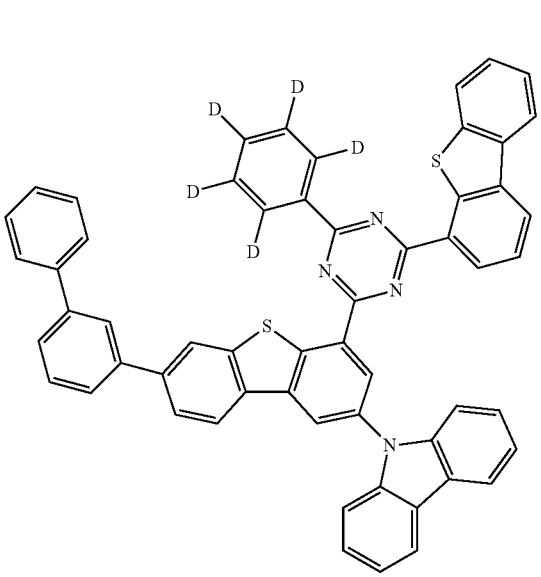
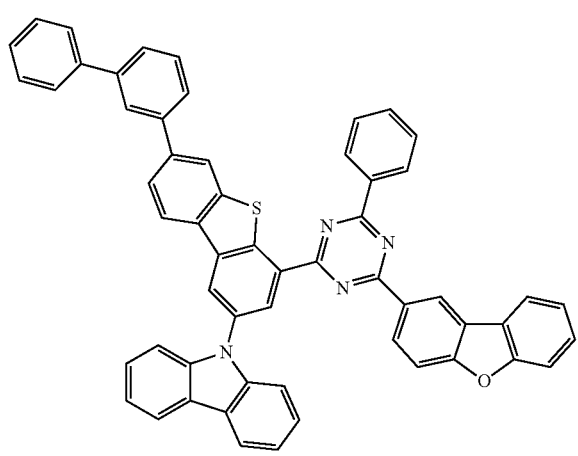
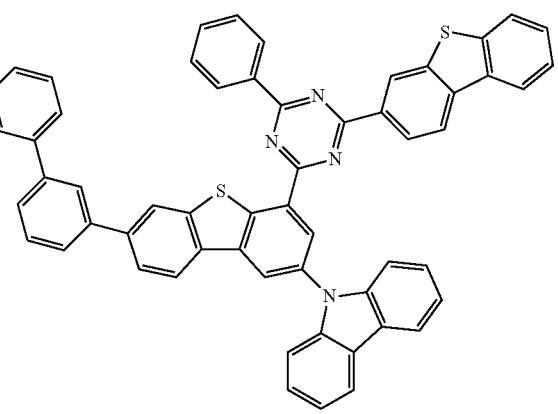

165
-continued
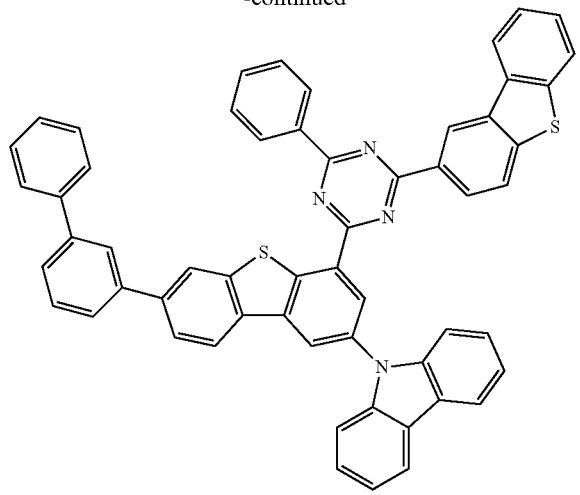
166
-continued
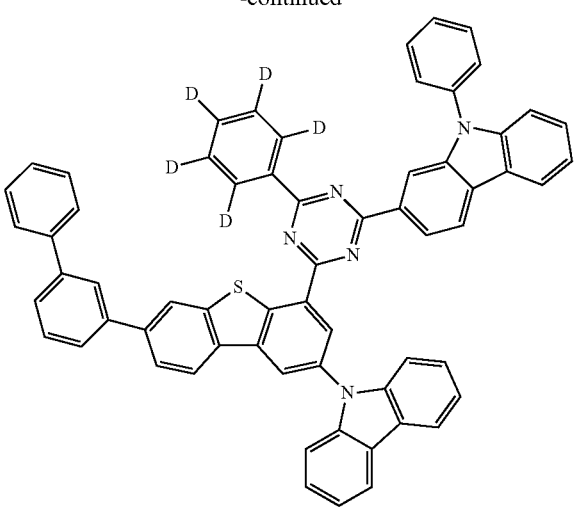
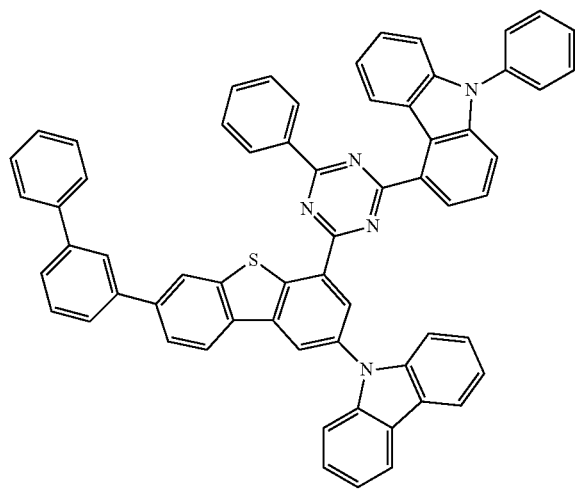
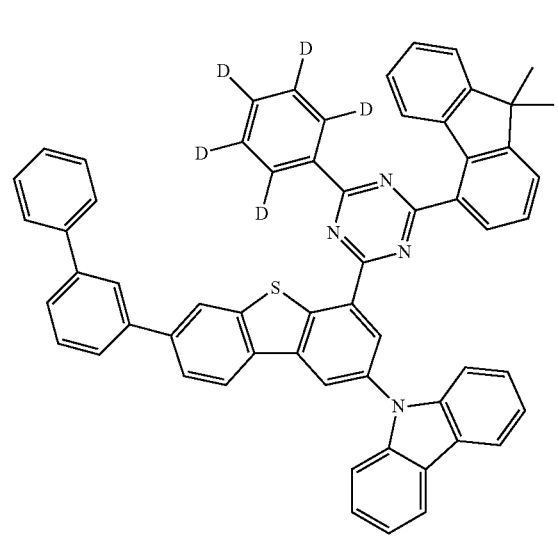
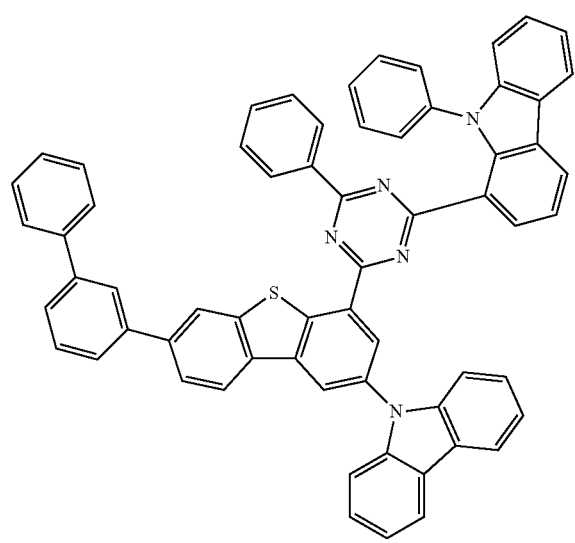

167
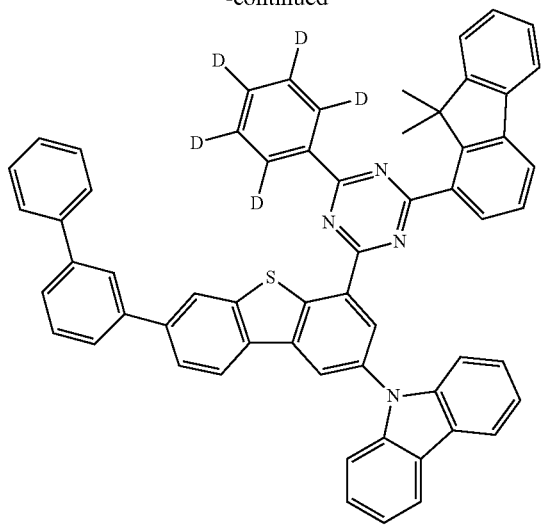
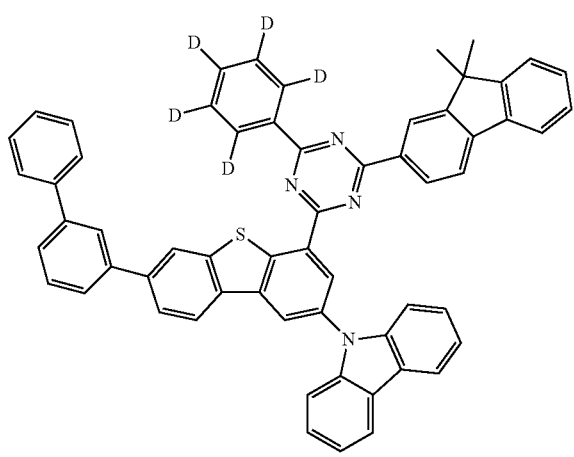
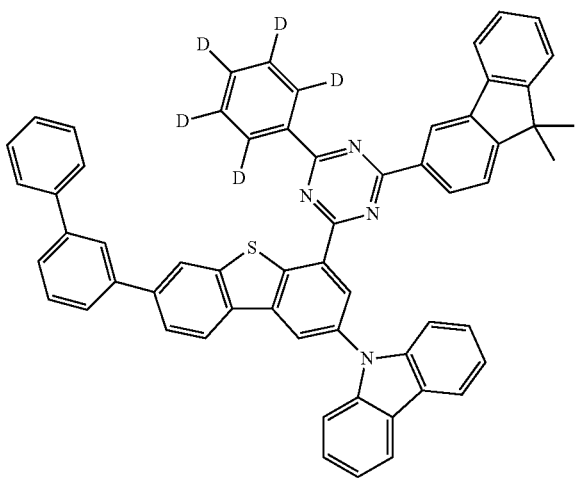
168
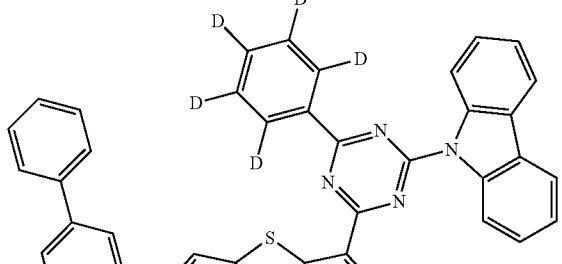
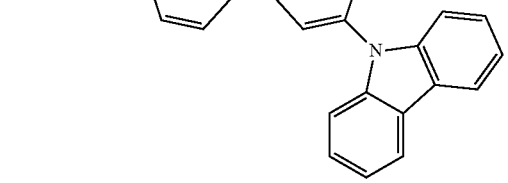
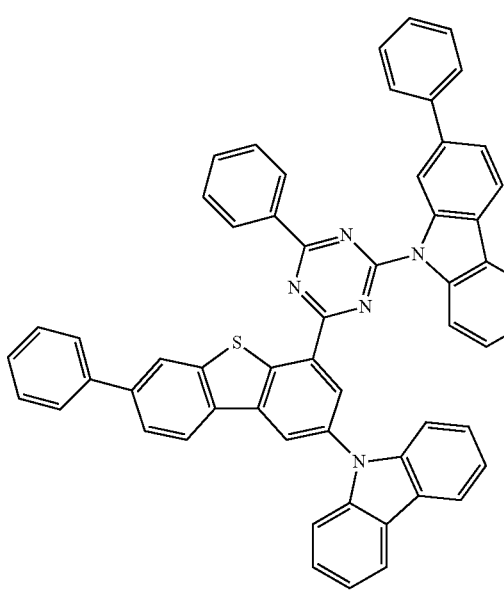
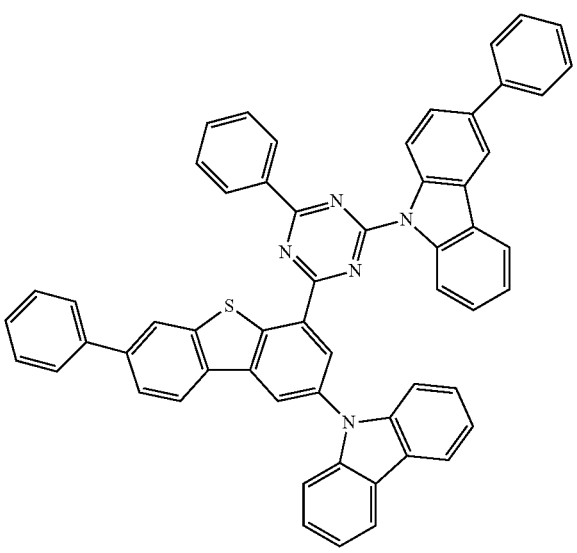

169
-continued
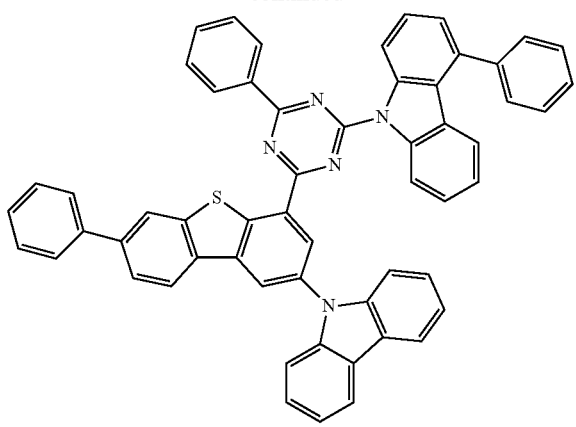
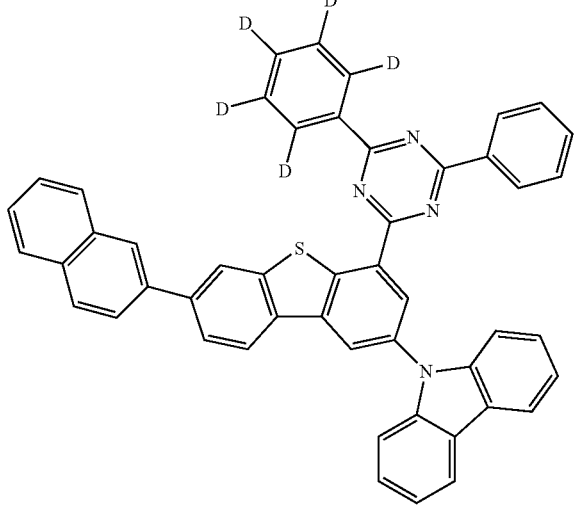
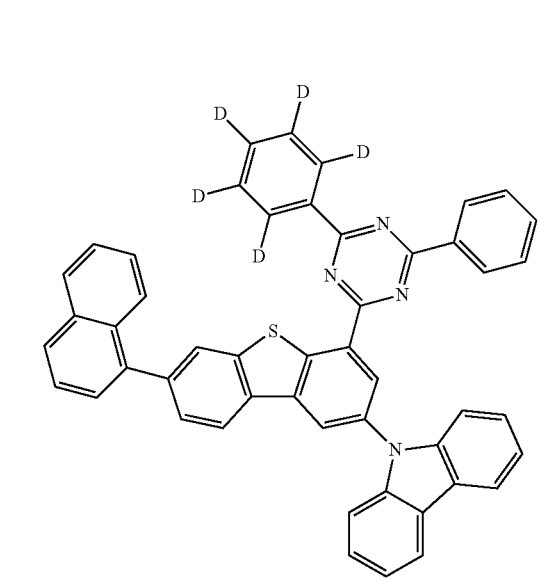
170
-continued
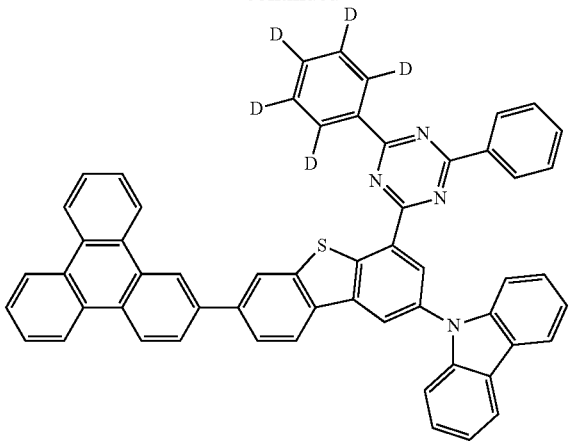
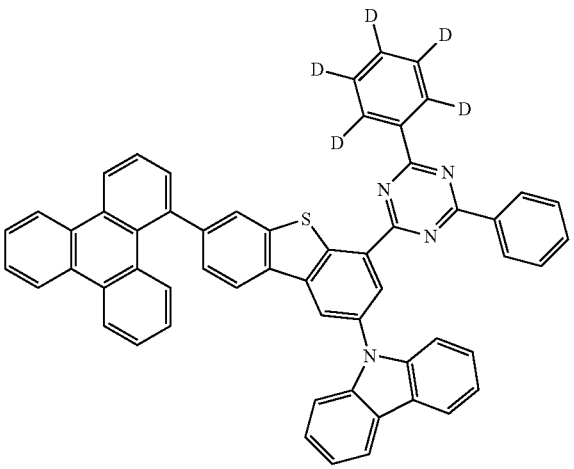
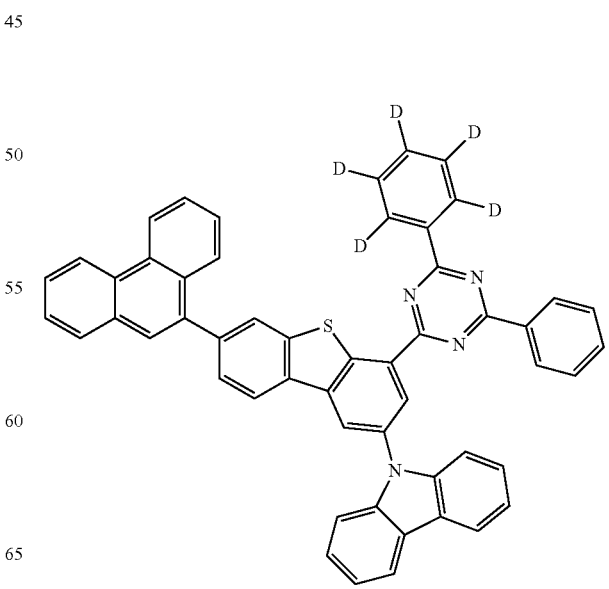

-continued
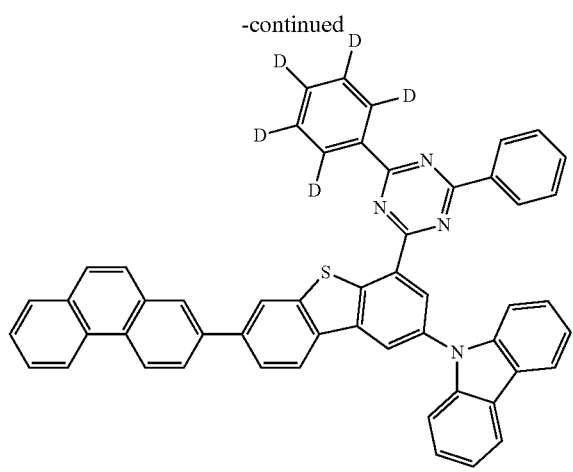
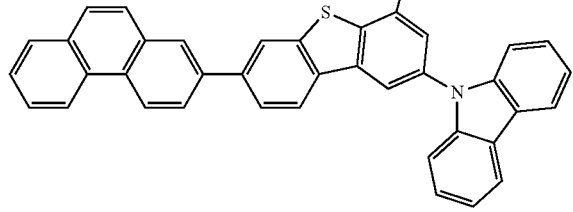
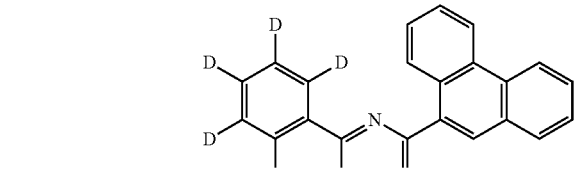
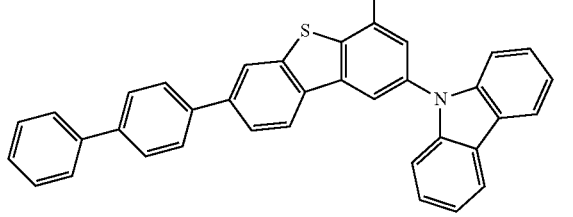
-continued
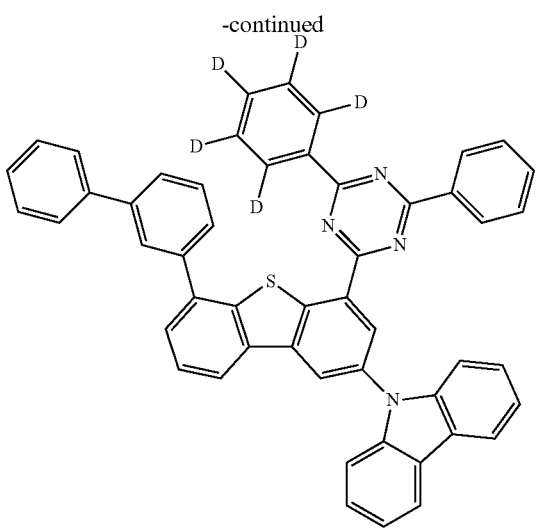
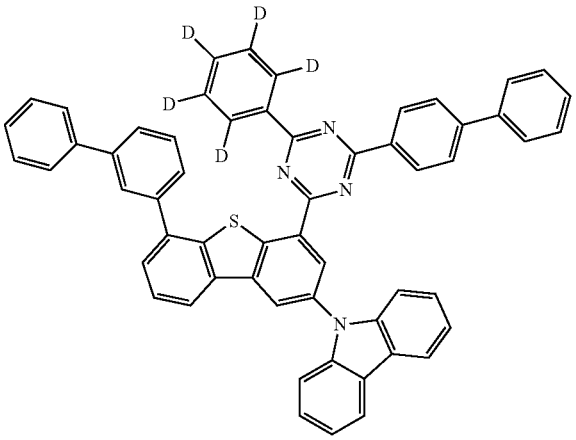
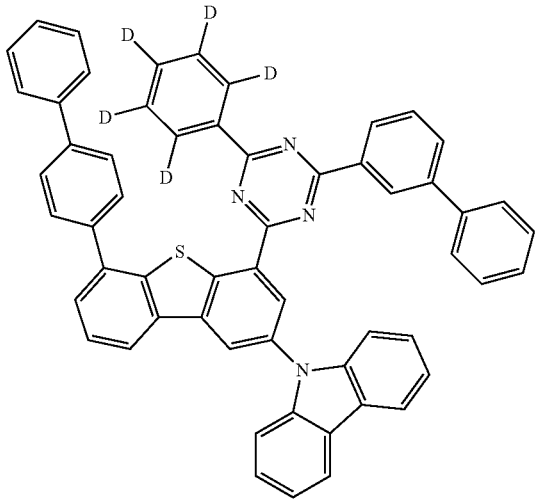

173
-continued
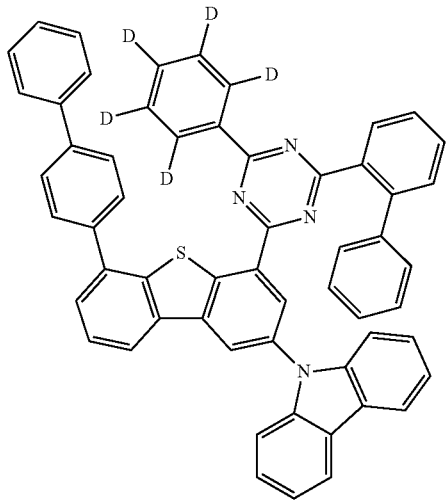
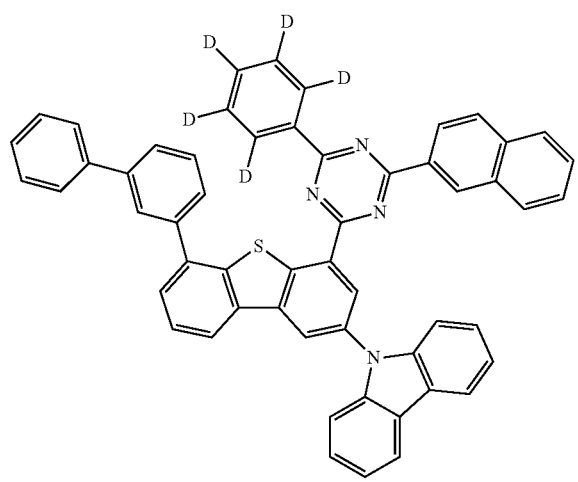
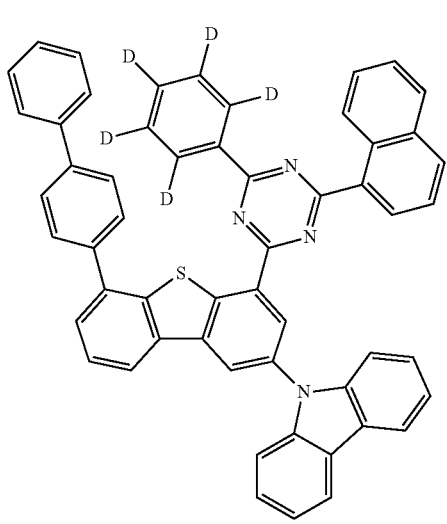
174
-continued
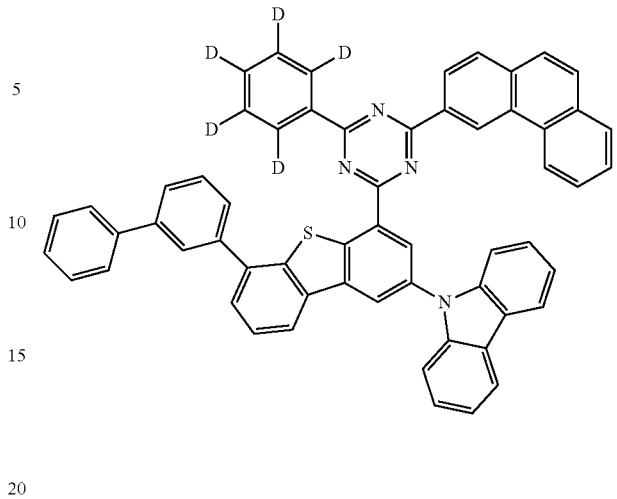
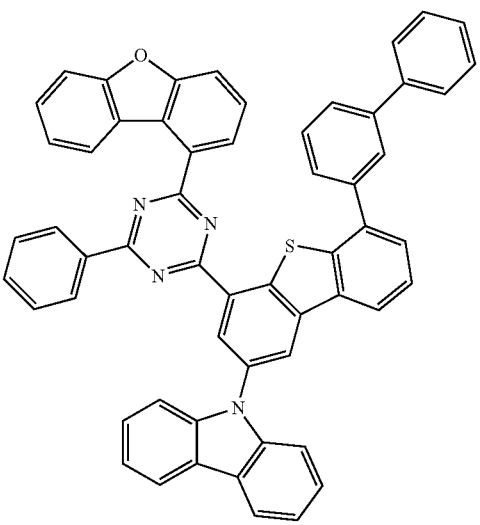

175
-continued
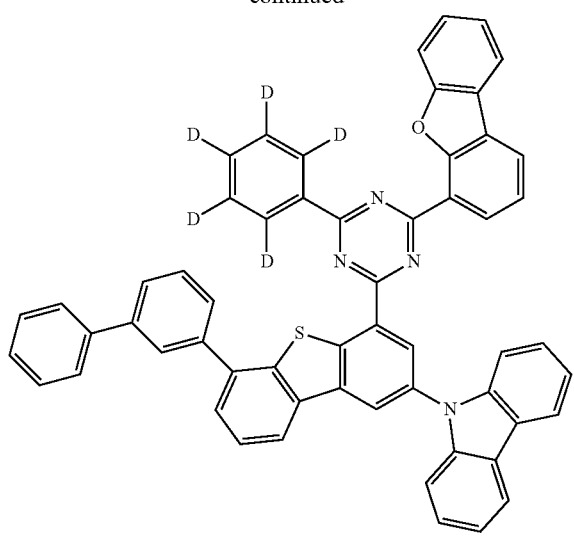
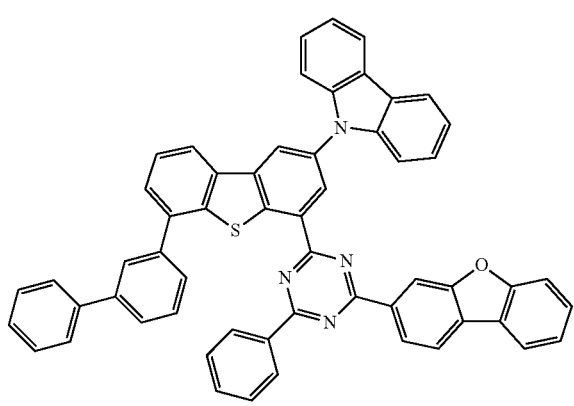
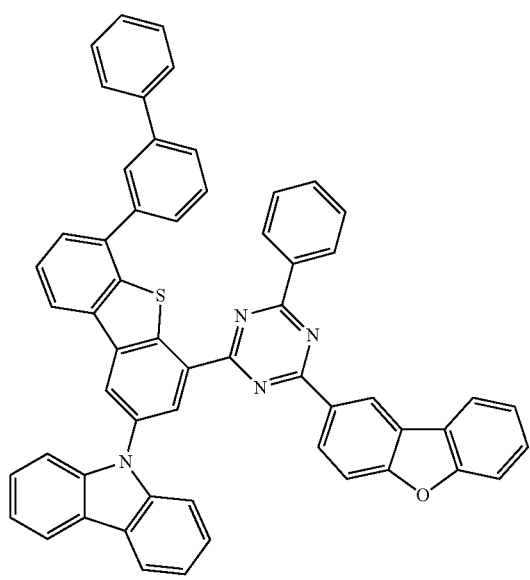
176
-continued
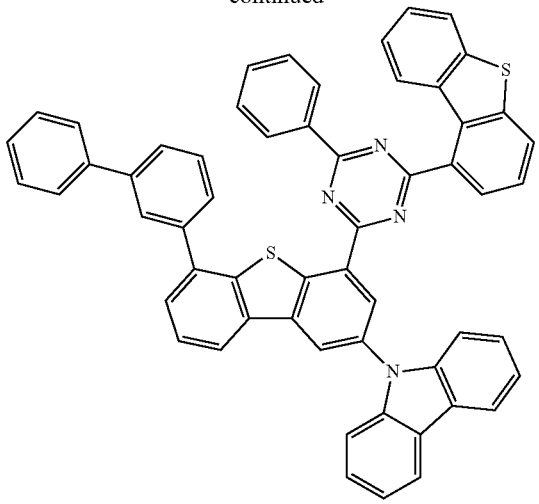
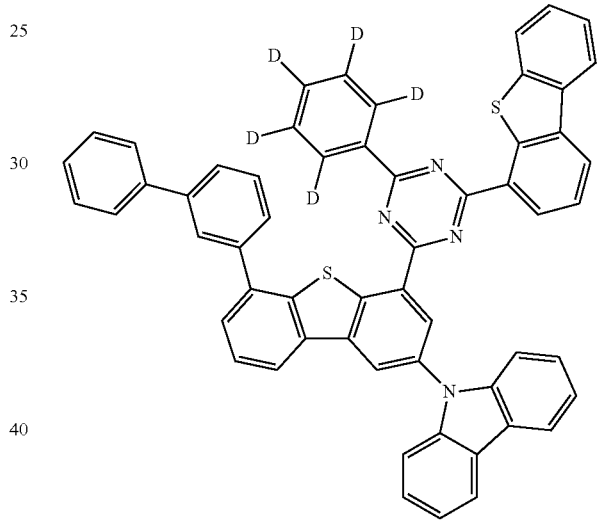
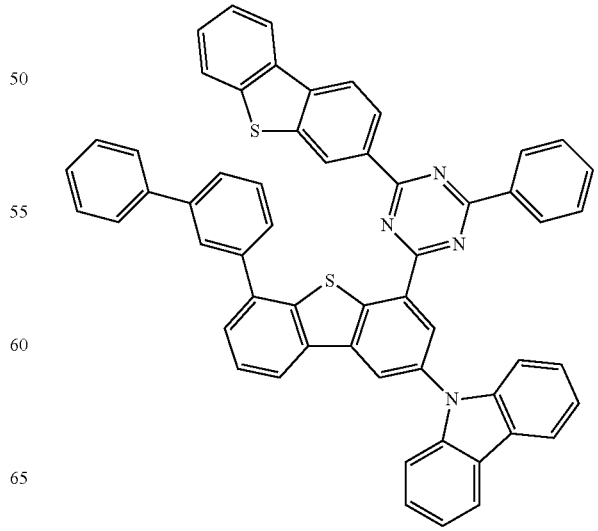

177
-continued
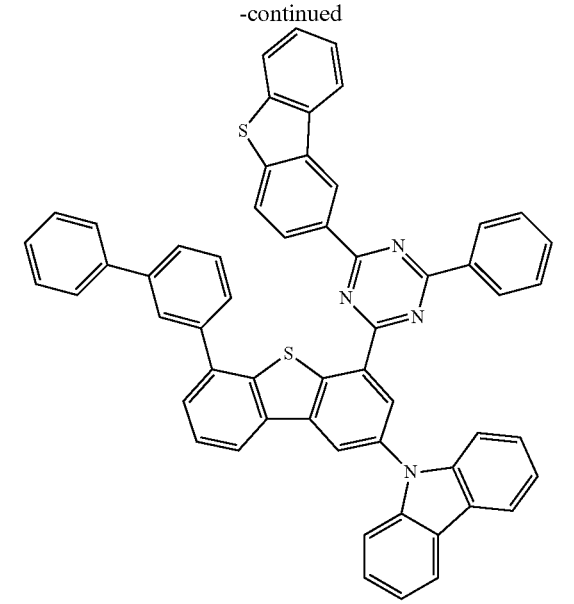
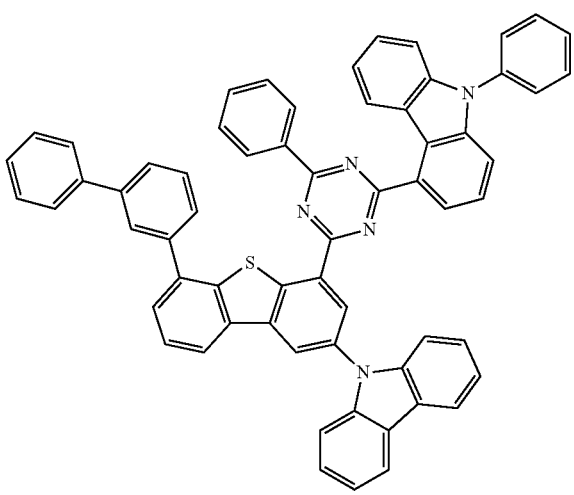
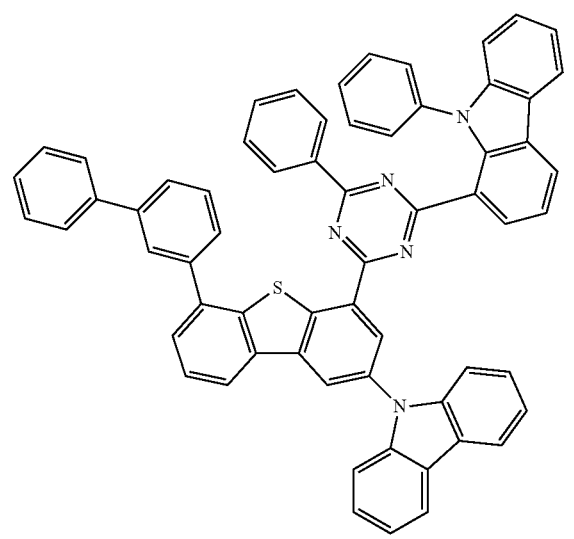
178
-continued
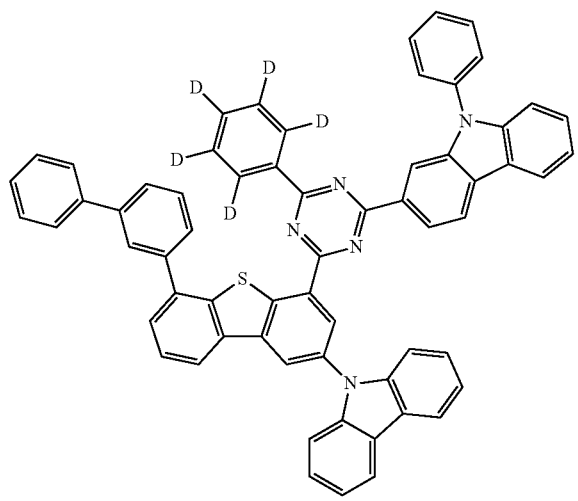
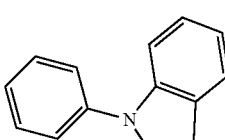
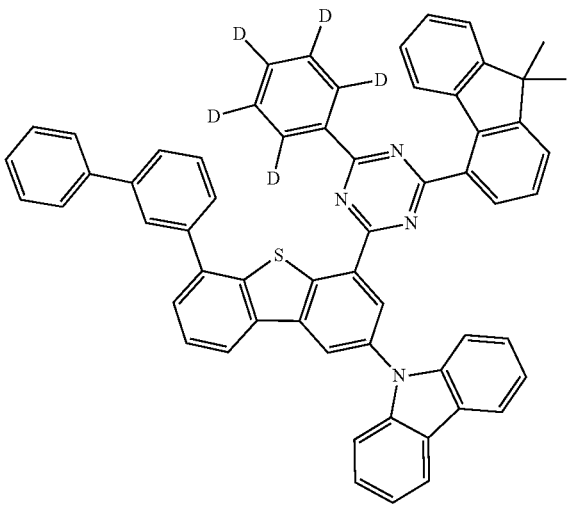

179
-continued
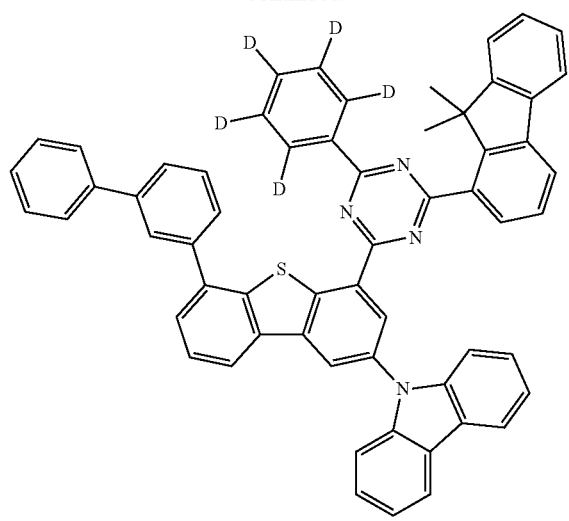
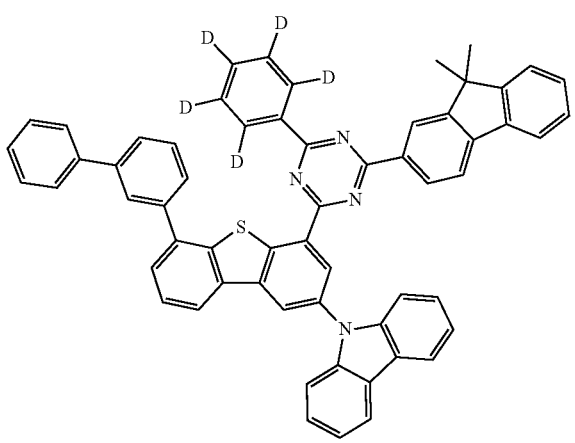
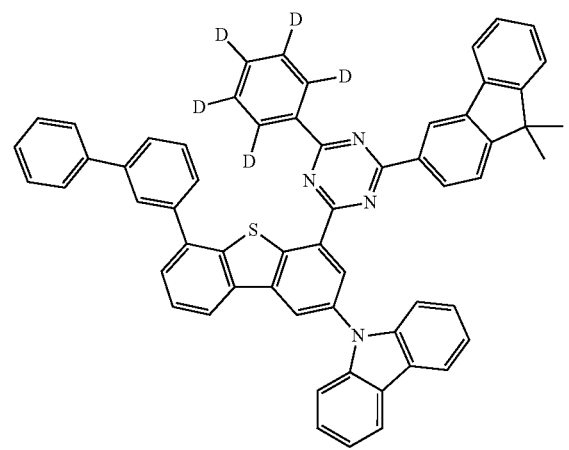
180
-continued
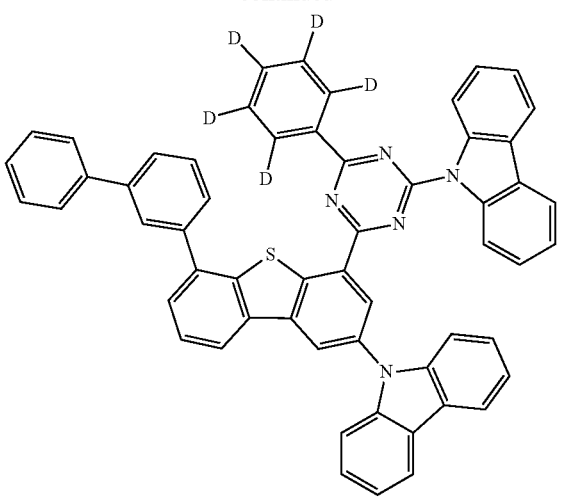
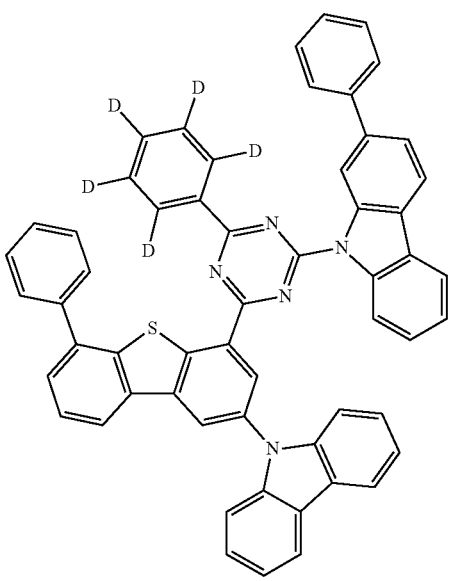

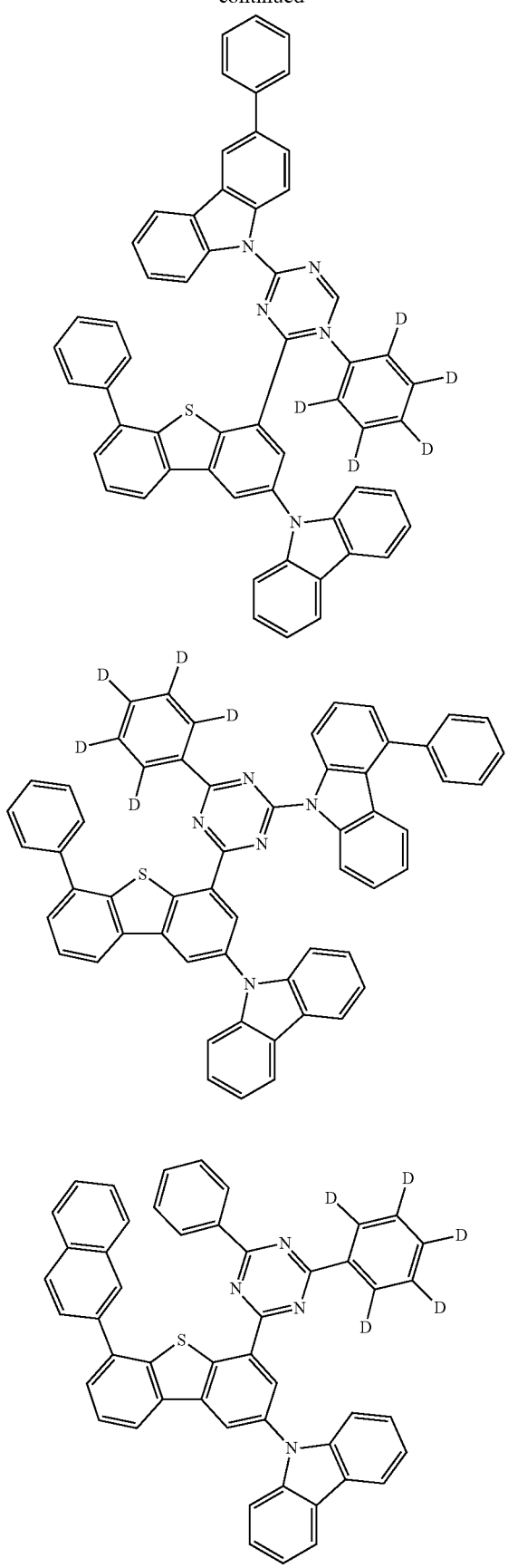
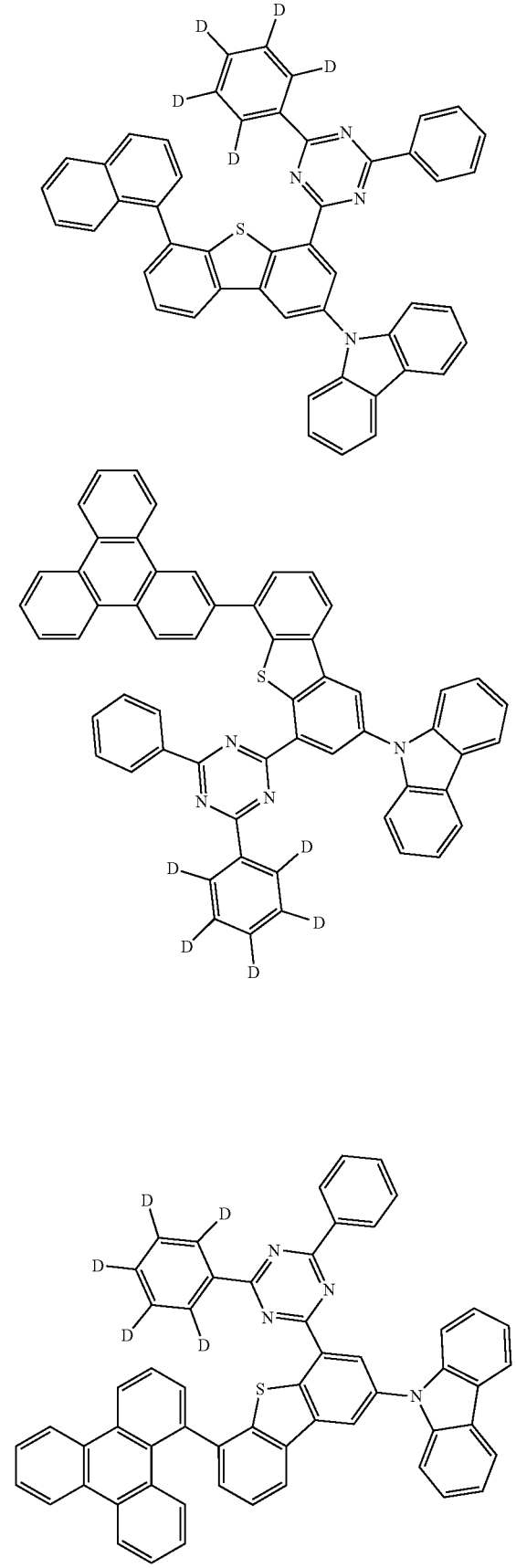

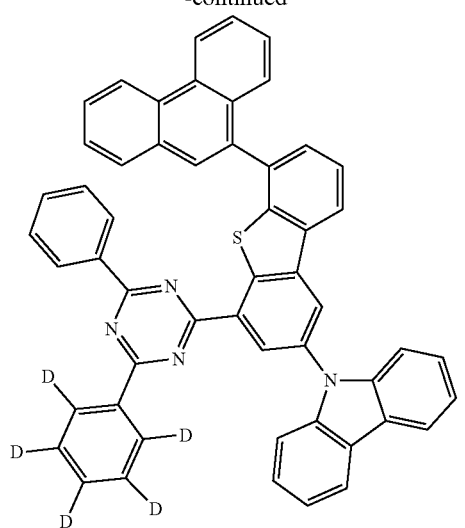
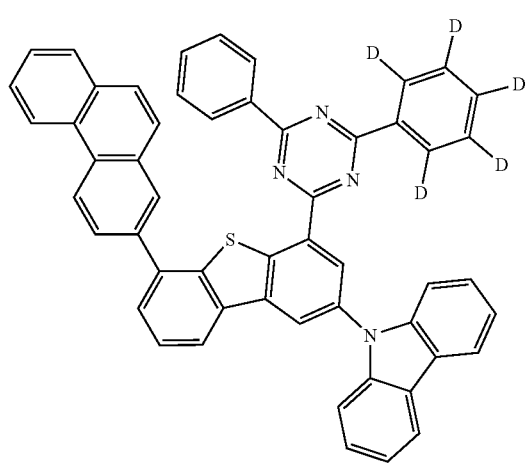
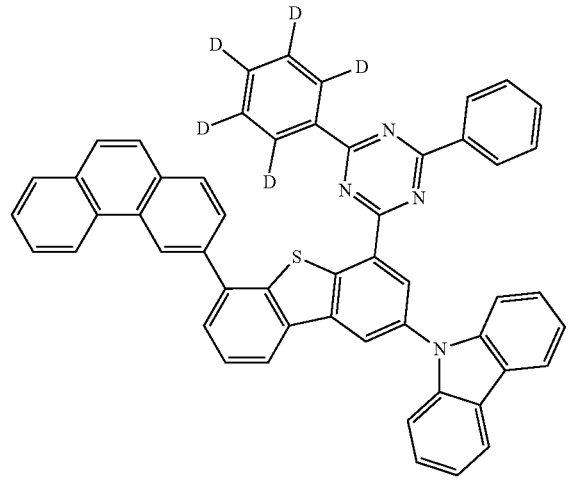
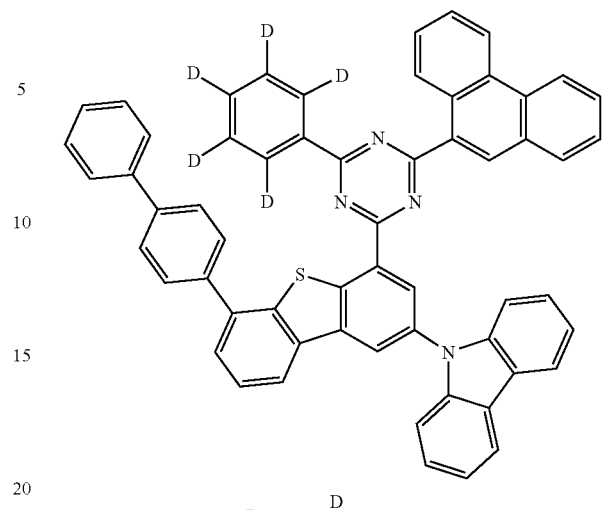
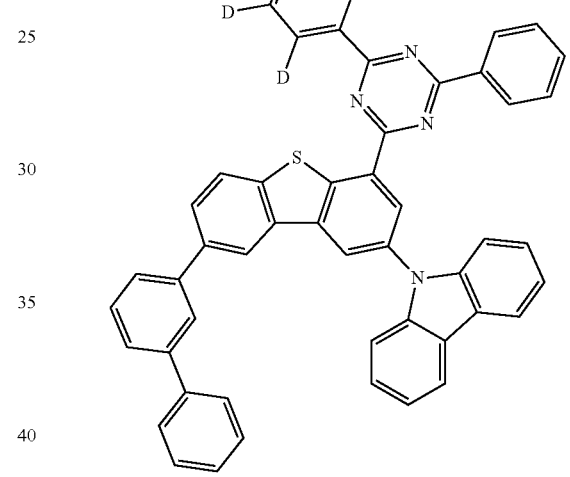
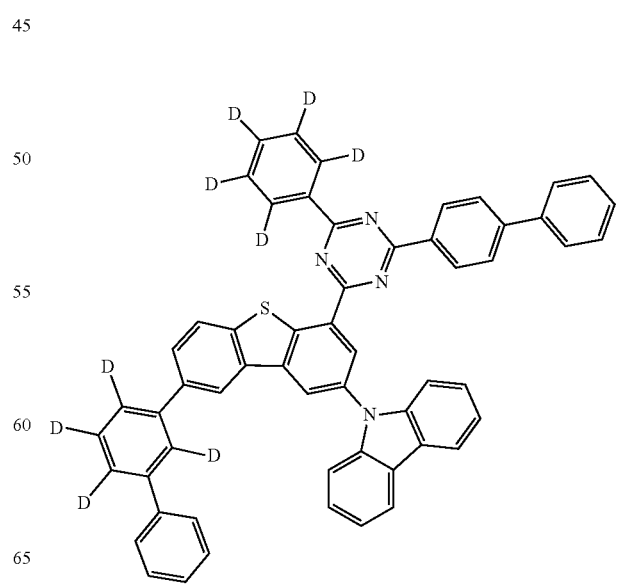

185
-continued
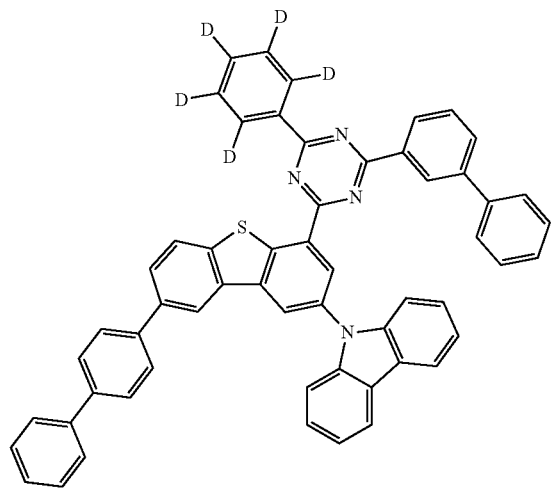
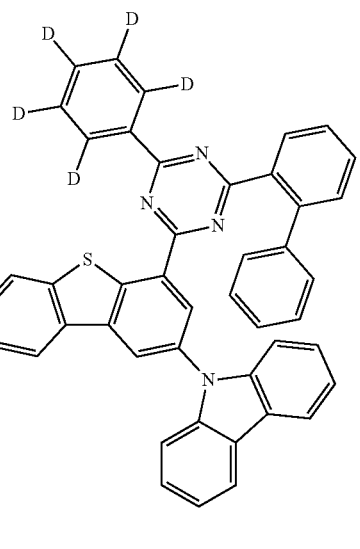
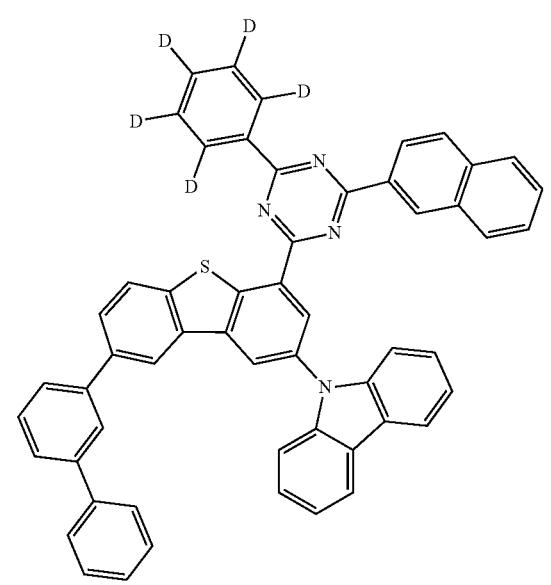
186
-continued
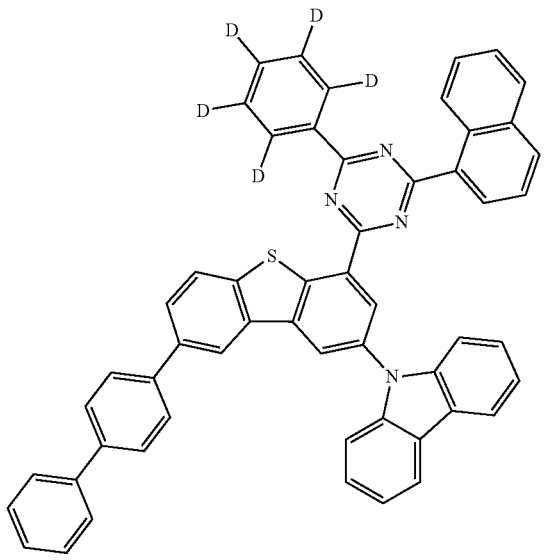
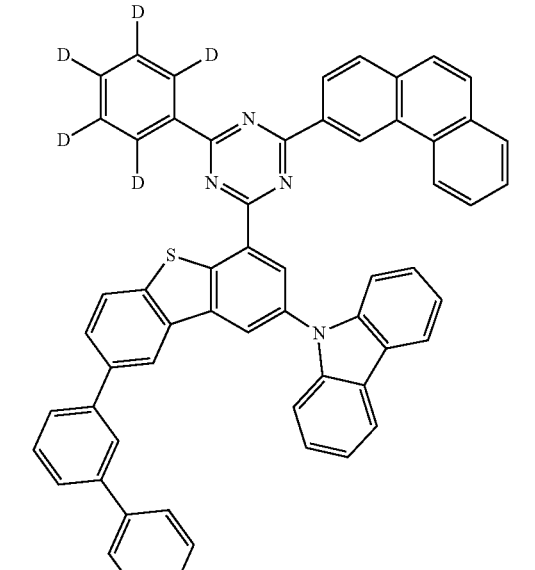

187
-continued
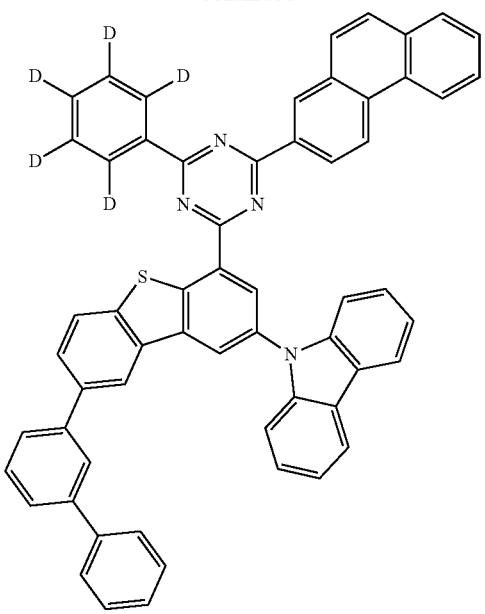
188
-continued
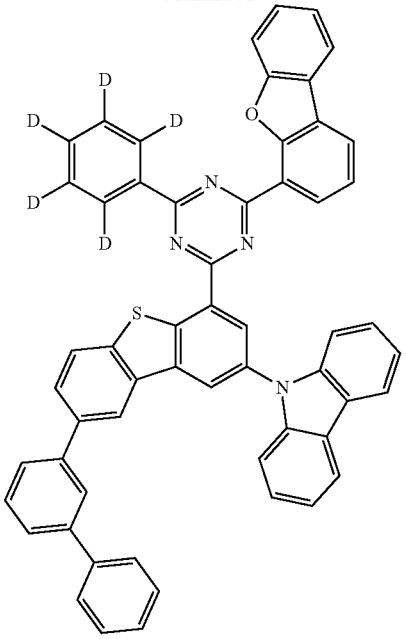
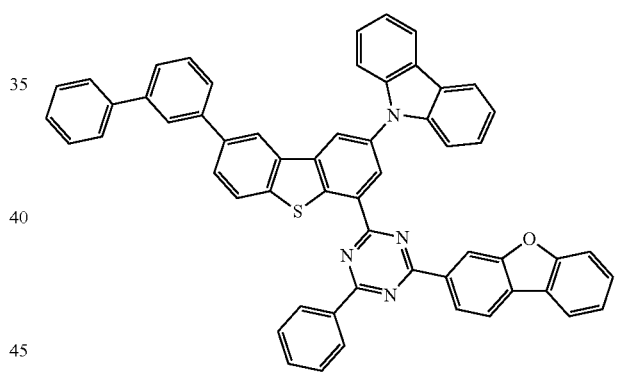
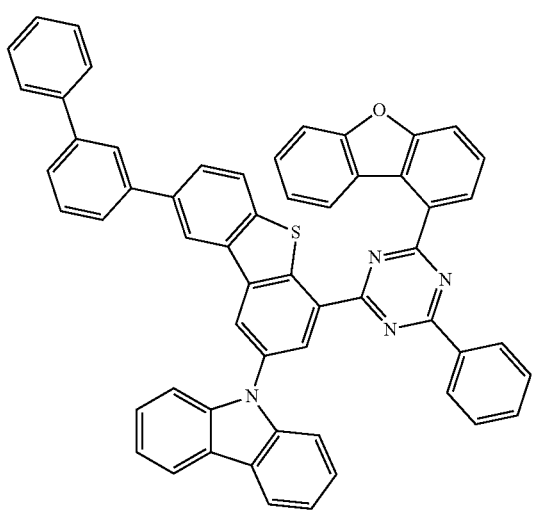
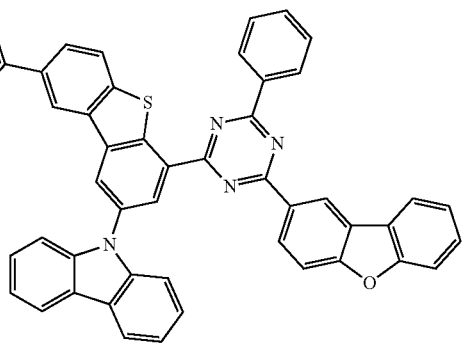

189
-continued
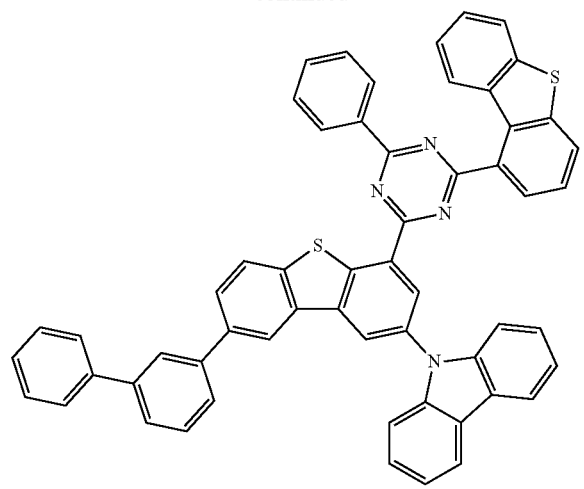
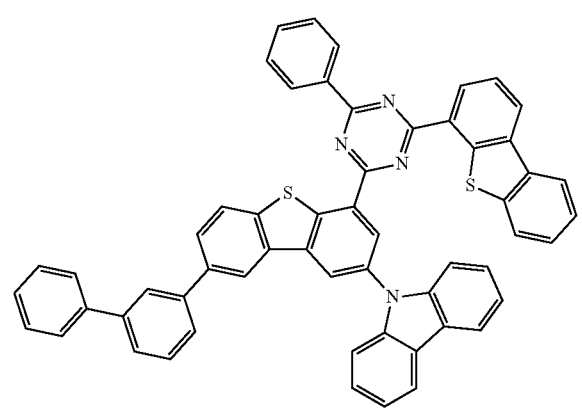
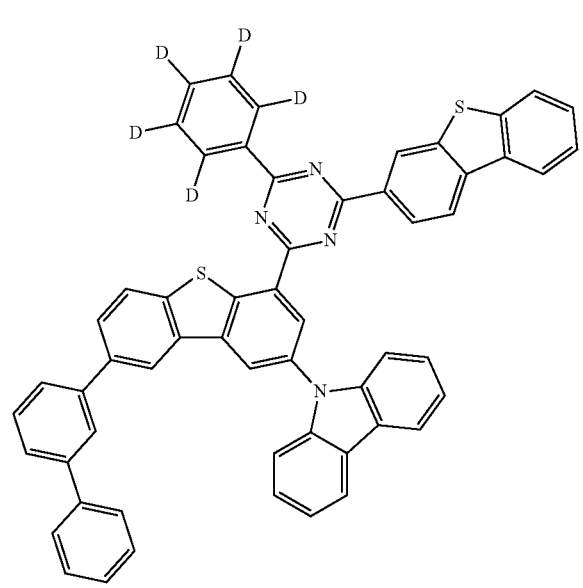
190
-continued
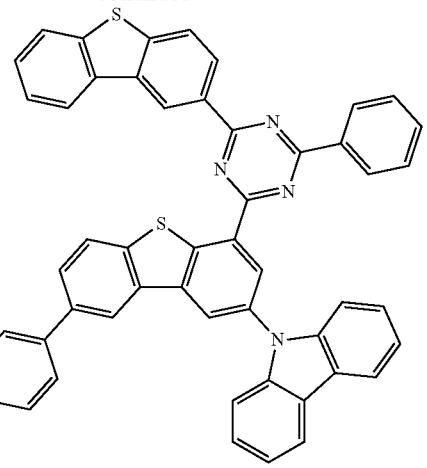
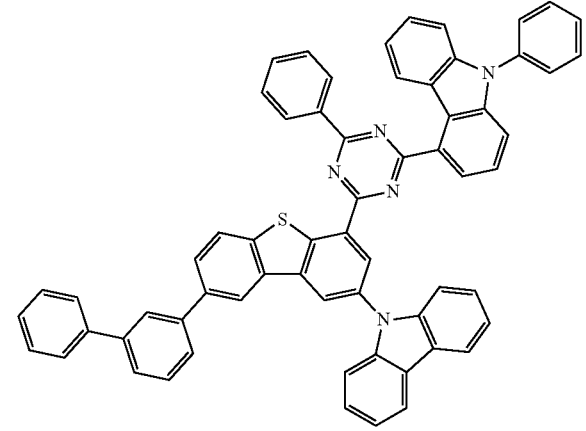
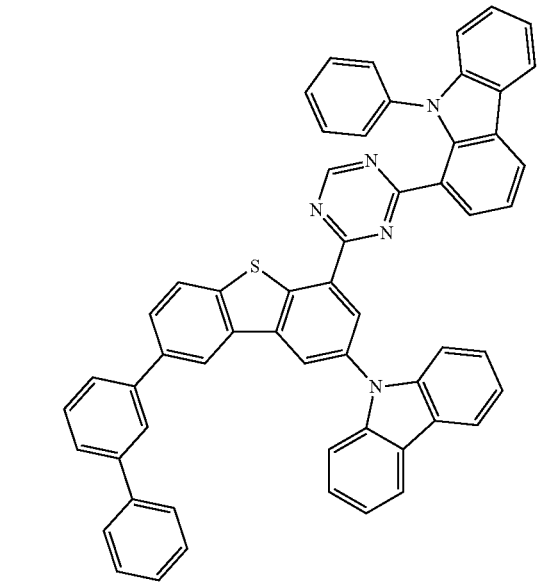

191
-continued
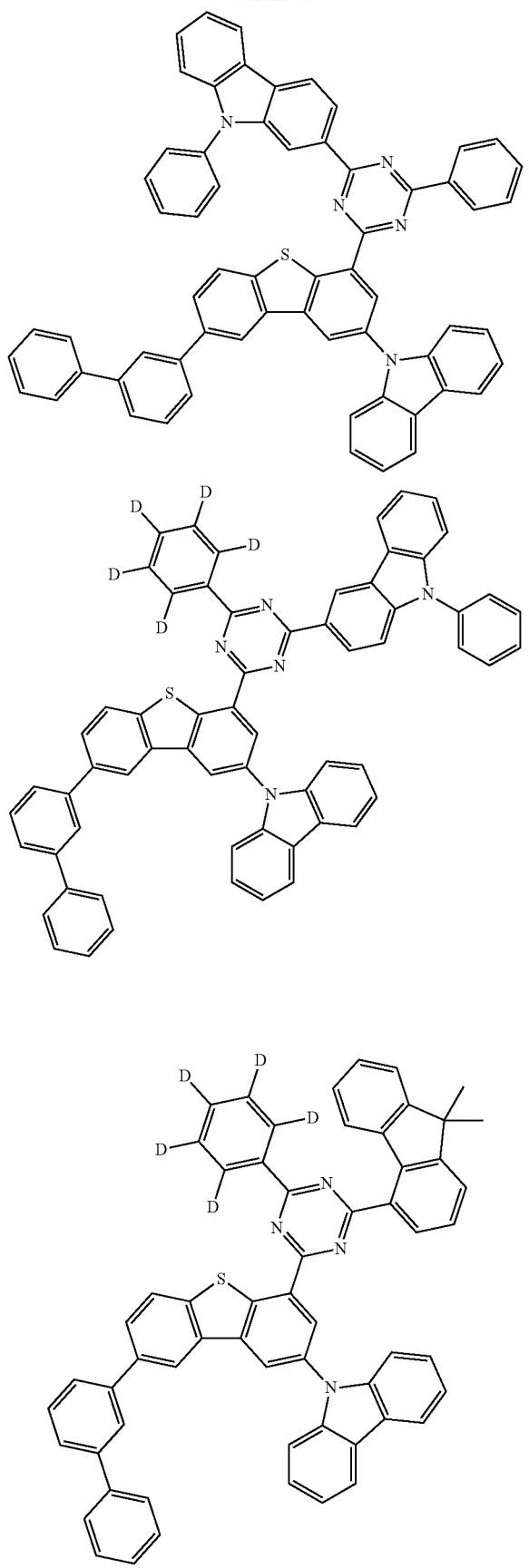
192
-continued
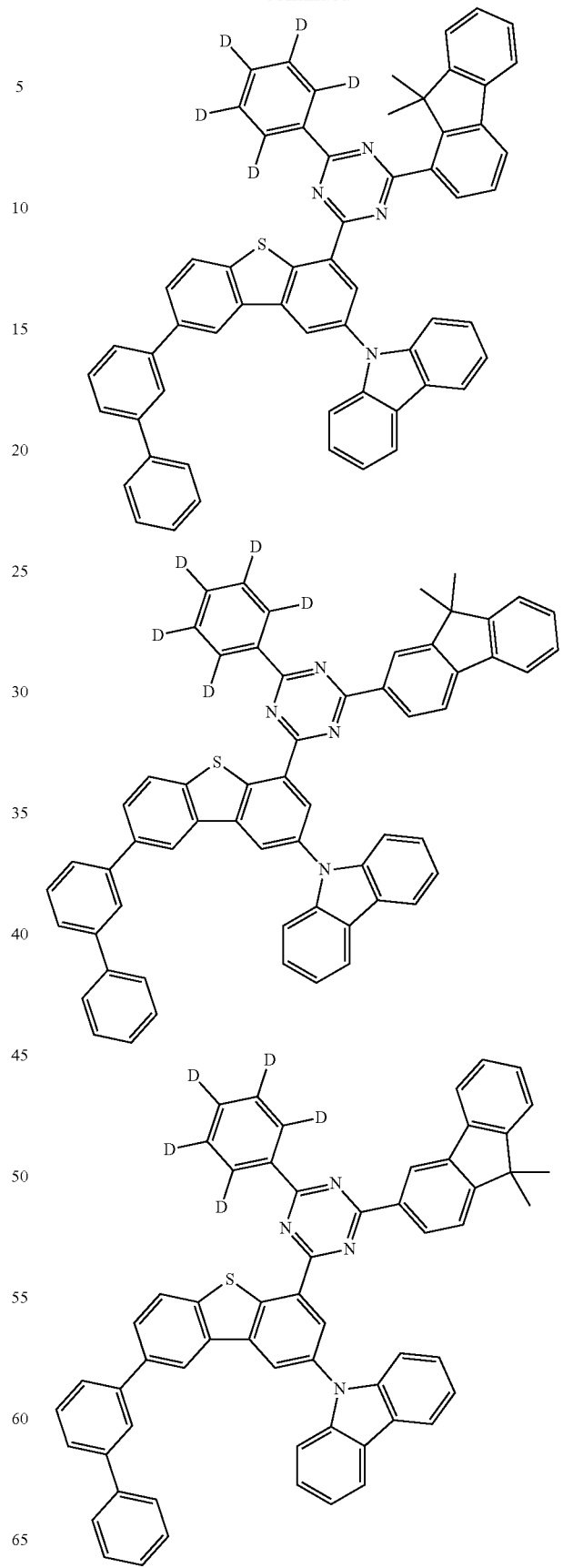

193
-continued
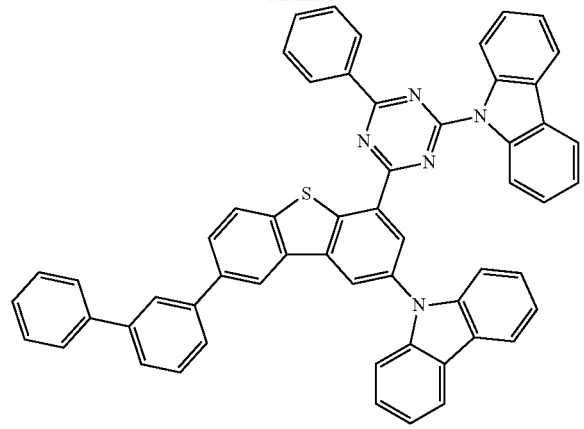
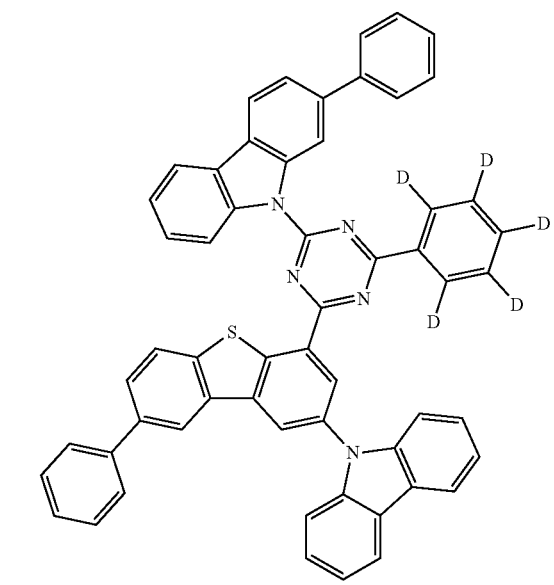
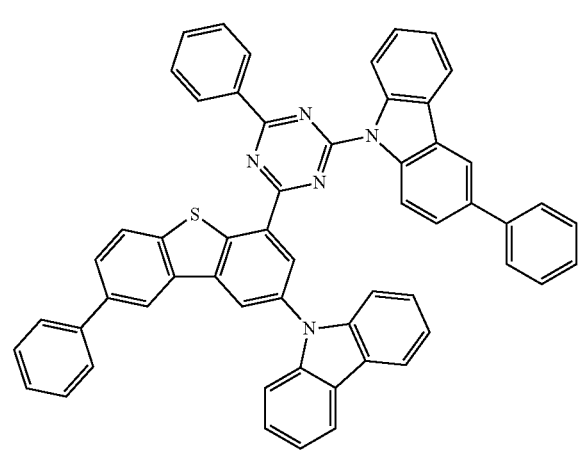
194
-continued
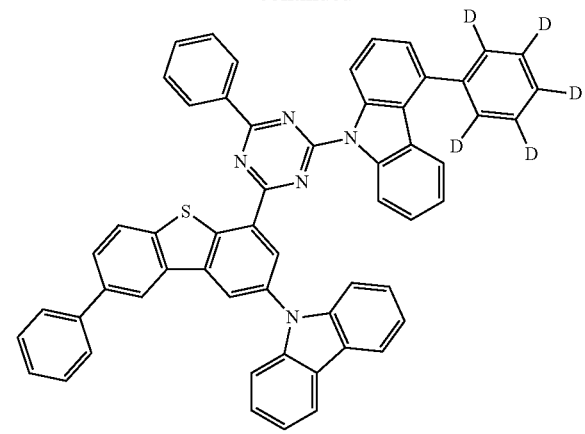
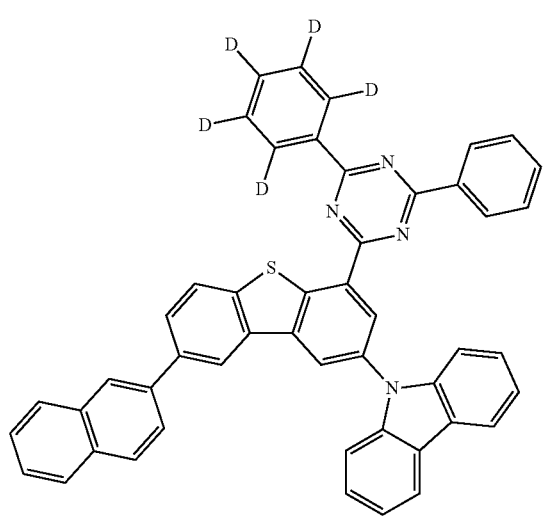
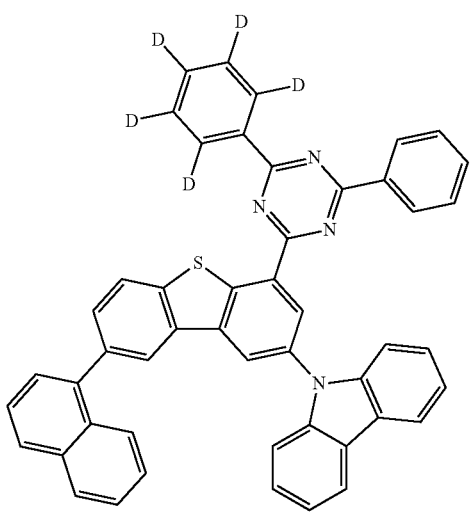

195
-continued
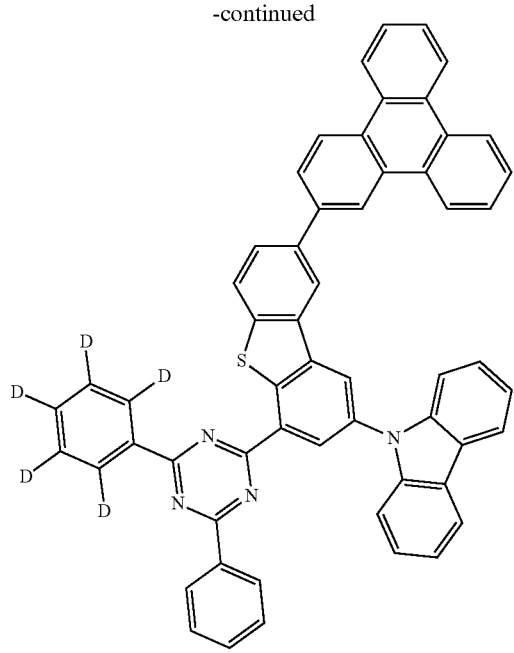
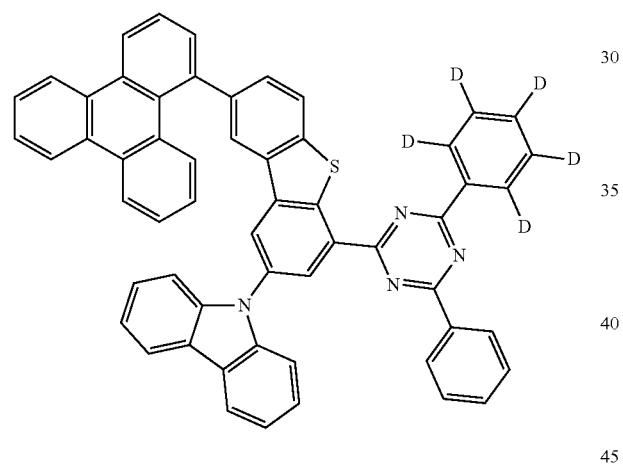
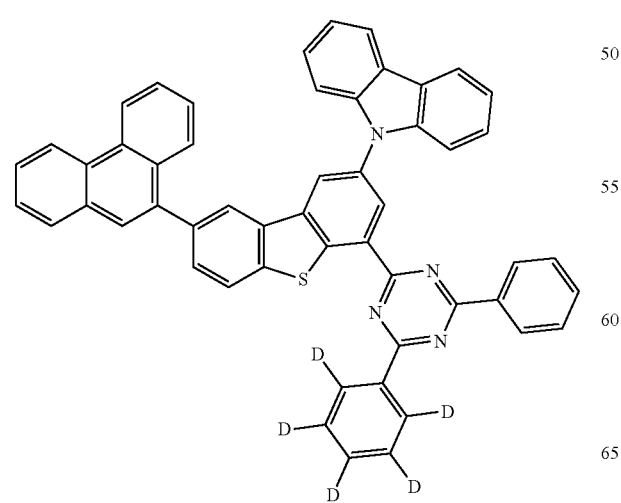
196
-continued
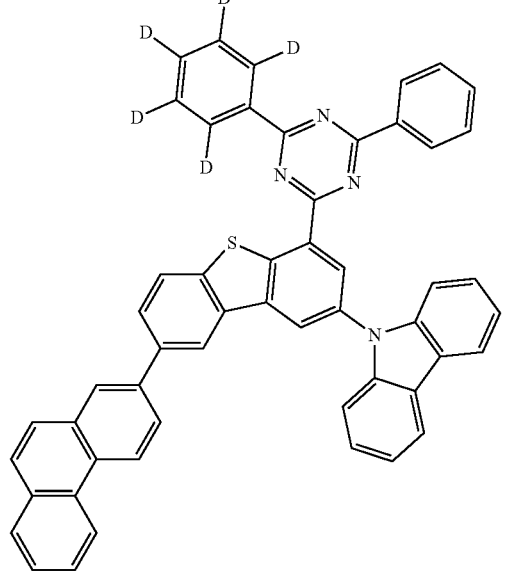
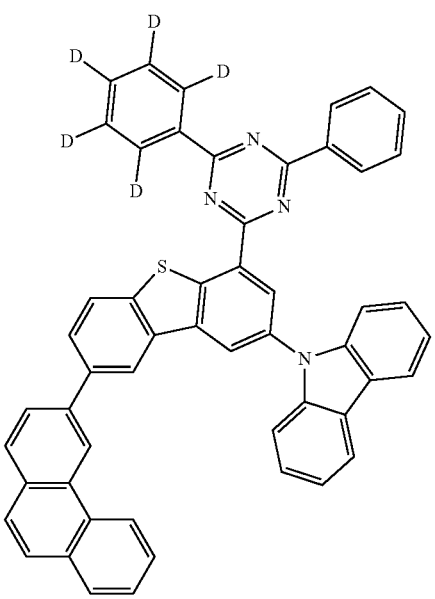

197
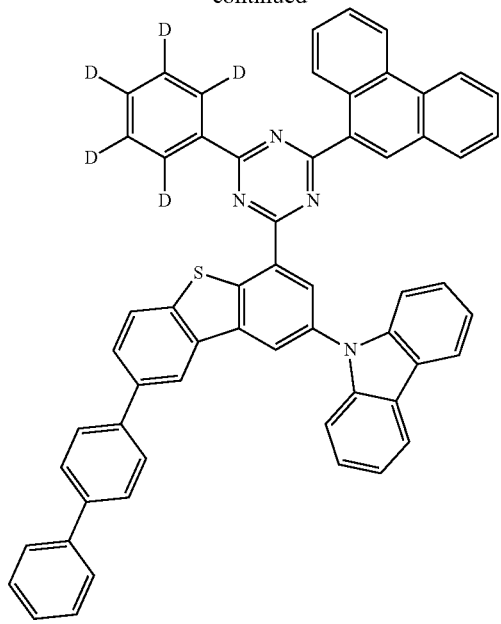
198
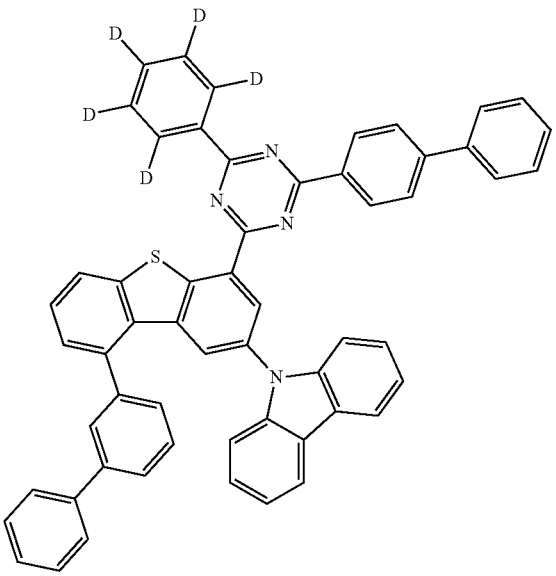
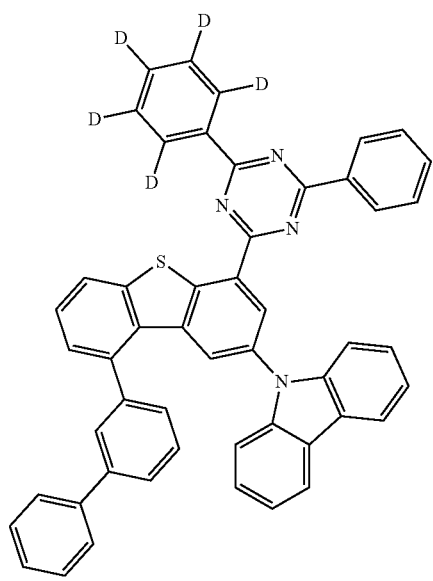
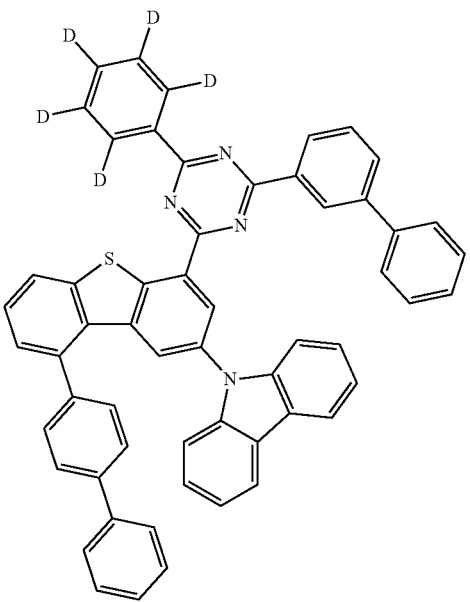

199
-continued
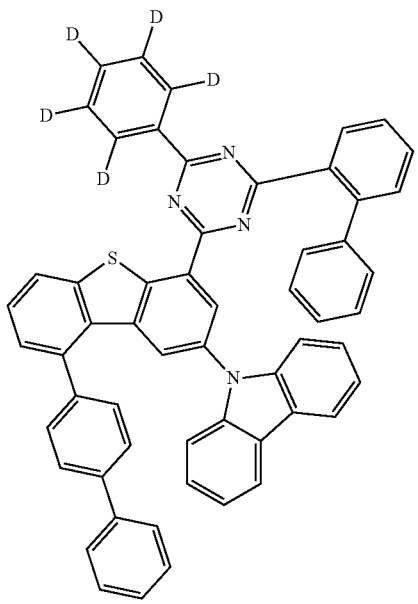
200
-continued
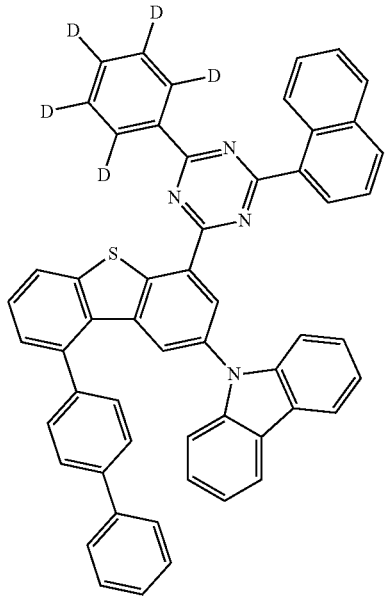
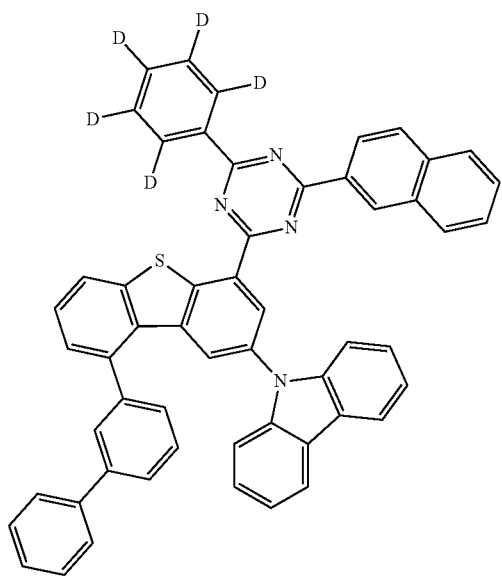
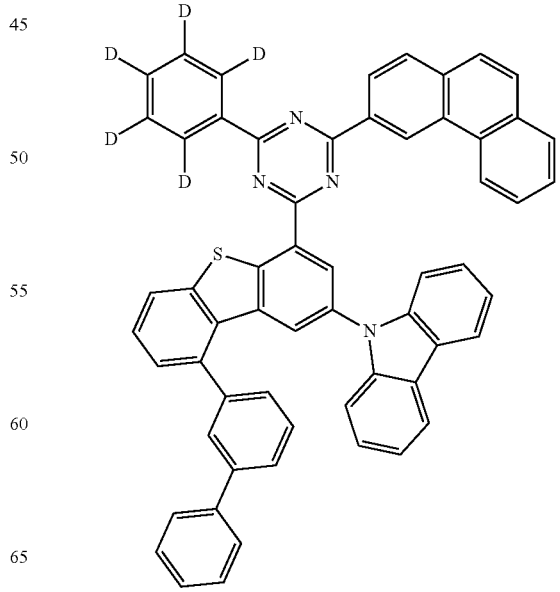

201
-continued
202
-continued
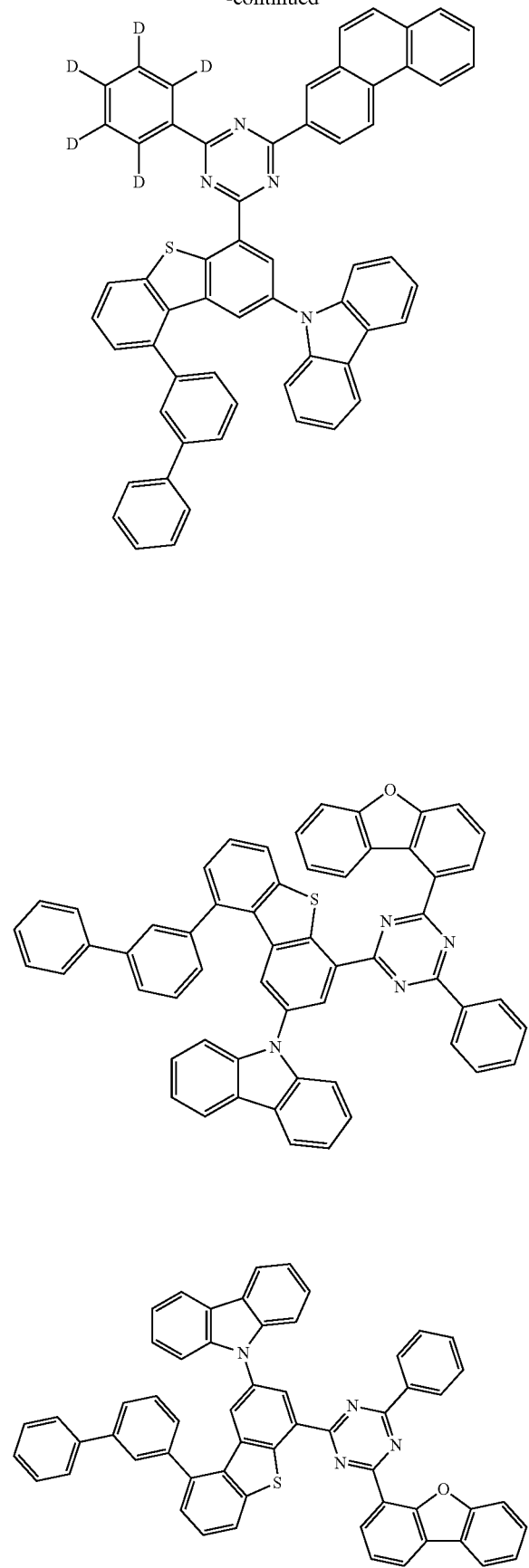
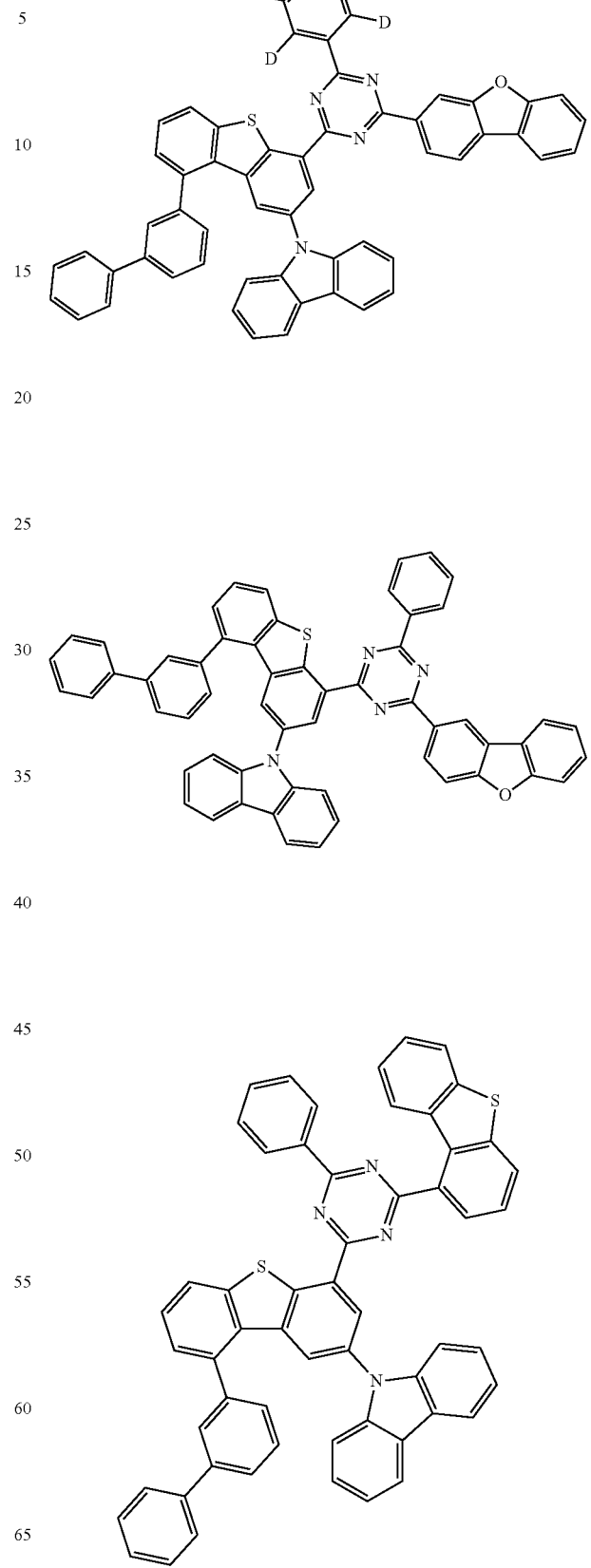

203
-continued
204
-continued
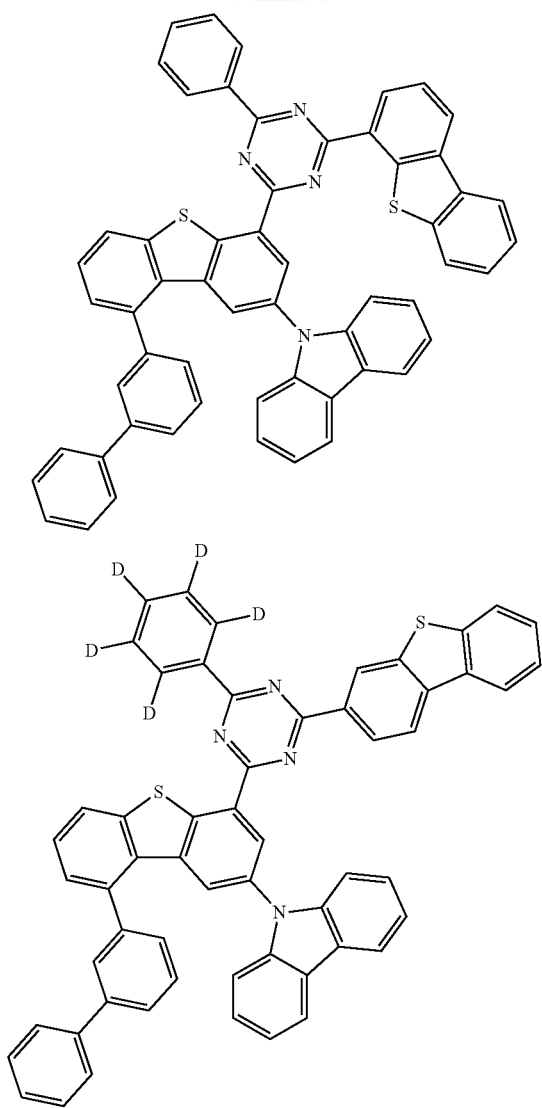

205
-continued
206
-continued
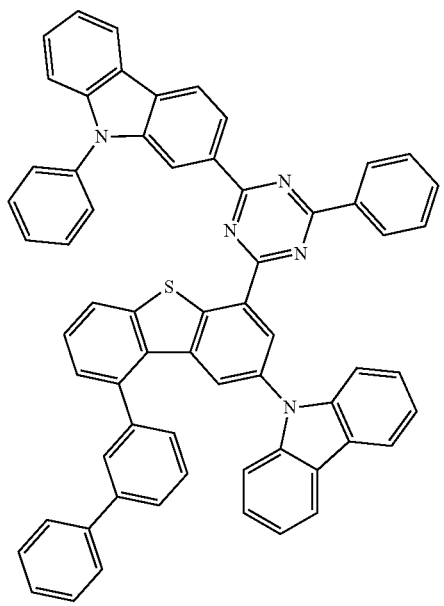
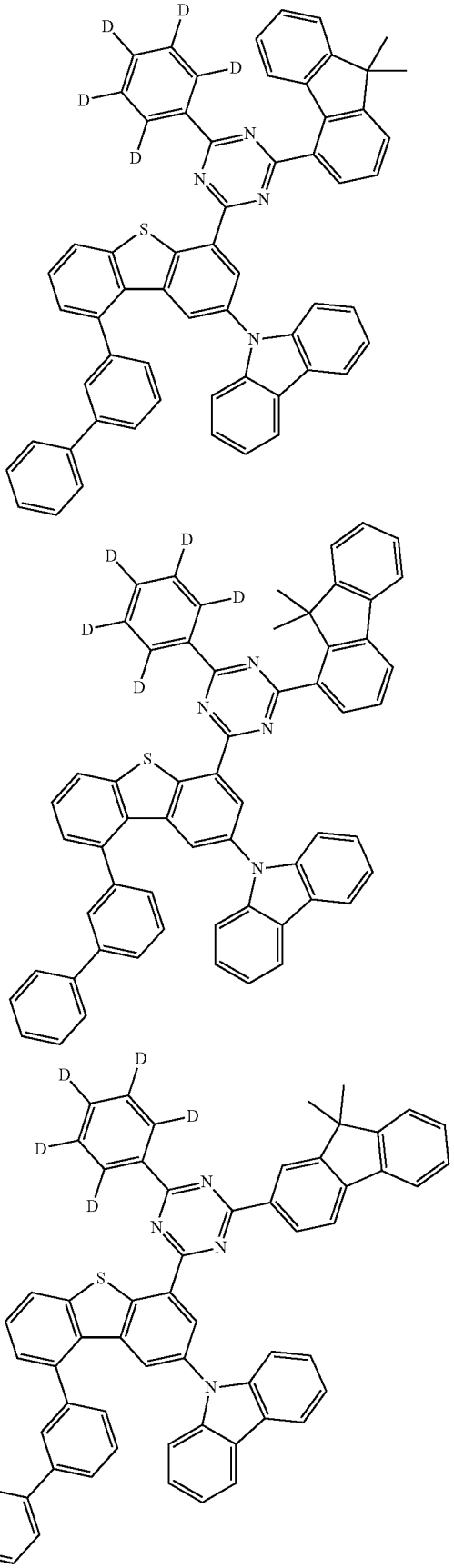

207
-continued
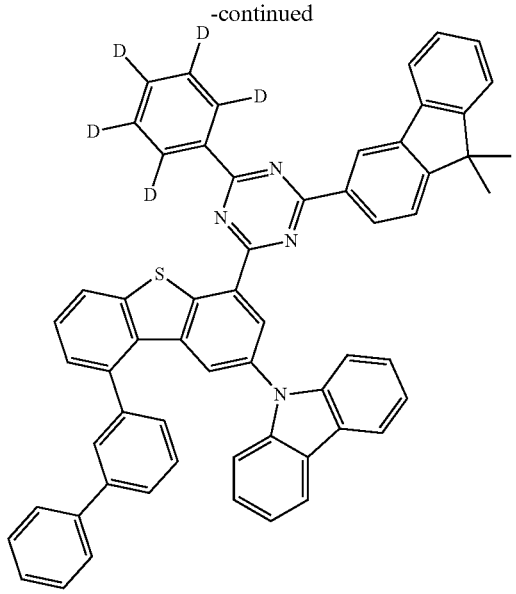
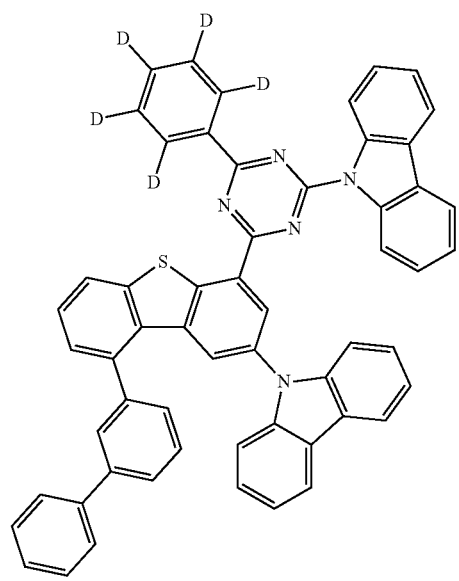
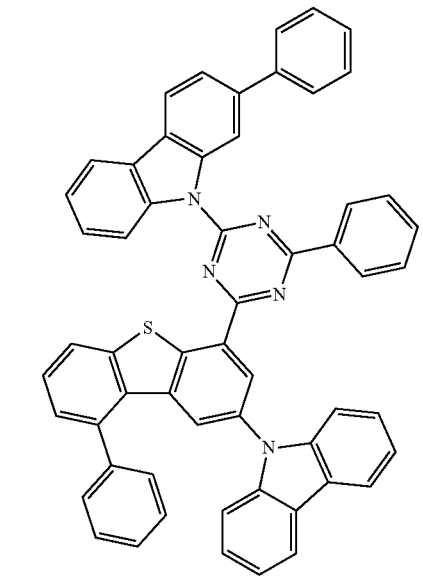
208
-continued
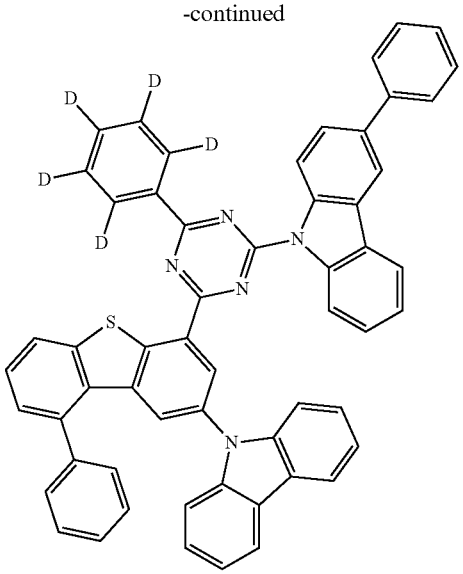
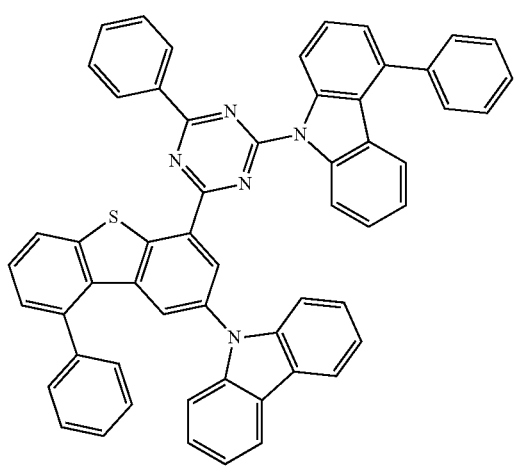
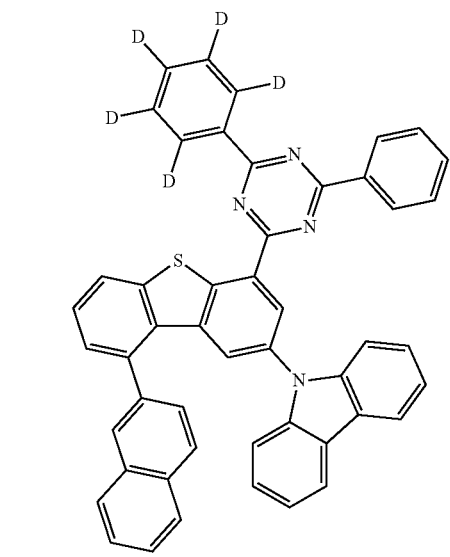

209
-continued
210
-continued
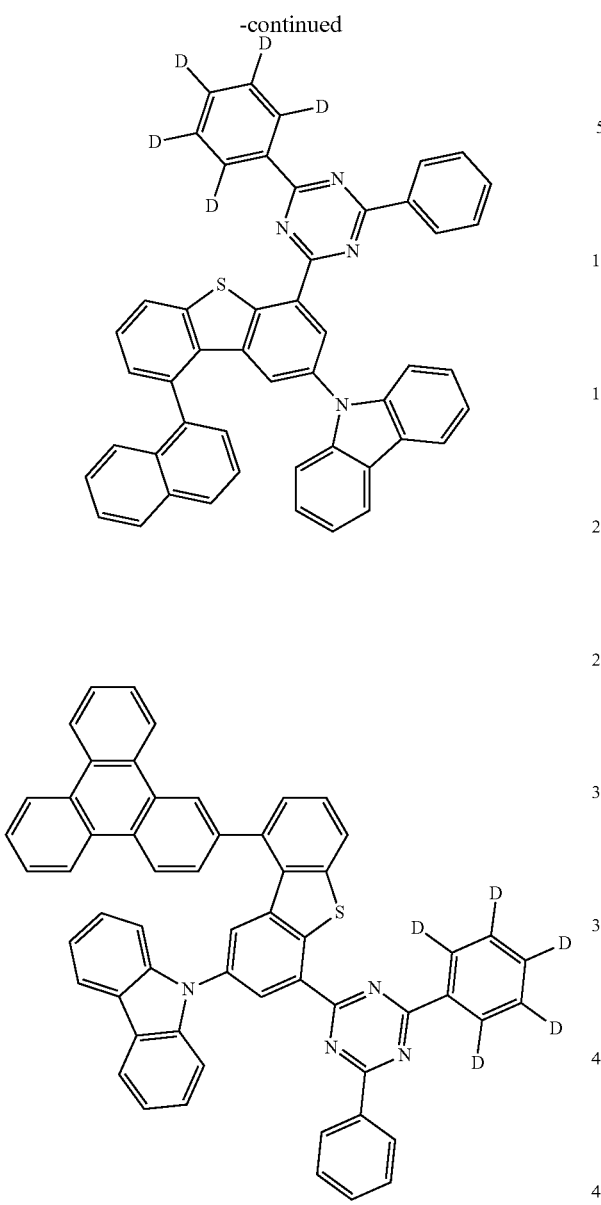
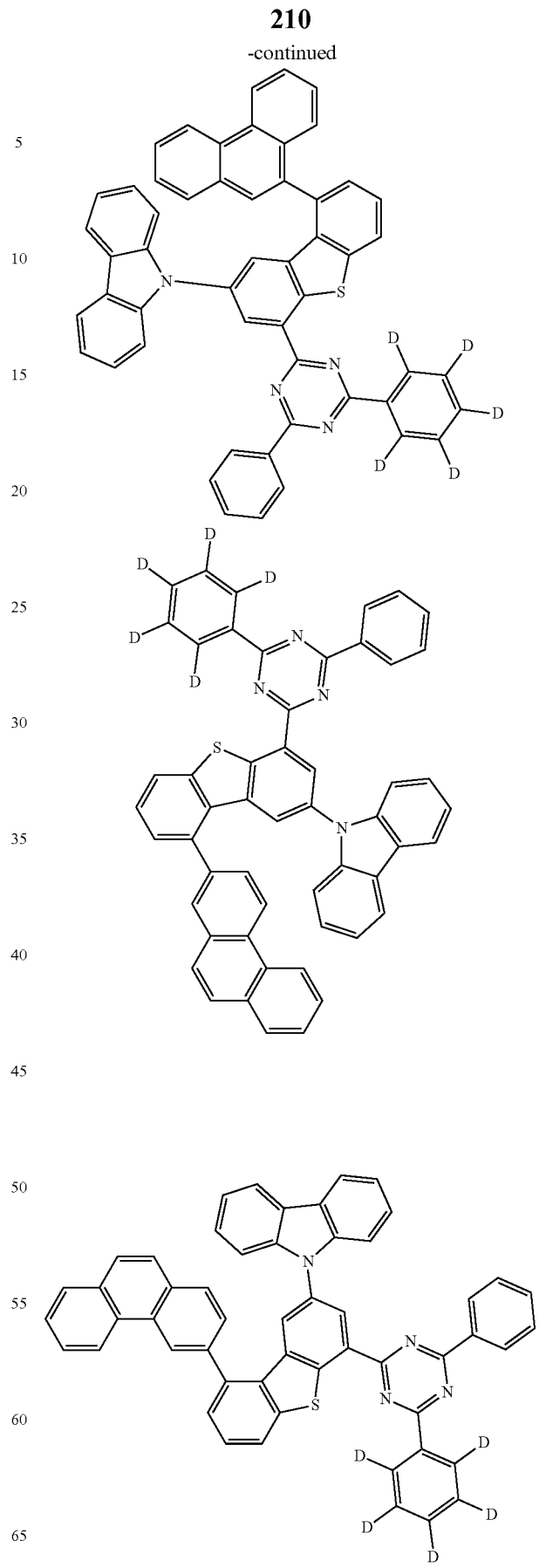

211
-continued
212
-continued
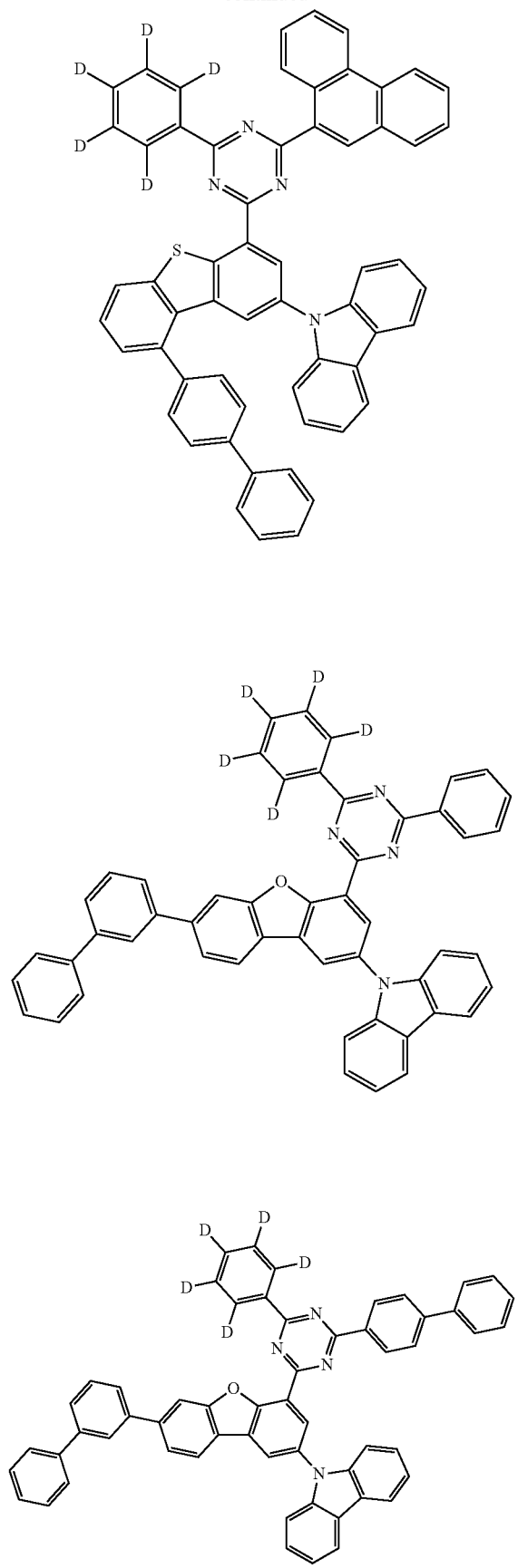
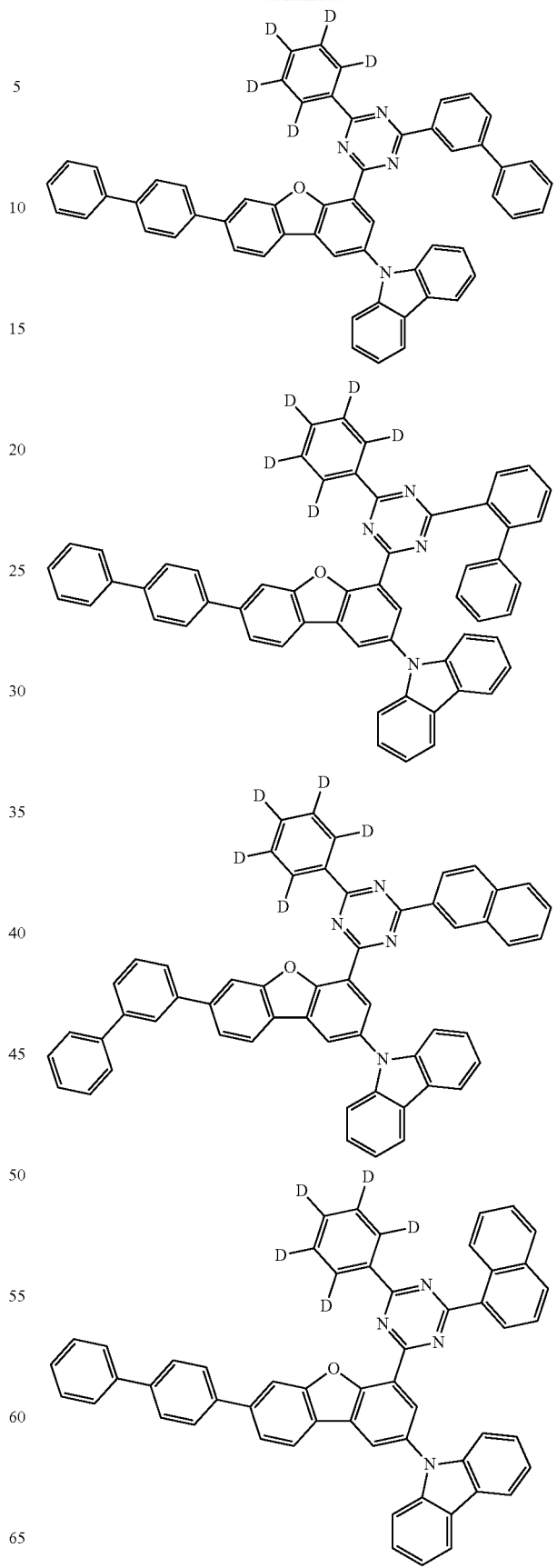

213
-continued
214
-continued
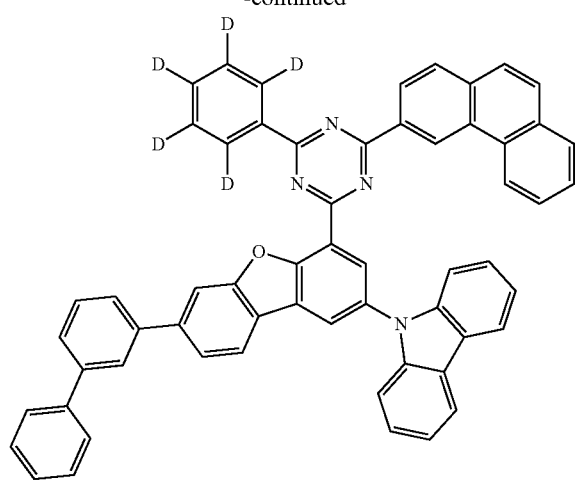
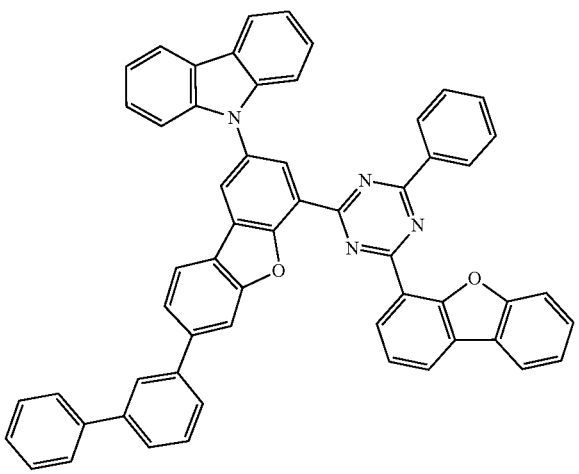
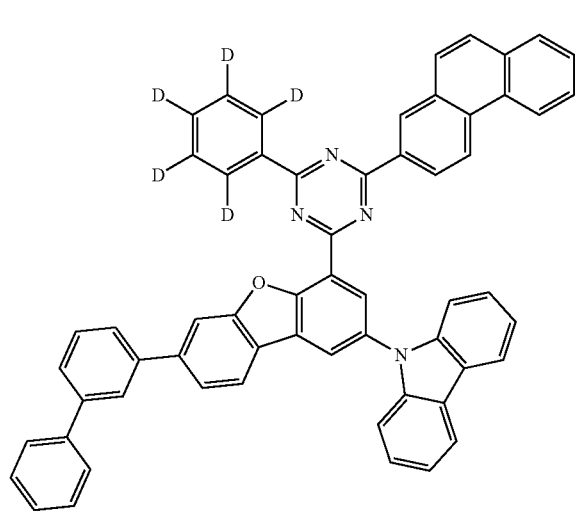
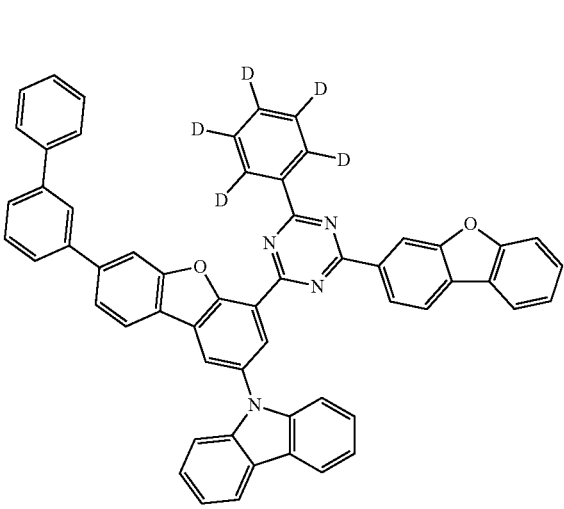
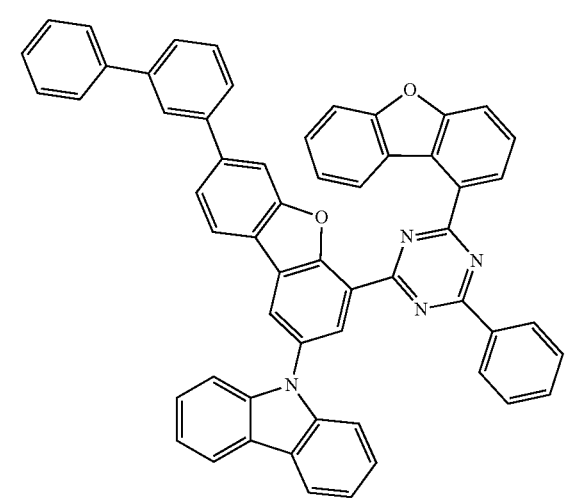
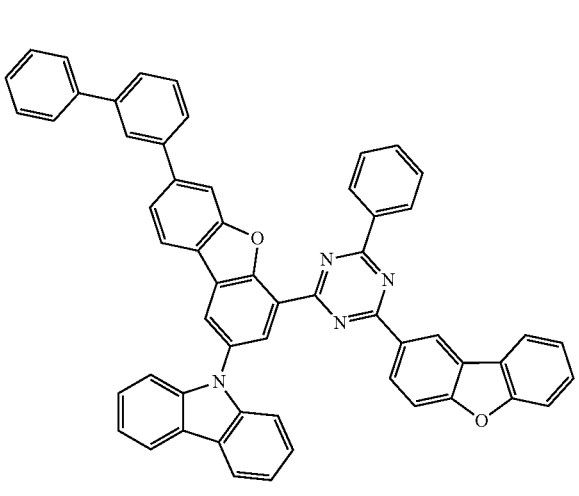

215
-continued
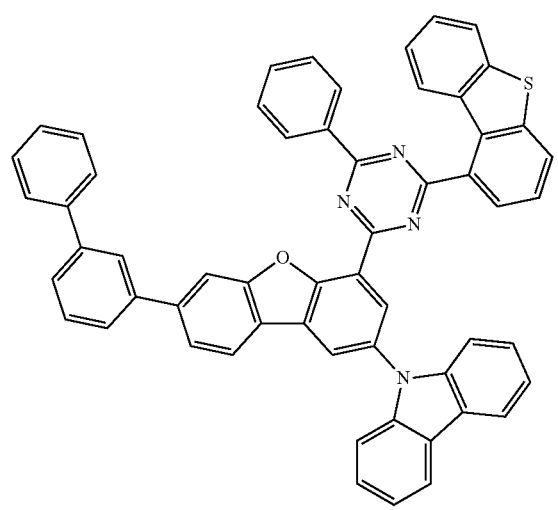
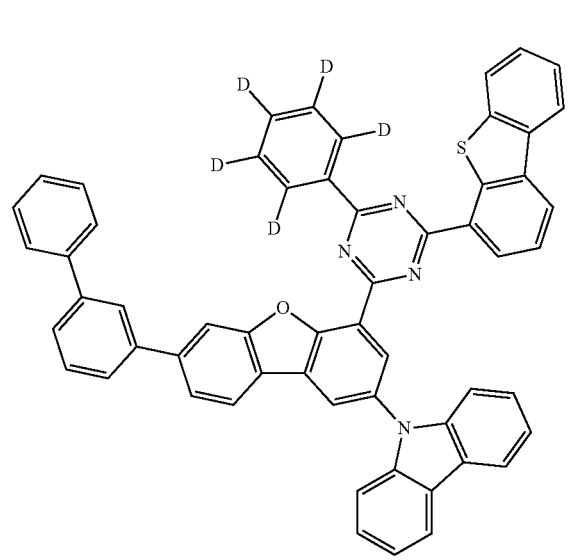
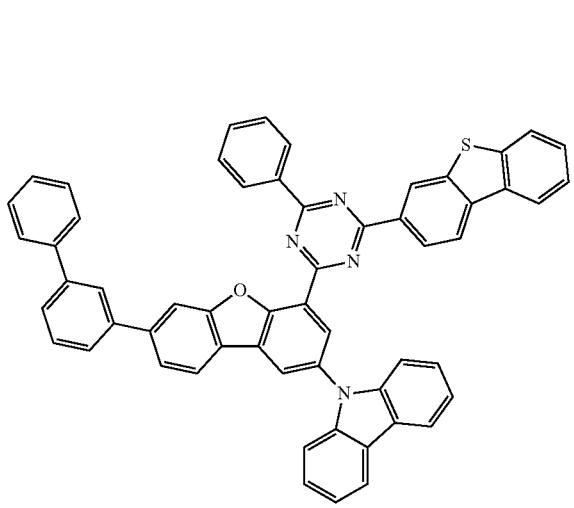
216
-continued
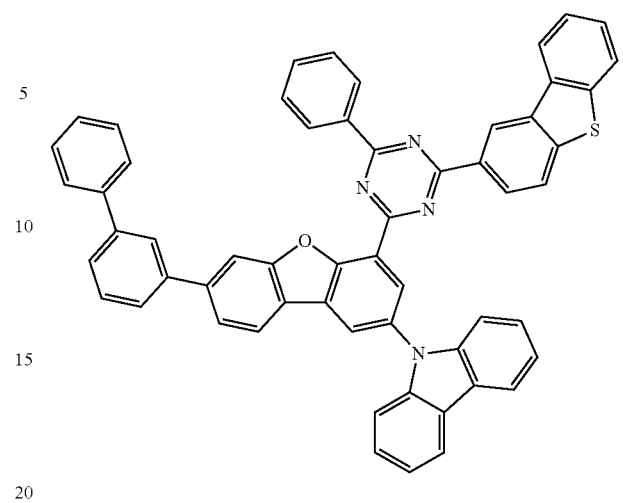
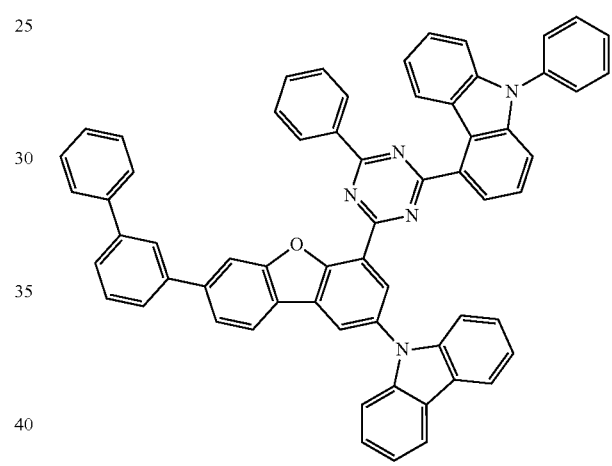
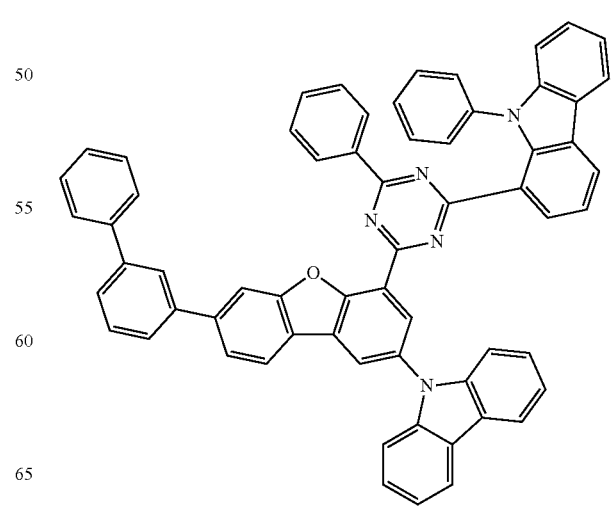

217
-continued
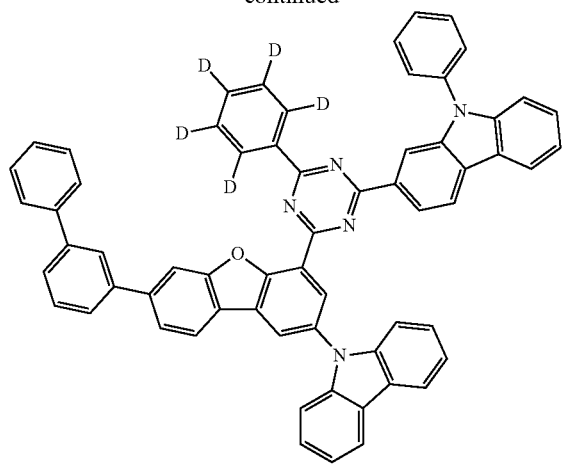
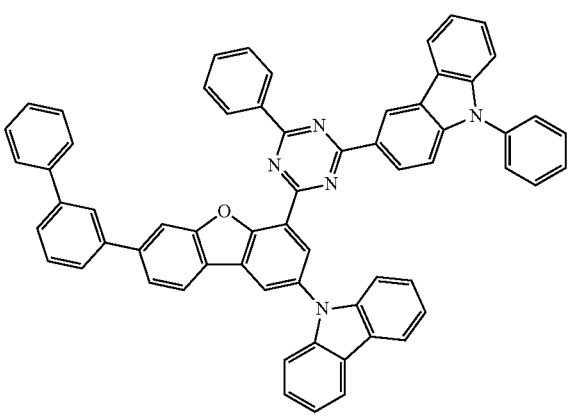
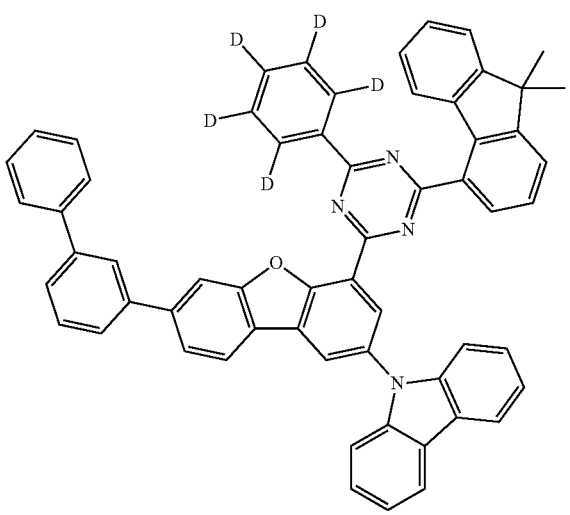
218
-continued
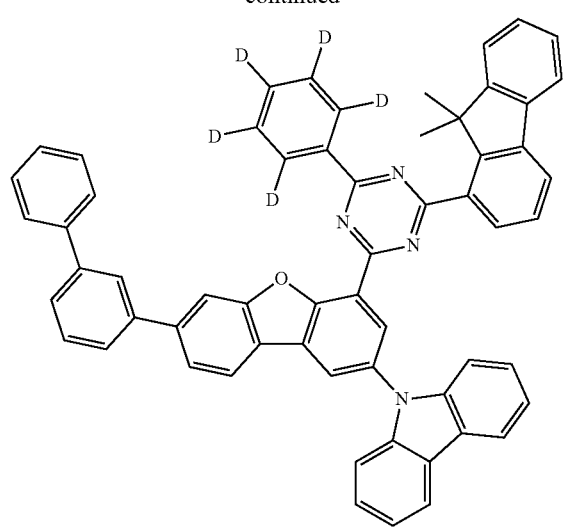
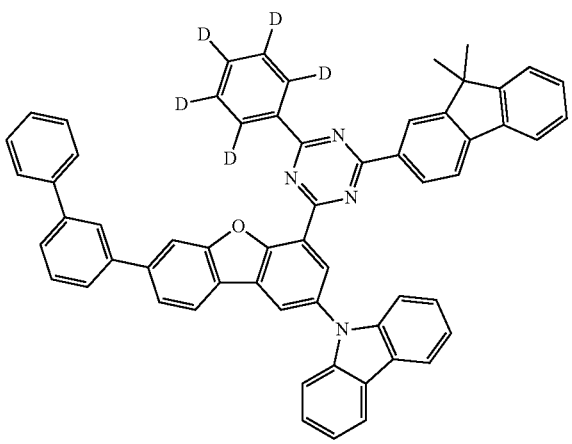
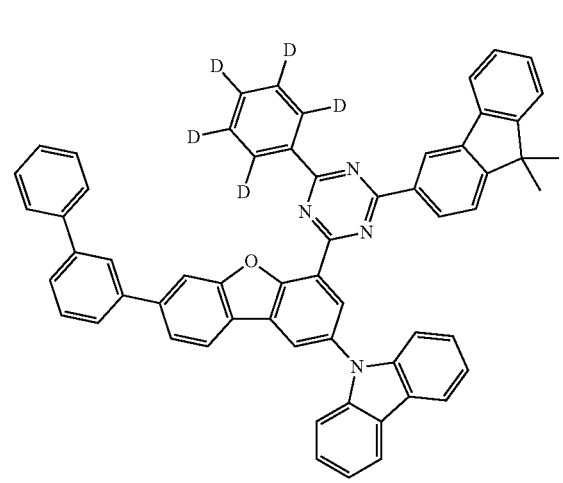

219
-continued
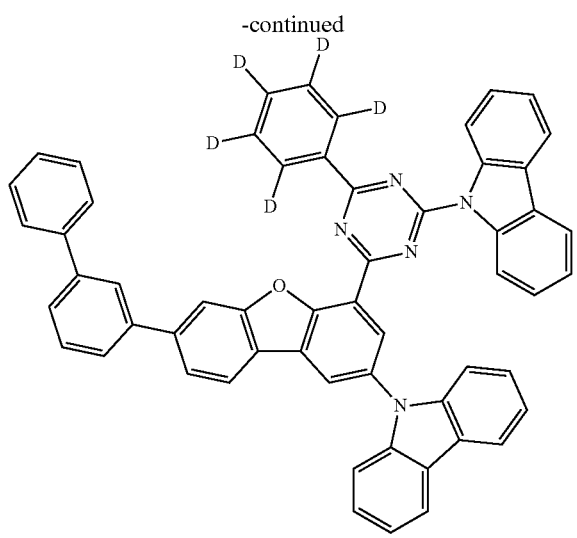
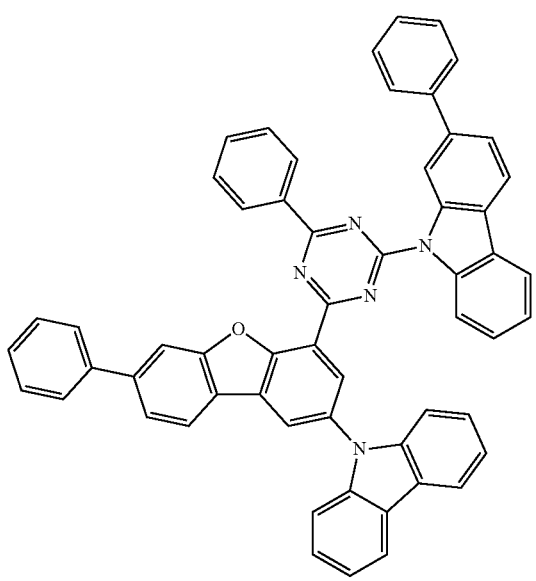
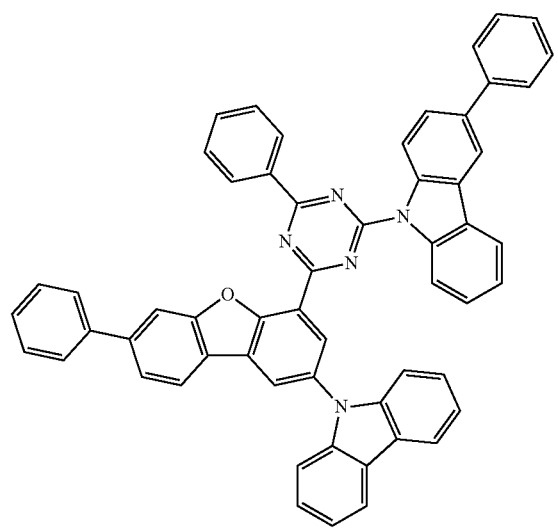
220
-continued
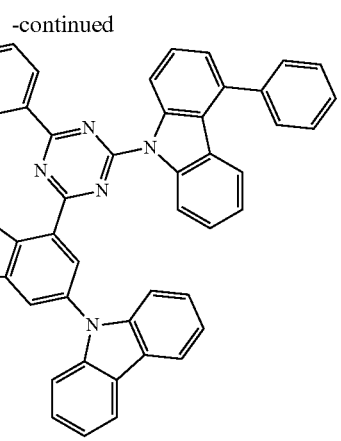
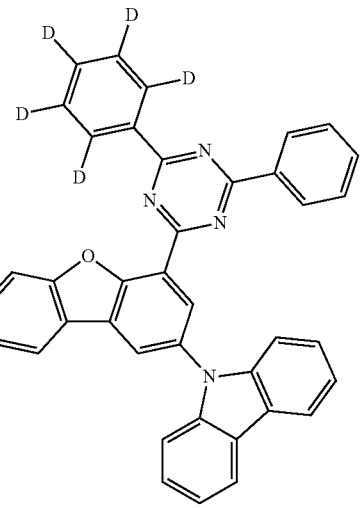
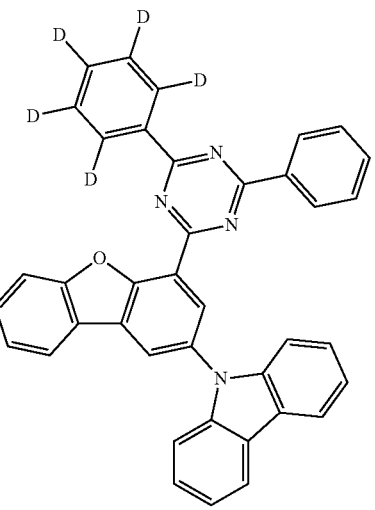

221
-continued
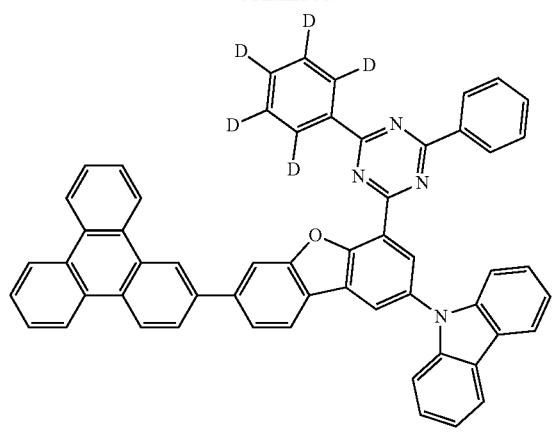
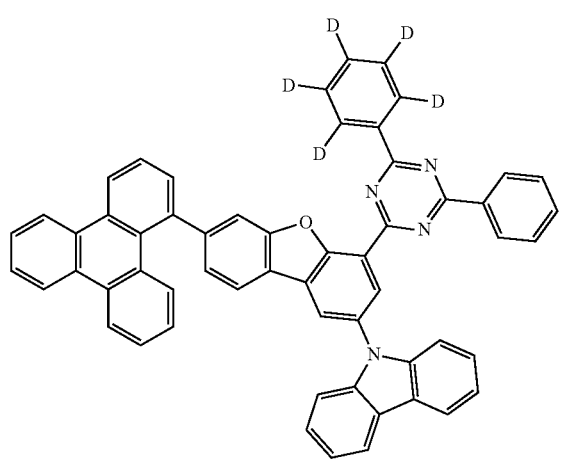
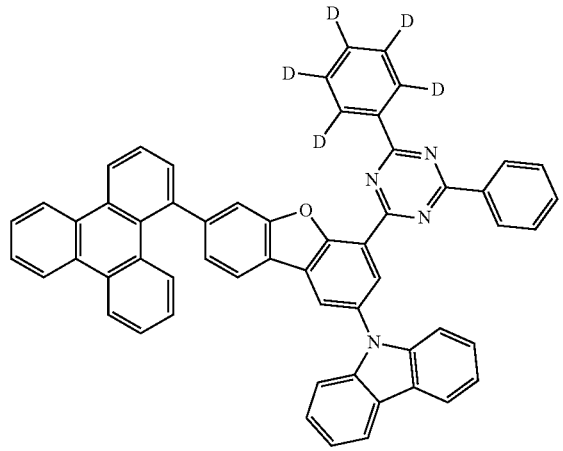
222
-continued
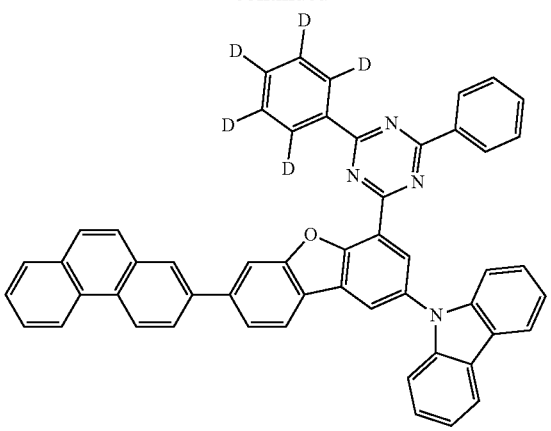
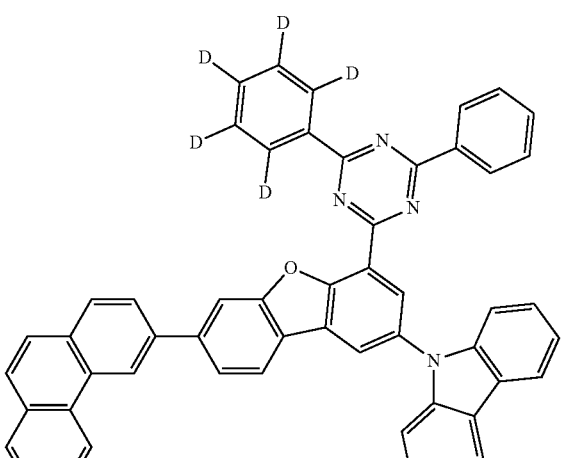
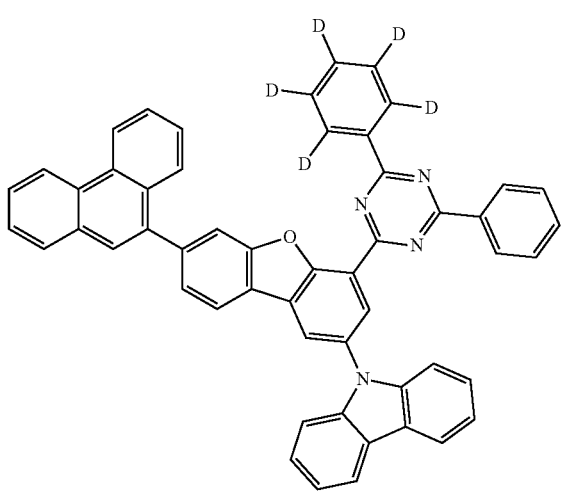
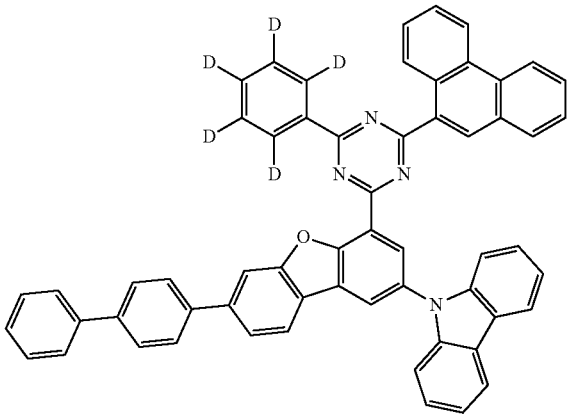

223
-continued
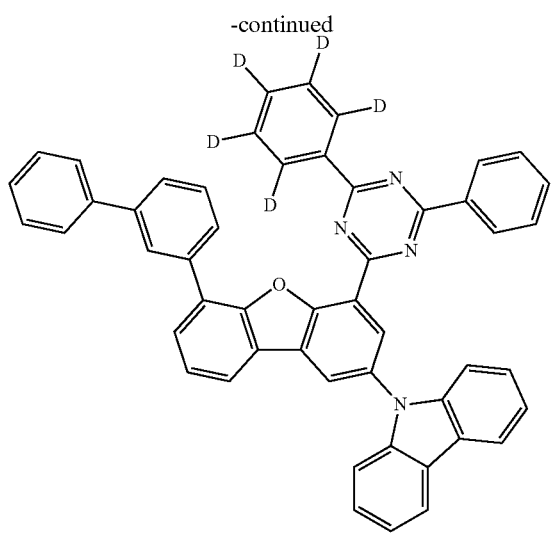
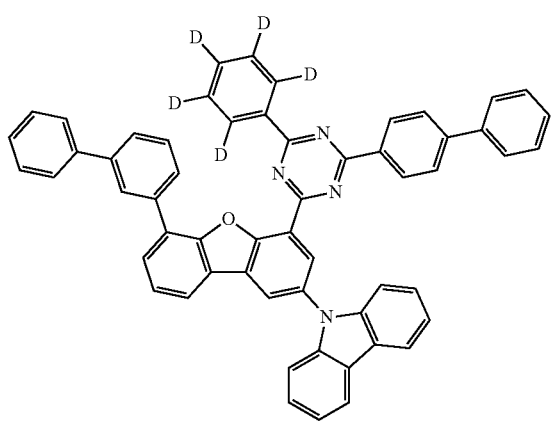
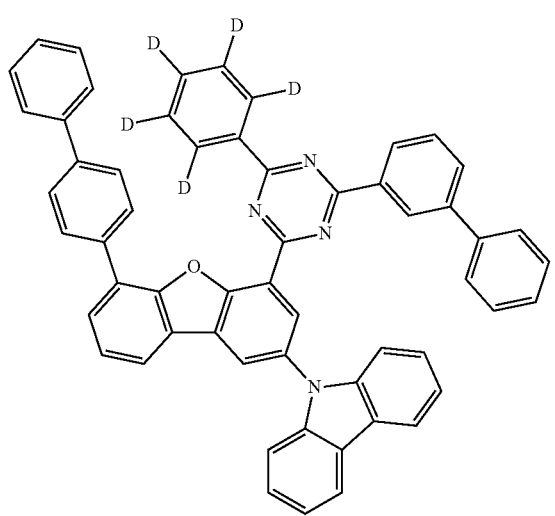
224
-continued
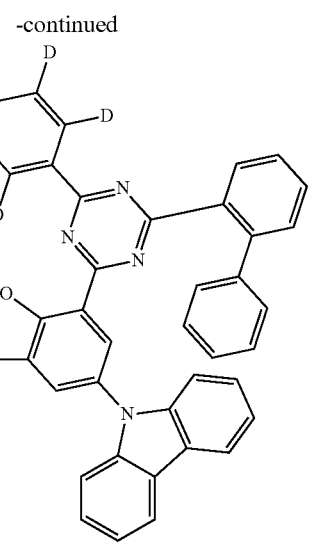
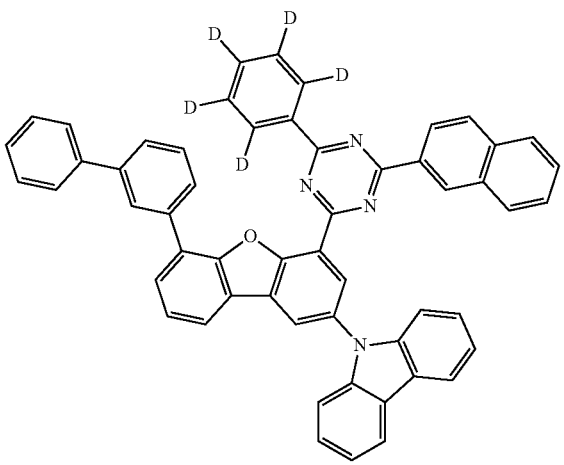
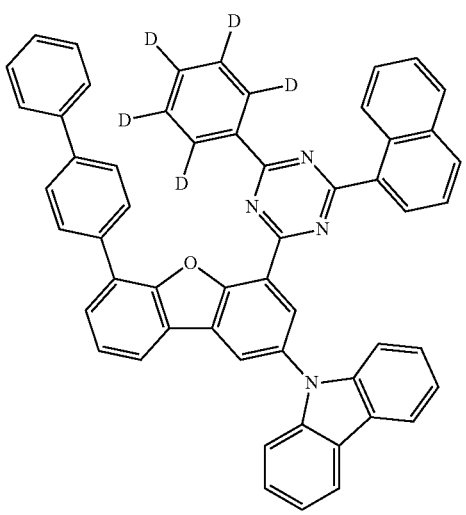

225
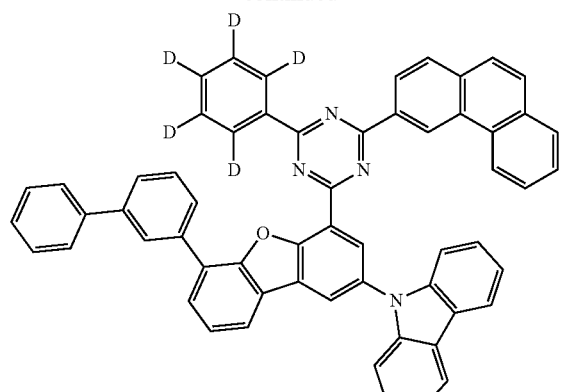
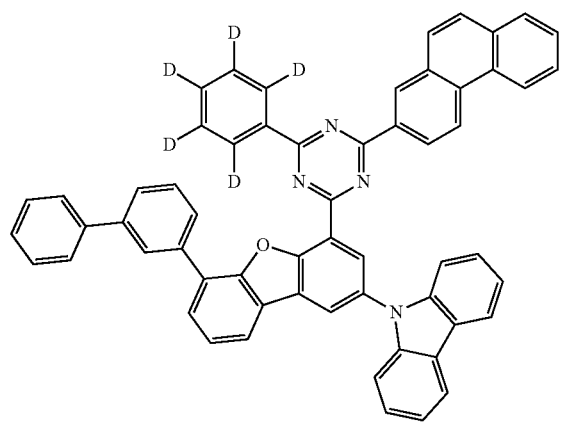
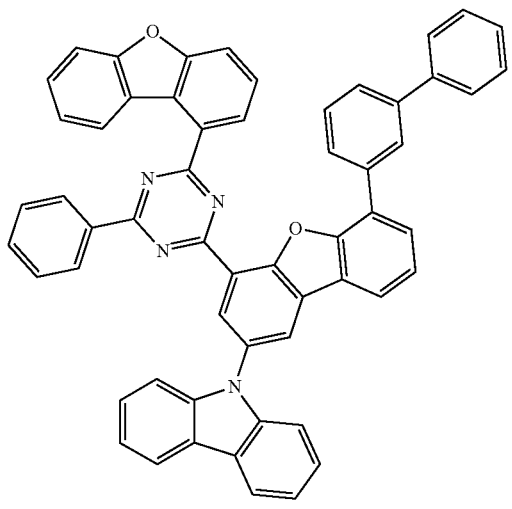
226
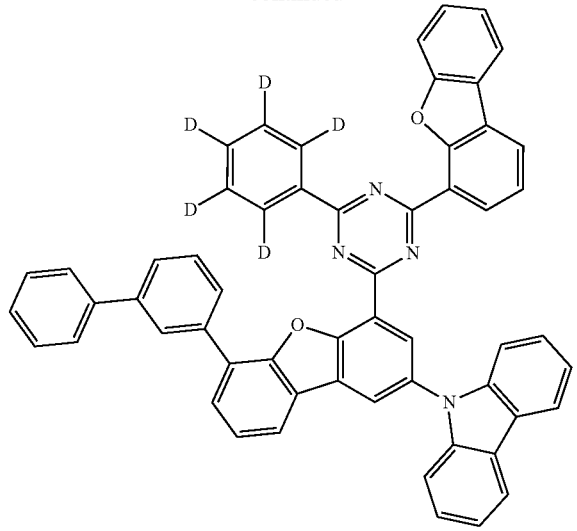
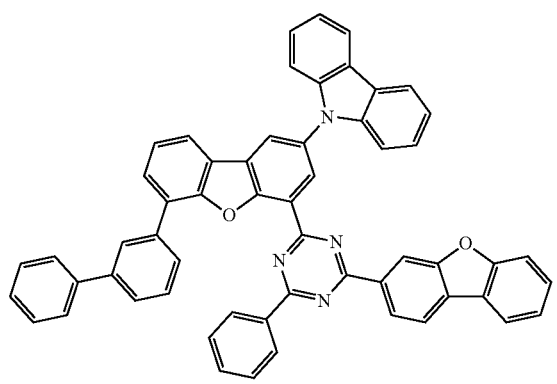

227
-continued
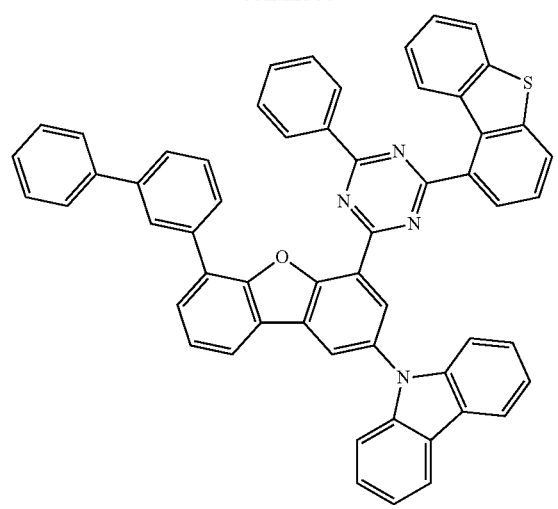
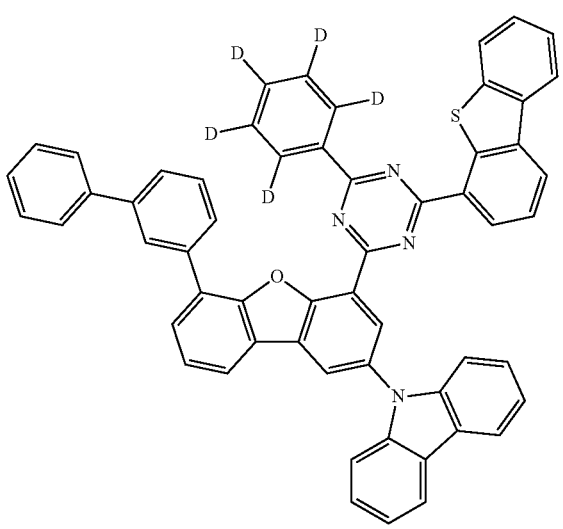
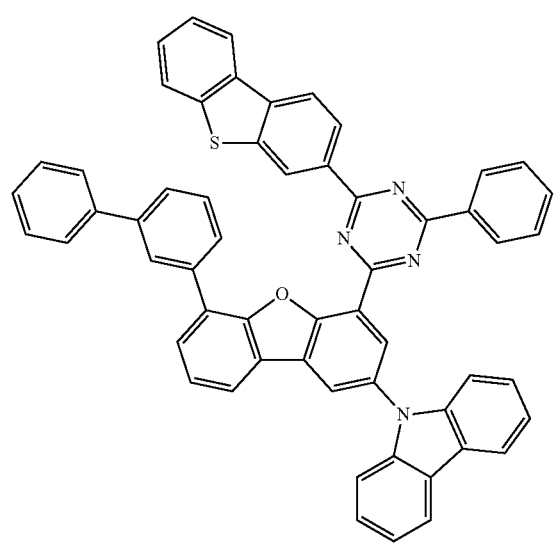
228
-continued
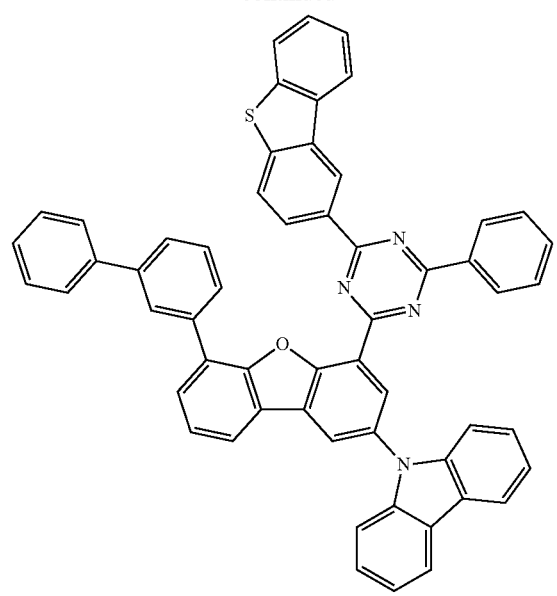
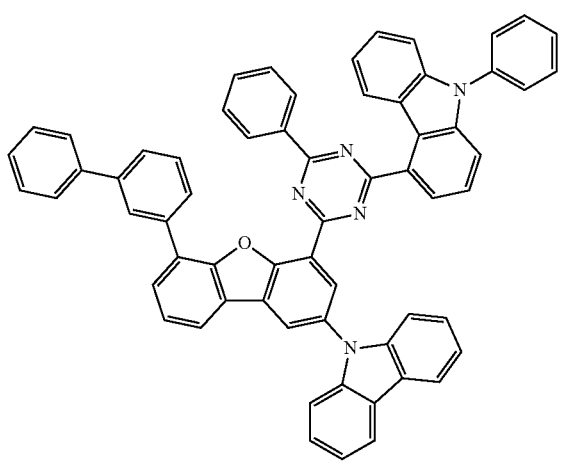
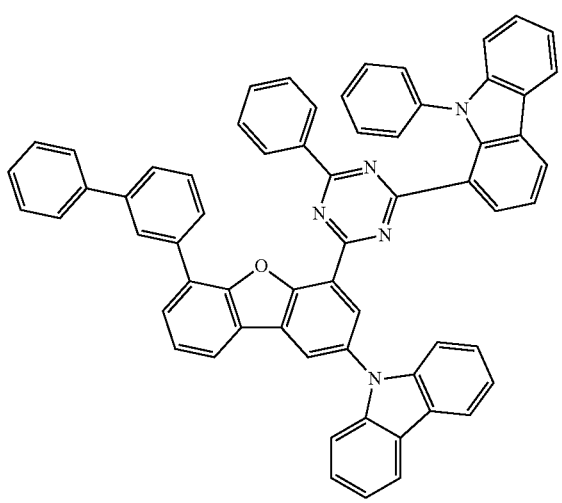

229
-continued
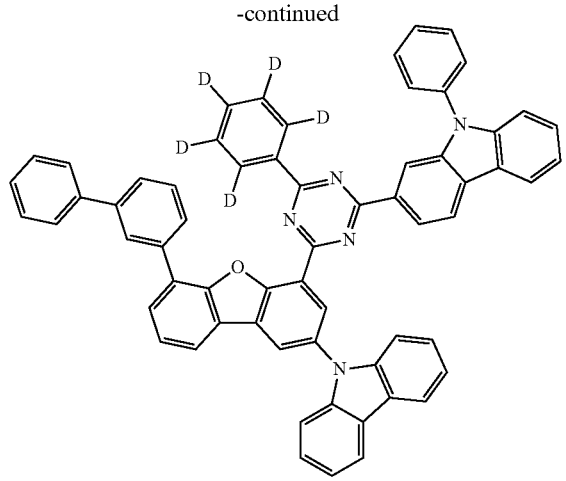
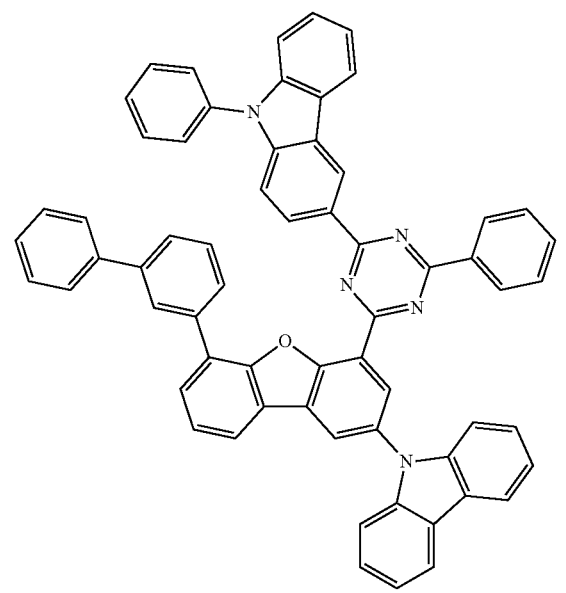
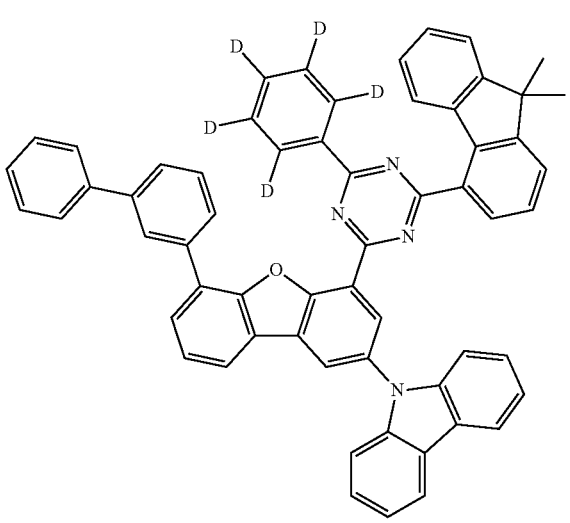
230
-continued
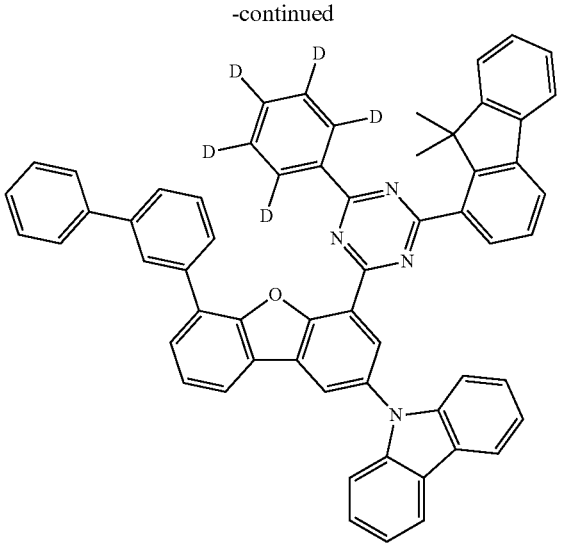
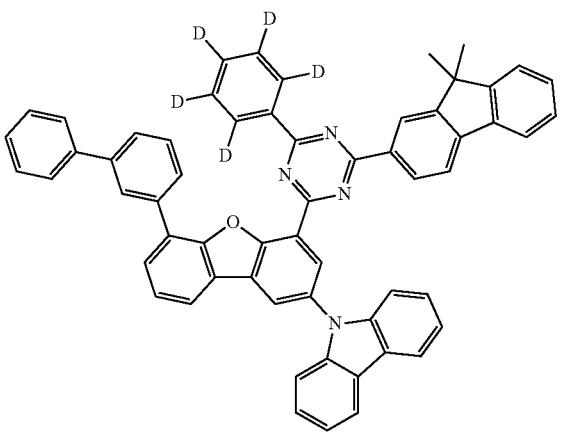
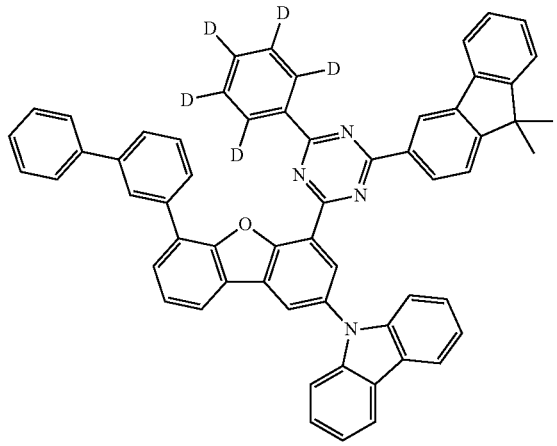

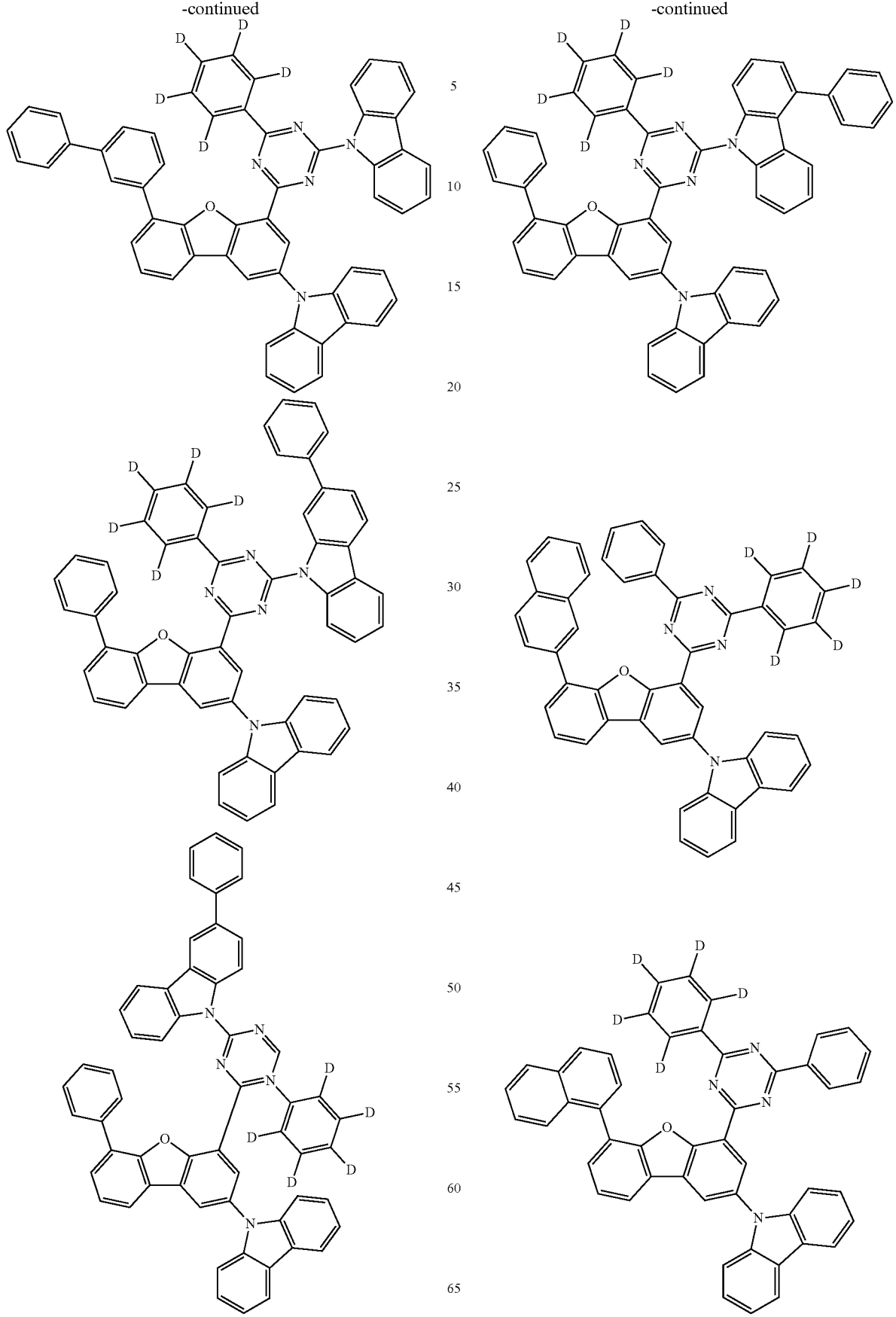

233
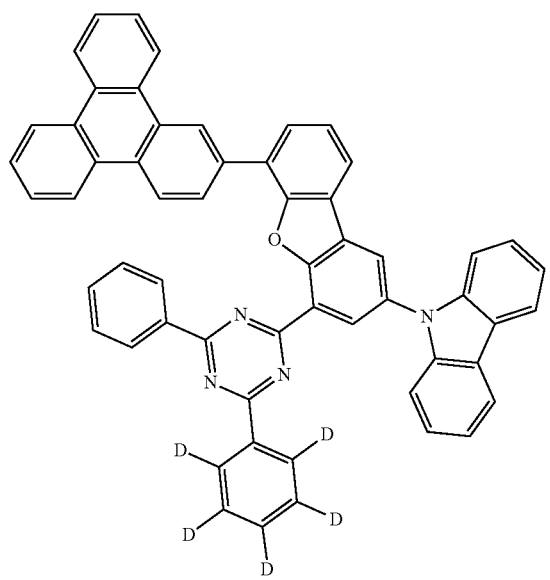
234
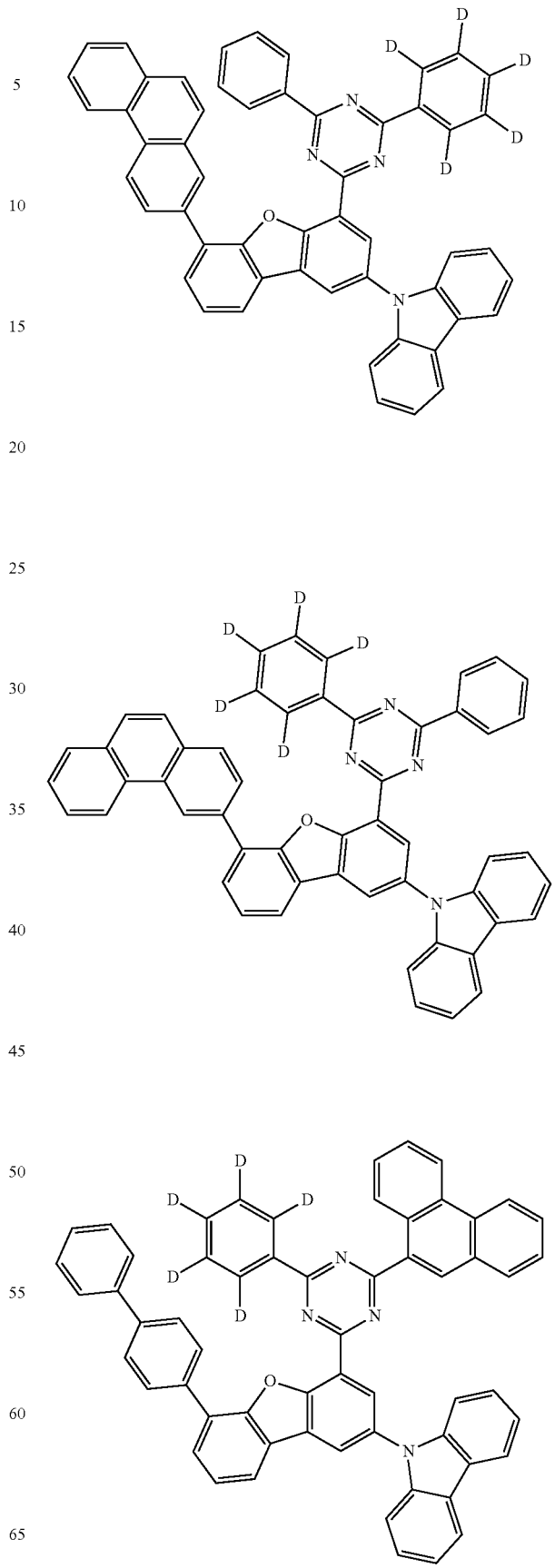

235
-continued
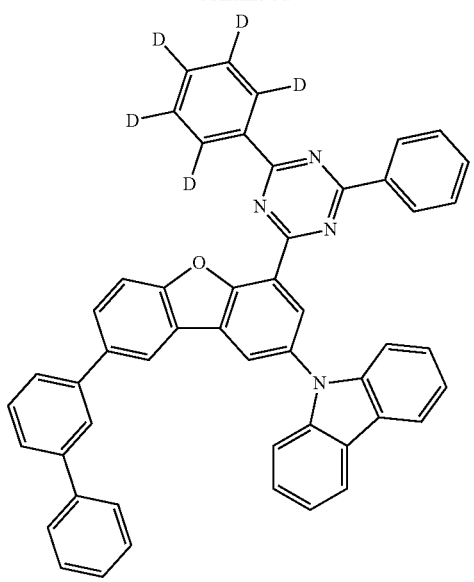
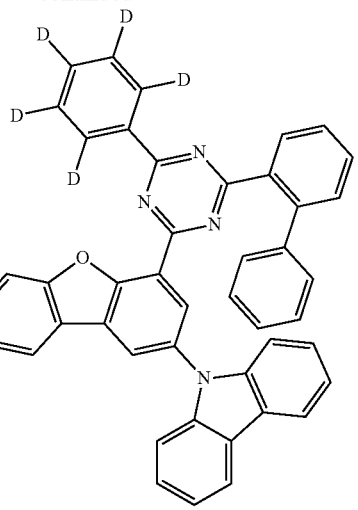
236
-continued
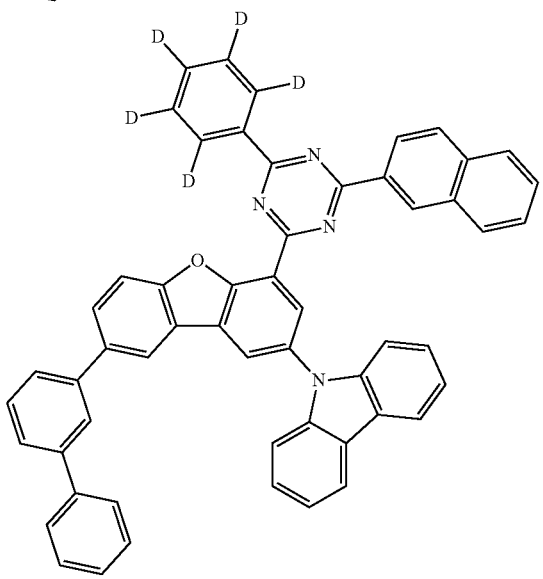
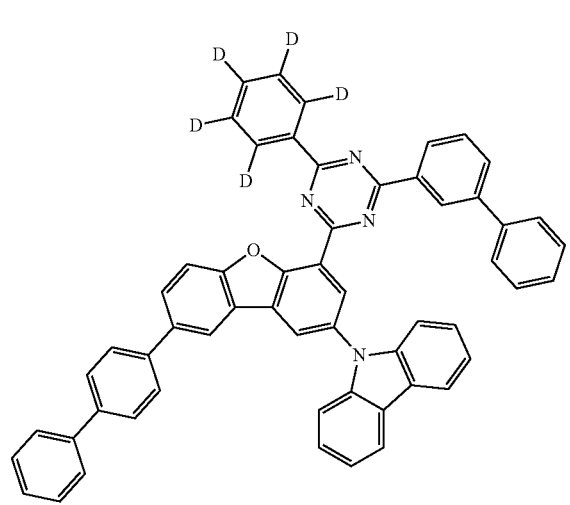
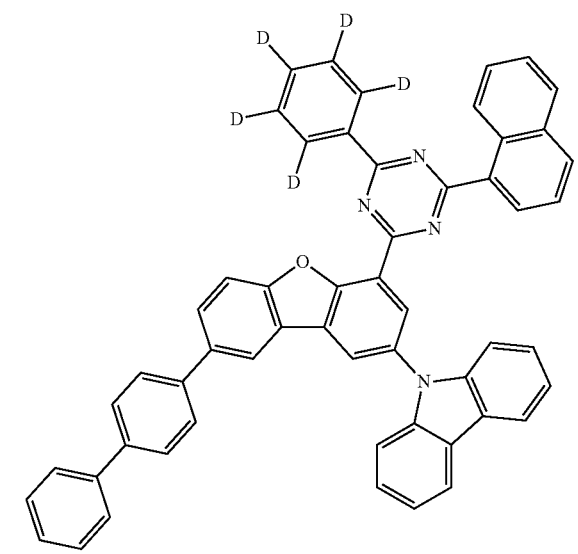

237
-continued
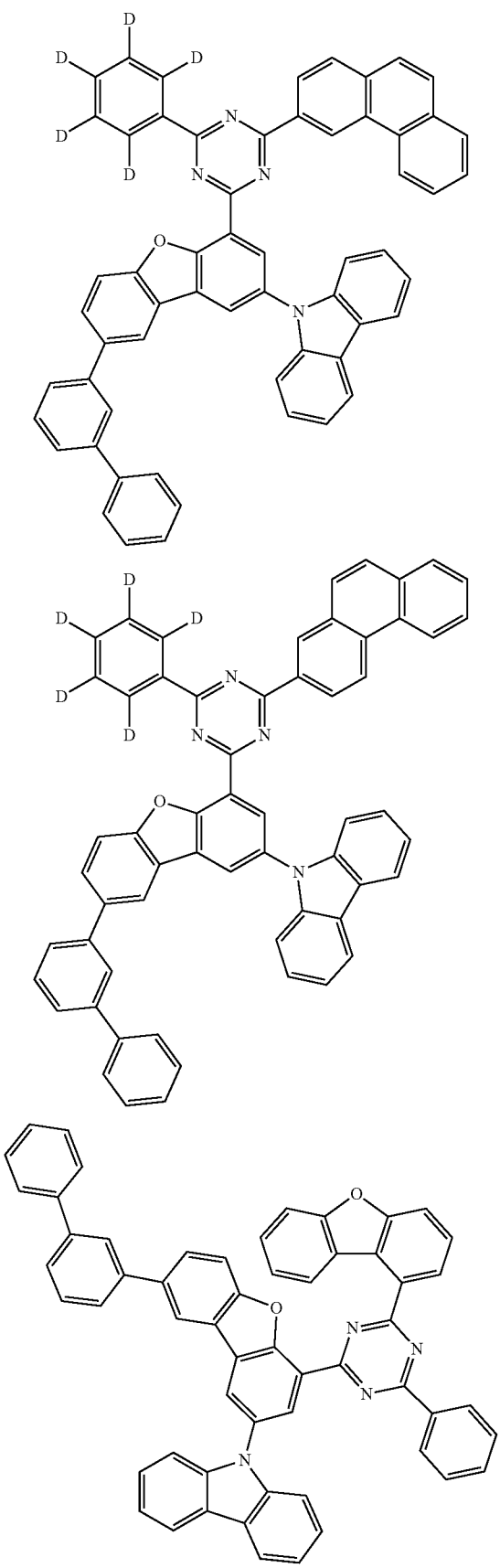
238
-continued
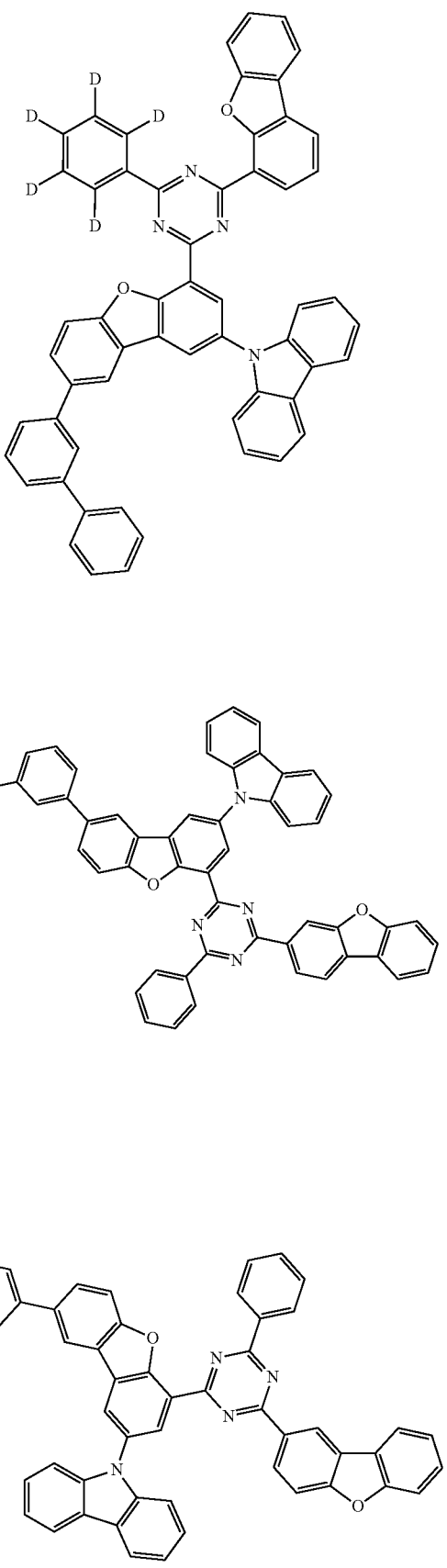

239
-continued
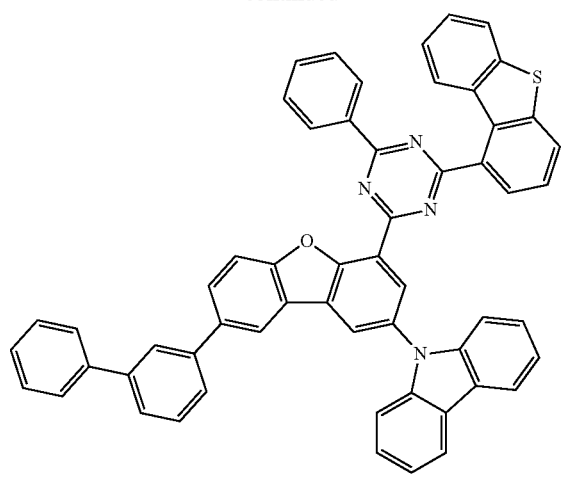
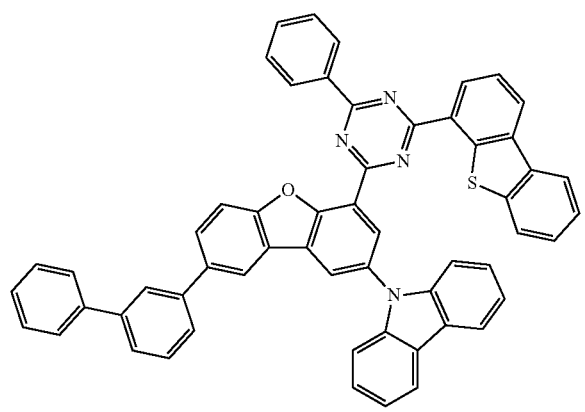
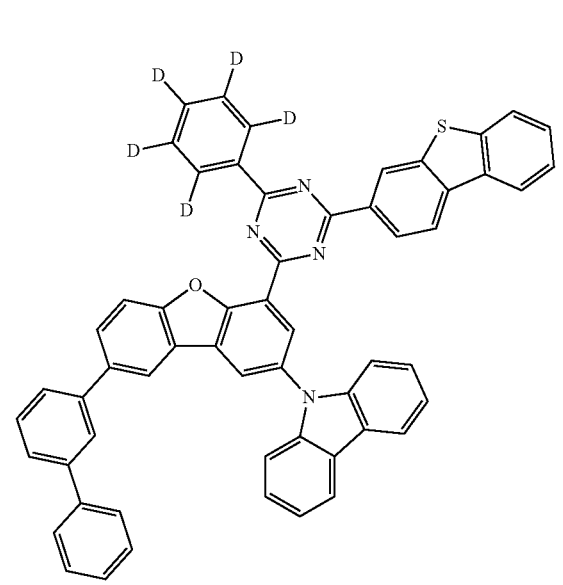
240
-continued
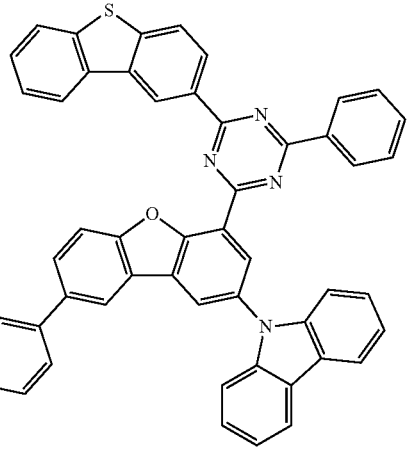
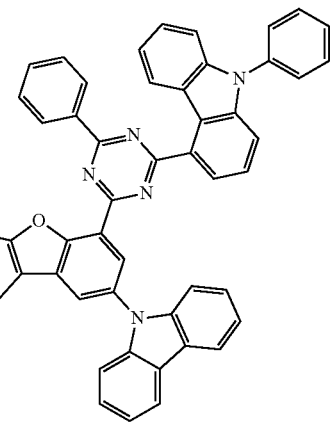
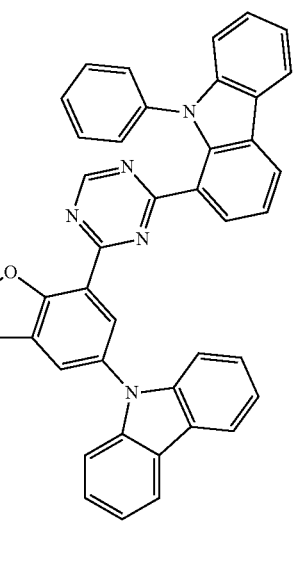

241
-continued
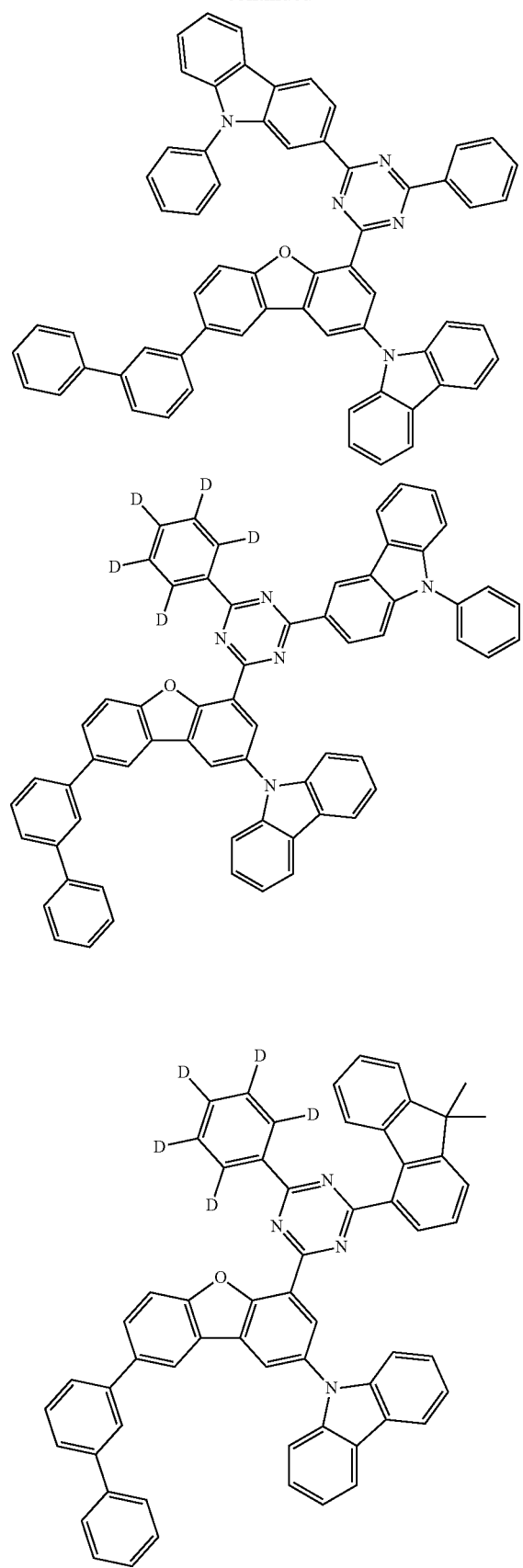
242
-continued
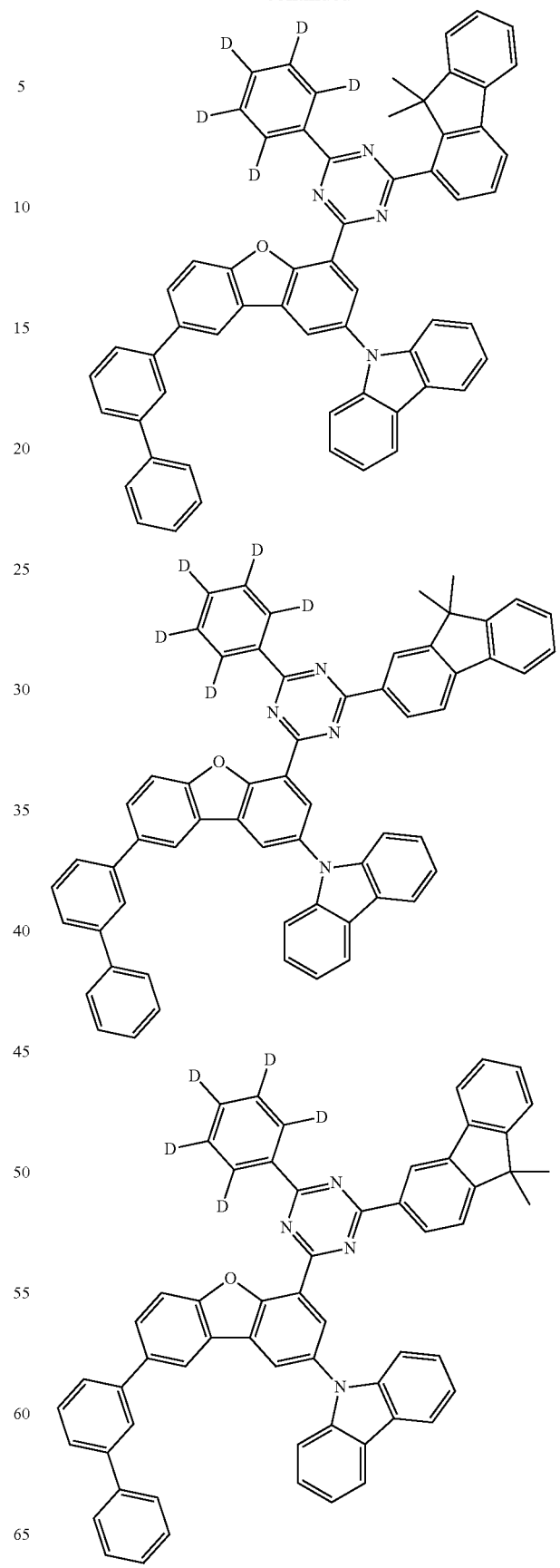

243
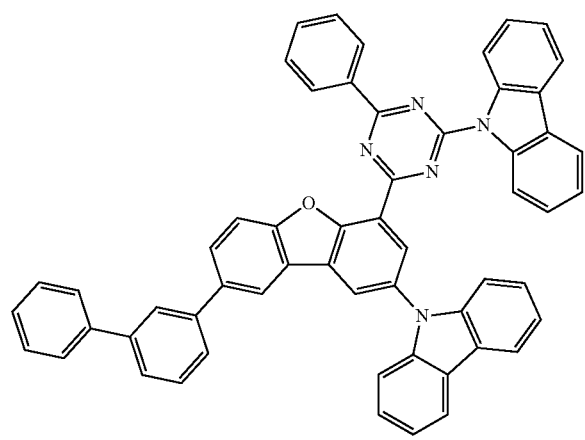
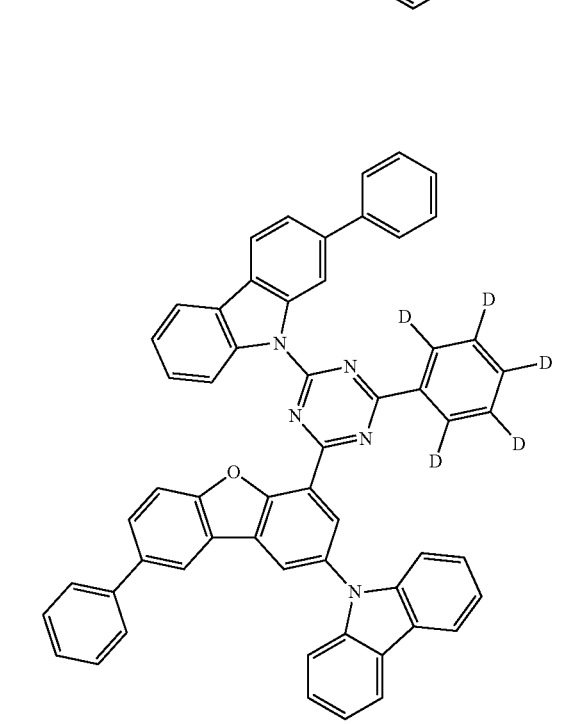
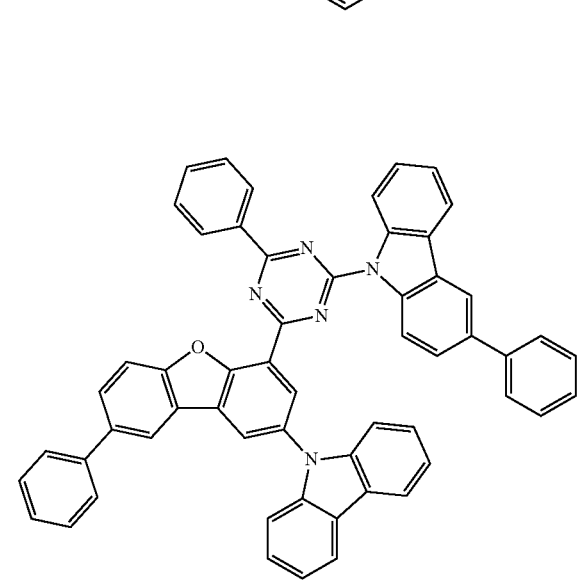
244
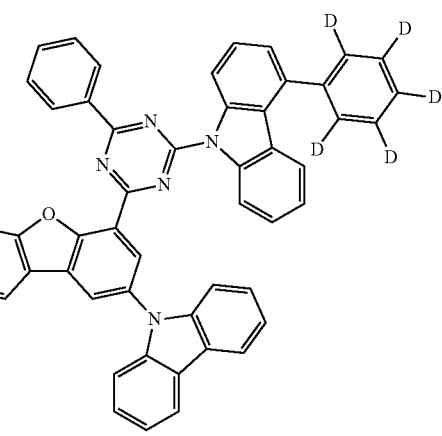
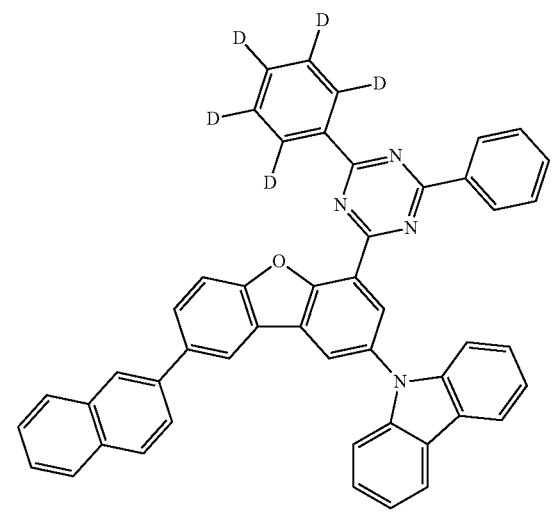
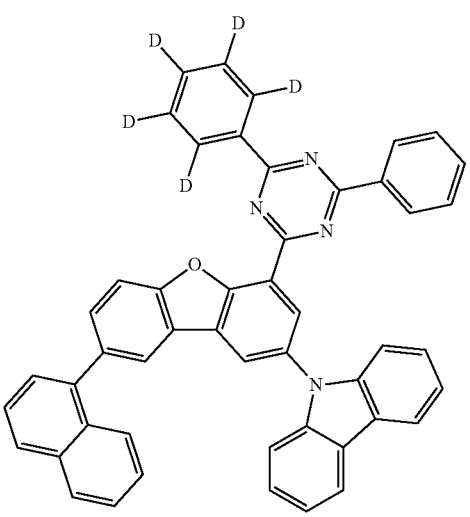

245
-continued
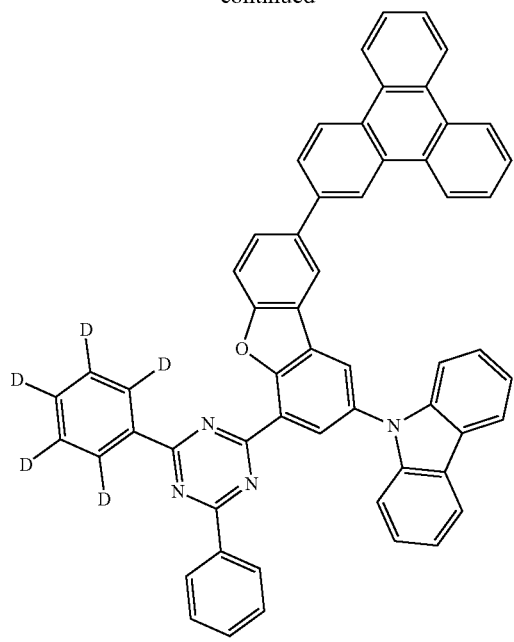
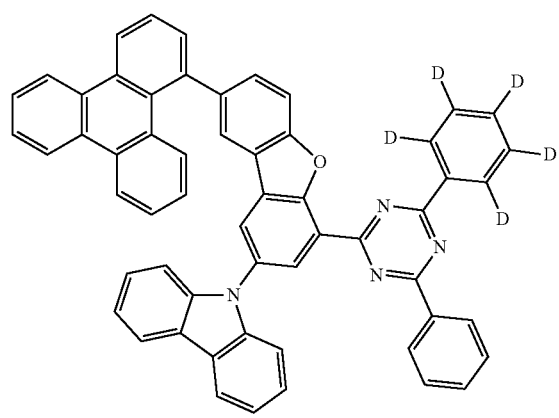
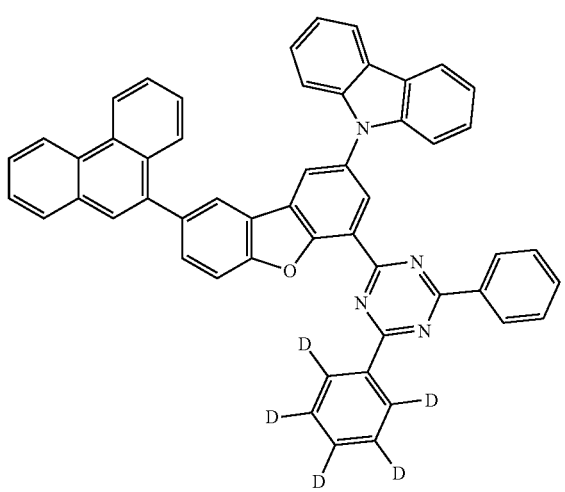
246
-continued
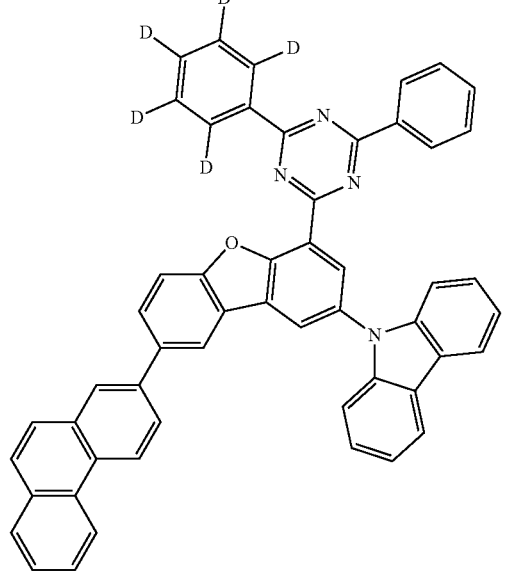
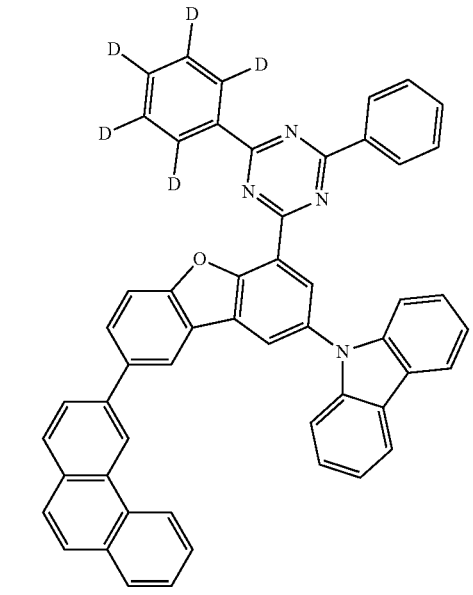

247
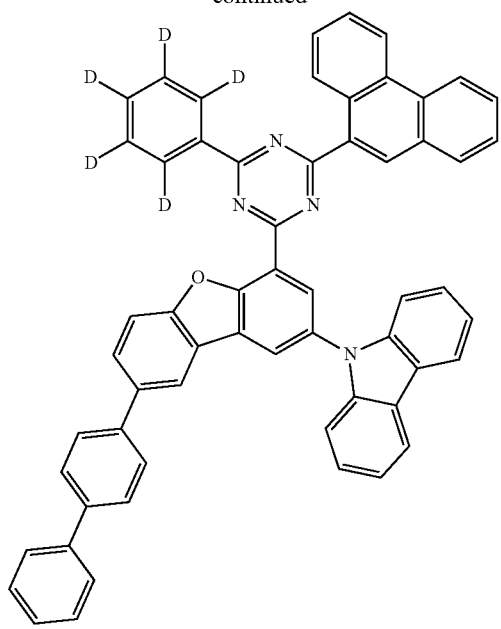
248
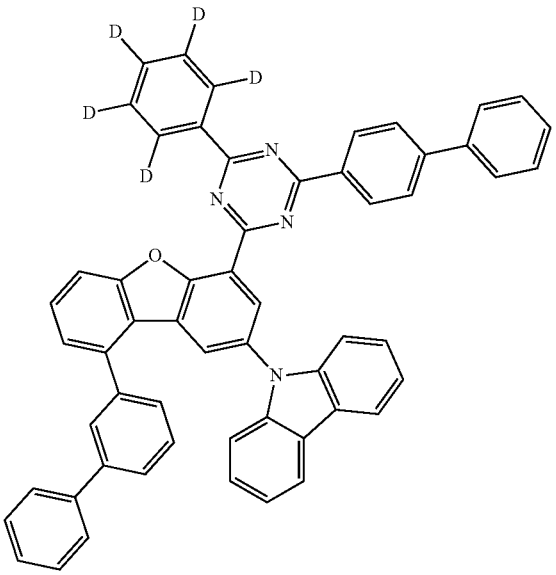
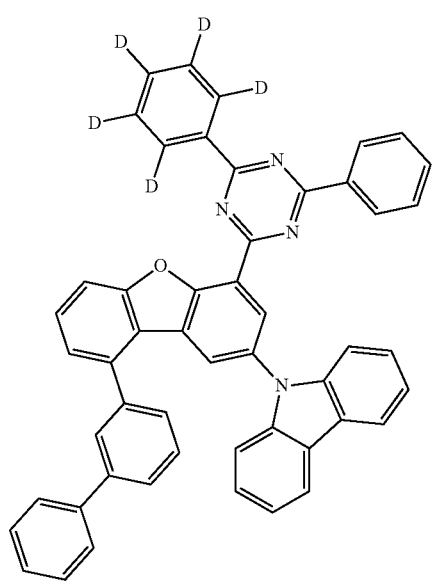
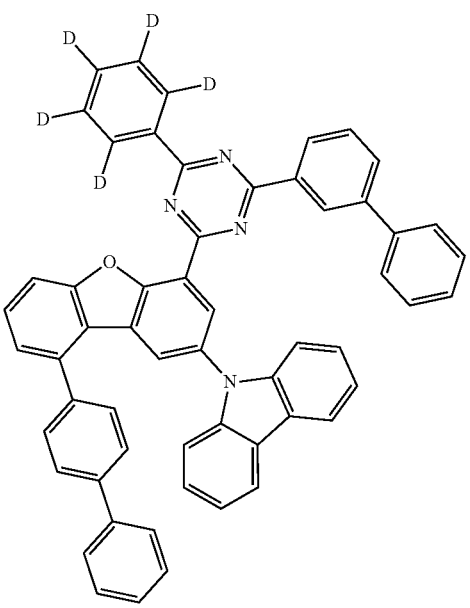

249
-continued
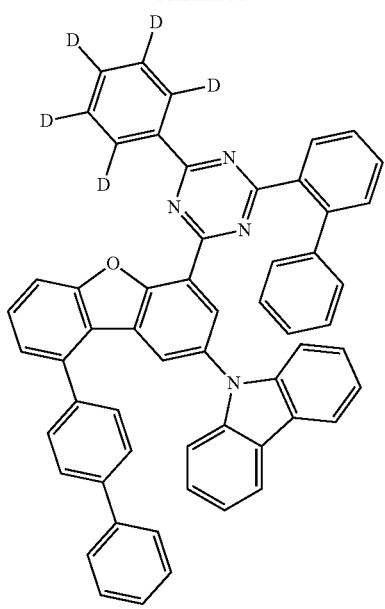
250
-continued
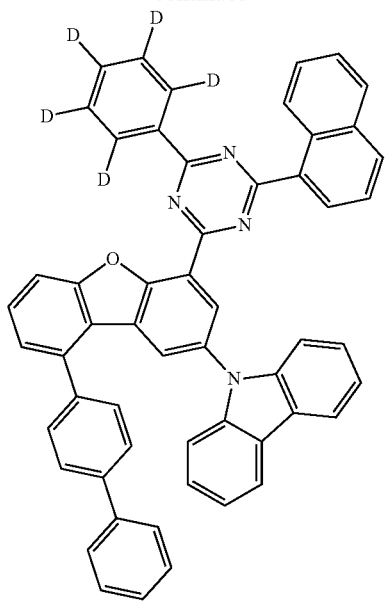
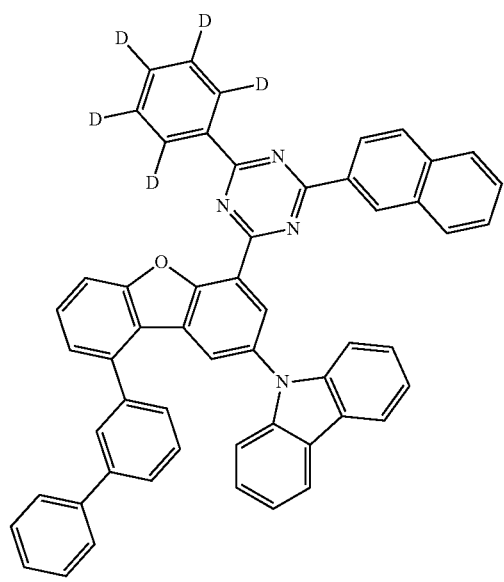
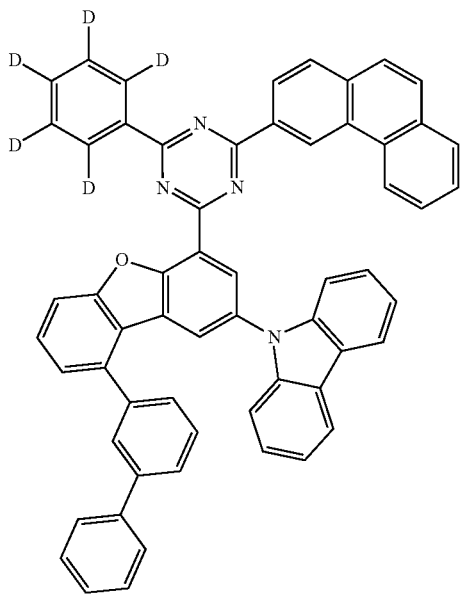

251
-continued
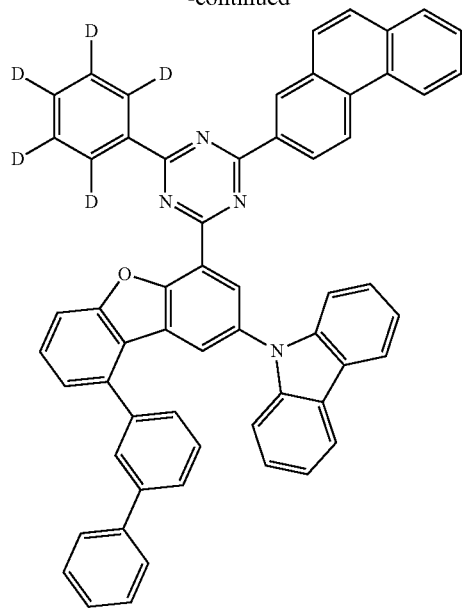
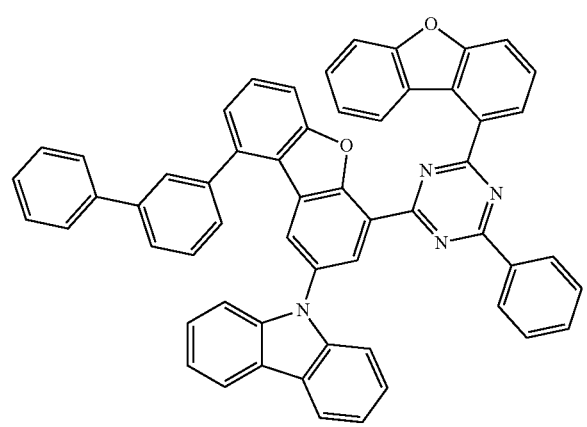
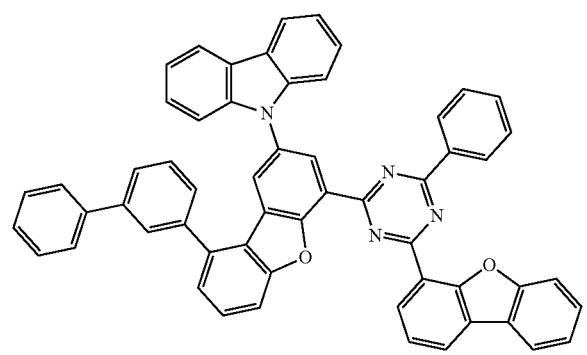
252
-continued
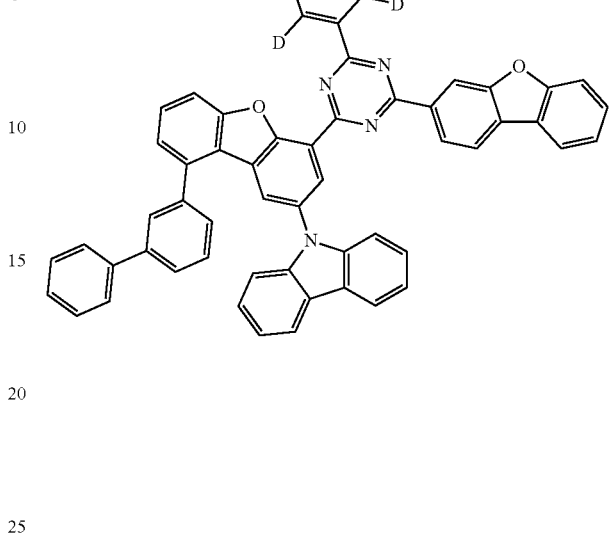
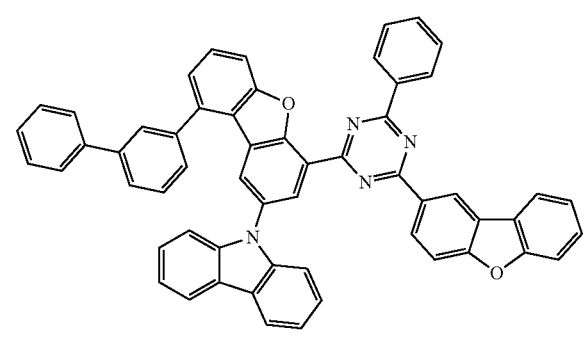
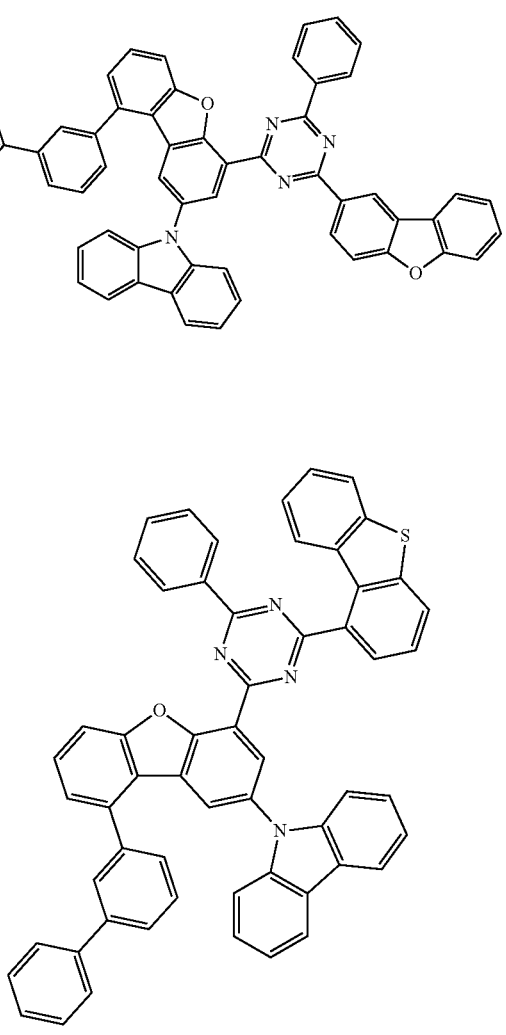

253
-continued
254
-continued
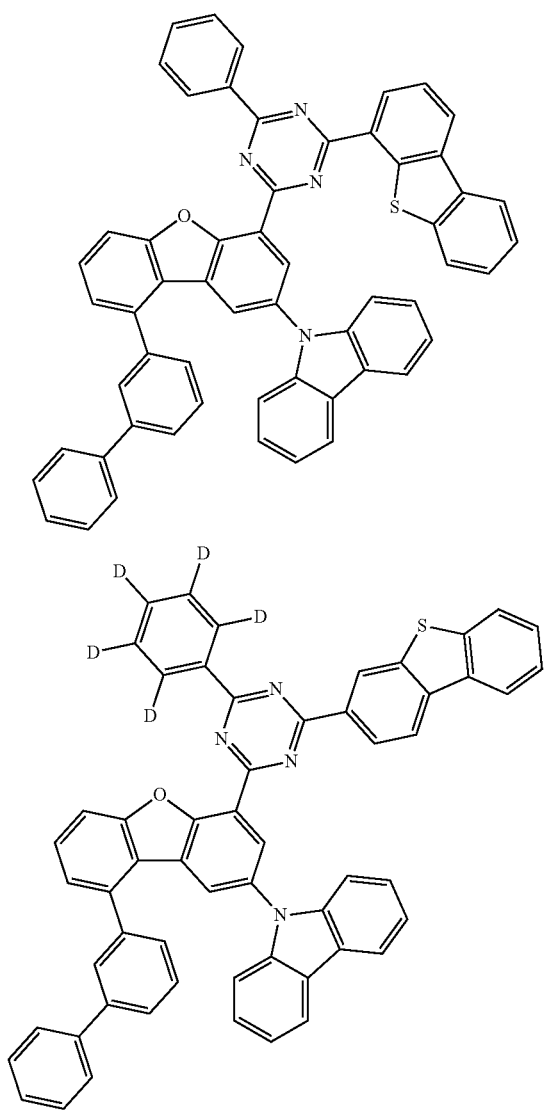

255
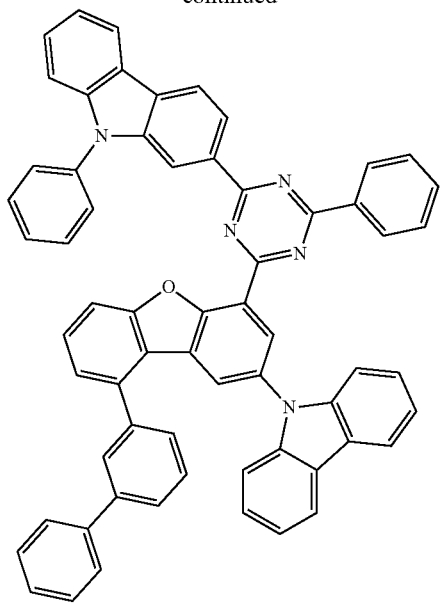
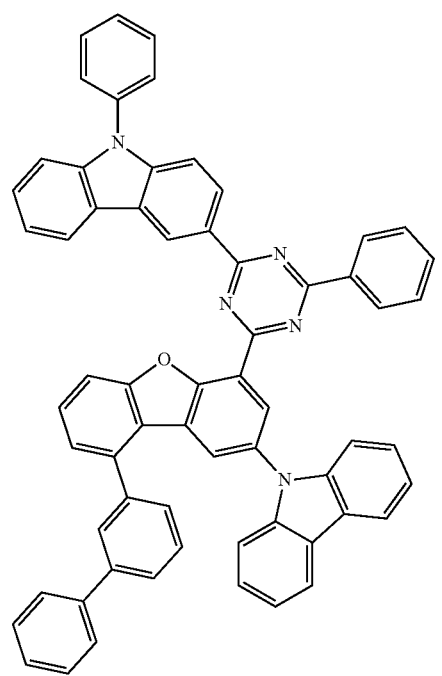
256
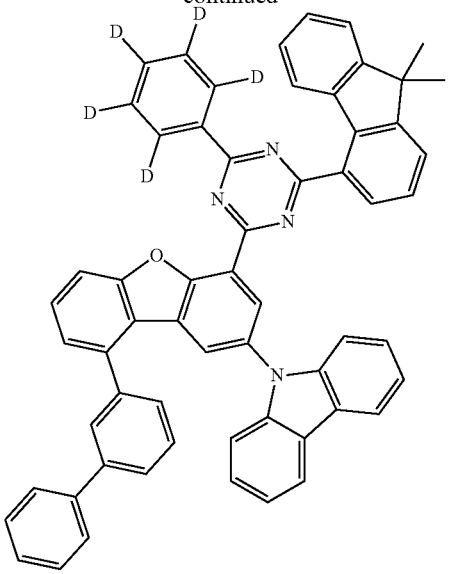
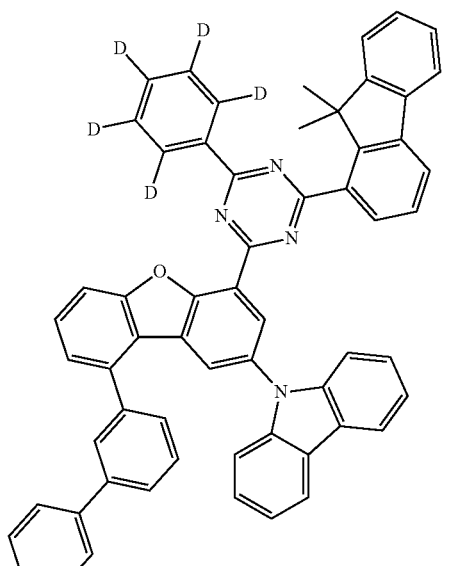
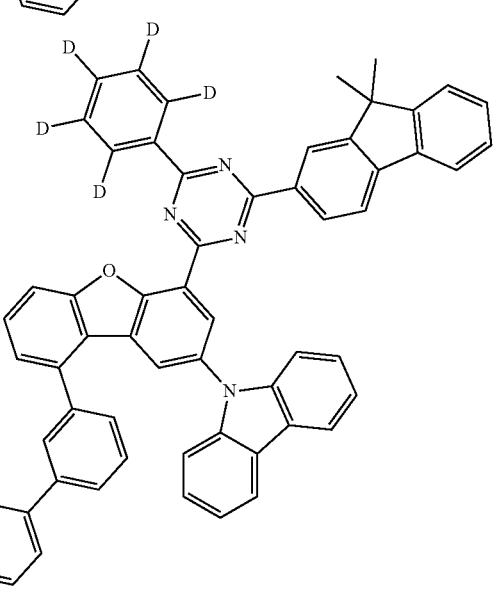

257
-continued
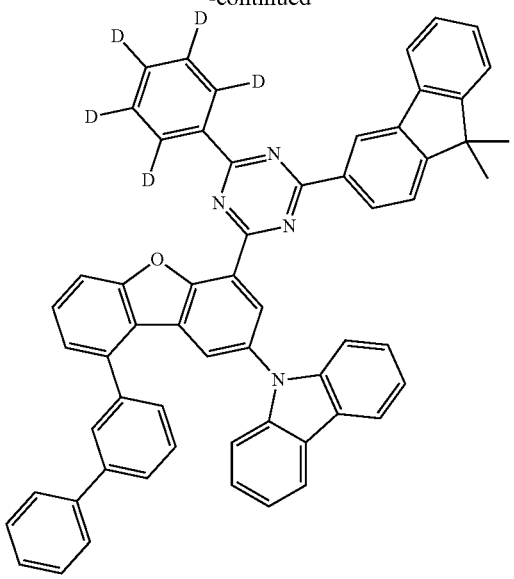
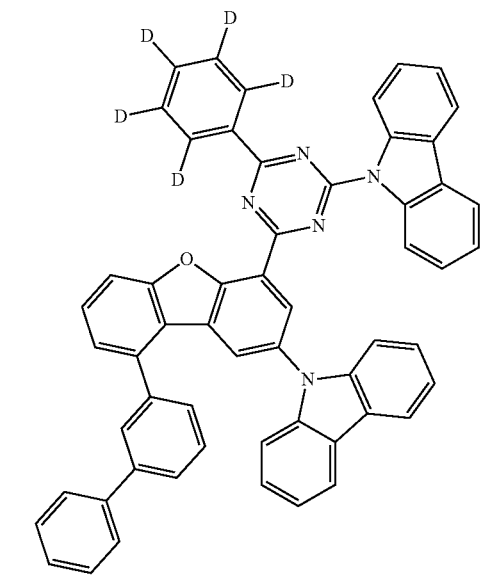
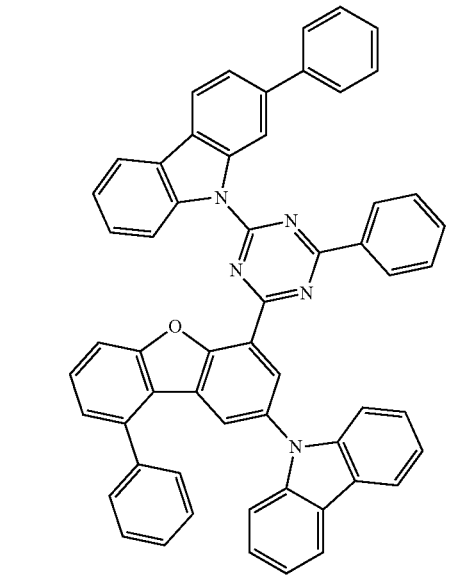
258
-continued
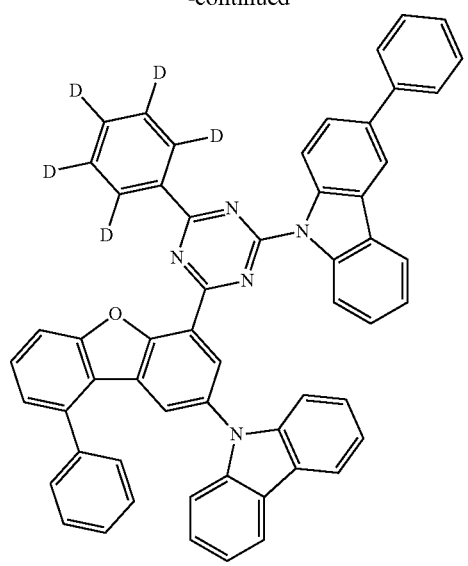
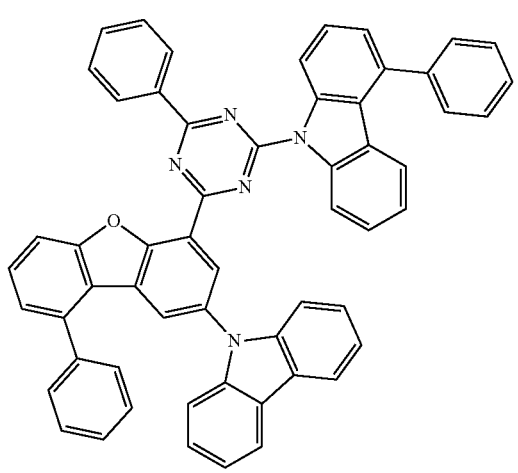
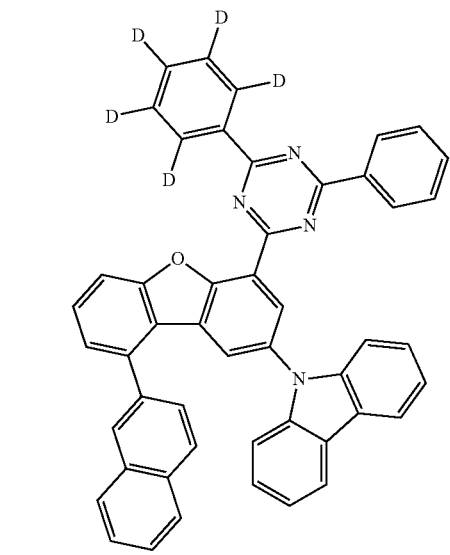

259
-continued
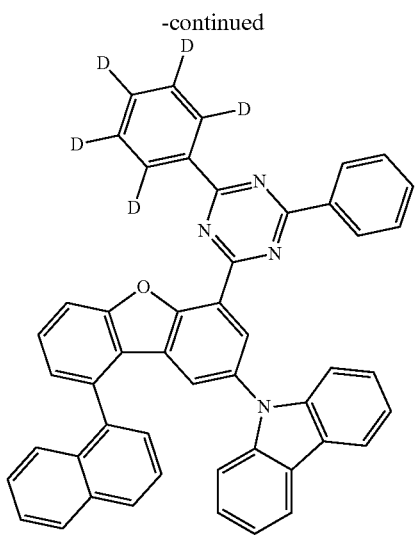
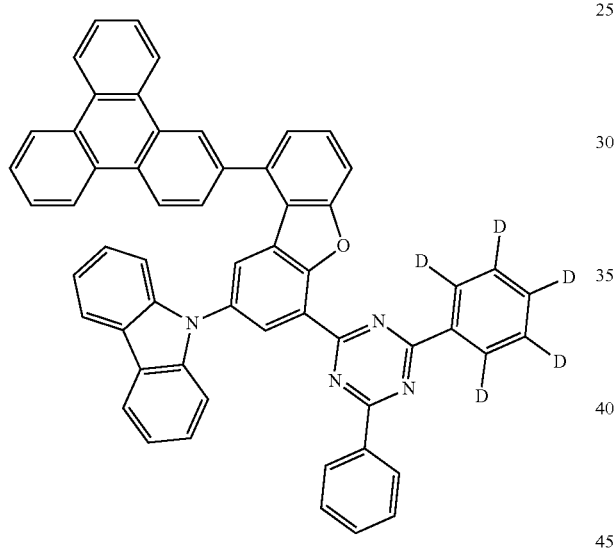
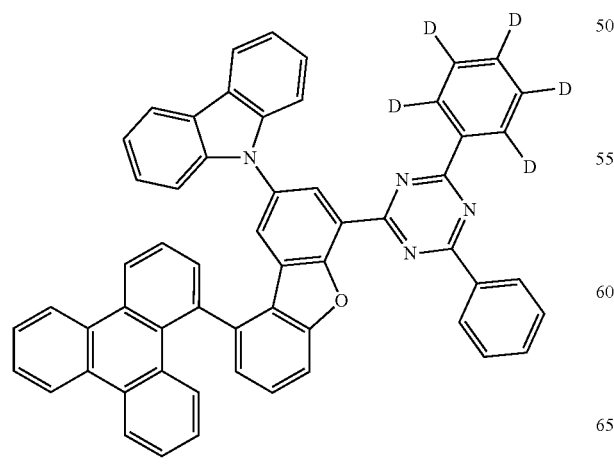
260
-continued
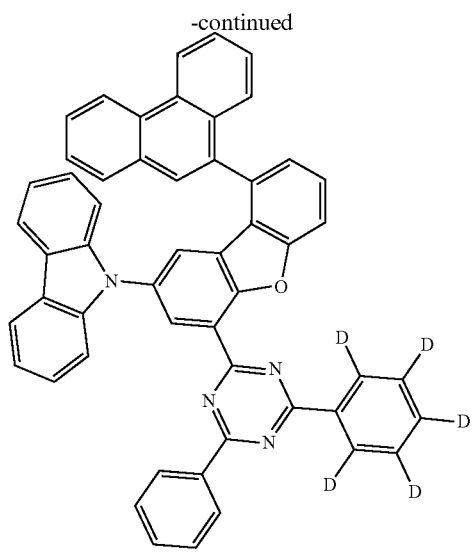
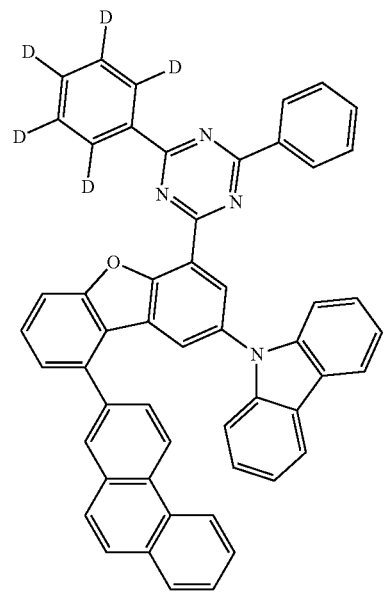
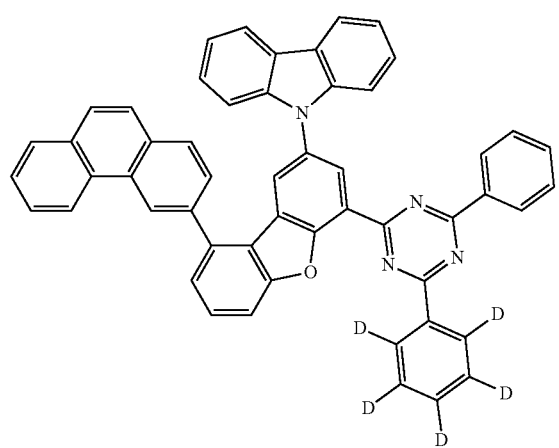

-continued

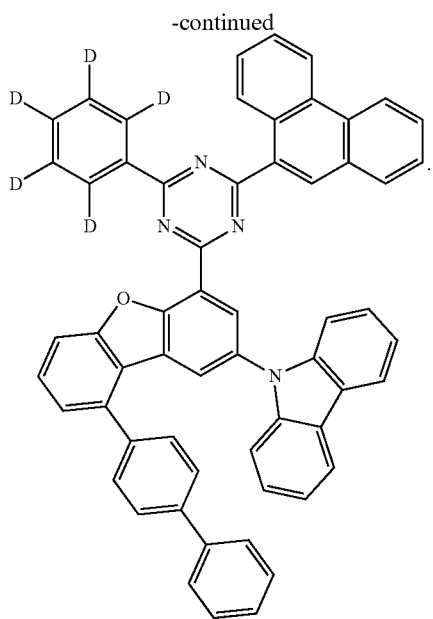

The compound of Chemical Formula 1 according to the present disclosure has structural properties that it simulataneously contains a carbazole-based substituent and a triazine (pyrimidine)-based substituent on one benzene ring of the core structure of dibenzofuran (dibenzothiophene), and contains an aryl substituent on the other benzene ring, and due to these properties, the compound can have improved thermal stability, and at the same time, can have high efficiency, low driving voltage, high luminance, and long lifetime. In particular, in the present disclosure, when $Ar_1$, $Ar_2$ and $Ar_3$ are the same or different substituted or unsubstituted $C_{6-60}$ aryl at the same time, any one of $Ar_1$, $Ar_2$ and $Ar_3$ is substituted with 4 or more deuteriums, which stabilizes LUMO. Thus, the present disclosure can have improved long lifetime properties as compared with an organic light-emitting device that employs a compound having a structure in which all of the terminal $Ar_1$, $Ar_2$ and $Ar_3$ are aryl, without being substituted with deuterium. In addition, as a heteroaryl group is substituted with a triazine having strong electronic properties, a balance between holes and electrons is appropriately aligned, which can be advantageous in terms of the efficiency and lifetime of a device.

The compound of Chemical Formula 1 can be prepared through the following Reaction Schemes 1-1 and 1-2.

Reaction Scheme 1-1

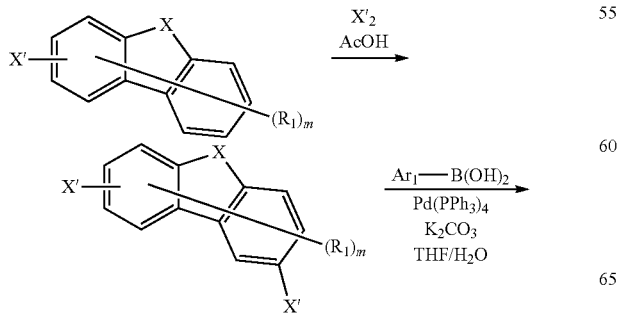

-continued

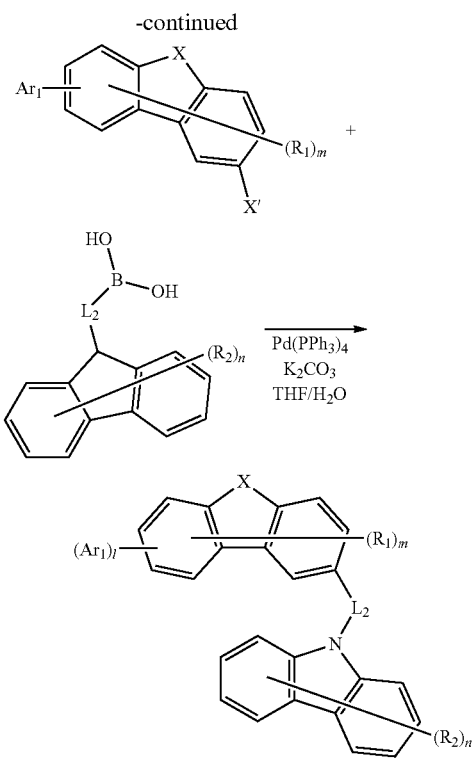

Reaction Scheme 1-2

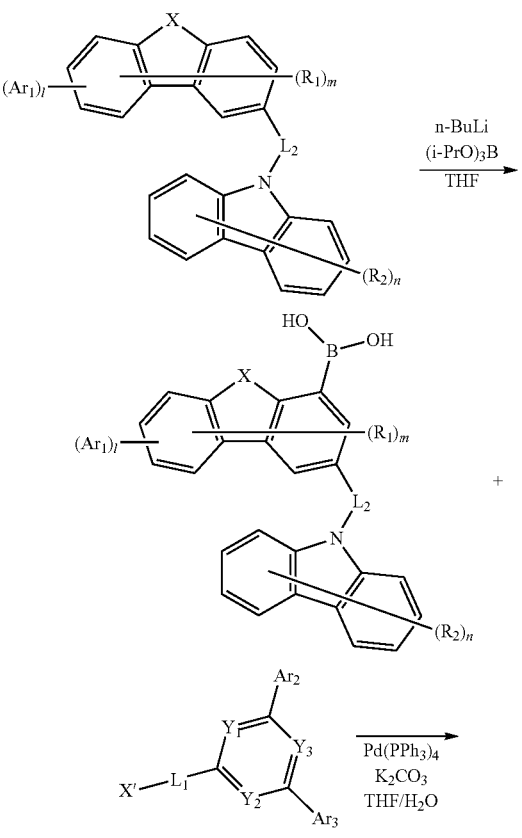

-continued

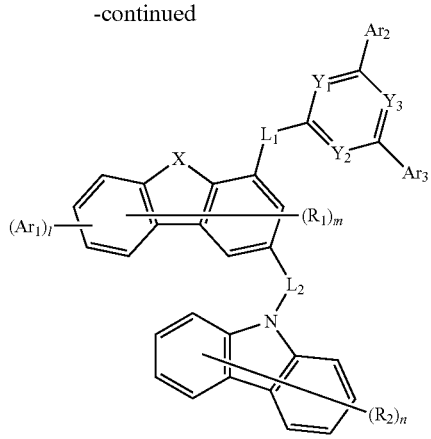

In Reaction Schemes 1-1 and 1-2, X' is halogen, preferably, bromo or chloro, and the definition of the remaining substituents is the same as defined above.

The above-mentioned reaction is a Suzuki coupling reaction, which is preferably carried out in the presence of a palladium catalyst and a base, and a reactant, catalyst and the like for the reaction can be modified as known in the art. The above preparation method can be further embodied in the Preparation Examples described hereinafter. In addition, when a plurality of substituents are introduced, it can be implemented by repeatedly performing the steps (for example, the introduction of a plurality of Ar1 can be implemented by performing the first step several times in Reaction Scheme 1-1. In this case, a protecting group and a deprotecting group reaction known in the art can also be performed together to introduce the desired structure.)

Another embodiment of the invention provides an organic light emitting device including a compound of Chemical Formula 1 described above. As an example, provided is an organic light emitting device including a first electrode; a second electrode that is provided opposite to the first electrode; and one or more organic material layers that are provided between the first electrode and the second electrode, wherein one or more layers of the organic material layers include the compound of Chemical Formula 1.

The organic material layer of the organic light emitting device of the present disclosure can have a single-layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport include the compound of Chemical Formula 1.

Further, the organic material layer can include a light emitting layer, wherein the light emitting layer includes the compound of Chemical Formula 1.

Further, the organic material layer can include an electron transport layer, or an electron injection layer, wherein the electron transport layer, or the electron injection layer includes the compound of Chemical Formula 1.

Further, the electron transport layer, the electron injection layer, and the layer for simultaneously performing electron injection and electron transport includes the compound of Chemical Formula 1. In particular, the compound of Chemical Formula 1 according to the present disclosure has excellent thermal stability, a deep HOMO level of 6.0 eV or higher, high triplet energy (ET) and hole stability. In addition, when the compound of Chemical Formula 1 is used for the organic material layer capable of simultaneously performing electron injection and electron transport, an n-type dopant used in the art can be mixed and used.

Further, the organic material layer includes a light emitting layer and an electron transport layer, wherein the electron transport layer can include a compound of Chemical Formula 1.

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Chemical Formula 1 can be included in one or more layers of the hole injection layer, the hole transport layer, the light emitting layer, and the electron transport layer.

The organic light emitting device according to the present disclosure can be manufactured by materials and methods known in the art, except that one or more layers of the organic material layers include the compound of Chemical Formula 1. In addition, when the organic light emitting device includes a plurality of organic material layers, the organic material layer can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as $LiF/Al$ or $LiO_2/Al$, and the like, but are not limited thereto.

The hole injection material is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole compound, a benzothiazole compound, a benzimidazole-based compound, a poly(p-phenylenevinylene)(PPV)-based polymer; a spiro compound, polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]-quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only and are not intended to limit the scope of the present disclosure.

PREPARATION EXAMPLES

Preparation Example 1-1: Preparation of Intermediate Compound B

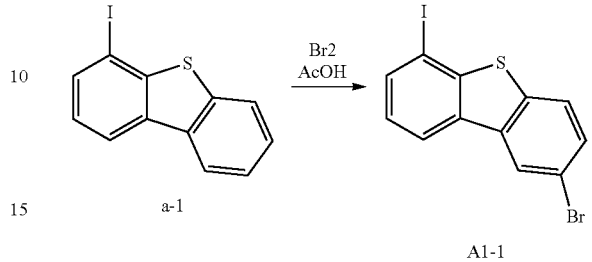

Compound a-1 (4-iododibenzothiophene) (20 g, 96.73 mmol) was added to a dried round flask under a nitrogen atmosphere and then 500 ml of chloroform was added thereto. Then, 2.5 eq of bromine (12.4 ml, 24.1 mmol) was added dropwise and reacted at room temperature for 12 hours. After completion of the reaction, the mixture was extracted with dichloromethane and an aqueous sodium thiosulfate solution, and the organic layer was dried over anhydrous magnesium sulfate and filtered. The filtered organic layer was concentrated under reduced pressure and then crystallized from ethyl acetate and hexane to give a white compound A1-1 (28 g, 75%, MS: [M+H]$^+$=388).

Preparation Examples 1-2 to 1-8: Preparation of Intermediate Compound B

Intermediate Compound B was prepared in the same manner as in the method for preparing Compound A1-1, except that the reactant A shown in Table 1 below was used instead of Compound a-1 (4-iododibenzothiophene) as the reactant in Preparation Example 1-1.

TABLE 1

| Category | Reactant A | Intermediate Compound B | Color | Yield (%) | MS: [M + H]$^+$ |
|---|---|---|---|---|---|
| Preparation Example 1-1 | a-1 | A1-1 | white | 75% | 388 |
| Preparation Example 1-2 | a-2 | A1-2 | white | 82% | 388 |

TABLE 1-continued
| Category | Reactant A | Intermediate Compound B | Color | Yield (%) | MS: [M + H]+ |
|---|---|---|---|---|---|
| Preparation Example 1-3 | 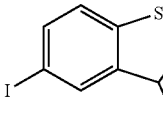 a-3 | 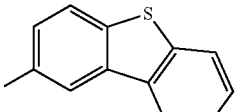 A1-3 | white | 69% | 388 |
| Preparation Example 1-4 | 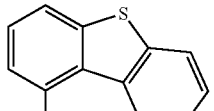 a-4 | 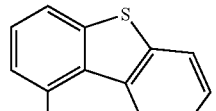 A1-4 | white | 71% | 388 |
| Preparation Example 1-5 | 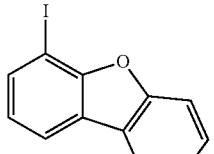 b-1 | 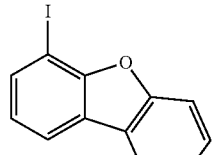 B1-1 | white | 55% | 388 |
| Preparation Example 1-6 | 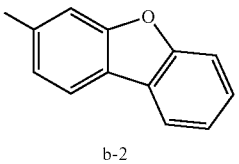 b-2 | 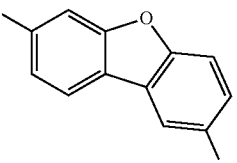 B1-2 | white | 60% | 388 |
| Preparation Example 1-7 | 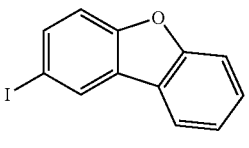 b-3 | 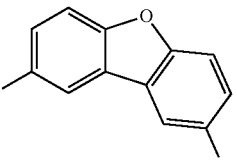 B1-3 | white | 62% | 388 |
| Preparation Example 1-8 | 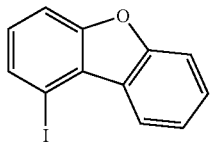 b-4 | 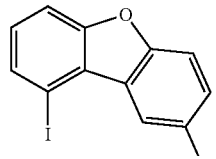 B1-4 | white | 59% | 388 |

Preparation Example 2-1: Preparation of Intermediate Compound D

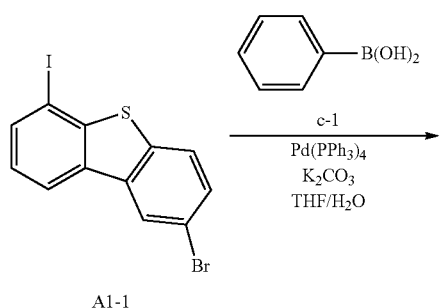

Compound A1-1 (20 g, 51.41 mmol) and Compound c-1 (phenylboronic acid) (6.27 g, 51.41 mmol) were dissolved in tetrahydrofuran (150 mL) under a nitrogen atmosphere, and then potassium carbonate (21.3 g, 154.2 mmol) was dissolved in water (50 mL) and added thereto, and tetrakis(triphenylphosphine)palladium (1.8 g, 1.54 mmol) was added, and the mixture was heated and stirred at 60° C. for 9 hours. The temperature was lowered to room temperature, and the reaction mixture was filtered, washed with water and ethanol, and dried to prepare Compound A2-1 (15.2 g, yield: 87%, MS: [M+H]$^+$=33 8).

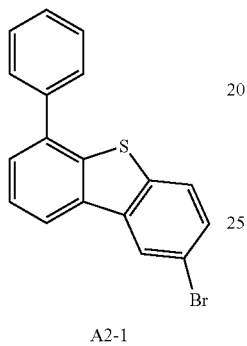

Preparation Examples 2-2 to 2-9: Preparation of Intermediate Compound D

Intermediate Compound D was prepared in the same manner as in Preparation Example 2-1, except that Intermediate Compound B and Intermediate Compound C shown in Table 2 below were used instead of Compound A1-1 and Compound c-1 (phenylboronic acid) in Preparation Example 2-1.

TABLE 2

| Category | Intermediate Compound B | Intermediate Compound C | Intermediate Compound D | Color | Yield | MS [M + H]$^+$ |
|---|---|---|---|---|---|---|
| Preparation Example 2-1 | A1-1 | c-1 | A2-1 | white | 87% | 338 |
| Preparation Example 2-2 | A1-1 | c-2 | A2-2 | white | 77% | 344 |

TABLE 2-continued

| Category | Intermediate Compound B | Intermediate Compound C | Intermediate Compound D | Color | Yield | MS [M + H]+ |
|---|---|---|---|---|---|---|
| Preparation Example 2-3 | A1-2 | c-3 | A2-3 | white | 89% | 415 |
| Preparation Example 2-4 | A1-3 | c-1 | A2-4 | white | 94% | 338 |
| Preparation Example 2-5 | A1-4 | c-1 | A2-5 | white | 81% | 338 |
| Preparation Example 2-6 | B1-1 | c-1 | B2-1 | white | 87% | 323 |
| Preparation Example 2-7 | B1-2 | c-1 | B2-2 | white | 92% | 323 |

TABLE 2-continued

| Category | Intermediate Compound B | Intermediate Compound C | Intermediate Compound D | Color | Yield | MS [M + H]+ |
|---|---|---|---|---|---|---|
| Preparation Example 2-8 | B1-3 | c-1 | B2-3 | white | 90% | 323 |
| Preparation Example 2-9 | B1-4 | c-2 | B2-4 | white | 89% | 328 |

Preparation Example 3-1: Preparation of Intermediate Compound F

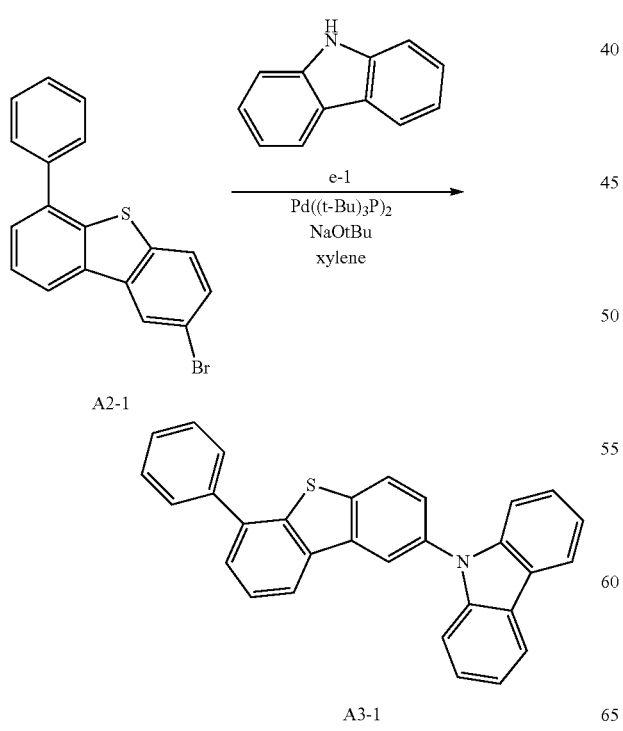

Compound A2-1 (15 g, 44.22 mmol) and Compound e-1 (9H-carbazole) (7.39 g, 44.22 mmol) were dissolved in xylene (150 mL) under a nitrogen atmosphere, to which NaOtBu (6.4 g, 66.32 mmol) was added and bis(tri-tert-butylphosphine)palladium(0) (0.7 g, 1.33 mmol) was added, and the mixture was heated and stirred for 12 hours. The temperature was lowered to room temperature, and the reaction mixture was filtered, washed with water and ethanol, and dried to prepare Compound A3-1 (13.9 g, yield: 74%, MS: [M+H]+=426).

Preparation Examples 3-2 to 3-10: Preparation of Intermediate Compound F

Intermediate Compound F was prepared in the same manner as in Preparation Example 3-1, except that Intermediate Compound D and Intermediate Compound E shown in Table 3 below were used instead of Compound A2-1 and Compound e-1 (phenylboronic acid) in Preparation Example 3-1.

TABLE 3

| Category | Intermediate Compound D | Intermediate Compound | Intermediate Compound F | Color | Yield | MS: [M + H]+ |
|---|---|---|---|---|---|---|
| Preparation Example 3-1 | A2-1 | e-1 | A3-1 | yellow | 74% | 426 |
| Preparation Example 3-2 | A2-1 | e-2 | A3-2 | yellow | 75% | 591 |
| Preparation Example 3-3 | A2-2 | e-1 | A3-3 | yellow | 72% | 431 |
| Preparation Example 3-4 | A2-3 | e-1 | A3-4 | yellow | 65% | 502 |
| Preparation Example 3-5 | A2-4 | e-1 | A3-5 | yellow | 88% | 426 |

TABLE 3-continued
| Category | Intermediate Compound D | Intermediate Compound | Intermediate Compound F | Color | Yield | MS: [M + H]+ |
|---|---|---|---|---|---|---|
| Preparation Example 3-6 | 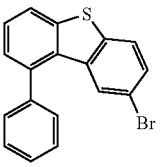<br>A2-5 | 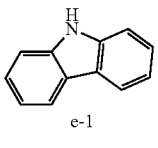 [SMILES: c1ccc2c(c1)[nH]c1ccccc12]<br>e-1 | 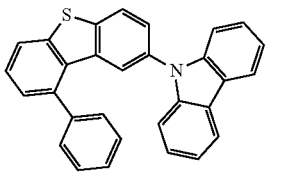<br>A3-6 | yellow | 72% | 338 |
| Preparation Example 3-7 | 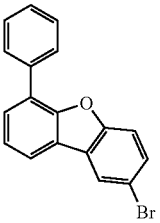<br>B2-1 | 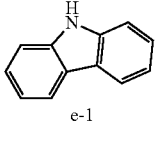<br>e-1 | 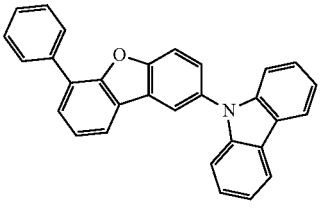<br>B3-1 | yellow | 86% | 410 |
| Preparation Example 3-8 | 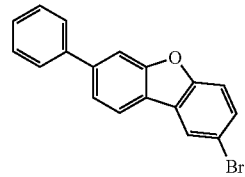<br>B2-2 | 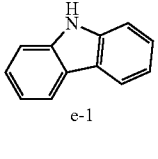<br>e-1 | 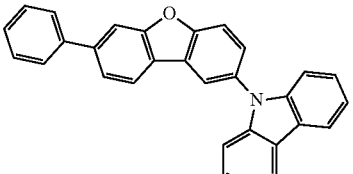<br>B3-2 | yellow | 81% | 410 |
| Preparation Example 3-9 | 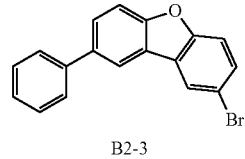 [SMILES: Brc1ccc2oc3ccc(-c4ccccc4)cc3c2c1]<br>B2-3 | 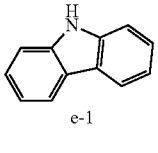<br>e-1 | 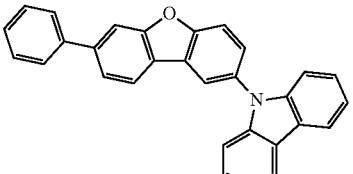<br>B3-3 | yellow | 79% | 410 |
| Preparation Example 3-10 | 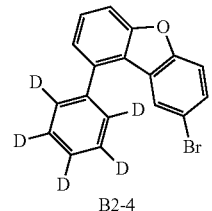 [SMILES: [2H]c1c([2H])c([2H])c(-c2cccc3oc4ccc(Br)cc4c23)c([2H])c1[2H]]<br>B2-4 | 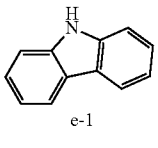<br>e-1 | 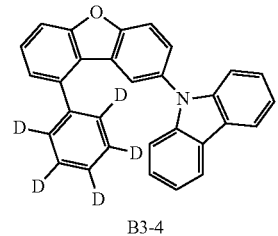 [SMILES: [2H]c1c([2H])c([2H])c(-c2cccc3oc4ccc(-n5c6ccccc6c6ccccc65)cc4c23)c([2H])c1[2H]]<br>B3-4 | yellow | 77% | 415 |

Preparation Example 4-1: Preparation of Compound A1-4

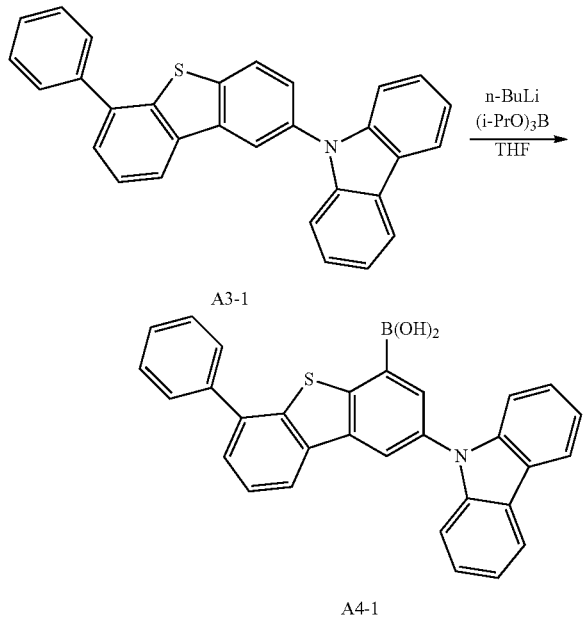

A3-1

A4-1

Compound A3-1 (14 g, 32.90 mmol) was dissolved in 150 mL of THF in a dried round bottom flask under a nitrogen atmosphere, to which 1.6M n-BuLi (26.73 mL, 42.77 mmol) was slowly added dropwise at −78° C., and the mixture was stirred at room temperature for 1 hour. Isopropylborate (i-PrO)3B (26.5 mL, 115.1 mmol) was added dropwise to the reaction mixture at −78° C., and then stirred at room temperature for 1 hour. After completion of the reaction, the mixture was extracted with an aqueous ammonium chloride solution at room temperature, and the organic layer was dried over MgSO$_4$, concentrated, and recrystallized from ethyl acetate to give Compound A4-1. (10 g, yield: 65%, MS: [M+H]$^+$=470)

Preparation Examples 4-2 to 4-10: Preparation of Intermediate Compound G

Intermediate Compound G was prepared in the same manner as in Preparation Example 4-1, except that Intermediate Compound F shown in Table 4 below was used instead of Compound A3-1 in Preparation Example 4-1.

TABLE 4

| Category | Intermediate Compound F | Intermediate Compound G | Color | Yield | MS [M + H]$^+$ |
|---|---|---|---|---|---|
| Preparation Example 4-1 | A3-1 | A4-1 | white | 65% | 470 |

TABLE 4-continued

| Category | Intermediate Compound F | Intermediate Compound G | Color | Yield | MS [M + H]+ |
|---|---|---|---|---|---|
| Preparation Example 4-2 | A3-2 | A4-2 | white | 62% | 635 |
| Preparation Example 4-3 | A3-3 | A4-3 | white | 69% | 475 |
| Preparation Example 4-4 | A3-4 | A4-4 | white | 70% | 546 |
| Preparation Example 4-5 | A3-5 | A4-5 | white | 67% | 470 |

TABLE 4-continued

| Category | Intermediate Compound F | Intermediate Compound G | Color | Yield | MS [M + H]+ |
|---|---|---|---|---|---|
| Preparation Example 4-6 | A3-6 | A4-6 | white | 63% | 470 |
| Preparation Example 4-7 | B3-1 | B4-1 | white | 71% | 454 |
| Preparation Example 4-8 | B3-2 | B4-2 | white | 76% | 454 |
| Preparation Example 4-9 | B3-3 | B4-3 | white | 59% | 454 |
| Preparation Example 4-10 | B3-4 | B4-4 | white | 77% | 459 |

EXAMPLES

Example 1: Preparation of Compound 1

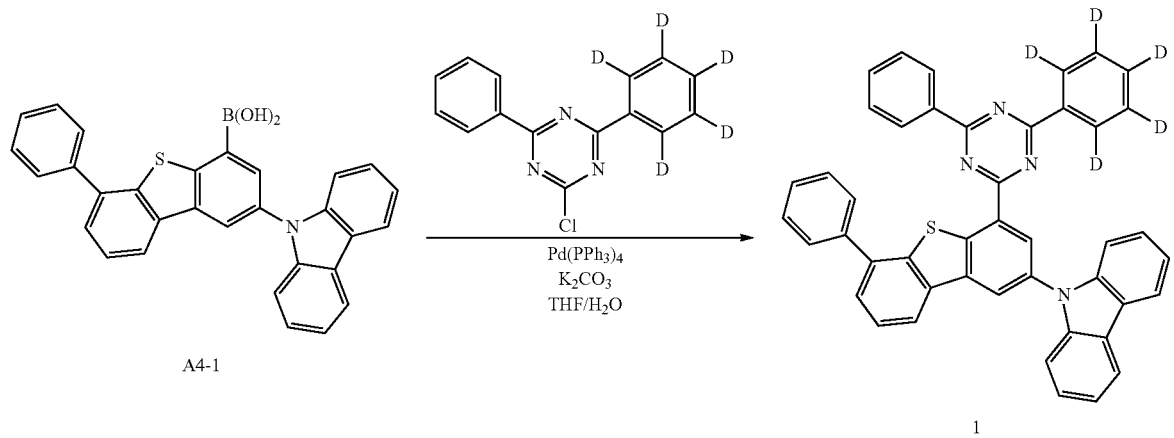 [SMILES: OB(O)c1cc(-n2c3ccccc3c3ccccc32)cc2c1sc1c(-c3ccccc3)cccc12 ; [2H]c1c([2H])c([2H])c(-c2nc(Cl)nc(-c3ccccc3)n2)c([2H])c1[2H] ; [2H]c1c([2H])c([2H])c(-c2nc(-c3ccccc3)nc(-c3cc(-n4c5ccccc5c5ccccc54)cc4c3sc3c(-c5ccccc5)cccc34)n2)c([2H])c1[2H]]

After Compound A4-1 (15 g, 31.96 mmol) and 2-chloro-4-phenyl-6-(phenyl-d5)-1,3,5-triazine (8.71 g, 31.96 mmol) were dissolved in THF (150 mL), potassium carbonate (13.3 g, 211.10 mmol) was added and tetrakis(triphenylphosphine)palladium (1.1 g, 0.96 mmol) was added, and the mixture was heated and stirred for 8 hours. The temperature was lowered to room temperature and the aqueous layer was separated and removed. The result was dried over anhydrous magnesium sulfate, filtered, concentrated under reduced pressure, recrystallized using ethyl acetate, filtered and dried to prepare Compound 1 (15.7 g, yield: 74%, MS: $[M+H]^+=662$).

Example 2: Preparation of Compound 2

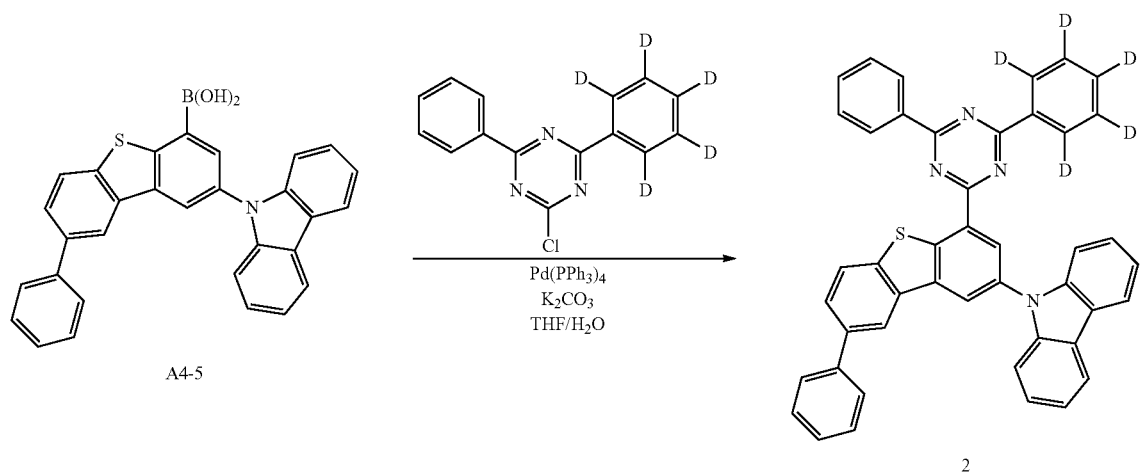 [SMILES: OB(O)c1cc(-n2c3ccccc3c3ccccc32)cc2c1sc1ccc(-c3ccccc3)cc12 ; [2H]c1c([2H])c([2H])c(-c2nc(Cl)nc(-c3ccccc3)n2)c([2H])c1[2H] ; [2H]c1c([2H])c([2H])c(-c2nc(-c3ccccc3)nc(-c3cc(-n4c5ccccc5c5ccccc54)cc4c3sc3ccc(-c5ccccc5)cc34)n2)c([2H])c1[2H]]

Compound 2 was prepared in the same manner as in the method for preparing Compound 1, except that Compound A4-5 was used instead of Compound A4-1. (15.0 g, yield: 71%; MS: $[M+H]^+=662$)

Example 3: Preparation of Compound 3
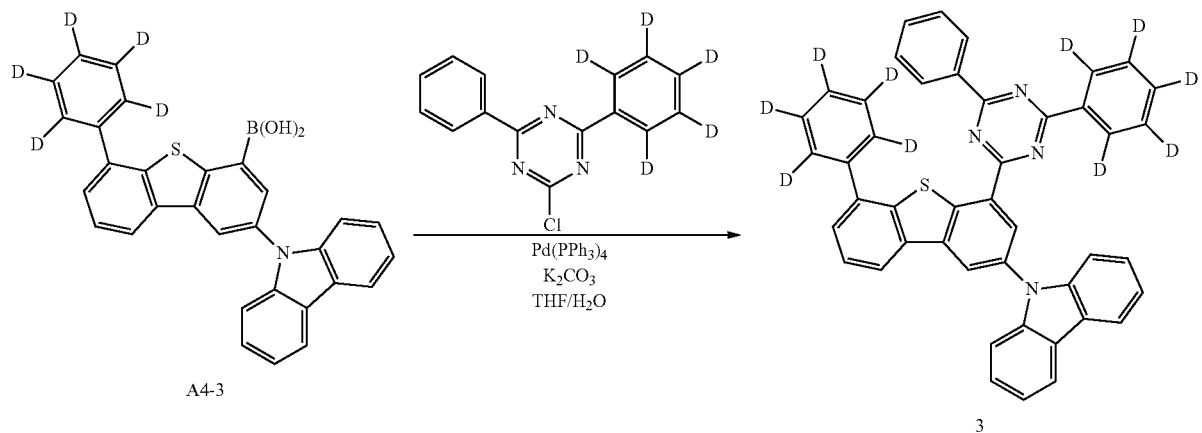 [SMILES: [2H]c1c([2H])c([2H])c(-c2cccc3c2sc2c(B(O)O)cc(-n4c5ccccc5c5ccccc54)cc23)c([2H])c1[2H] ; [2H]c1c([2H])c([2H])c(-c2nc(Cl)nc(-c3ccccc3)n2)c([2H])c1[2H] ; [2H]c1c([2H])c([2H])c(-c2nc(-c3ccccc3)nc(-c3cc(-n4c5ccccc5c5ccccc54)cc4c3sc3c(-c5c([2H])c([2H])c([2H])c([2H])c5[2H])cccc34)n2)c([2H])c1[2H]]
Compound 3 was prepared in the same manner as the method for preparing Compound 1, except that Compound A4-3 was used instead of Compound A4-1. (15.0 g, yield: 71%; MS: [M+H]$^+$=667)
Example 4: Preparation of Compound 4
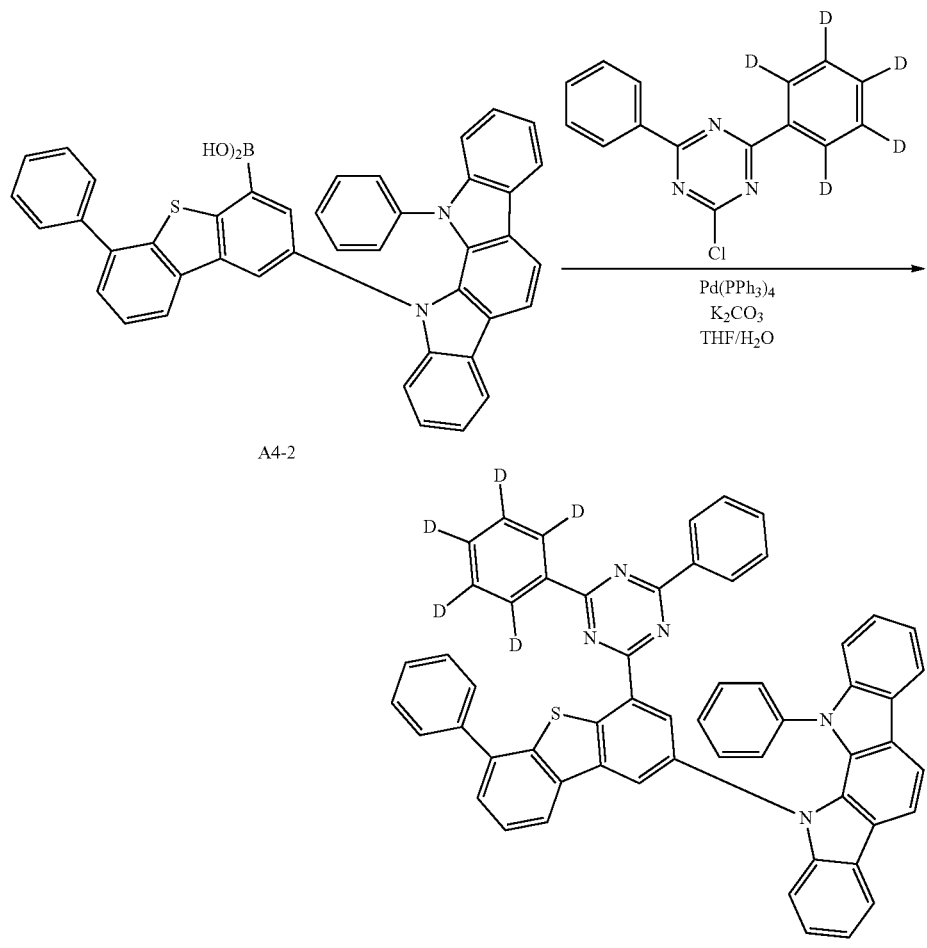

Compound 4 was prepared in the same manner as in the method for preparing Compound 1, except that Compound A4-2 was used instead of Compound A4-1. (16.0 g, yield: 82%; MS: [M+H]⁺=827)

Example 5: Preparation of Compound 5

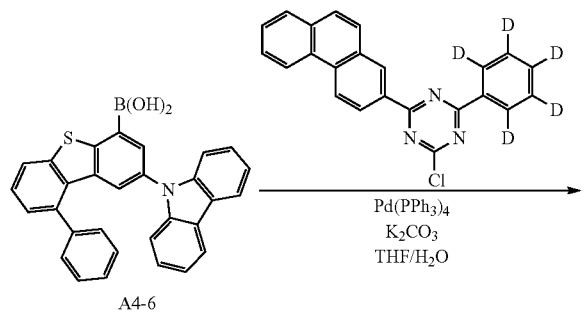

A4-6

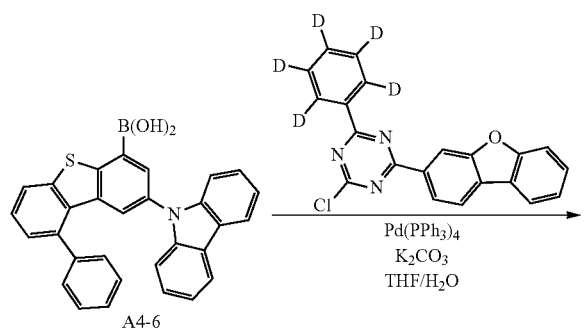

5

Compound 5 was prepared in the same manner as in the method for preparing Compound 1, except that Compounds A4-6 and 2-chloro-4-(phenanthren-2-yl)-6-(phenyl-d5)-1,3,5-triazine were used instead of Compounds A4-2 and 2-chloro-4-phenyl-6-(phenyl-d5)-1,3,5-triazine. (16.0 g, yield: 82%; MS: [M+H]⁺=827)

Example 6: Preparation of Compound 6

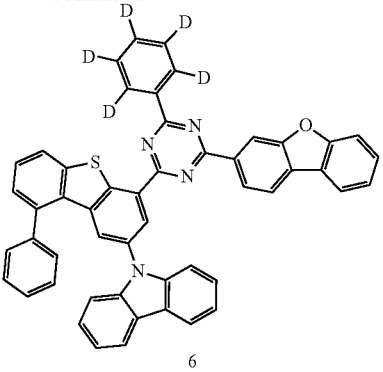

6

Compound 6 was prepared in the same manner as the method for preparing Compound 1, except that Compound A4-6 and 2-chloro-4-(dibenzo[b,d]furan-3-yl)-6-(phenyl-d5)-1,3,5-triazine were used instead of Compound A4-1 and 2-chloro-4-phenyl-6-(phenyl-d5)-1,3,5-triazine. (17.8 g, yield: 74%; MS: [M+H]⁺=752)

Example 7: Preparation of Compound 7

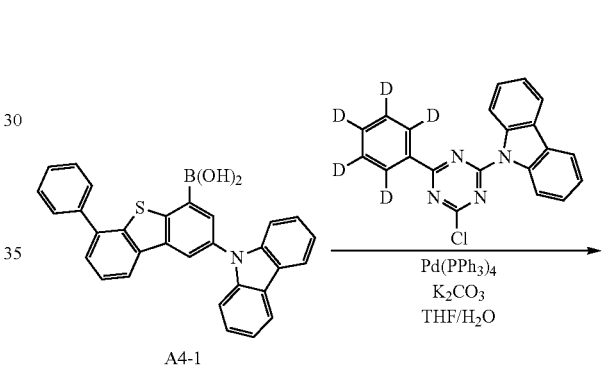

A4-1

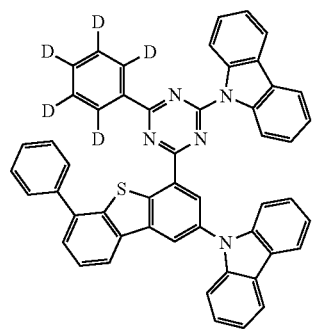

7

Compound 7 was prepared in the same manner as in the method for preparing Compound 1, except that 9-(4-chloro-6-(phenyl-d5)-1,3,5-triazin-2-yl)-9H-carbazole was used instead of 2-chloro-4-phenyl-6-(phenyl-d5)-1,3,5-triazine. (16.5 g, yield: 69%; MS: [M+H]⁺=751)

Example 8: Preparation of Compound 8
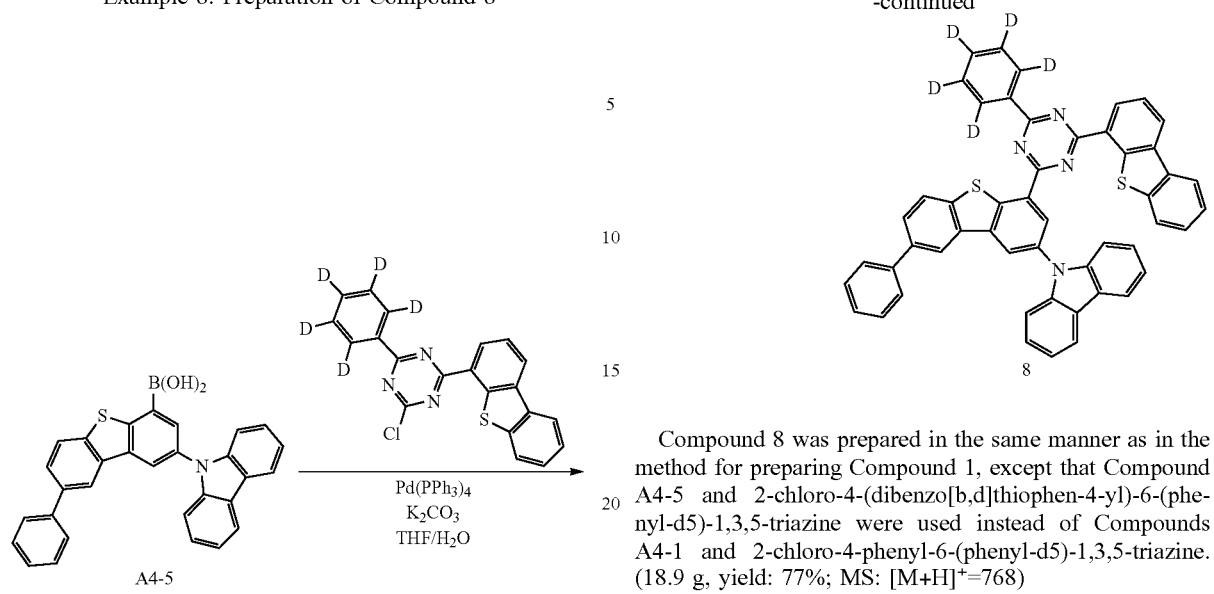
Compound 8 was prepared in the same manner as in the method for preparing Compound 1, except that Compound A4-5 and 2-chloro-4-(dibenzo[b,d]thiophen-4-yl)-6-(phenyl-d5)-1,3,5-triazine were used instead of Compounds A4-1 and 2-chloro-4-phenyl-6-(phenyl-d5)-1,3,5-triazine. (18.9 g, yield: 77%; MS: [M+H]$^+$=768)
Example 9: Preparation of Compound 9

Compound 9 was prepared in the same manner as in the method for preparing Compound 1, except that Compound A4-4 and 9-(4-chloro-6-(phenyl-d5)-1,3,5-triazin-2-yl)-9H-carbazole were used instead of Compound A4-1 and 2-chloro-4-phenyl-6-(phenyl-d5)-1,3,5-triazine. (14.8 g, yield: 65%; MS: [M+H]⁺=827)

Example 10: Preparation of Compound 10

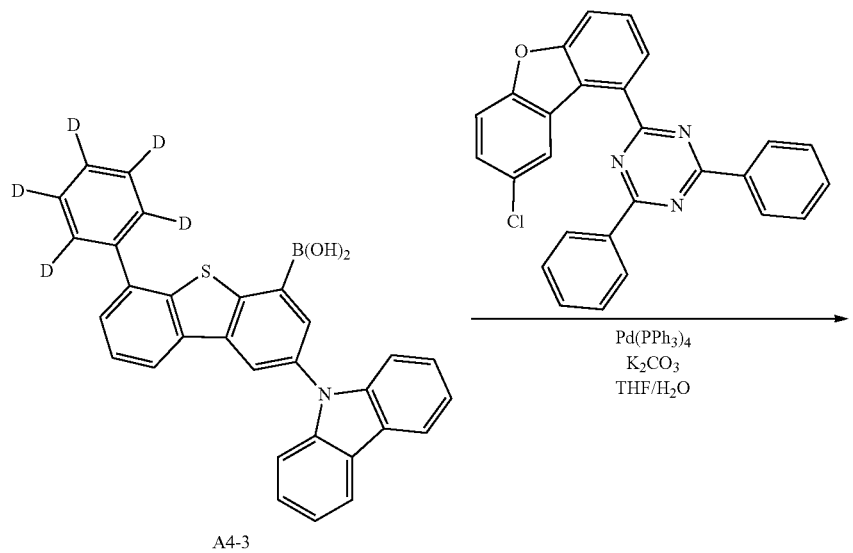

Compound 10 was prepared in the same manner as in the method for preparing Compound 1, except that Compound A4-3 and 2-(8-chlorodibenzo[b,d]furan-1-yl)-4,6-diphenyl-1,3,5-triazine were used instead of Compound A4-1 and 2-chloro-4-phenyl-6-(phenyl-d5)-1,3,5-triazine. (18.3 g, yield 70%; MS: [M+H]⁺=828)

Example 11: Preparation of Compound 11
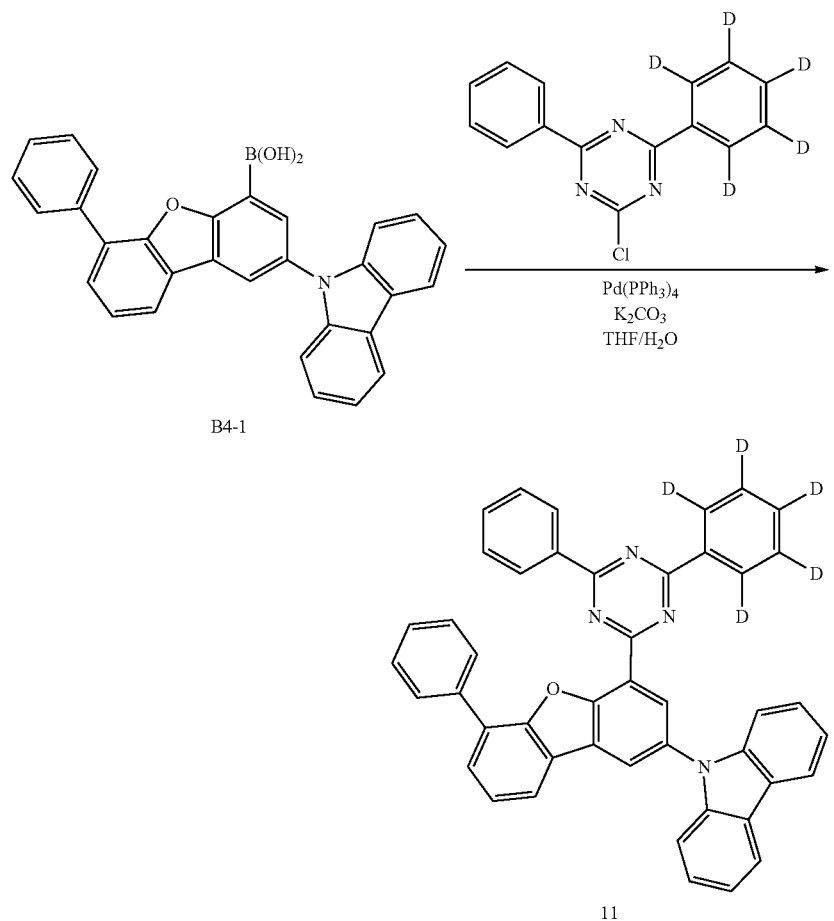
Compound 11 was prepared in the same manner as in the method for preparing Compound 1, except that Compound B4-1 was used instead of Compound A4-1. (16.2 g, yield: 76%; MS: [M+H]$^+$=646)
Example 12: Preparation of Compound 12
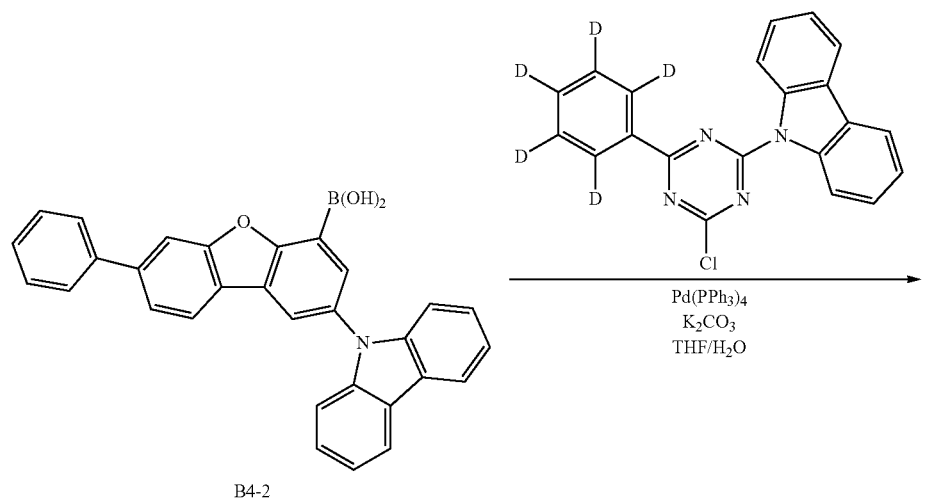

-continued
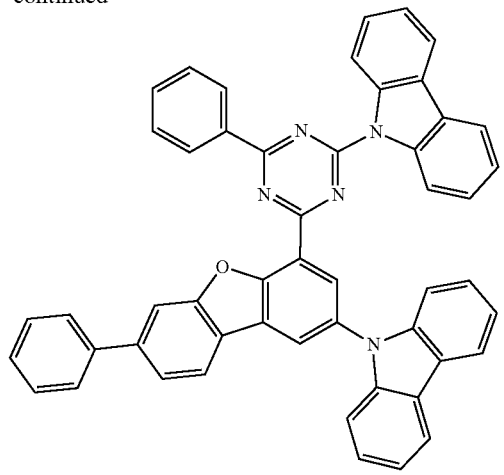
12
Compound 12 was prepared in the same manner as in the method for preparing Compound 1, except that Compounds B4-2 and 9-(4-chloro-6-(phenyl-d5)-1,3,5-triazin-2-yl)-9H-carbazole were used instead of Compound A4-1 and 2-chloro-4-phenyl-6-(phenyl-d5)-1,3,5-triazine. (19.3 g, yield: 80%; MS: [M+H]$^+$=730)
Example 13: Preparation of Compound 13
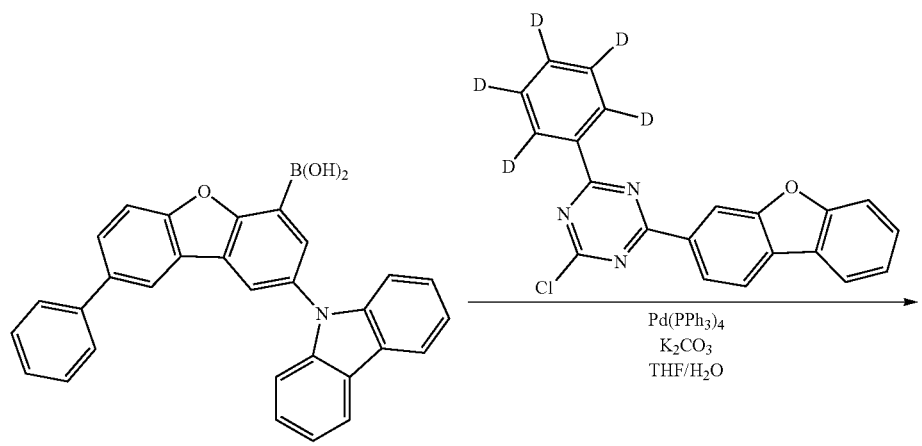
B4-3

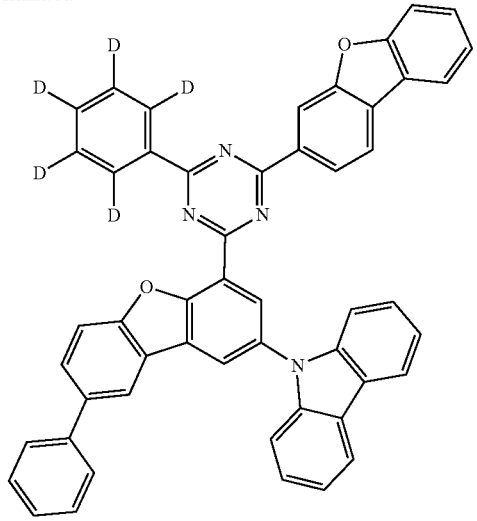
13
Compound 13 was prepared in the same manner as in the method for preparing Compound 1, except that Compound B4-3 and 2-chloro-4-(dibenzo[b,d]furan-3-yl)-6-(phenyl-d5)-1,3,5-triazine were used instead of Compound A4-1 and 2-chloro-4-phenyl-6-(phenyl-d5)-1,3,5-triazine. (16.6 g, yield: 68%; MS: [M+H]⁺=736)
Example 14: Preparation of Compound 14
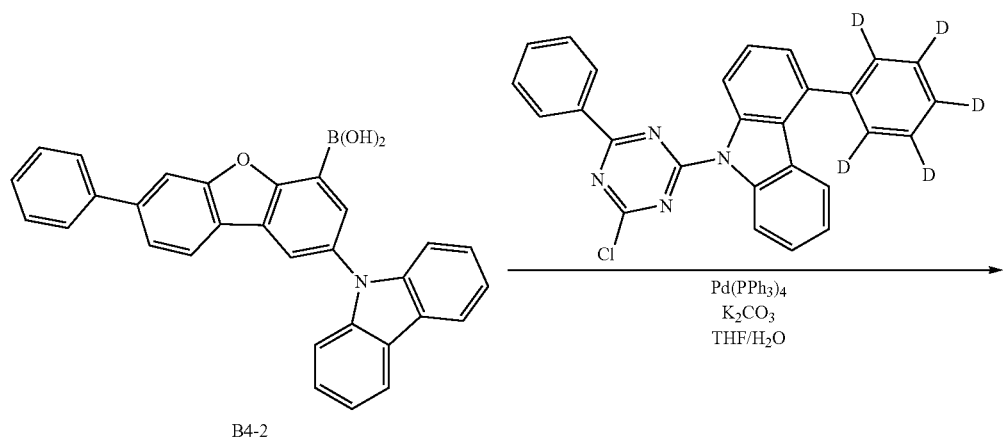
B4-2

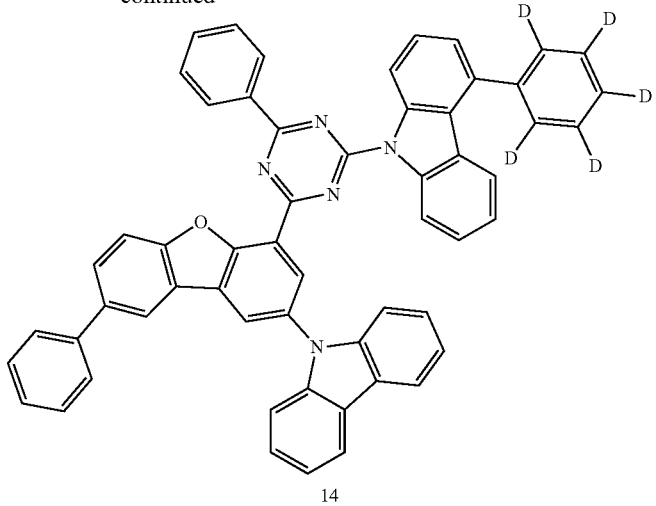

14

Compound 14 was prepared in the same manner as in the method for preparing Compound 1, except that Compounds B4-2 and 9-(4-chloro-6-phenyl-1,3,5-triazin-2-yl)-4-(phenyl-d5)-9H-carbazole were used instead of Compound A4-1 and 2-chloro-4-phenyl-6-(phenyl-d5)-1,3,5-triazine. (19.3 g, yield: 72%; MS: [M+H]$^+$=811)

Example 15: Preparation of Compound 15

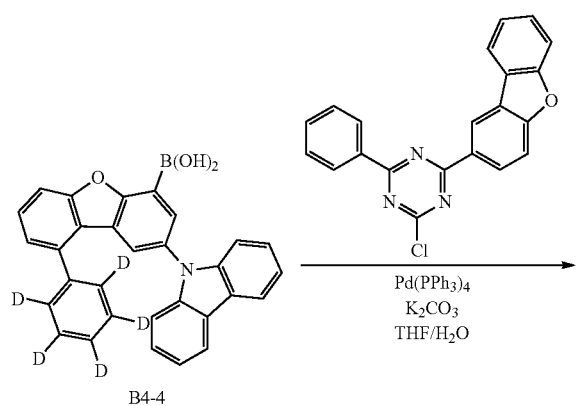

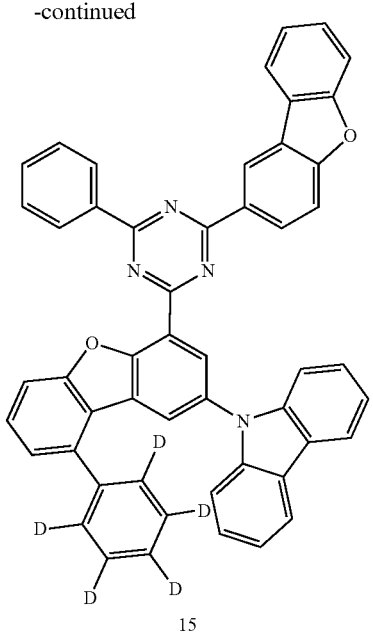

15

Compound 15 was prepared in the same manner as in the method for preparing Compound 1, except that Compound B4-4 and 2-chloro-4-(dibenzo[b,d]furan-3-yl)-6-(phenyl-d5)-1,3,5-triazine were used instead of Compound A4-4 and 2-chloro-4-phenyl-6-(phenyl-d5)-1,3,5-triazine. (18.8 g, yield: 78%; MS: [M+H]$^+$=736)

EXPERIMENTAL EXAMPLES

Experimental Example 1

A glass substrate on which ITO (indium tin oxide) was coated as a thin film to a thickness of 130 nm was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, the following compound HI-1 was thermally vacuum-deposited to a thickness of 5 nm to form a hole injection layer. The following compound HT-1 was thermally vacuum-deposited on the hole injection layer to a thickness of 25 nm to form a hole transport layer, and the following compound HT-2 was vacuum-deposited on the HT-1 deposited layer to a thickness of 5 nm to form an electron blocking layer. Then, the compound 1 previously prepared and the following compound Dp-25 were co-deposited in a weight ratio of 88:12 on the HT-2 deposited layer to form a light emitting layer with a thickness of 40 nm. The following compound ET-1 was vacuum-deposited on the light emitting layer to a thickness of 25 nm to form an electron transport layer, and the following compound ET-2 and LiQ were vacuum-deposited (thickness of 10 nm) in a weight ratio of 98:2 thereon to form an electron injection layer. Aluminum was deposited on the electron injection layer to a thickness of 100 nm to form a cathode.

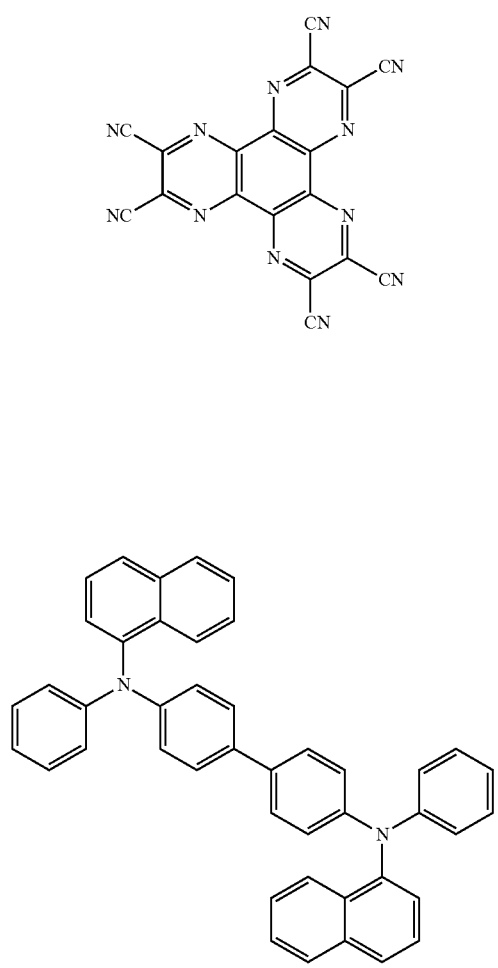

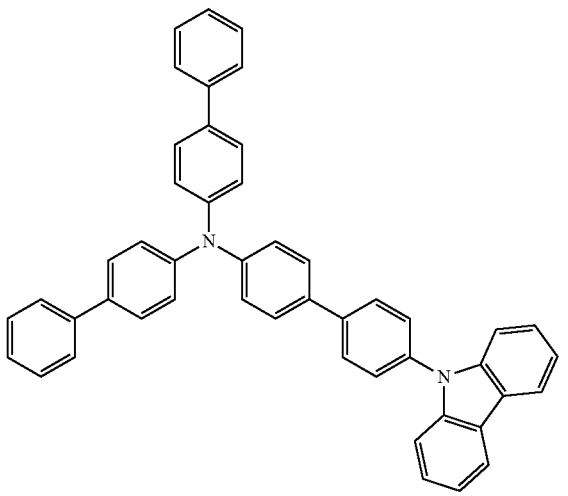

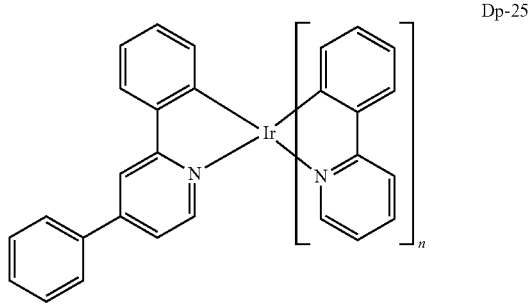

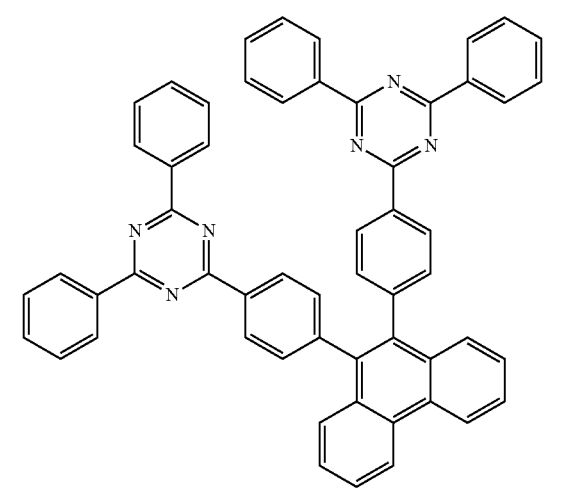

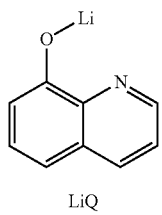

LiQ

In the above-mentioned process, the vapor deposition rate of the organic material was maintained at 0.04 nm/sec to 0.07 nm/sec, the deposition rate of aluminum was maintained at 0.2 nm/sec, and the degree of vacuum during the deposition was maintained at $1\times10^{-7}$ torr to $5\times10^{-8}$ torr.

Experimental Examples 2 to 21 and Comparative Experimental Examples 1 to 9

An organic light emitting device was manufactured in the same manner as in Experimental Example 1, except that the compounds shown in Table 1 below were used instead of Compound 1 in Experimental Example 1.

For reference, in Experimental Examples 16 to 21 and Comparative Experimental Examples 7 to 9, an organic light emitting device was manufactured by using the compounds shown in Table 5 below in the weight ratio of 1:1 instead of Compound 1 in Experimental Example 1. For example, in Example 16, Compound 1 and Compound H-2 were used in a weight ratio of 1:1 instead of Compound 1 in Experimental Example 1.

H-2

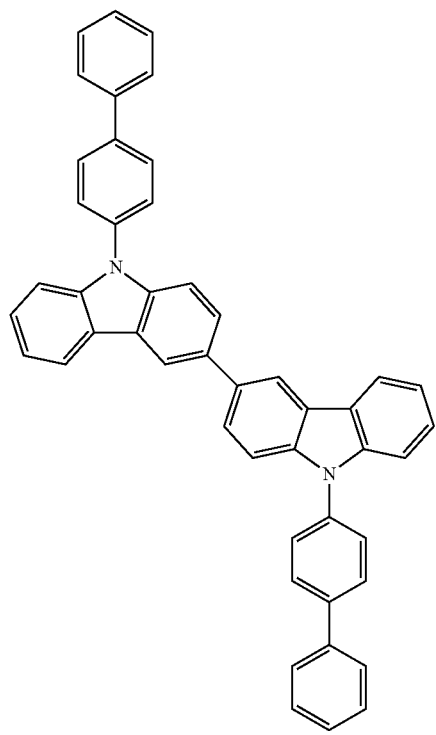

C1

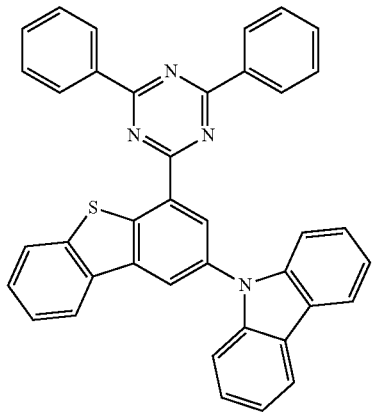

C2

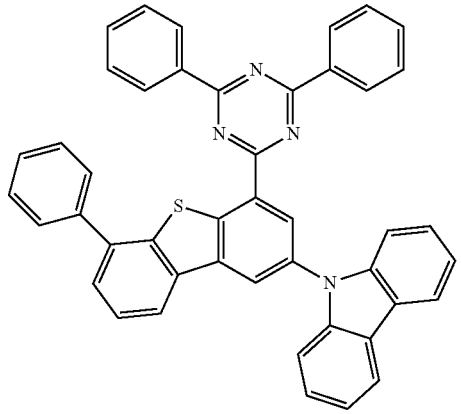

C3

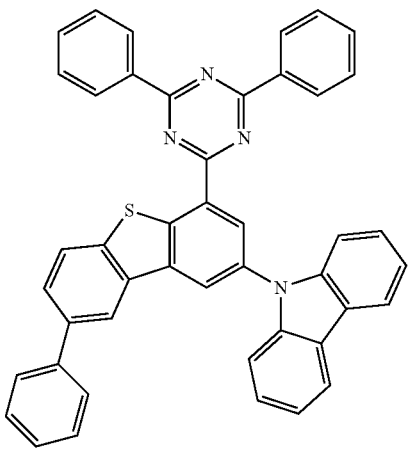

-continued

C4

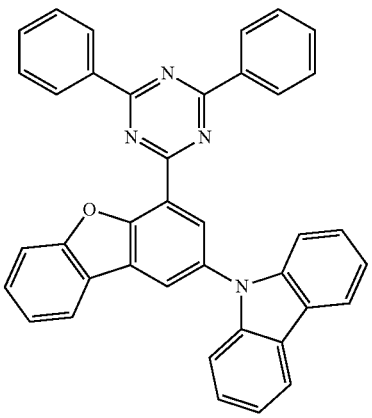

C5

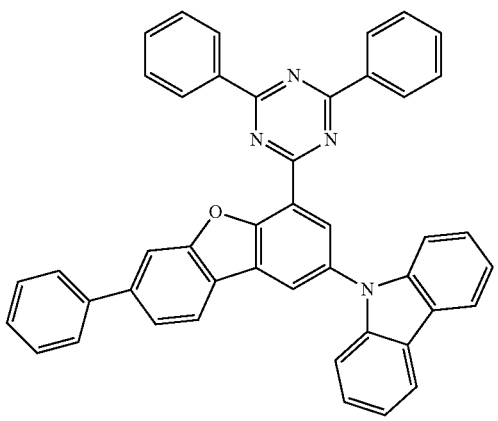

C6

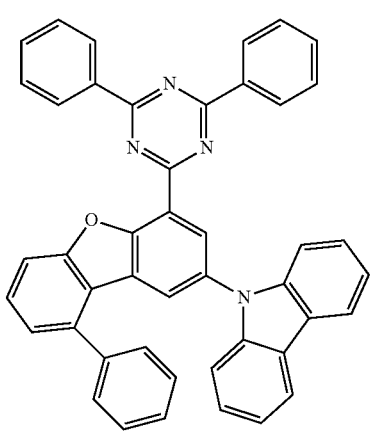

The voltage, efficiency, luminous color, and lifetime were measured by applying a current density of 10 mA/cm$^2$ for the organic light emitting devices of Experimental Examples and Comparative Experimental Examples, and the results are shown in Table 1 below. In this case, T95 means the time required for the luminance to be reduced to 95% when the initial luminance at the current density of 20 mA/cm2 is taken as 100%.

TABLE 5

| Category | Light emitting layer compound | Voltage (V) (@10 mA/cm$^2$) | Efficiency (cd/A) (@10 mA/cm$^2$) | Luminous color | T$_{95}$ (@20 mA/cm$^2$) |
|---|---|---|---|---|---|
| Experimental Example 1 | Compound 1 | 3.01 | 65.9 | green | 75 |
| Experimental Example 2 | Compound 2 | 3.00 | 65.8 | green | 79 |
| Experimental Example 3 | Compound 3 | 3.06 | 66.6 | green | 69 |
| Experimental Example 4 | Compound 4 | 2.97 | 66.1 | green | 67 |
| Experimental Example 5 | Compound 5 | 2.89 | 64.0 | green | 66 |
| Experimental Example 6 | Compound 6 | 2.84 | 66.1 | green | 79 |
| Experimental Example 7 | Compound 7 | 3.11 | 67.2 | green | 68 |
| Experimental Example 8 | Compound 8 | 2.98 | 67.9 | green | 63 |
| Experimental Example 9 | Compound 9 | 2.92 | 66.9 | green | 65 |
| Experimental Example 10 | Compound 10 | 3.05 | 68.0 | green | 58 |
| Experimental Example 11 | Compound 11 | 3.03 | 65.9 | green | 63 |
| Experimental Example 12 | Compound 12 | 3.04 | 63.5 | green | 62 |
| Experimental Example 13 | Compound 13 | 2.98 | 64.9 | green | 62 |
| Experimental Example 14 | Compound 14 | 2.94 | 63.1 | green | 66 |
| Experimental Example 15 | Compound 15 | 3.01 | 66.2 | green | 59 |
| Comparative Experimental Example 1 | Compound C1 | 3.01 | 60.0 | green | 50 |
| Comparative Experimental Example 2 | Compound C2 | 3.07 | 62.5 | green | 60 |
| Comparative Experimental Example 3 | Compound C3 | 3.11 | 59.5 | green | 62 |
| Comparative Experimental Example 4 | Compound C4 | 3.06 | 59.2 | green | 51 |
| Comparative Experimental Example 5 | Compound C5 | 3.12 | 61.2 | green | 53 |
| Comparative Experimental Example 6 | Compound C6 | 3.09 | 60.9 | green | 55 |
| Experimental Example 16 | Compound 1, Compound H-2 | 3.29 | 72.1 | green | 160 |
| Experimental Example 17 | Compound 2, Compound H-2 | 3.20 | 74.8 | green | 169 |
| Experimental Example 18 | Compound 6, Compound H-2 | 3.28 | 74.0 | green | 161 |
| Experimental Example 19 | Compound 10, Compound H-2 | 3.32 | 74.7 | green | 165 |
| Experimental Example 20 | Compound 11, Compound H-2 | 3.48 | 74.9 | green | 169 |
| Experimental Example 21 | Compound 15, Compound H-2 | 3.26 | 74.1 | green | 171 |

TABLE 5-continued

| Category | Light emitting layer compound | Voltage (V) (@10 mA/cm$^2$) | Efficiency (cd/A) (@10 mA/cm$^2$) | Luminous color | T$_{95}$ (@20 mA/cm$^2$) |
|---|---|---|---|---|---|
| Experimental Example 7 | Compound C1, Compound H-2 | 3.14 | 58.9 | green | 138 |
| Comparative Experimental Example 8 | Compound C2, Compound H-2 | 3.50 | 65.0 | green | 154 |
| Comparative Experimental Example 9 | Compound C5, Compound H-2 | 3.48 | 65.9 | green | 141 |

Experimental Examples 1 to 15 and Comparative Experimental Examples 1 to 6 are examples of devices in which a single host was used for the light emitting layer. Compounds C1 to C3 used in Comparative Experimental Examples 1 to 3 are compounds in which Ar$_1$ of dibenzothiophene is hydrogen or all of Ar$_1$, Ar$_2$ and Ar$_3$ are substituted with only an unsubstituted aryl group. From Table 5, the examples of devices of Experimental Examples 1 to 3 are compounds in which all of Ar$_1$, Ar$_2$, and Ar$_3$ are aryl groups, and are substituted with deuterium. It can be confirmed that the lifetime characteristics are superior by about 21% to 40% compared to Comparative Experimental Examples 1 to 3.

Compounds C4 to C6 used in Comparative Experimental Examples 4 to 6 are compounds in which Ar$_1$ of dibenzofuran is hydrogen or all of Ar$_1$, Ar$_2$ and Ar$_3$ are substituted with y only an unsubstituted aryl group. The example of device of Experimental Example 11 in Table 5 is a compound in which all of Ar$_1$, Ar$_2$, and Ar$_3$ are aryl groups and are substituted with deuterium. It can be confirmed that the lifetime characteristics are superior by about 11% to 21% compared to Comparative Experimental Examples 1 to 3.

The compounds used in Experimental Examples 6 to 9 and Experimental Examples 12-15 are compounds in which Ar$_1$ and Ar$_2$ are substituted with deuterium or a heteroaryl group. It can be confirmed that the lifetime characteristics are superior by about 11% to 26% compared to Comparative Experimental Examples 1 to 6 in which Ar$_1$ and Ar$_2$ are substituted by only an aryl group.

Experimental Examples 16 to 21 are examples of devices in which two types of hosts are used for the light emitting layer. Even when two types of hosts are used for the light emitting layer, it can be confirmed that the devices of Experimental Examples 16 to 21 using the compound of the present disclosure have superior current efficiency and lifetime characteristics compared to the devices of Comparative Experimental Examples 7 to 9.

DESCRIPTION OF SYMBOLS

<Description of Symbols>

1: substrate
2: anode
3: light emitting layer
4: cathode
5: hole injection layer
6: hole transport layer <Description of Symbols>

7: light emitting layer
8: electron transport layer

What is claimed is:

1. A compound of Chemical Formula 1:

Chemical Formula 1

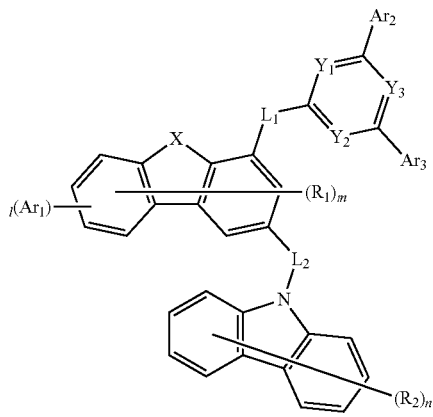

wherein, in Chemical Formula 1:

X is O or S;

Y$_1$, Y$_2$ and Y$_3$ are each independently CH or N, provided that at least one of Y$_1$, Y$_2$ and Y$_3$ is N;

L$_1$ and L$_2$ are each independently a direct bond, a substituted or unsubstituted C$_{6-60}$ arylene, or a substituted or unsubstituted C$_{5-60}$ heteroarylene containing at least one heteroatom selected from the group consisting of N, O and S;

Ar$_1$ is a substituted or unsubstituted C$_{6-60}$ aryl;

Ar$_2$ and Ar$_3$ are each independently any one selected from the group consisting of the following:

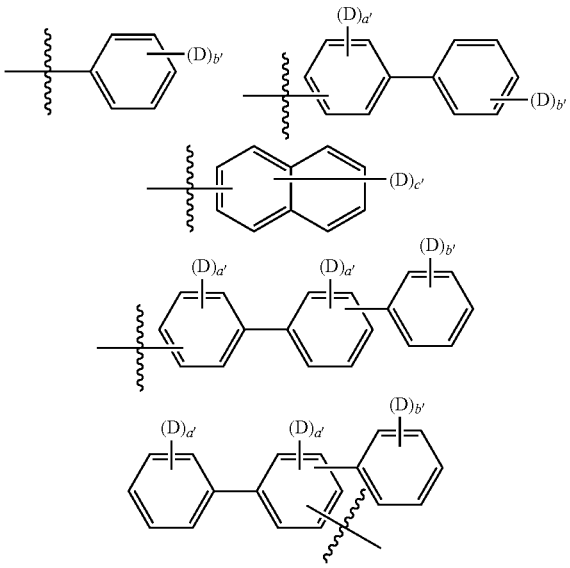

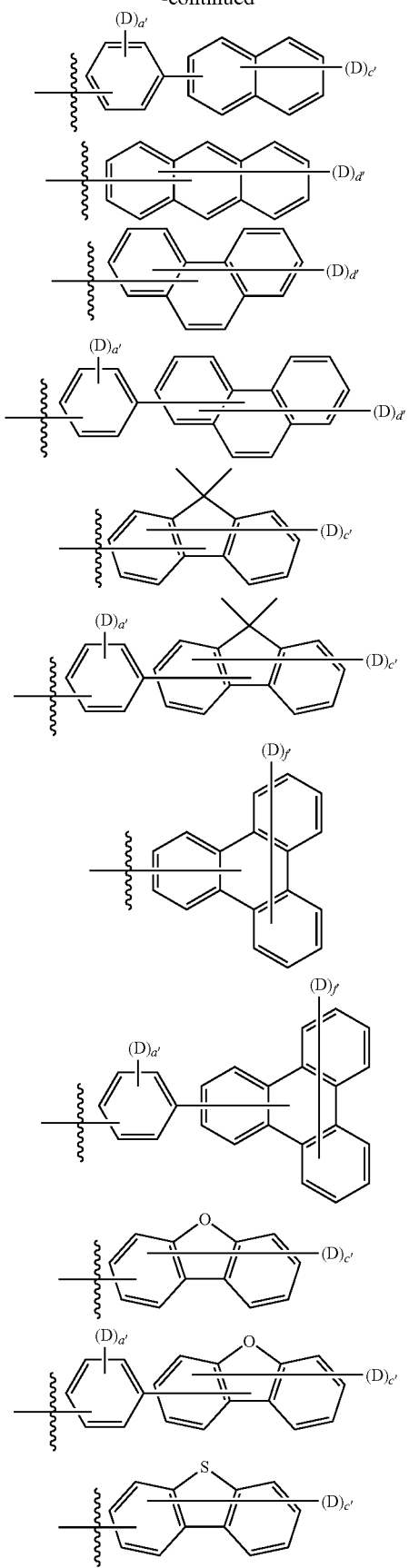
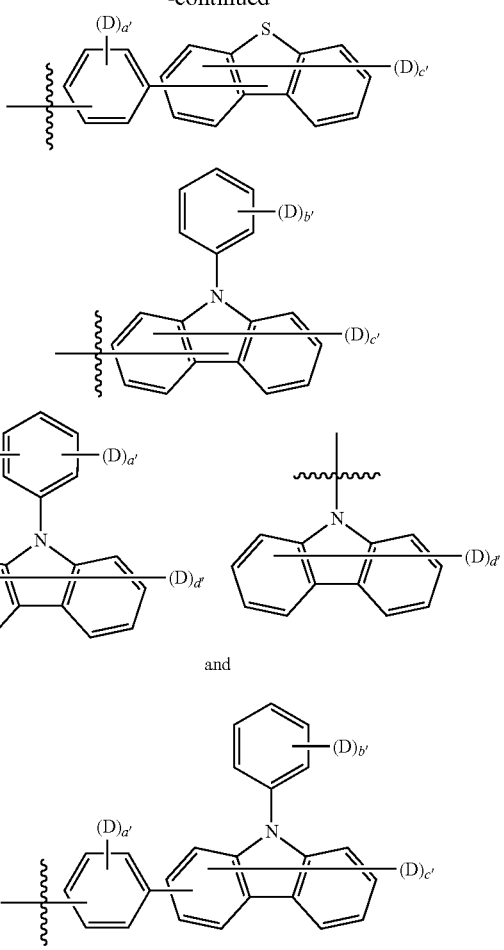
wherein in the above formulas:
a' is an integer from 0 to 4;
b' is an integer from 0 to 5;
c' is an integer from 0 to 7;
d' is an integer from 0 to 8;
e' is an integer from 0 to 9; and
f is an integer from 0 to 11,
provided that when Ar₁ is any one selected from the group consisting of the following:
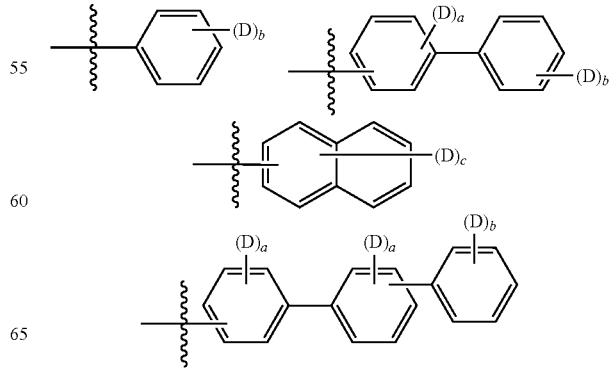

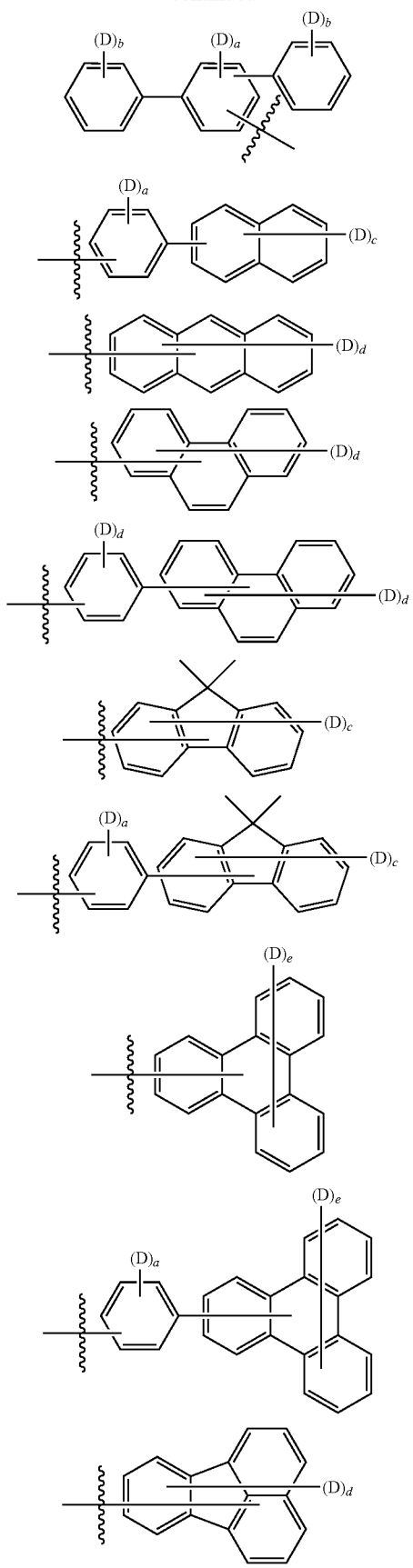
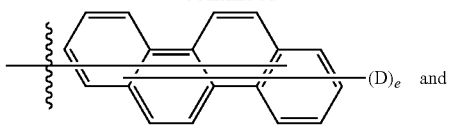
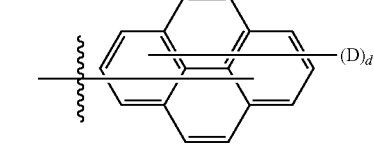
wherein in the above formulas:
a is an integer from 0 to 4;
b is an integer from 0 to 5;
c is an integer from 0 to 7;
d is an integer from 0 to 9; and
e is an integer from 0 to 11,
and Ar$_2$ and Ar$_3$ are each independently any one selected from the group consisting of the following:
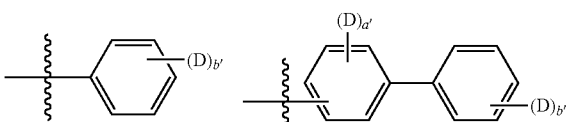
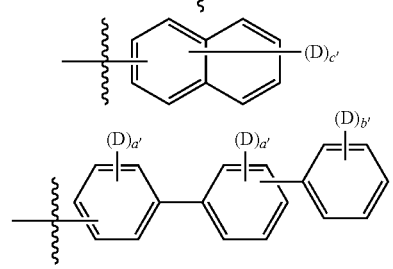
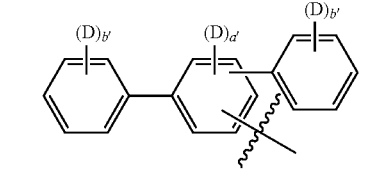
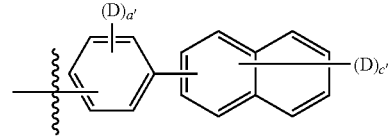

-continued

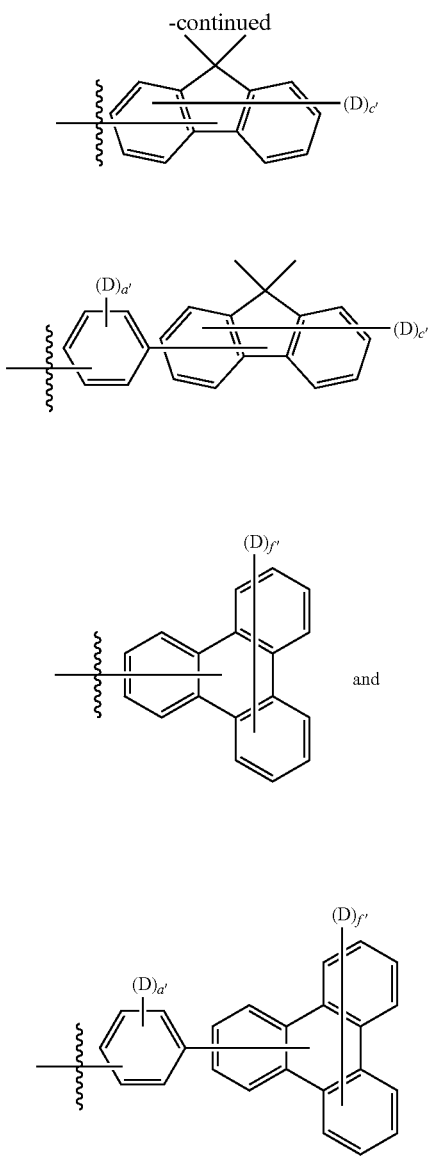

wherein in the above formulas:
a' is an integer from 0 to 4;
b' is an integer from 0 to 5;
c' is an integer from 0 to 7;
d' is an integer from 0 to 8;
e' is an integer from 0 to 9; and
f' is an integer from 0 to 11,
any one of $Ar_1$, $Ar_2$ and $Ar_3$ is substituted with 4 or more deuteriums;
each $R_1$ is independently hydrogen, deuterium, halogen, or a substituted or unsubstituted $C_{1-60}$ alkyl;
each $R_2$ is independently hydrogen, deuterium, halogen, cyano, a substituted or unsubstituted $C_{1-60}$ alkyl, a substituted or unsubstituted $C_{1-60}$ alkoxy, a substituted or unsubstituted $C_{3-60}$ cycloalkyl, a substituted or unsubstituted $C_{1-60}$ haloalkyl, a substituted or unsubstituted $C_{1-60}$ haloalkoxy, a substituted or unsubstituted $C_{6-60}$ arylamine, a substituted or unsubstituted $C_{1-60}$ alkylamine, a substituted or unsubstituted $C_{1-60}$ trifluoroalkyl, a substituted or unsubstituted $C_{1-60}$ trifluoroalkoxy, a substituted or unsubstituted $C_{6-60}$ aryl, or a substituted or unsubstituted $C_{5-60}$ heteroaryl containing at least one of N, O and S, or $R_2$ can bond with carbon atoms of the carbazole to form a condensed ring;
m is an integer from 0 to 3;
n is an integer from 0 to 6; and
l is 1 or 2.

2. The compound of claim 1,
wherein the compound of Chemical Formula 1 is any one compound selected from the group consisting of the compounds of the following Chemical Formulae 2 to 8:

Chemical Formula 2

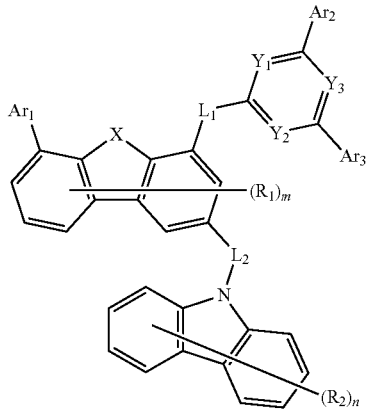

Chemical Formula 3

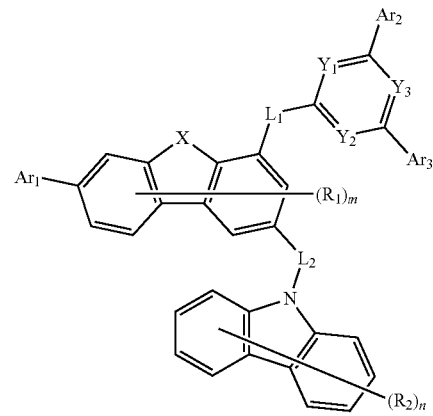

Chemical Formula 4

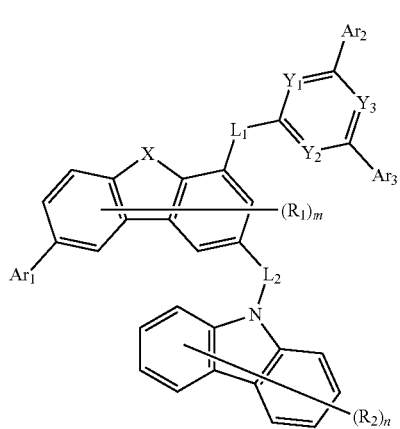

Chemical Formula 5
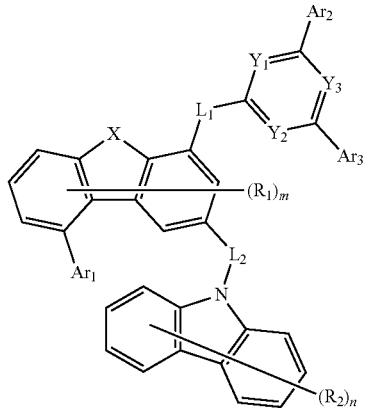
Chemical Formula 6
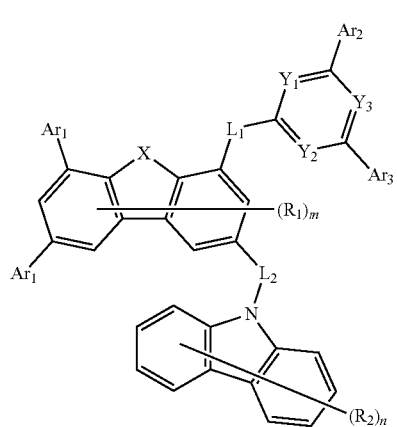
Chemical Formula 7
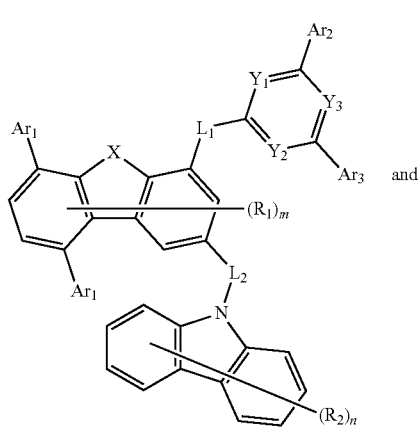
Chemical Formula 8
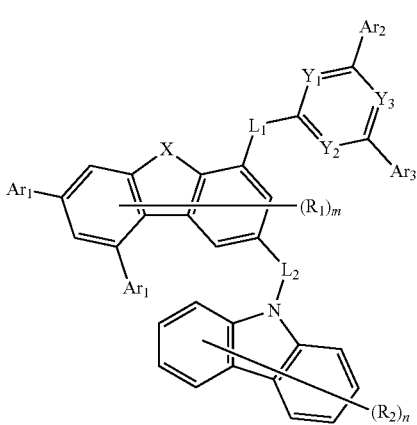
wherein, in Chemical Formulas 2 to 8:
X, $Y_1$, $Y_2$, $Y_3$, $L_1$, $L_2$, $Ar_1$, $Ar_2$, $Ar_3$, $R_1$, $R_2$, m and n are as defined in Chemical Formula 1.
3. The compound of claim 1,
wherein $L_1$ and $L_2$ are each independently a direct bond or any one group selected from the group consisting of the following:
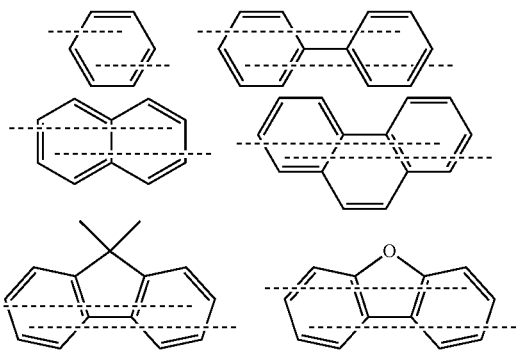
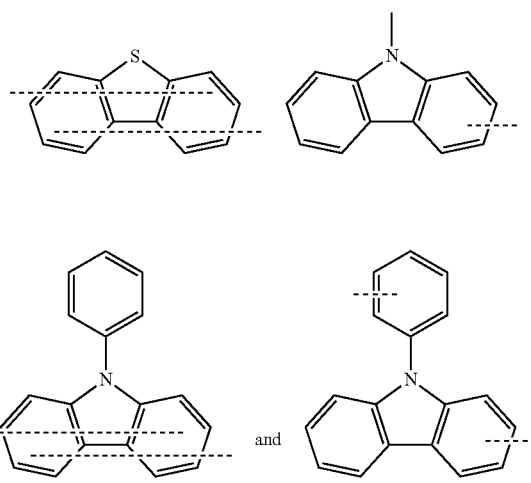

4. The compound of claim 1, wherein Ar₁ is any one selected from the group consisting of the following:

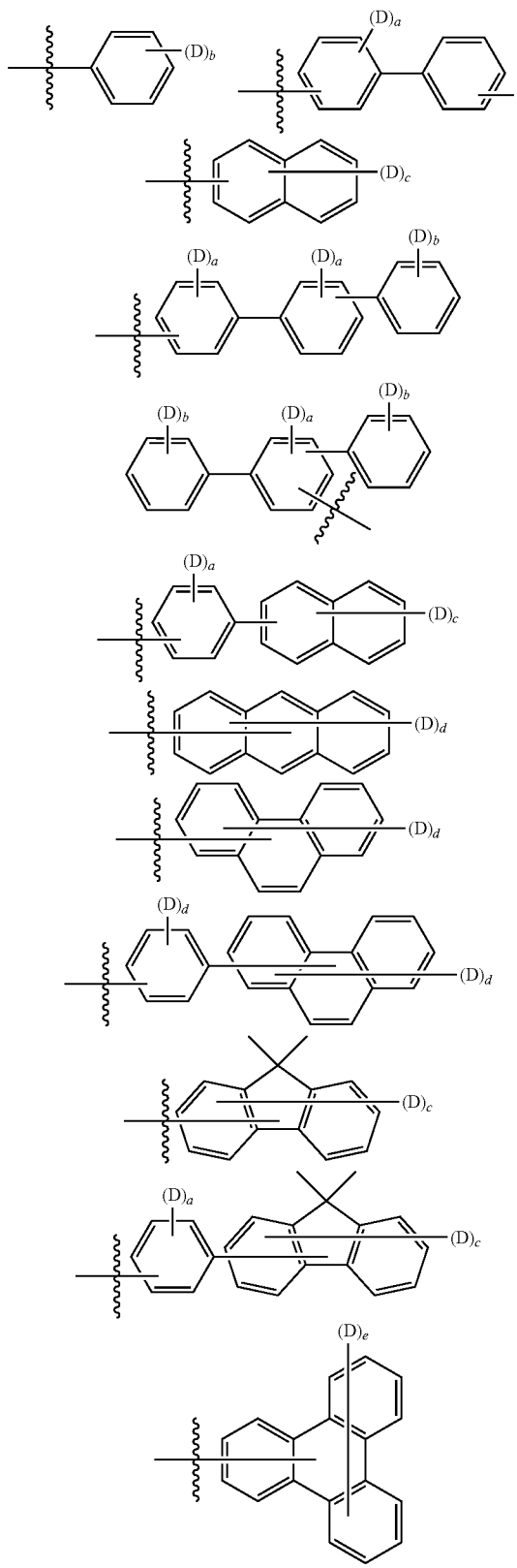

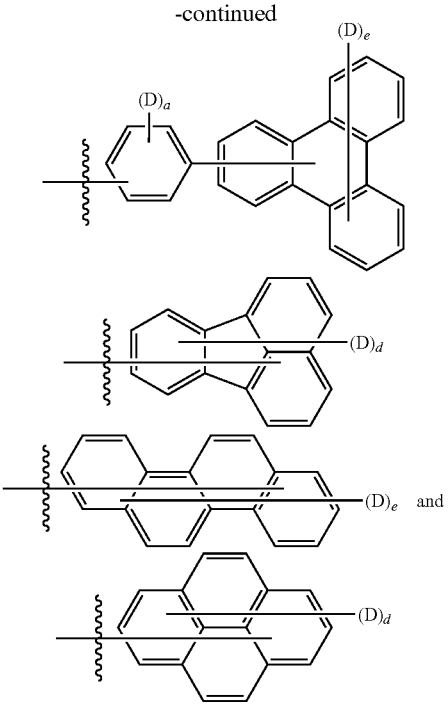

wherein in the above formulas:
a is an integer from 0 to 4;
b is an integer from 0 to 5;
c is an integer from 0 to 7;
d is an integer from 0 to 9; and
e is an integer from 0 to 11.

5. The compound of claim 1,
wherein each $R_1$ is independently hydrogen or deuterium.

6. The compound of claim 1,
wherein each $R_2$ is independently hydrogen, deuterium, halogen, cyano, methoxy, trifluoromethyl, trifluoromethoxy, phenyl, pyridinyl, isoquinolinyl, or any one substituent selected from the group consisting of the following substituents:

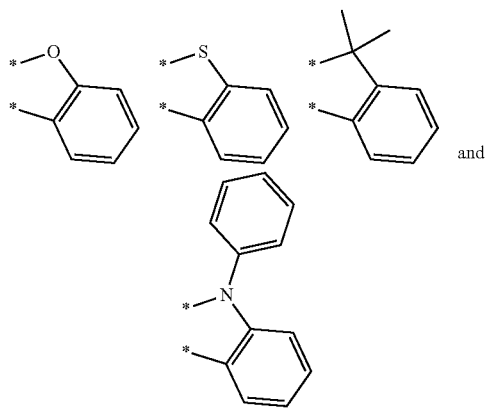

wherein in the above formulas, the two * are each connected to an adjacent carbon of the carbazole in Chemical Formula 1; and
the phenyl is unsubstituted or substituted with any one substituent selected from the group consisting of halogen, cyano, methoxy, trifluoromethyl and trifluoromethoxy.

7. A compound selected from the group consisting of the following compounds:
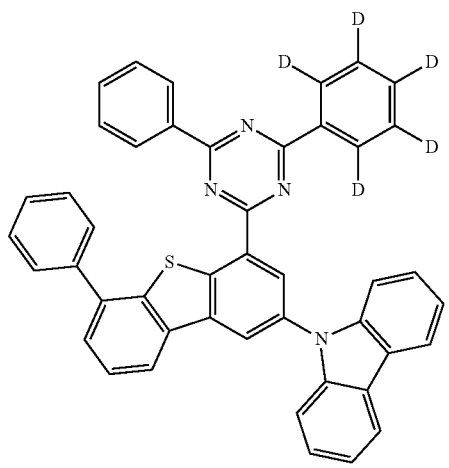
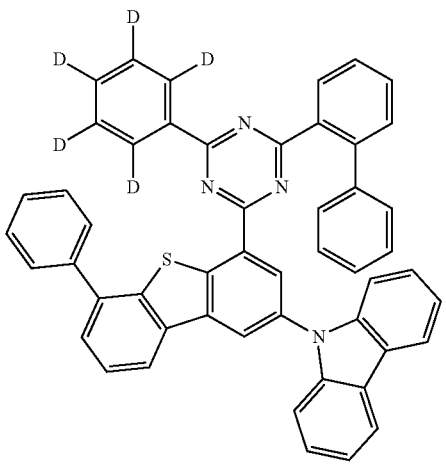
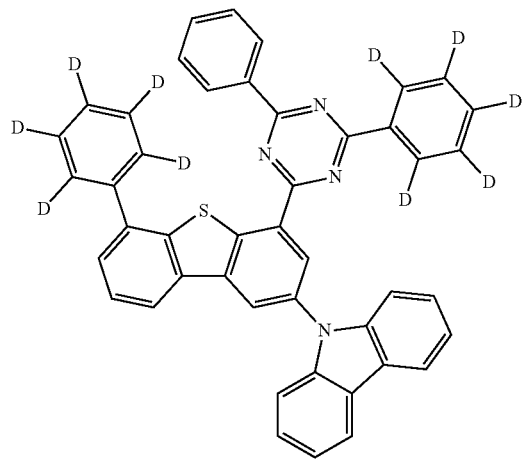
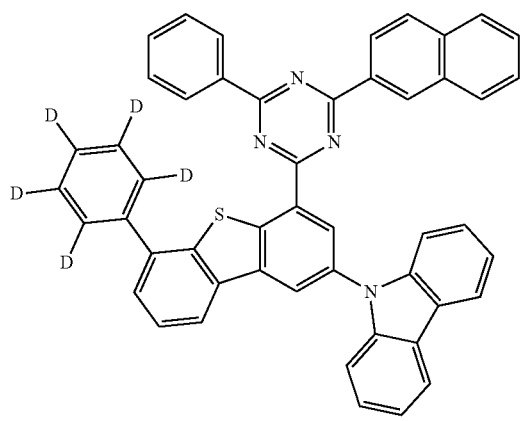
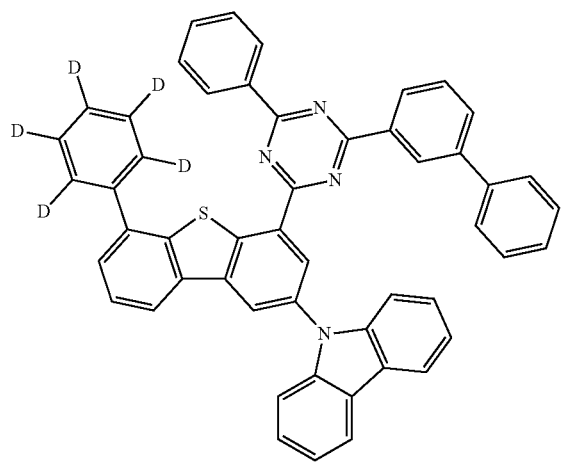
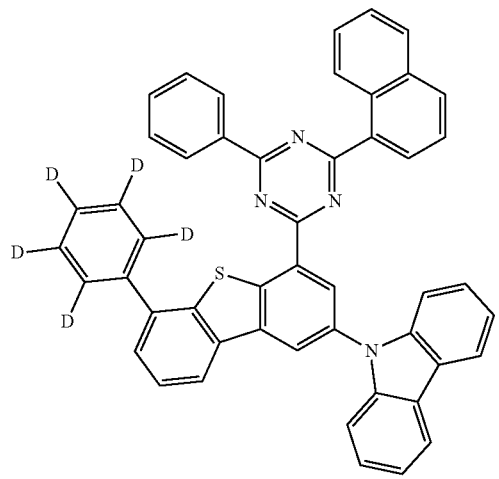

325
-continued
326
-continued
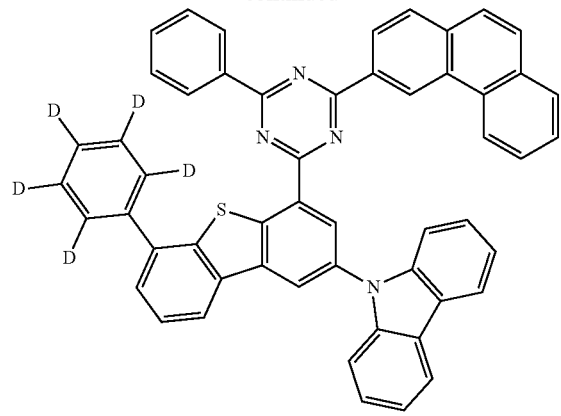
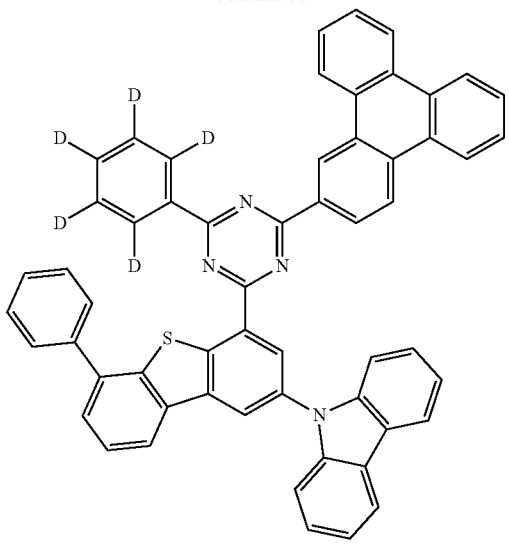
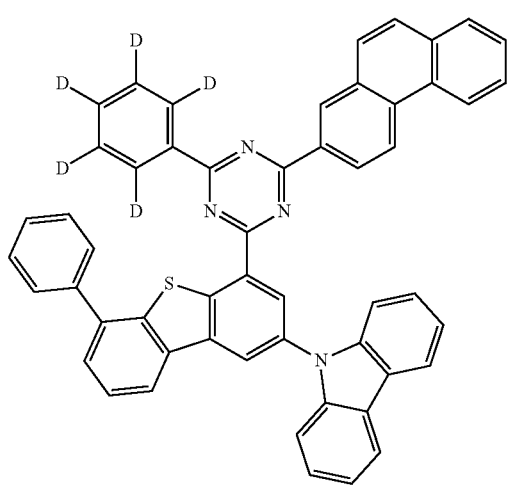
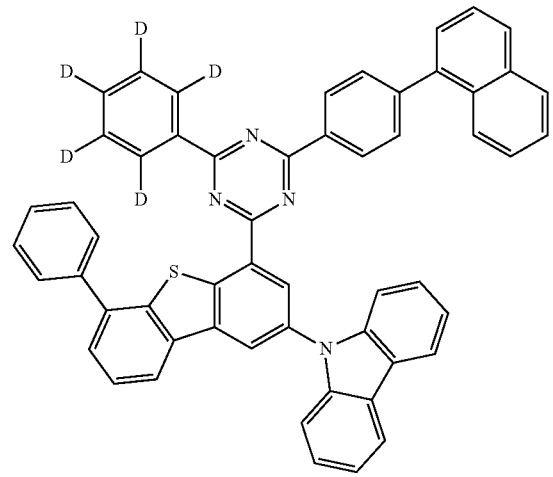
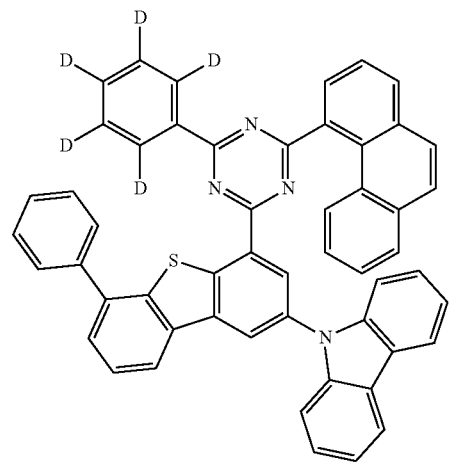

327
-continued
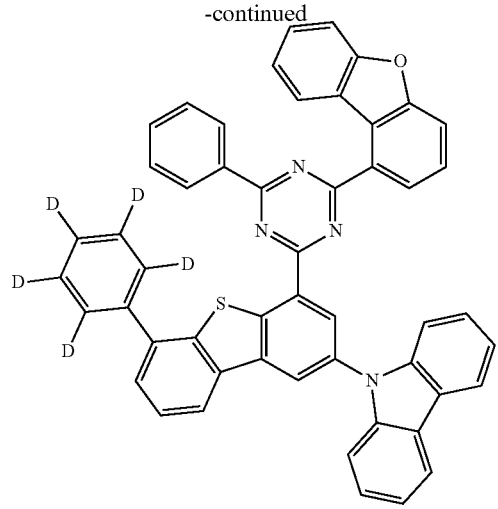
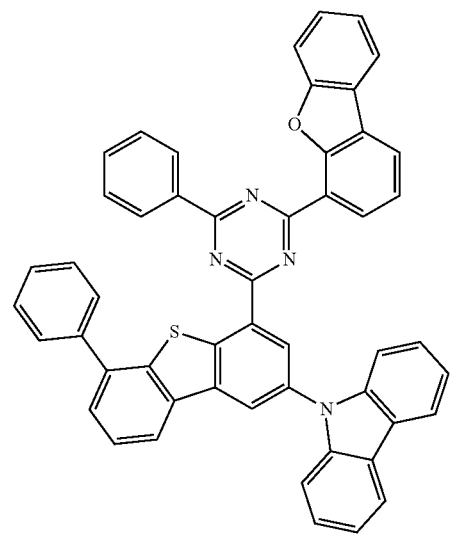
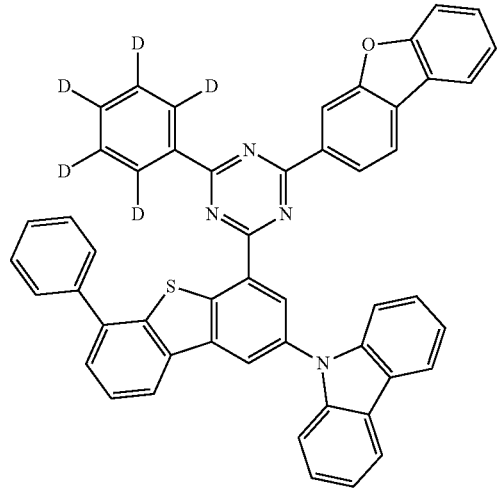
328
-continued
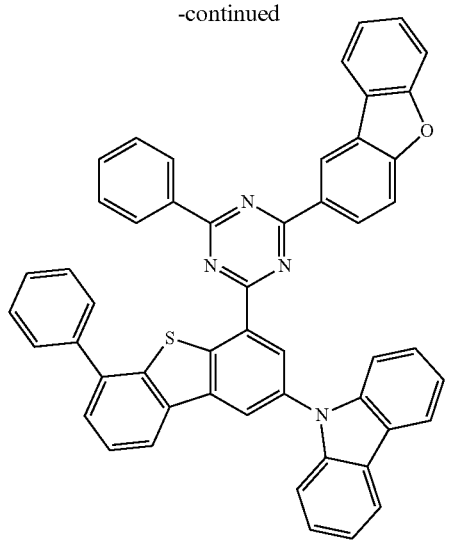
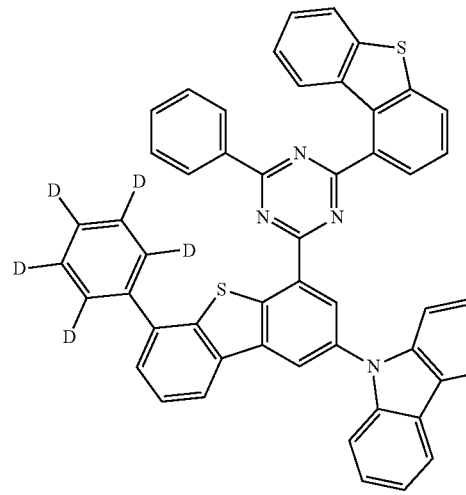
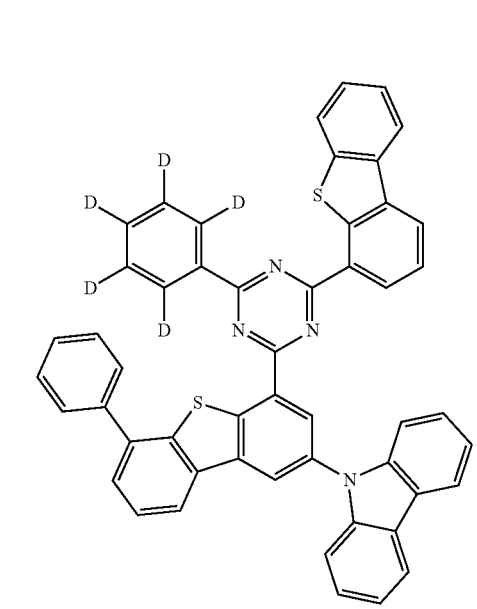

329
-continued
330
-continued
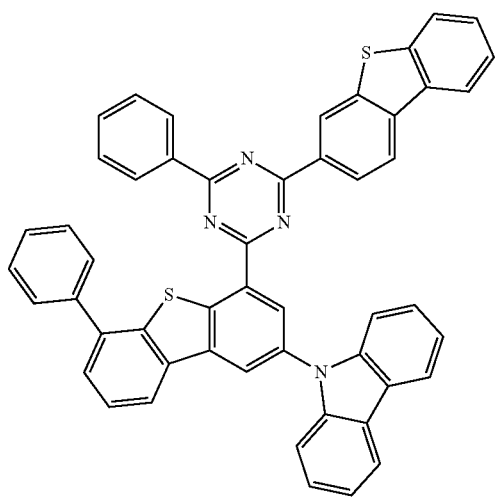
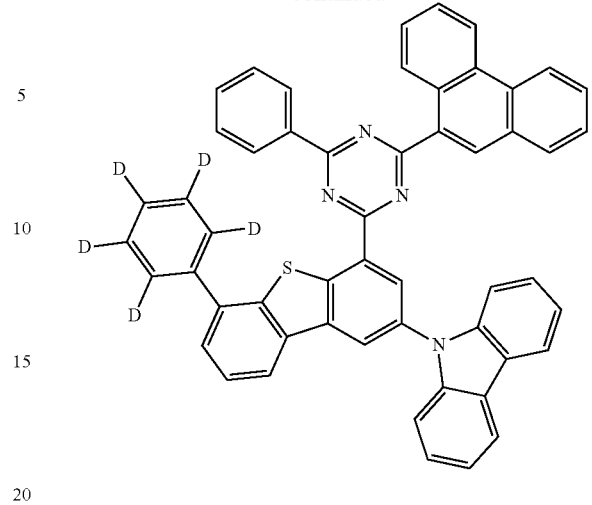
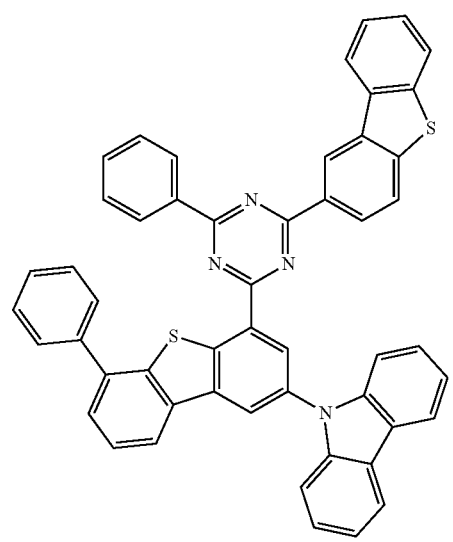
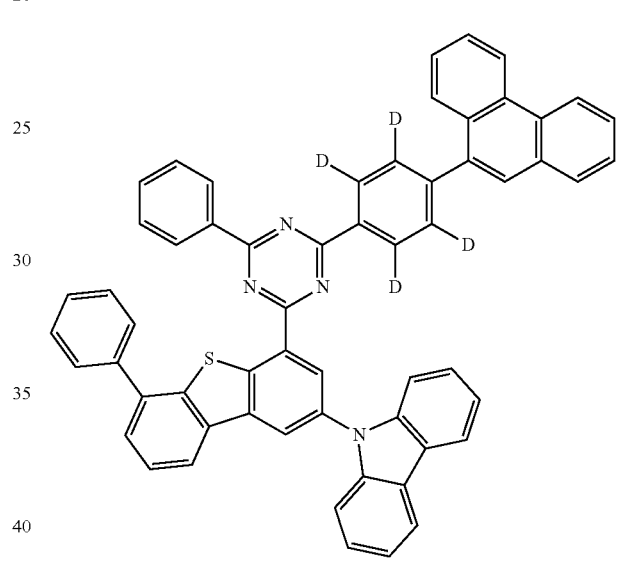
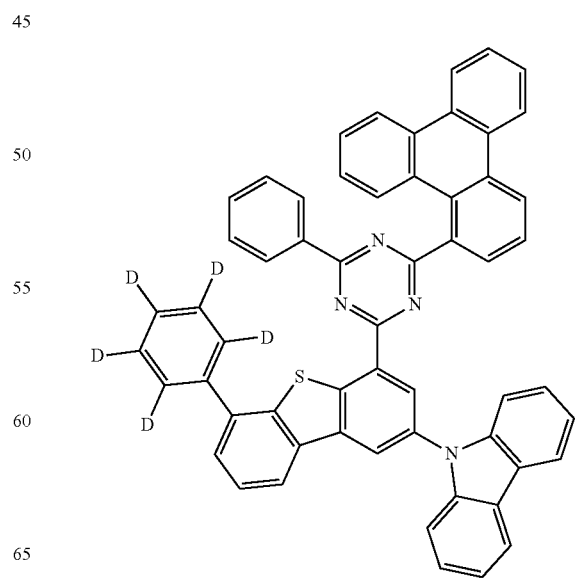

331
-continued
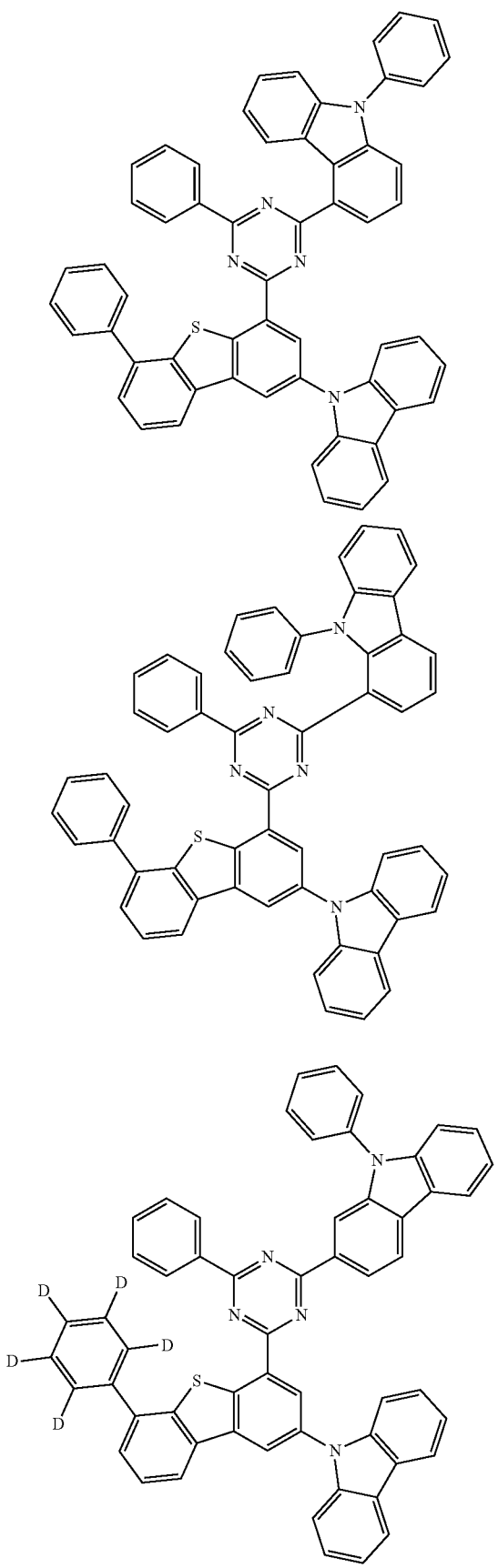
332
-continued
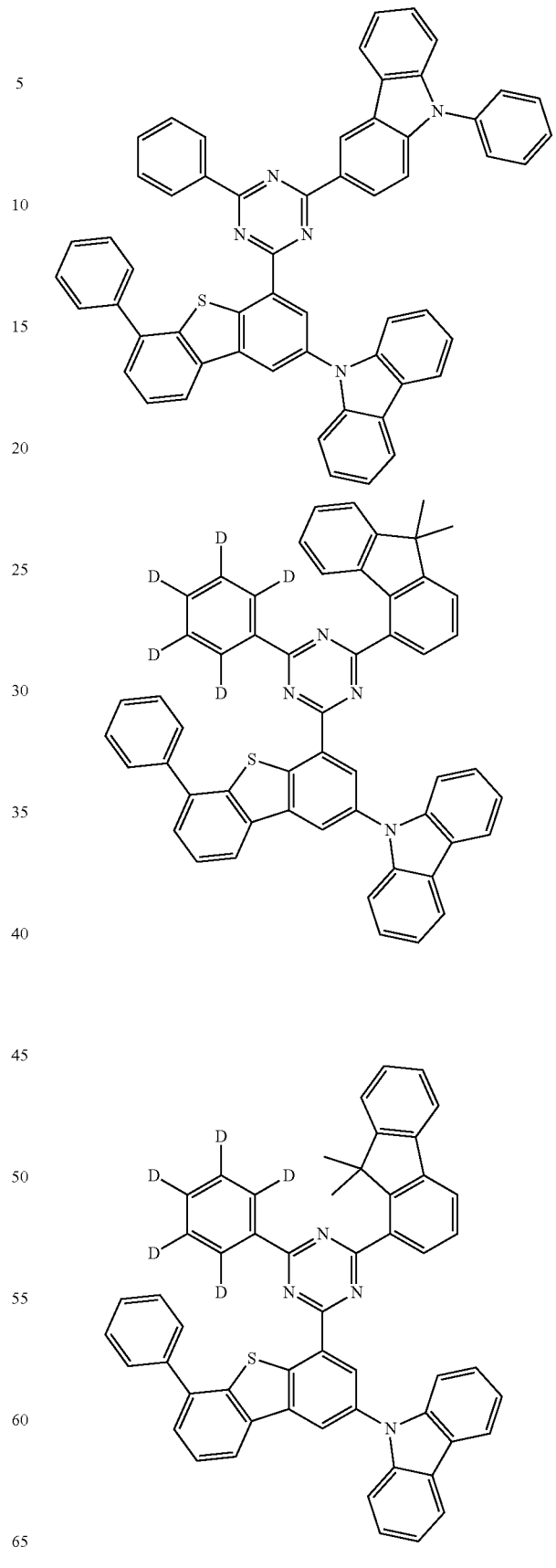

333
-continued
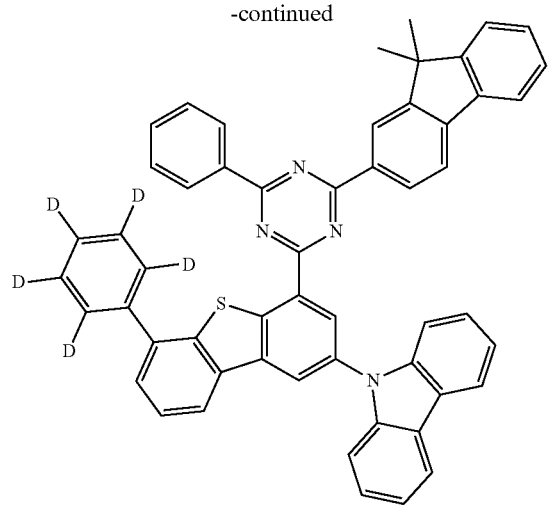
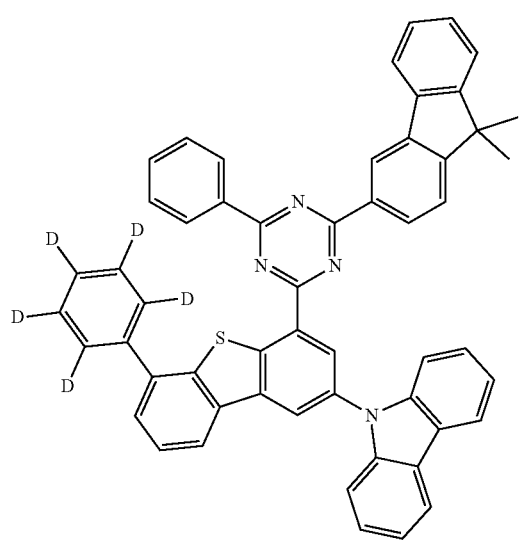
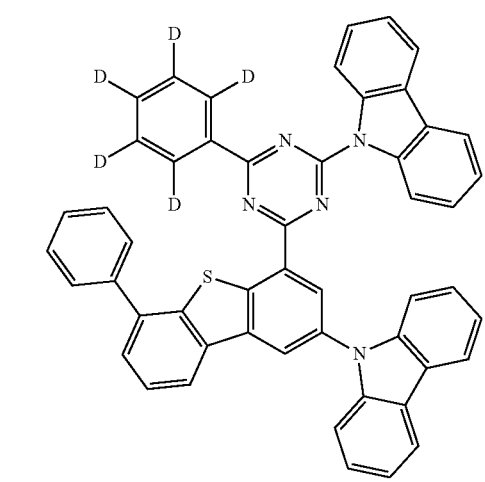
334
-continued
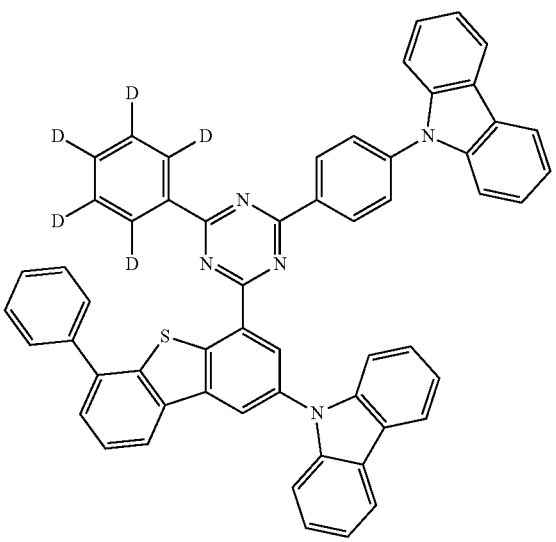
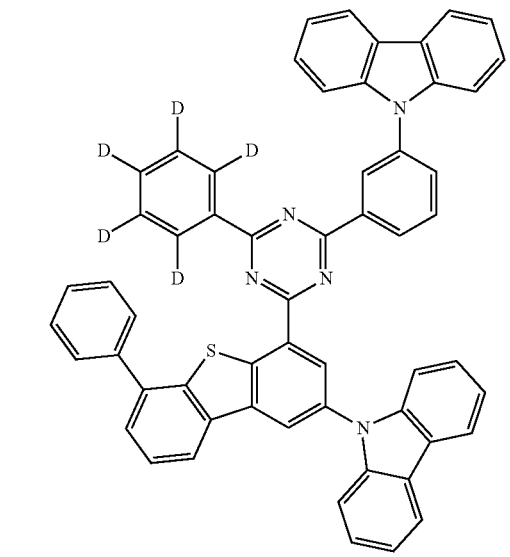
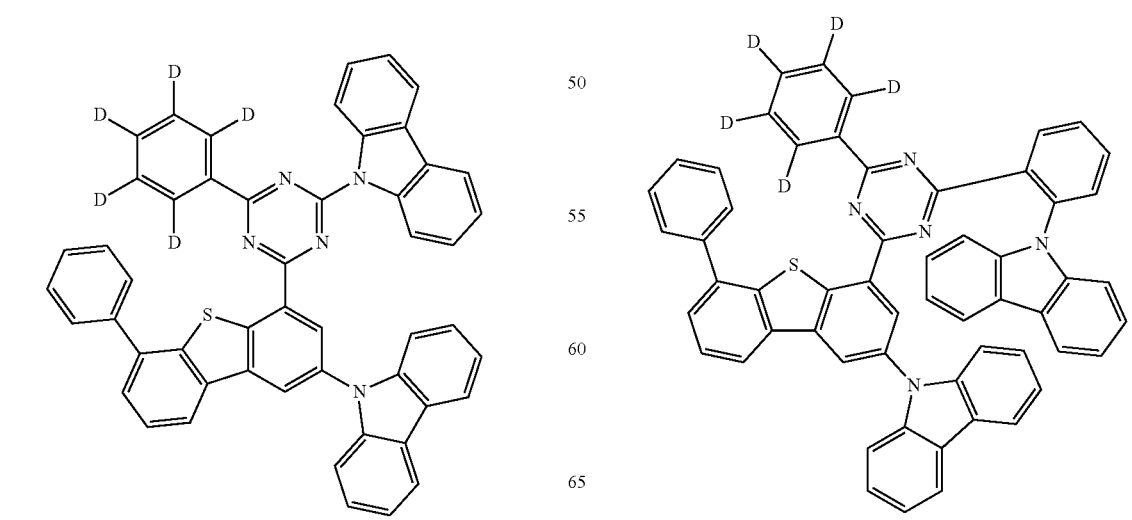

335
-continued
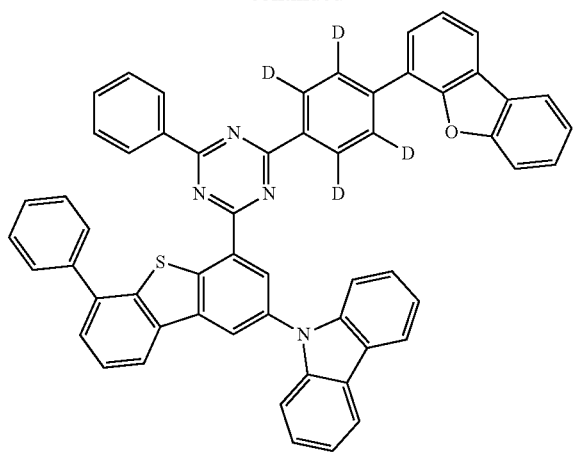
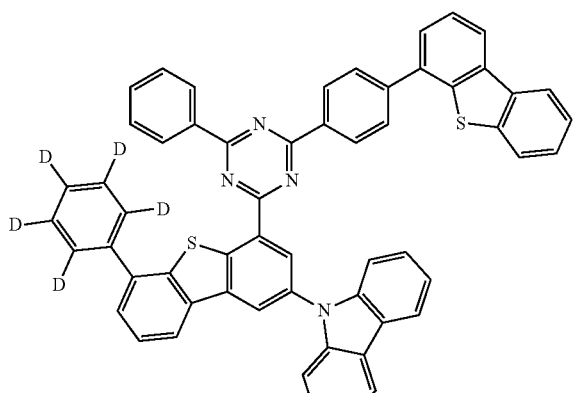
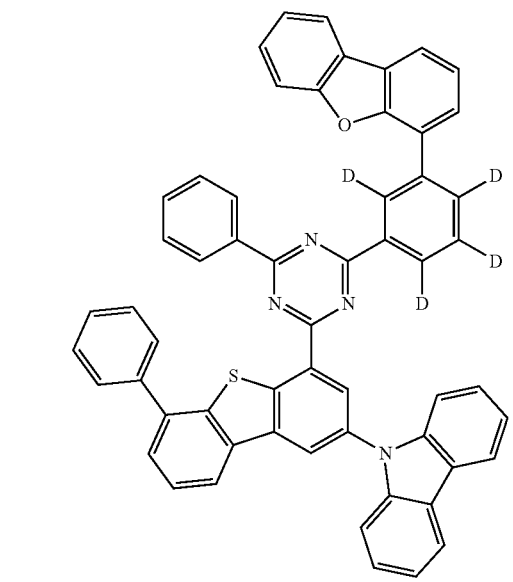
336
-continued
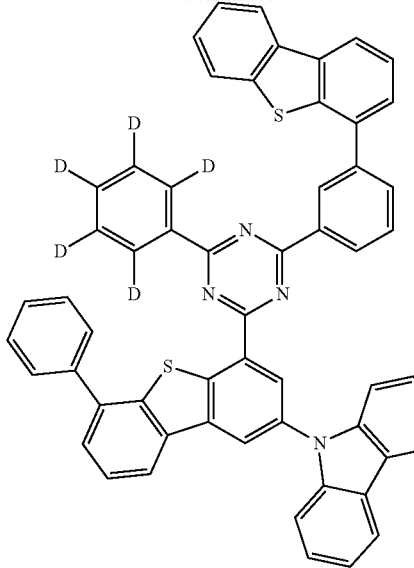
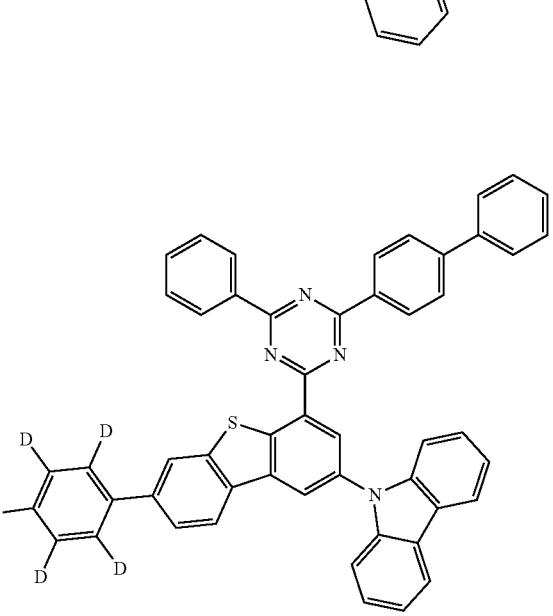

337
-continued
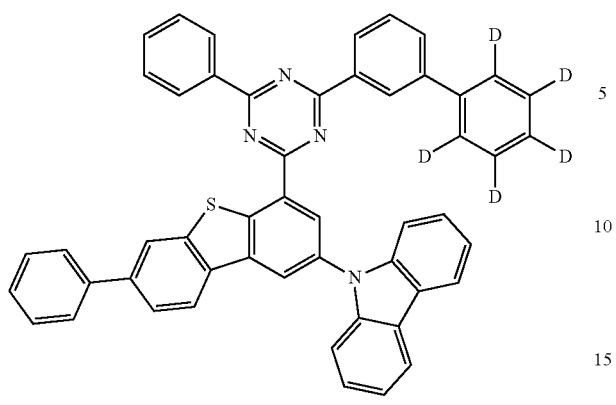
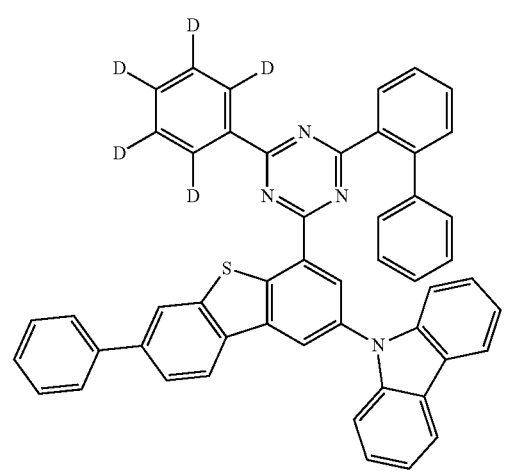
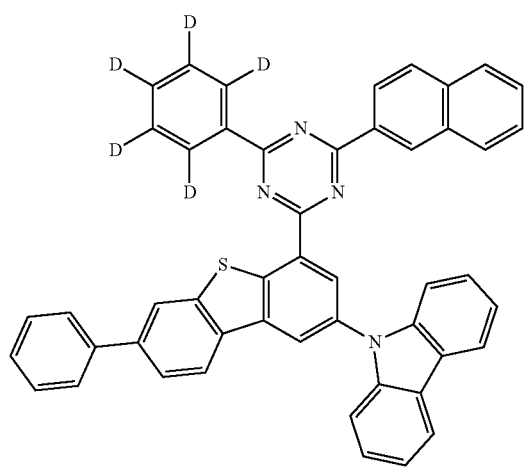
338
-continued
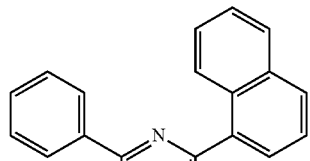
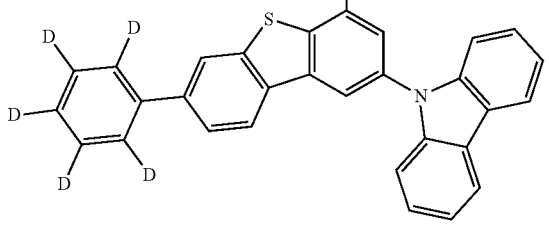
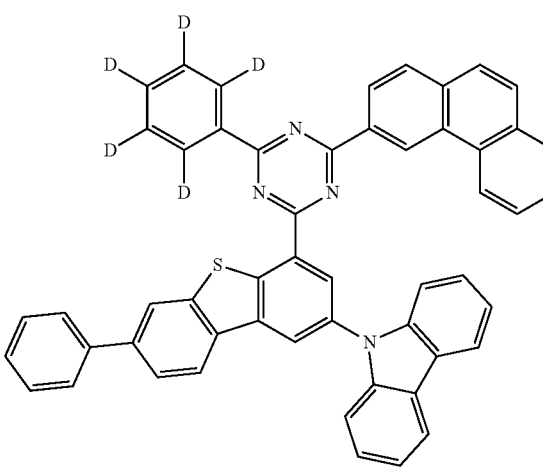
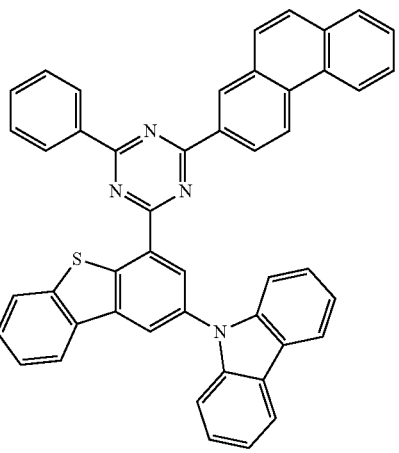

339
-continued
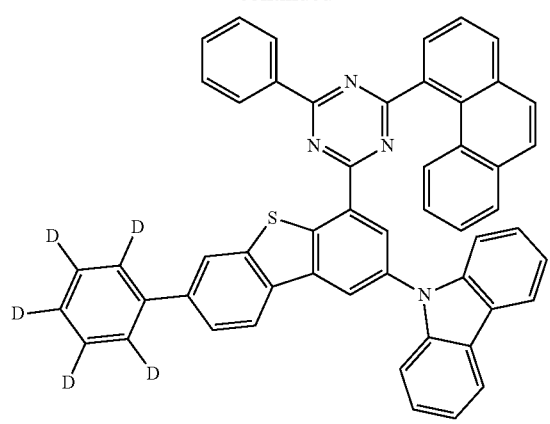
340
-continued
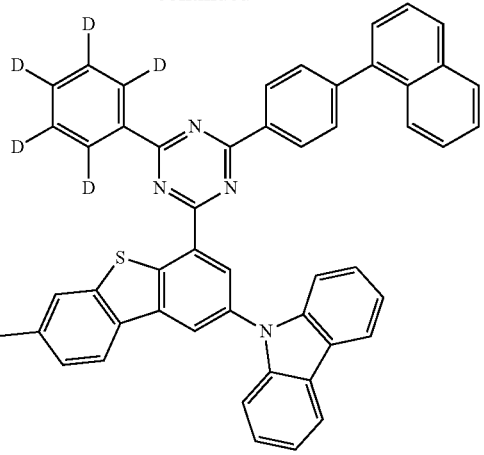
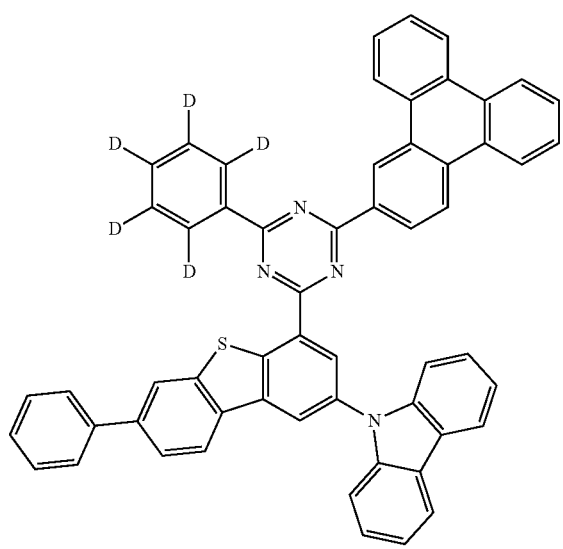
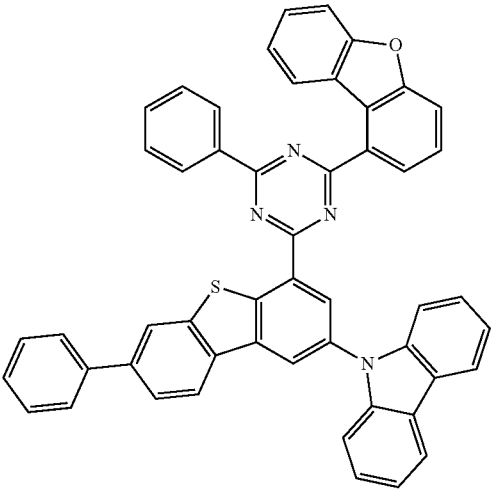
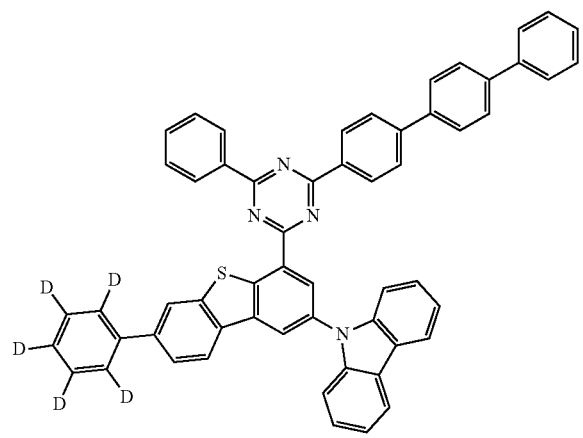
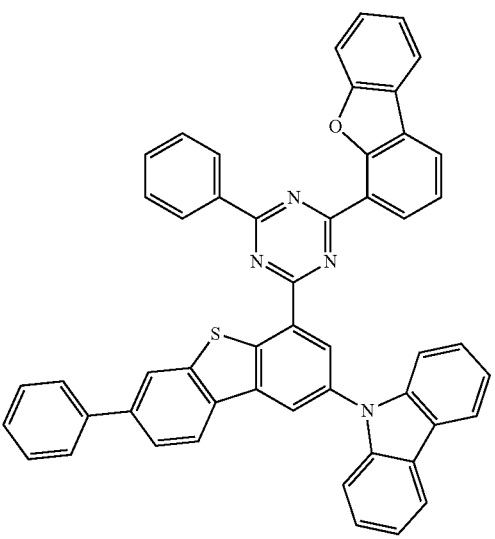

341
-continued
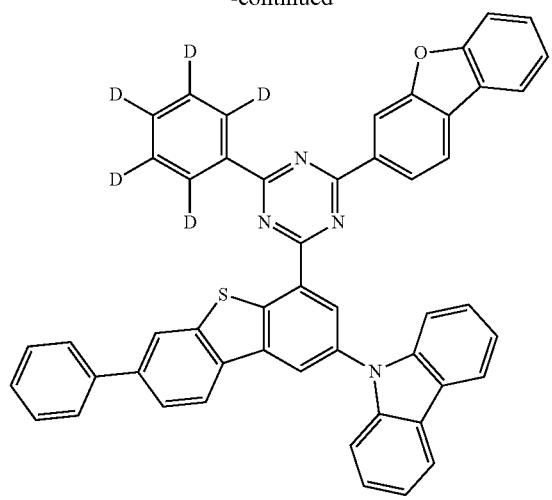
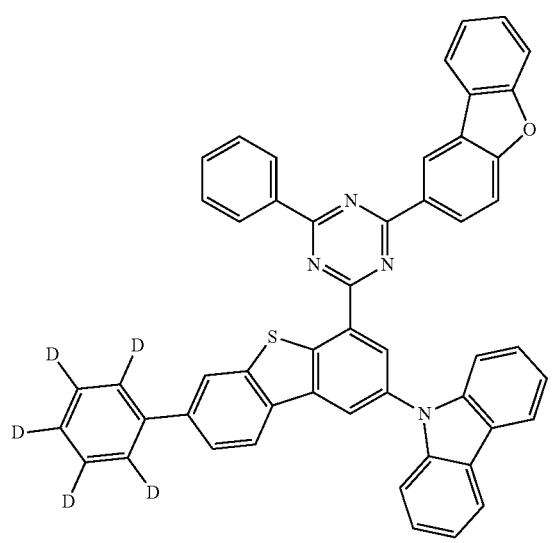
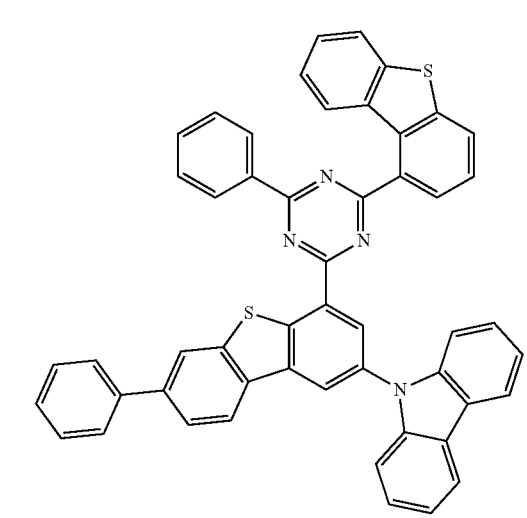
342
-continued
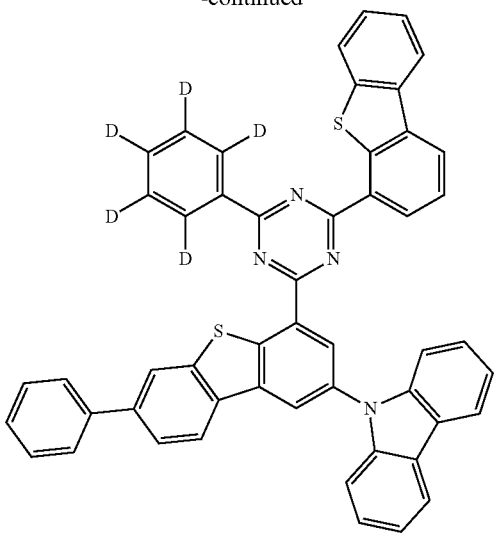
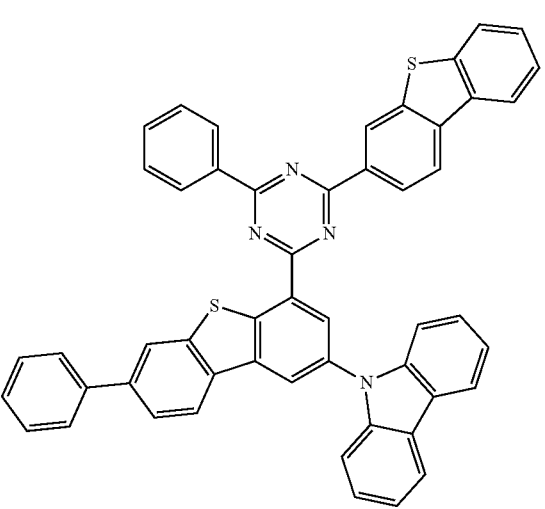
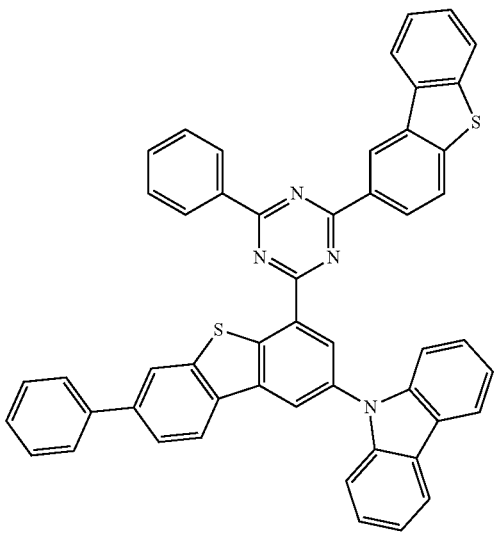

343
-continued
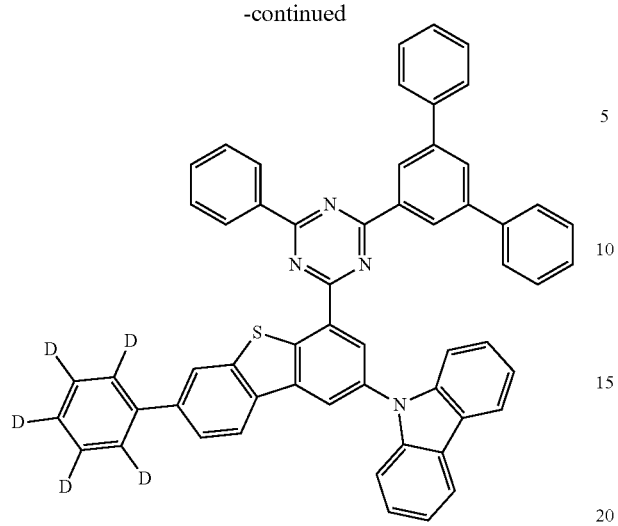
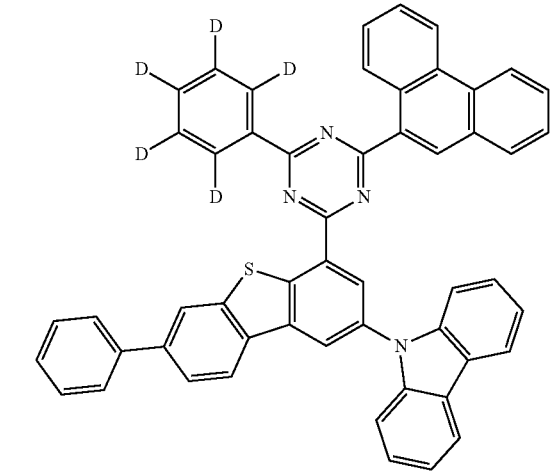
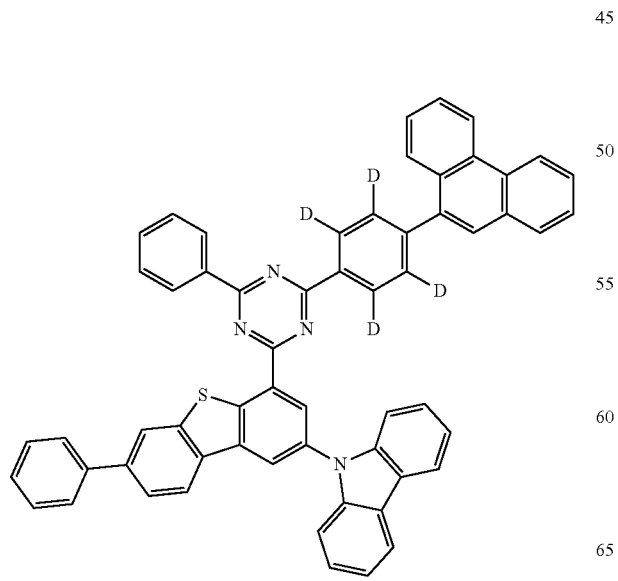
344
-continued
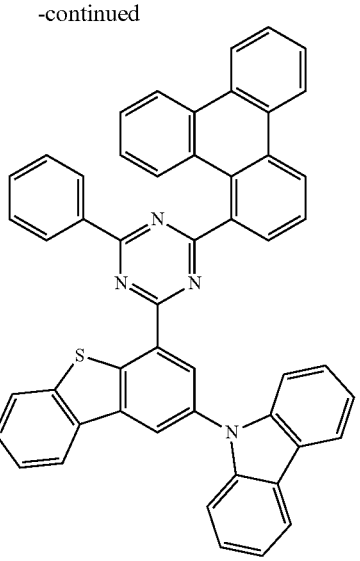
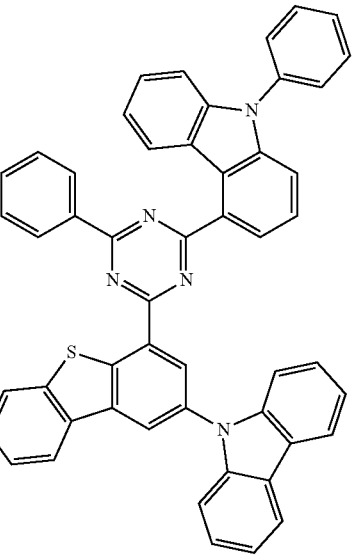
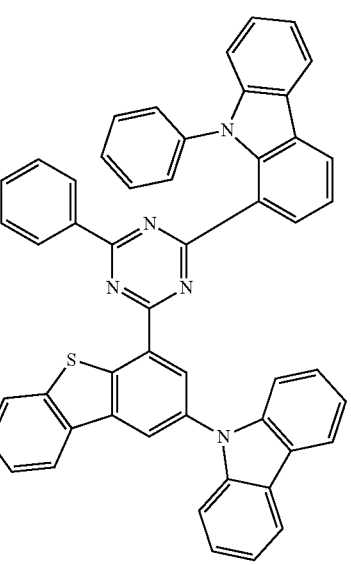

345
-continued
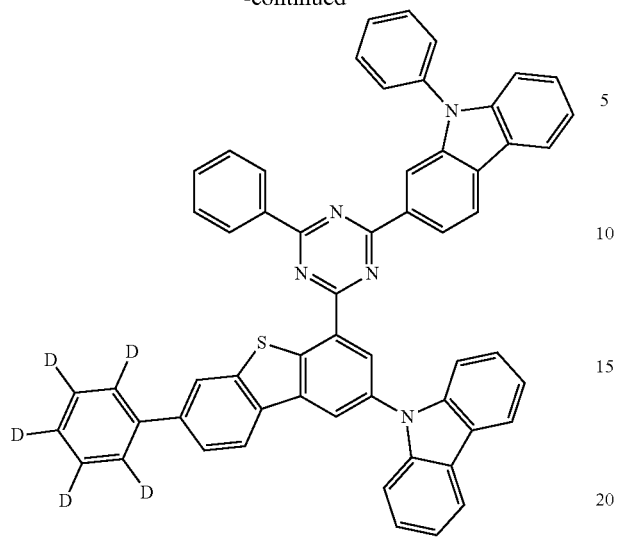
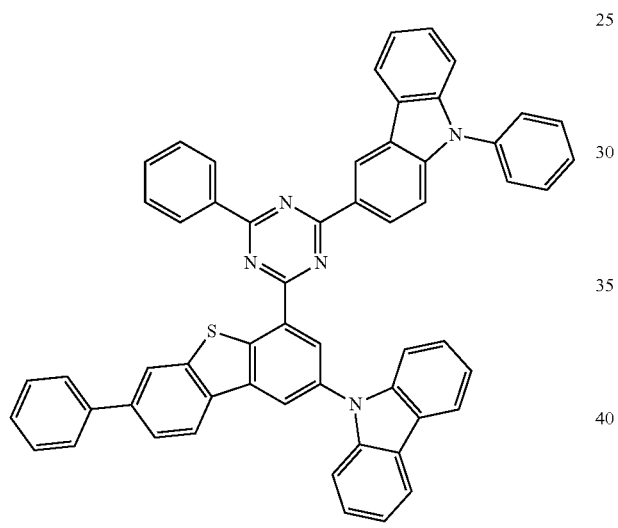
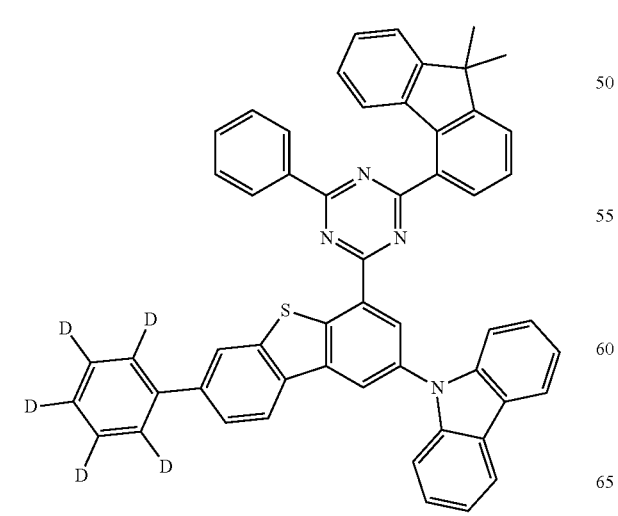
346
-continued
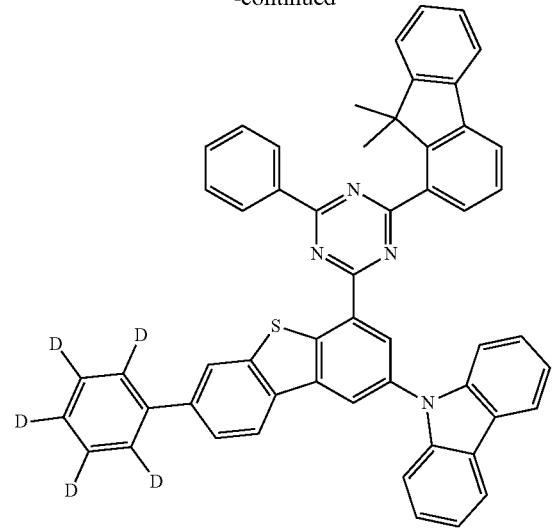
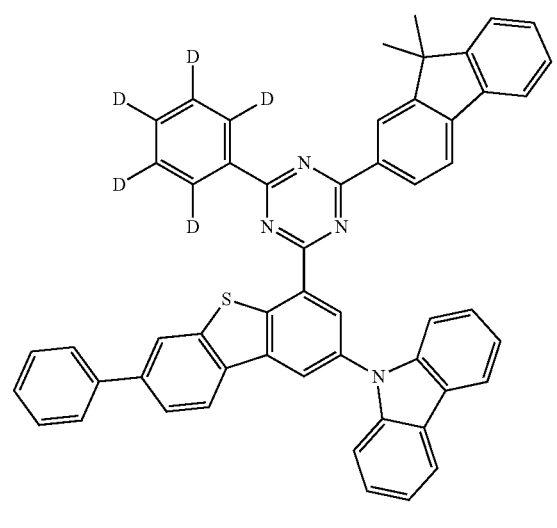
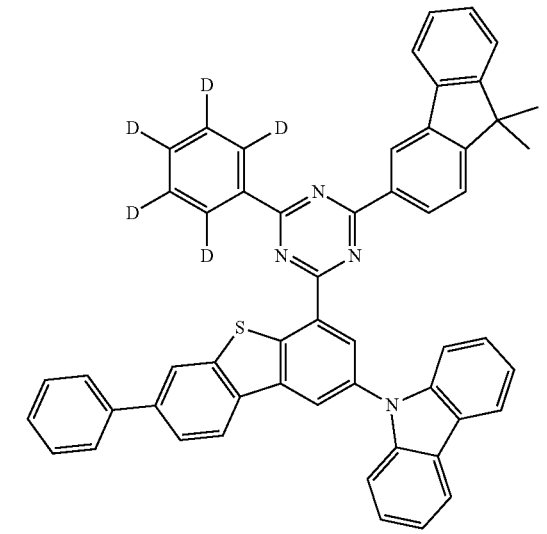

347
-continued
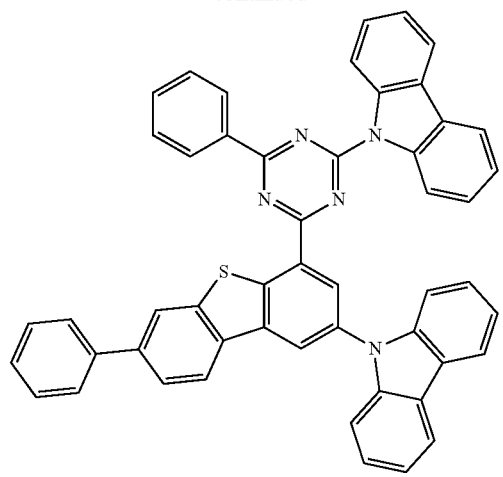
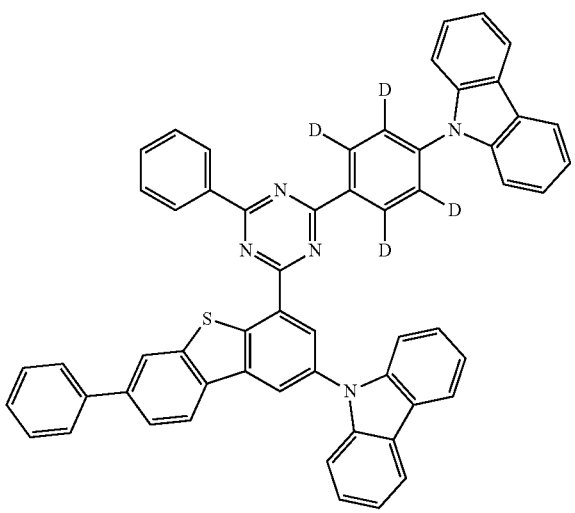
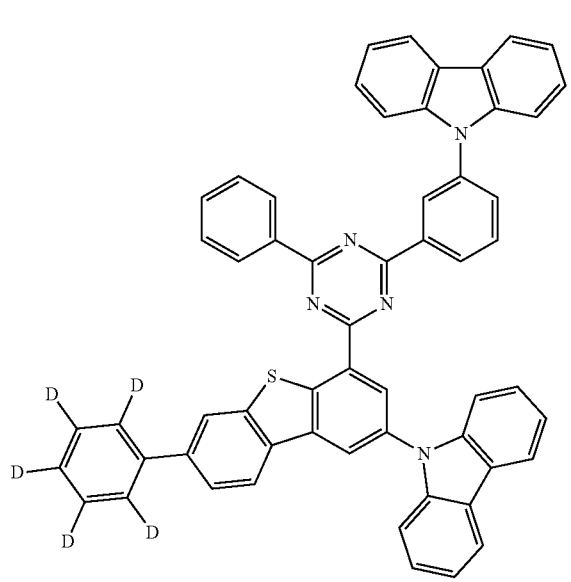
348
-continued
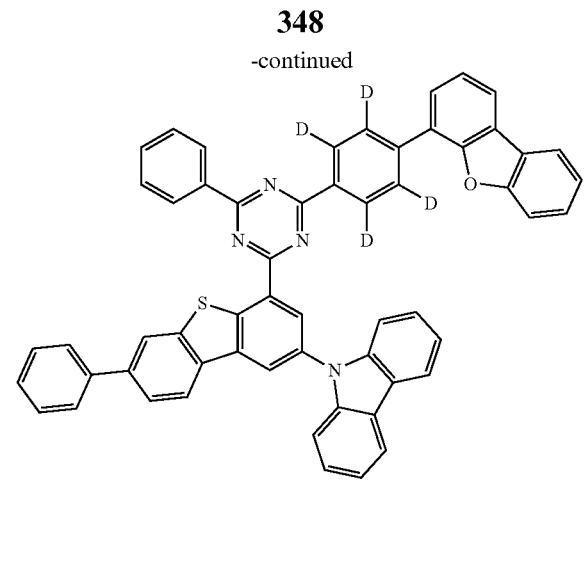
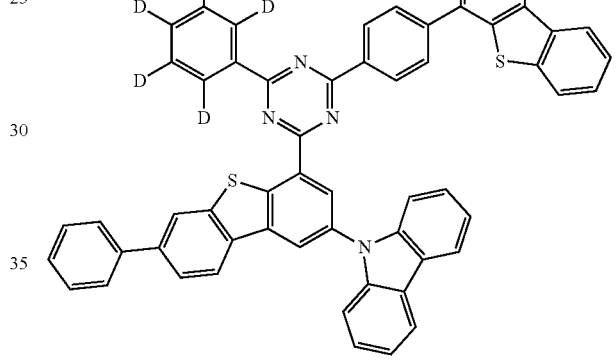
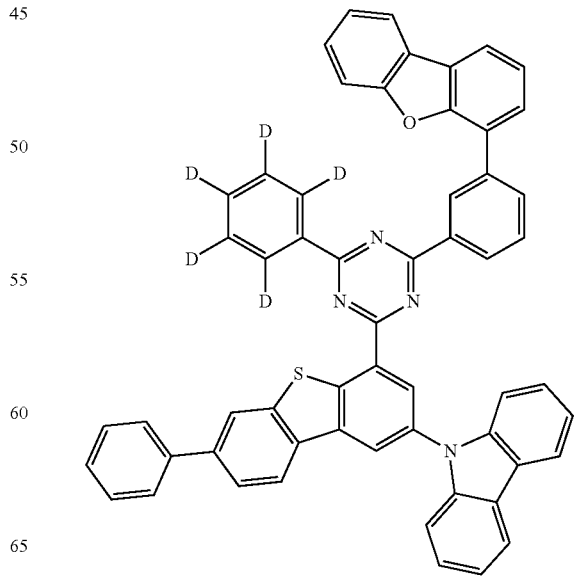

349
-continued
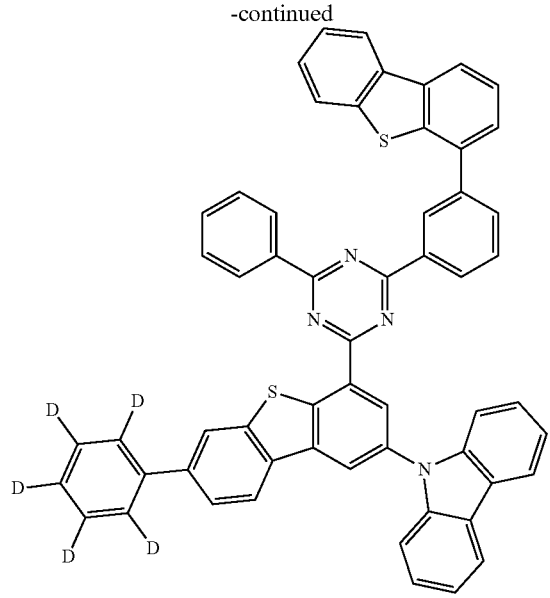
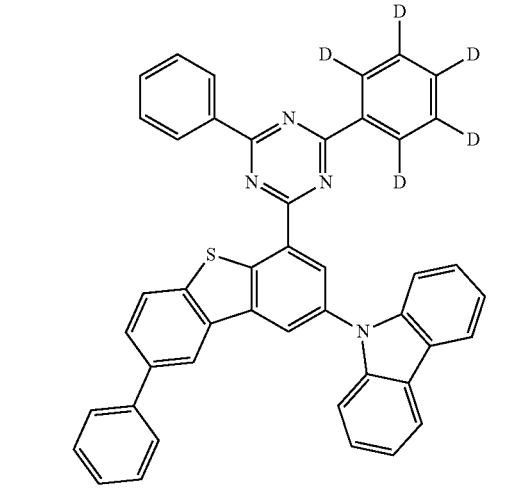
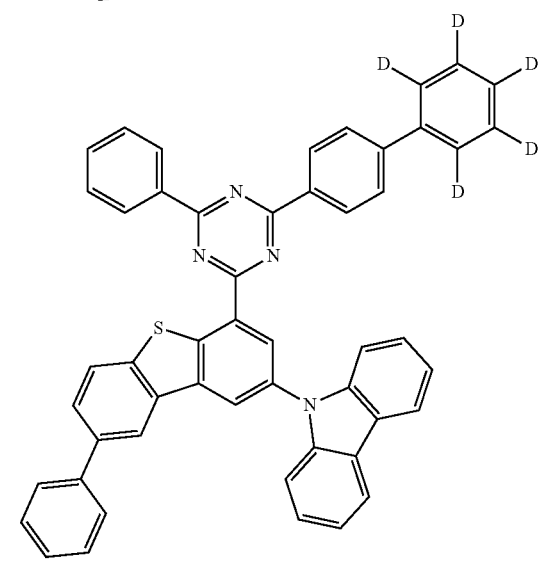
350
-continued
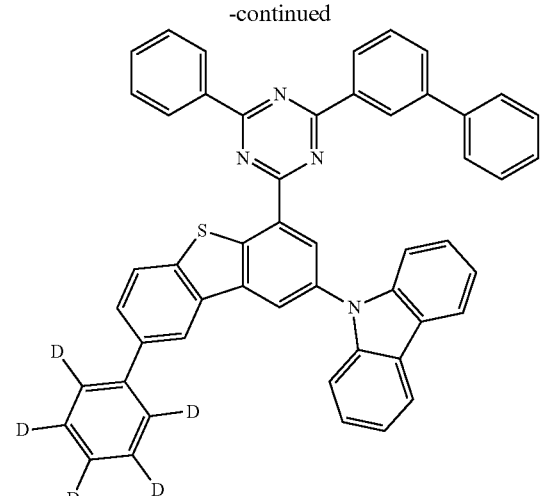
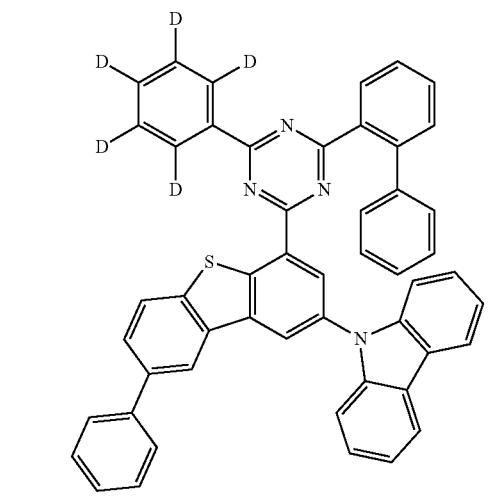
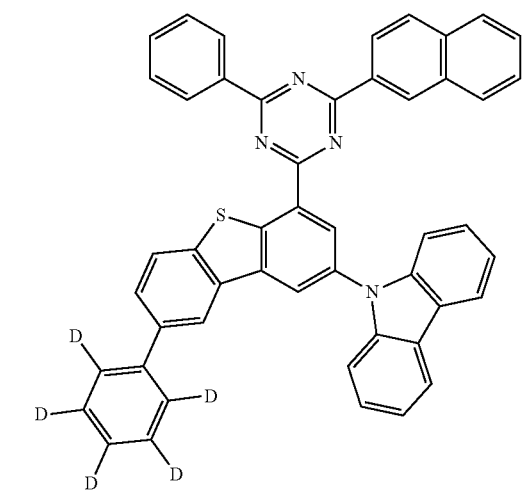

351
-continued
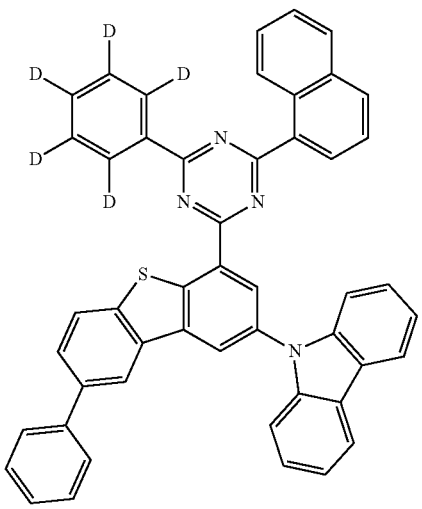
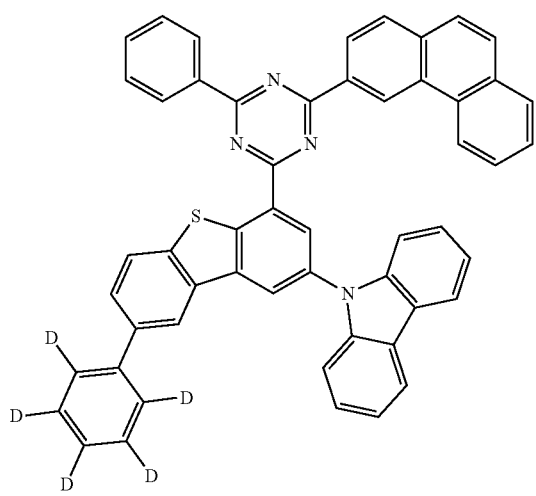
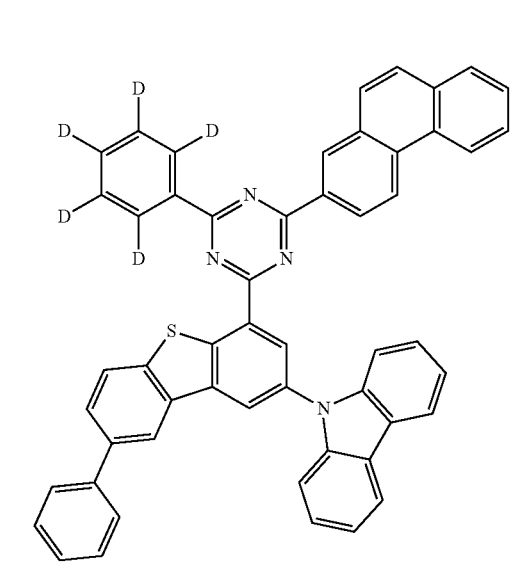
352
-continued
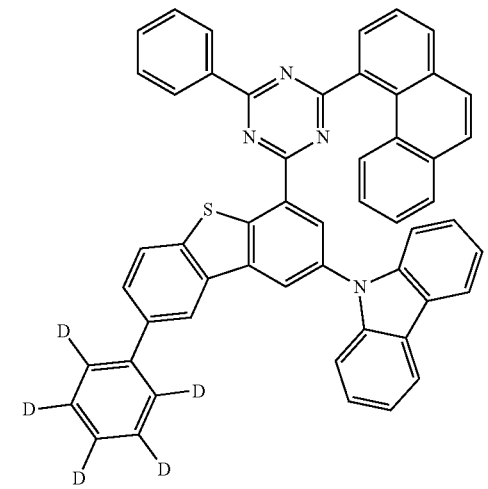
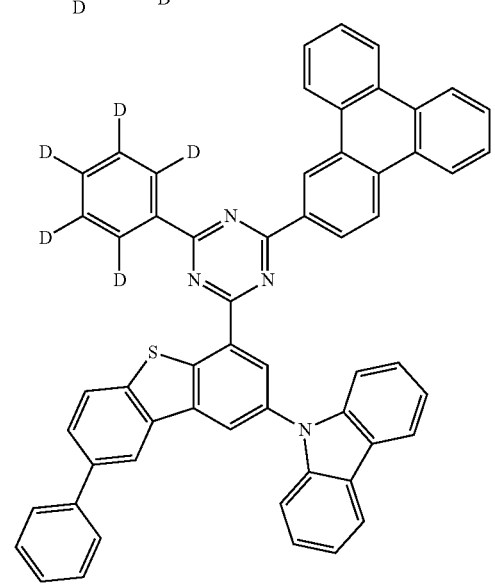
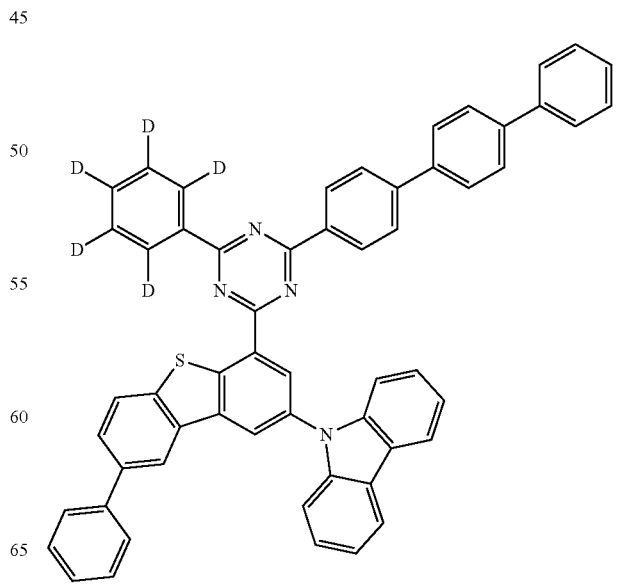

353
-continued
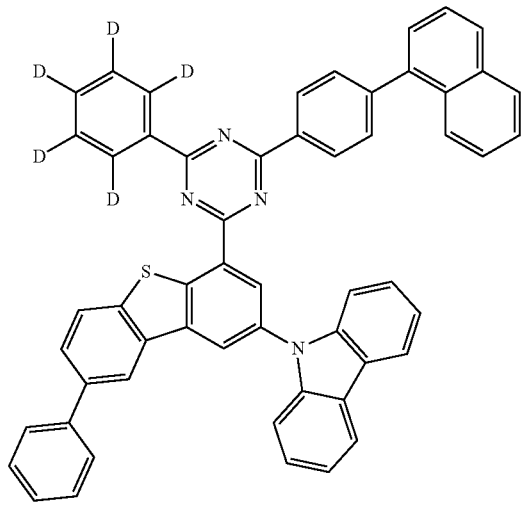
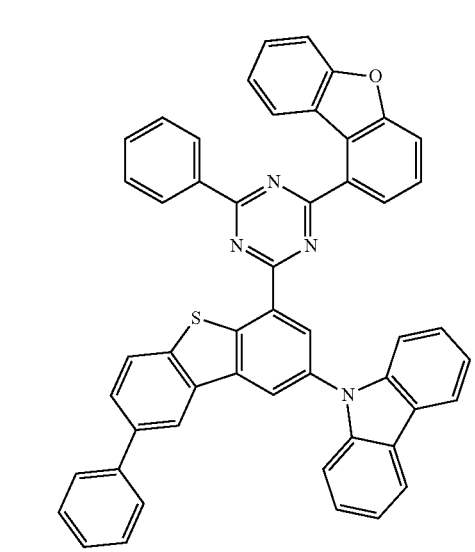
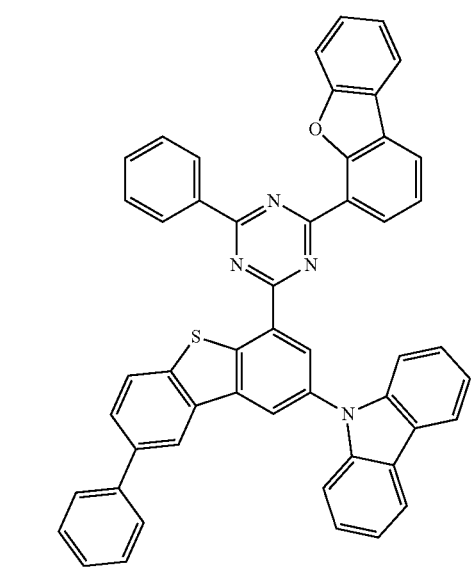
354
-continued
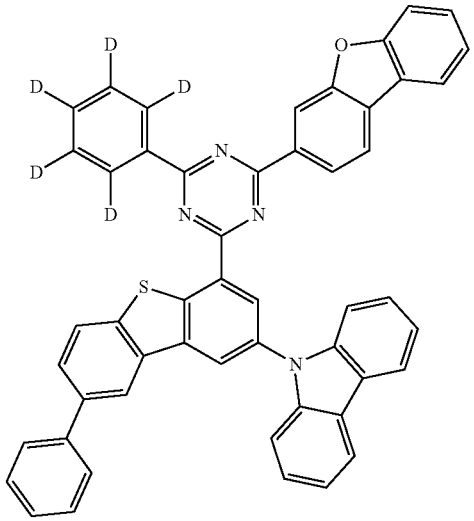
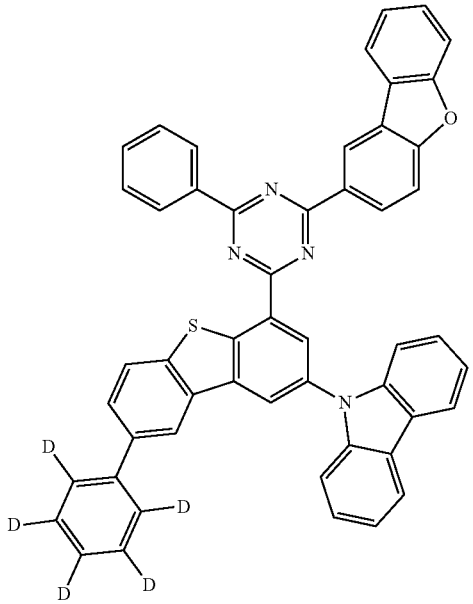
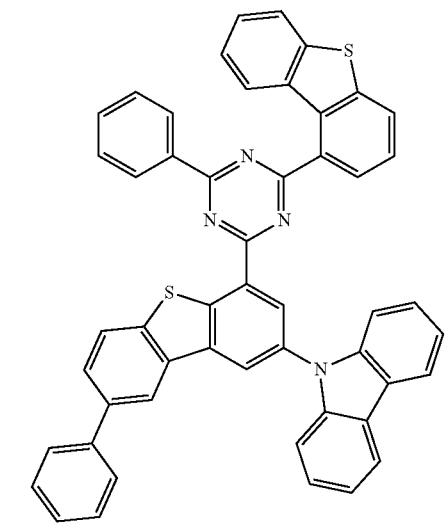

355
-continued
356
-continued
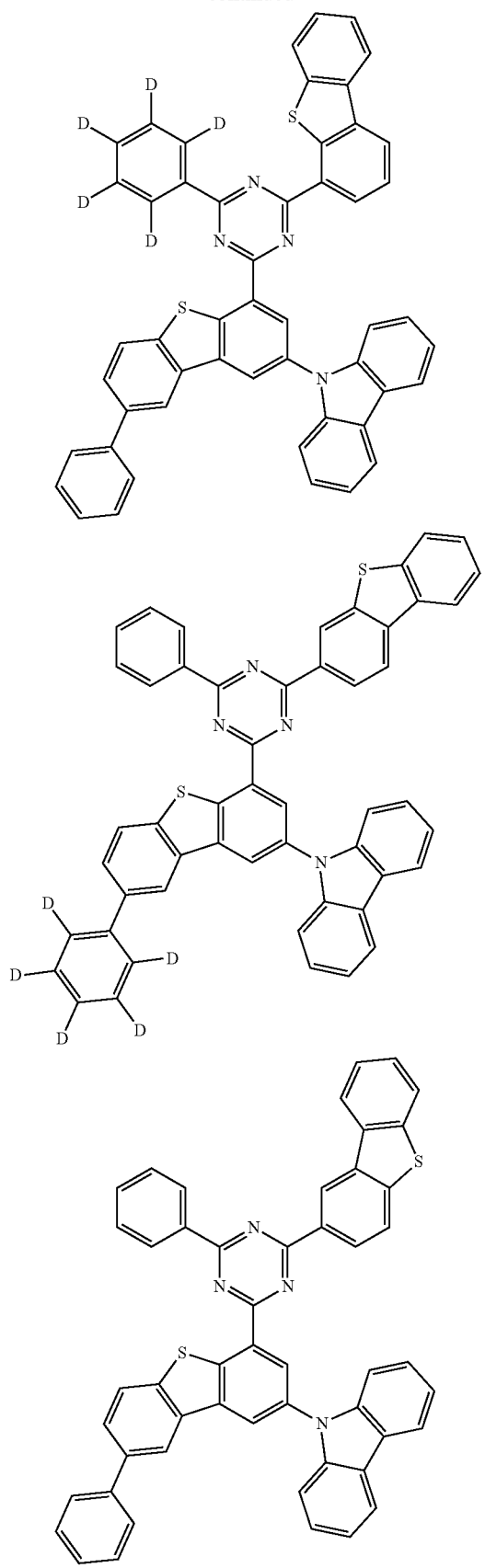
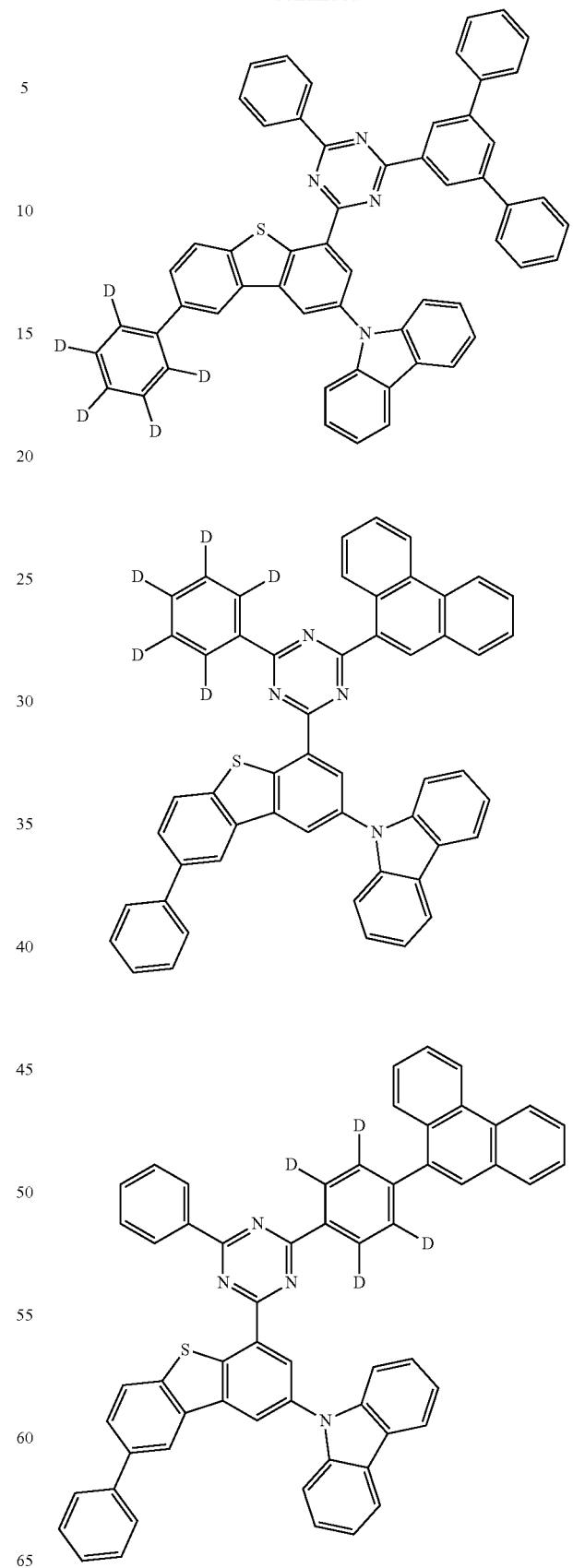

357
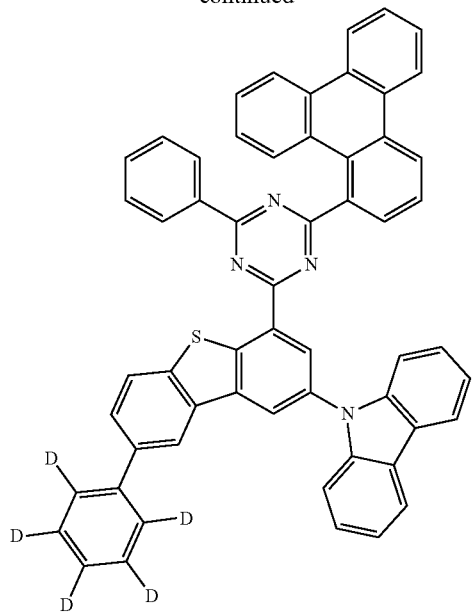
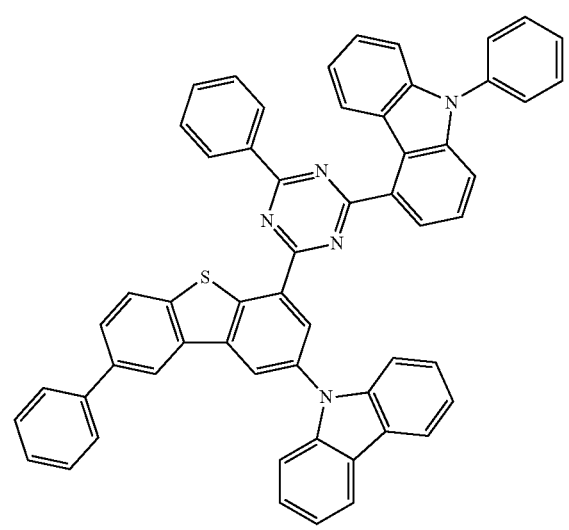
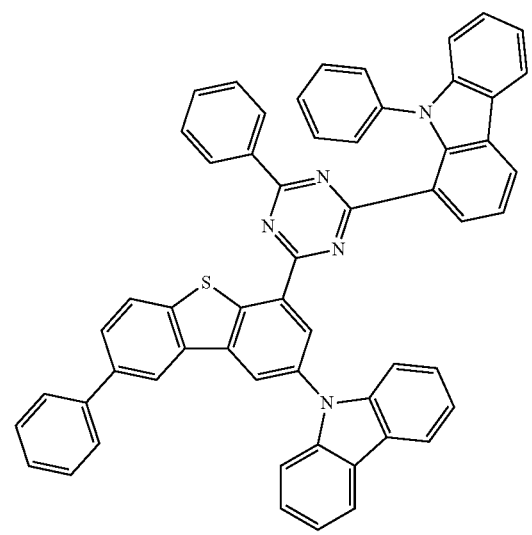
358
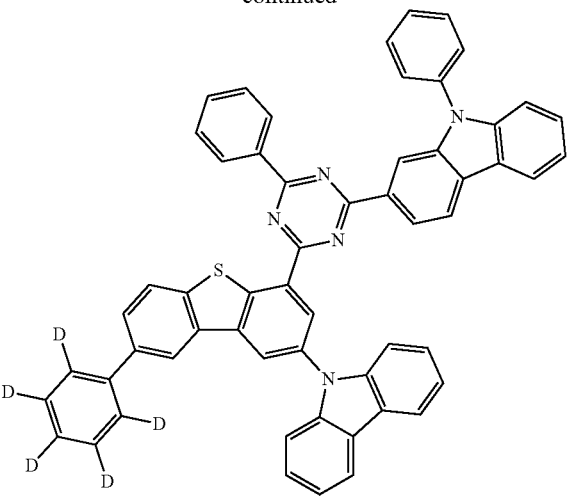
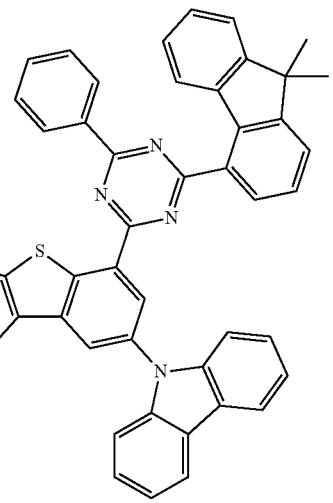

359
-continued
360
-continued
| | |
|---|---|
| 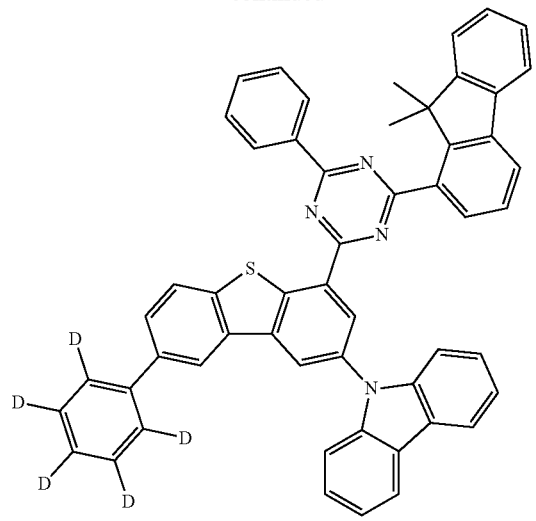 | 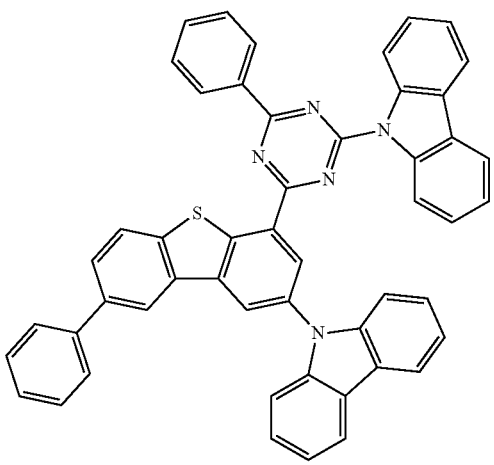 |
| 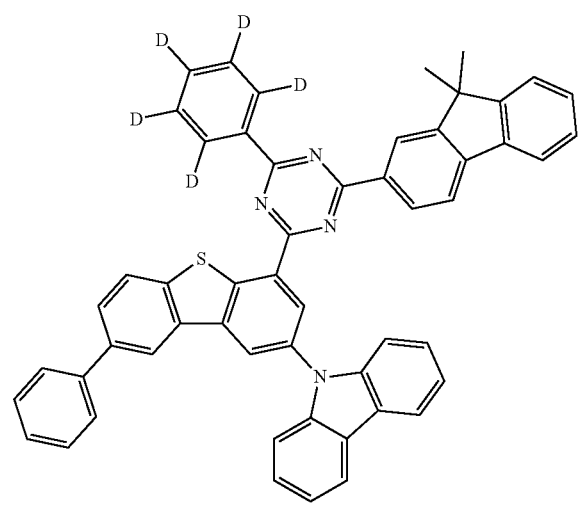 | 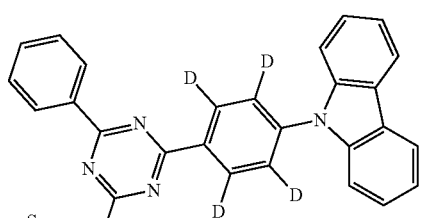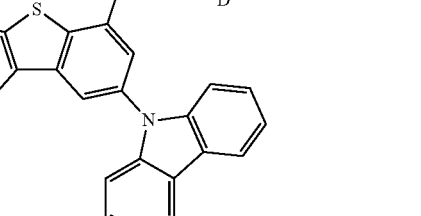 |
| 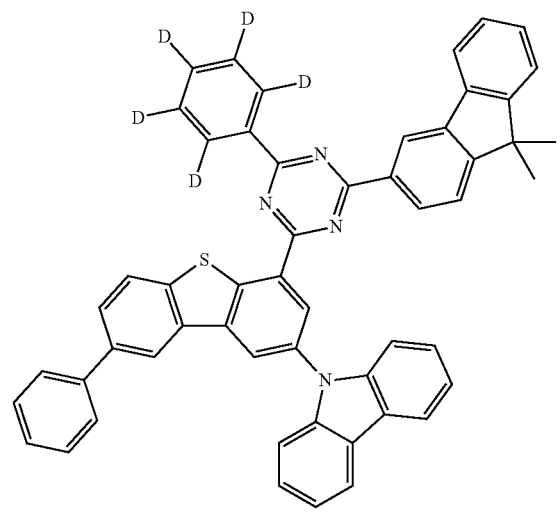 | 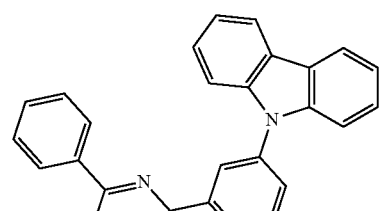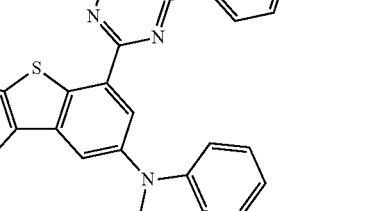 |

361
-continued
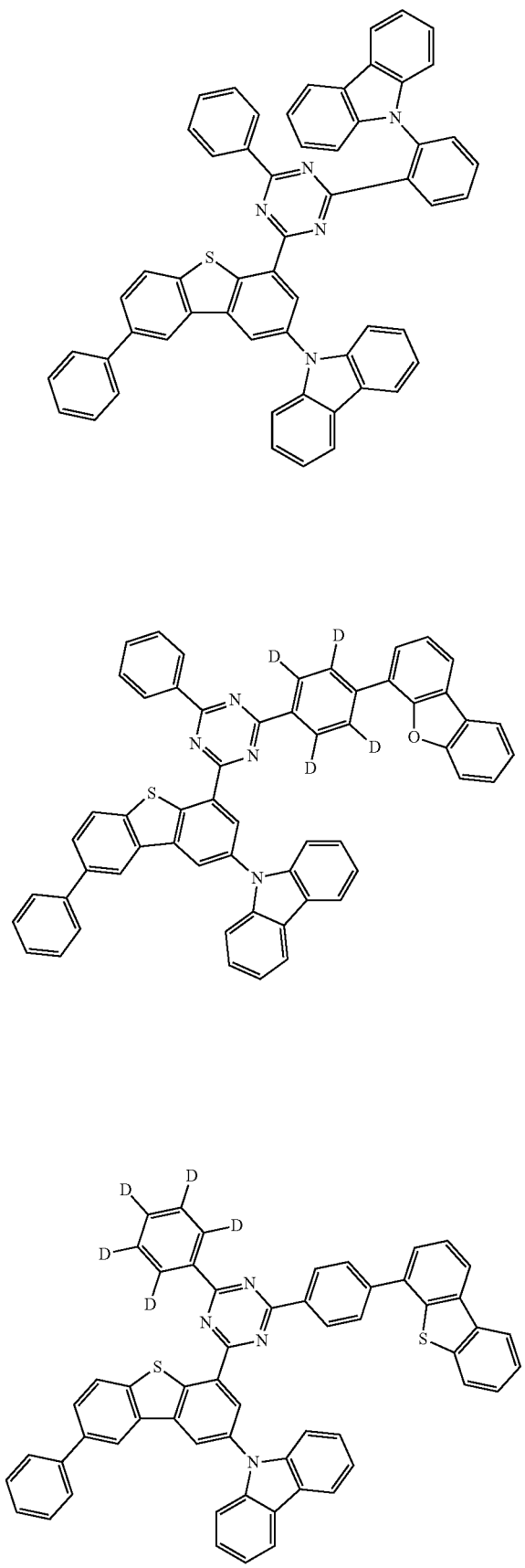
362
-continued
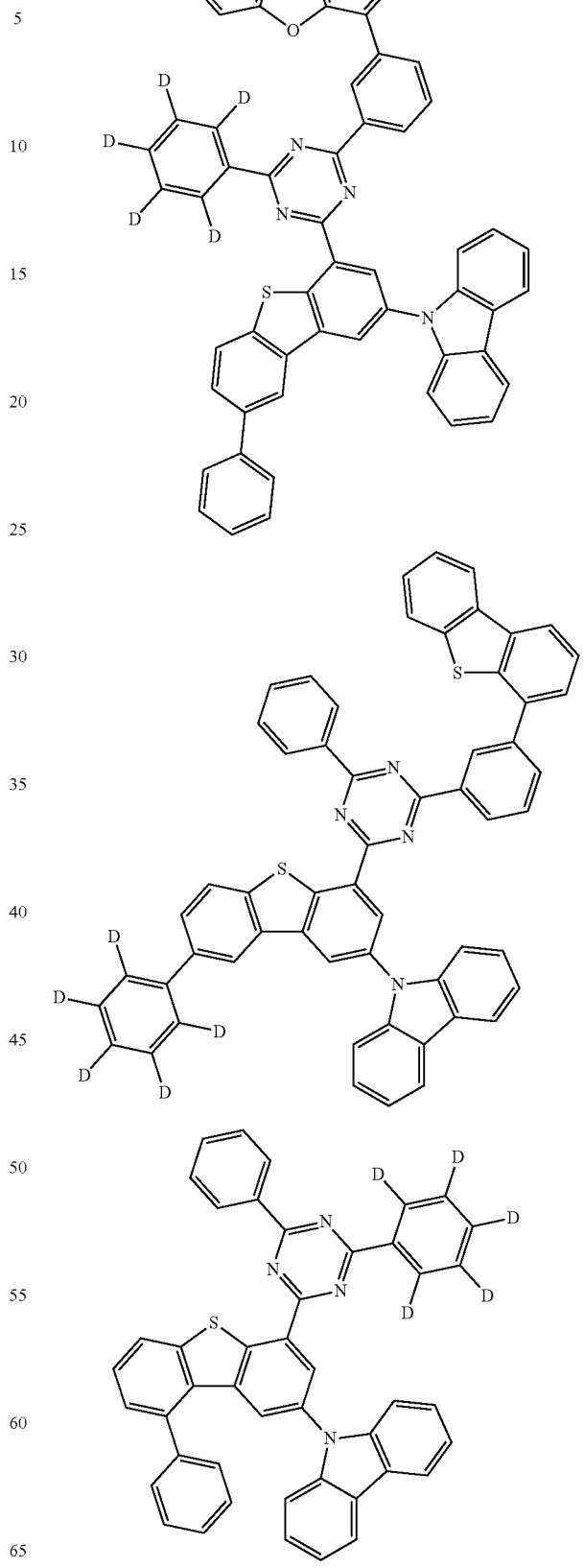

363
-continued
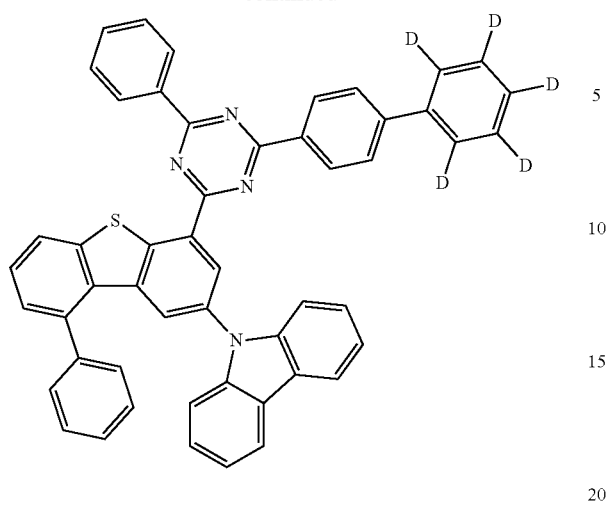
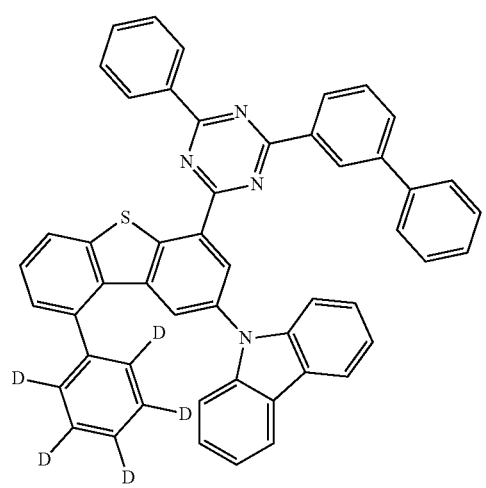
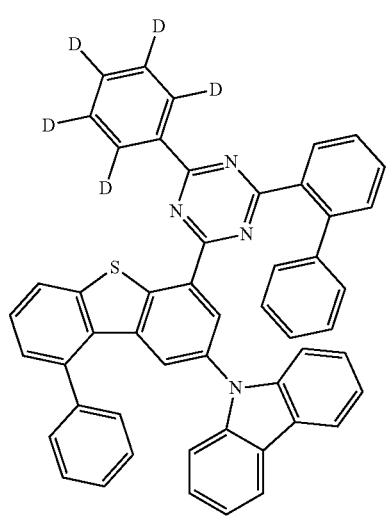
364
-continued
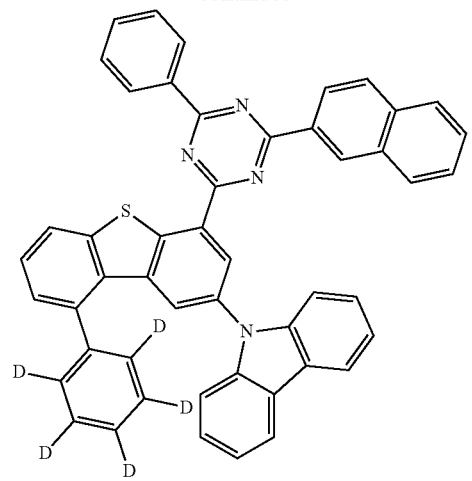
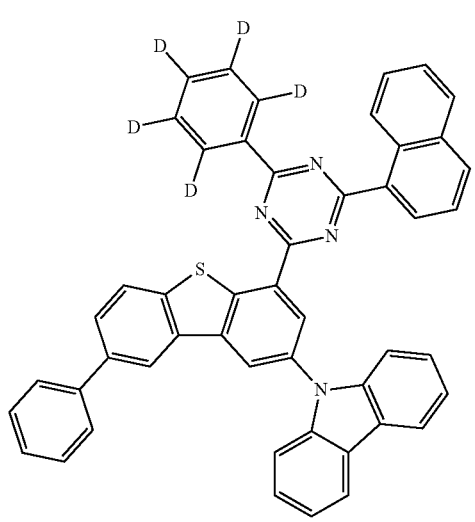
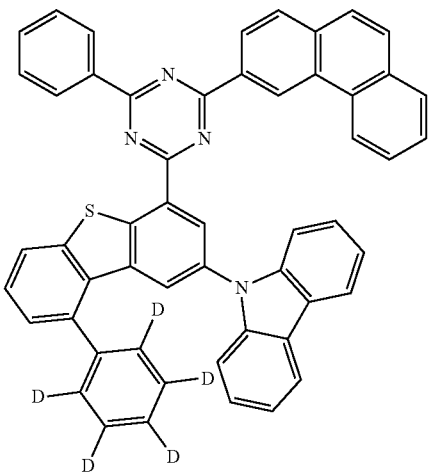

365
-continued
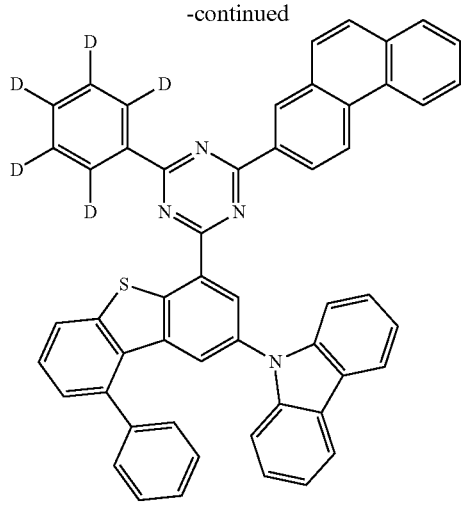
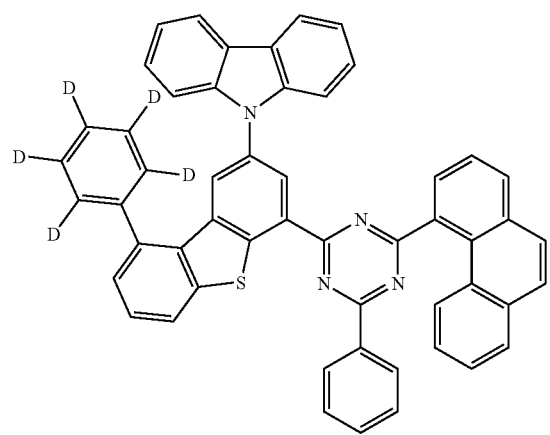
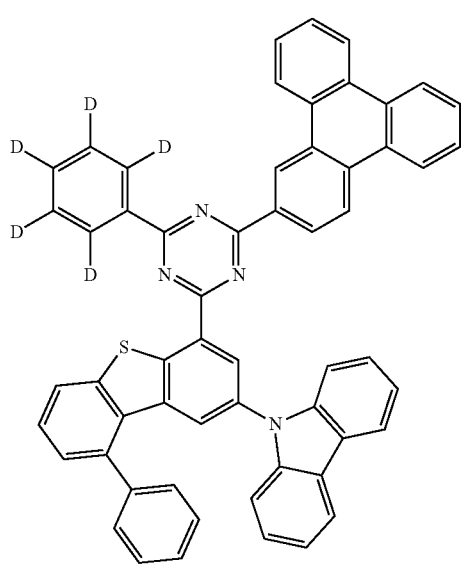
366
-continued
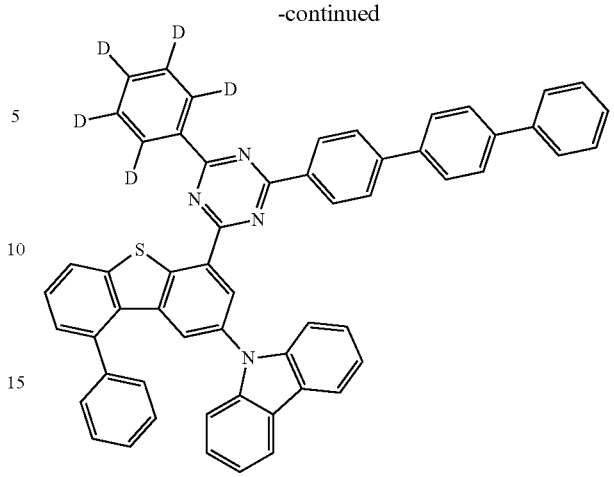
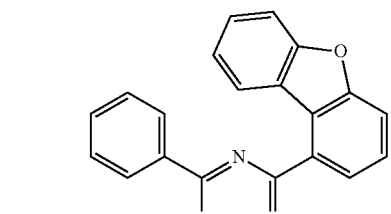
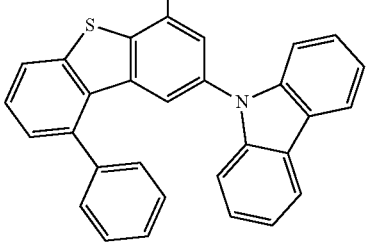

367
-continued
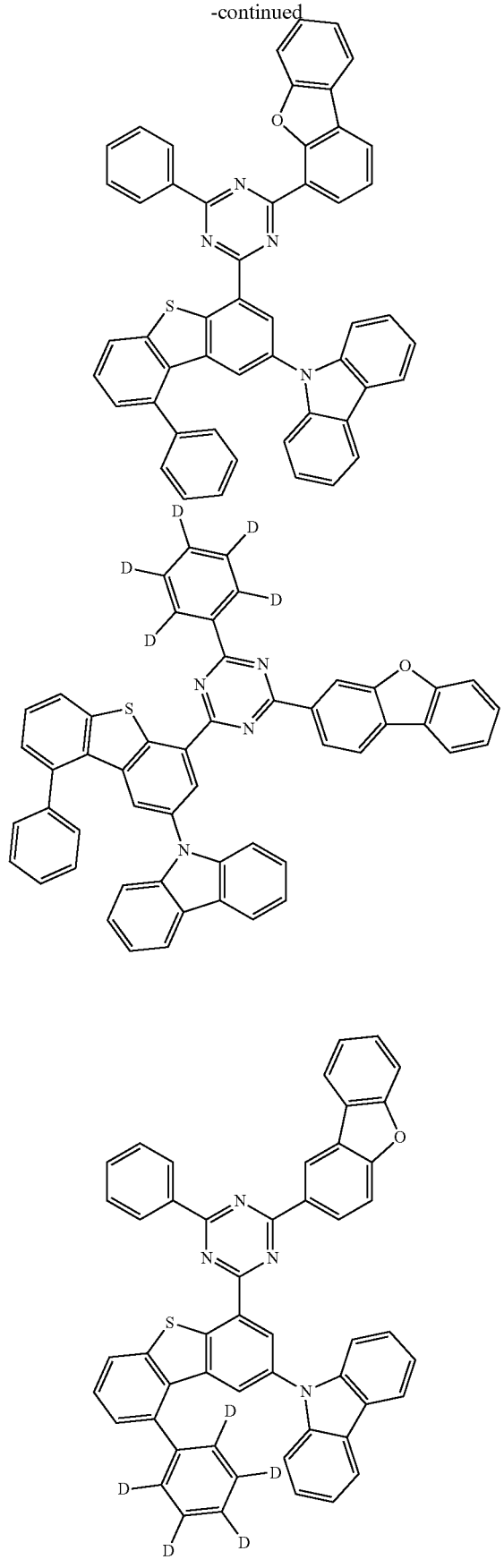
368
-continued
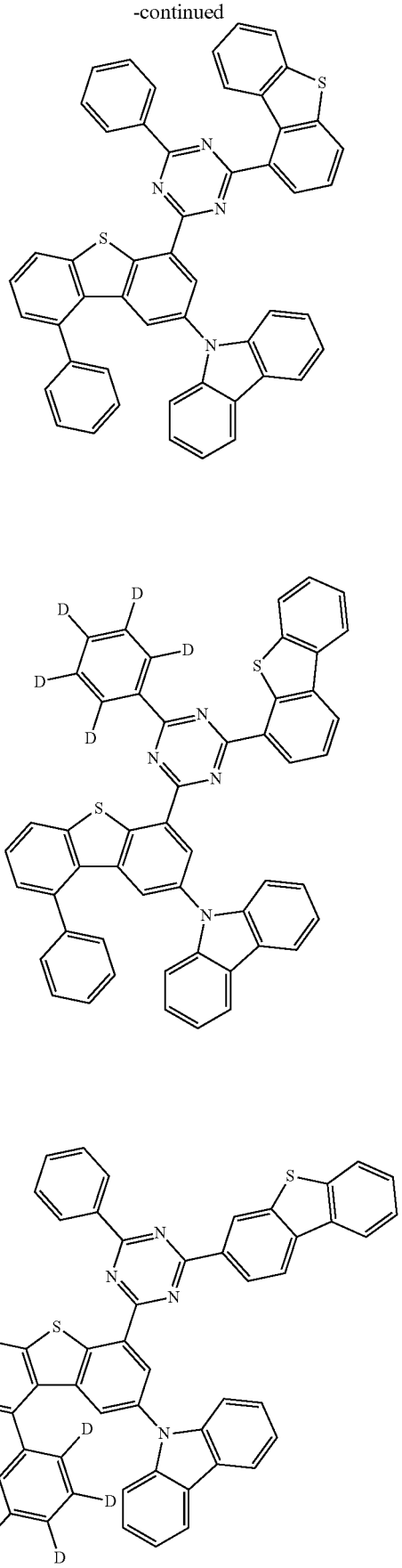

369
-continued
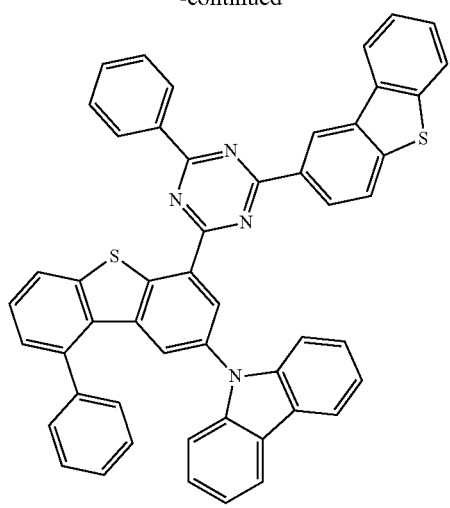
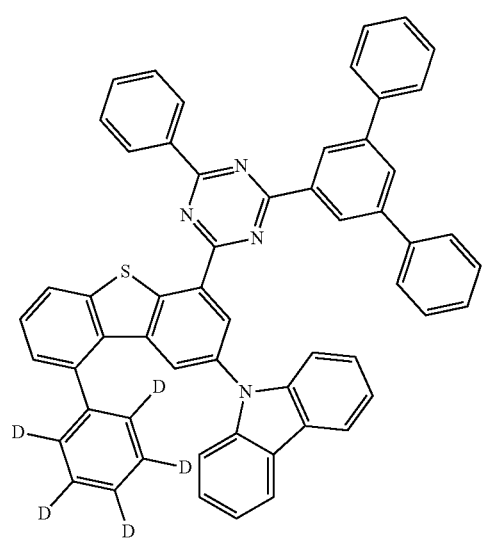
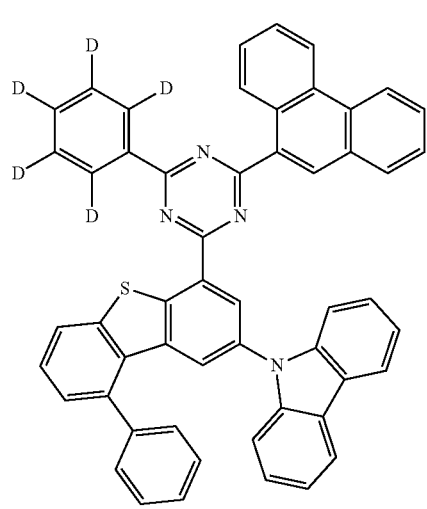
370
-continued
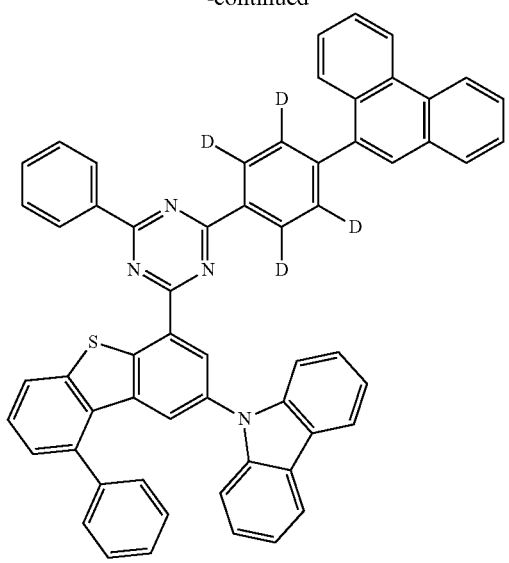
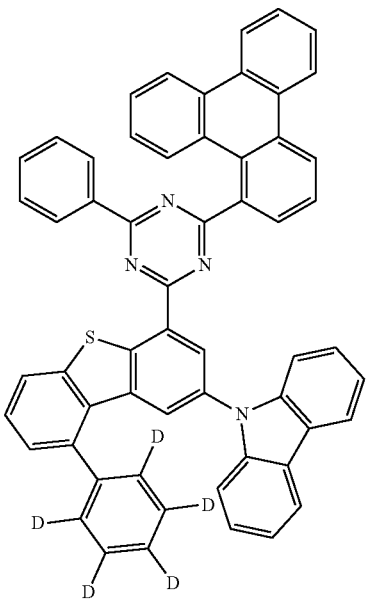
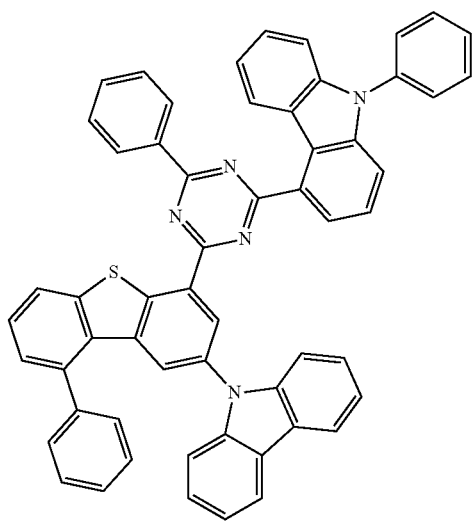

371
-continued
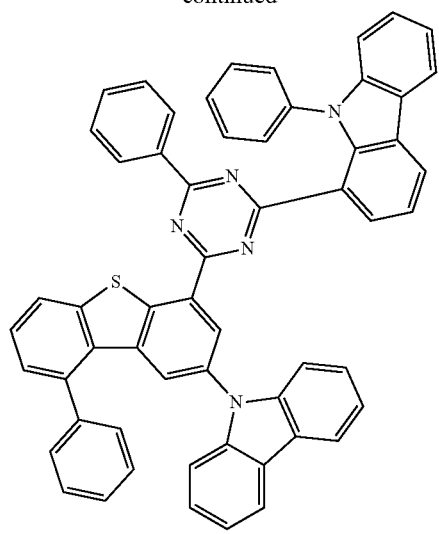
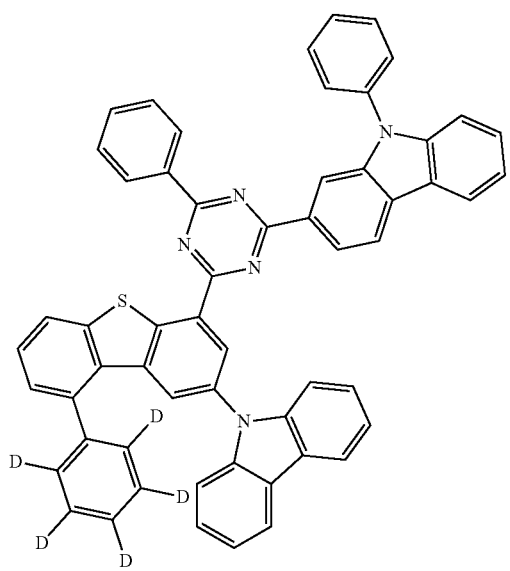
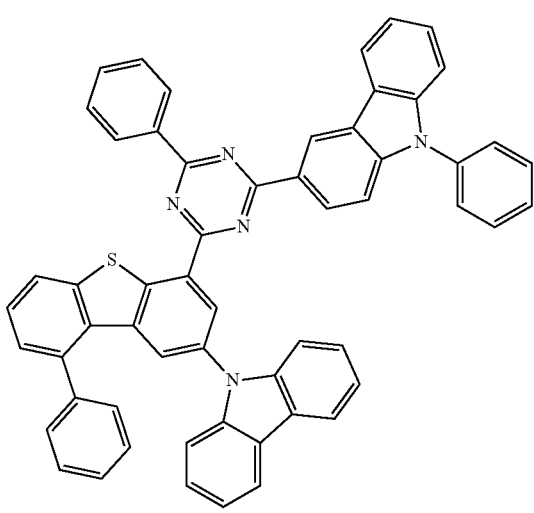
372
-continued
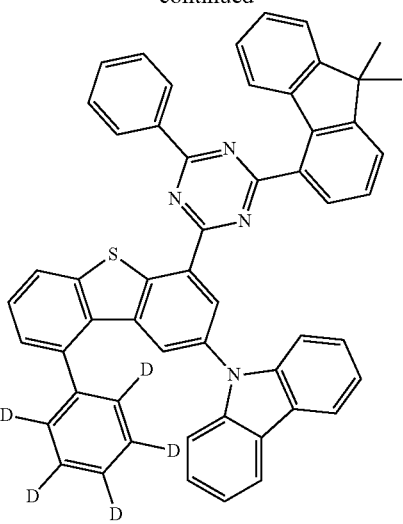
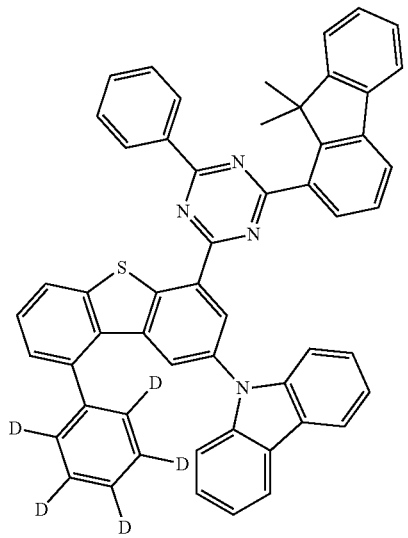
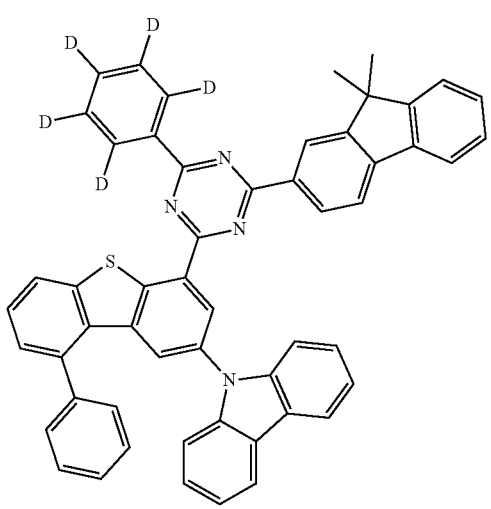

373
-continued
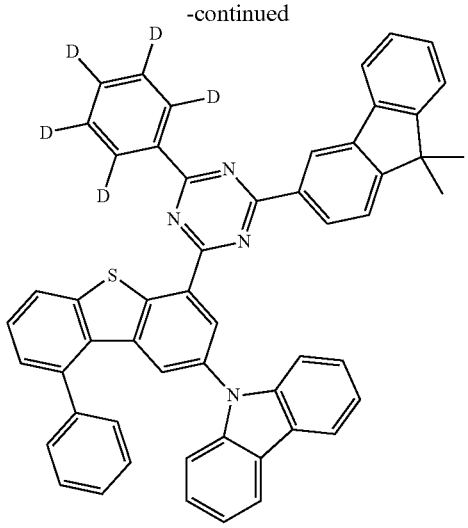
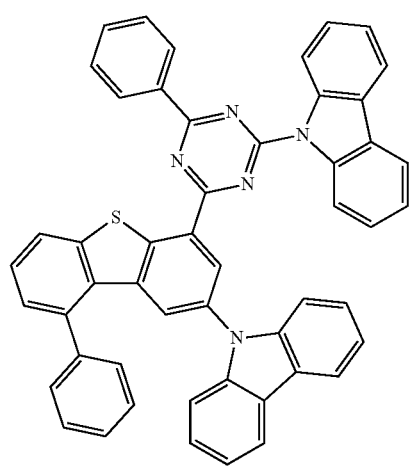
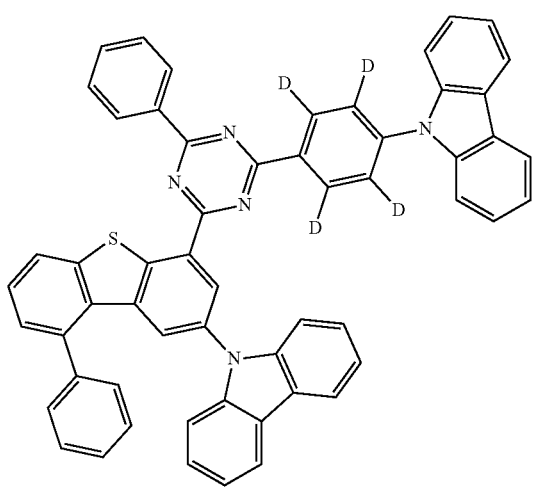
374
-continued
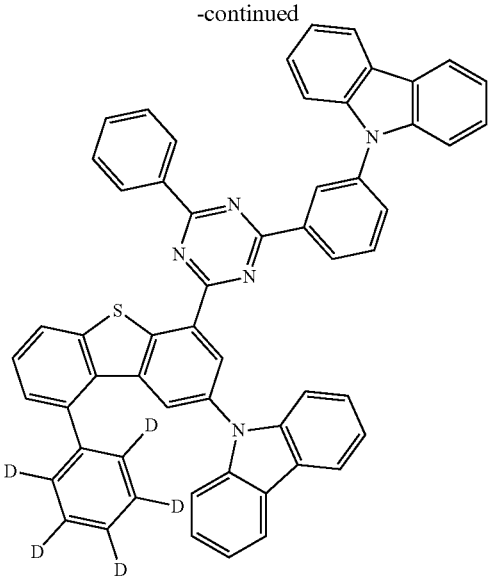
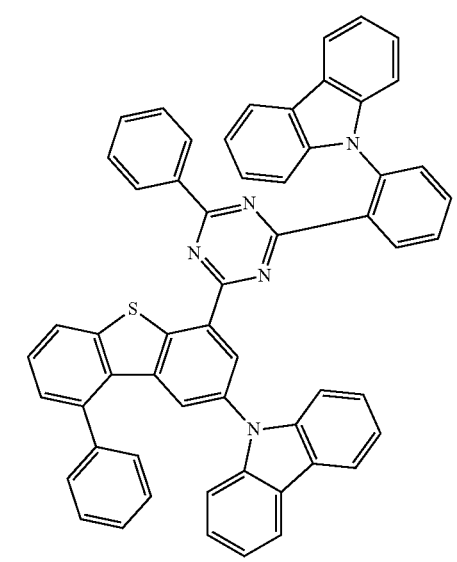
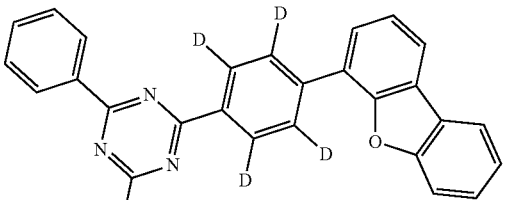
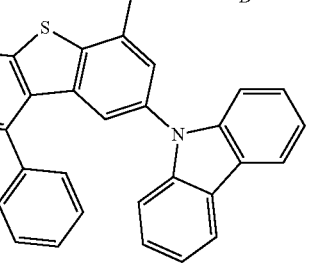

375
-continued
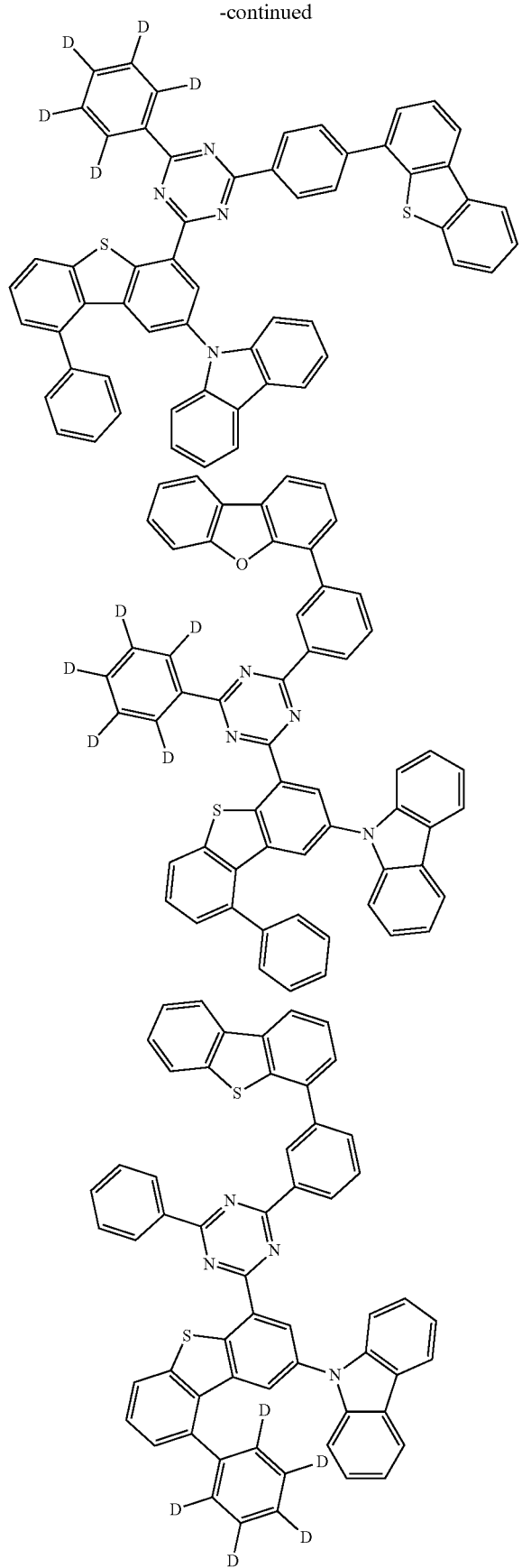
376
-continued
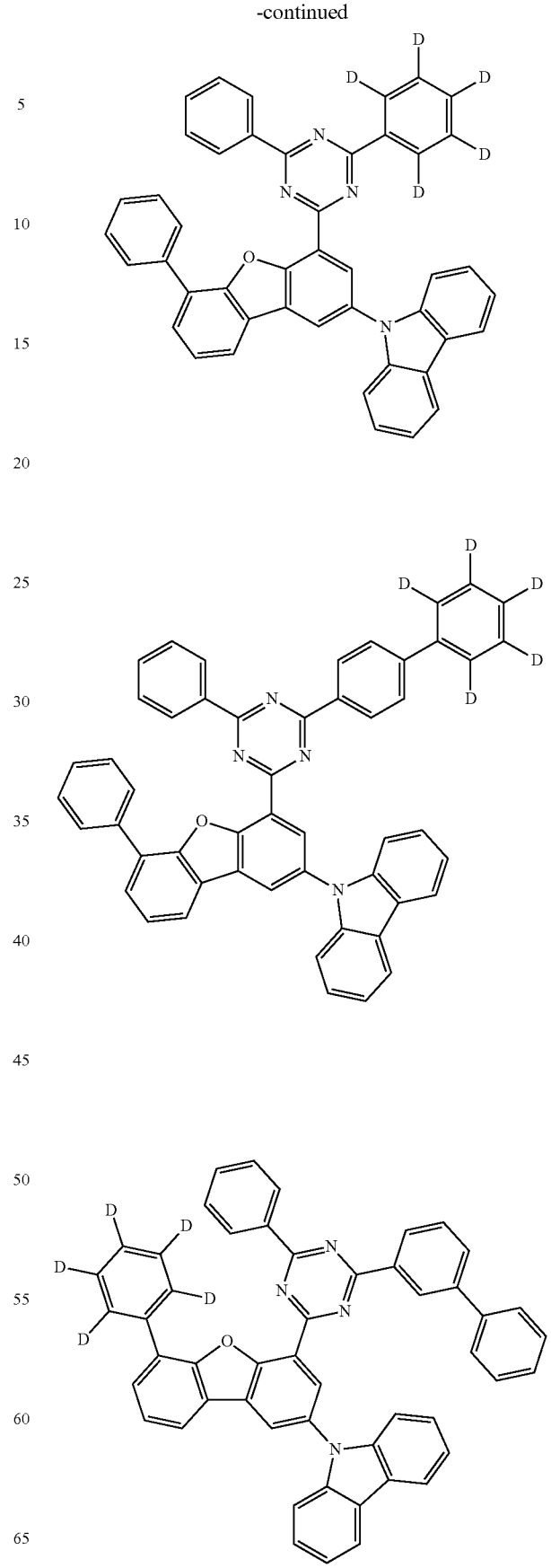

377
-continued
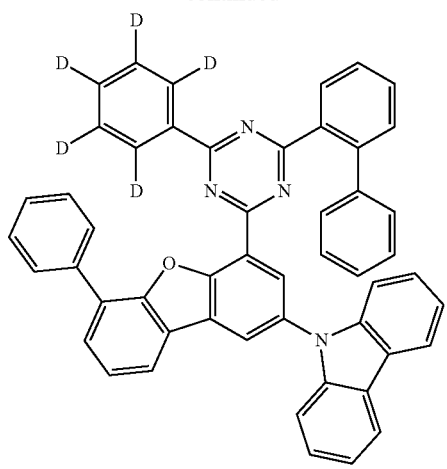
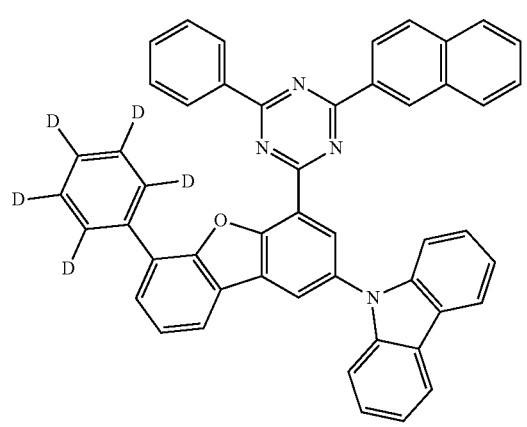
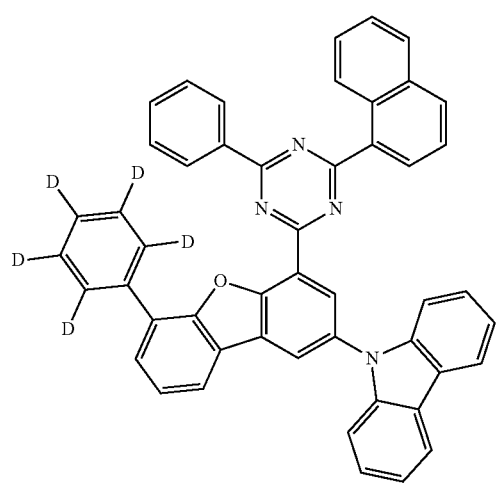
378
-continued
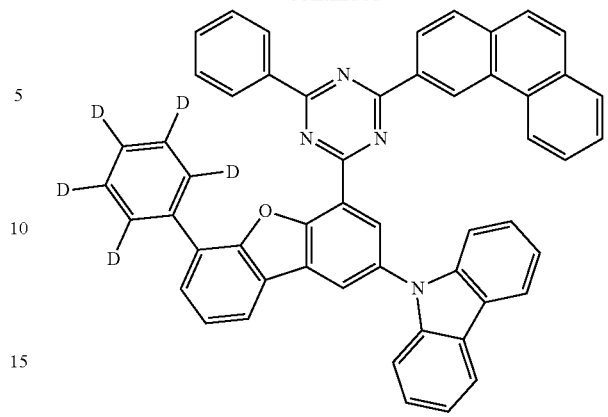
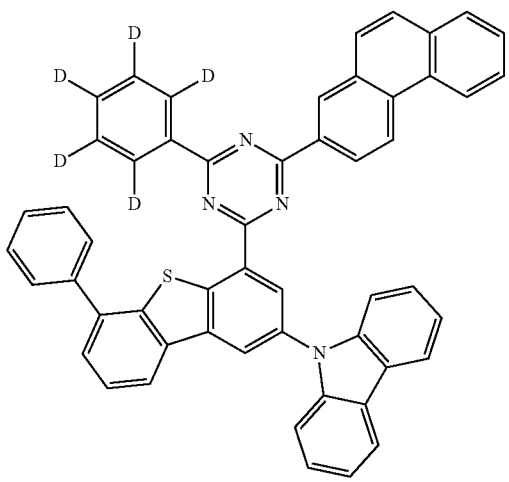
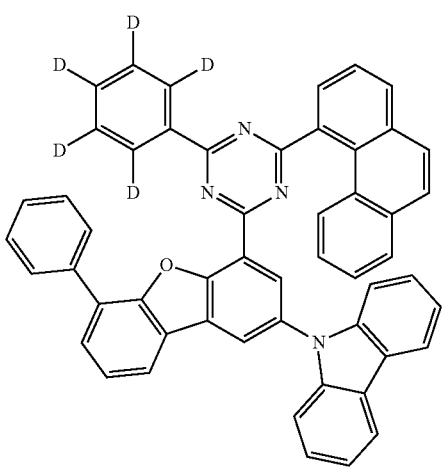

379
-continued
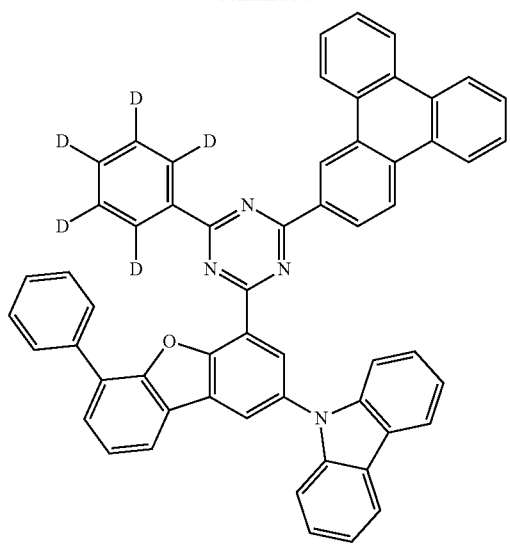
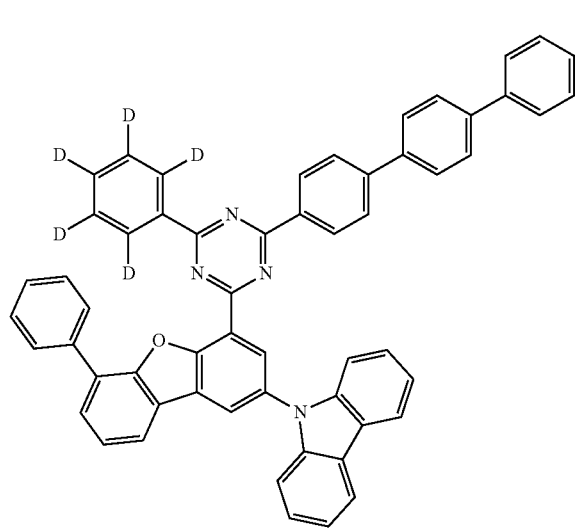
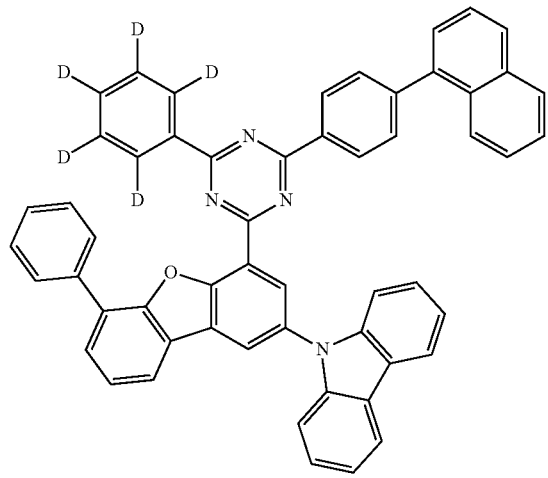
380
-continued
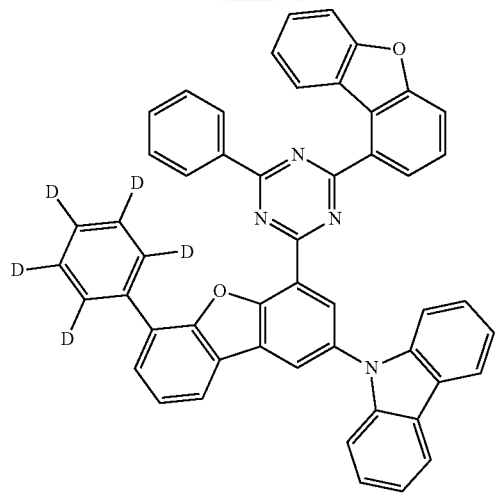
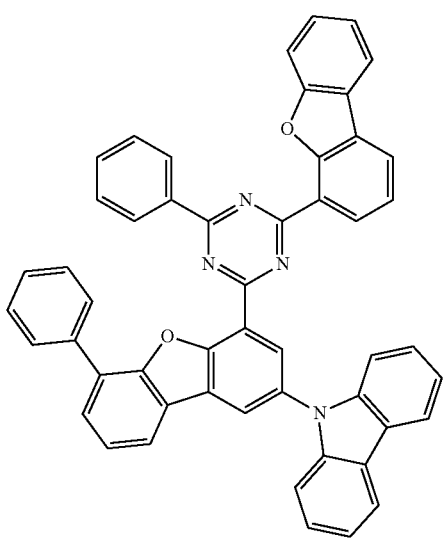
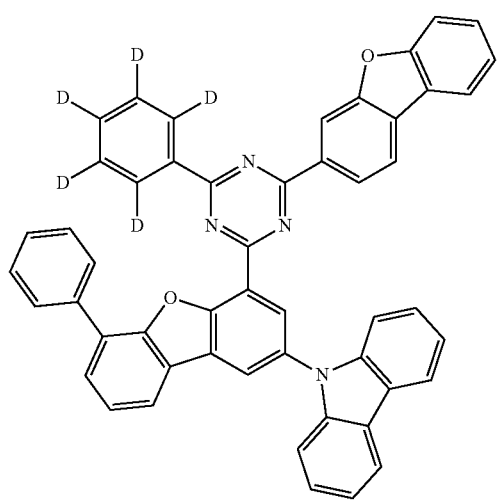

381
-continued
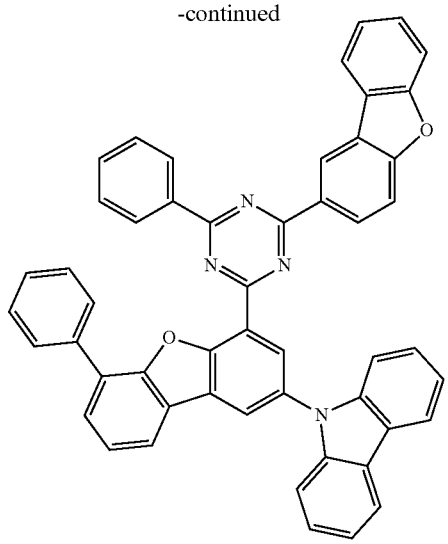
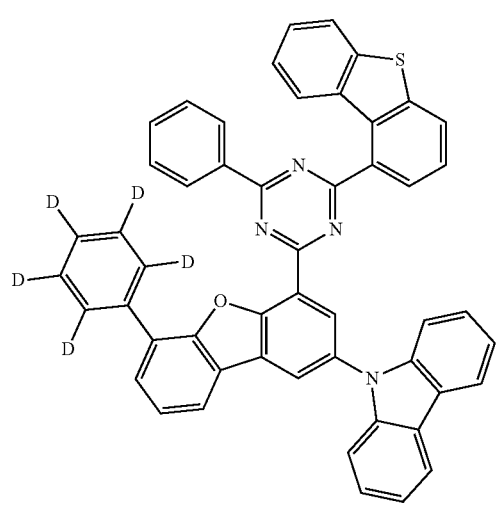
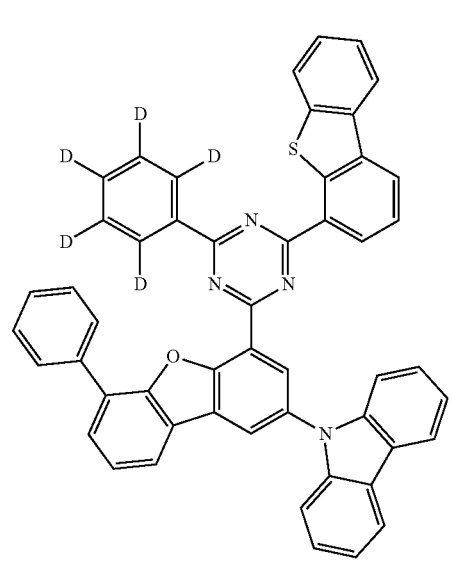
382
-continued
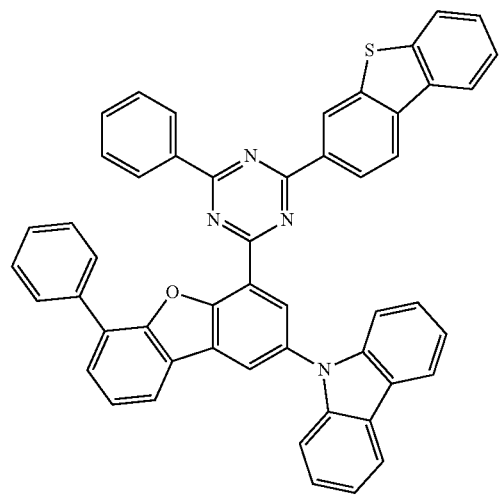
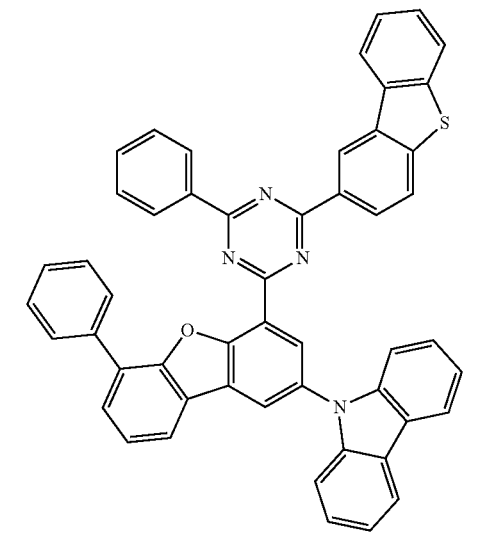
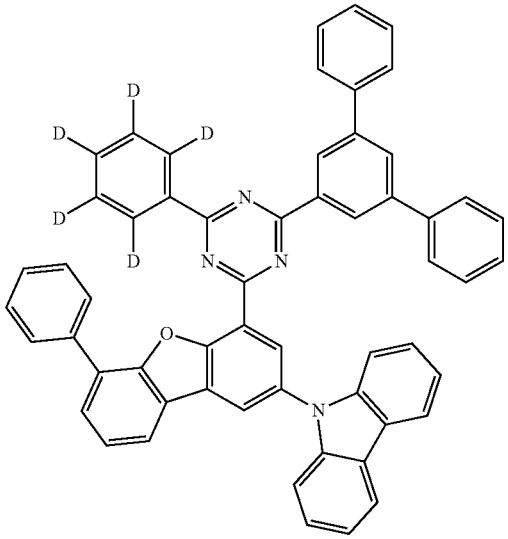

383
-continued
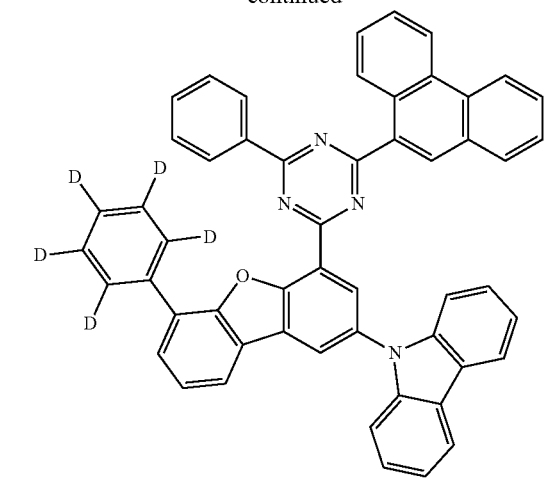
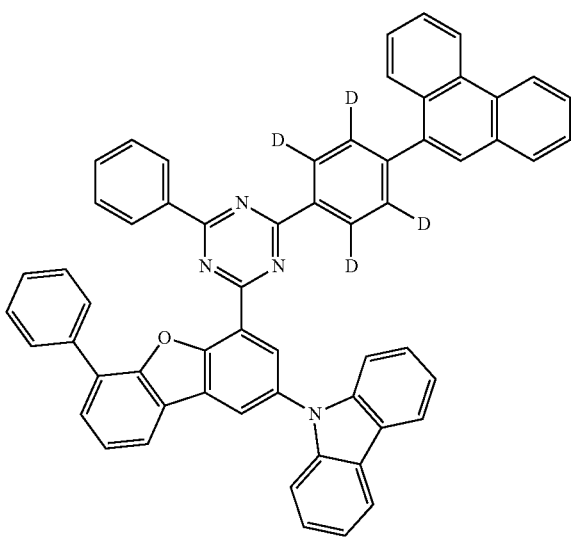
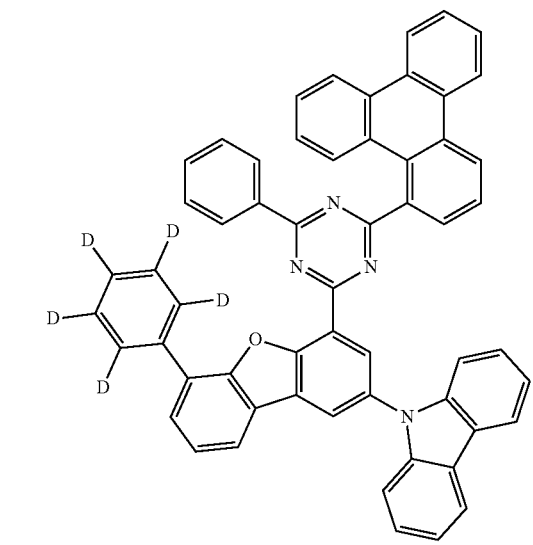
384
-continued
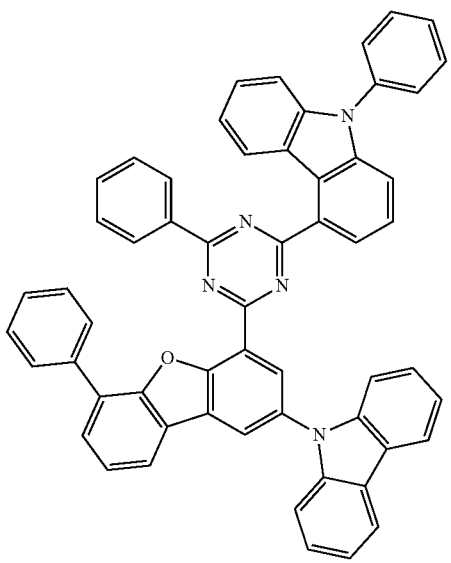
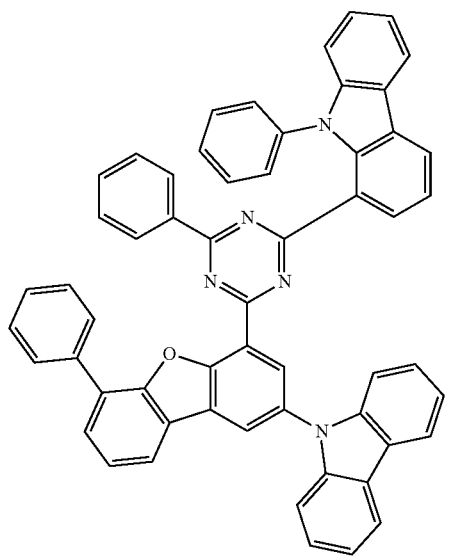
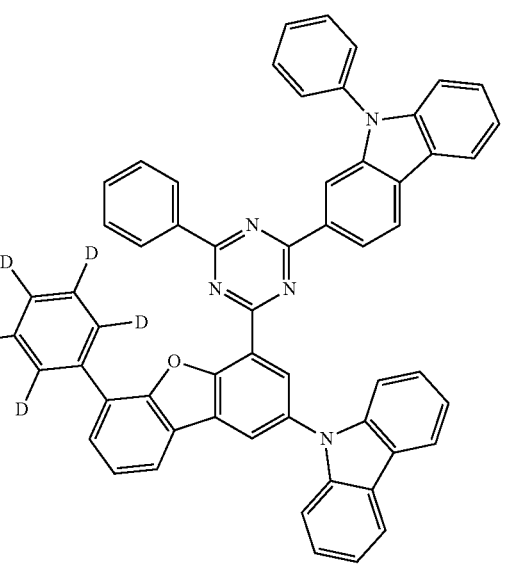

385
-continued
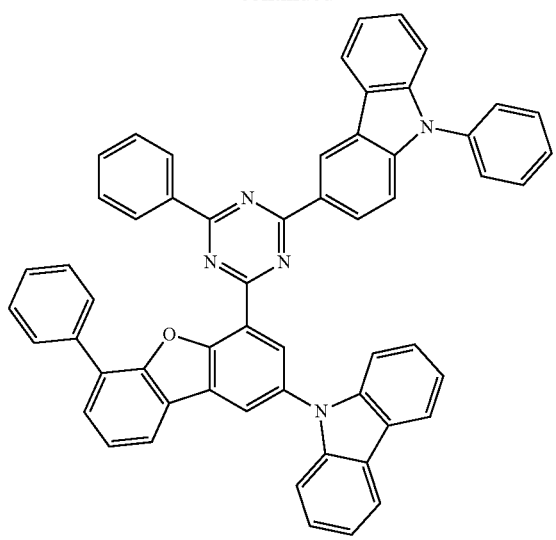
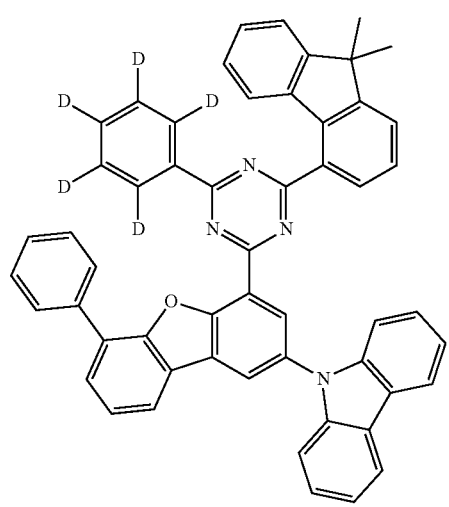
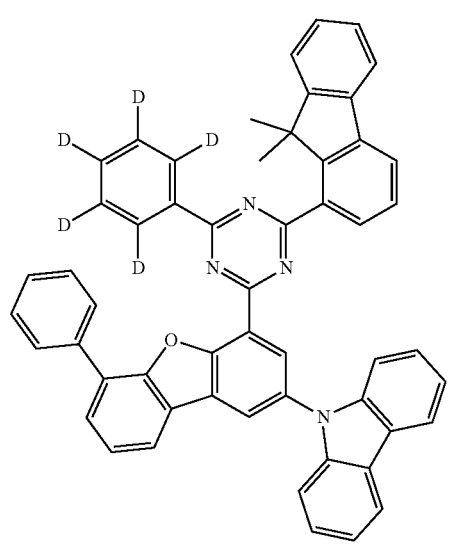
386
-continued
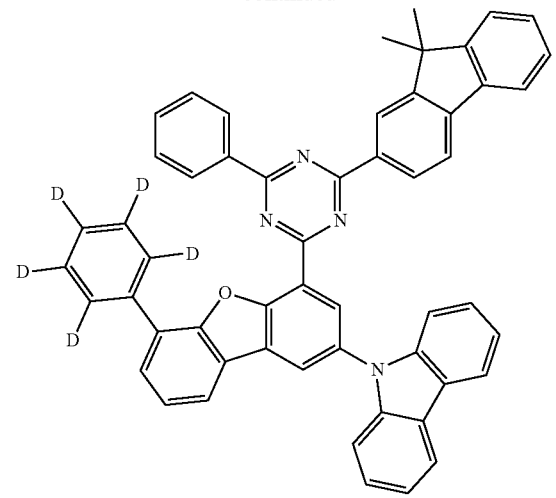
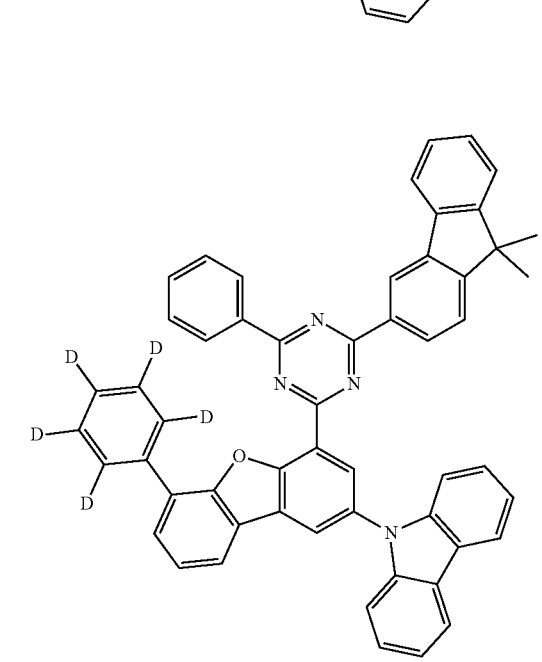
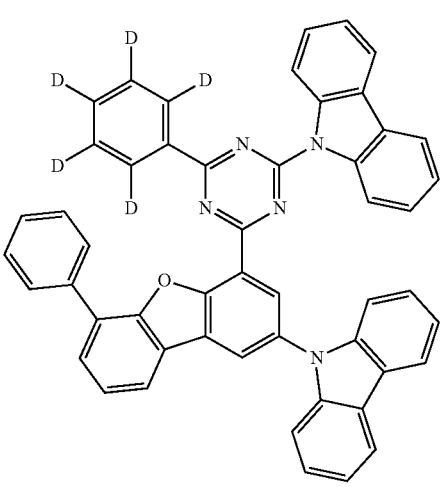

387
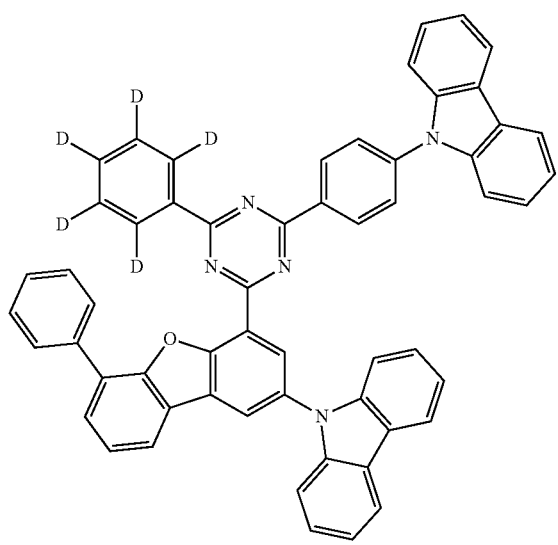
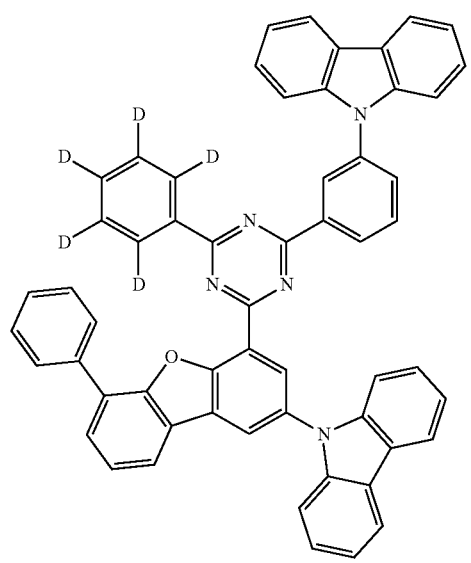
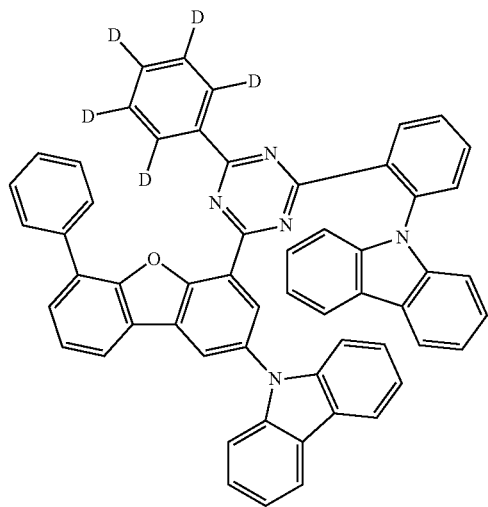
388
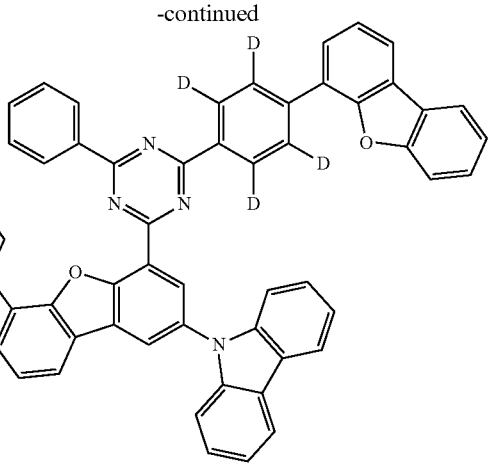
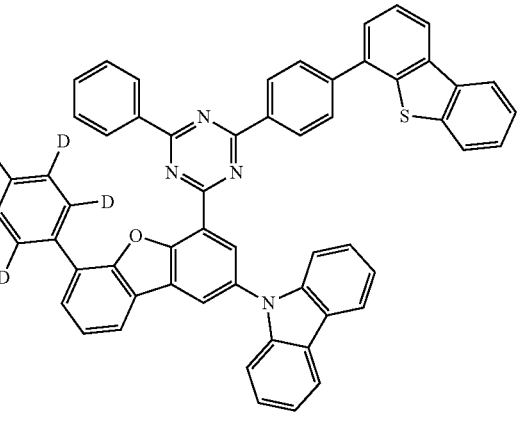
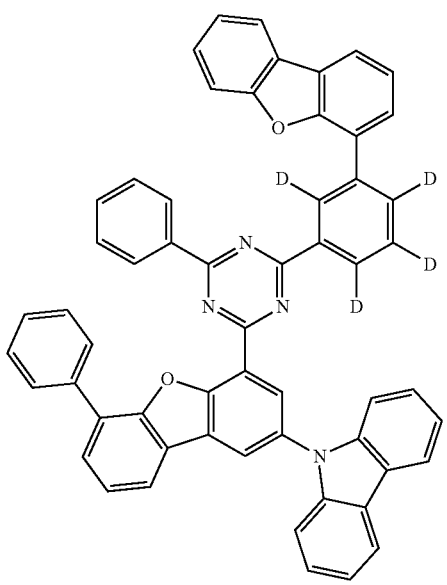

389
-continued
390
-continued
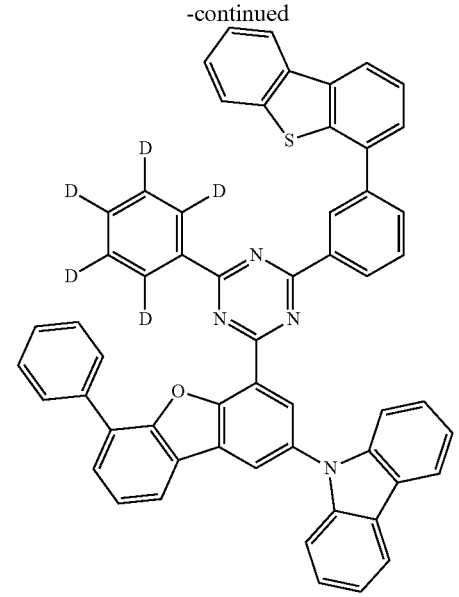
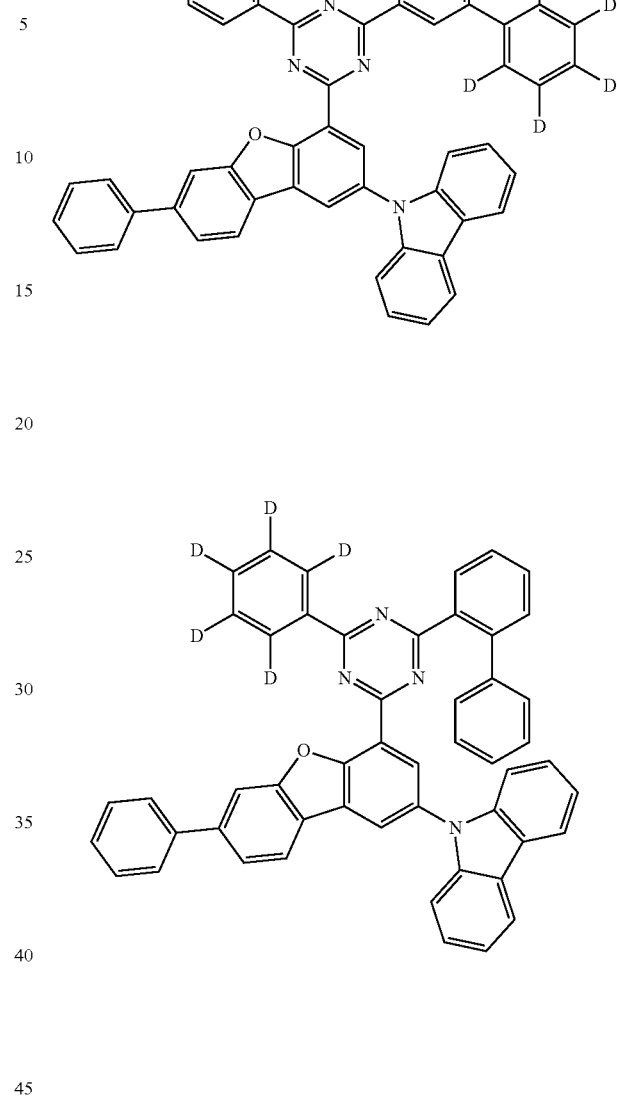
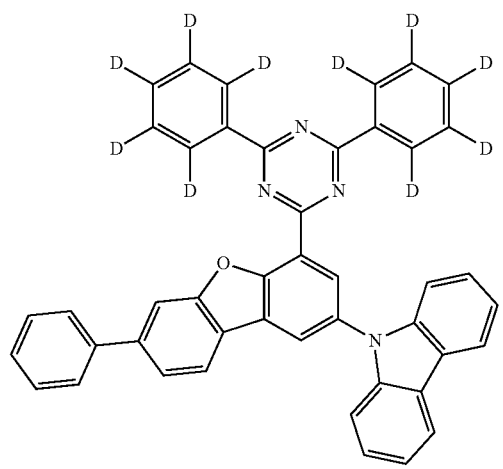
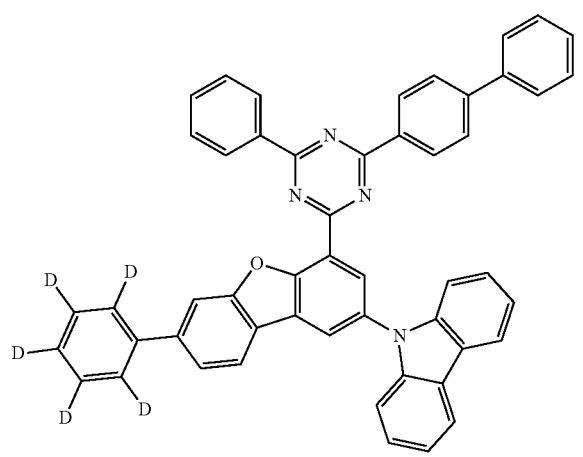
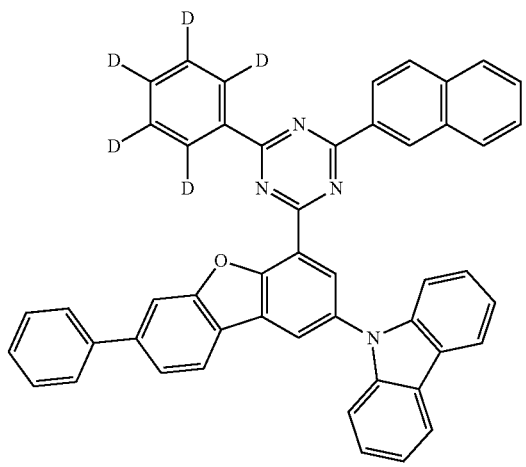

391
-continued
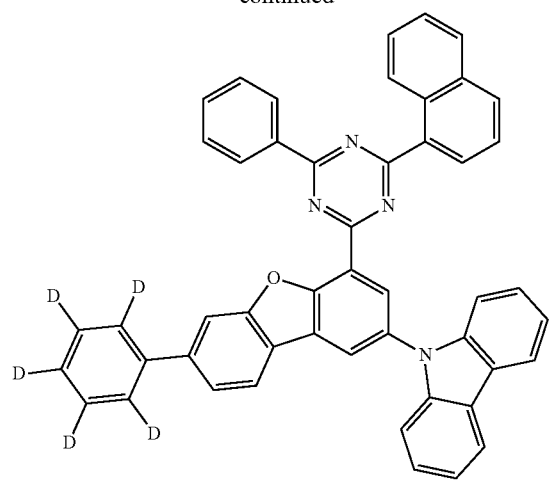
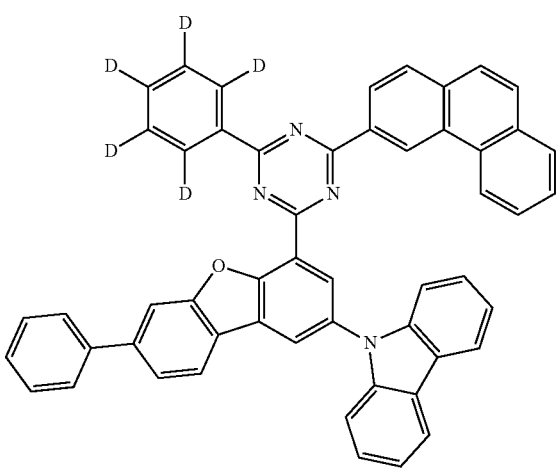
392
-continued
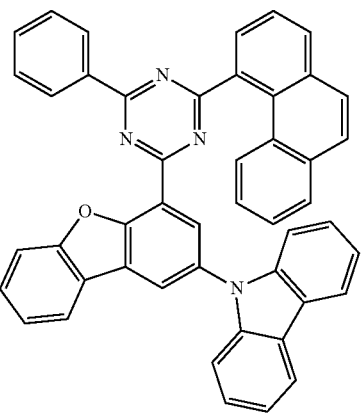
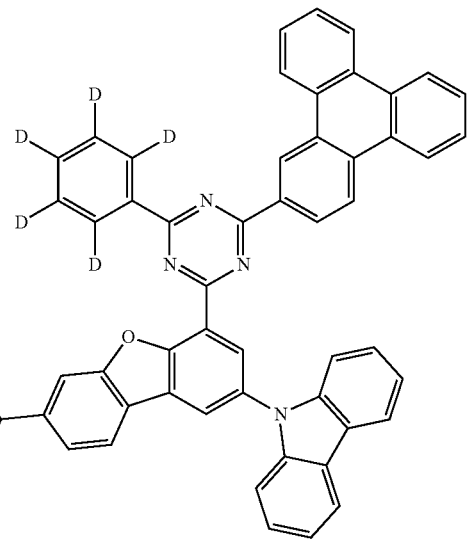
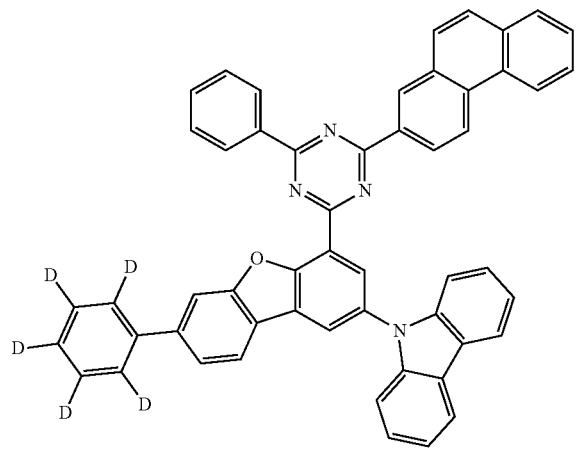
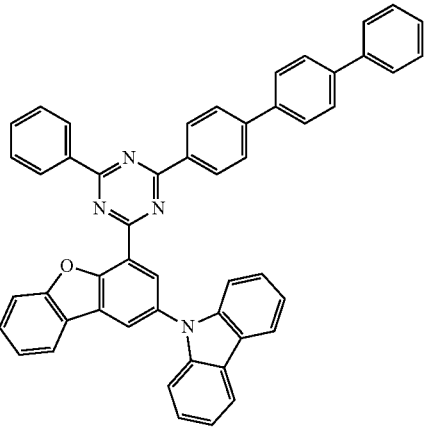

393
-continued
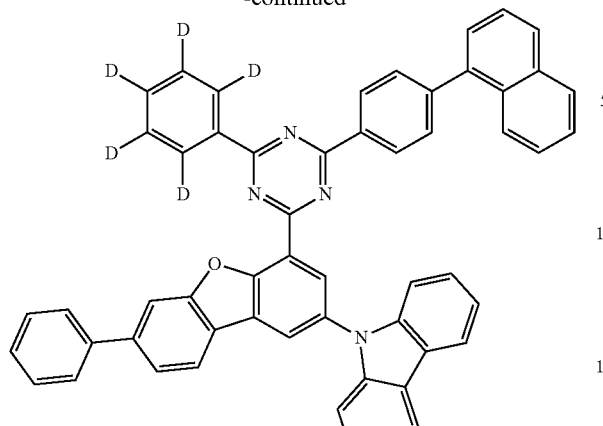
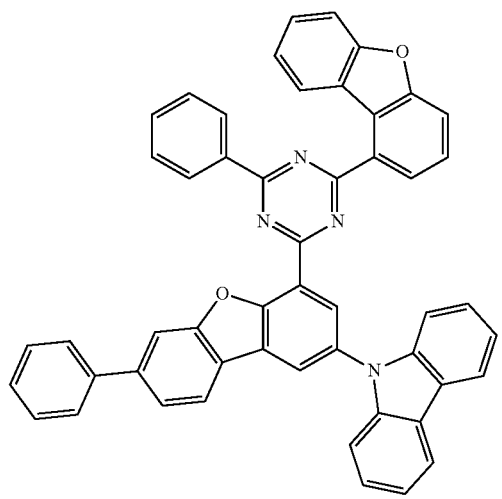
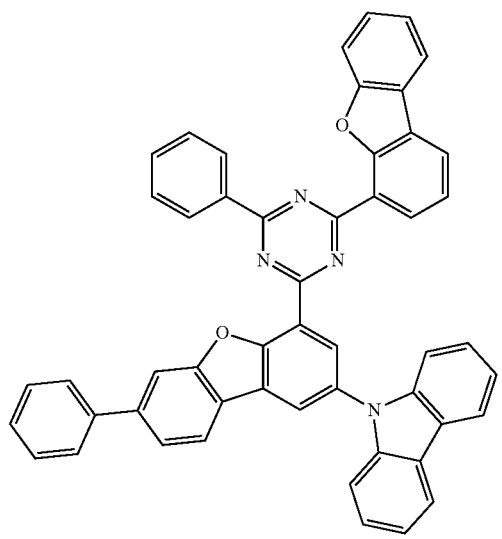
394
-continued
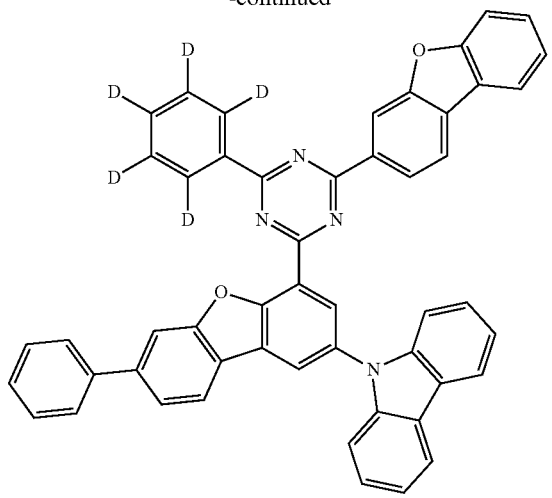
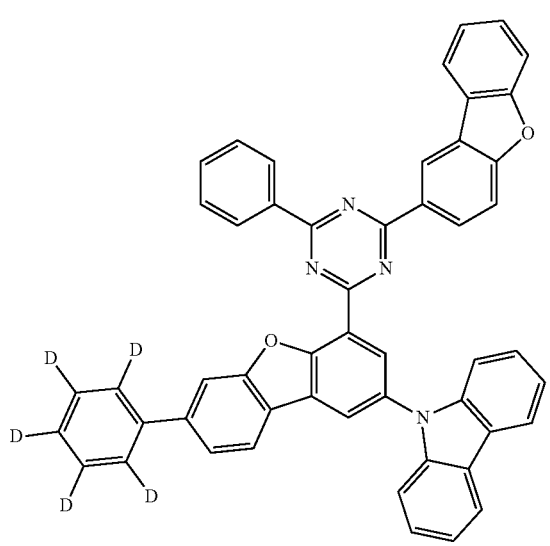
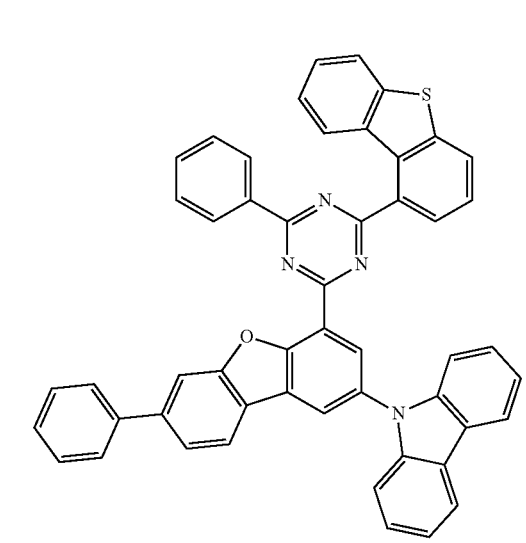

395
-continued
396
-continued
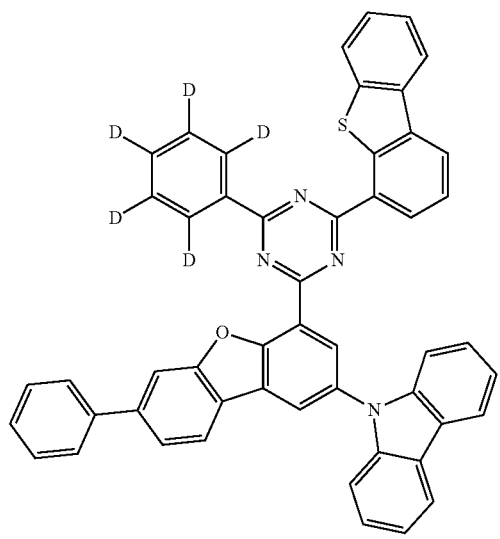
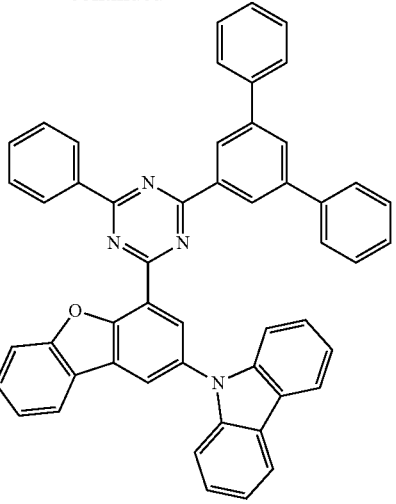
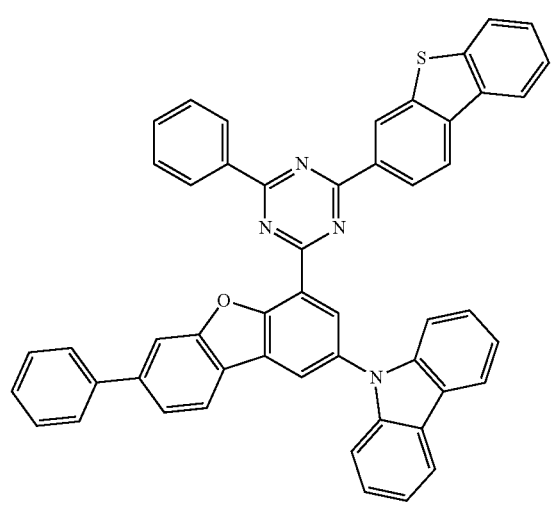
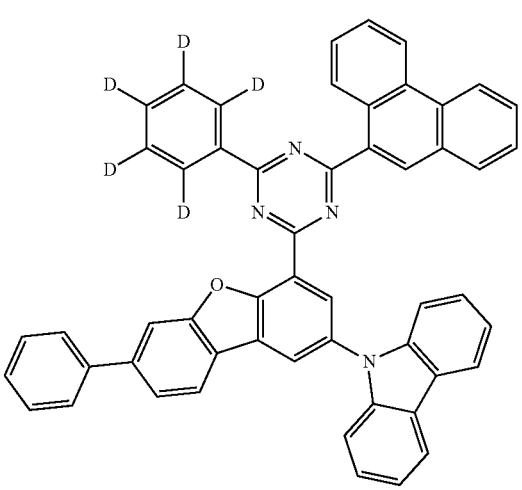
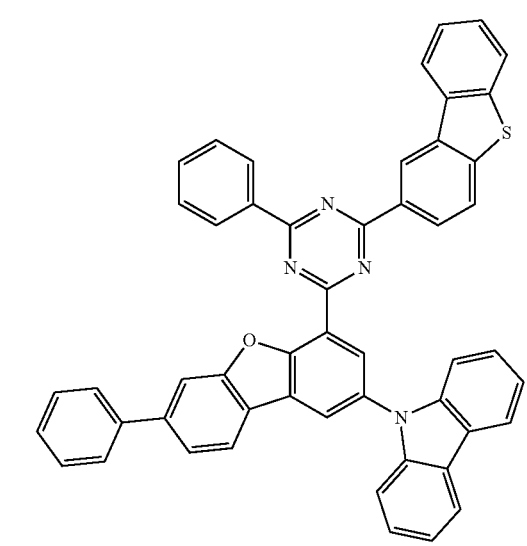
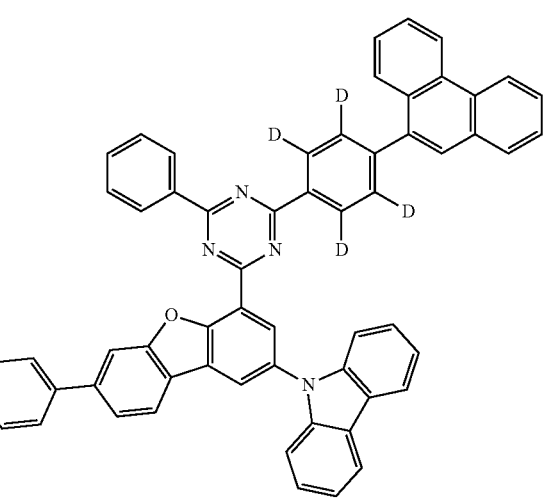

397
-continued
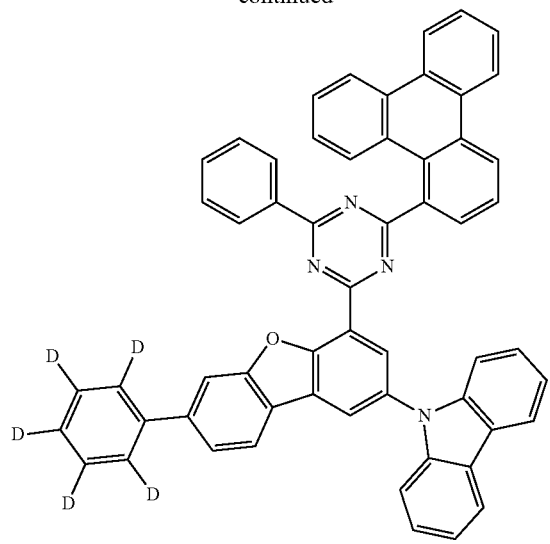
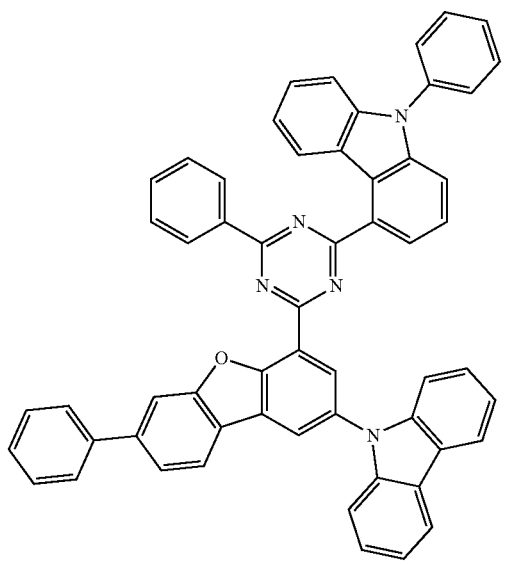
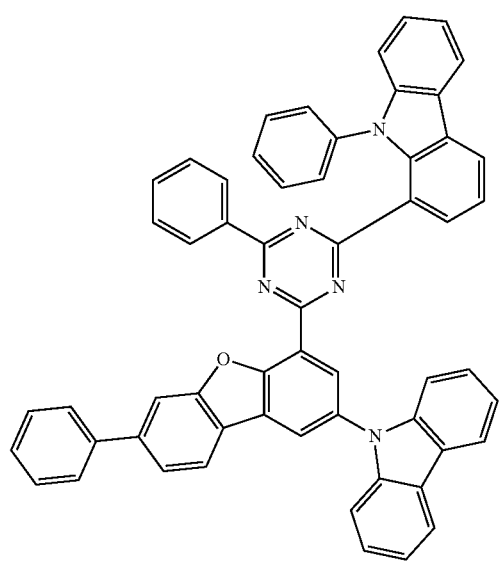
398
-continued
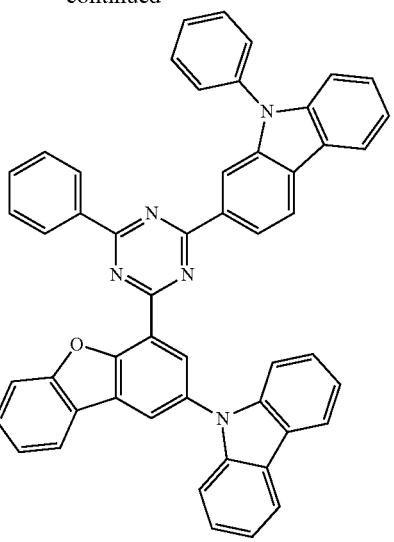
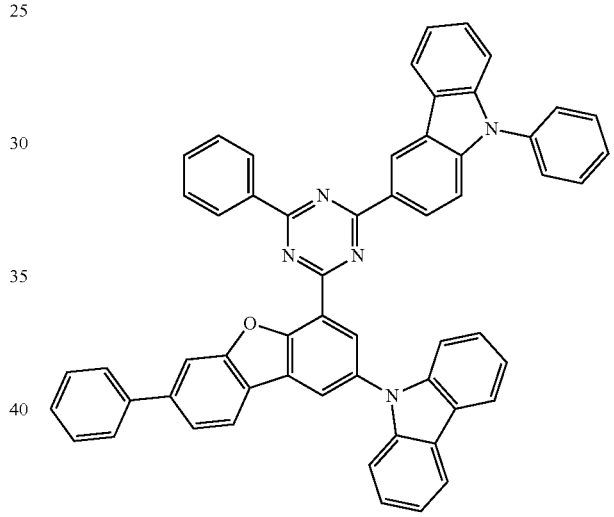
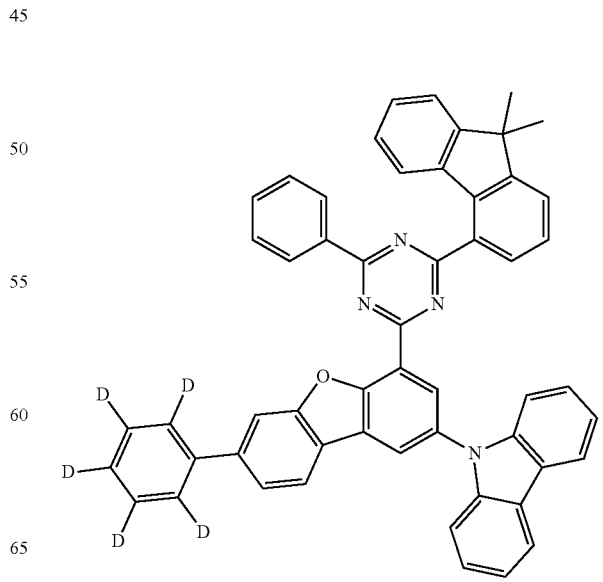

399
-continued
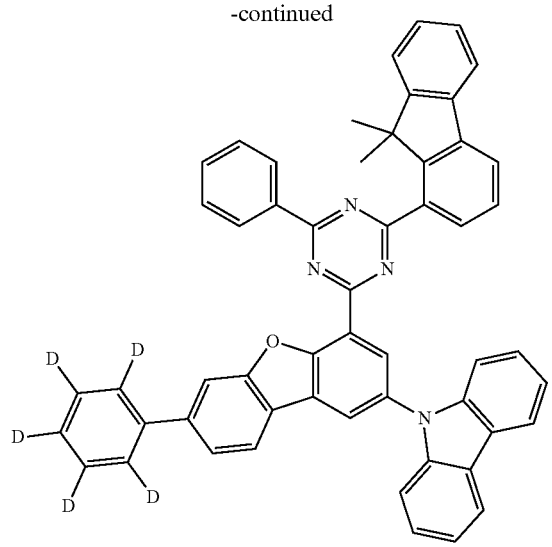
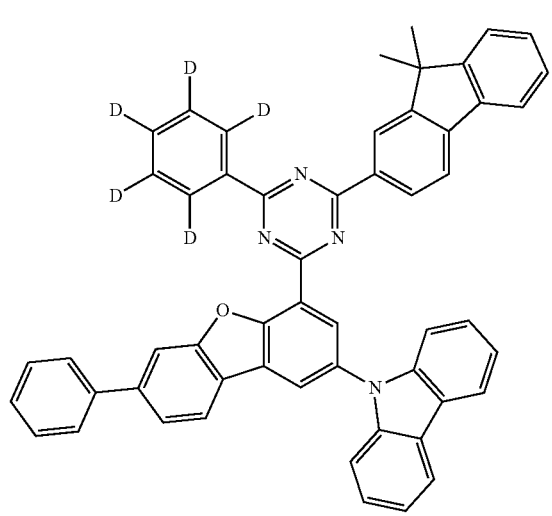
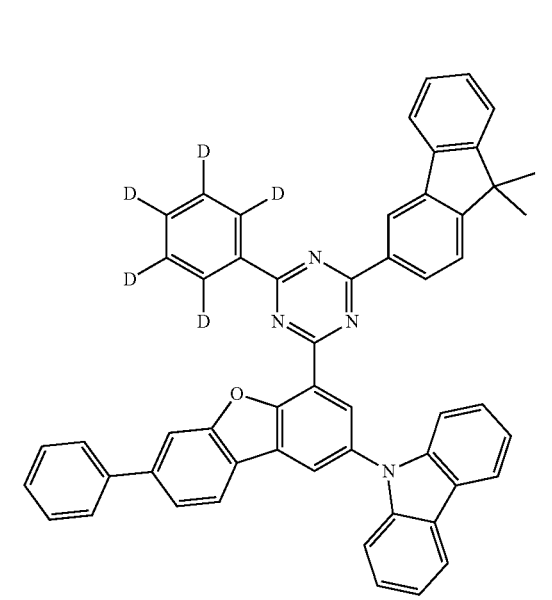
400
-continued
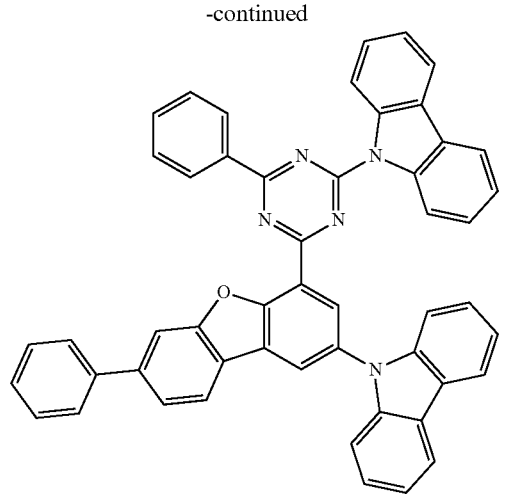
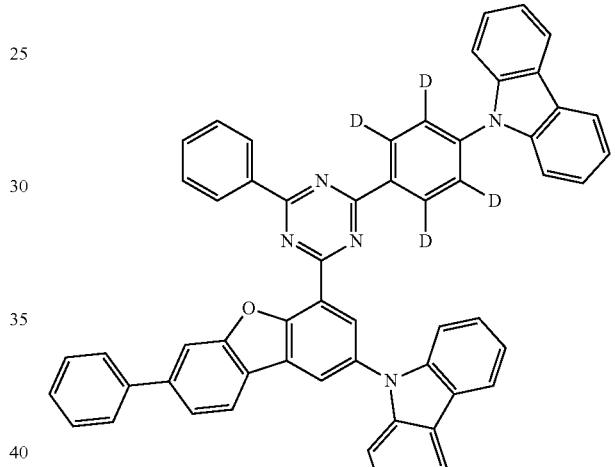
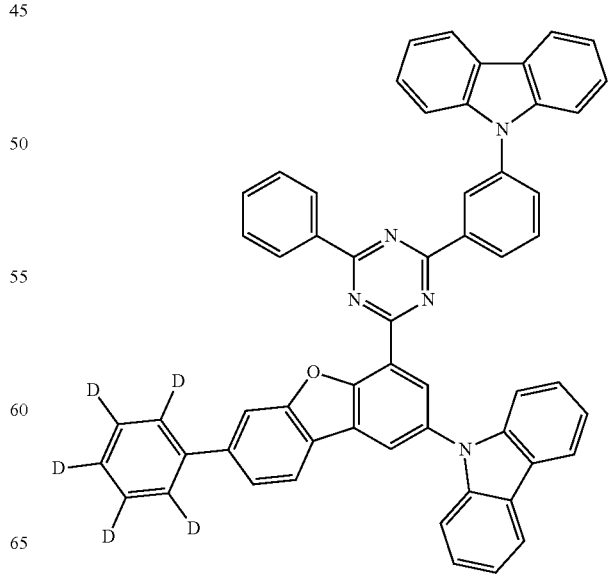

401
-continued
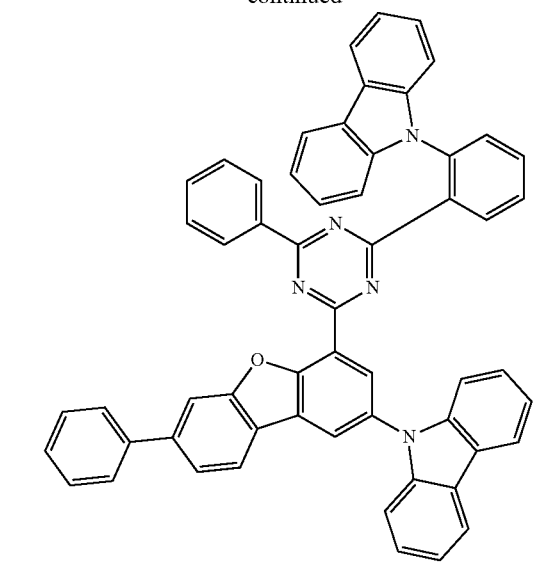
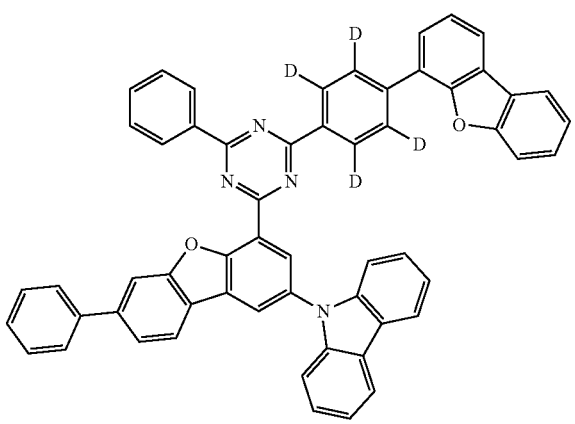
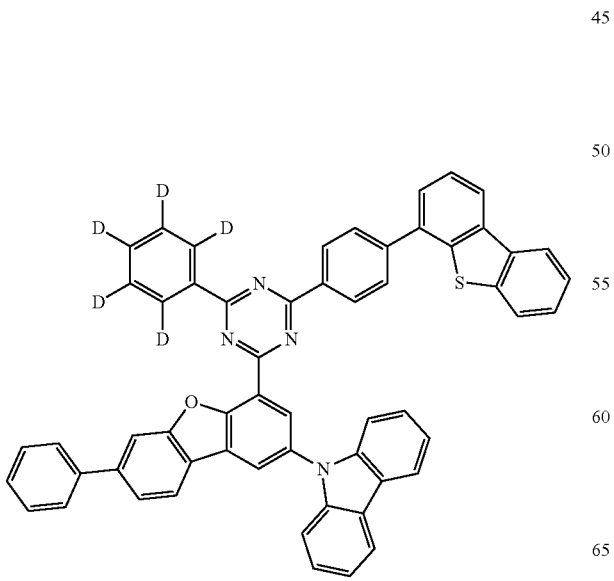
402
-continued
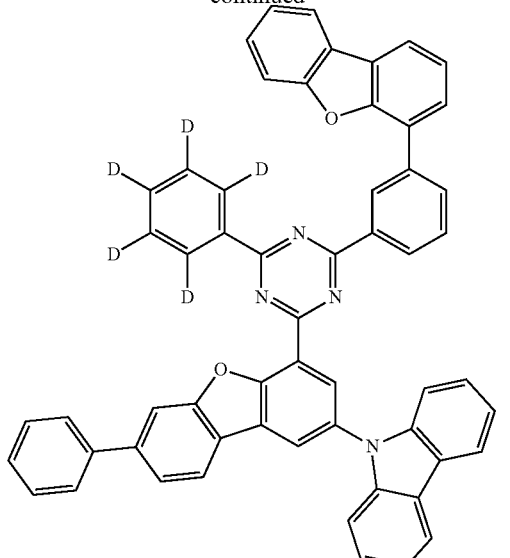
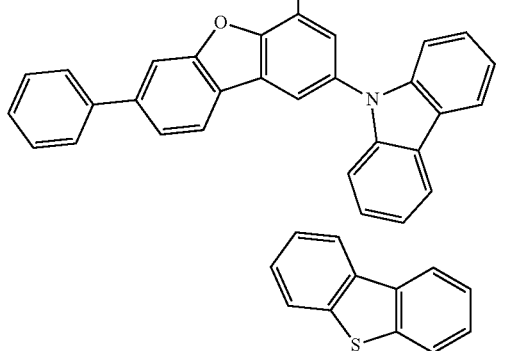
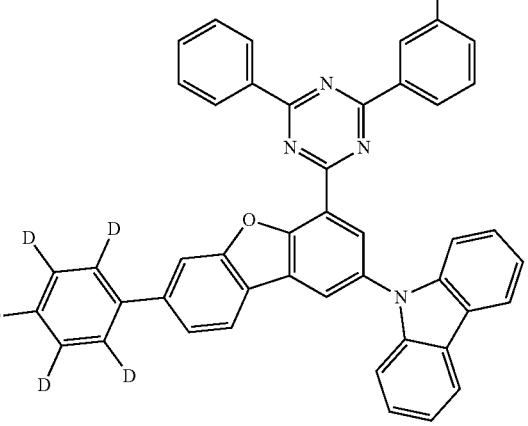
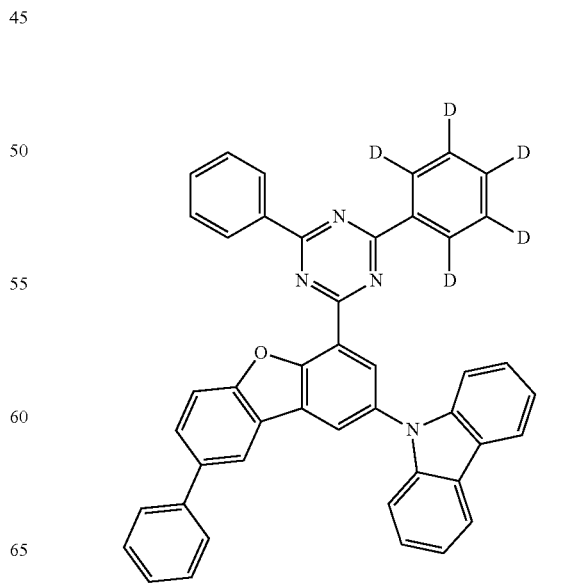

403
-continued
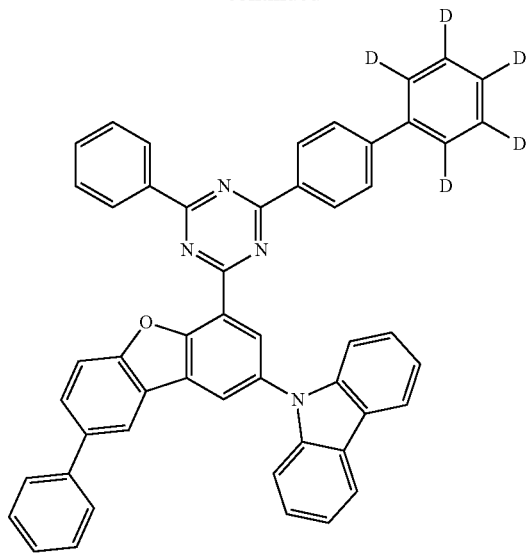
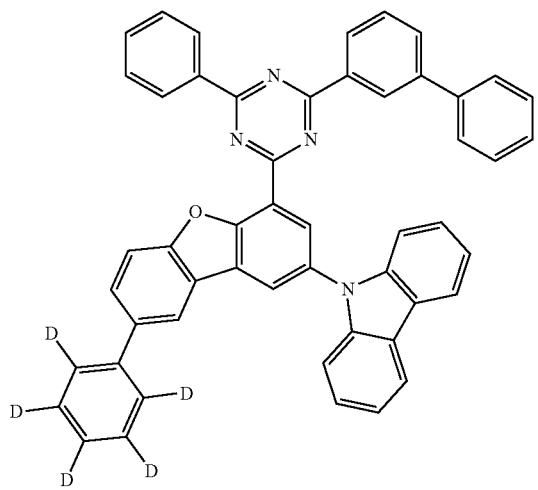
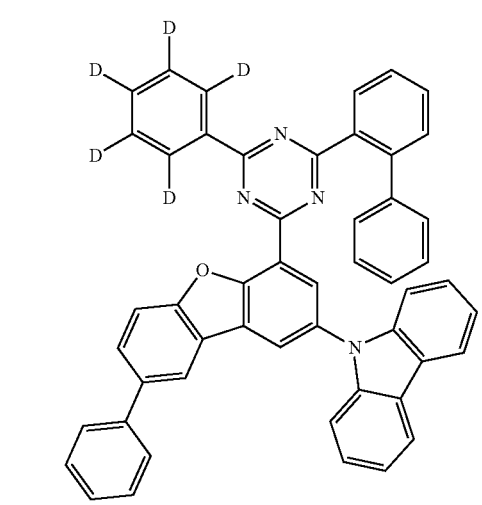
404
-continued
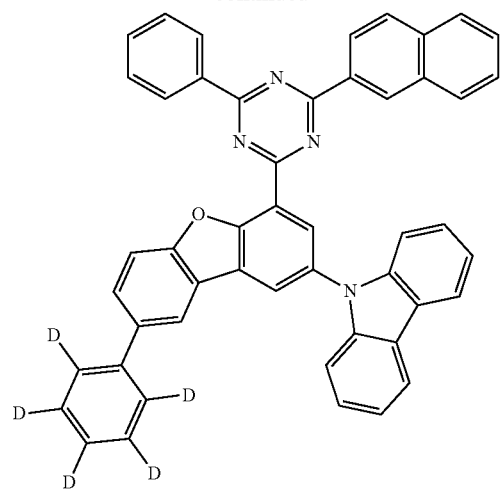
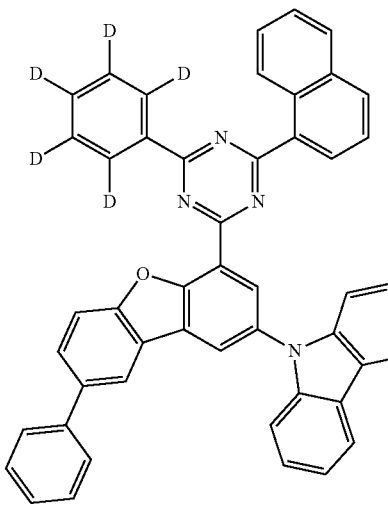
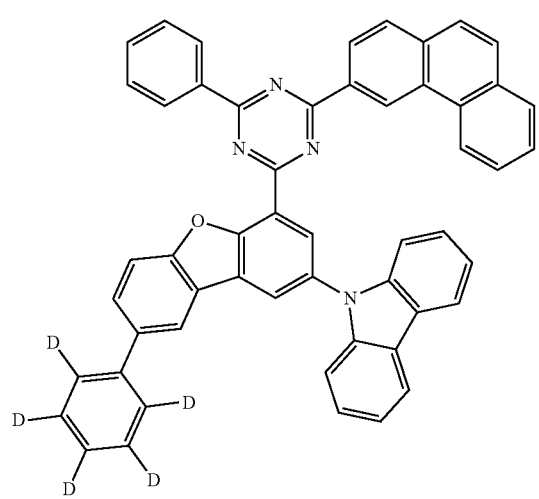

405
-continued
406
-continued
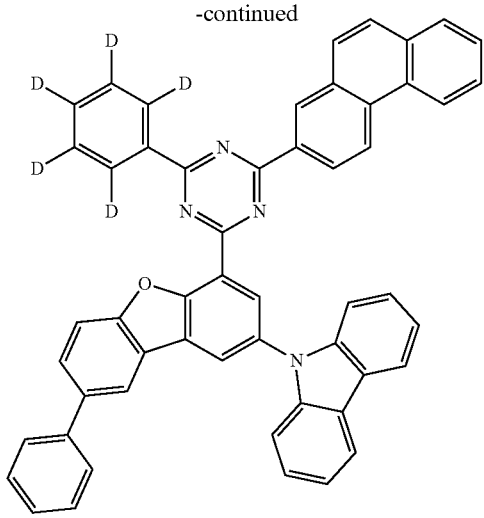
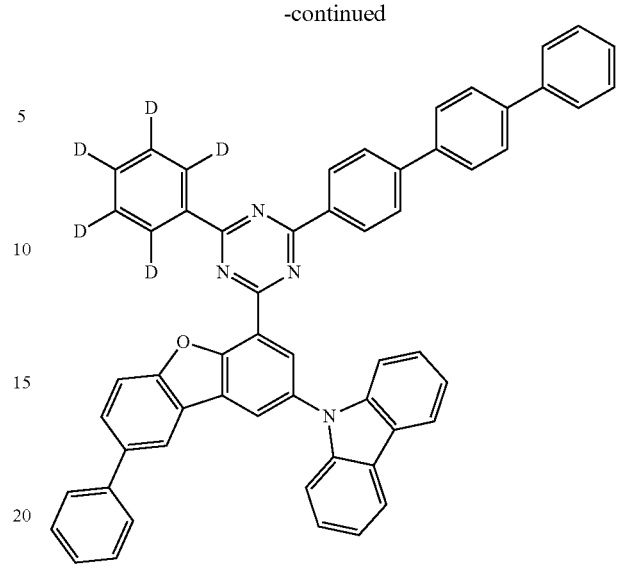
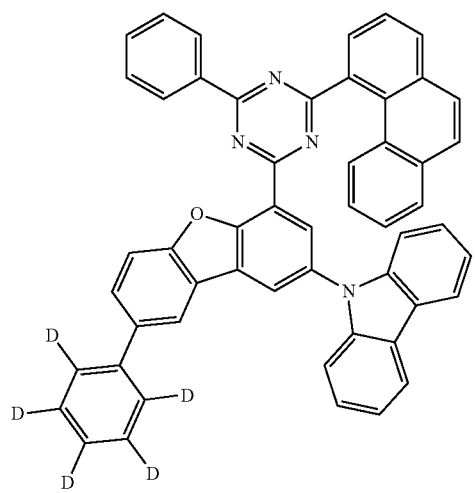
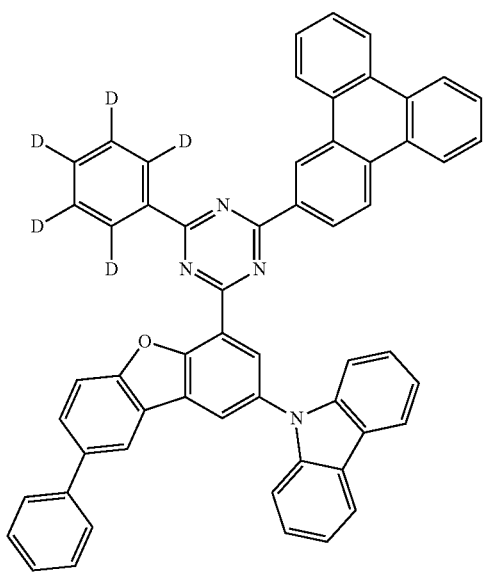

407
-continued
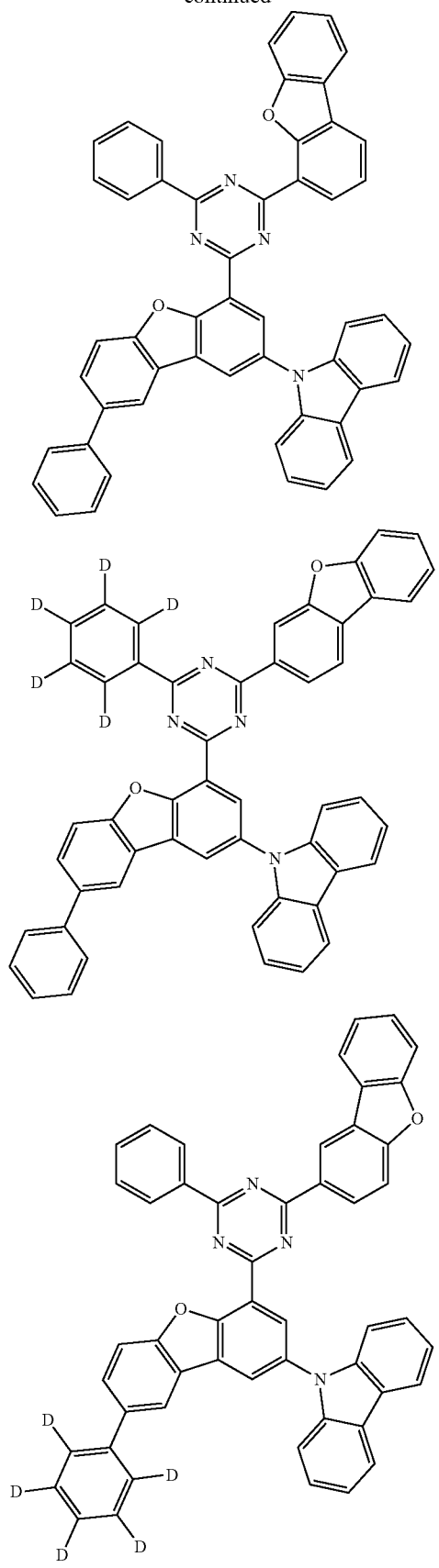
408
-continued
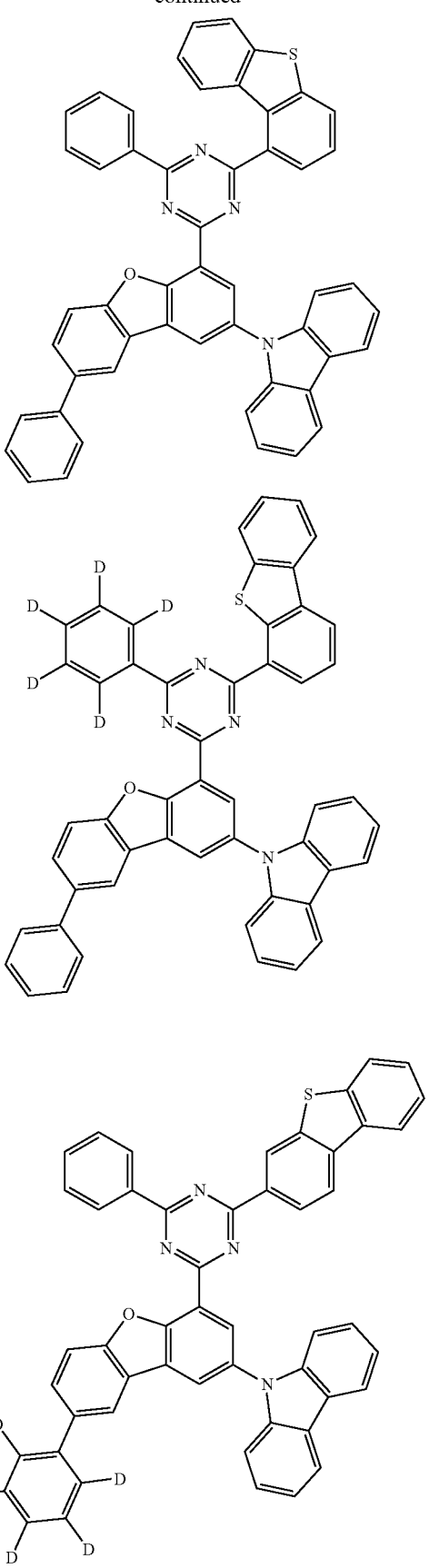

409
-continued
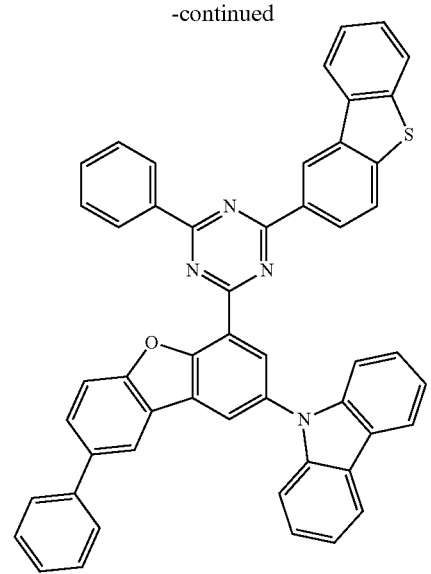
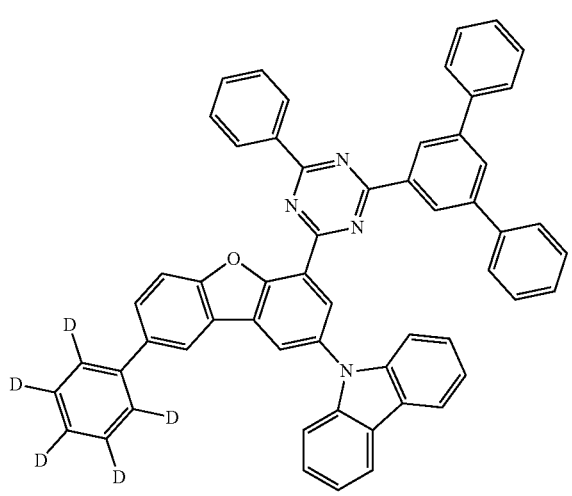
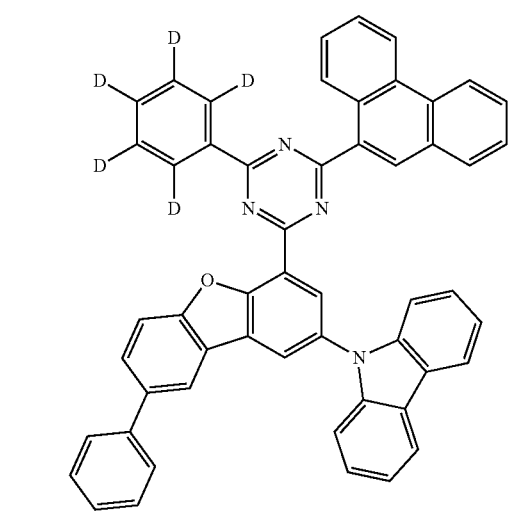
410
-continued
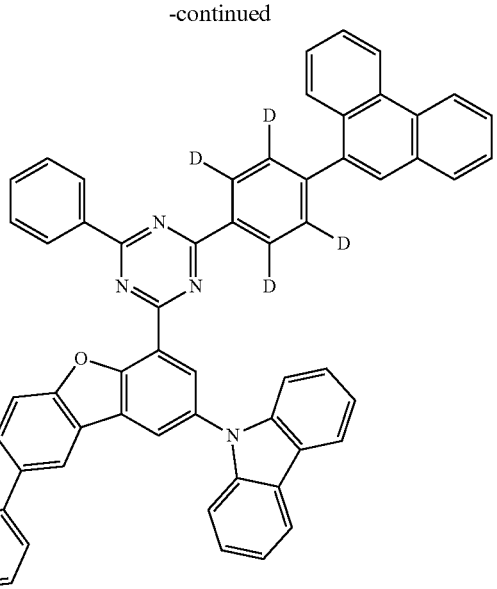
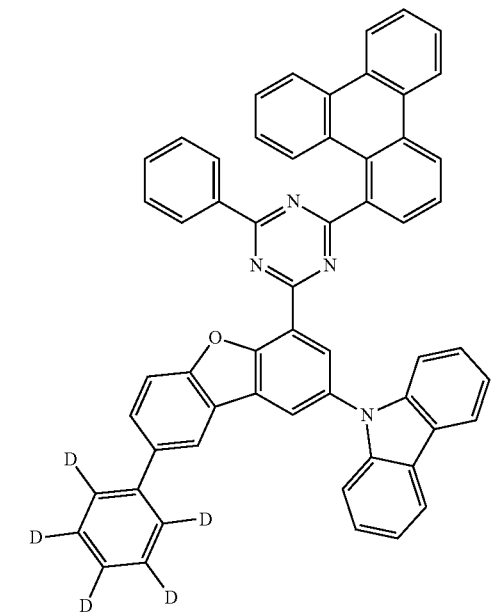
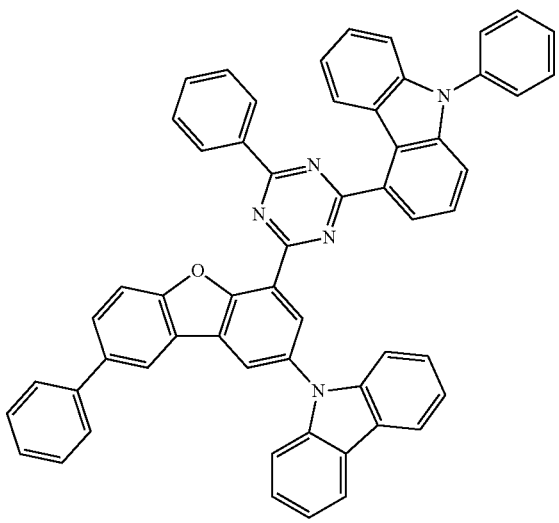

411
-continued
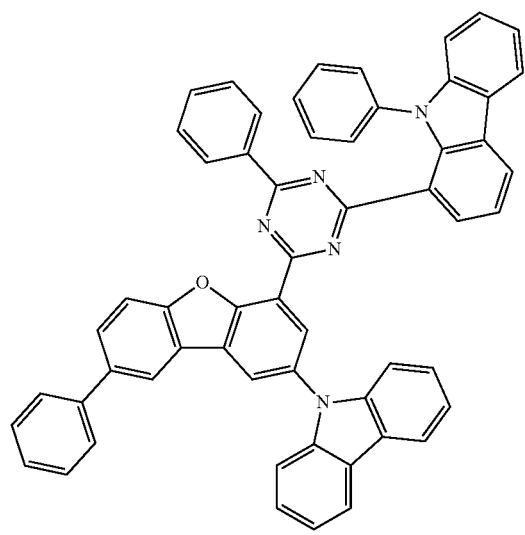
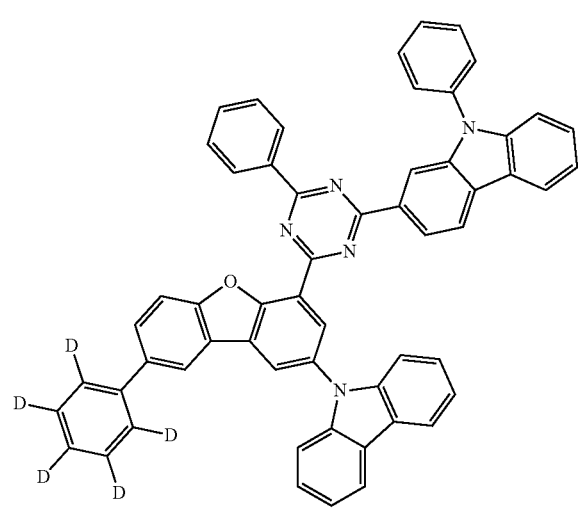
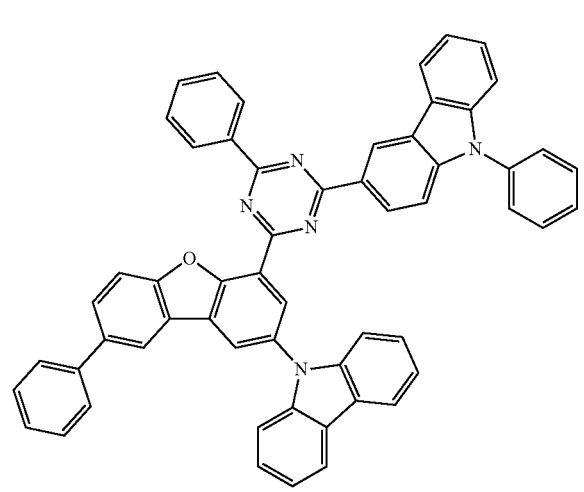
412
-continued
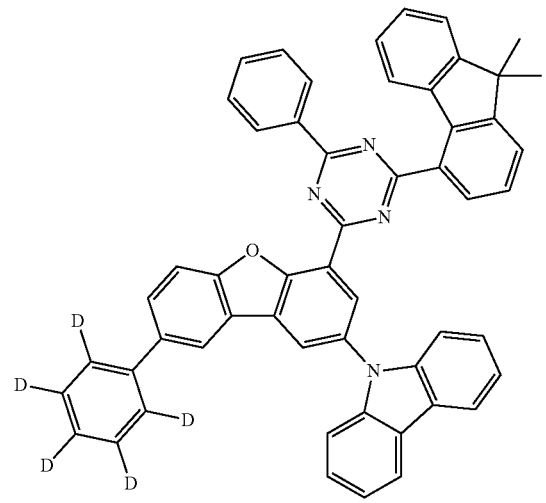
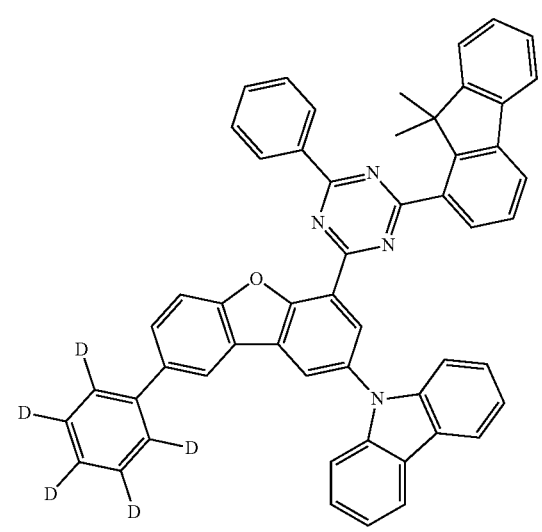
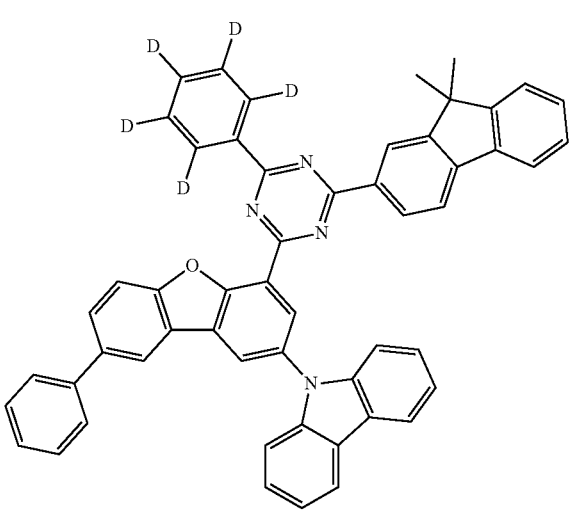

413          414
-continued    -continued
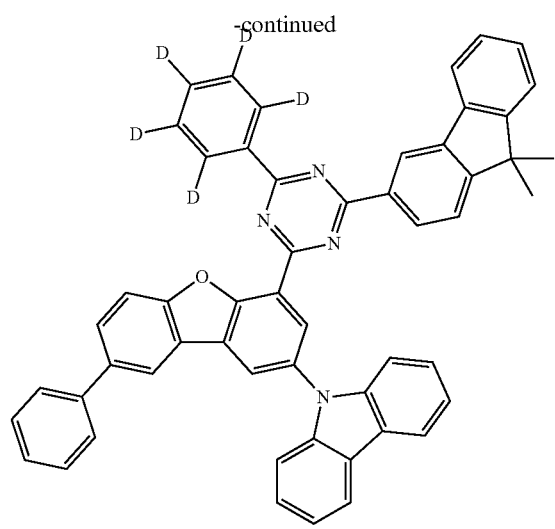
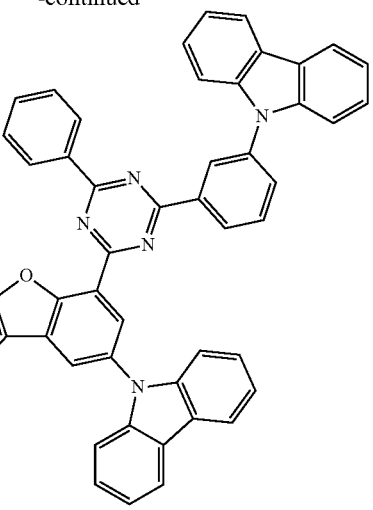
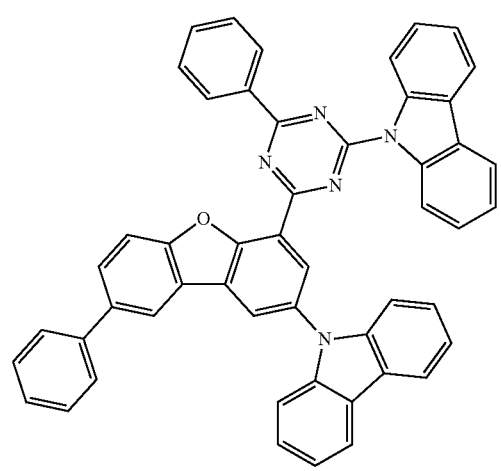
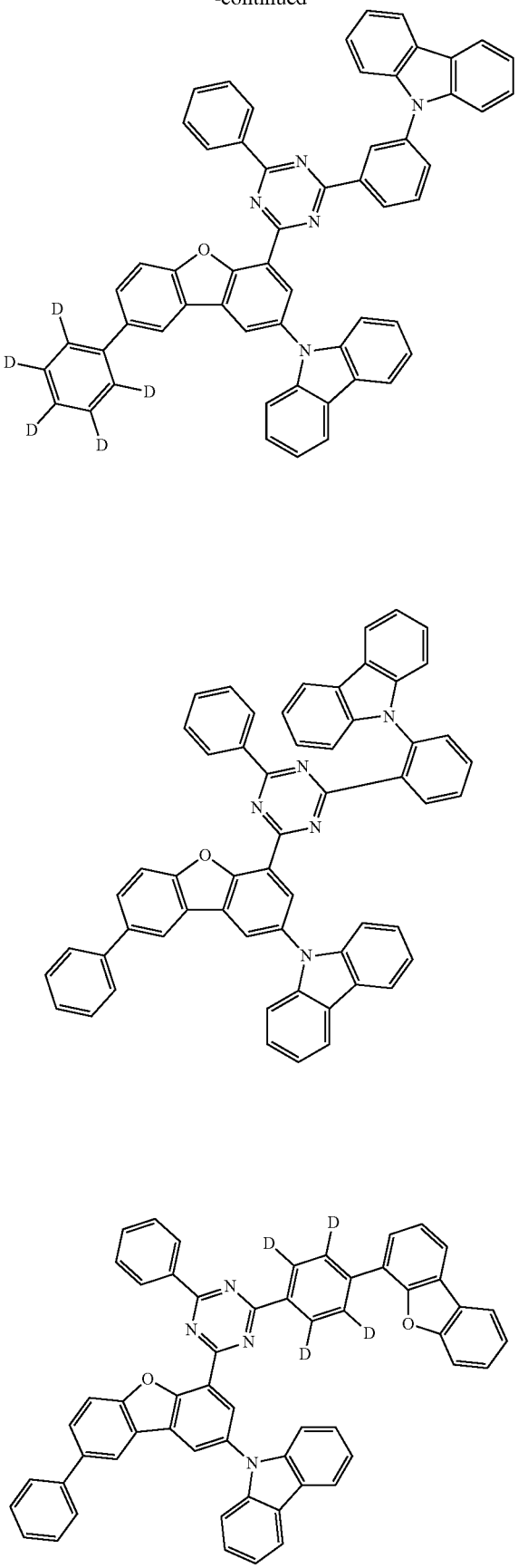
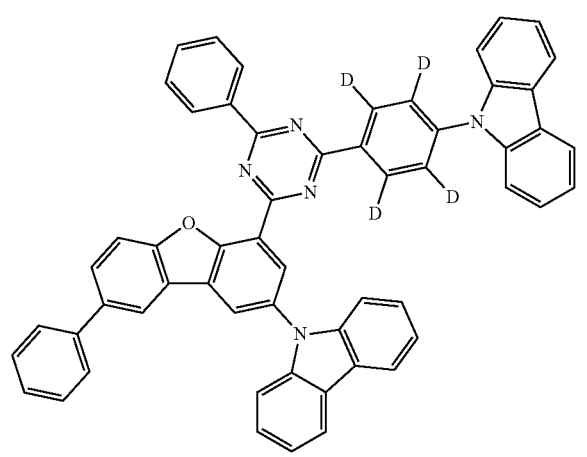

415
-continued
416
-continued
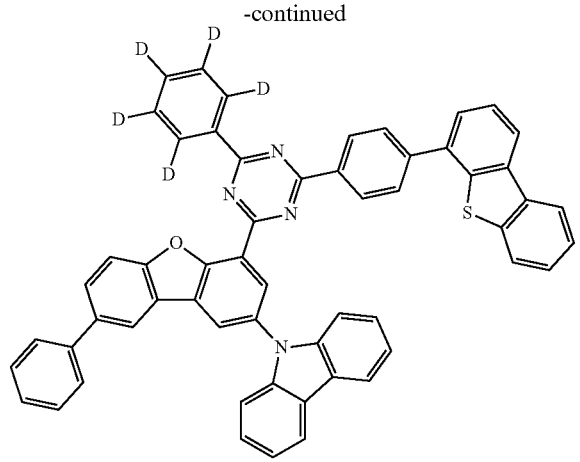
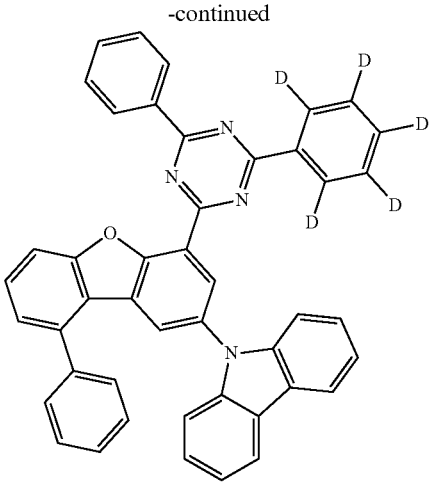
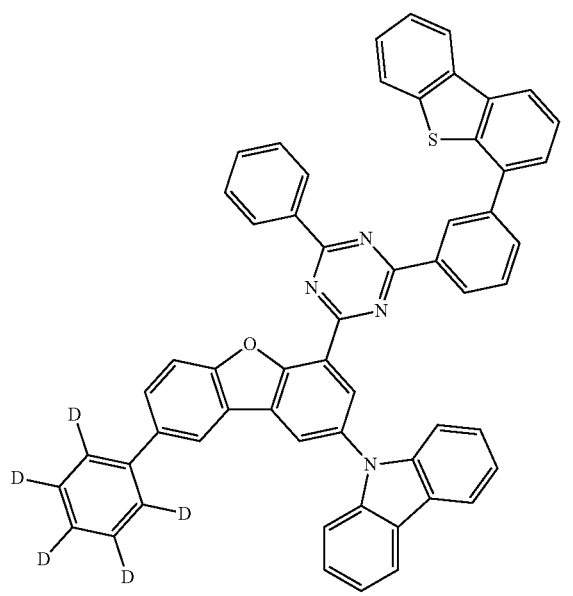
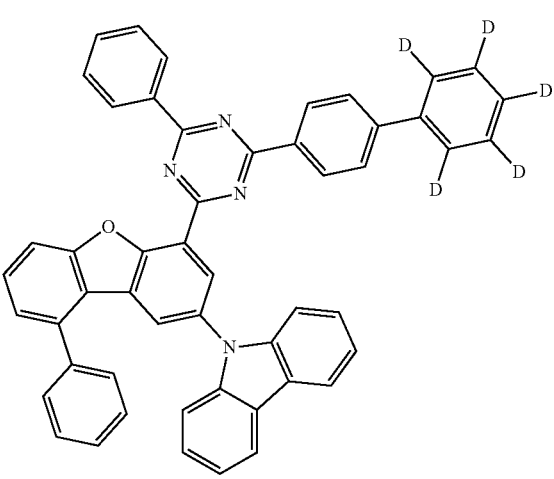

417
-continued
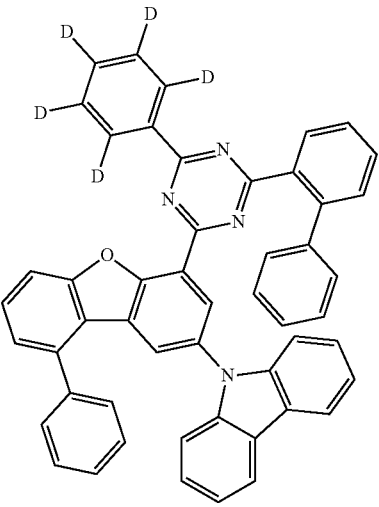
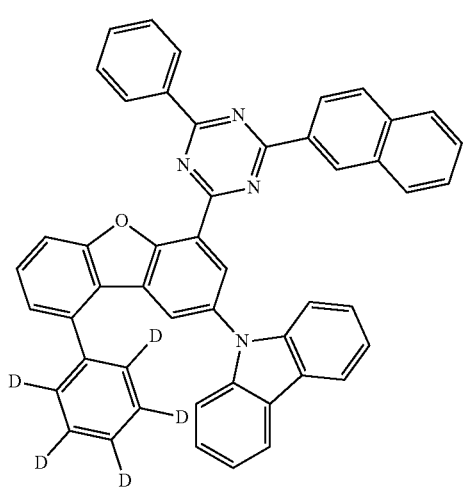
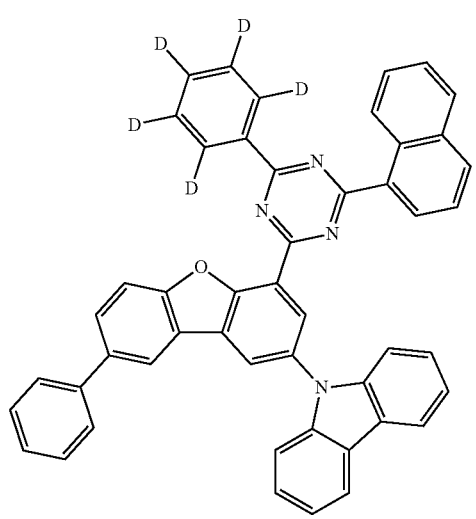
418
-continued
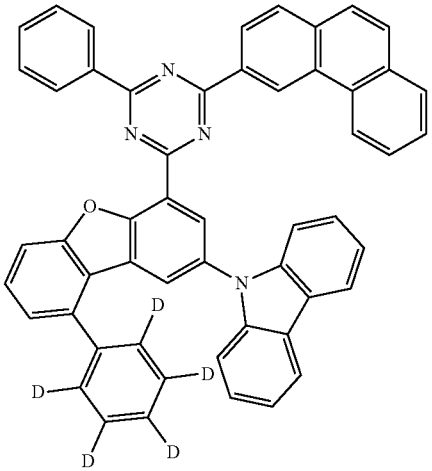
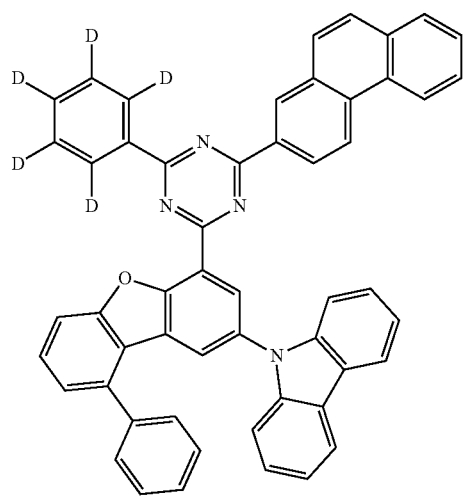
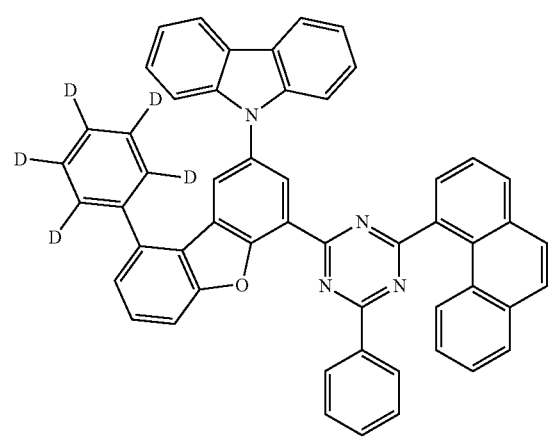

419
-continued
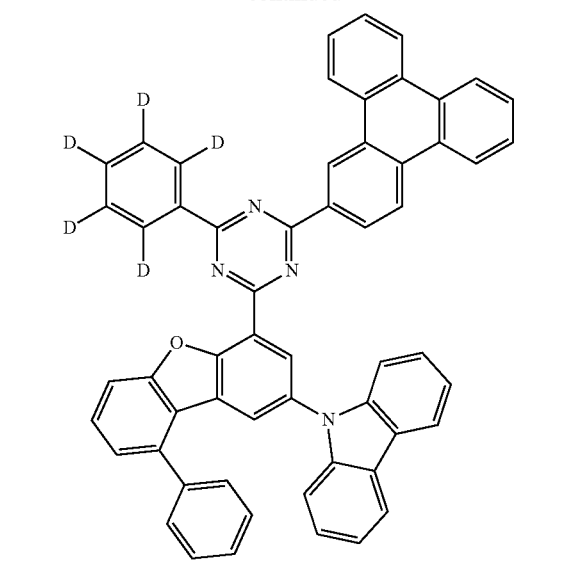
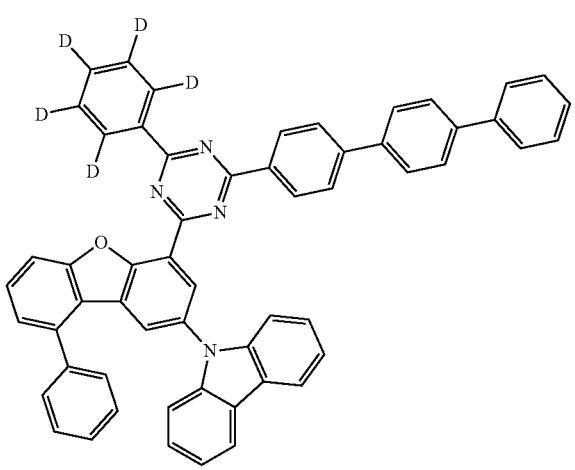
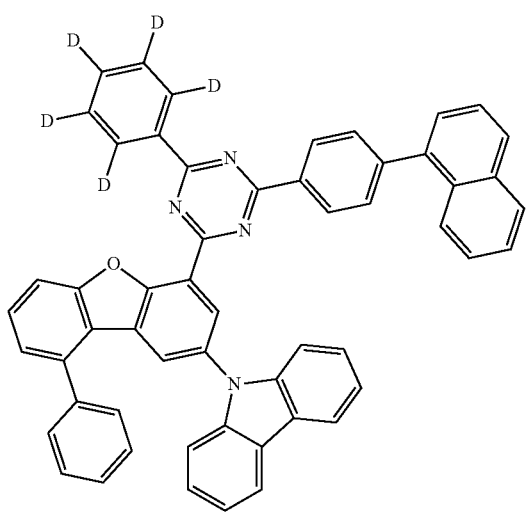
420
-continued
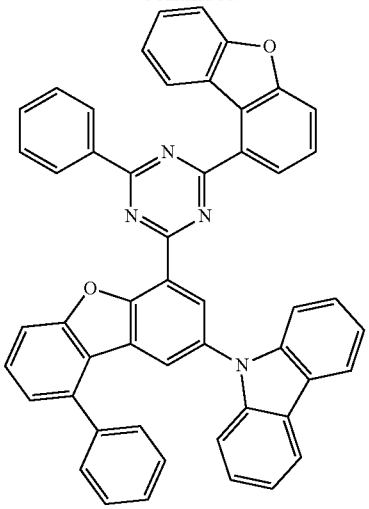
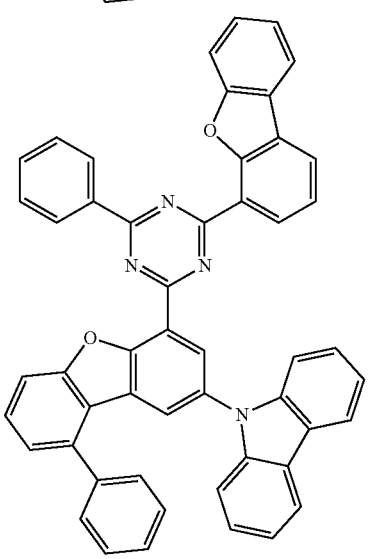
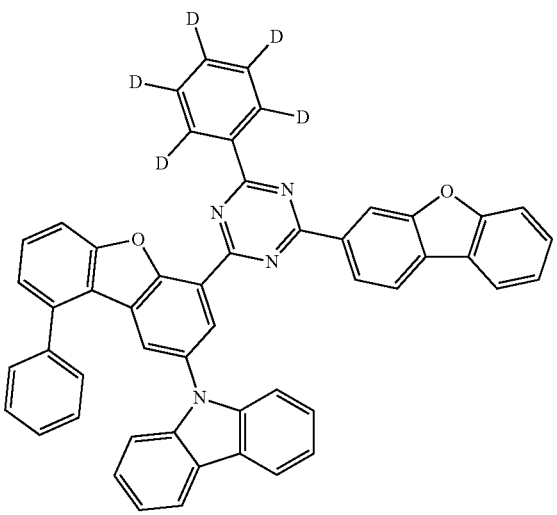

-continued
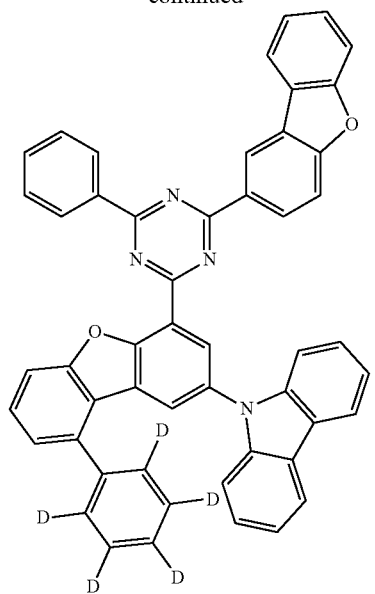
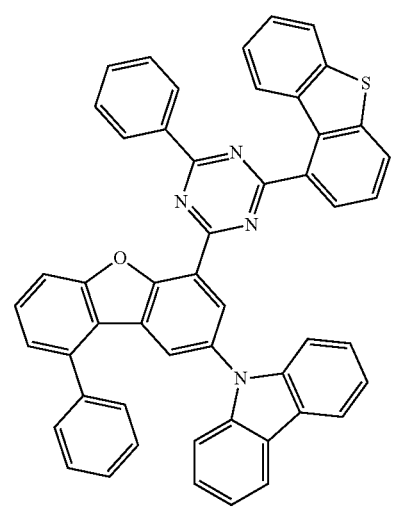
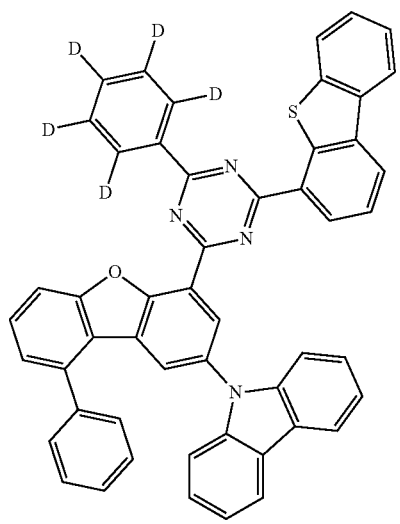
-continued
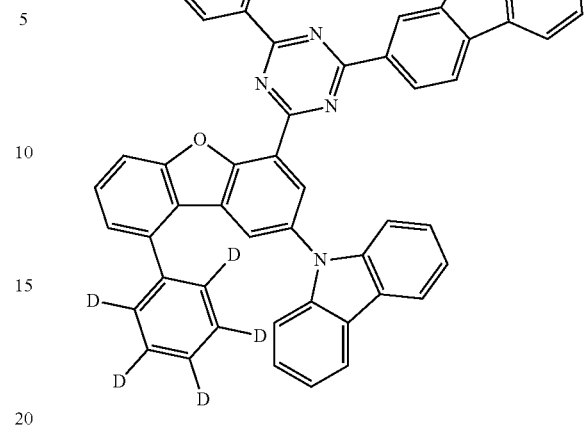
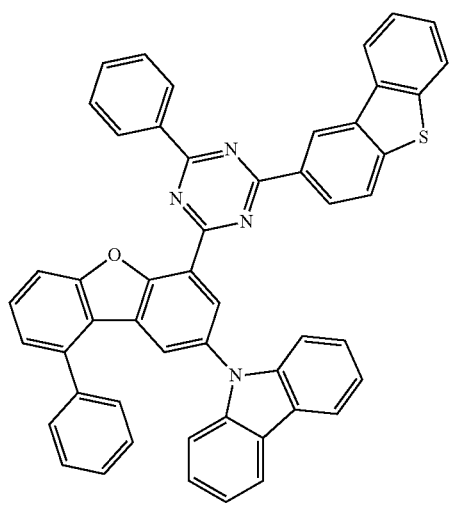
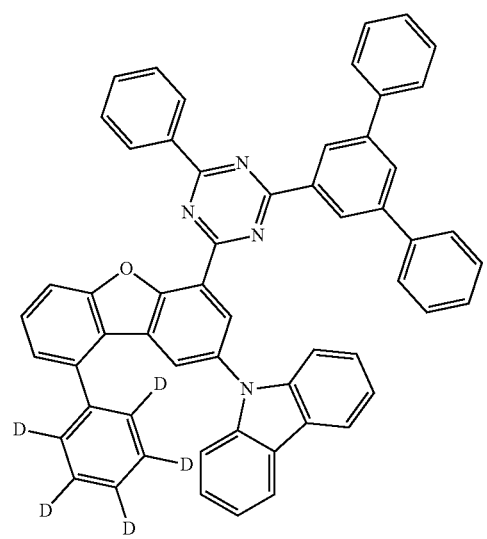

423
-continued
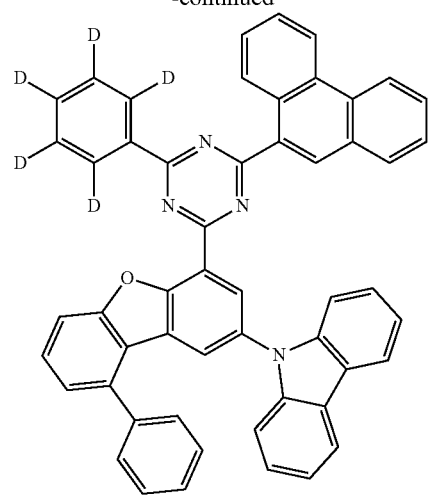
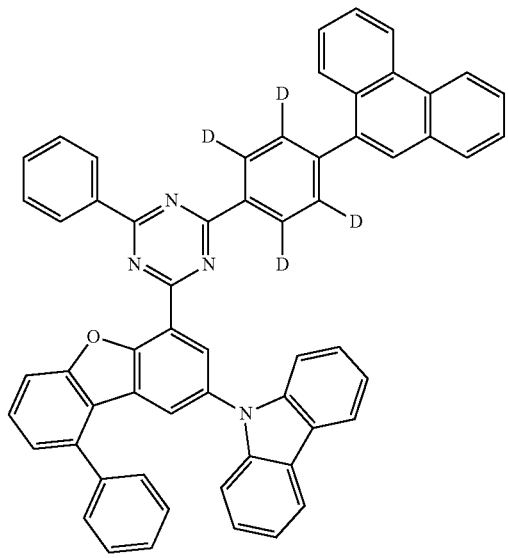
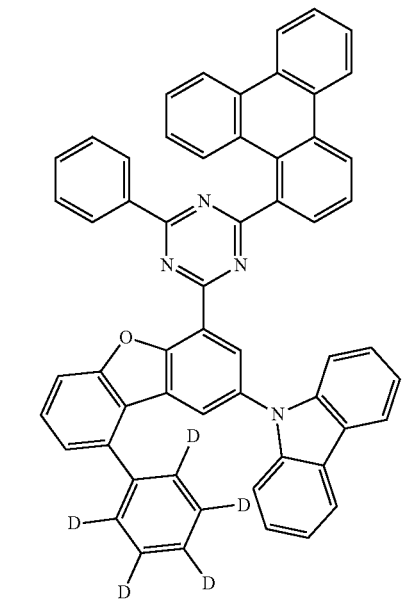
424
-continued
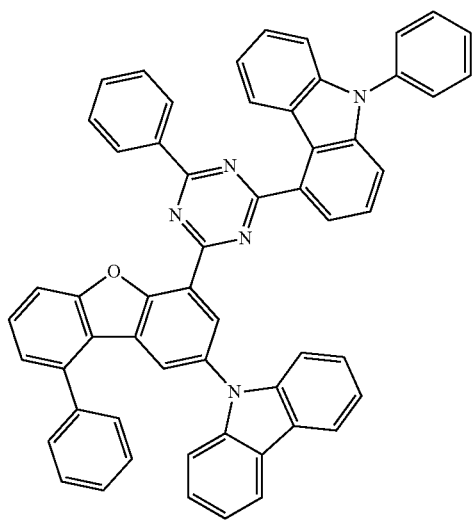
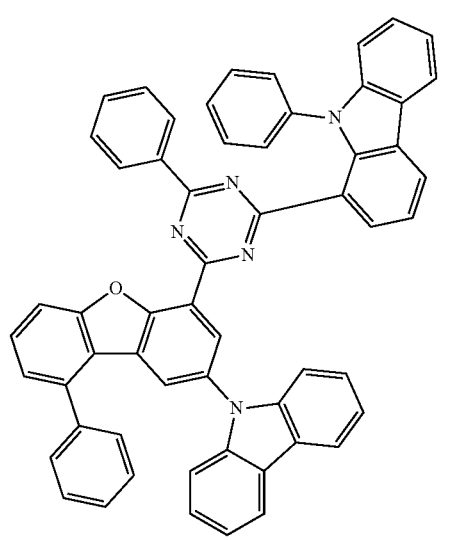
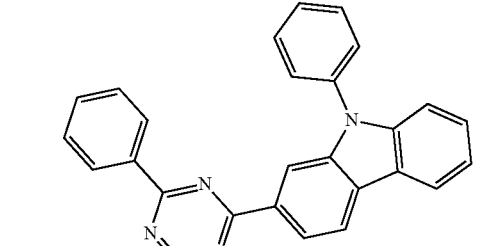
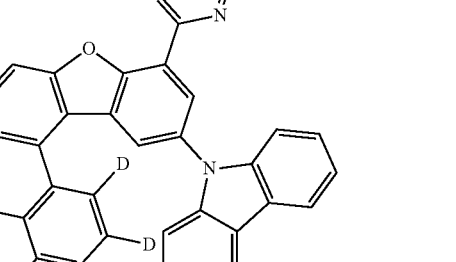
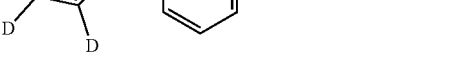

425
-continued
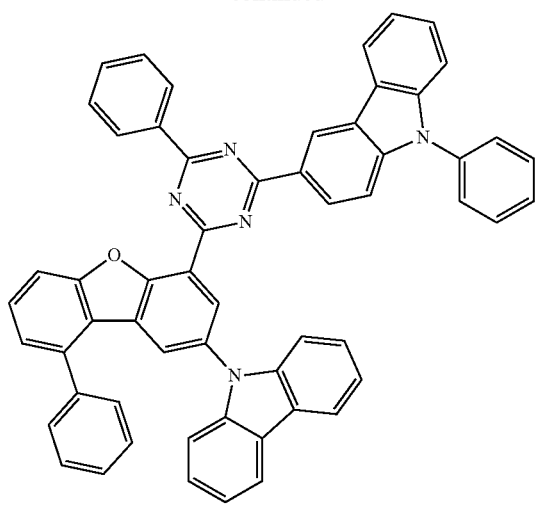
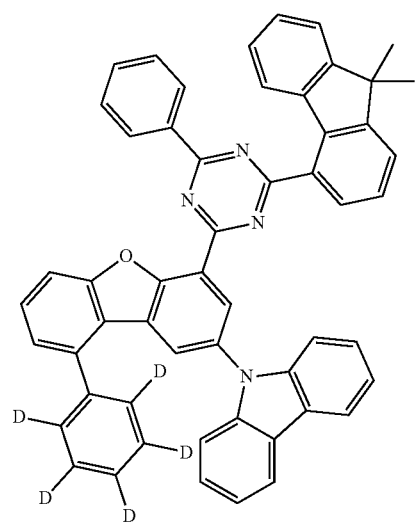
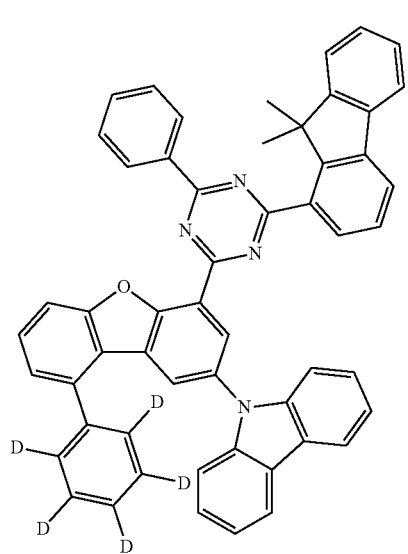
426
-continued
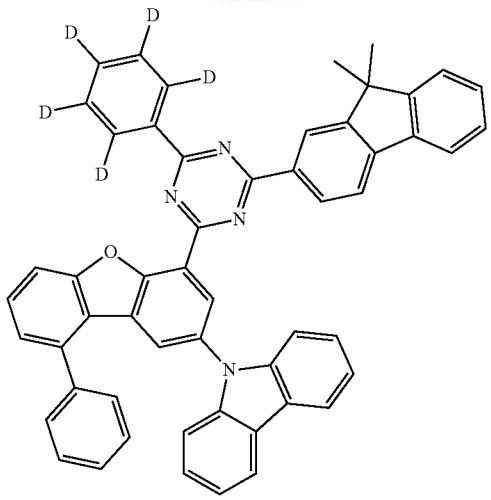
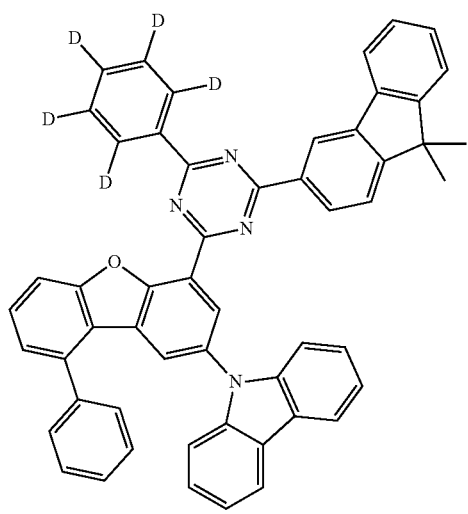
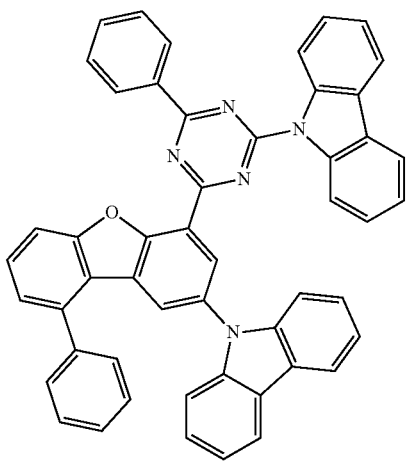

427
-continued
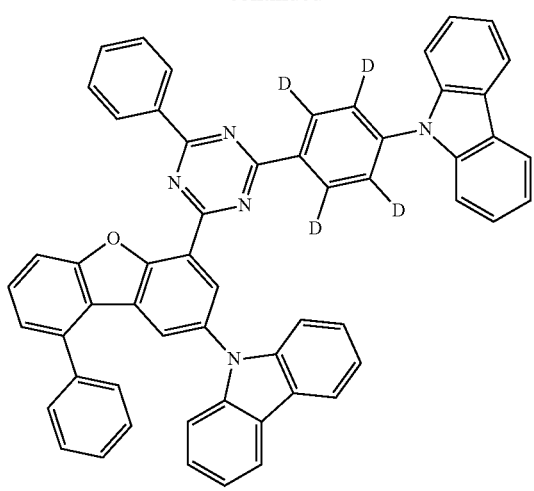
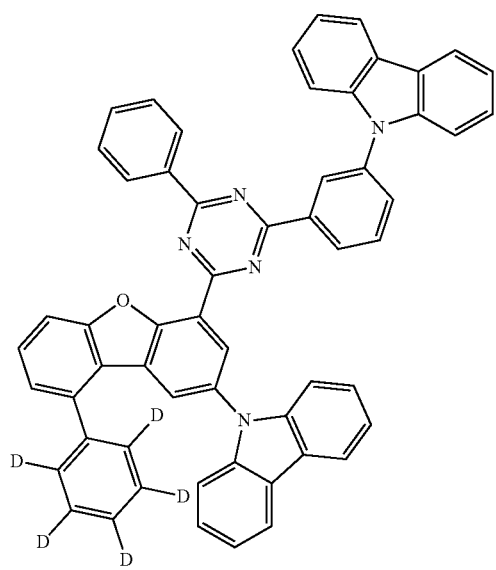
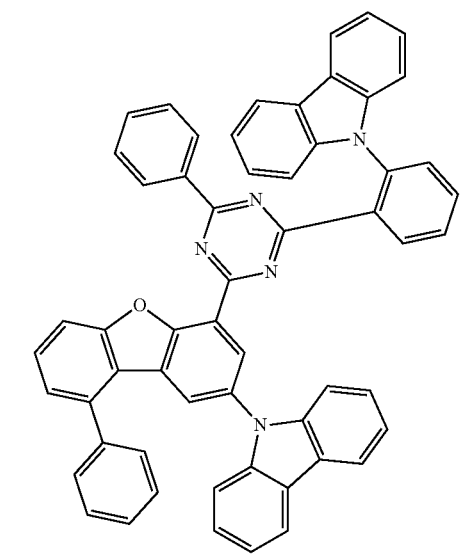
428
-continued
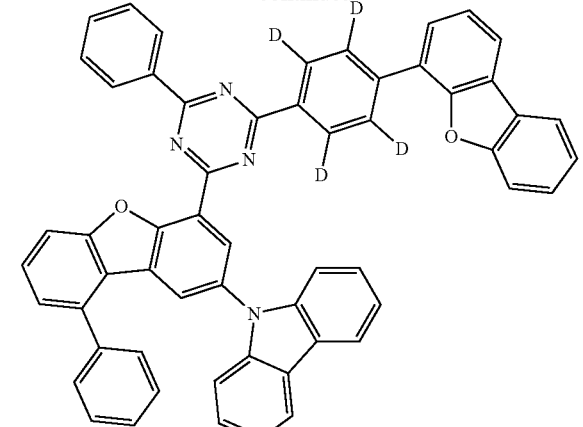
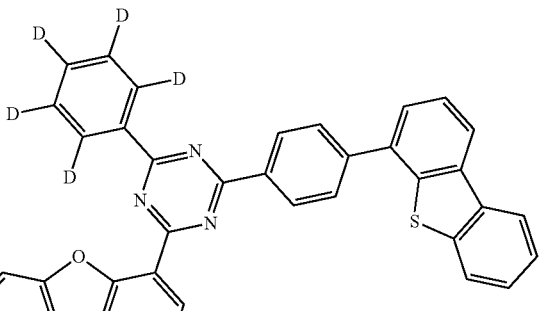
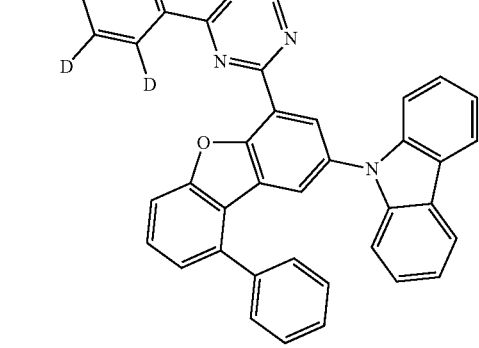

429
-continued
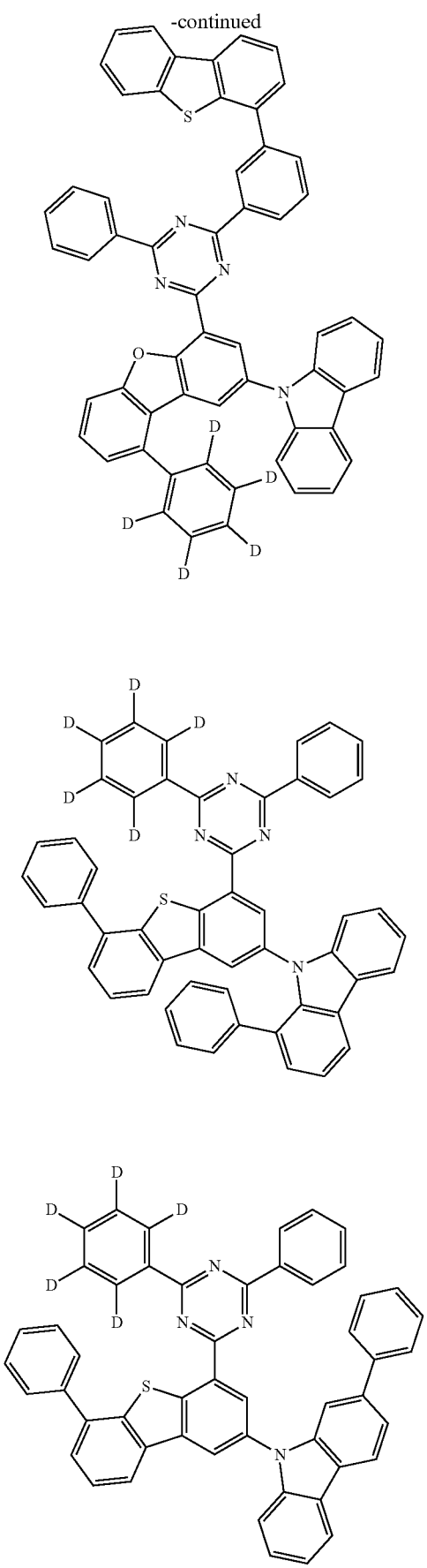
430
-continued
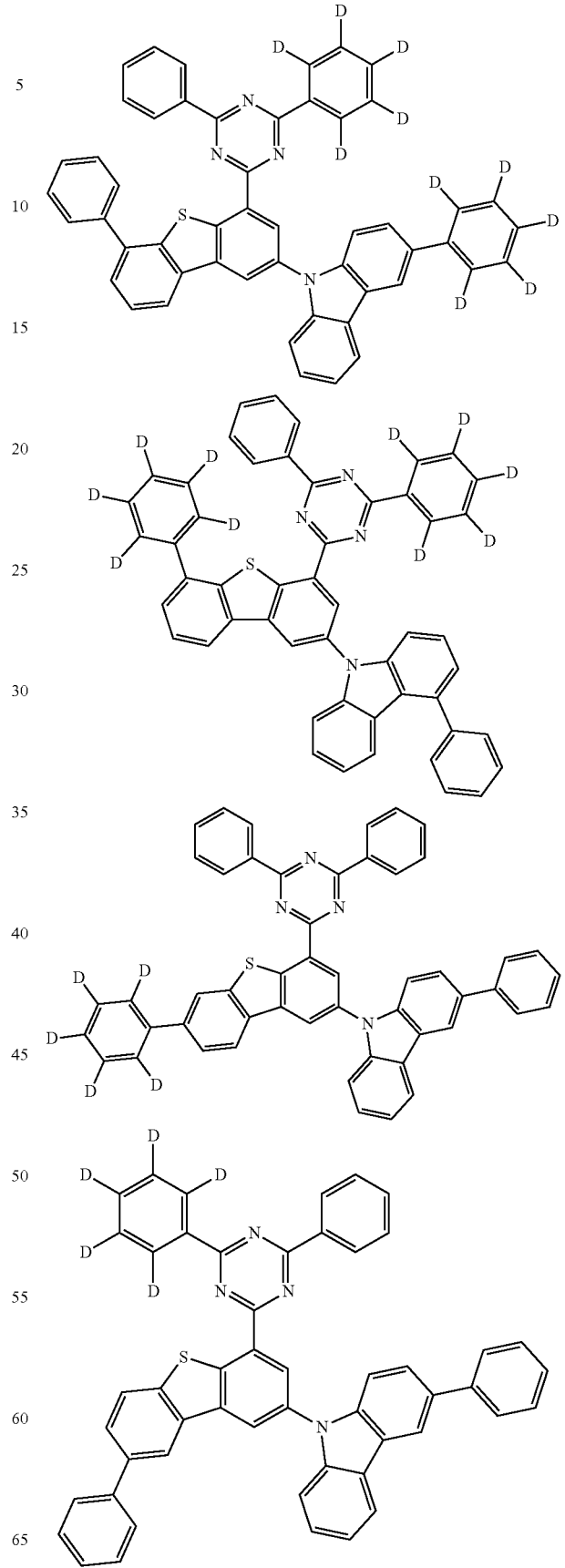

| 431 | 432 |
|---|---|
| -continued | -continued |
| 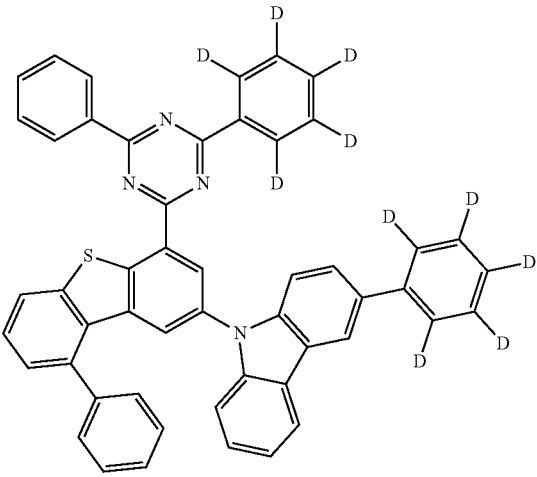 | 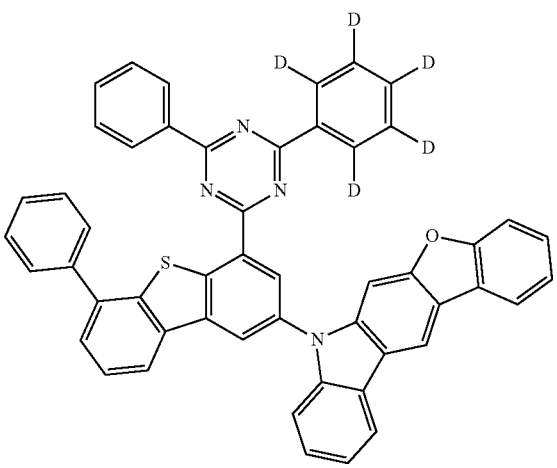 |
| 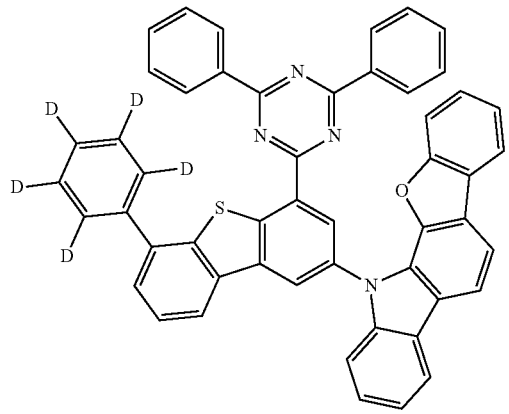 | 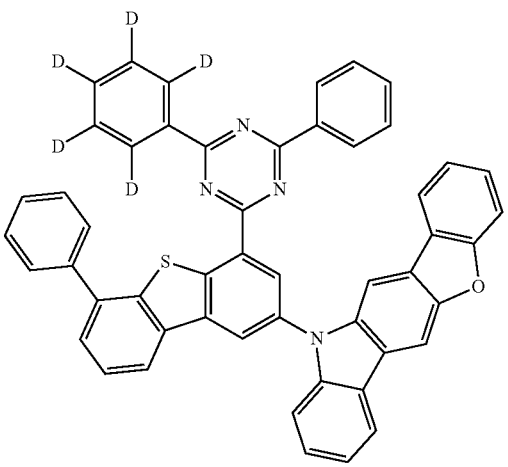 |
| 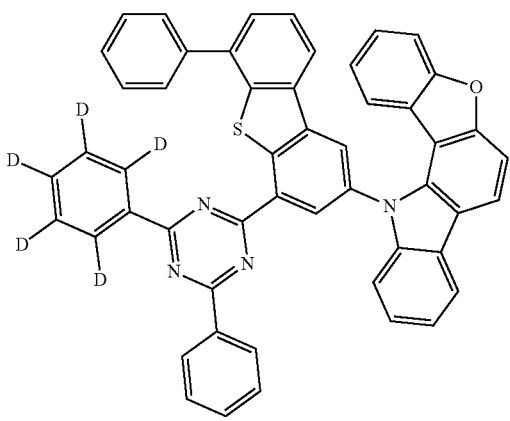 | 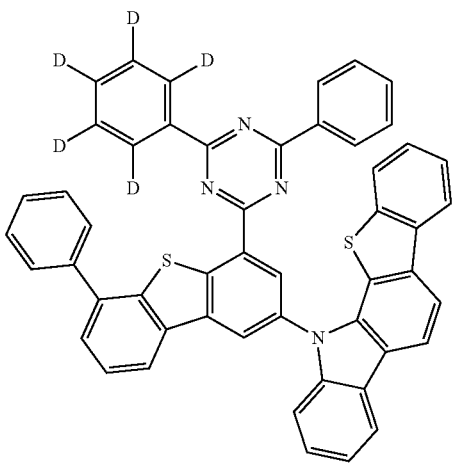 |

433
-continued
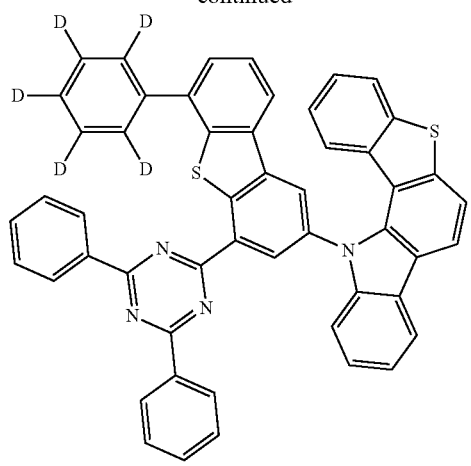
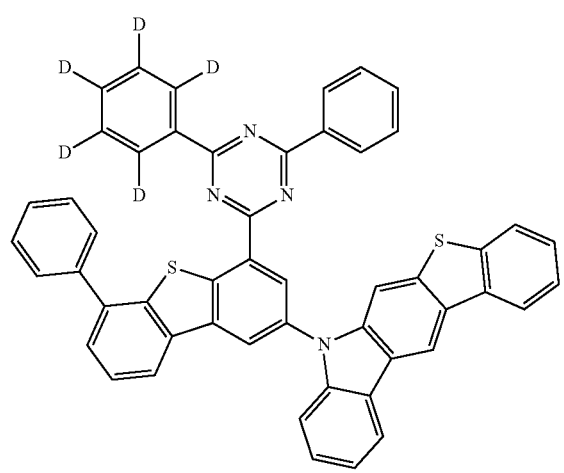
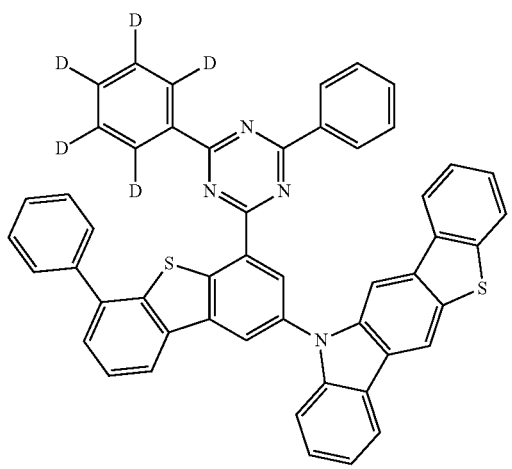
434
-continued
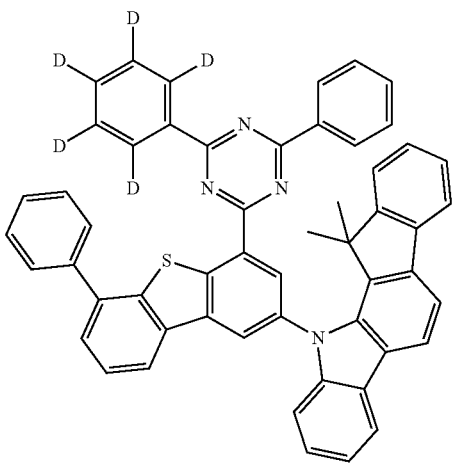
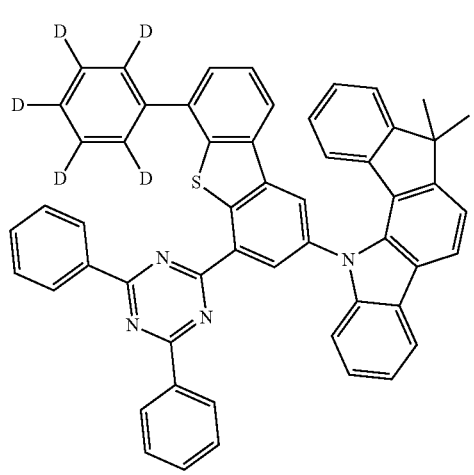
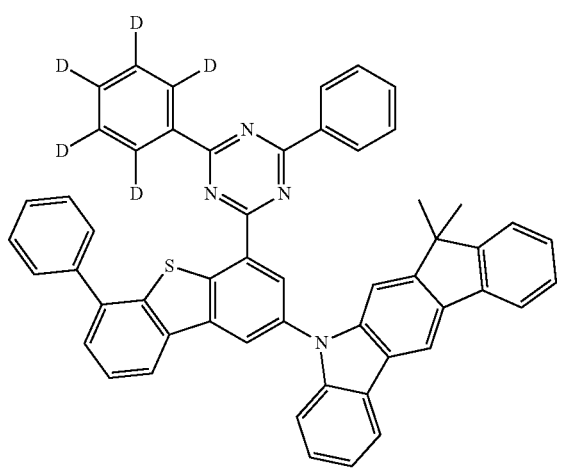

435
-continued
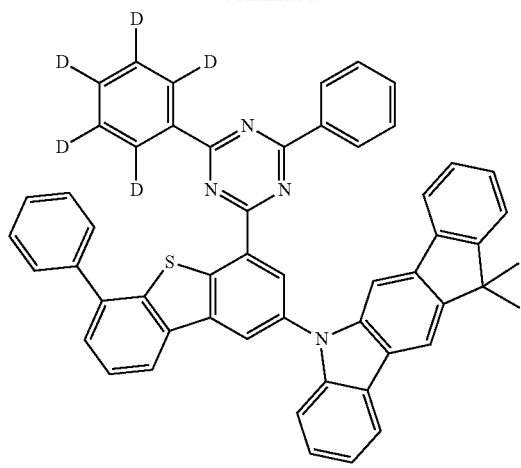
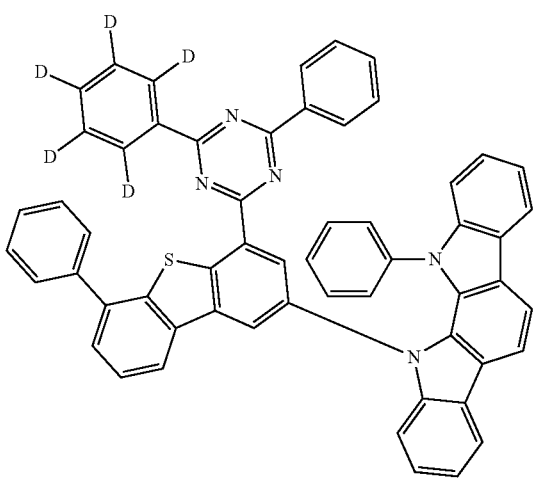
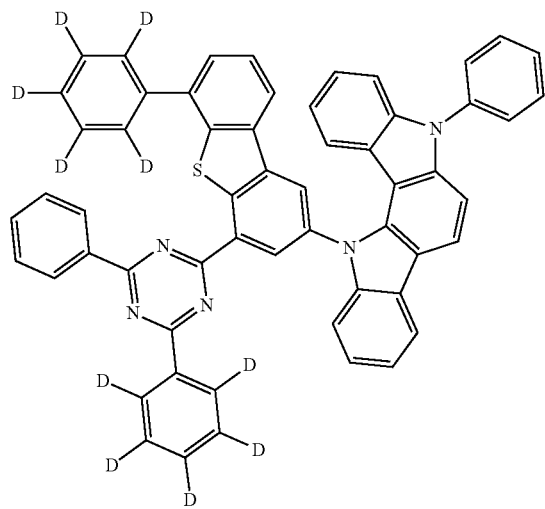
436
-continued
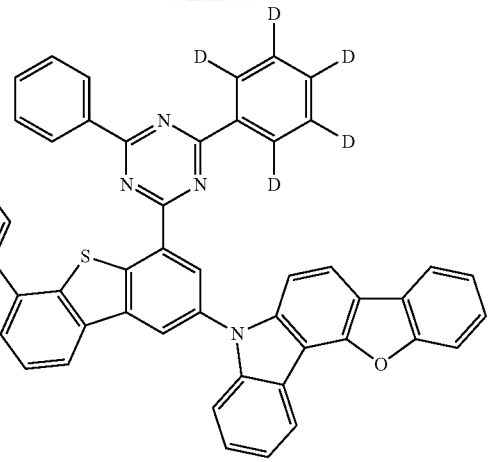
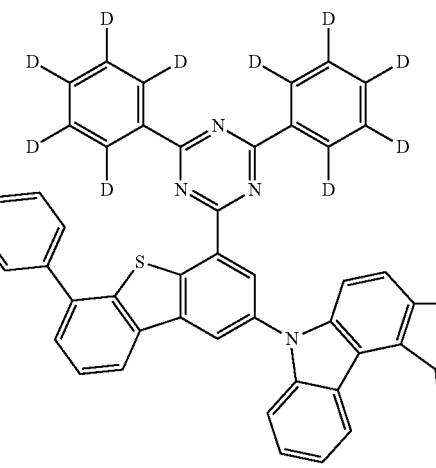
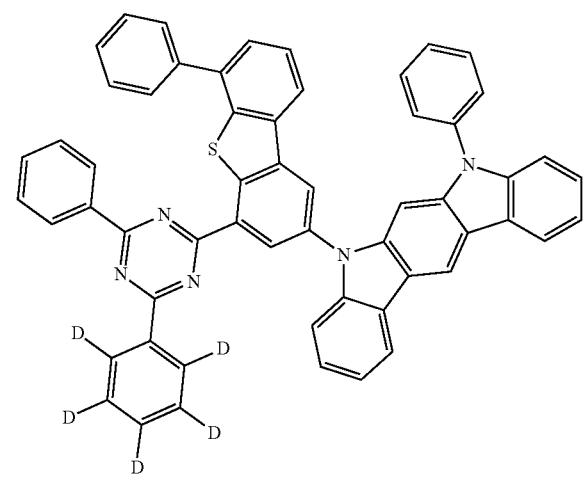

437
-continued
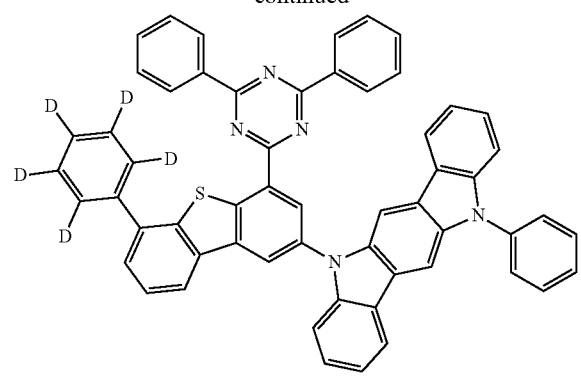
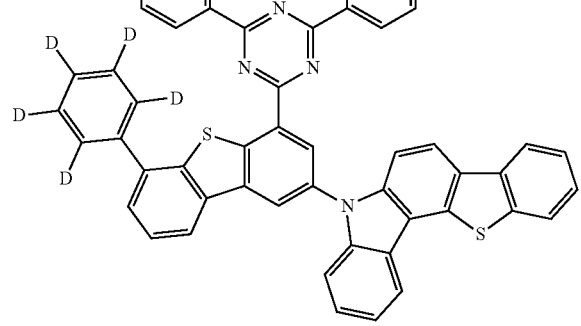
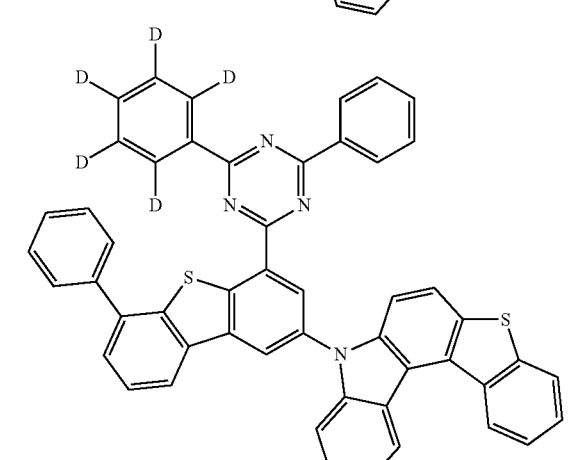
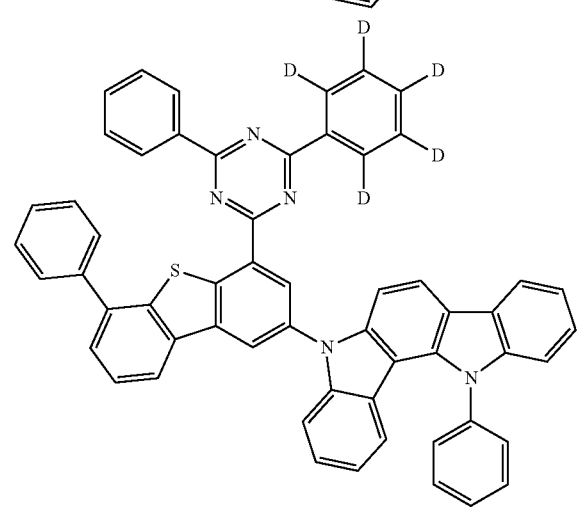
438
-continued
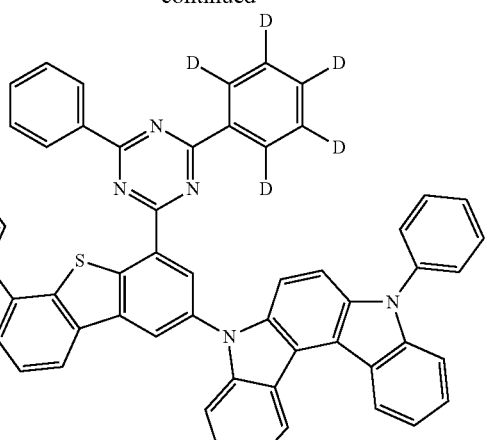
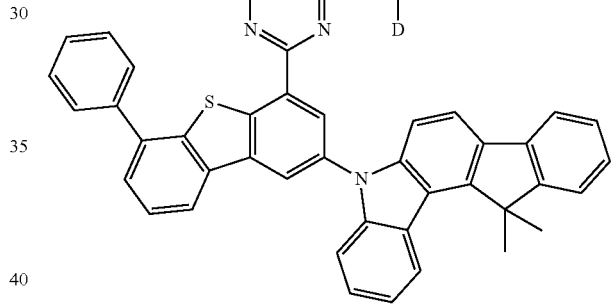
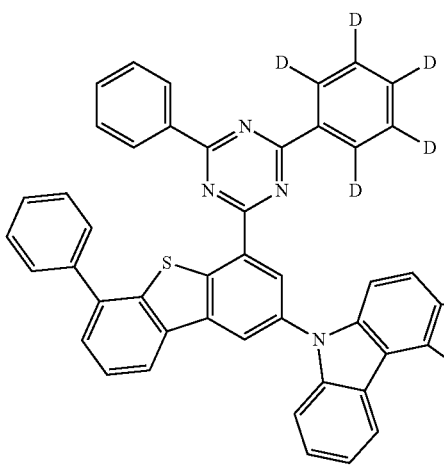

439
-continued
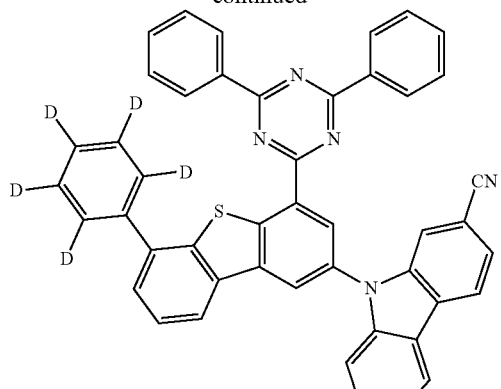
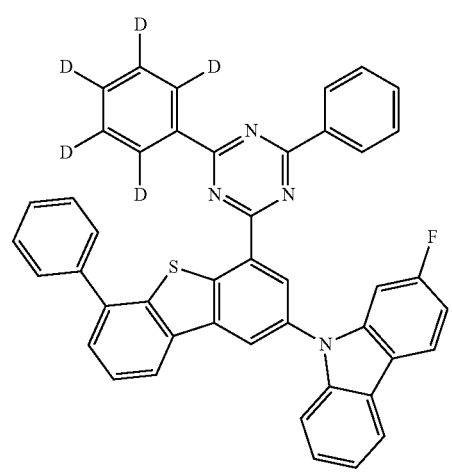
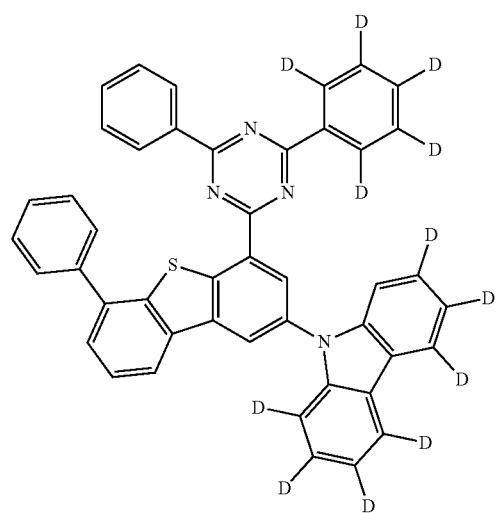
440
-continued
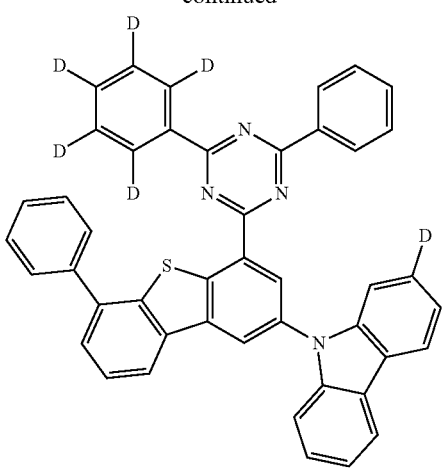
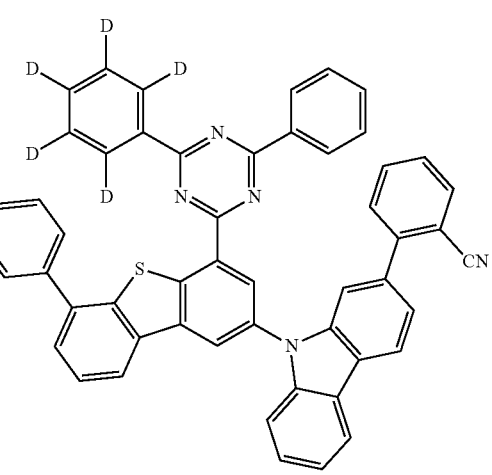
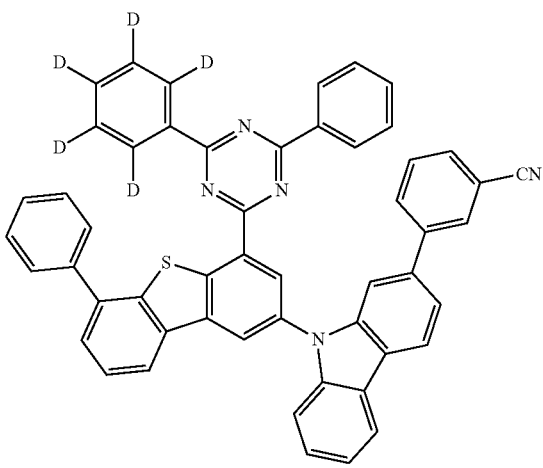

441
-continued
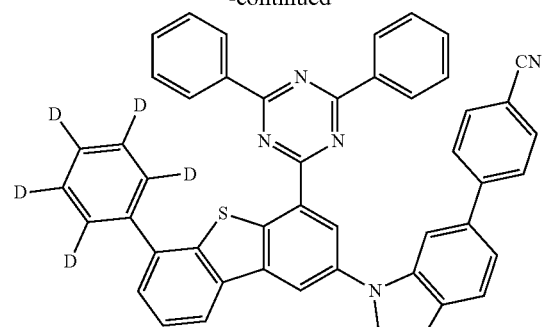
442
-continued
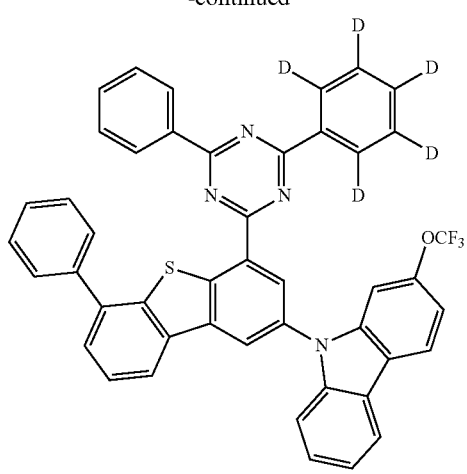
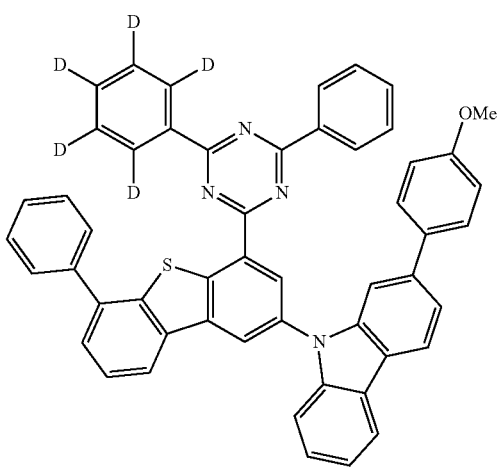
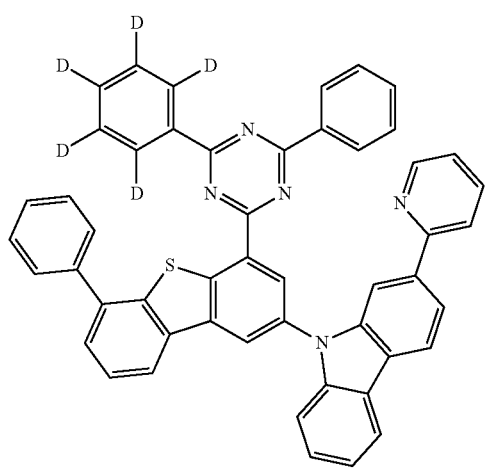

443
-continued
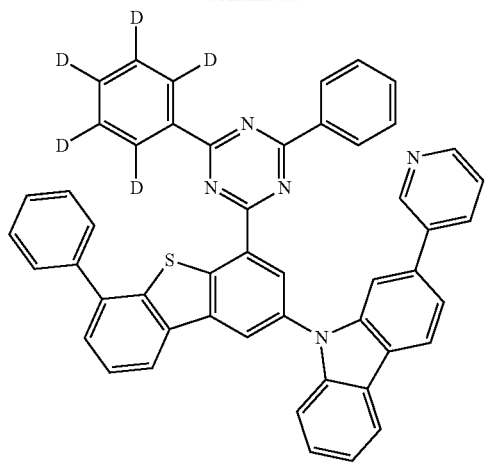
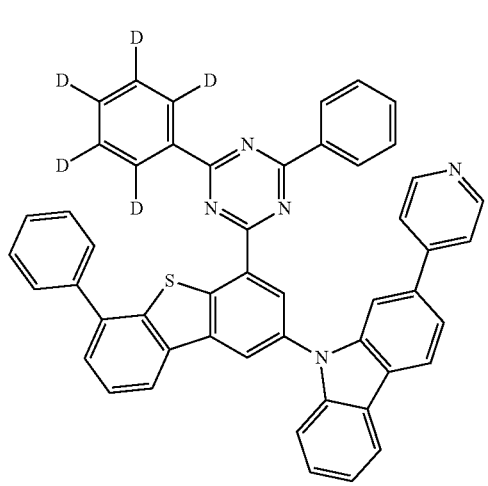
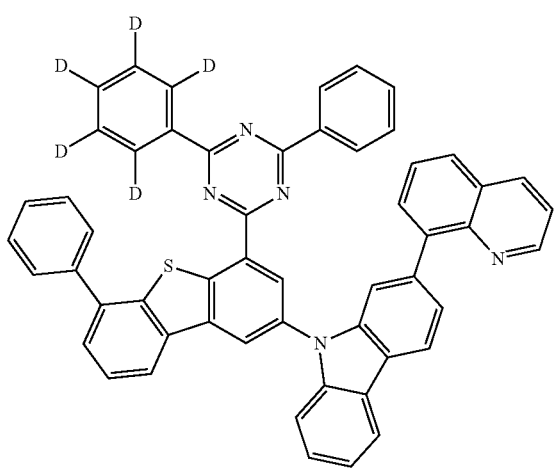
444
-continued
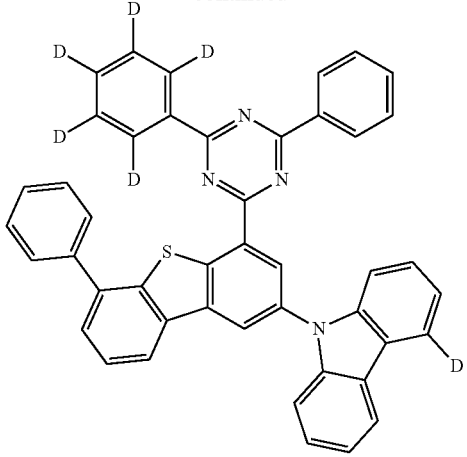
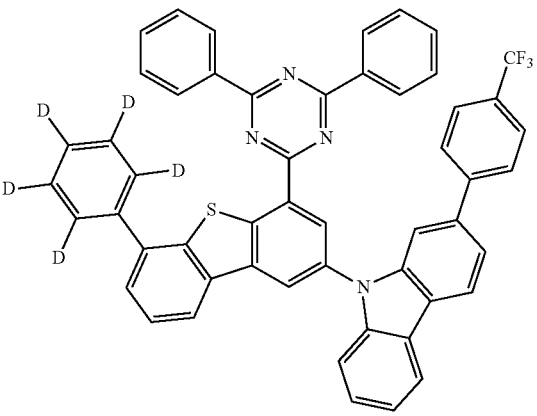
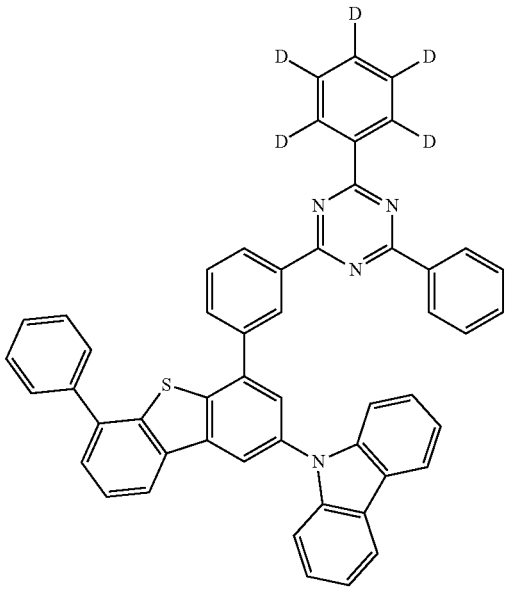

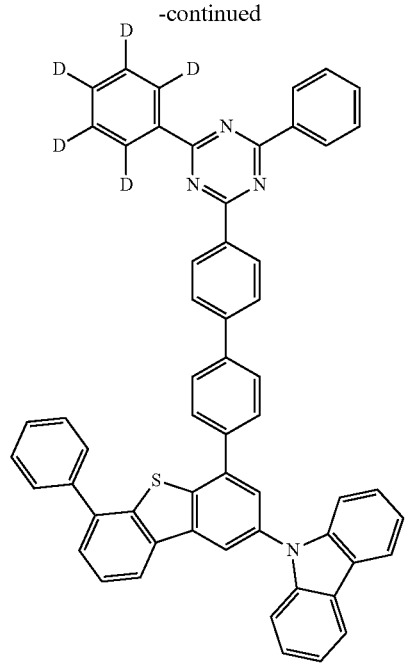
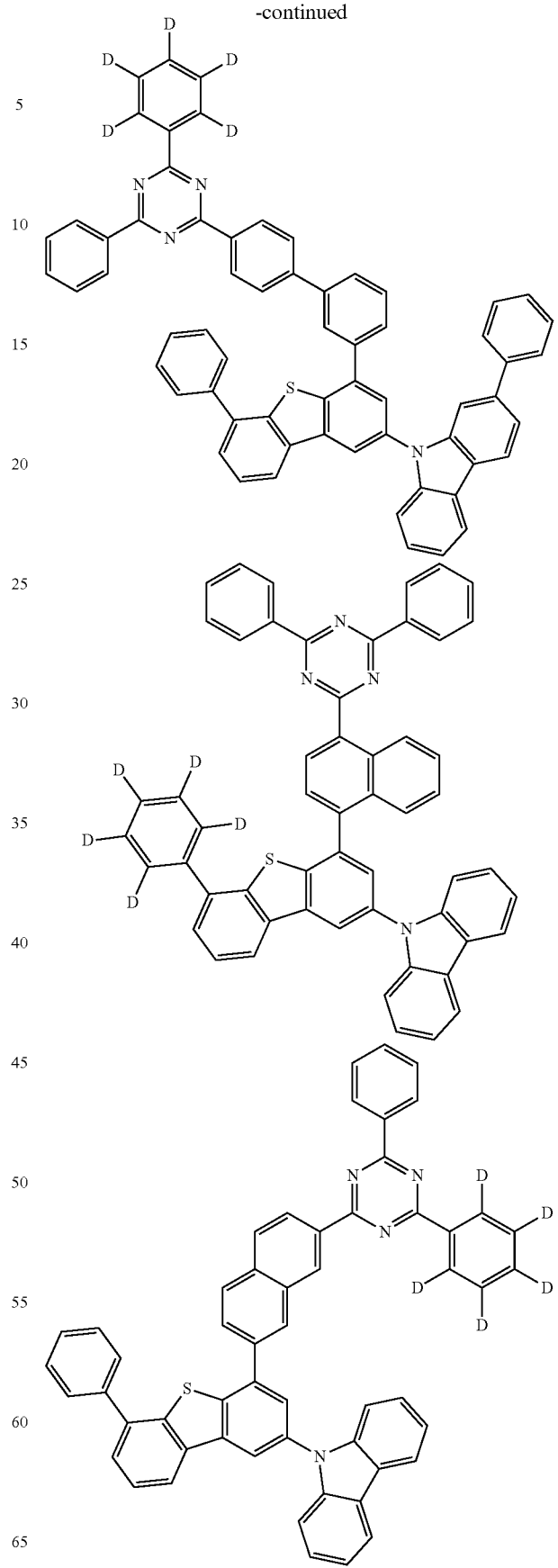

447
-continued
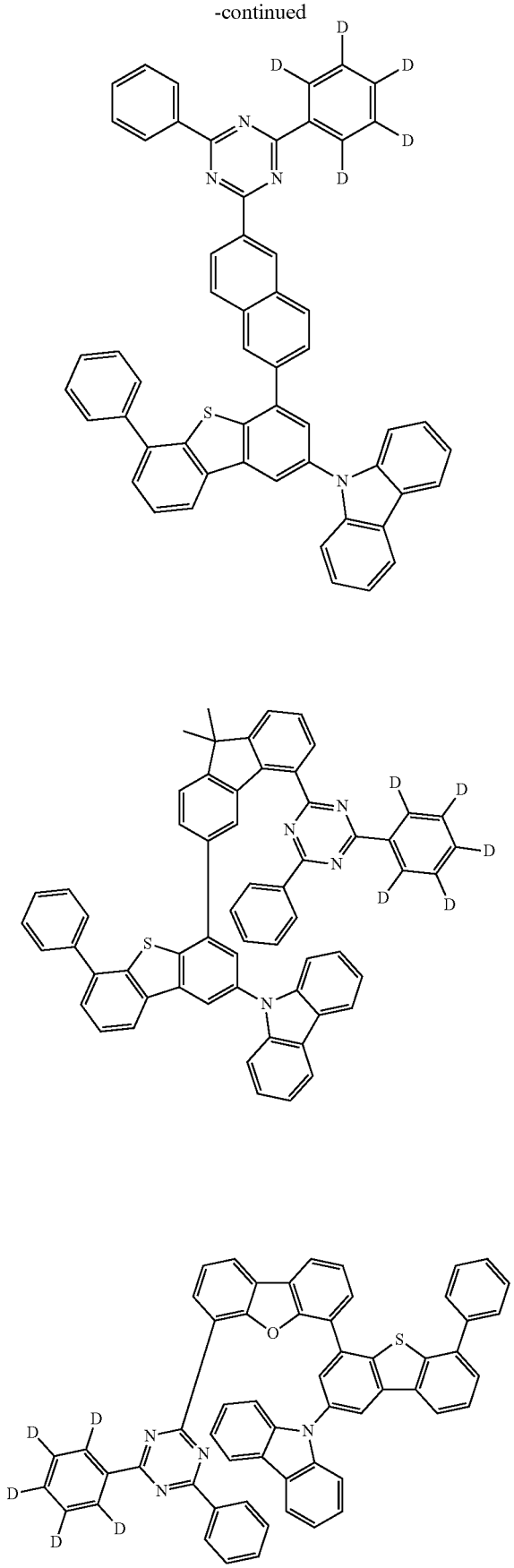
448
-continued
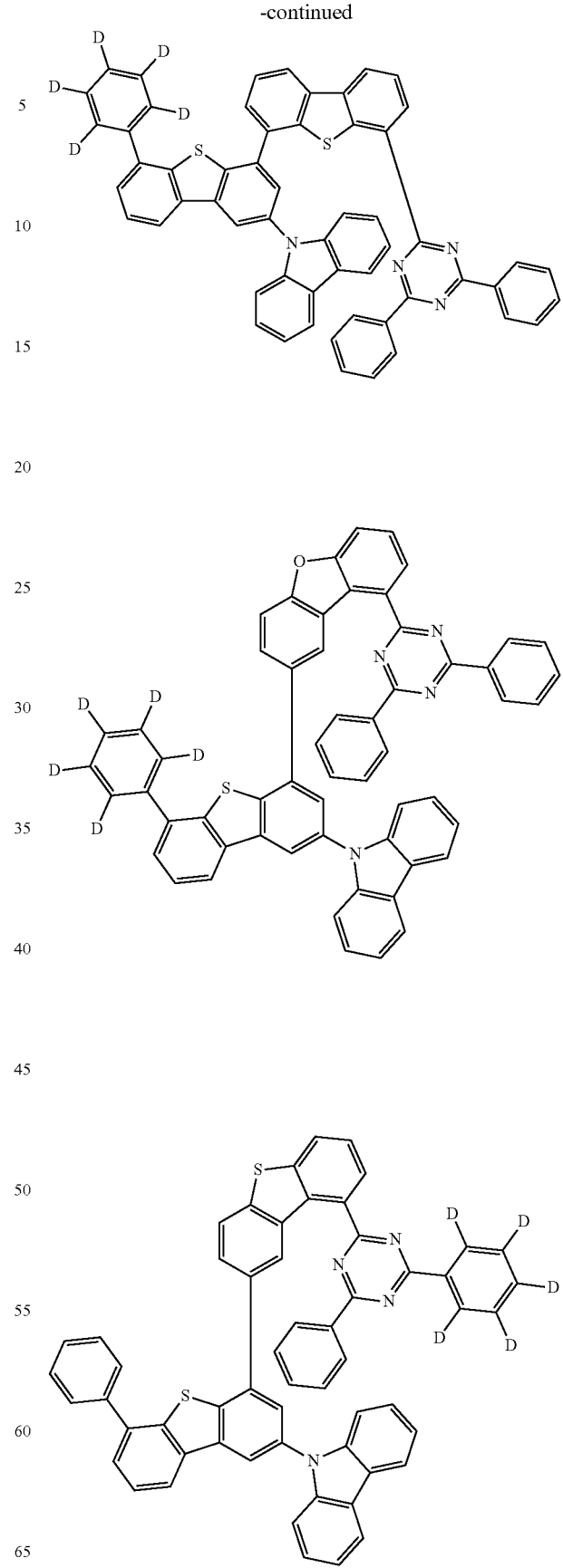

449
-continued
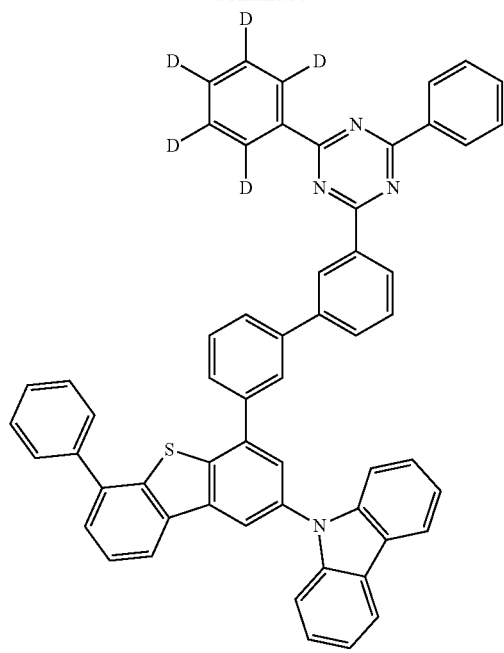
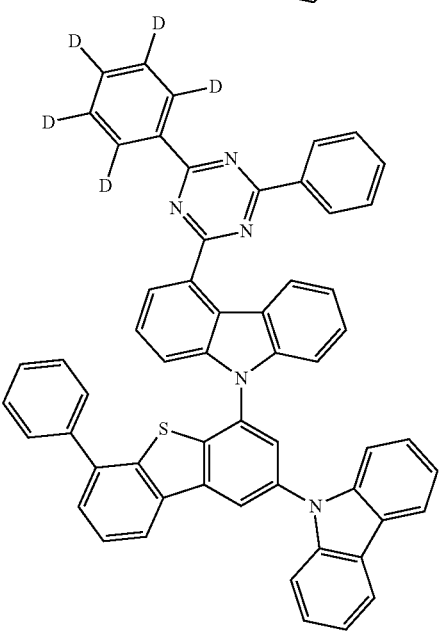
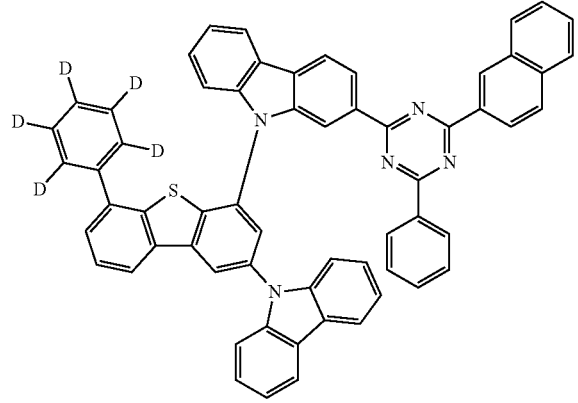
450
-continued
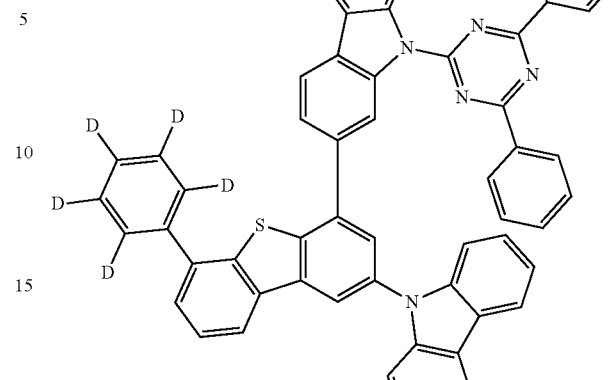
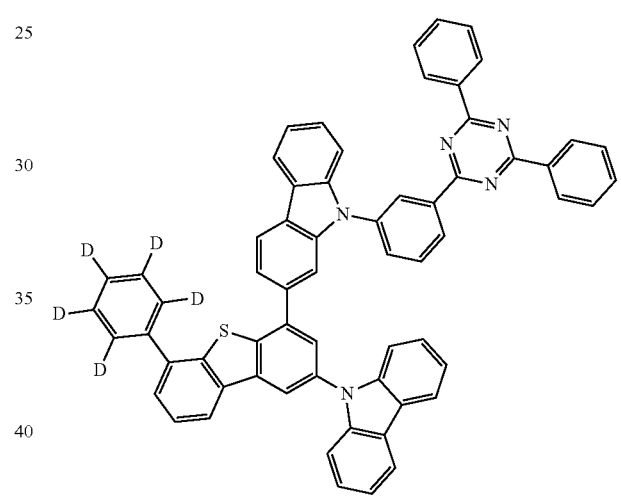
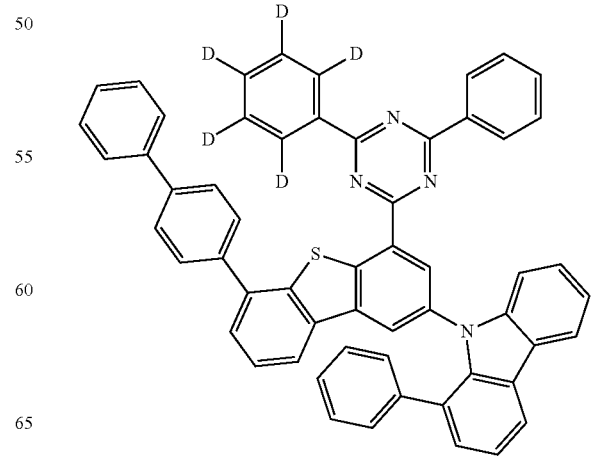

451
-continued
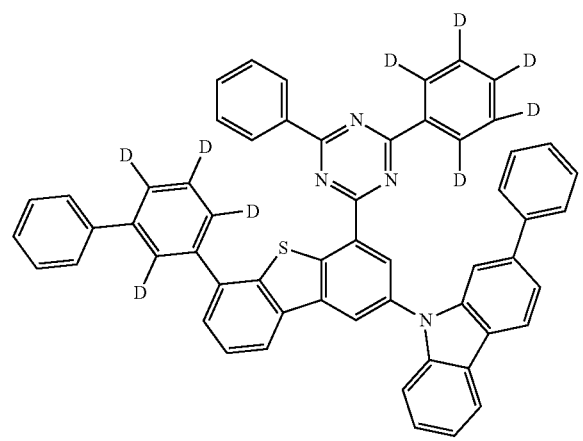
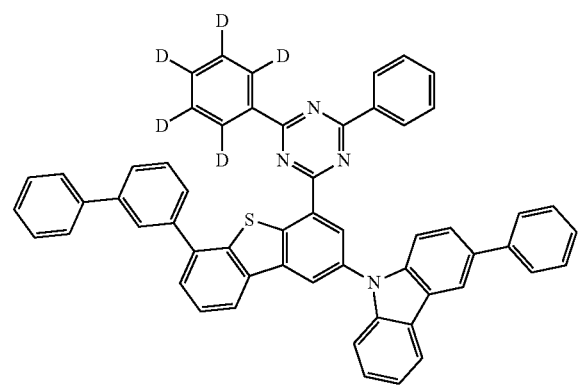
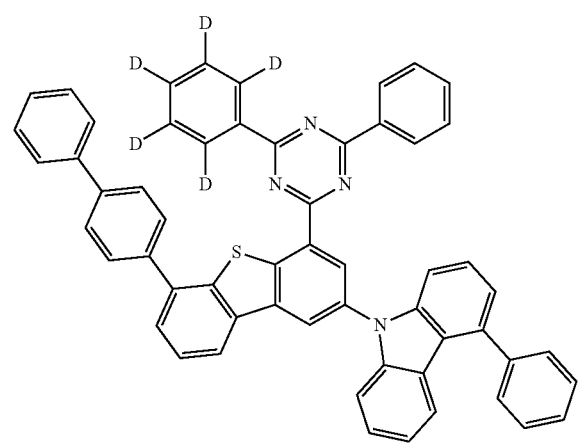
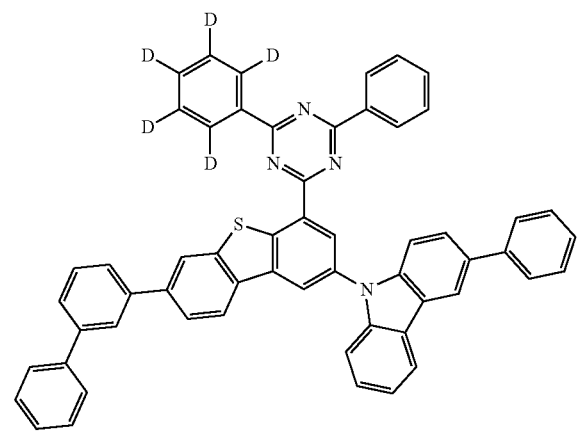
452
-continued
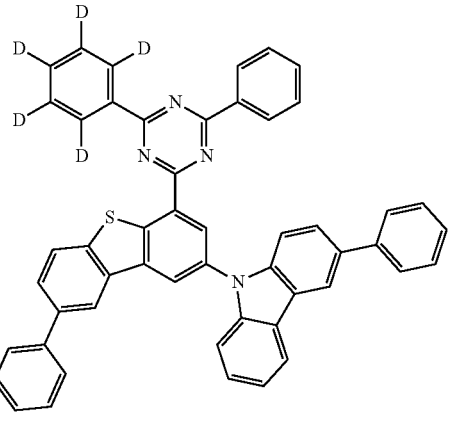
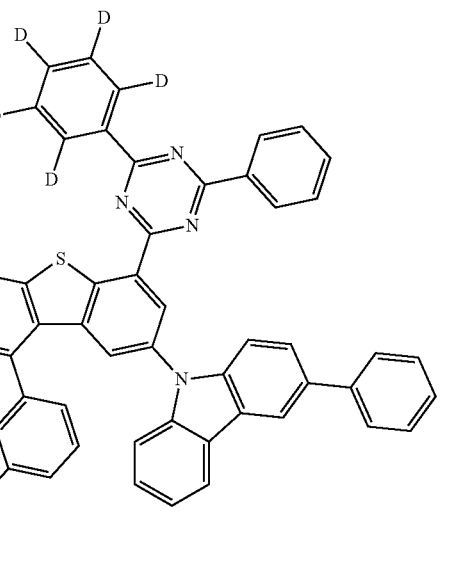
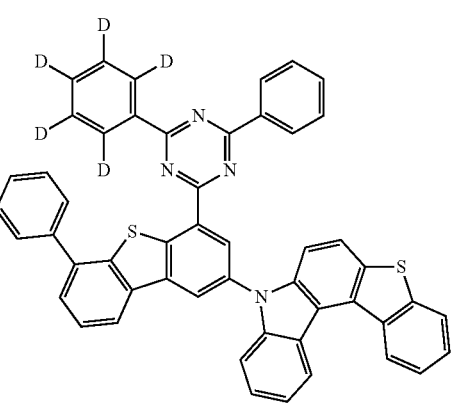

453
-continued
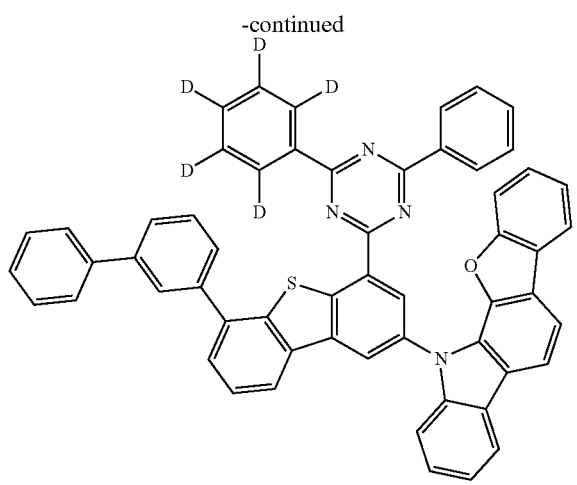
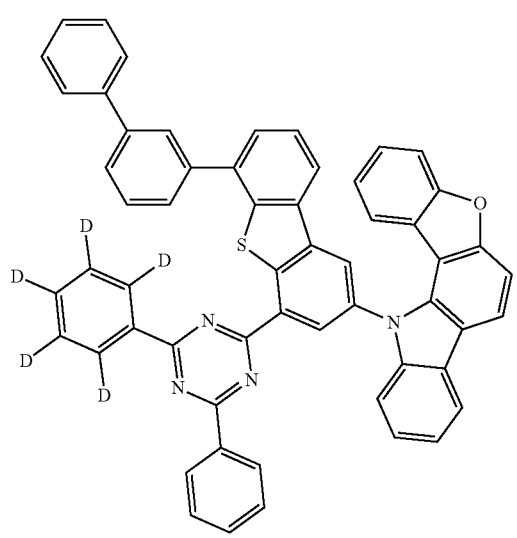
454
-continued
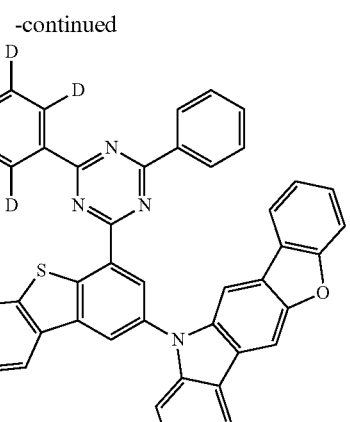
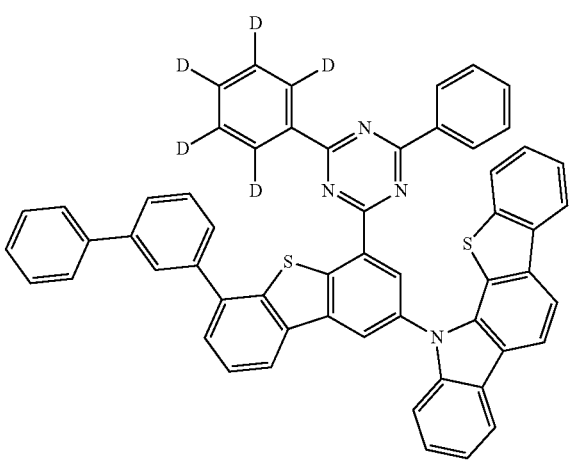
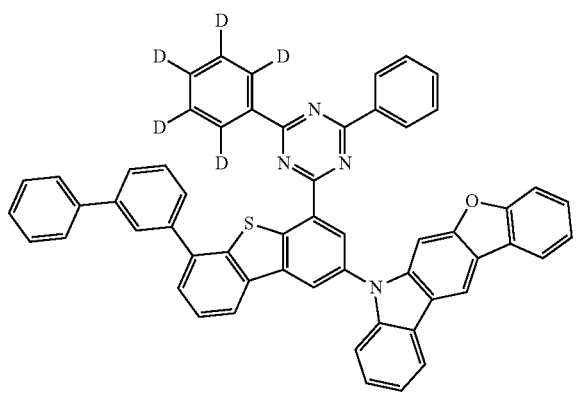
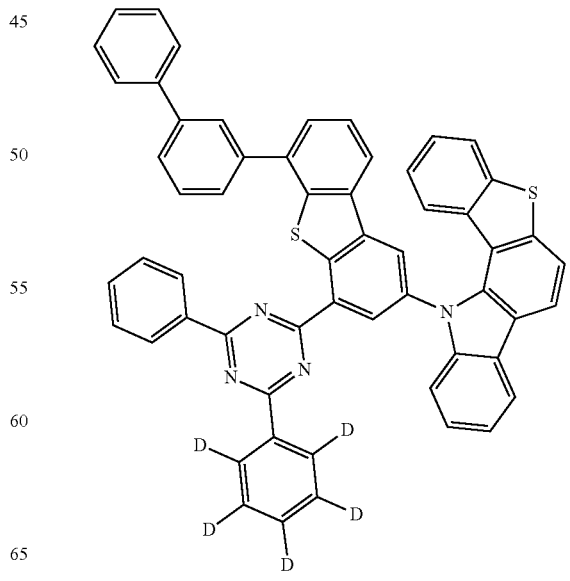

455
-continued
456
-continued
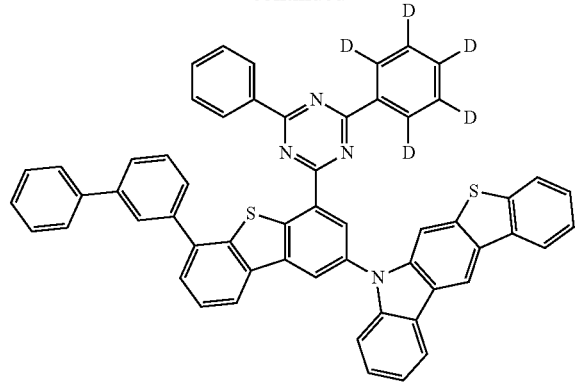
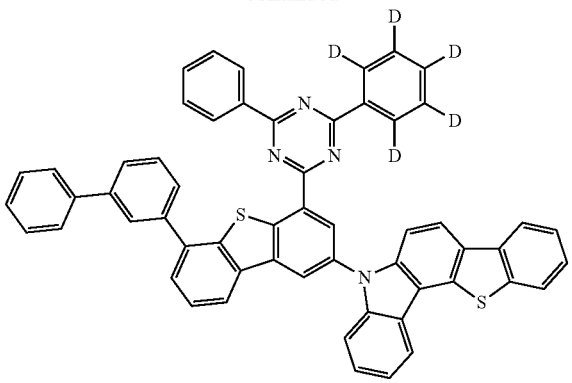

-continued
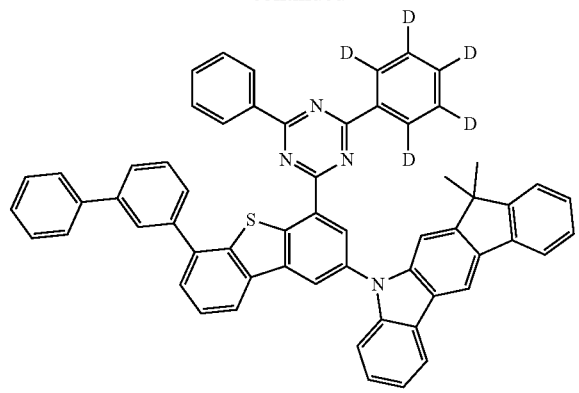
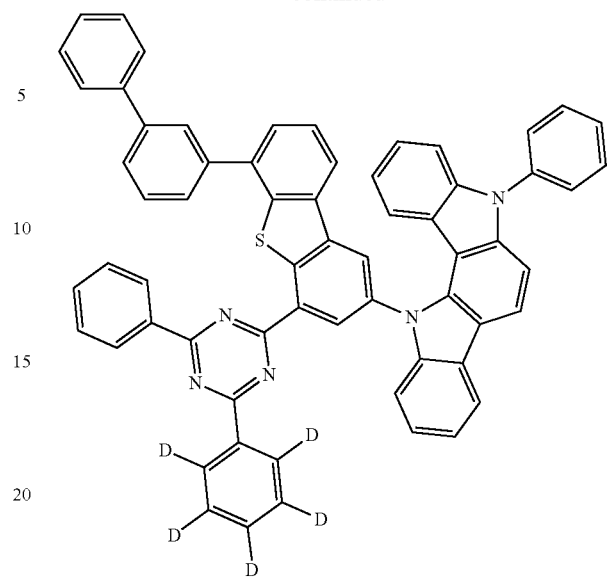
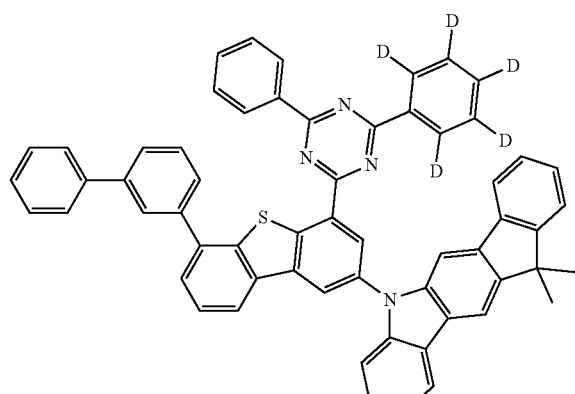
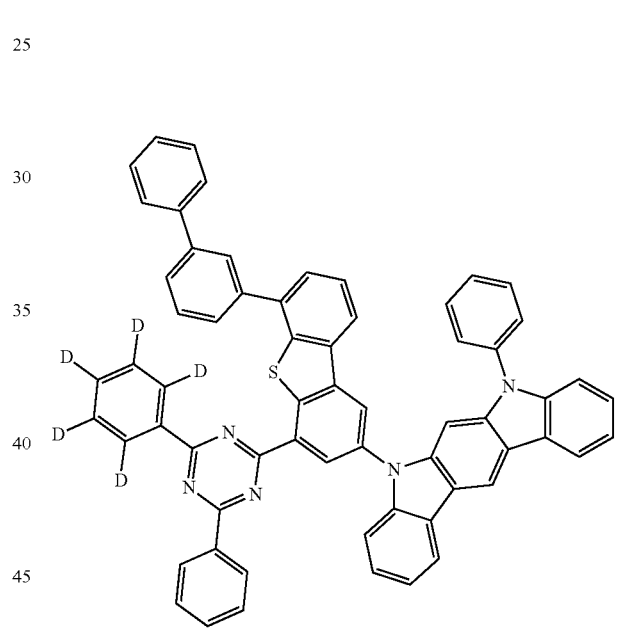
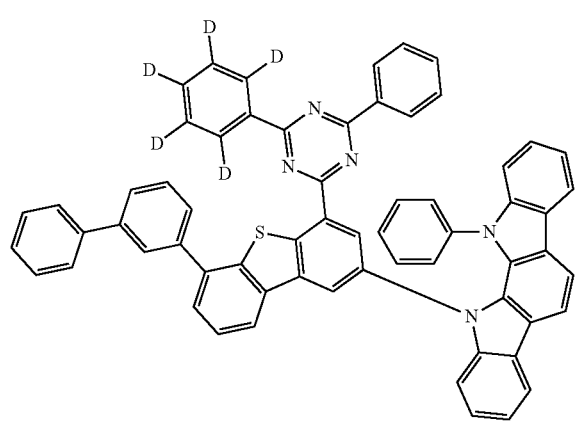
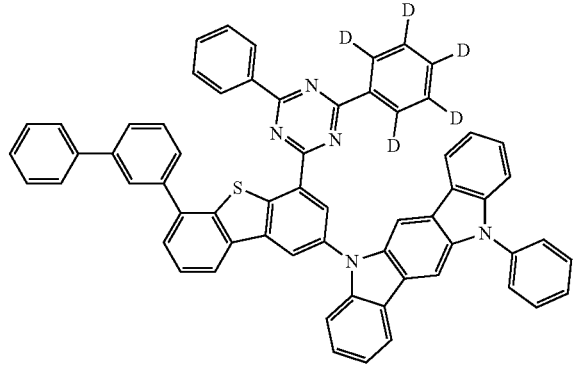

459
-continued
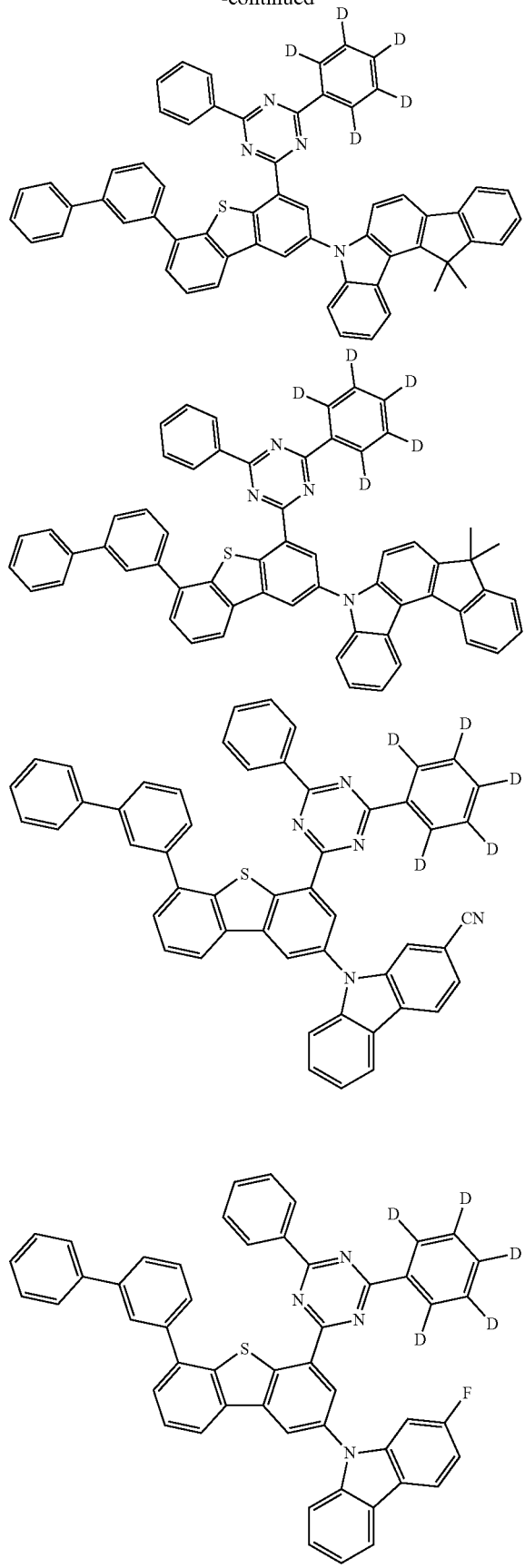
460
-continued
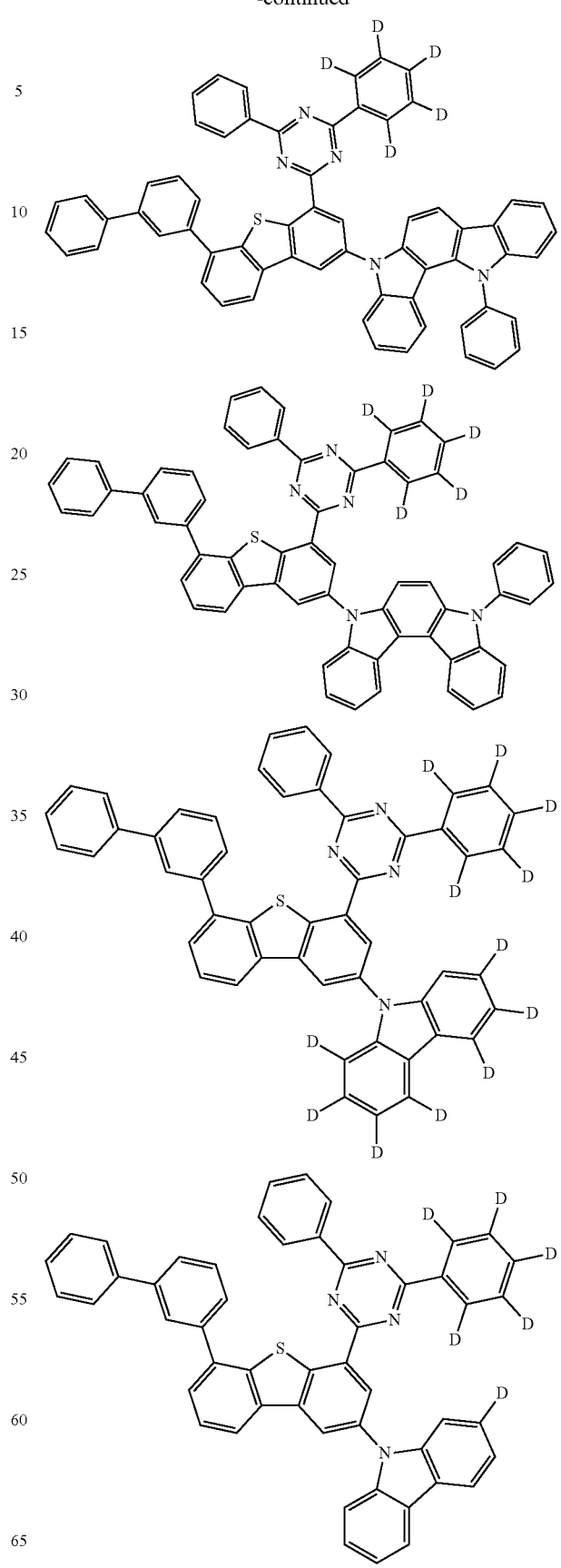

461
-continued
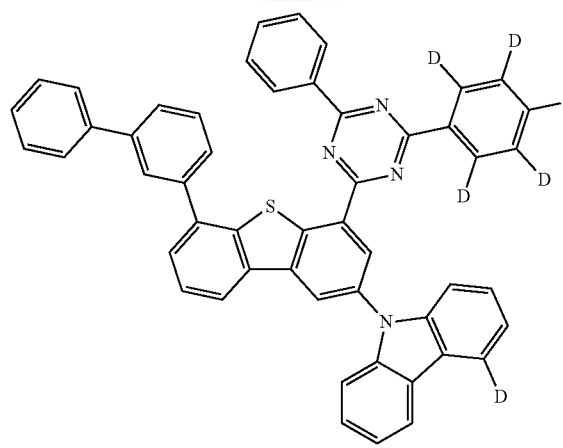
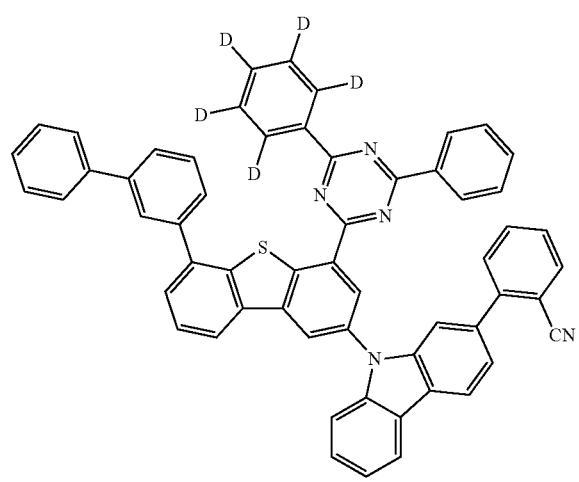
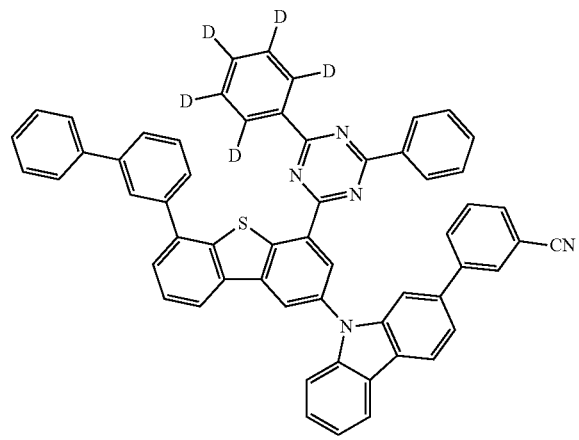
462
-continued
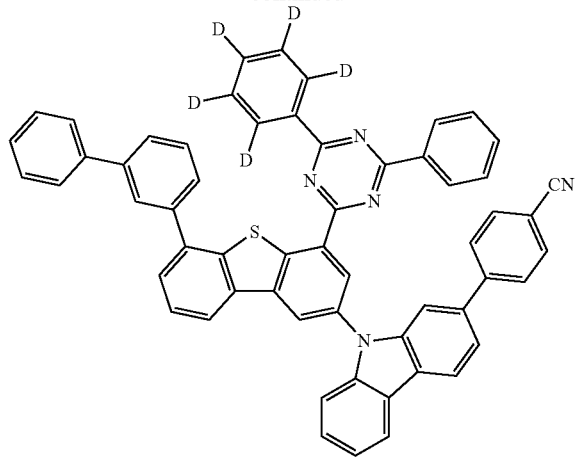
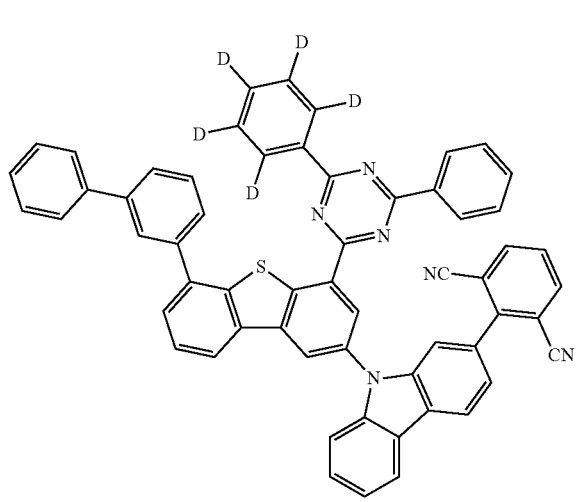
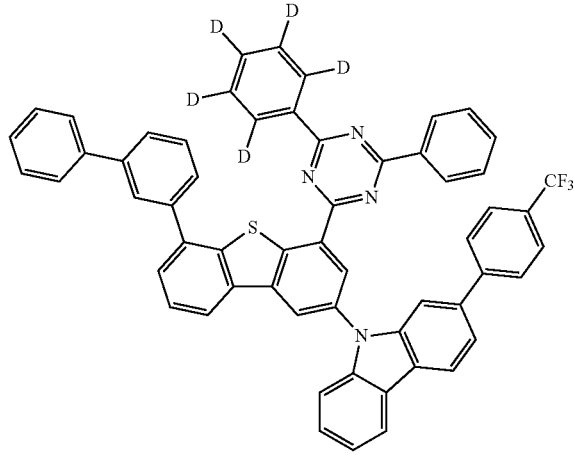

463
-continued
464
-continued
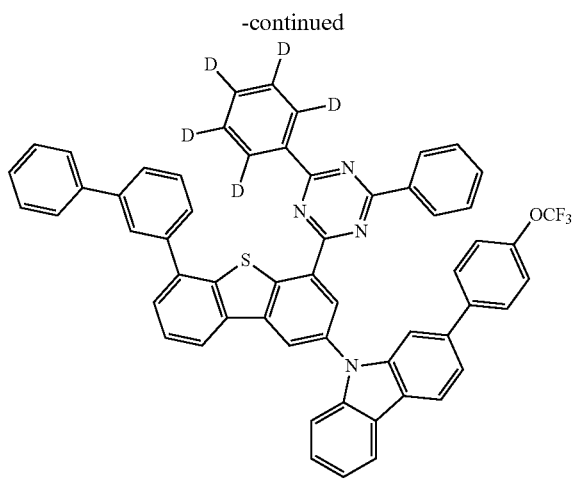
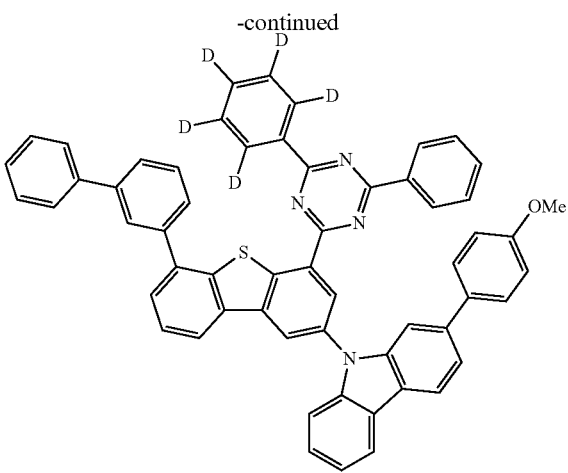
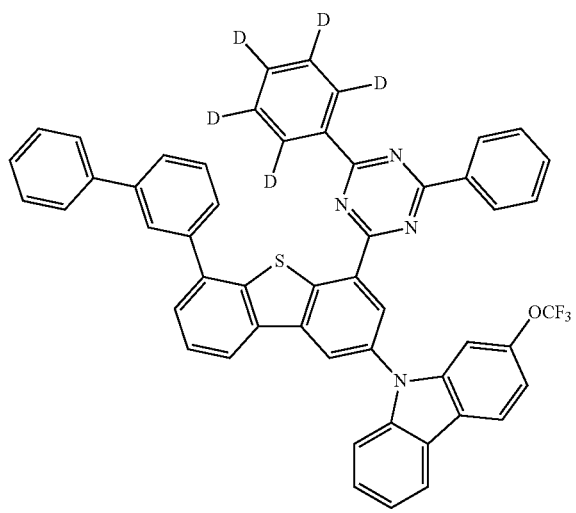

465
-continued
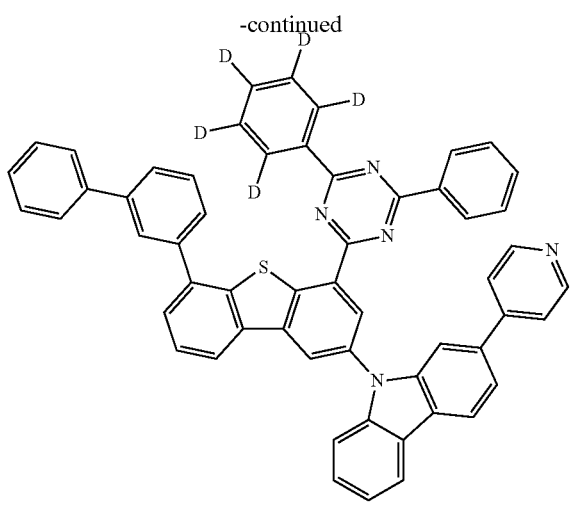
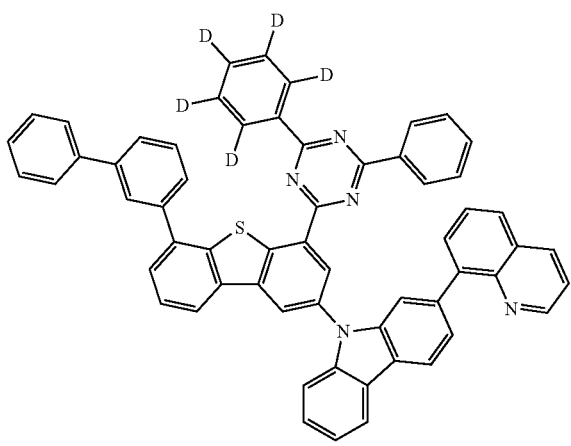
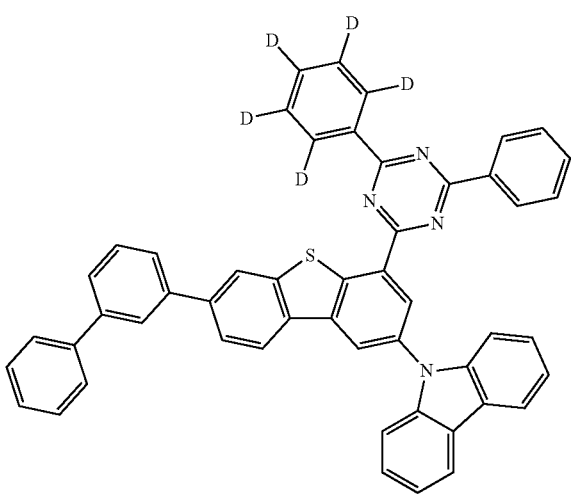
466
-continued
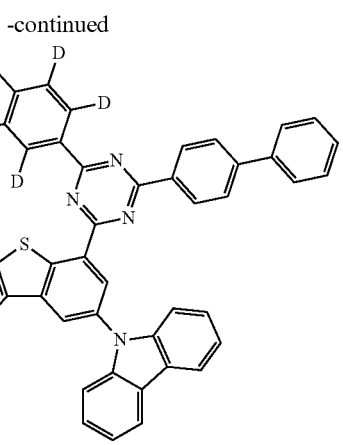
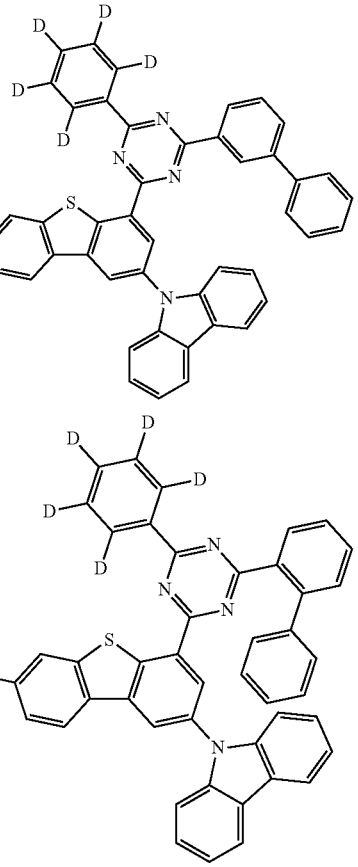
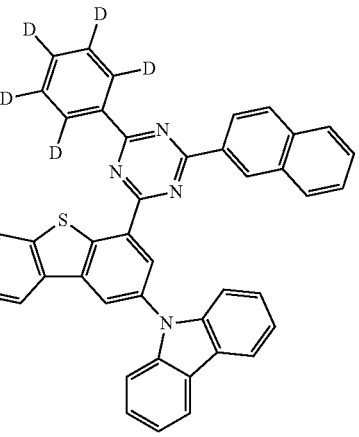

467
-continued
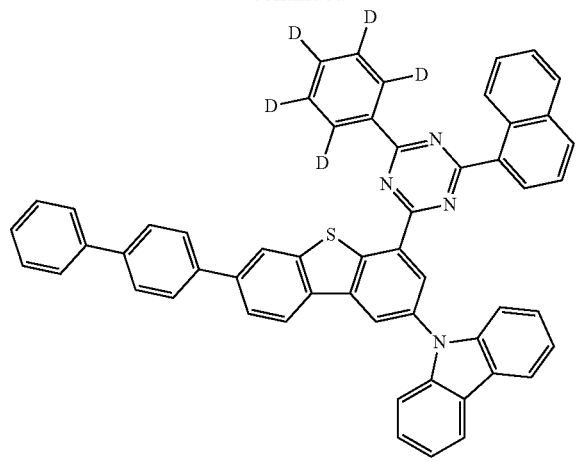
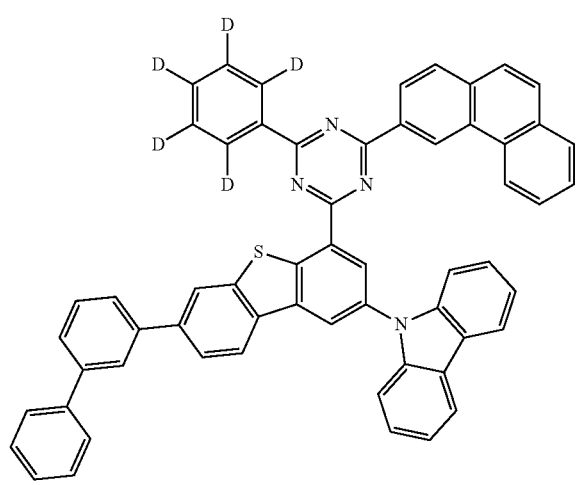
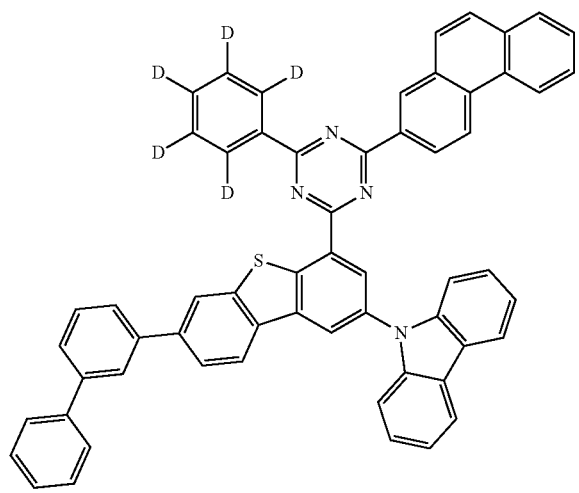
468
-continued
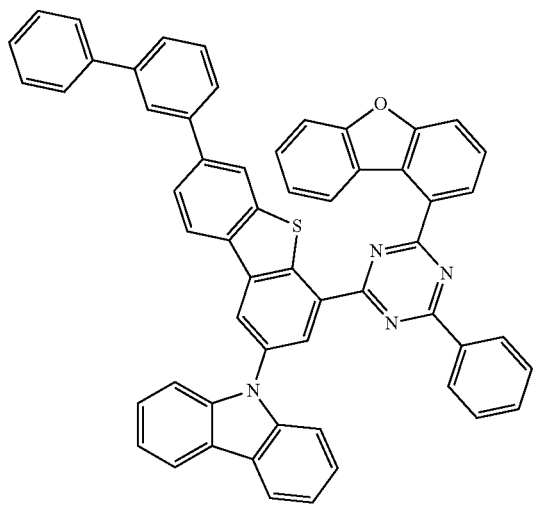
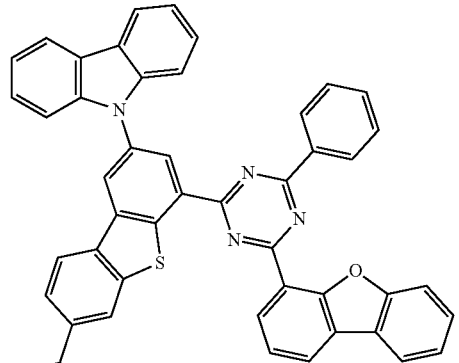
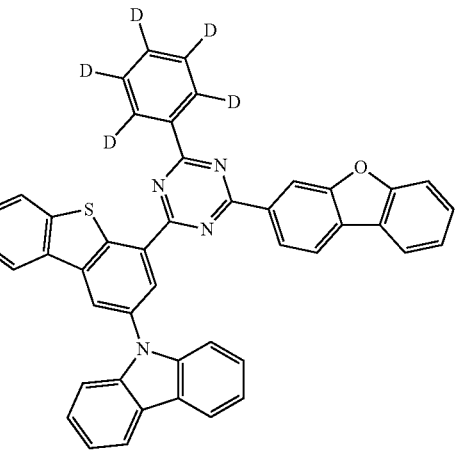

469
-continued
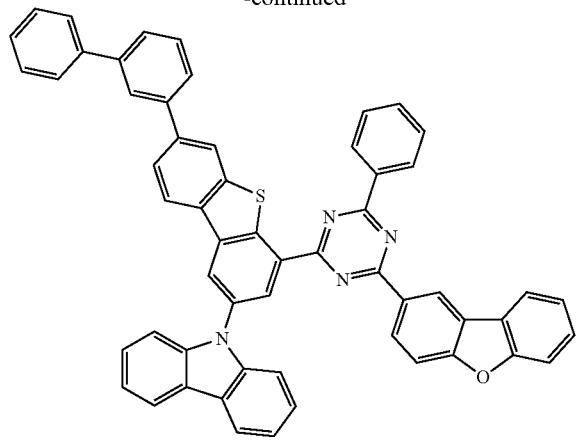
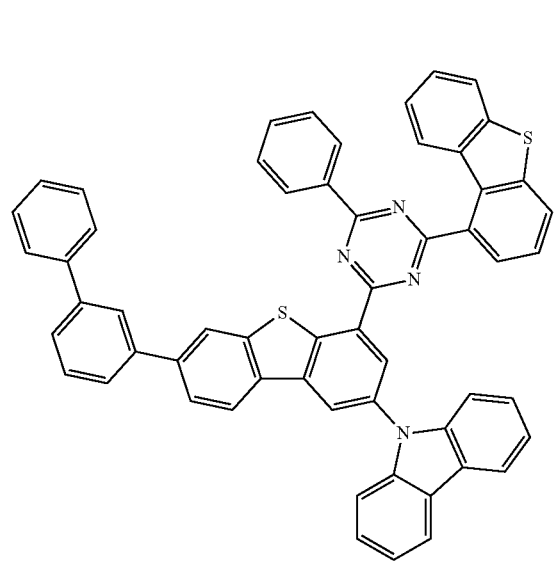
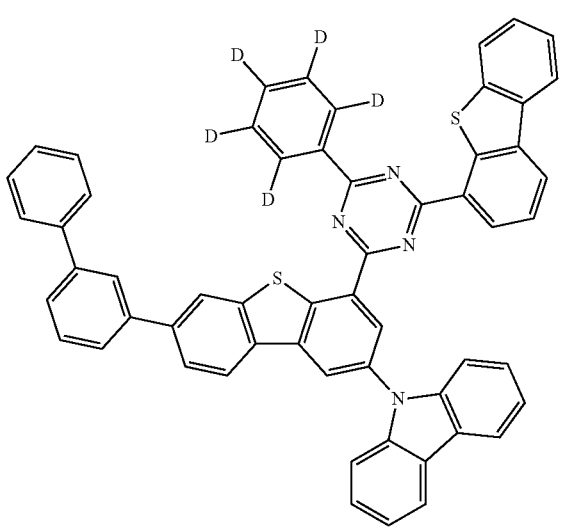
470
-continued
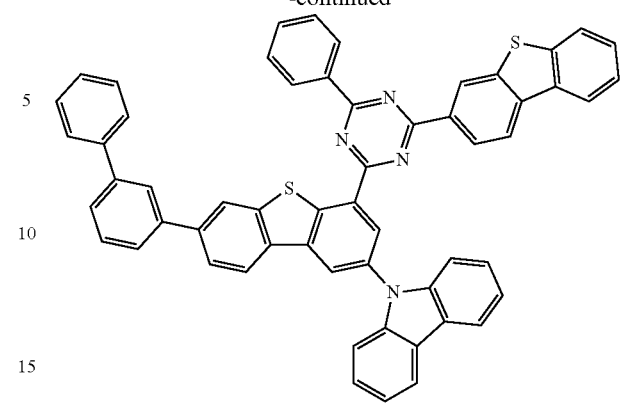
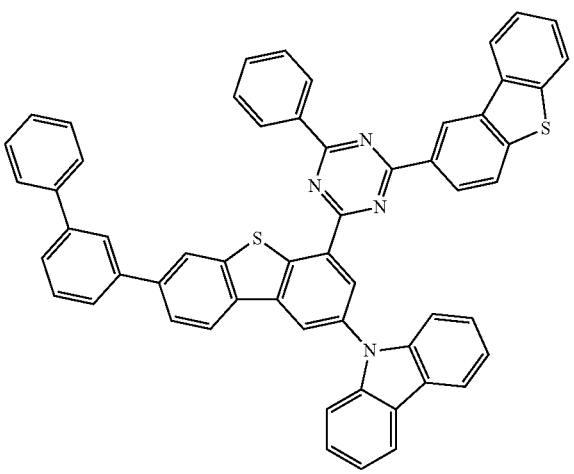
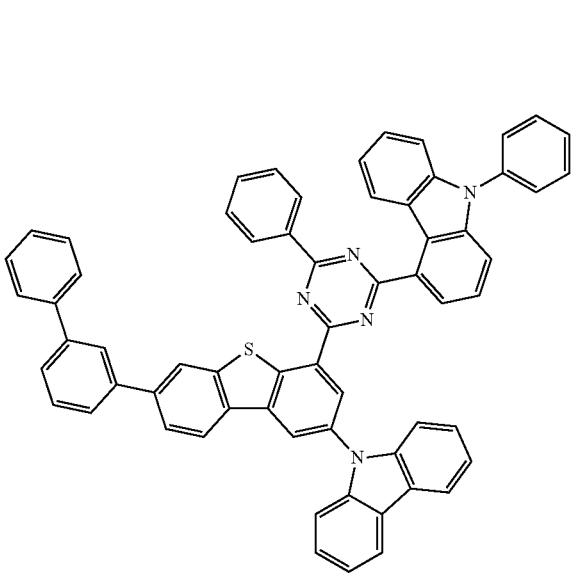

471
-continued
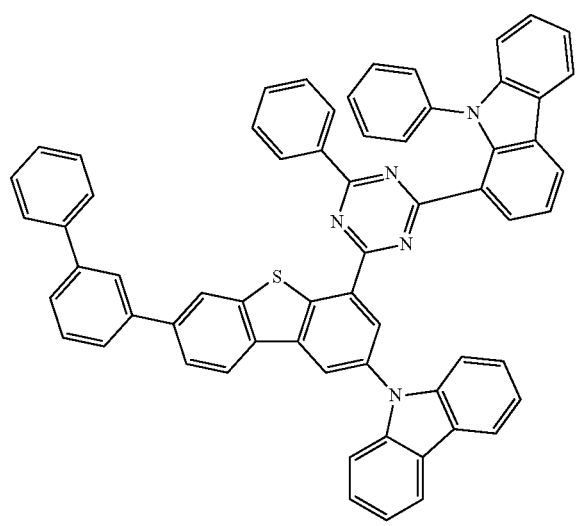
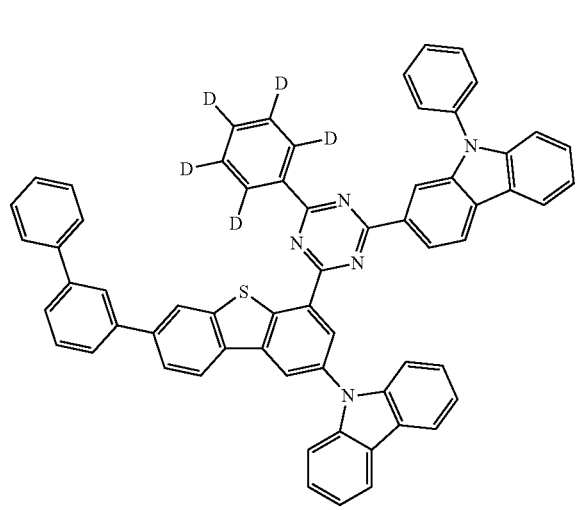
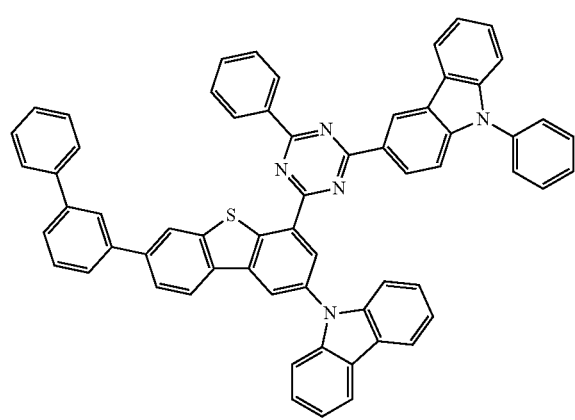
472
-continued
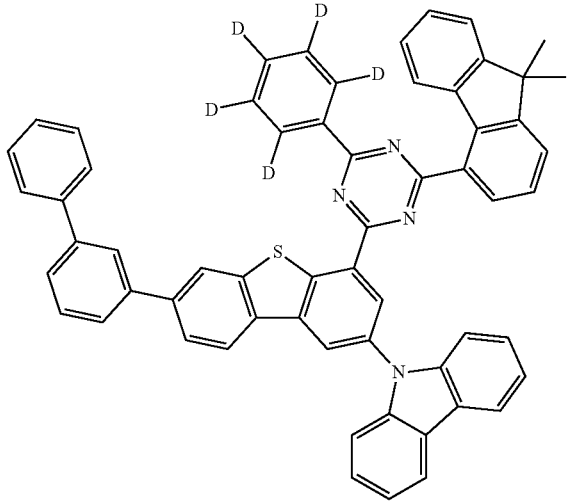
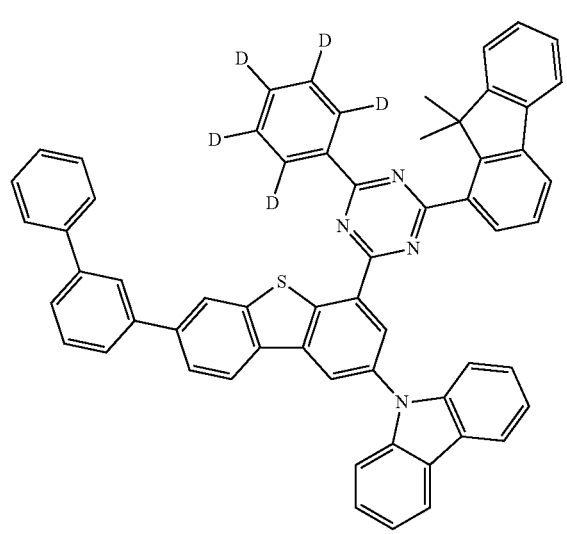
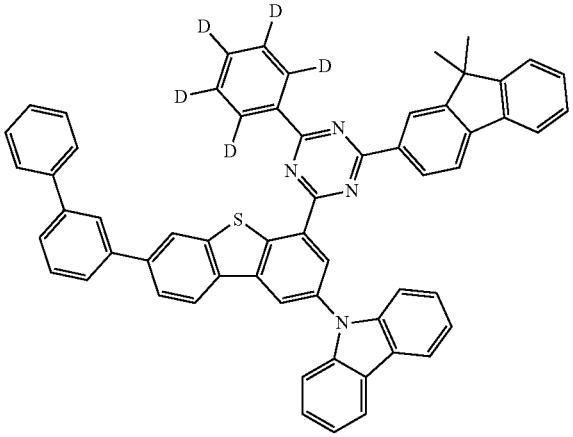

473
-continued
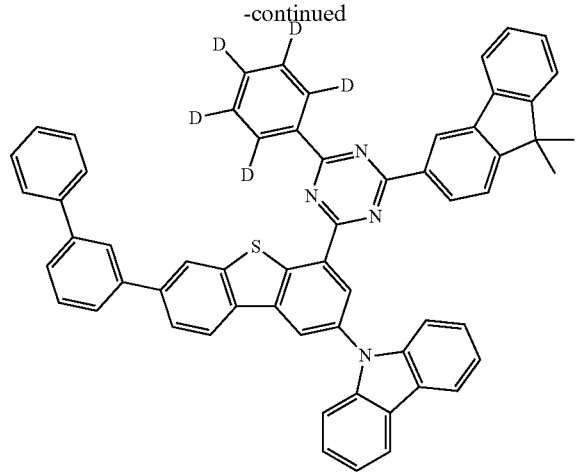
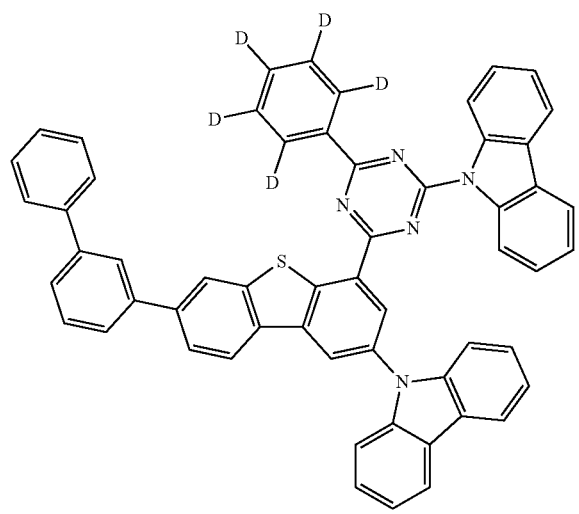
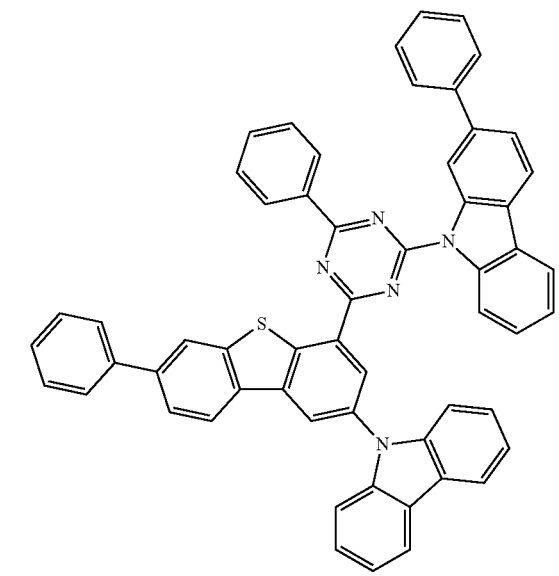
474
-continued
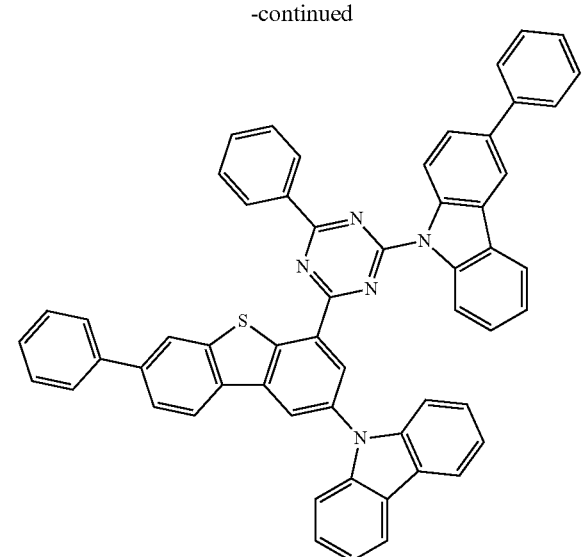
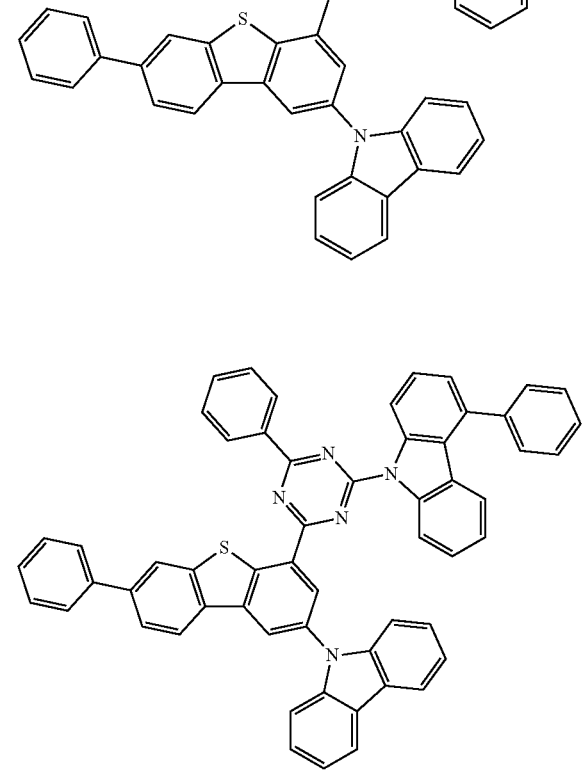
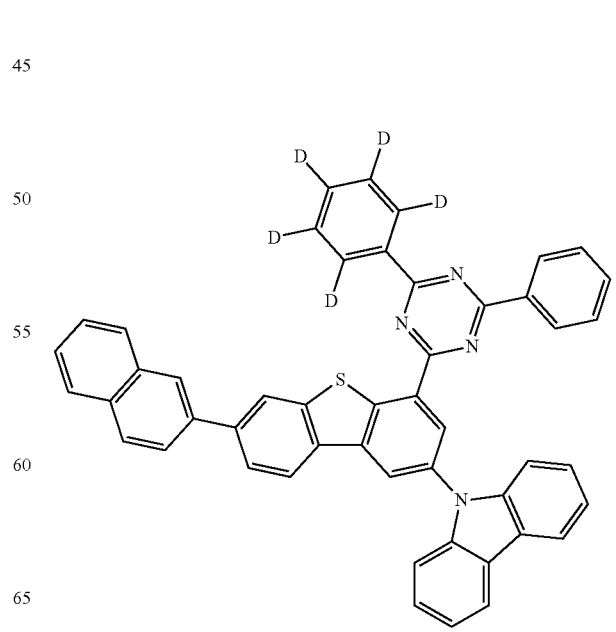

475
-continued
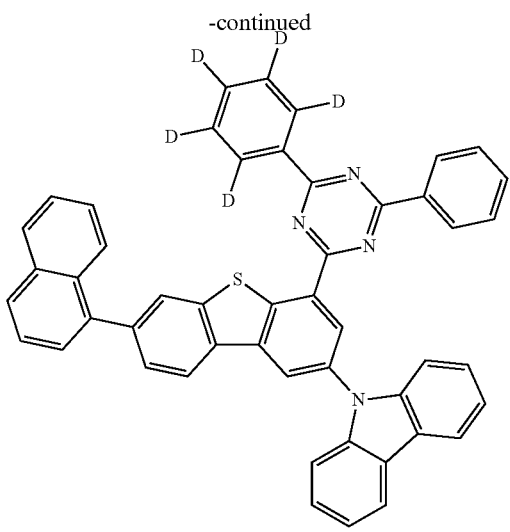
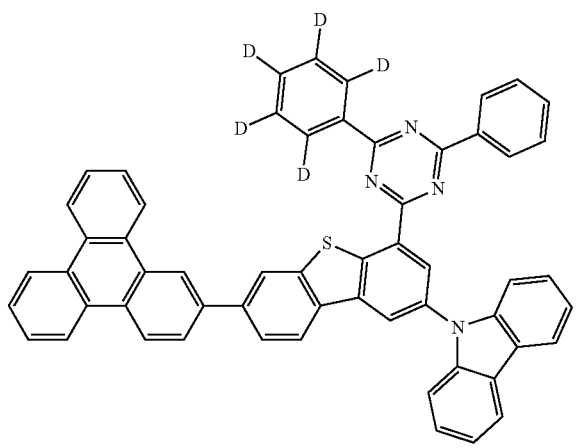
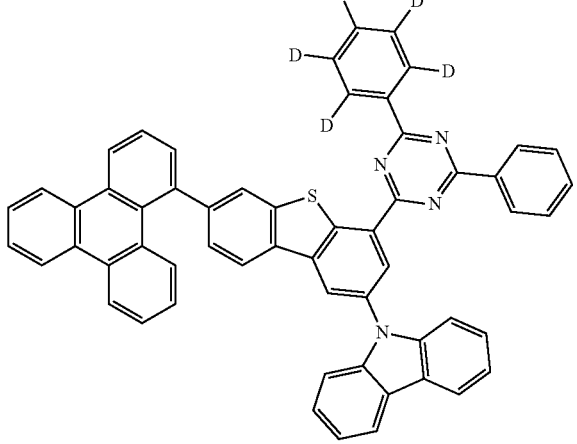
476
-continued
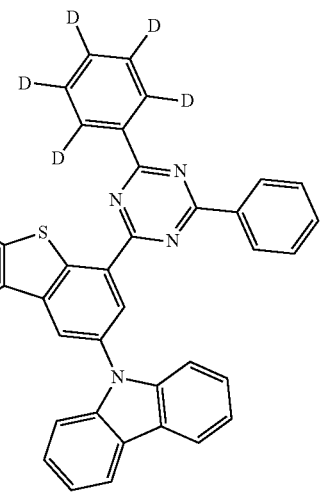
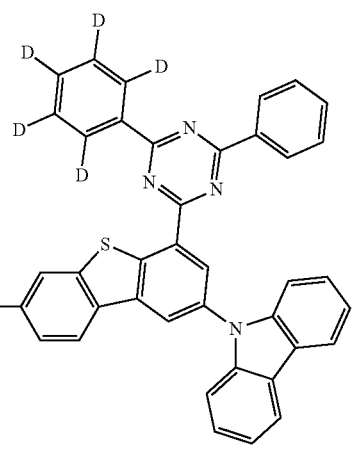
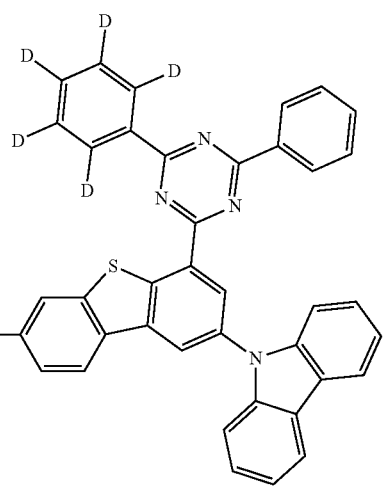

477
-continued
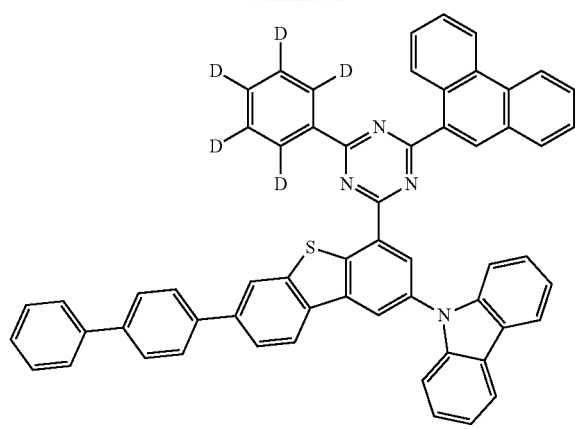
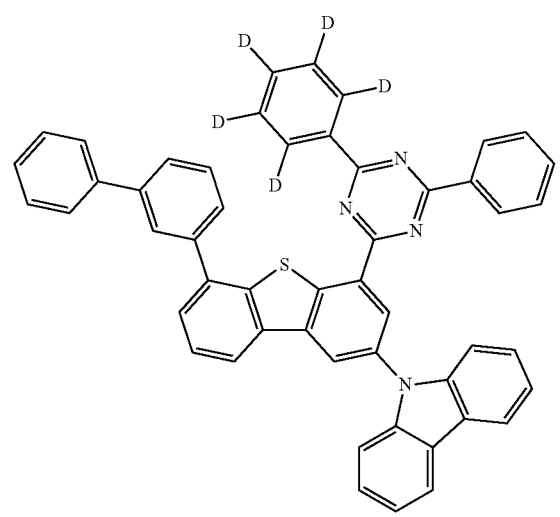
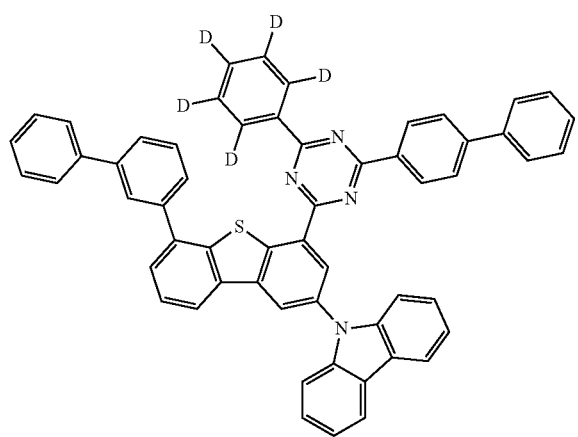
478
-continued
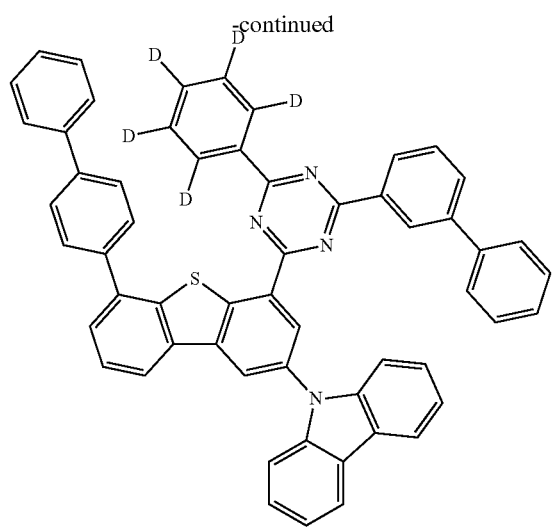
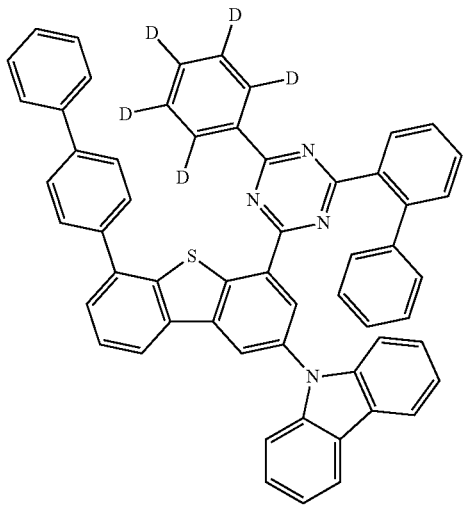
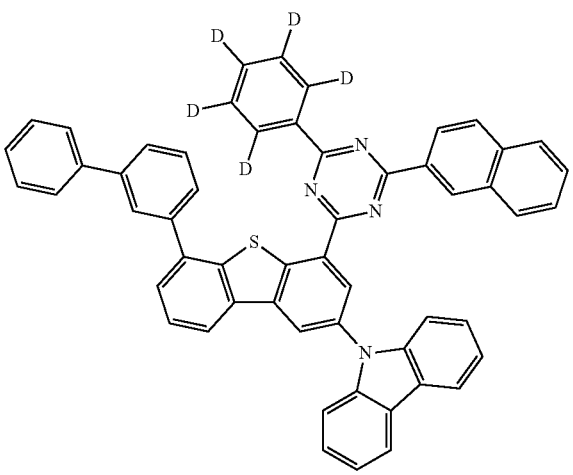

479
-continued
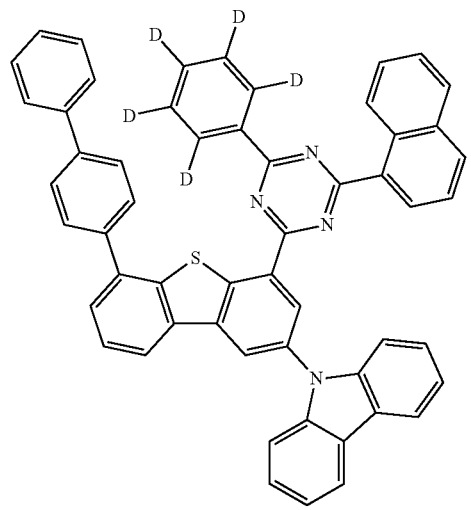
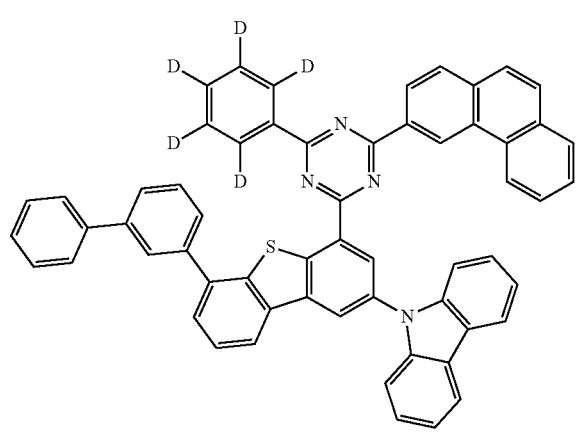
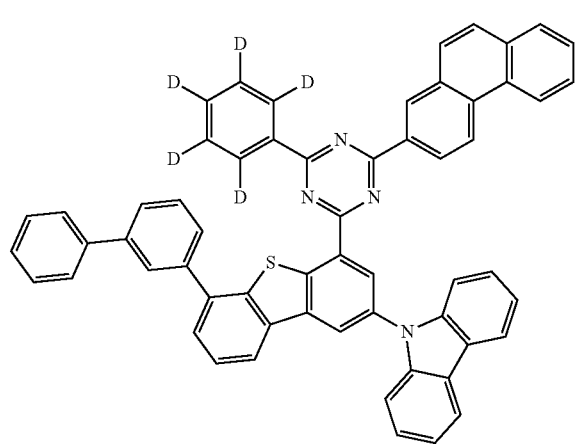
480
-continued
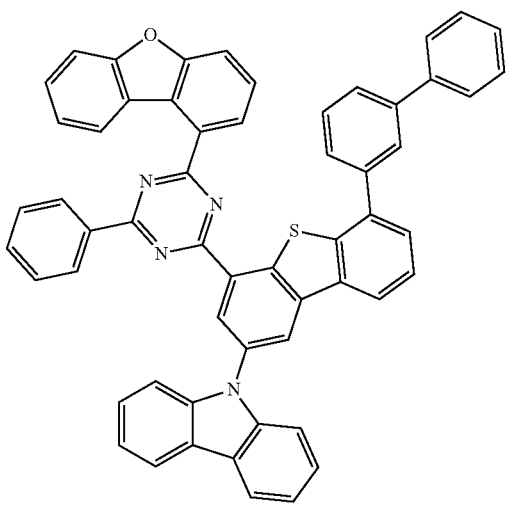
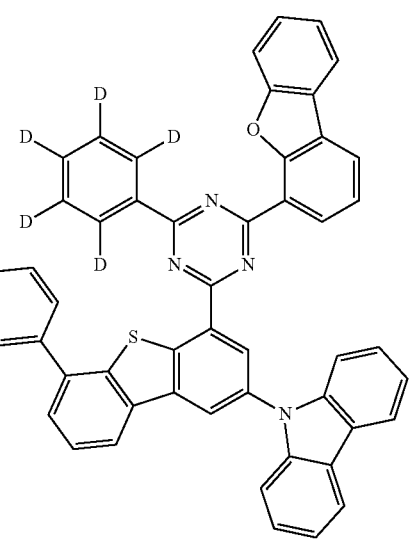
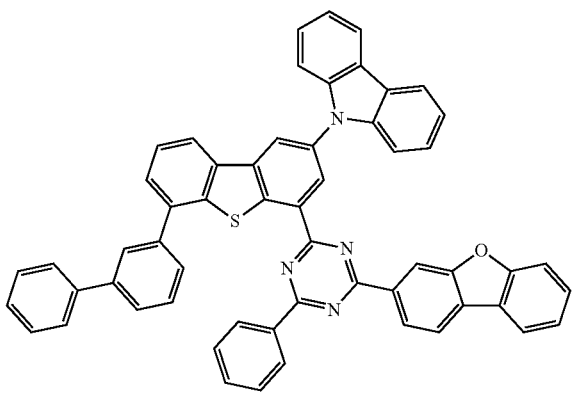

481
-continued
482
-continued
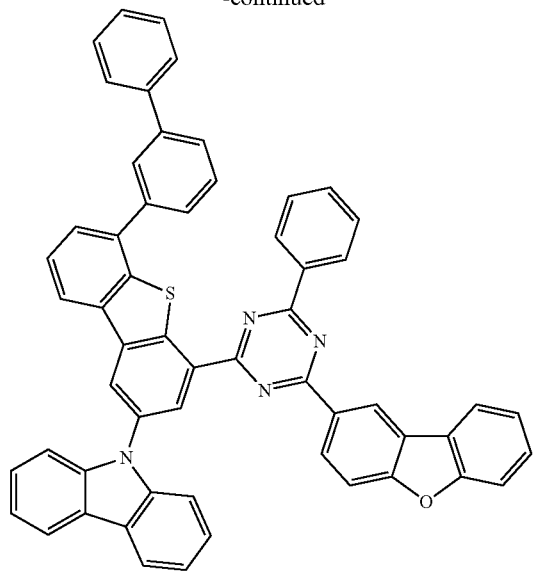
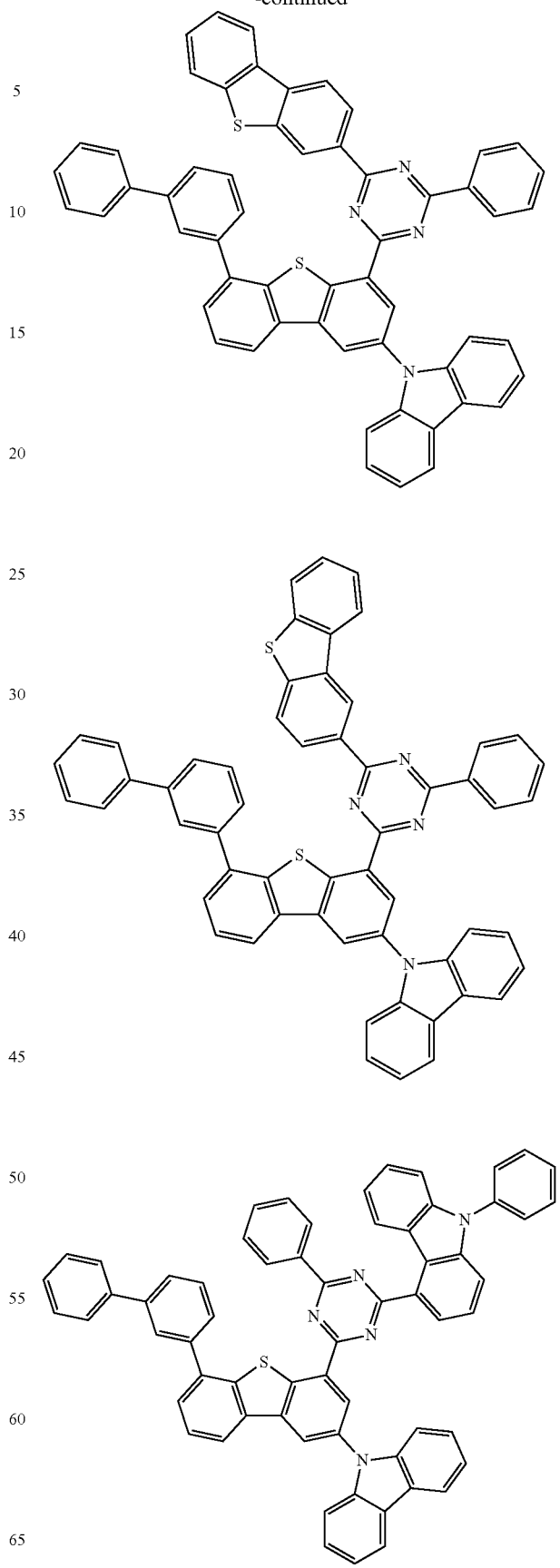

483
-continued
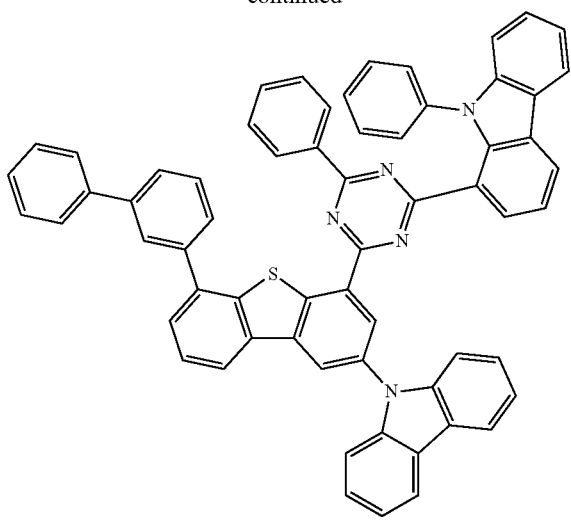
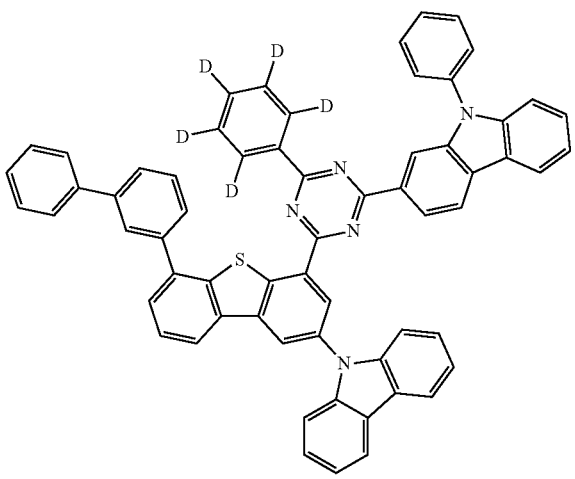
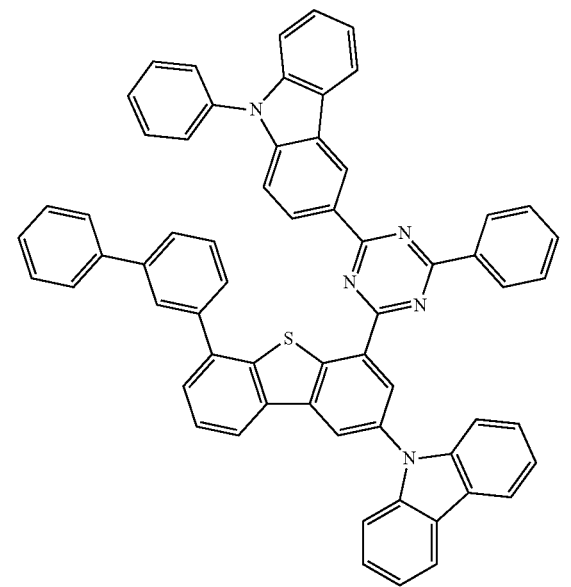
484
-continued
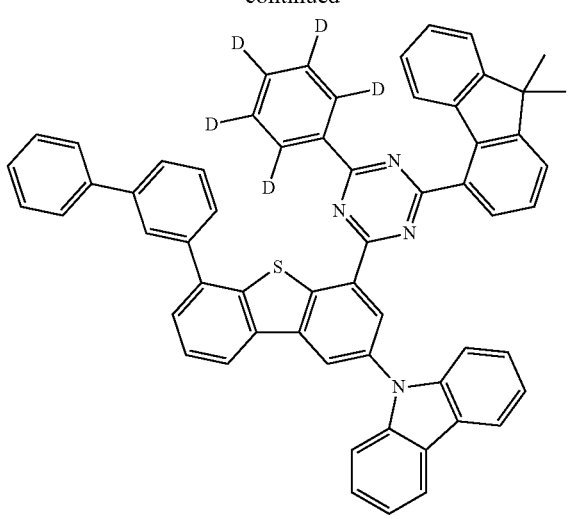
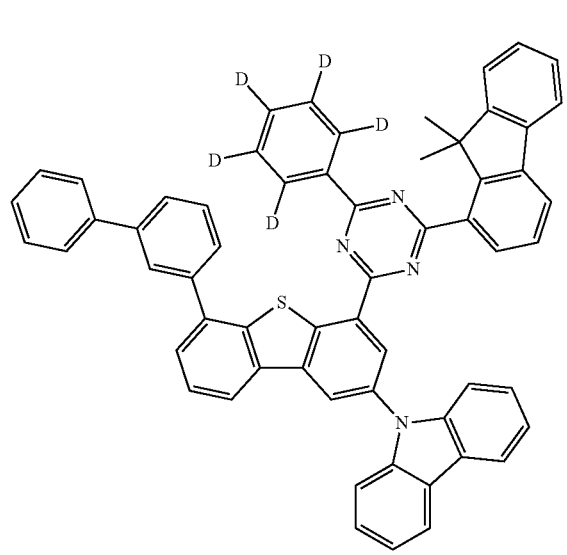
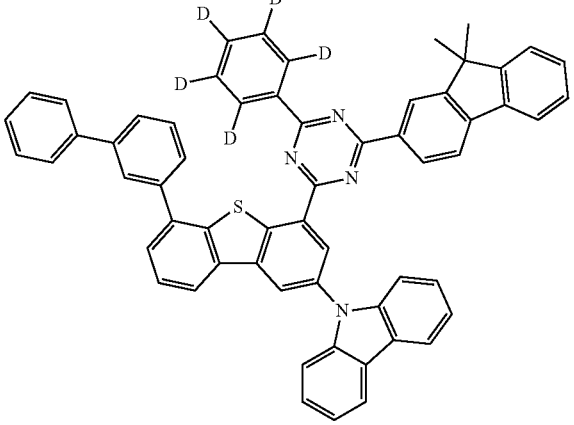

485
-continued
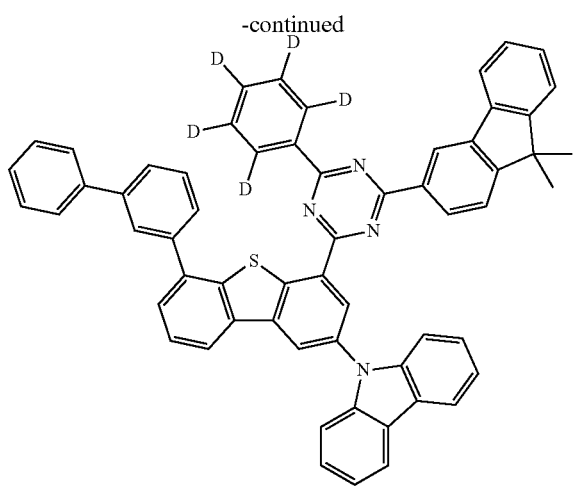
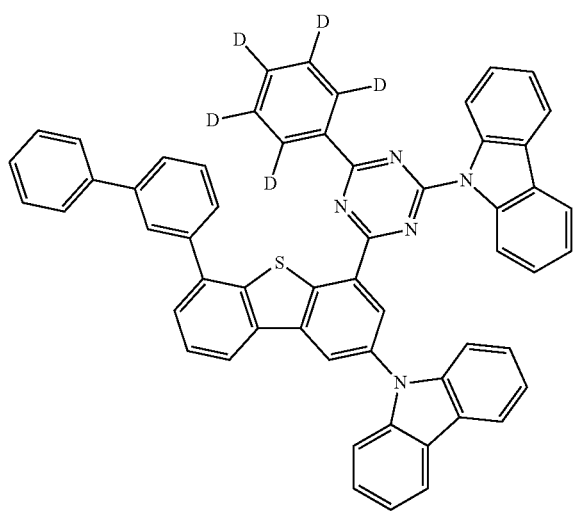
486
-continued
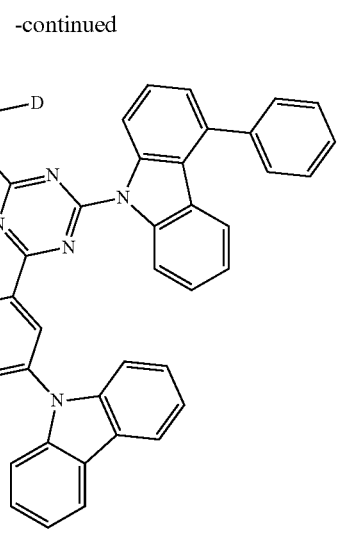
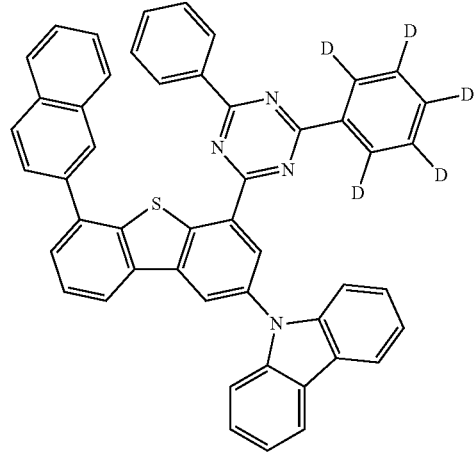
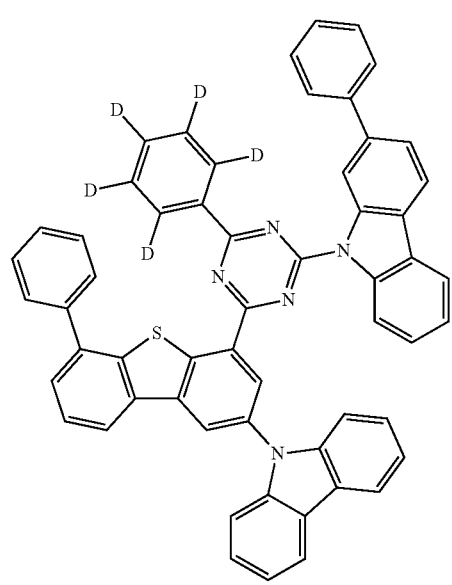
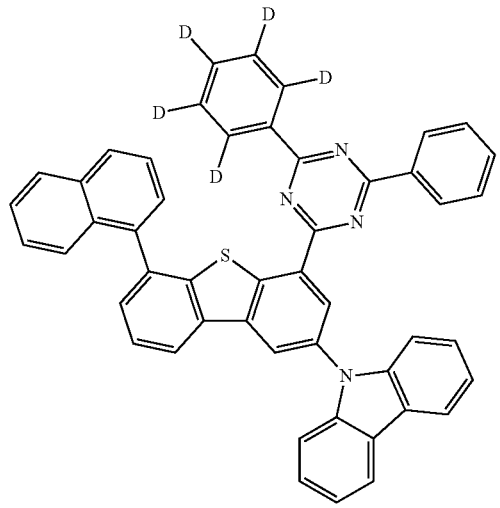

487
-continued
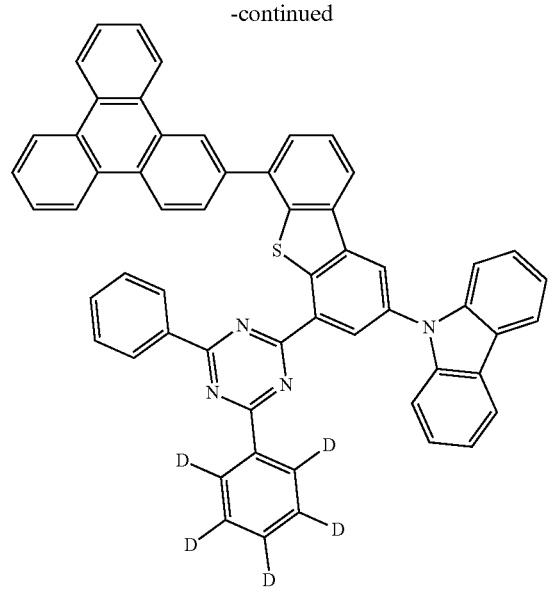
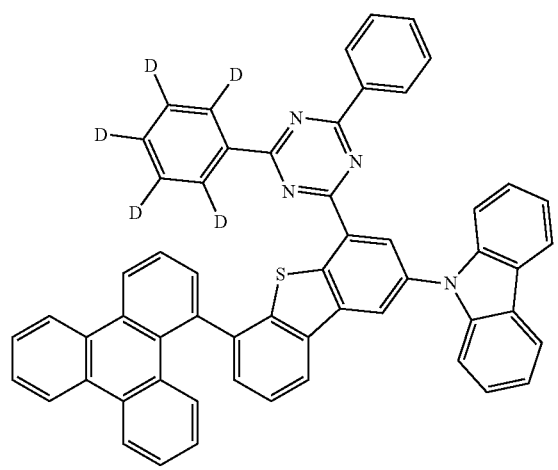
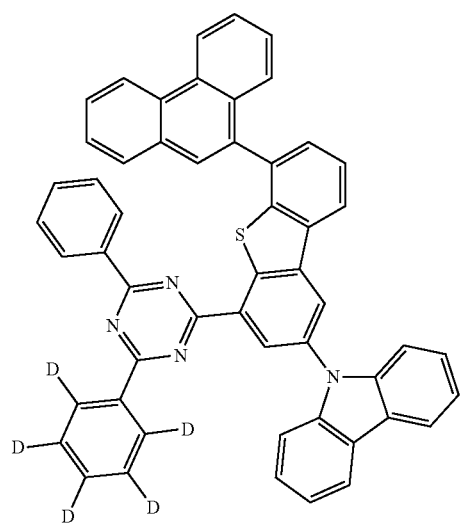
488
-continued
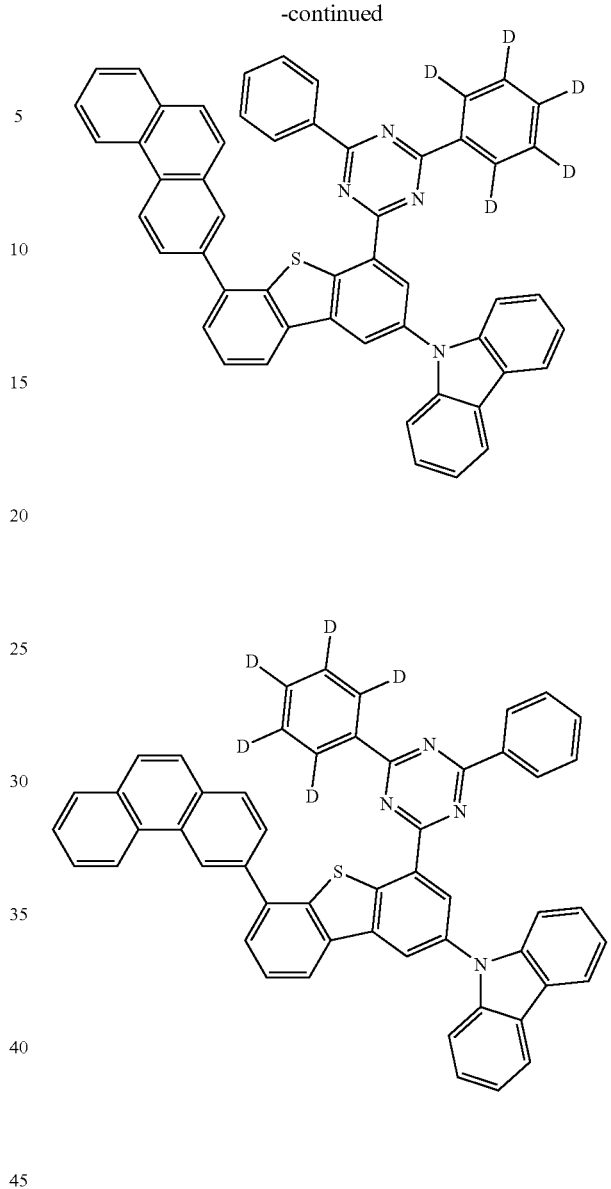
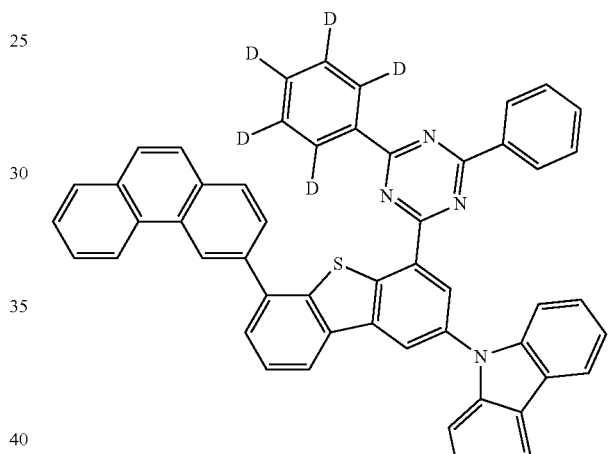
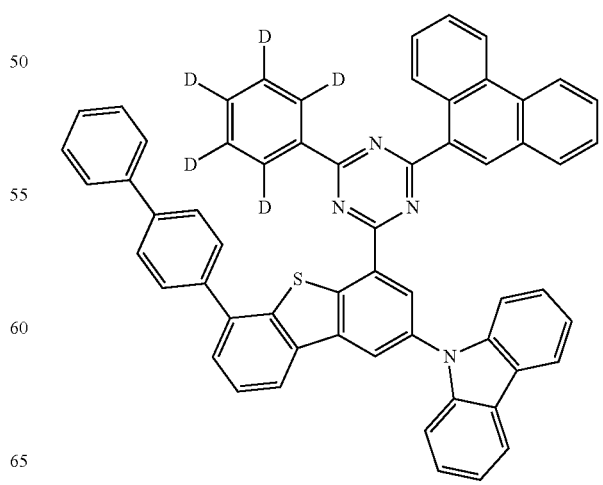

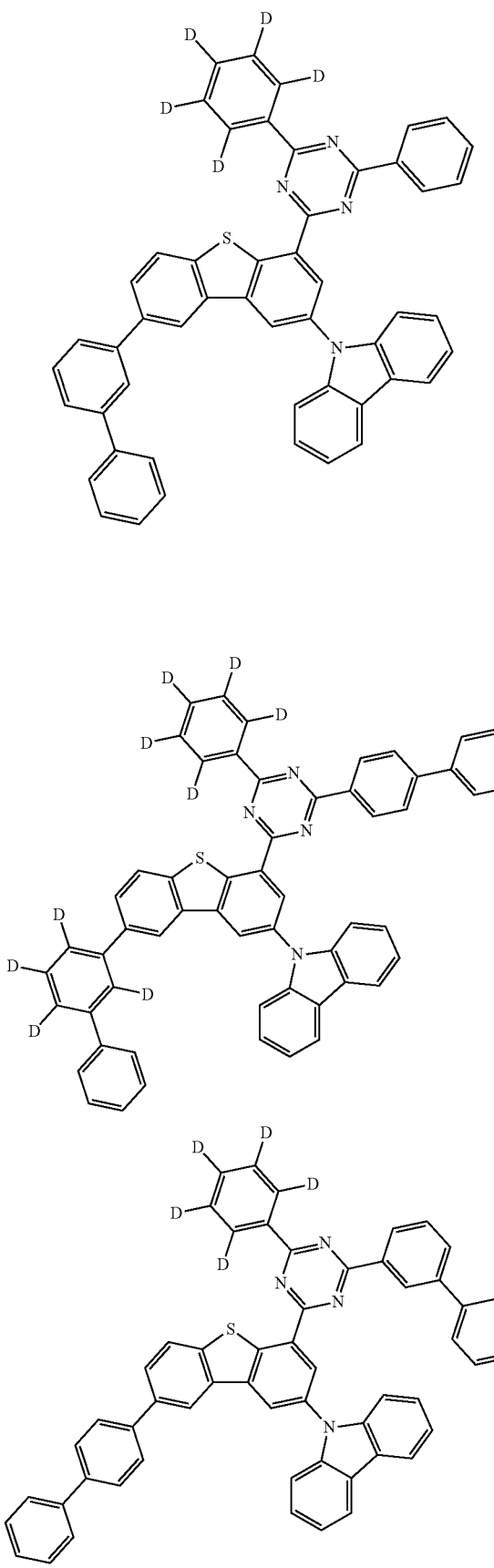

491
-continued
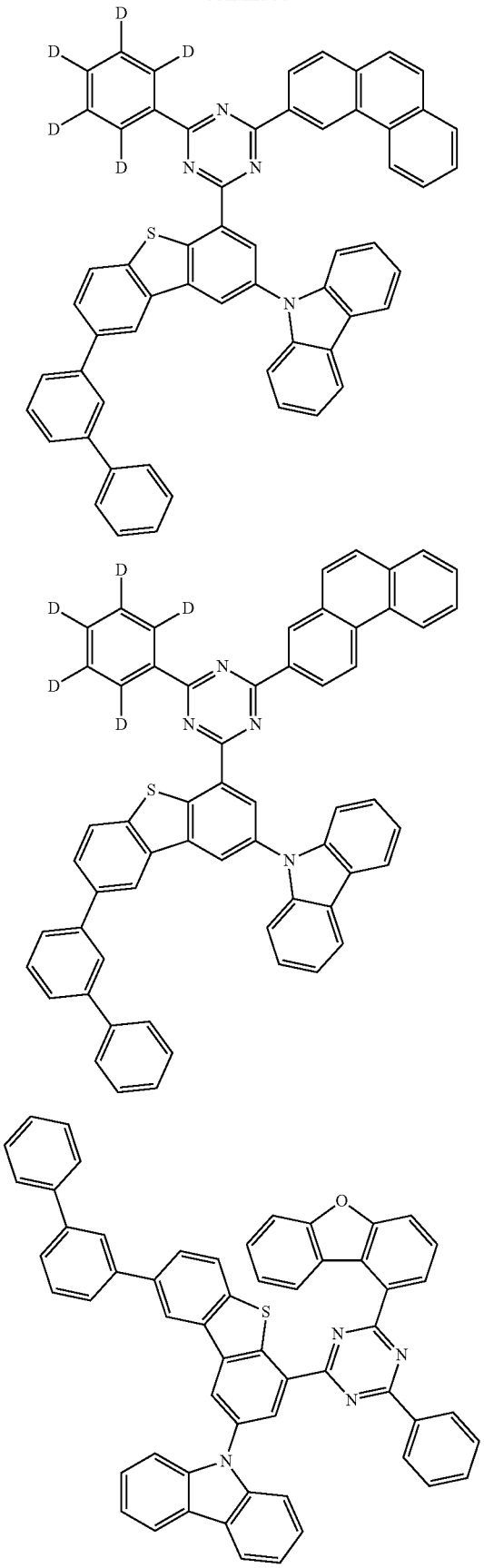
492
-continued
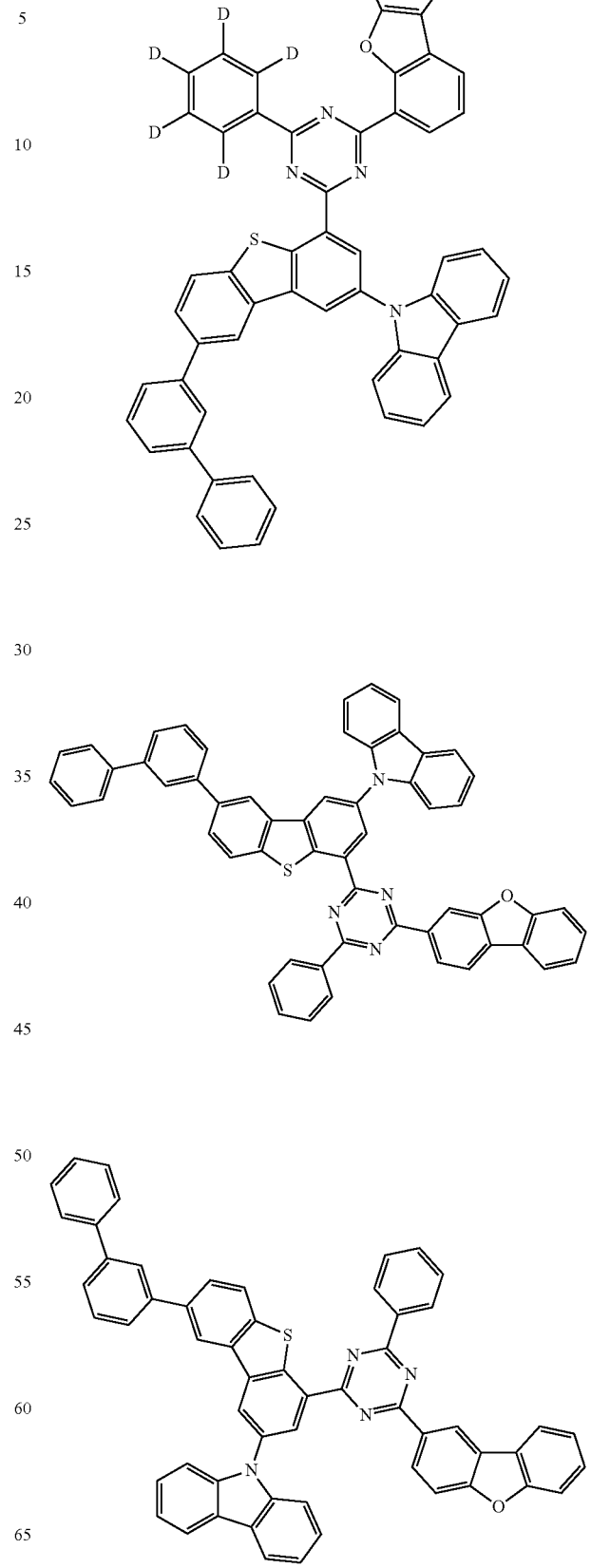

493
-continued
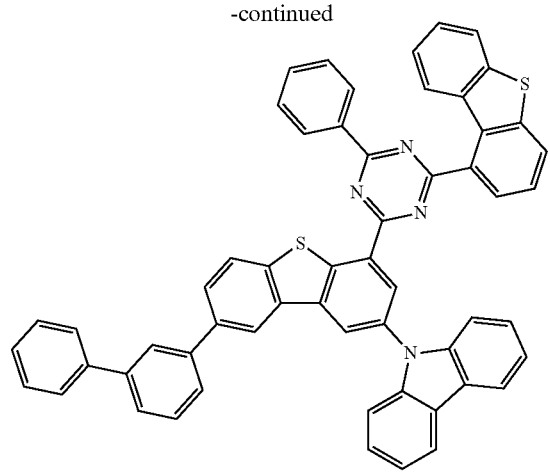
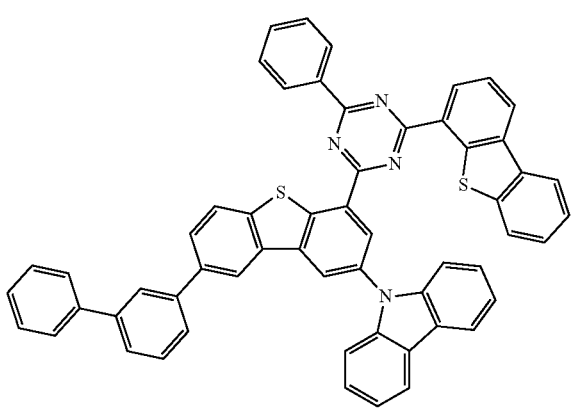
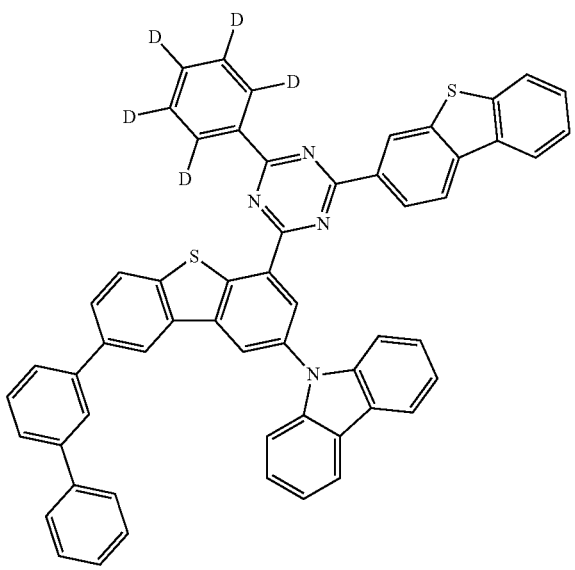
494
-continued
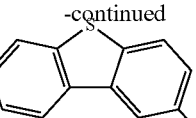
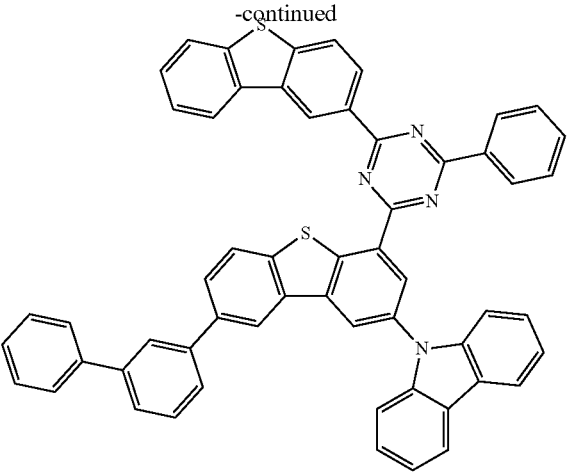
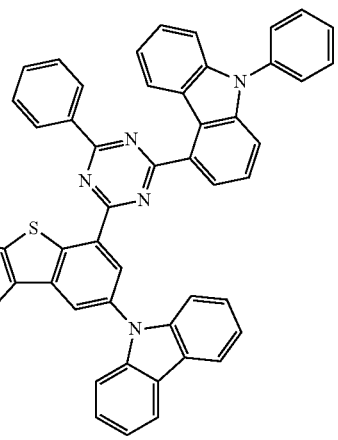
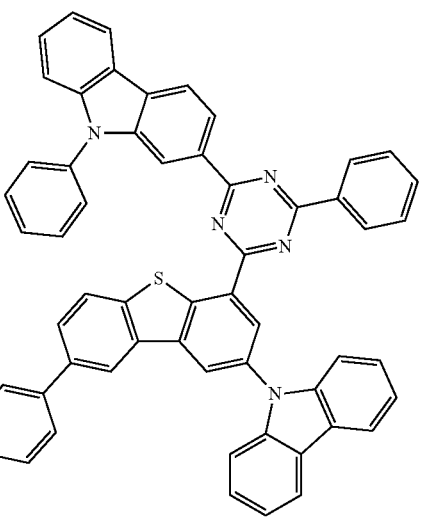

495
-continued
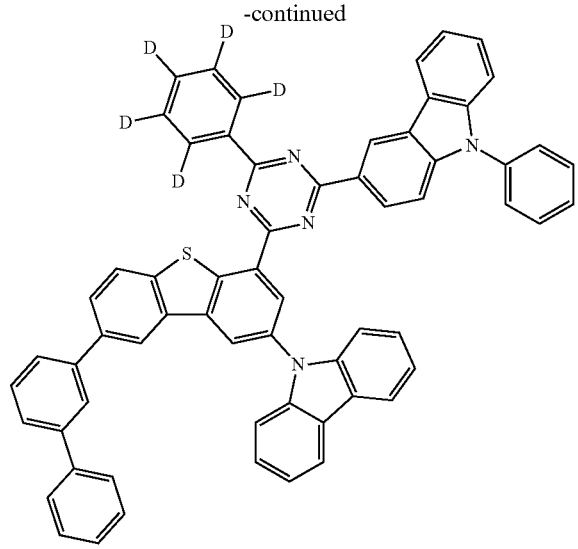
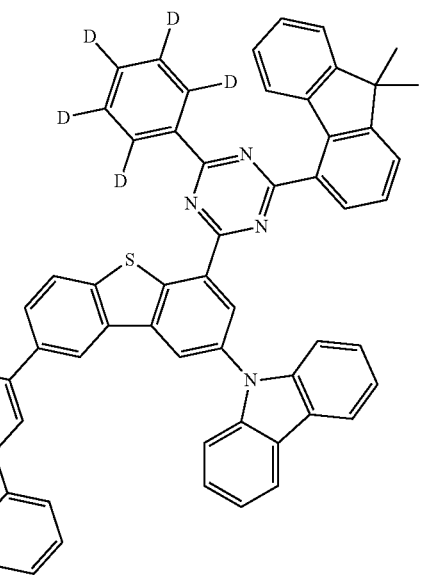
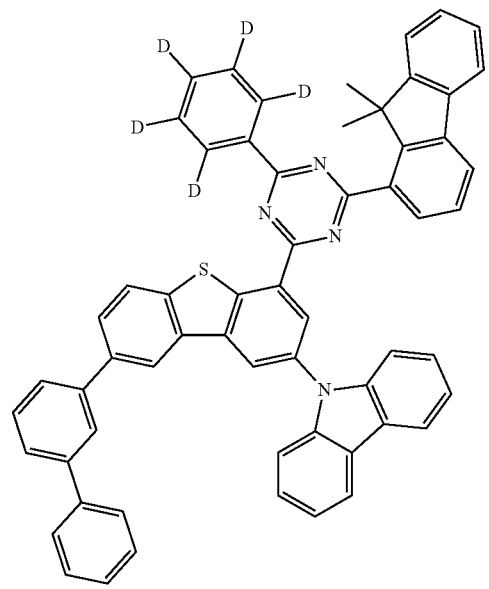
496
-continued
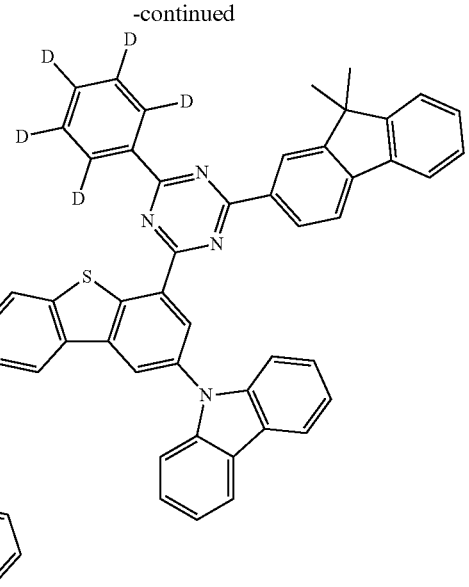
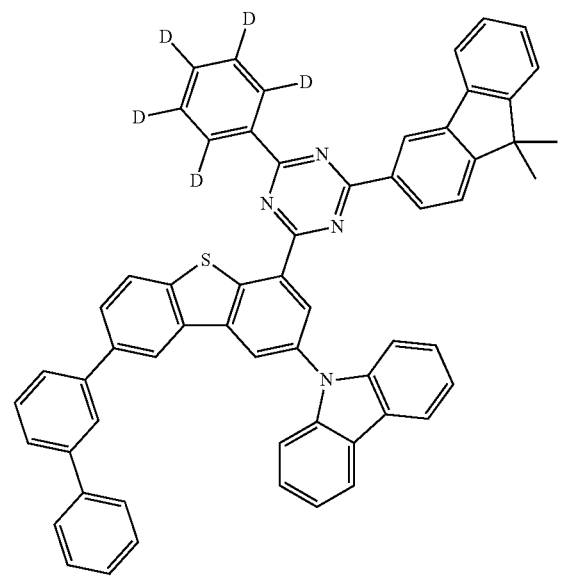
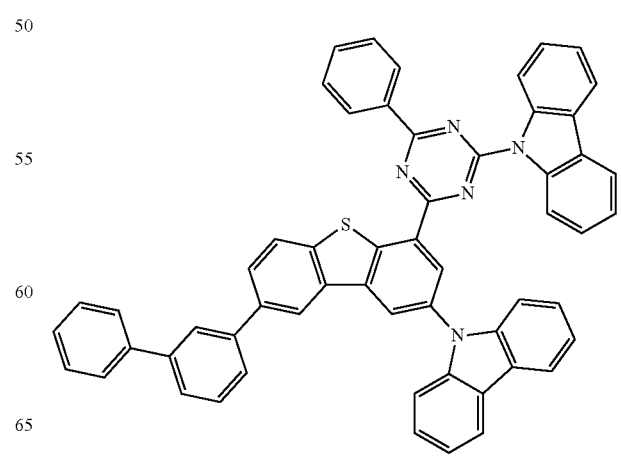

497
-continued
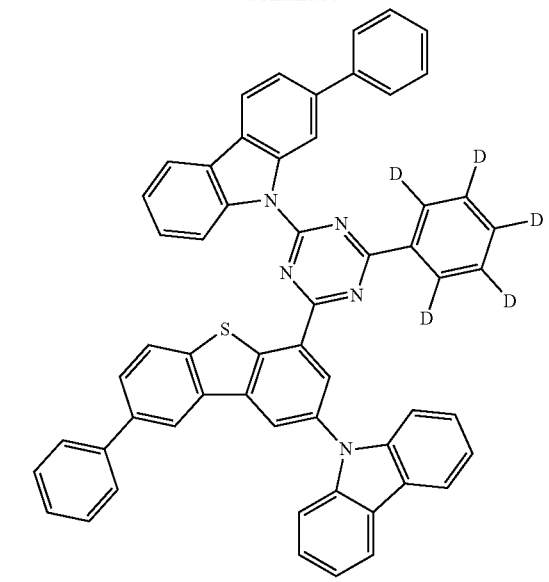
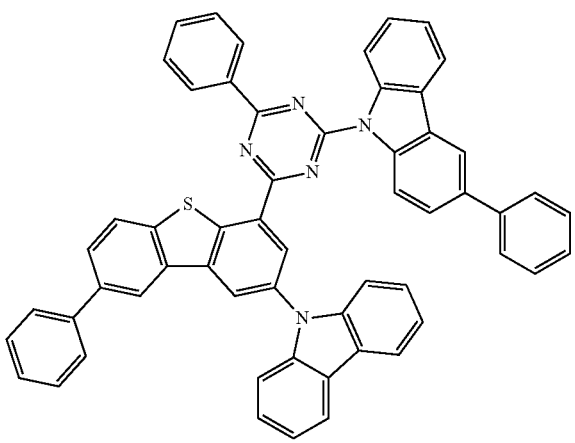
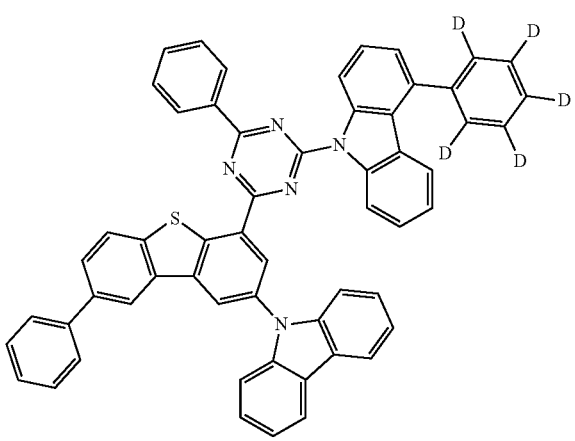
498
-continued
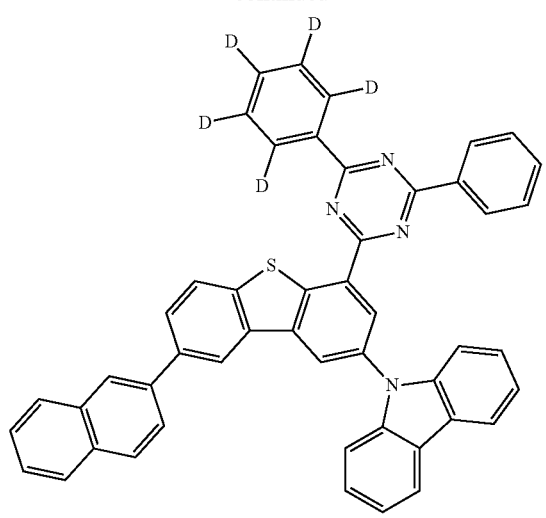
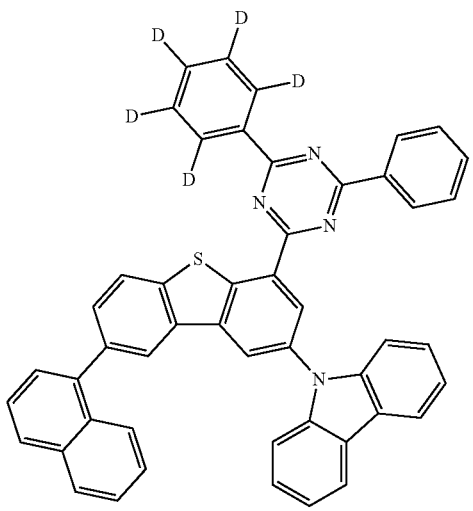
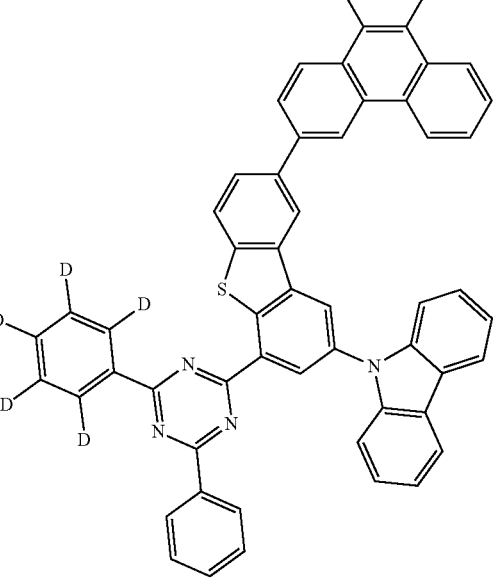

499
-continued
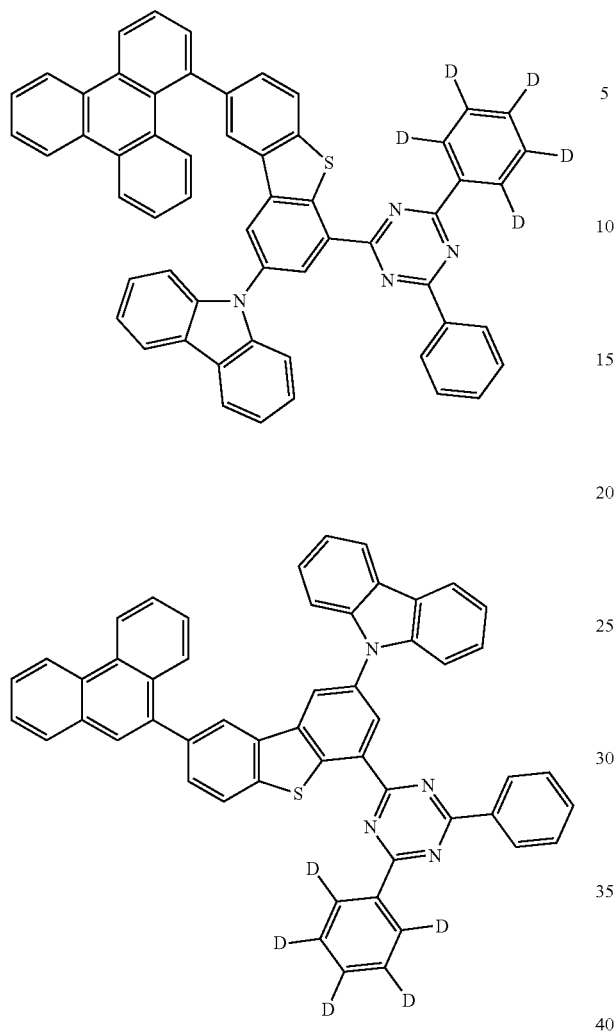
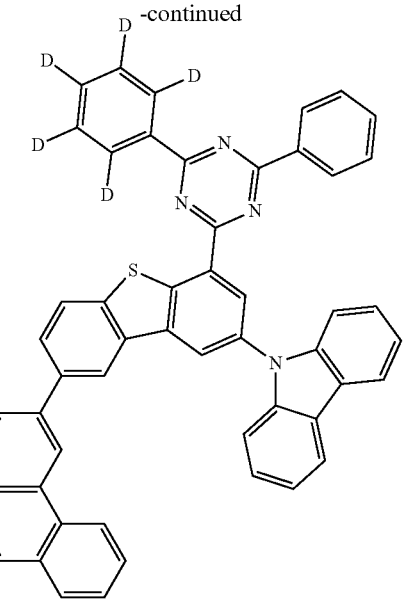
500
-continued
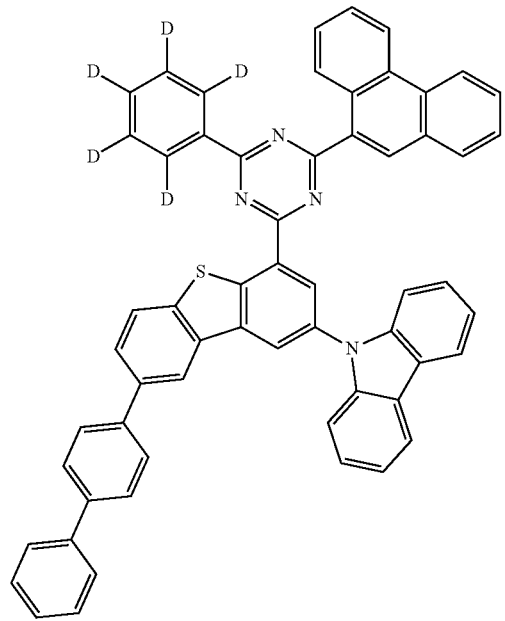
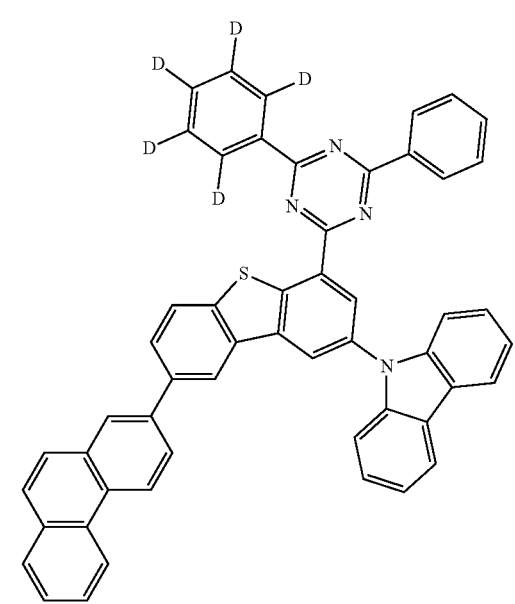

501
-continued
502
-continued
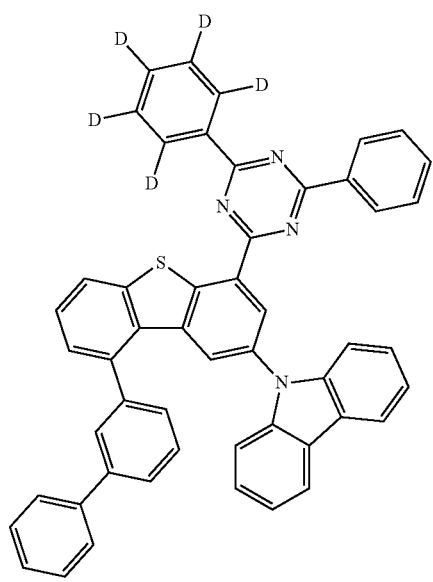
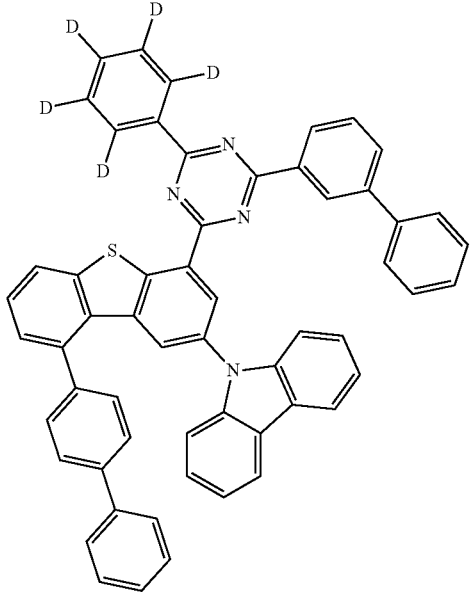
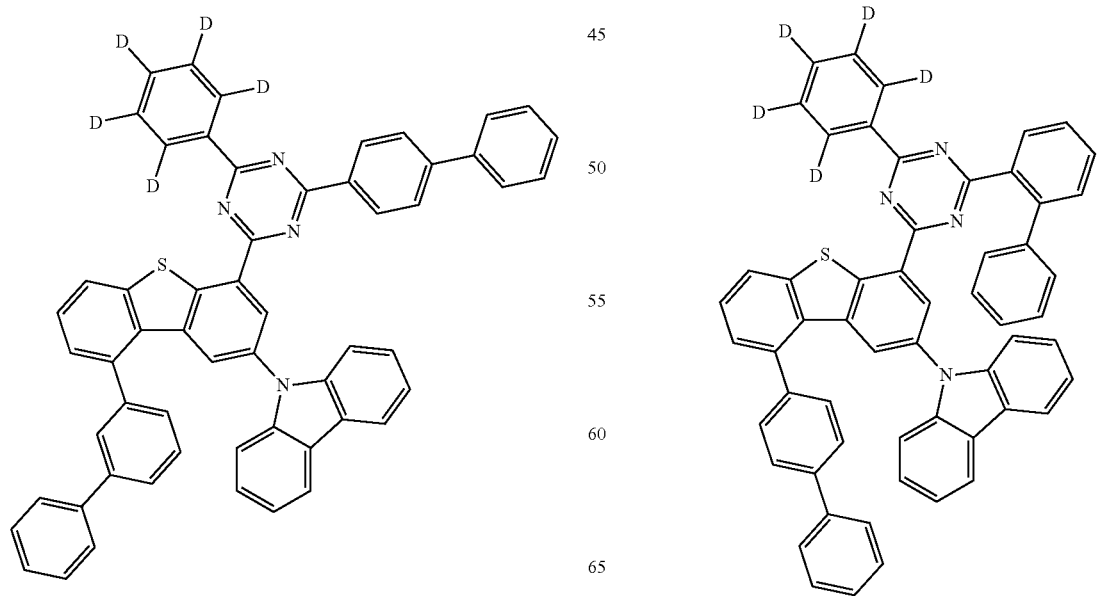

503
-continued
504
-continued
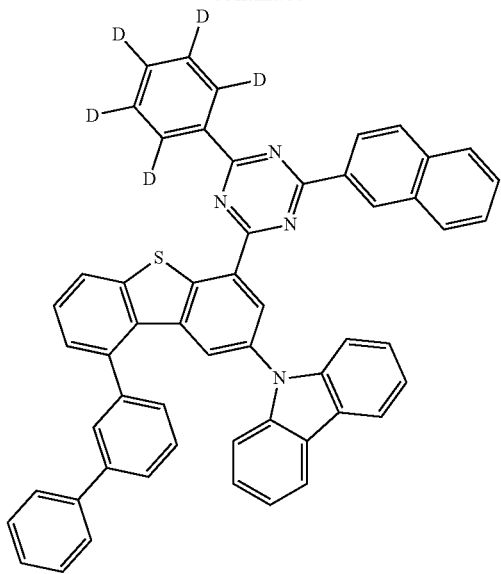
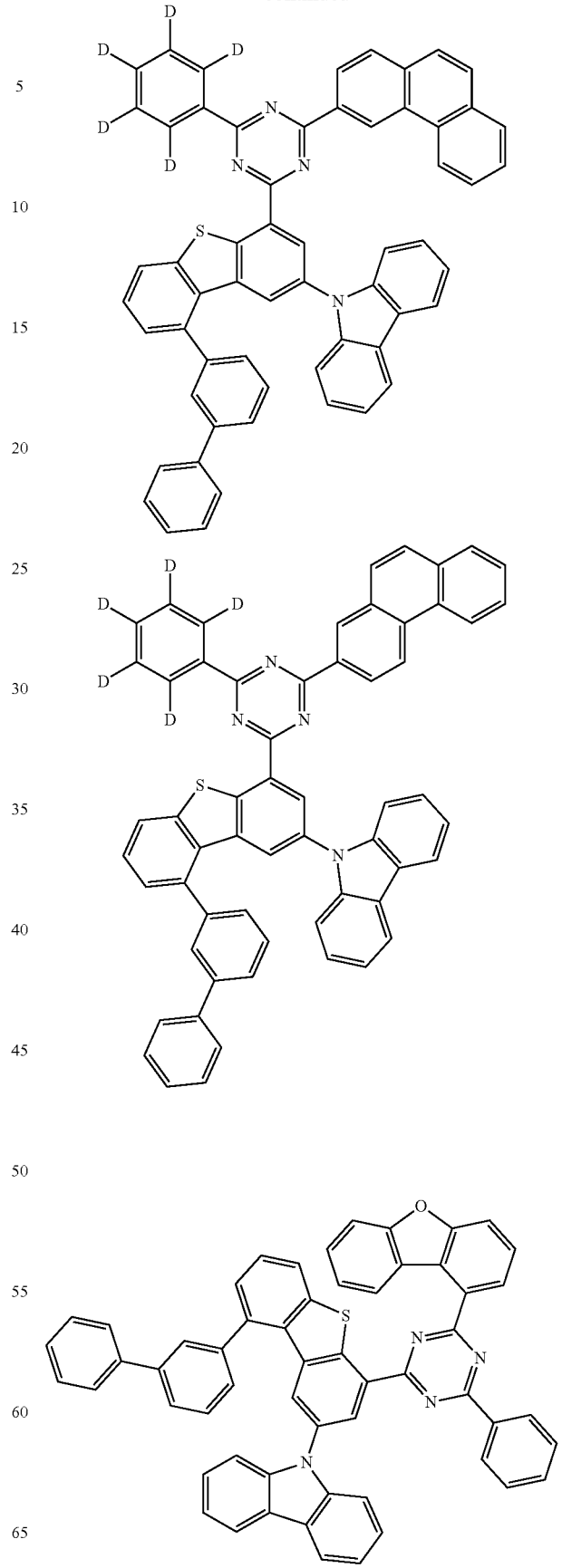

505
-continued
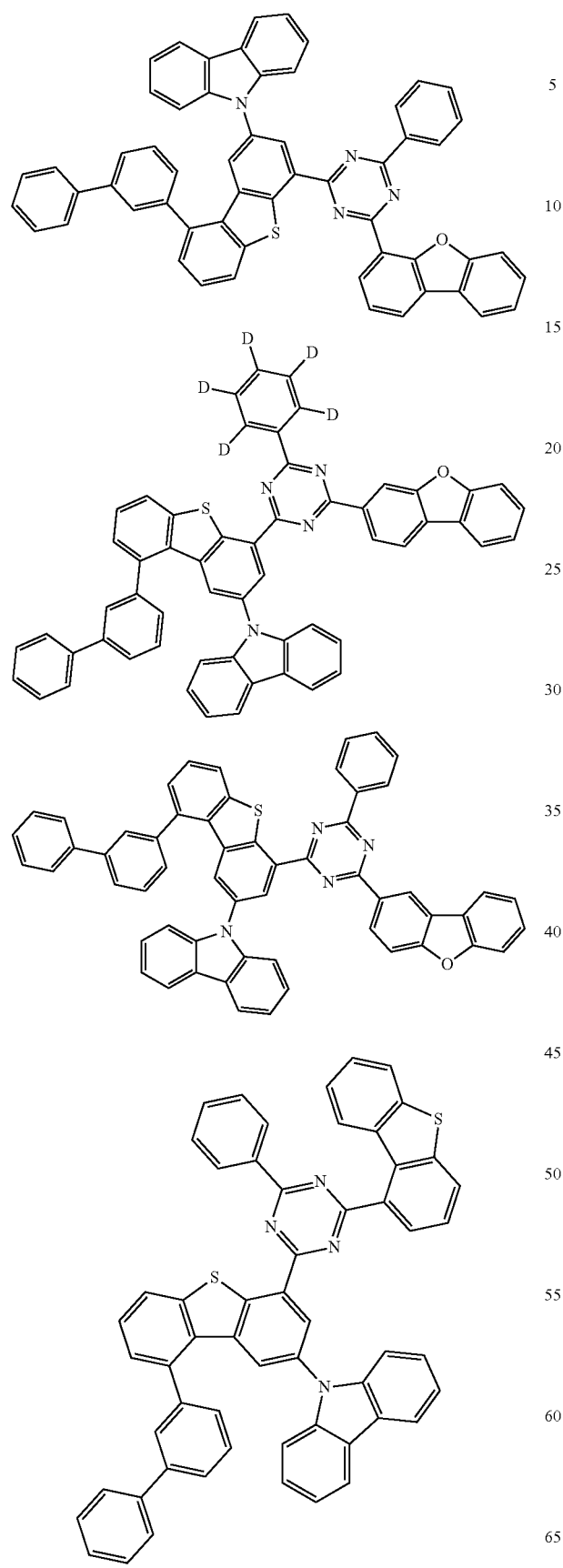
506
-continued
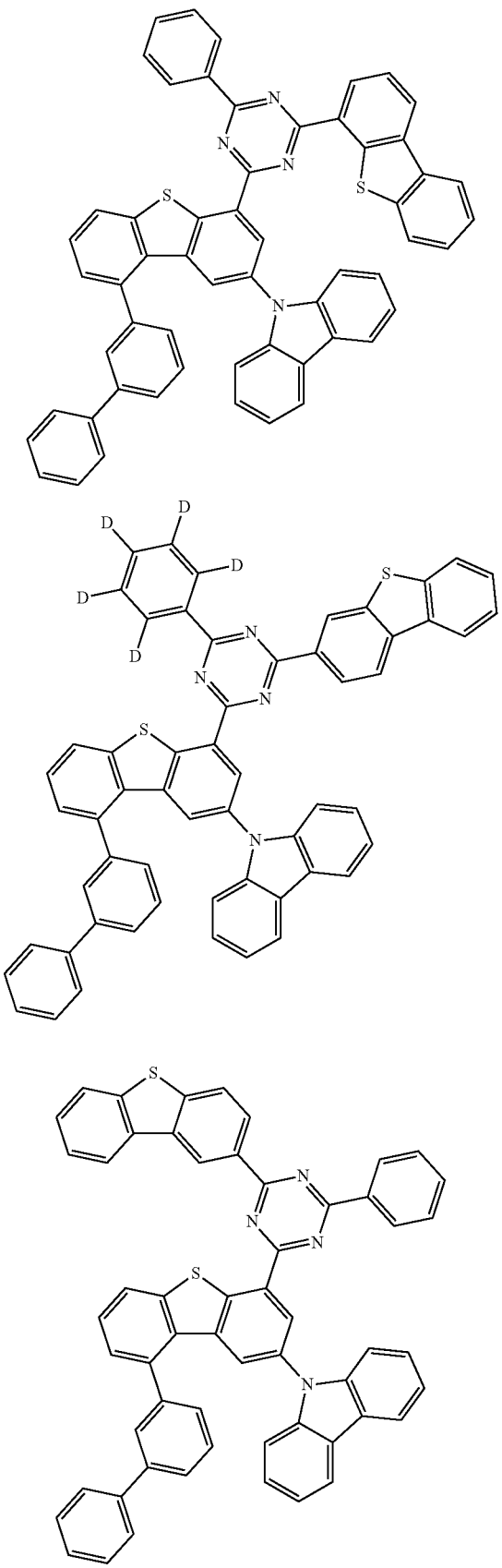

507
-continued
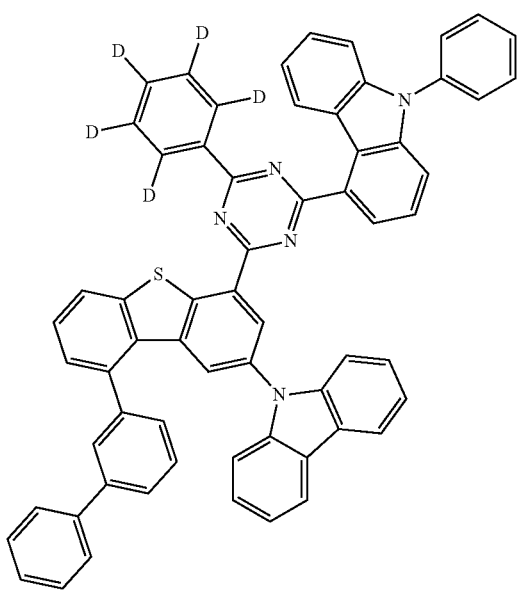
508
-continued
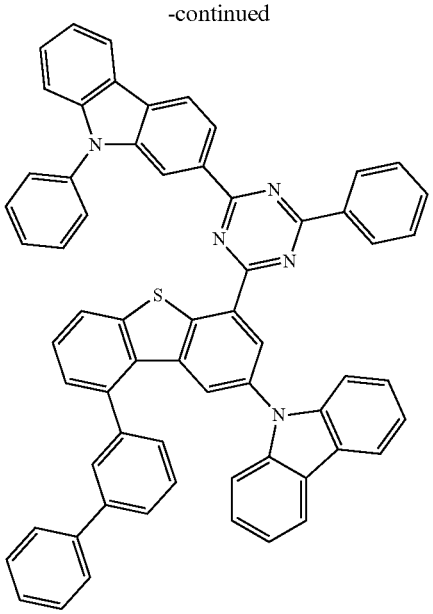
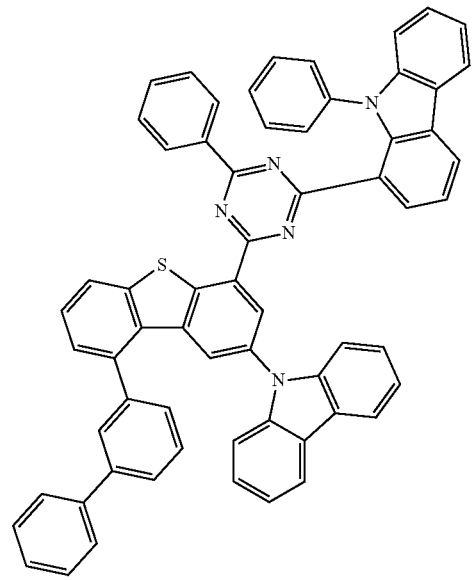
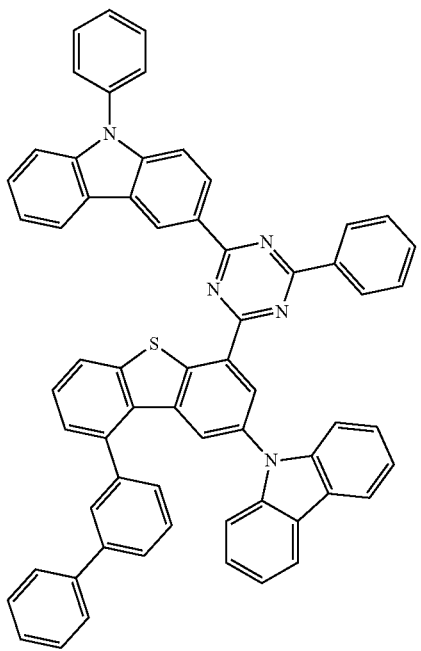

509
-continued
510
-continued
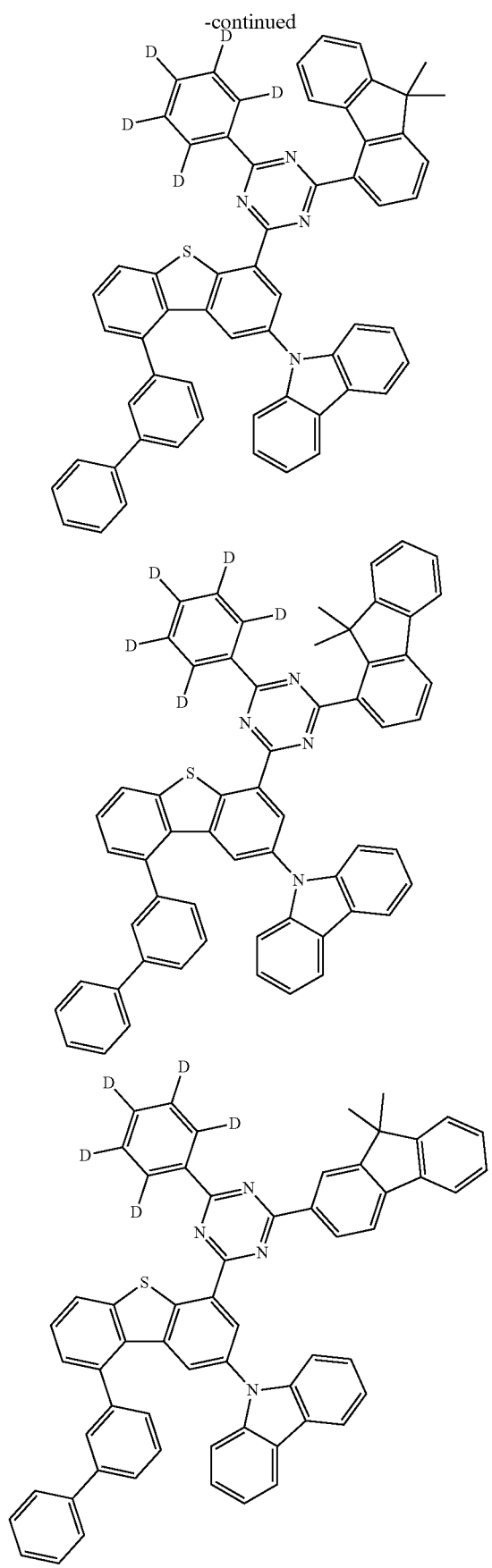
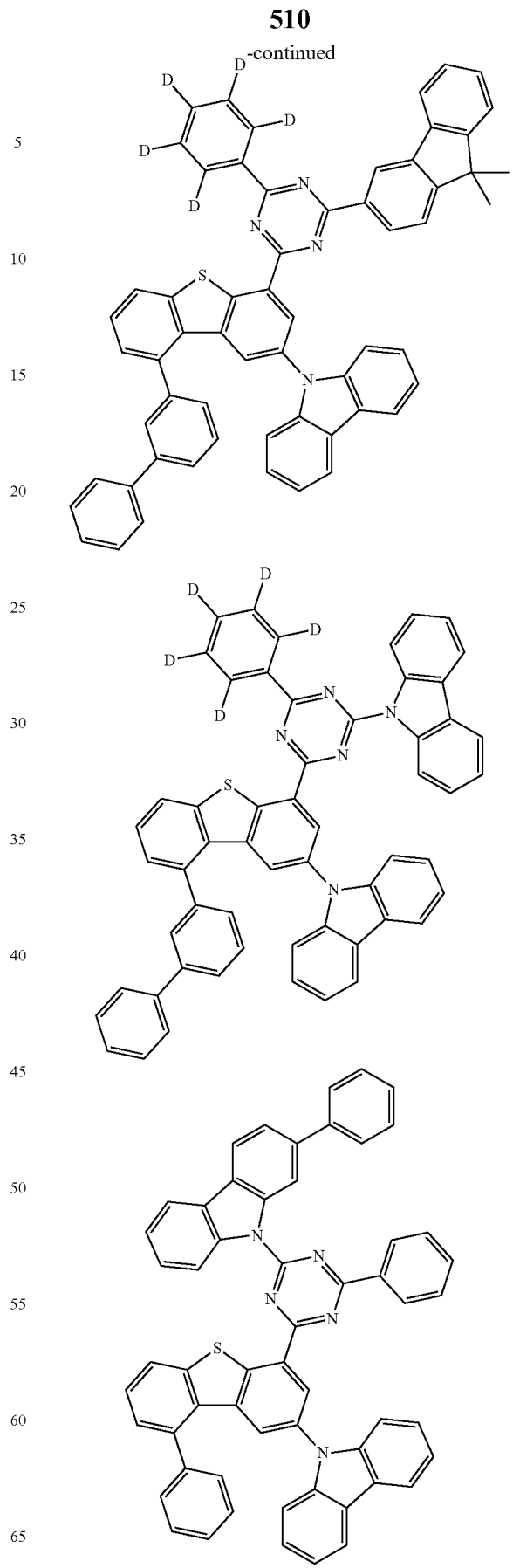

511
-continued
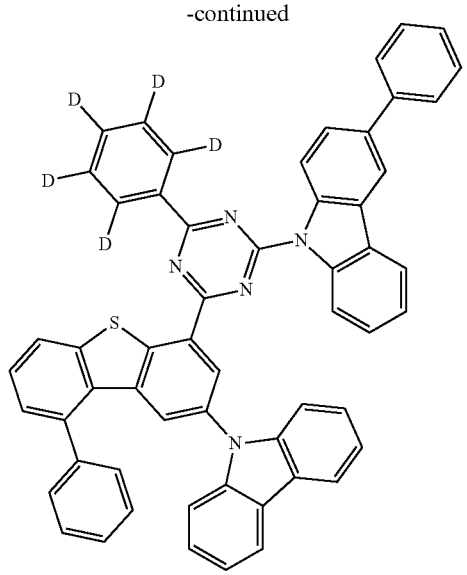
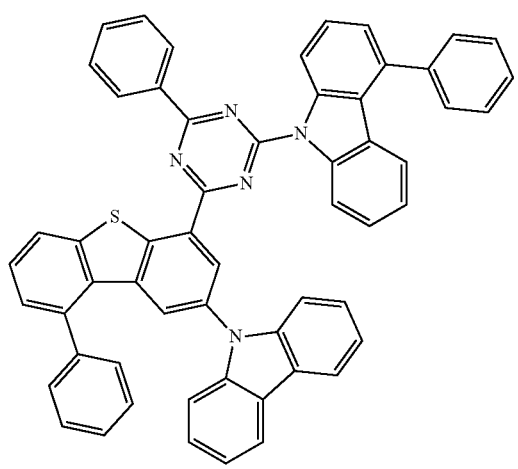
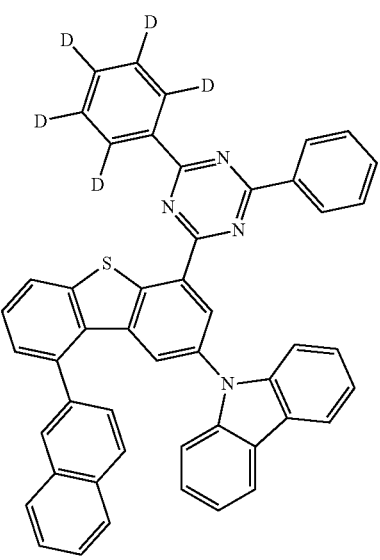
512
-continued
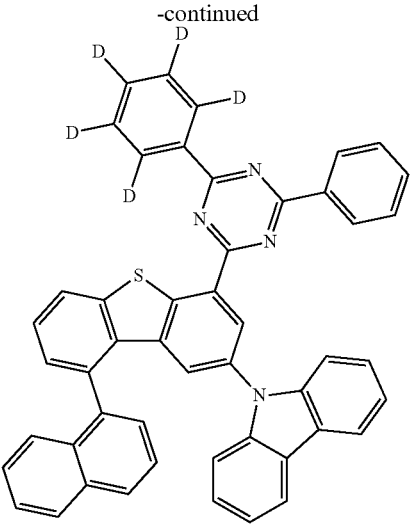
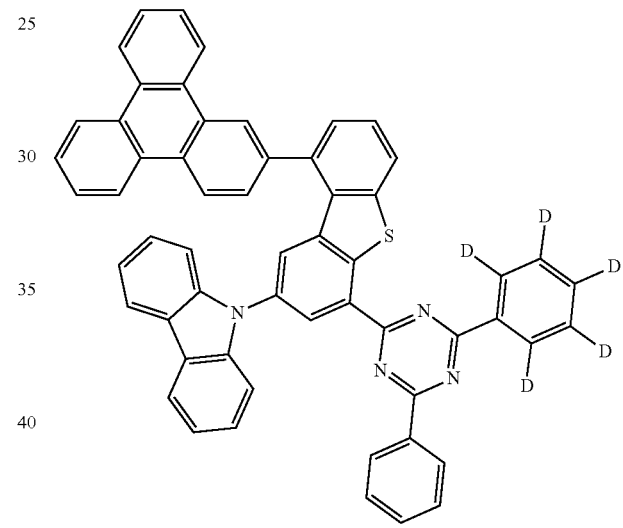
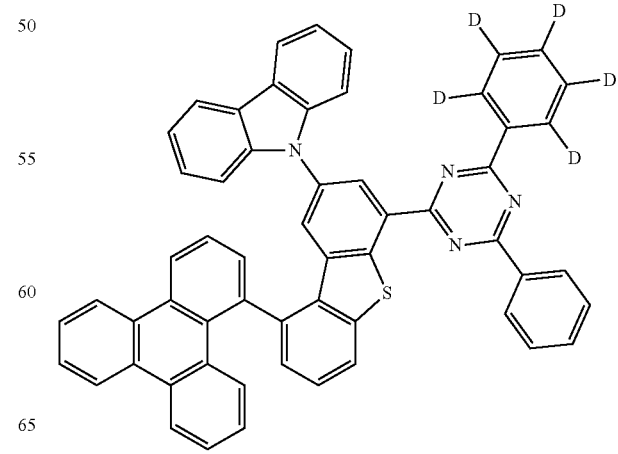

513
-continued
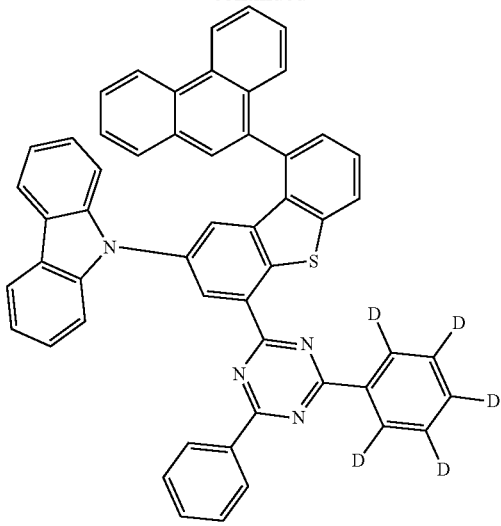
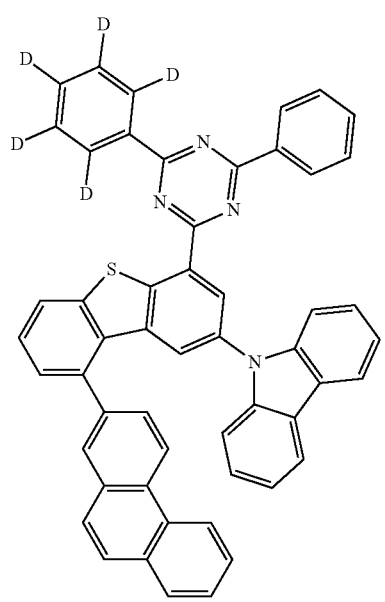
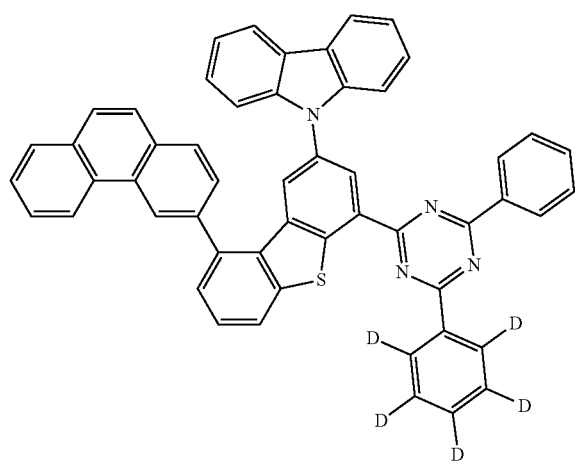
514
-continued
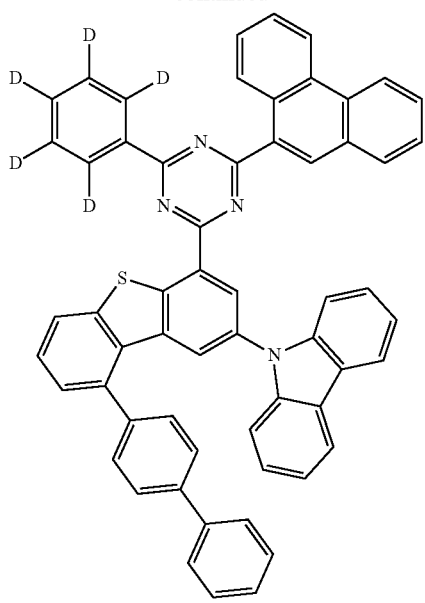
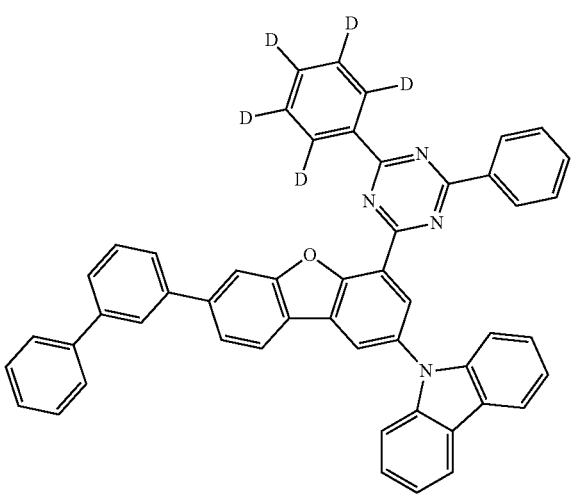
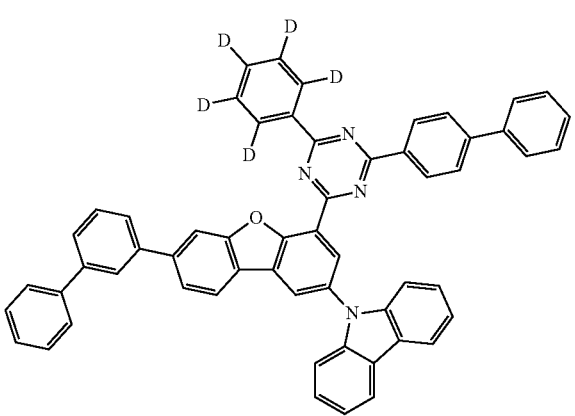

515
-continued
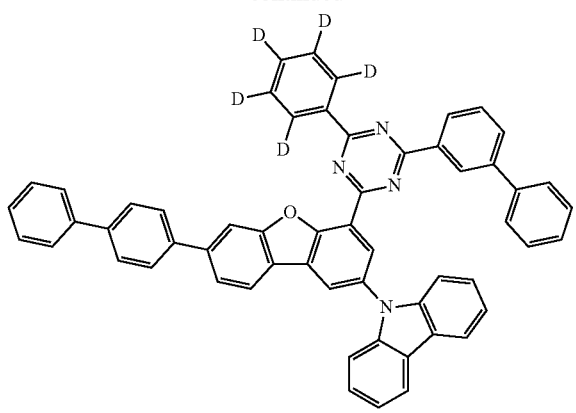
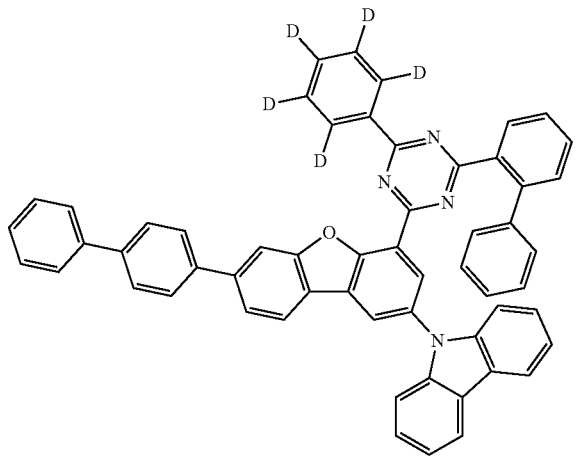
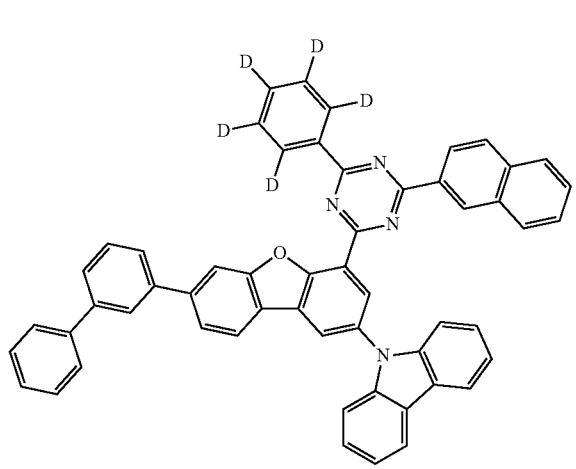
516
-continued
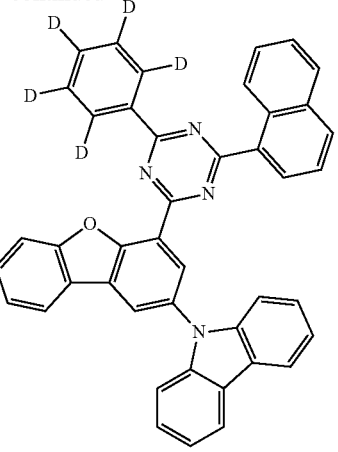
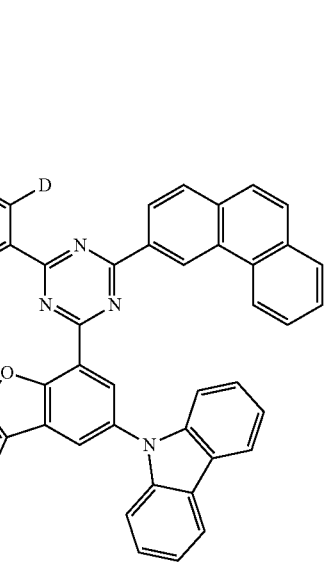
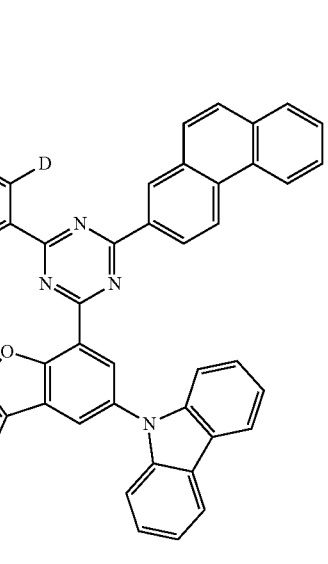

517
-continued
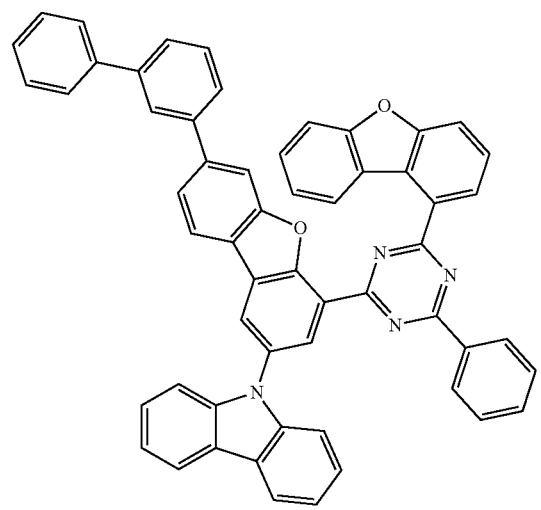
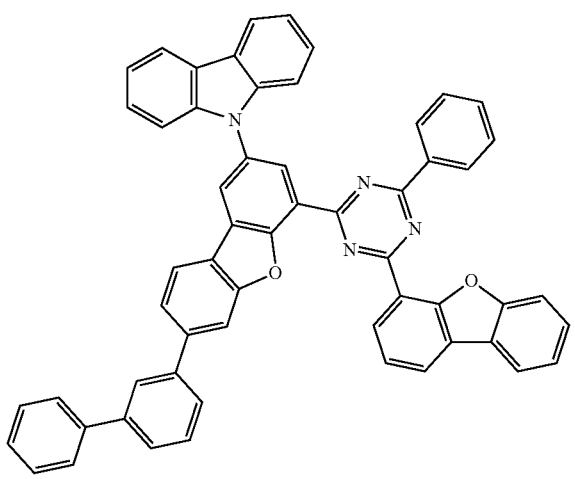
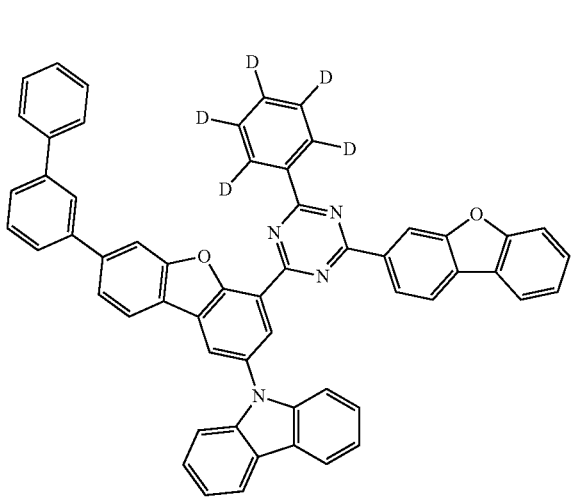
518
-continued
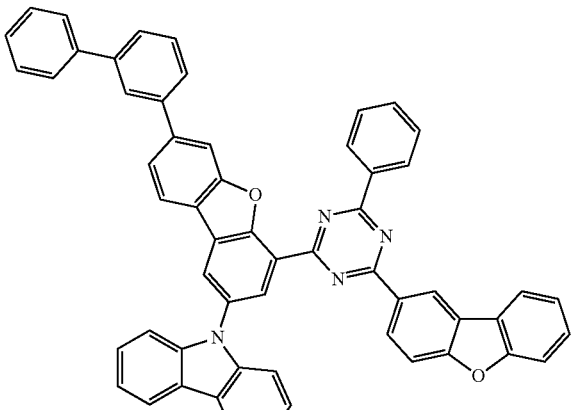
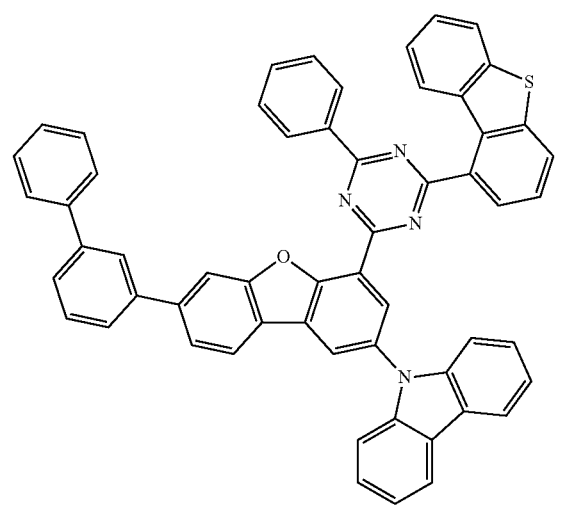
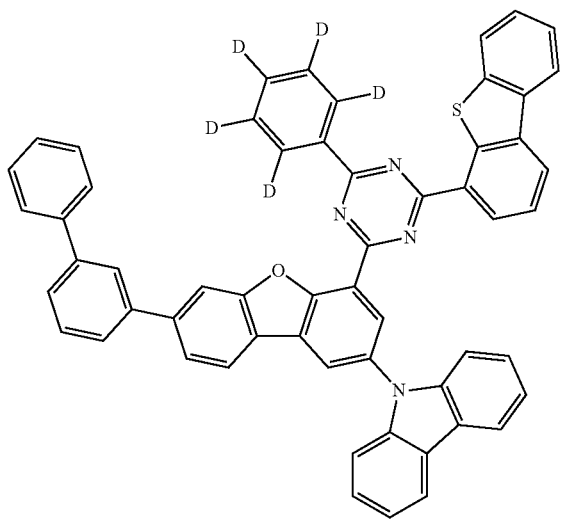

519
-continued
520
-continued
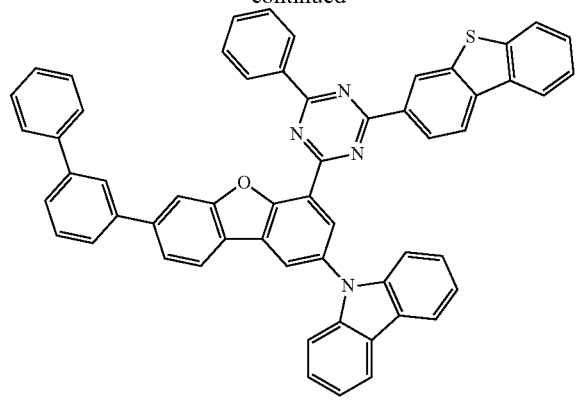
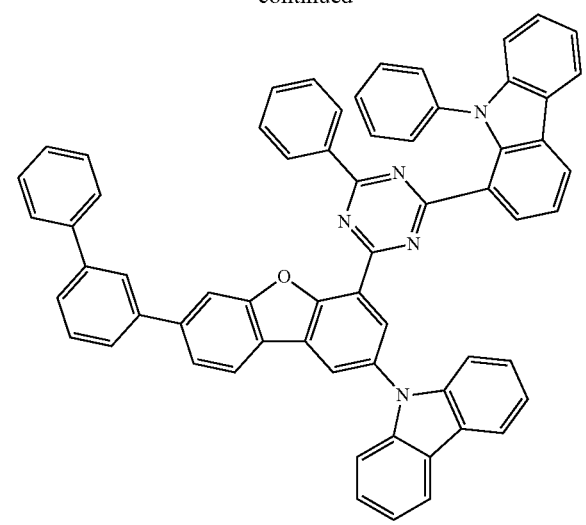
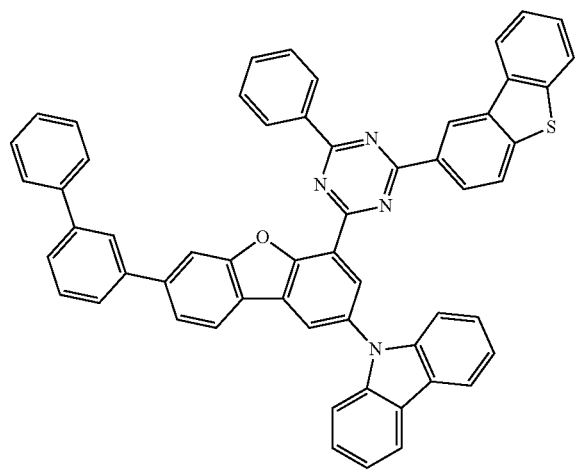
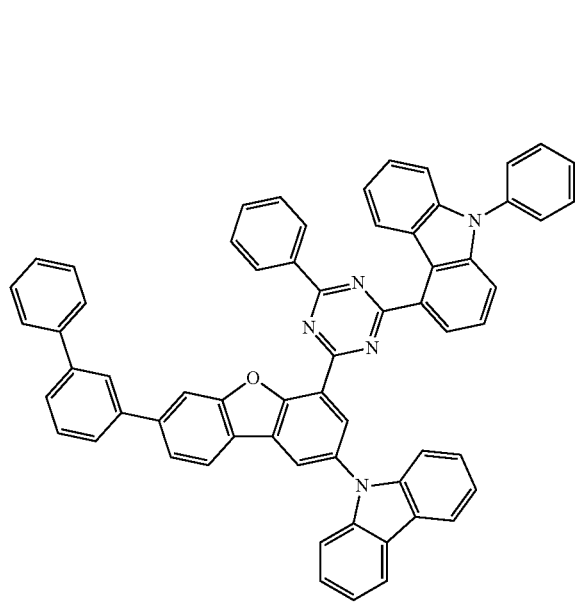

521
-continued
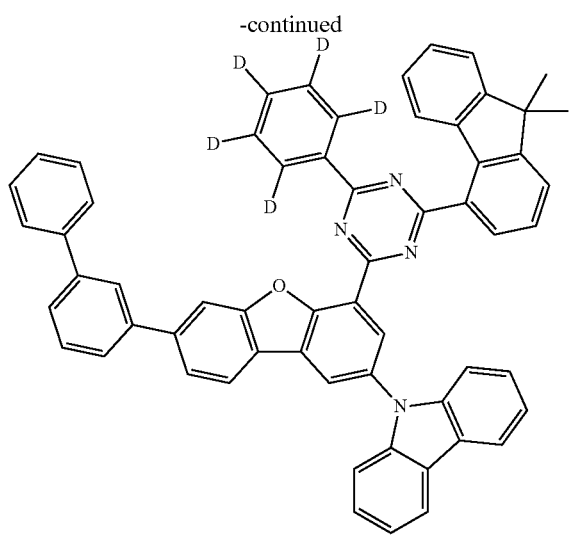
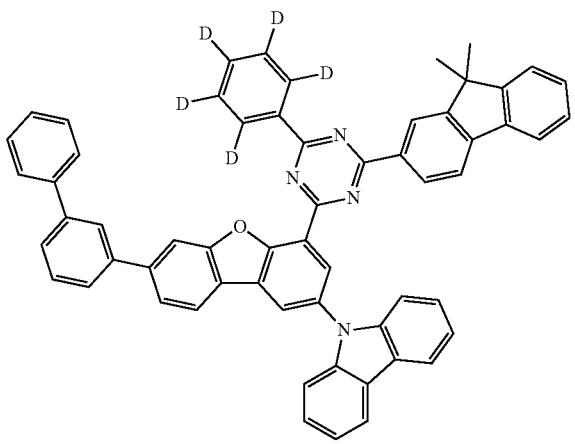
522
-continued
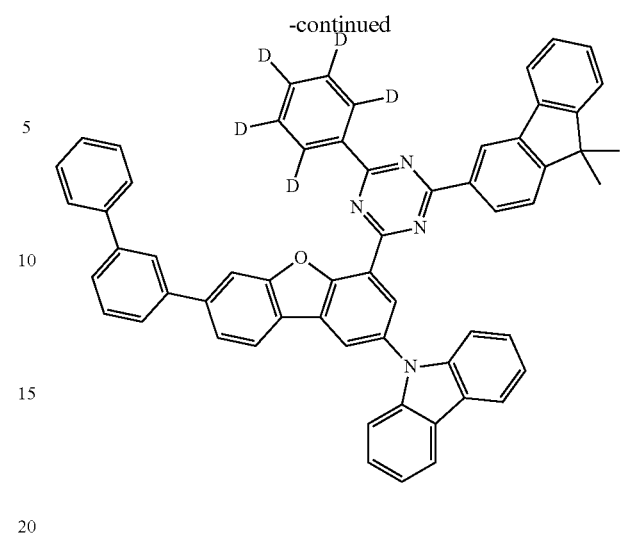
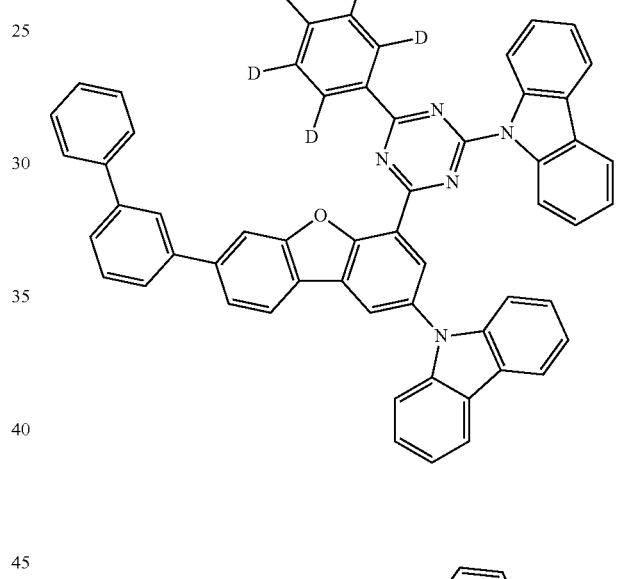
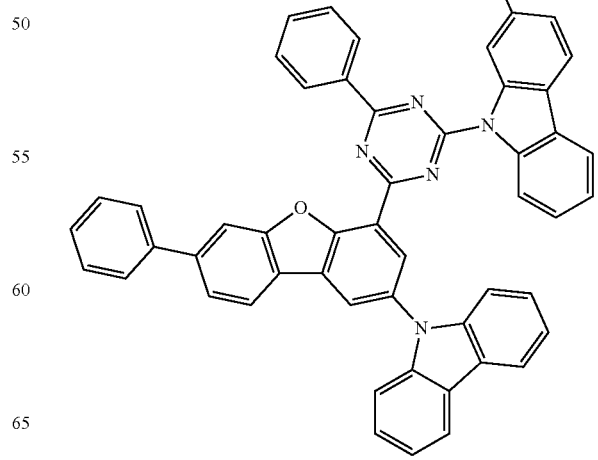

523
-continued
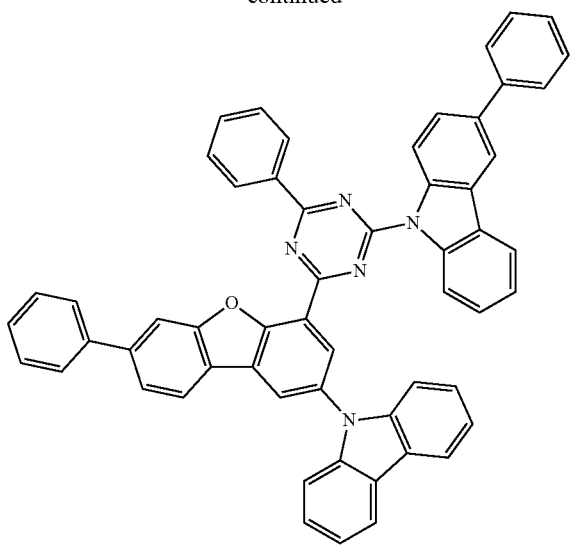
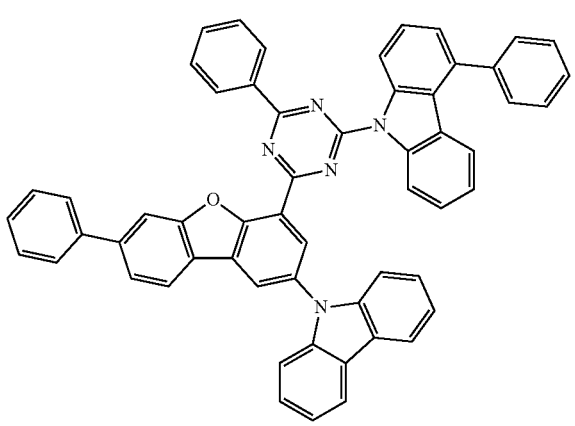
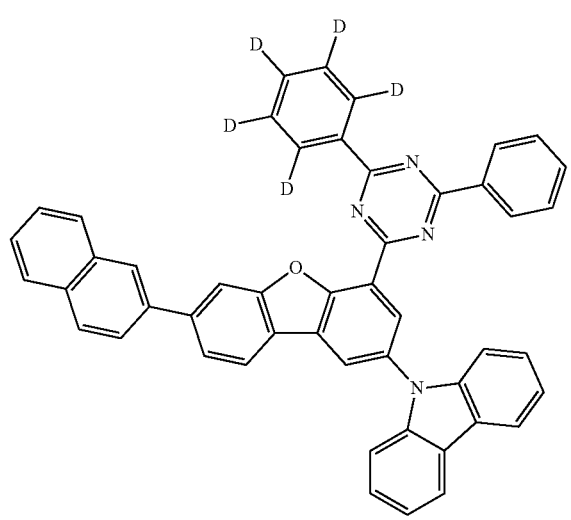
524
-continued
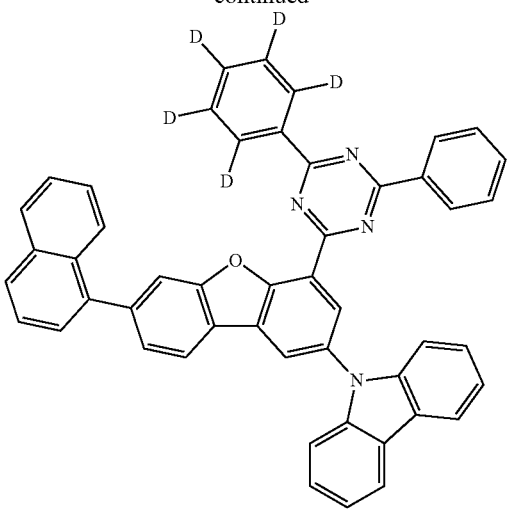
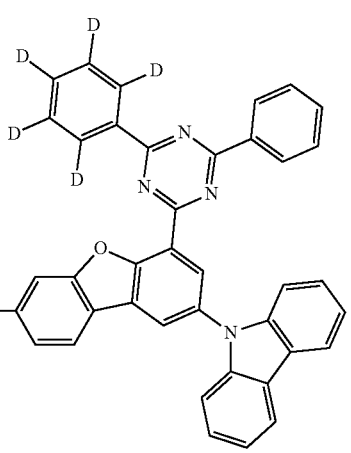
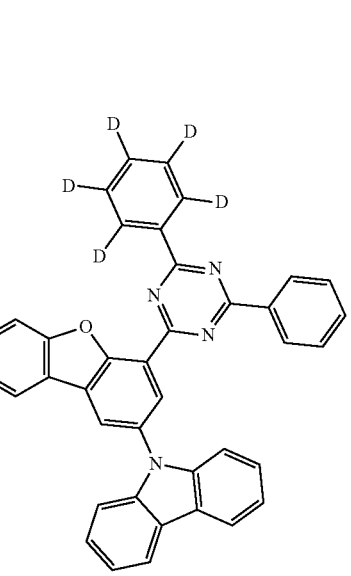

525
-continued
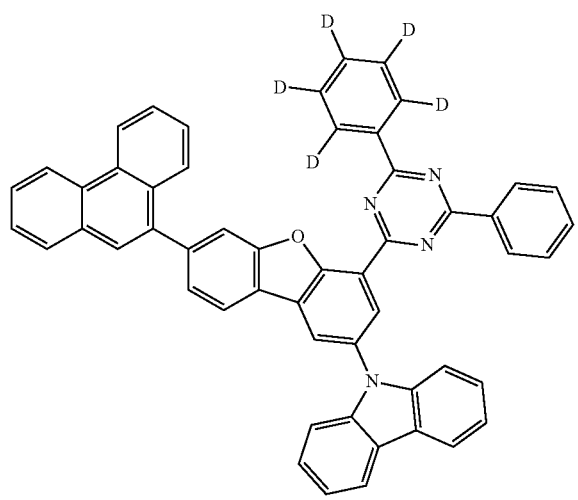
526
-continued
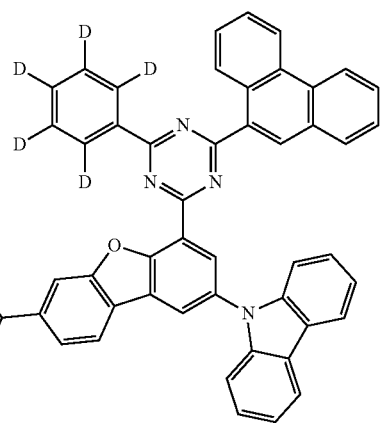
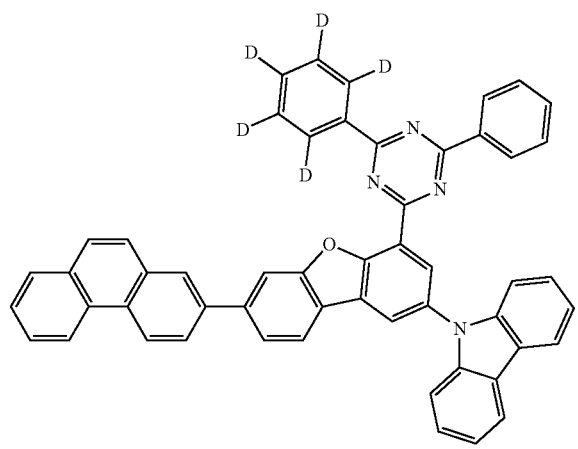
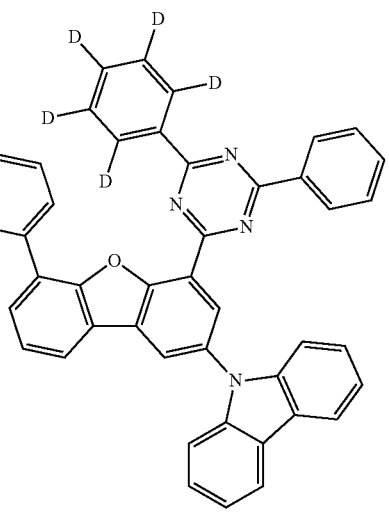
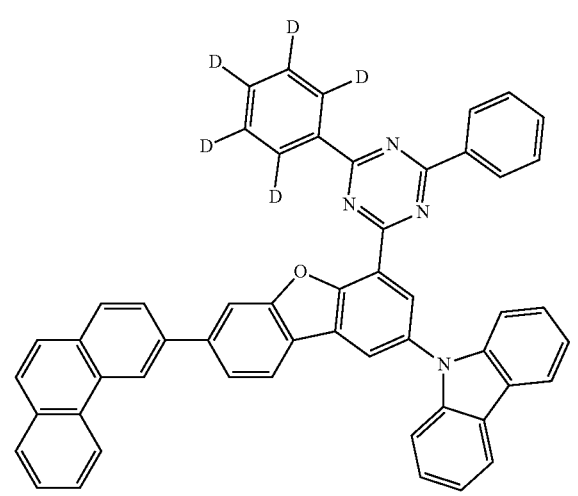
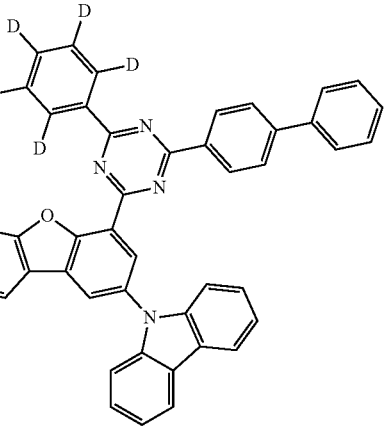

527
-continued
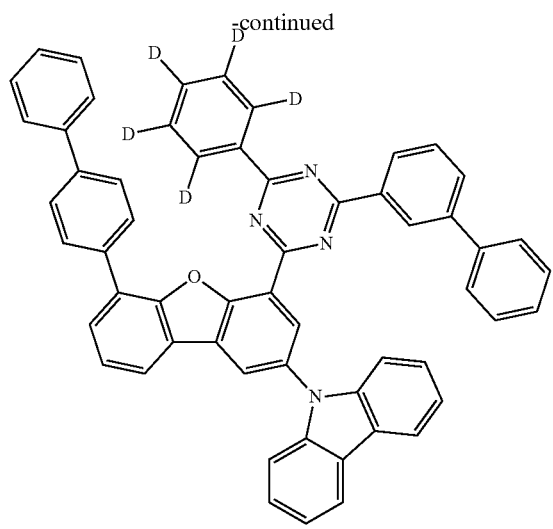
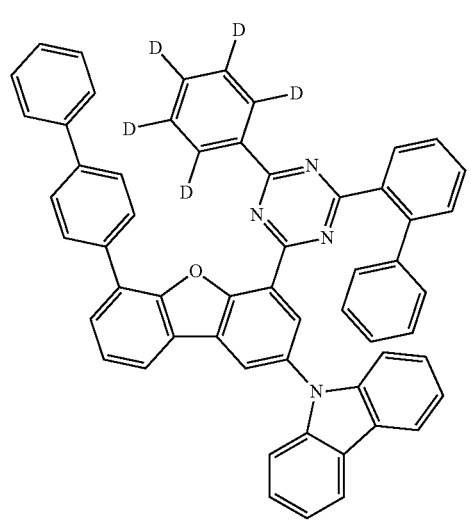
528
-continued
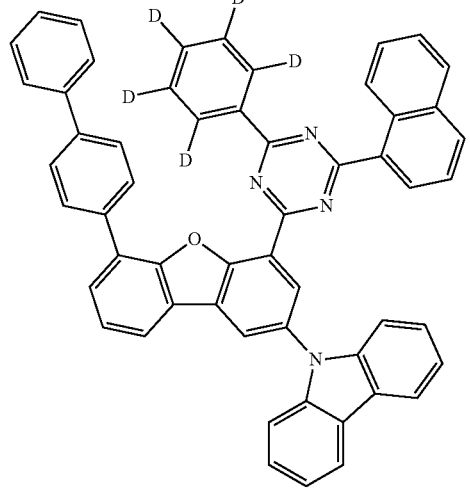
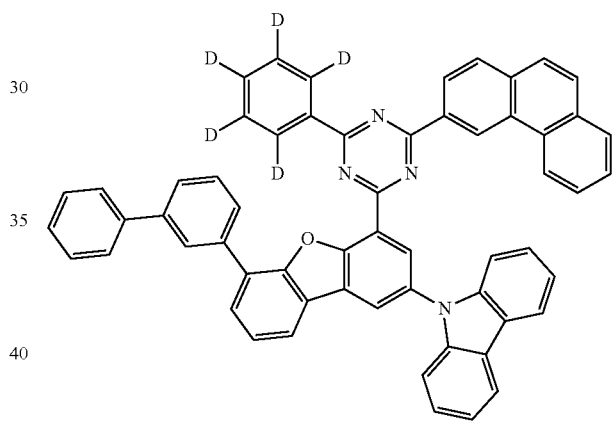
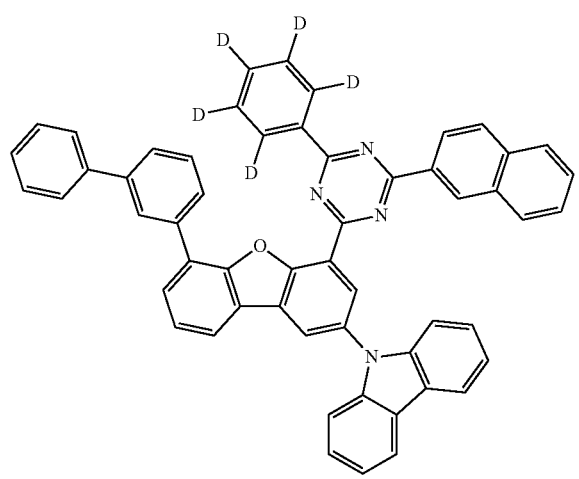
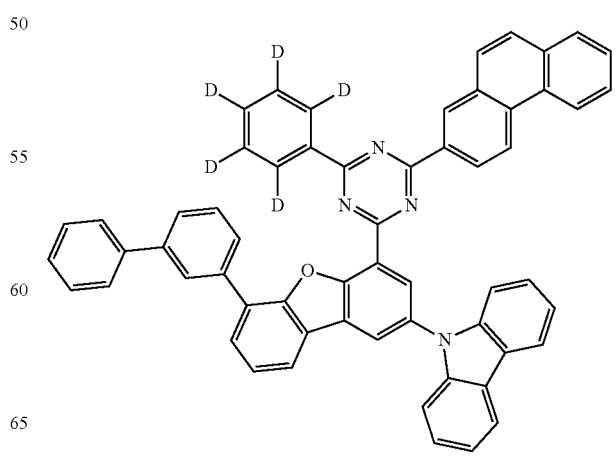

529
-continued
530
-continued
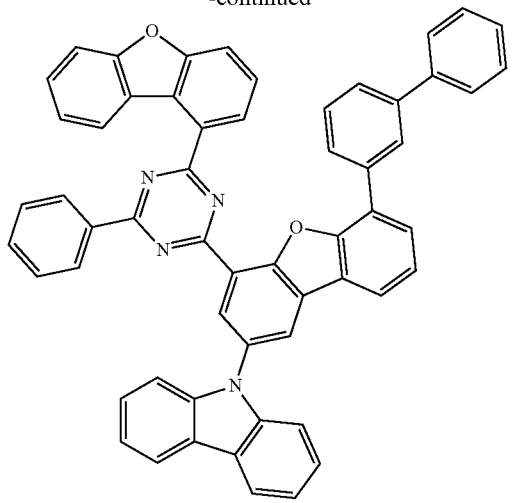
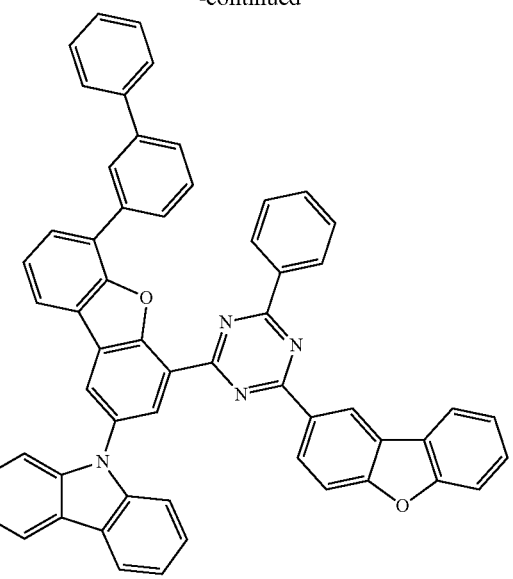
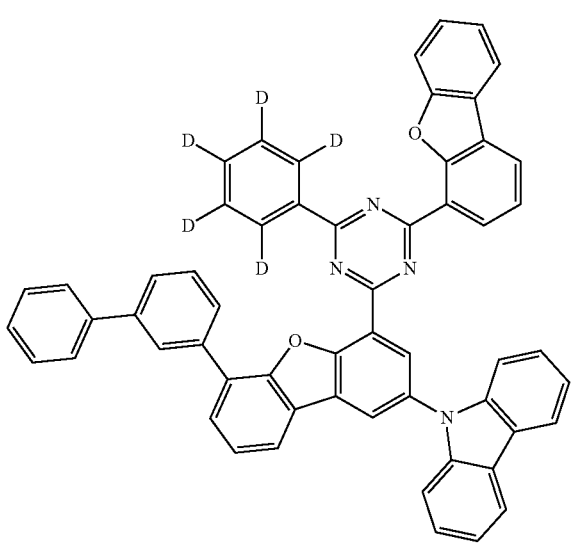
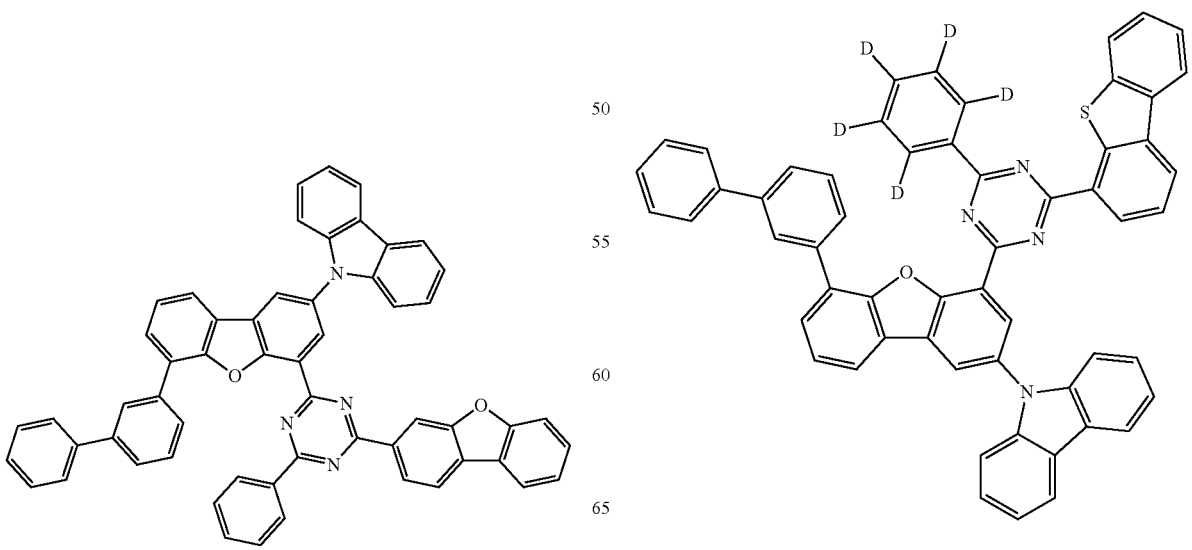

531
-continued
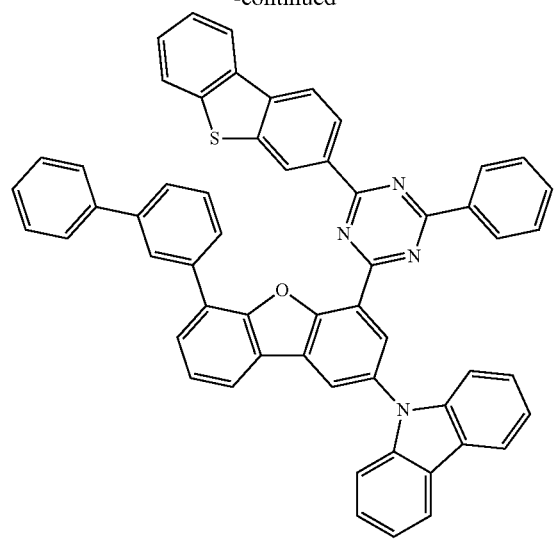
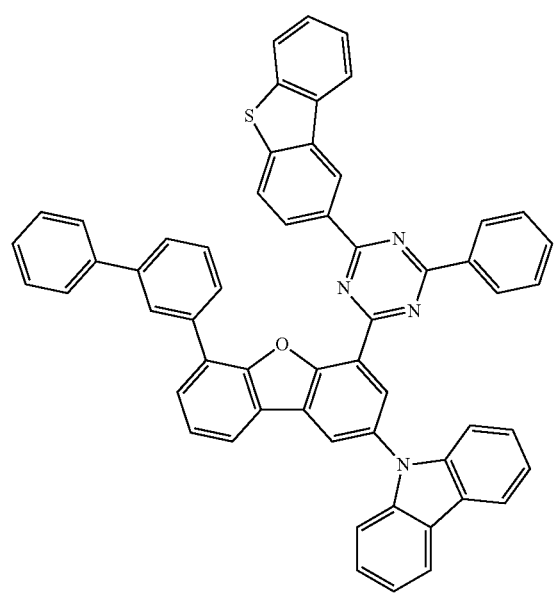
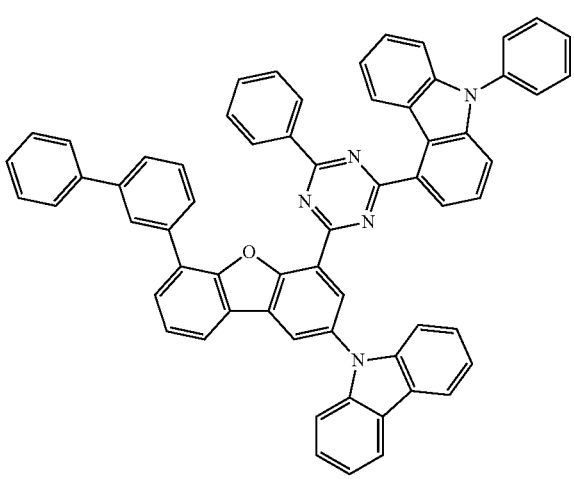
532
-continued
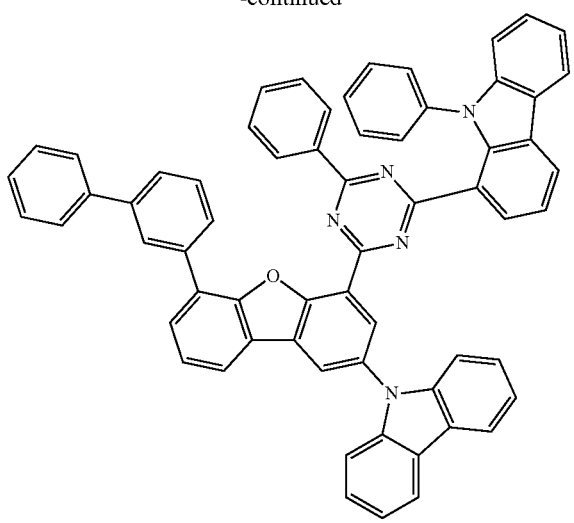
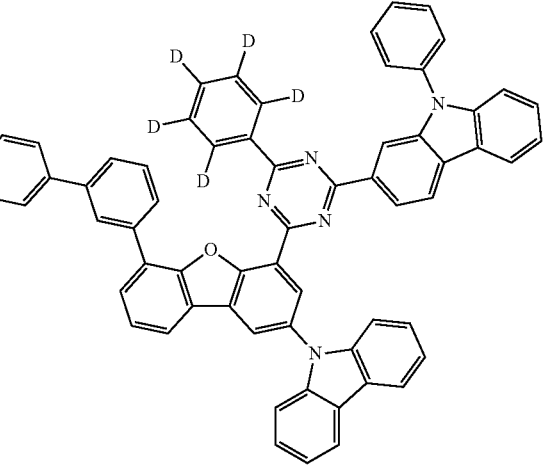
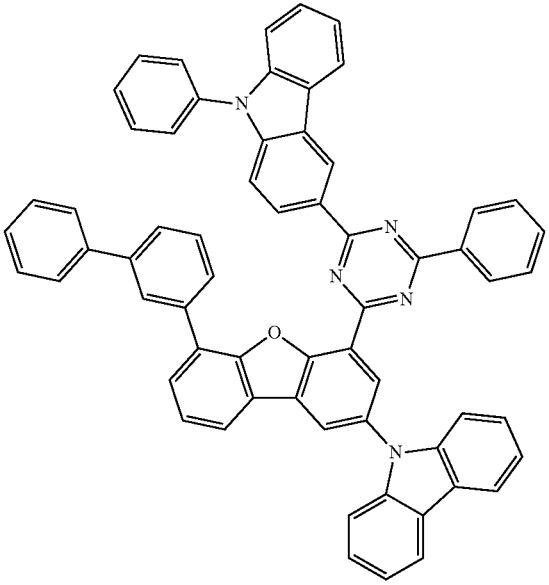

533
-continued
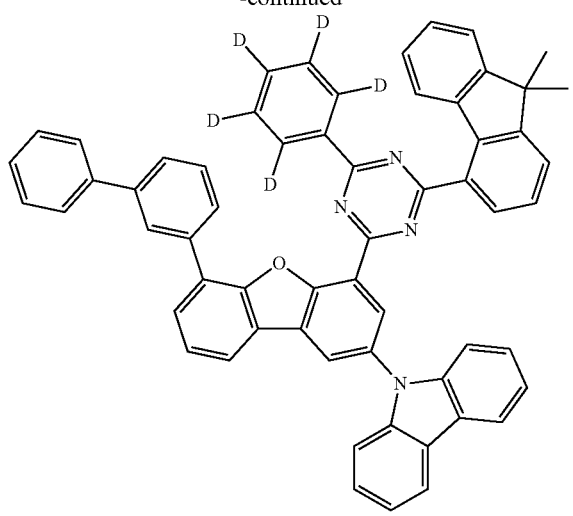
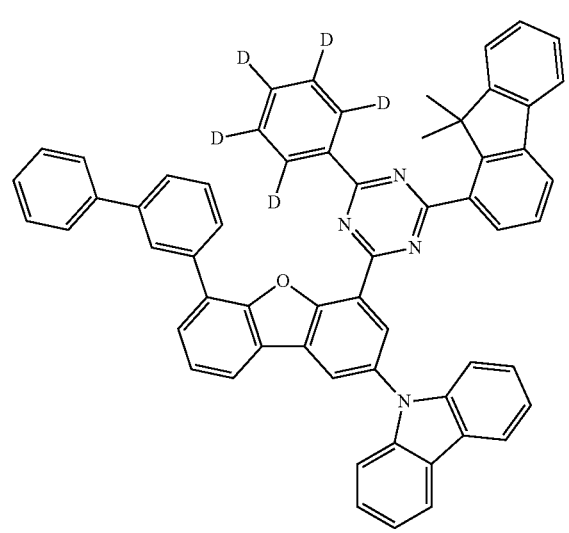
534
-continued
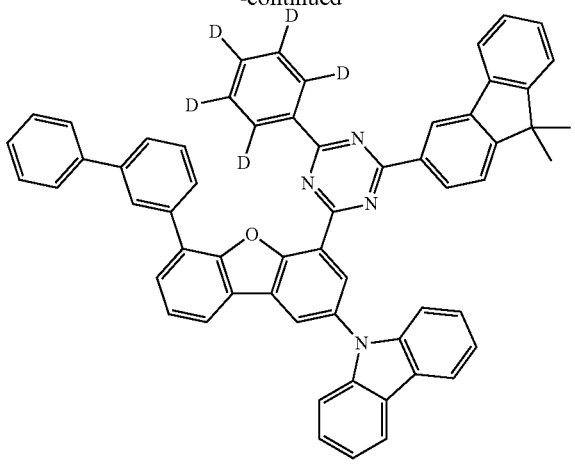
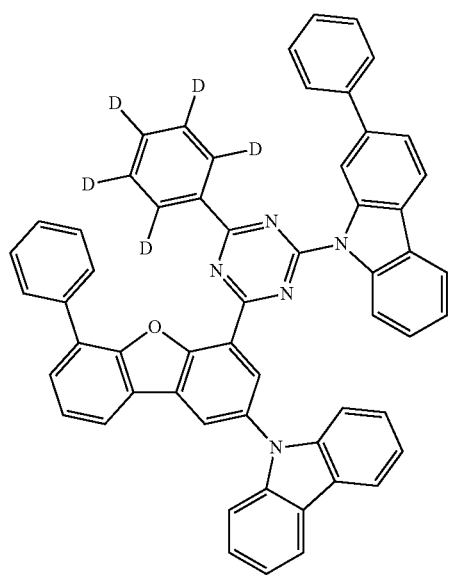

535
-continued
536
-continued
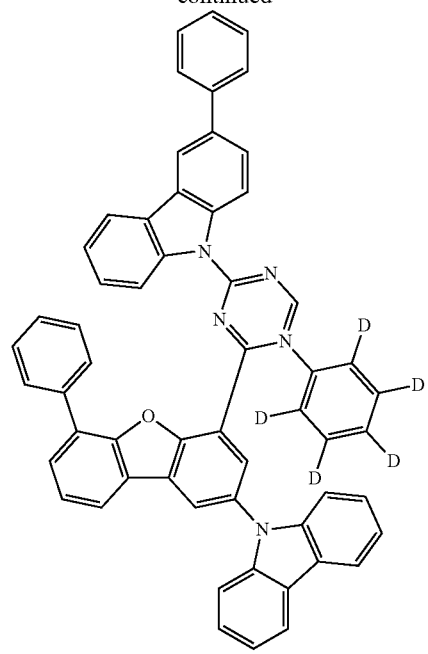
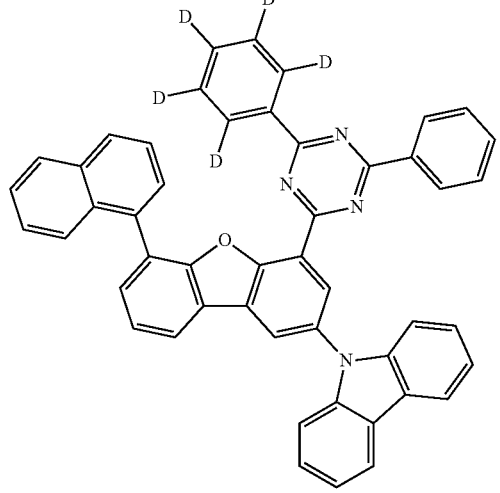
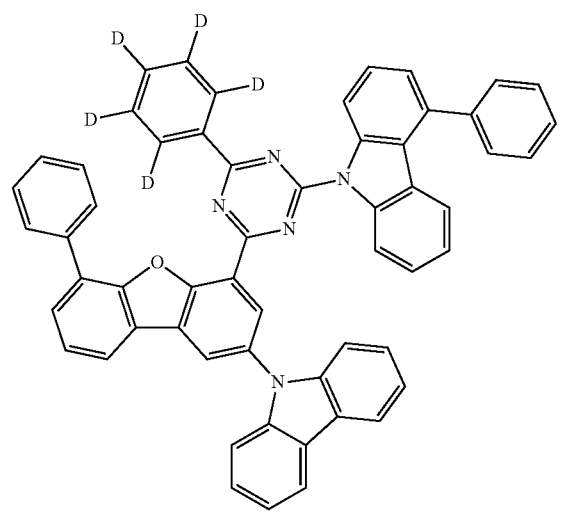
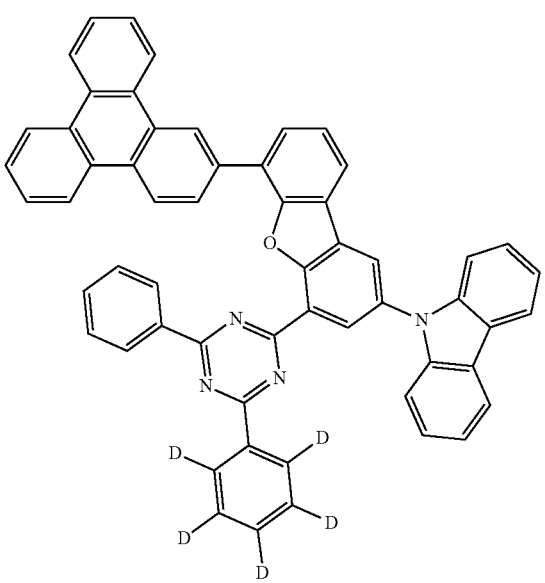
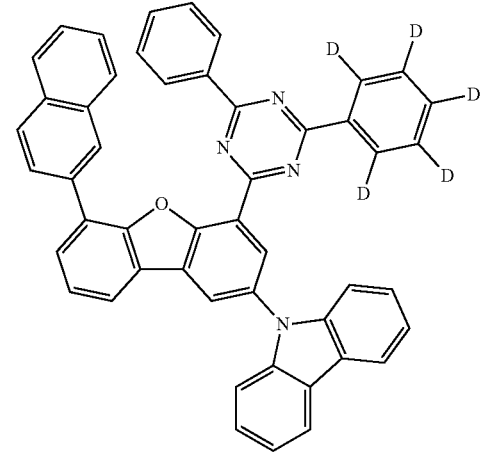
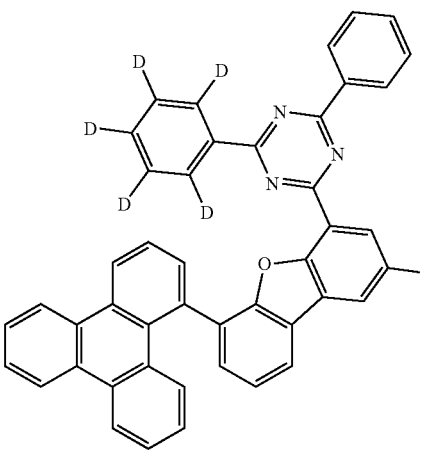

537
-continued
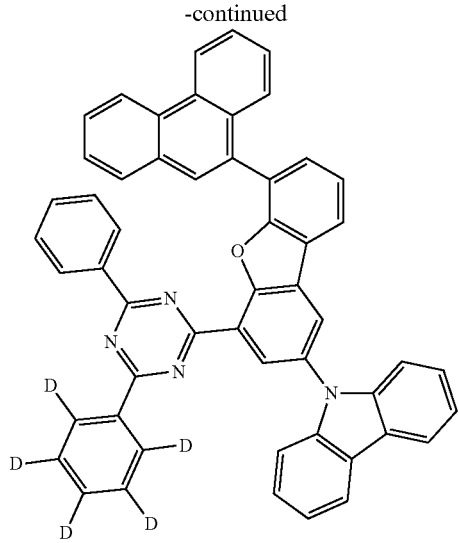
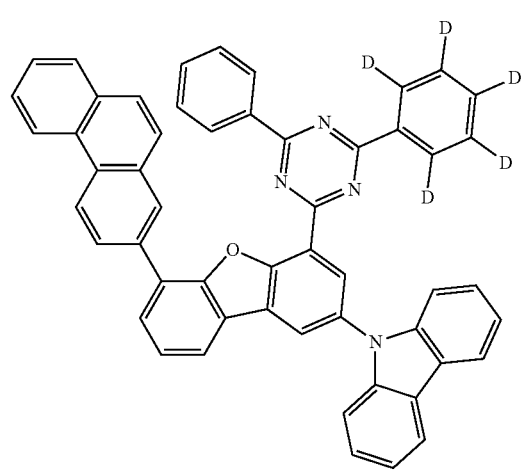
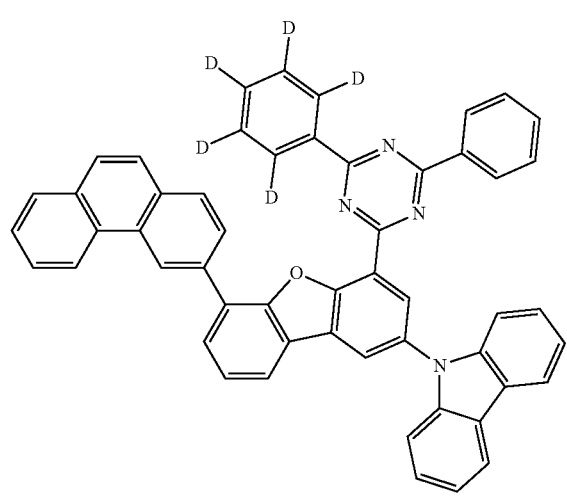
538
-continued
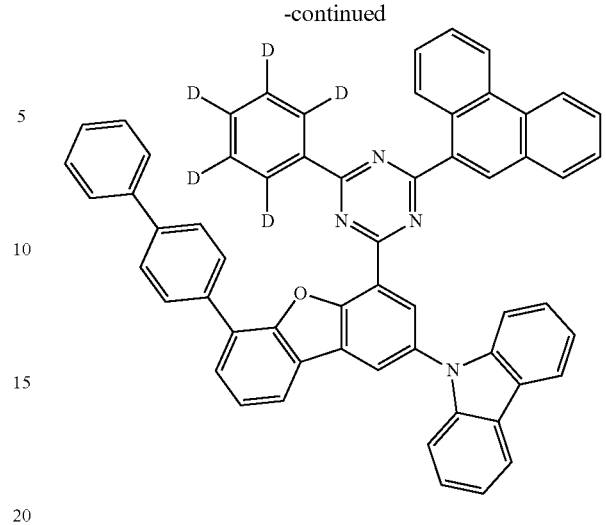
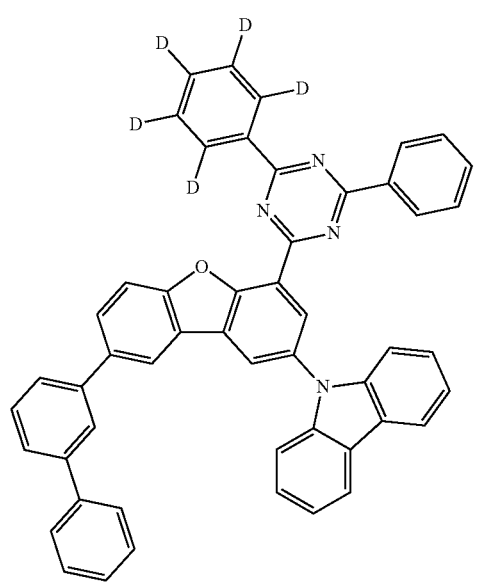
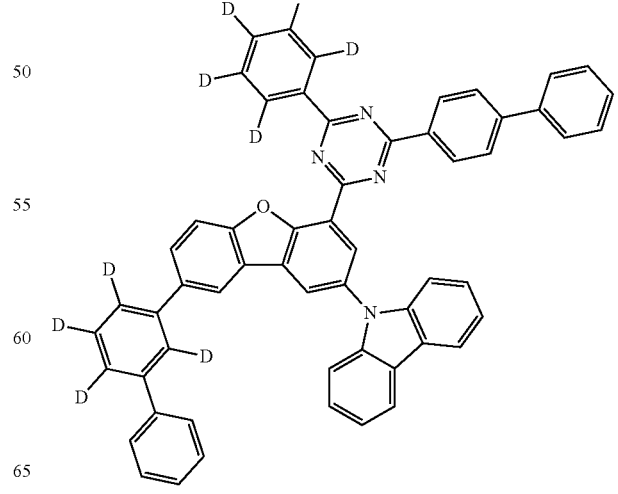

539
-continued
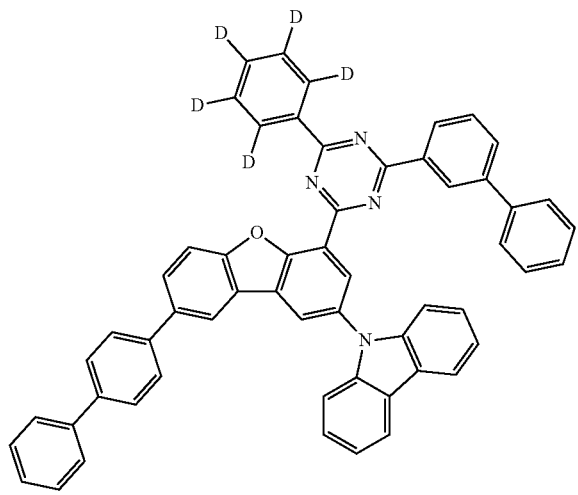
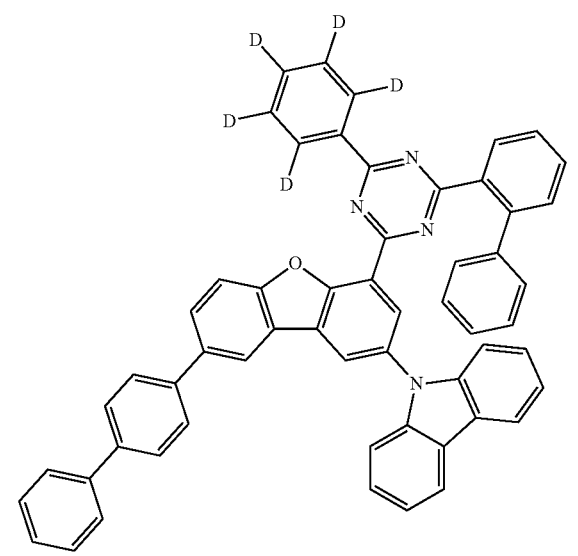
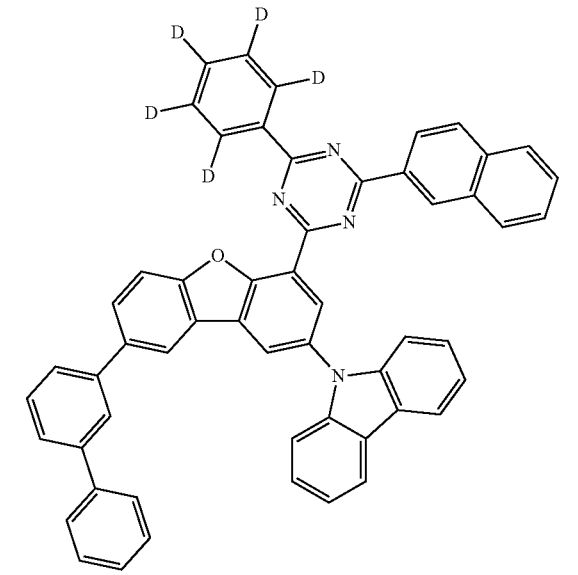
540
-continued
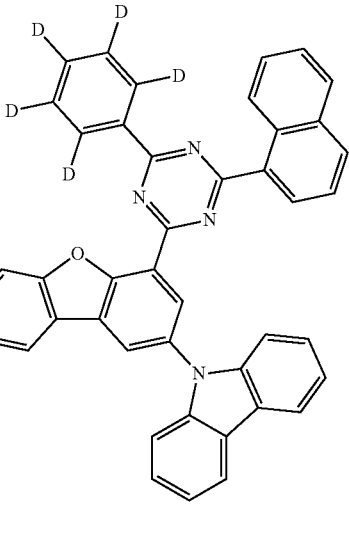

541
-continued
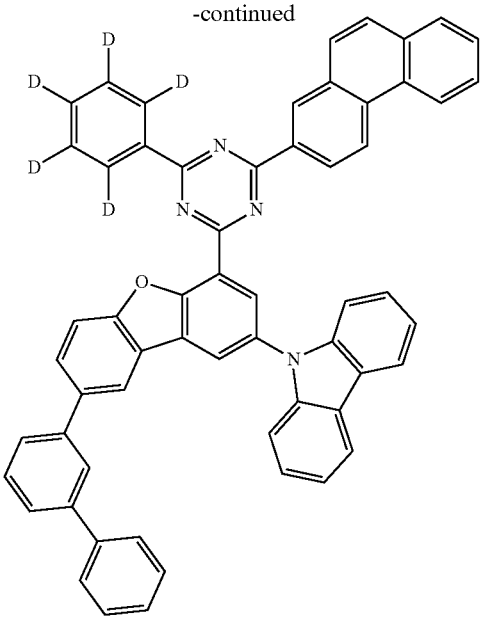
542
-continued
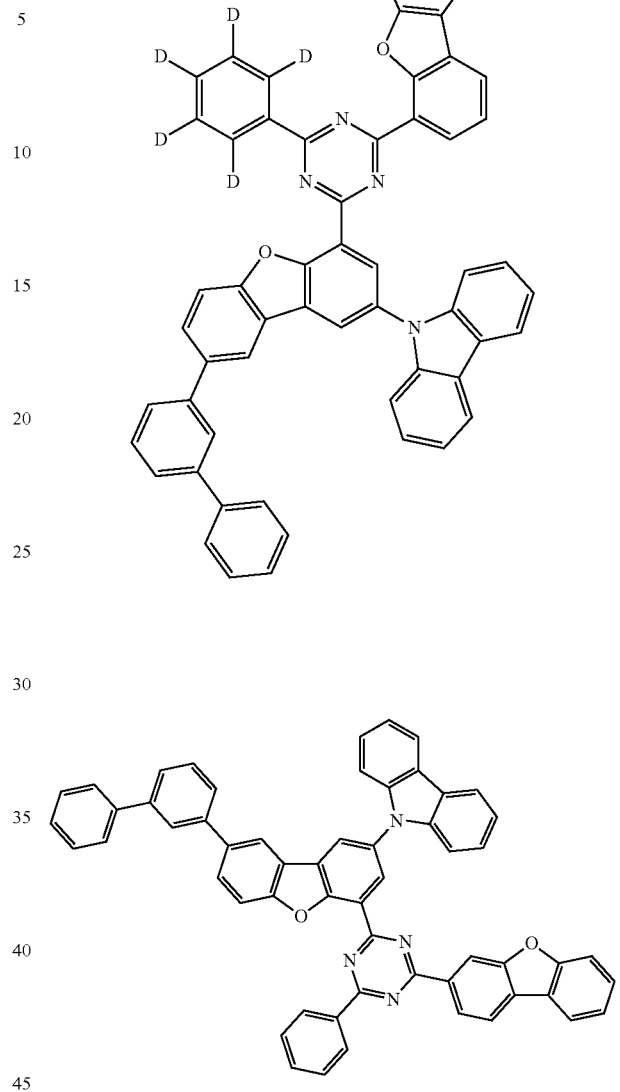
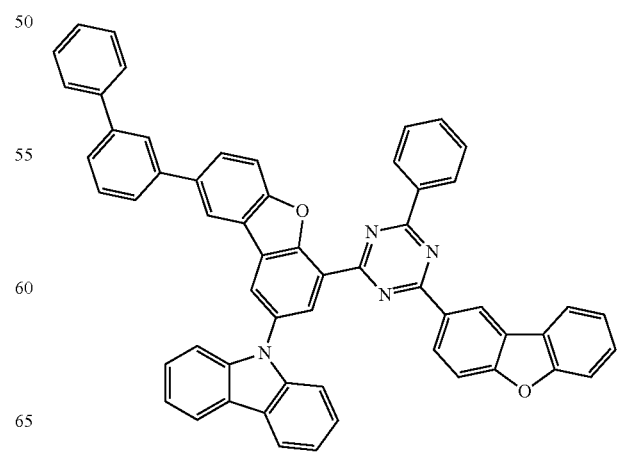
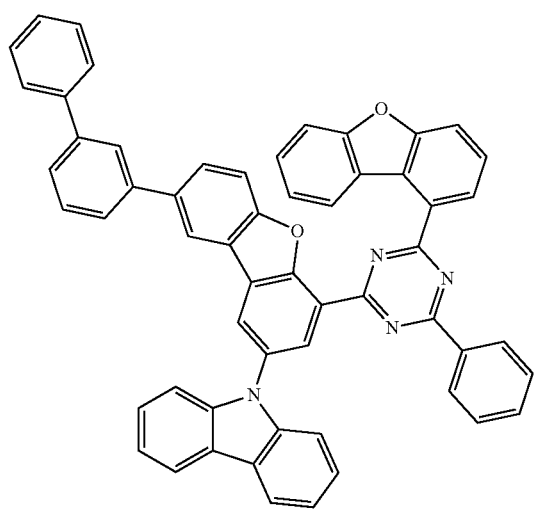

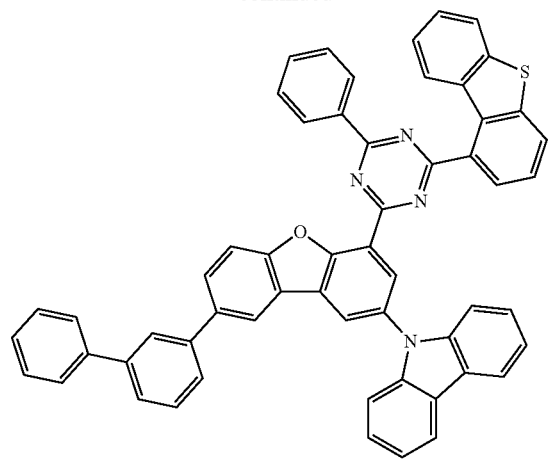
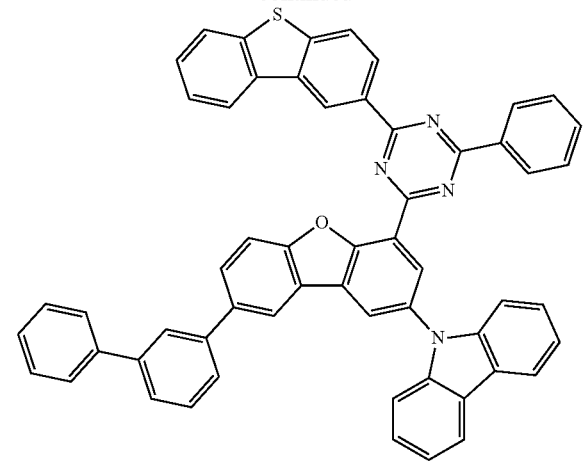
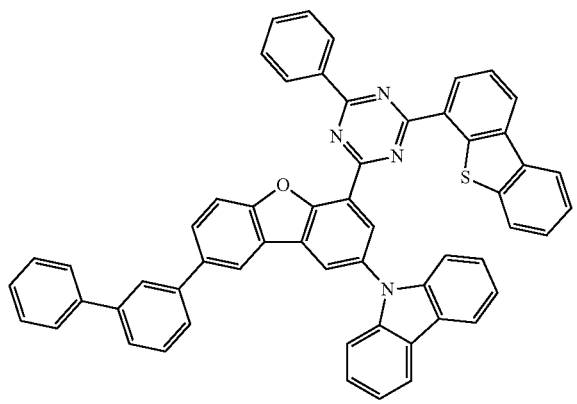
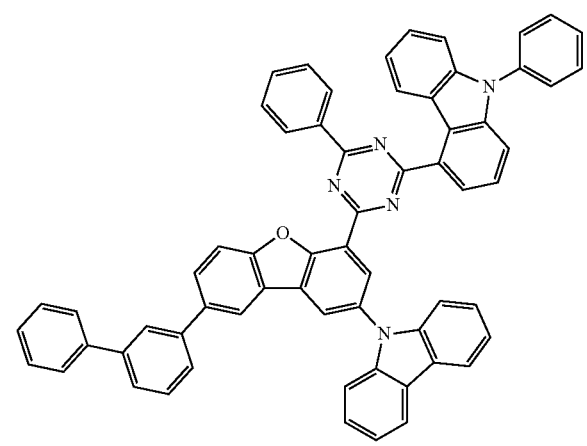
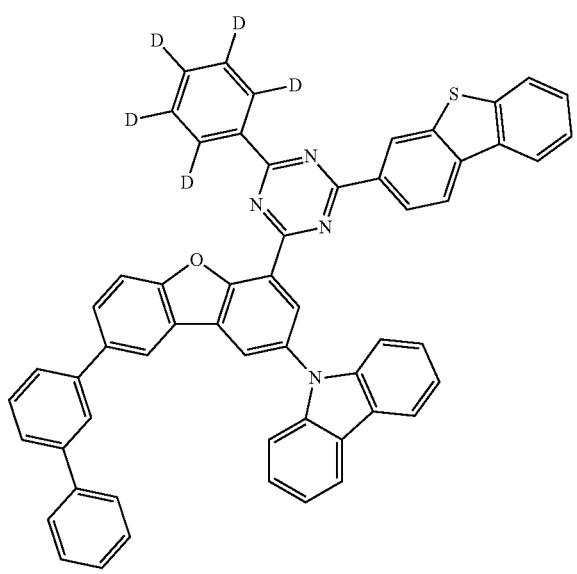
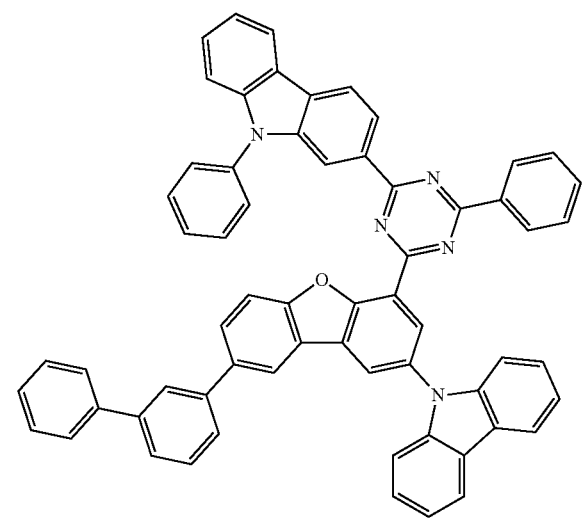

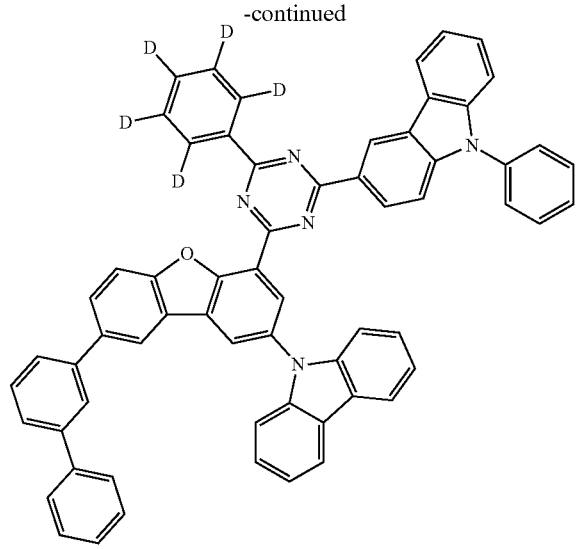
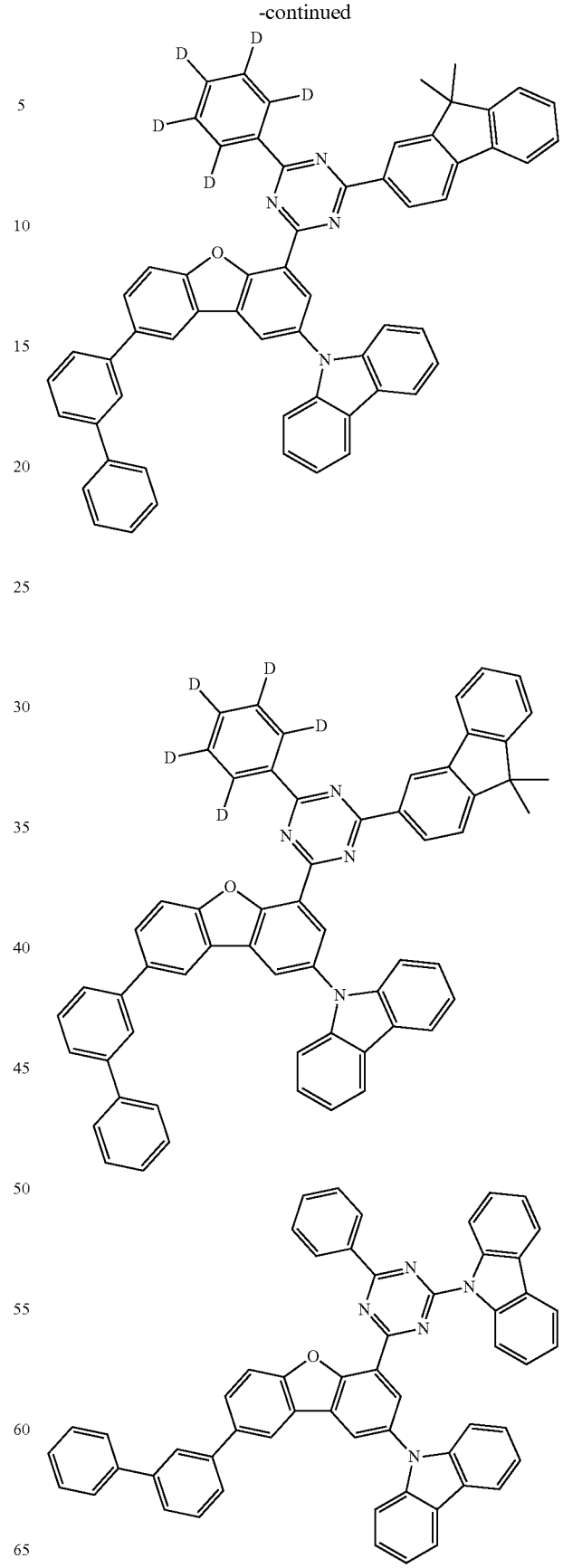

547
-continued
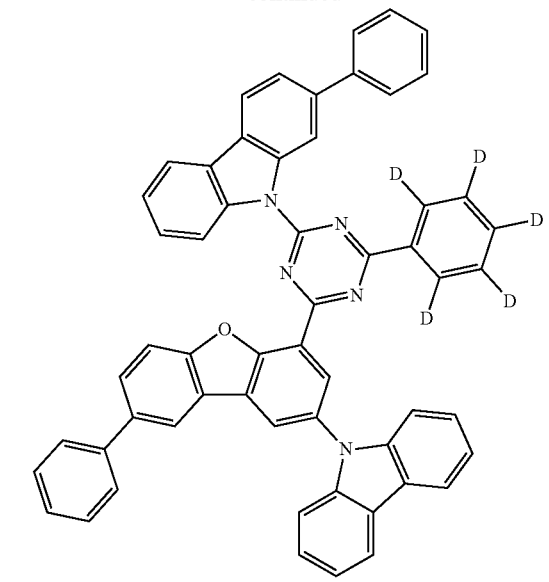
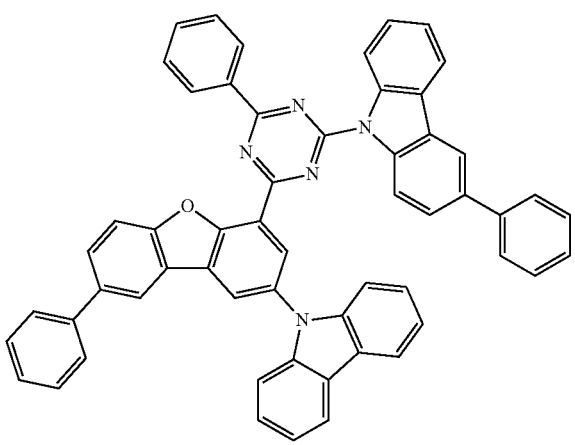
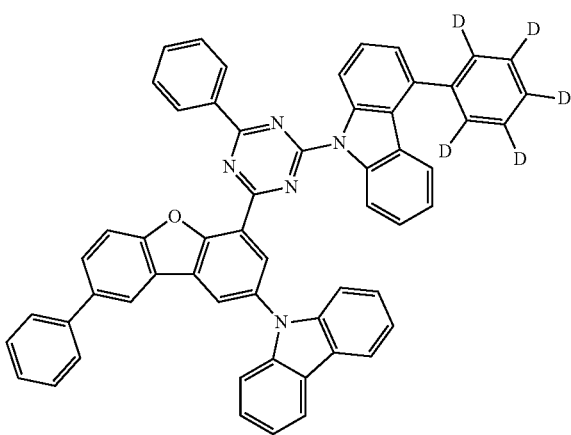
548
-continued
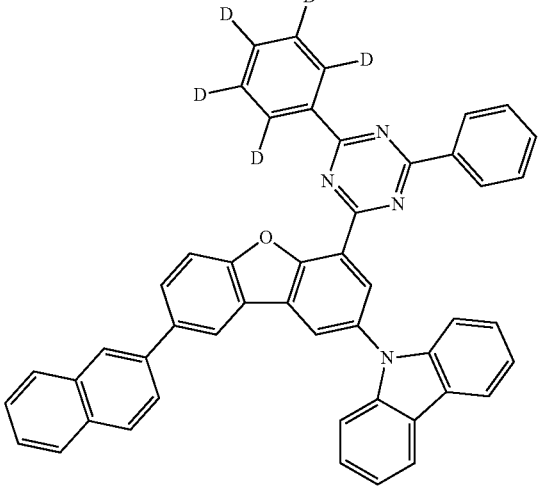
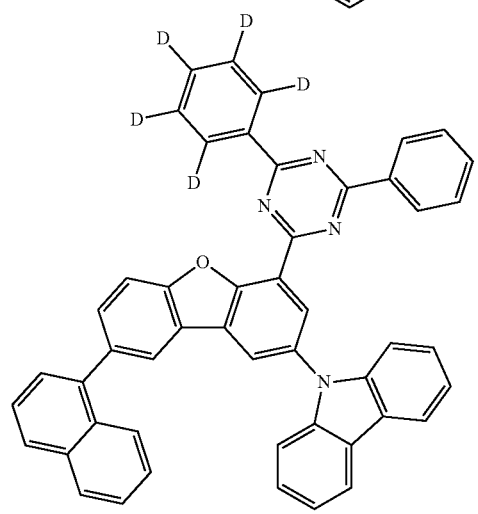
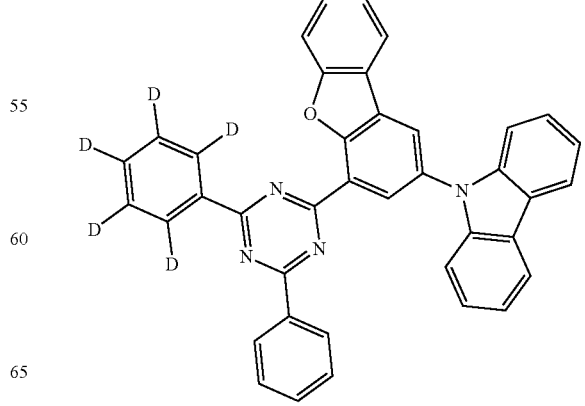

549
-continued
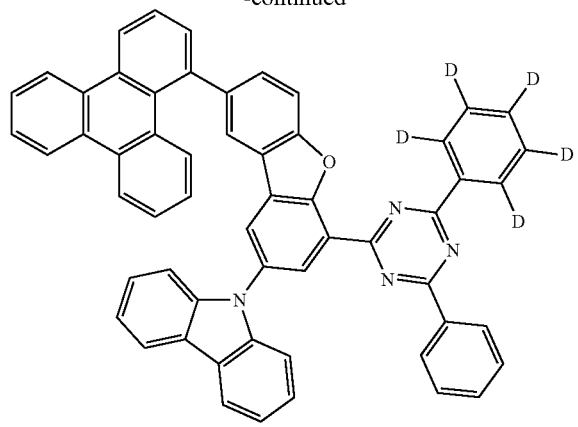
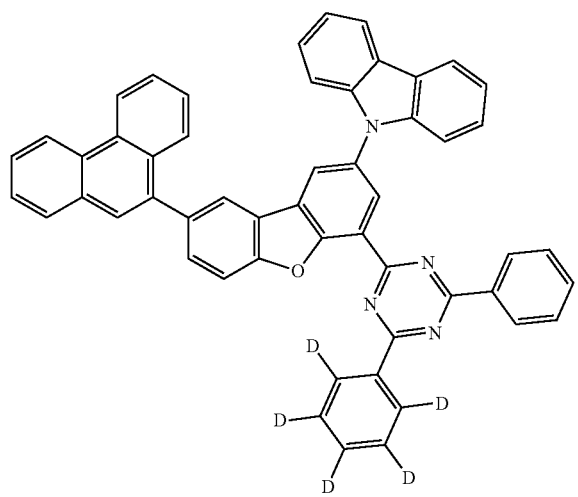
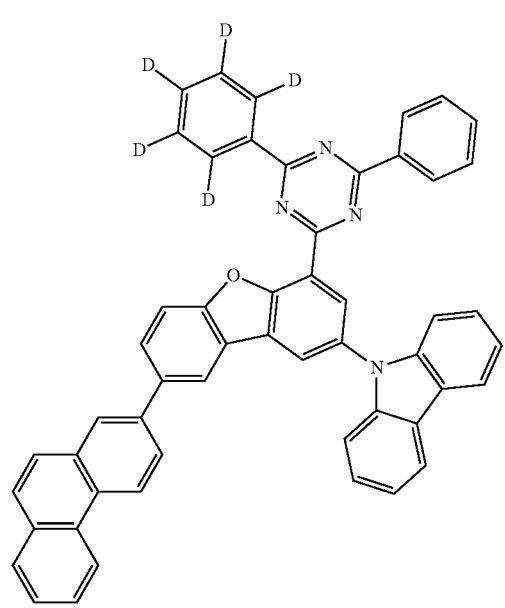
550
-continued
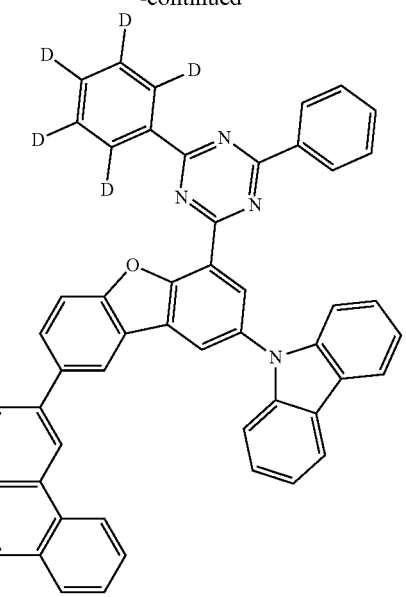
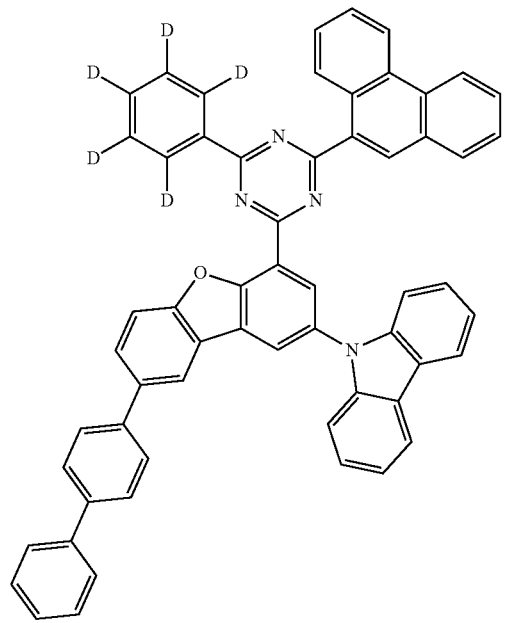

551
-continued
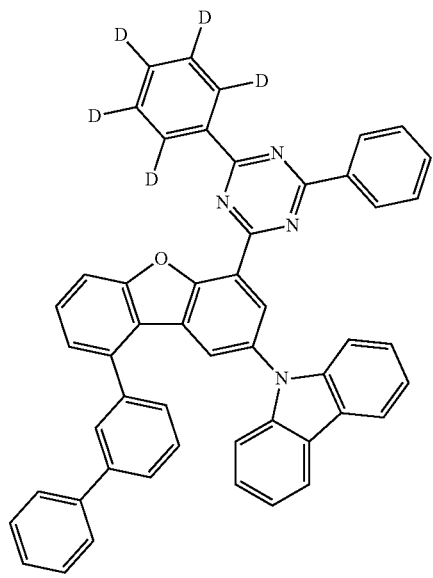
552
-continued
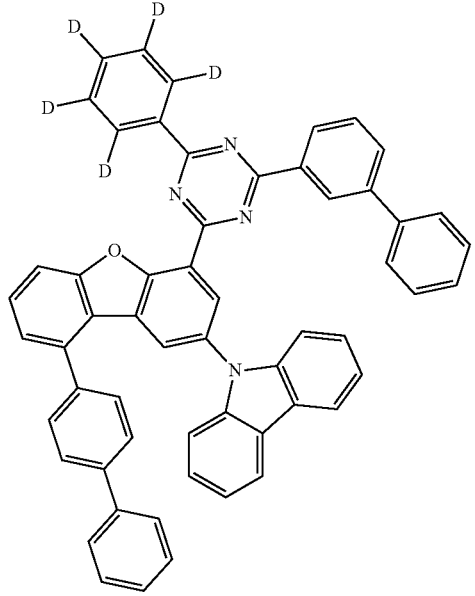
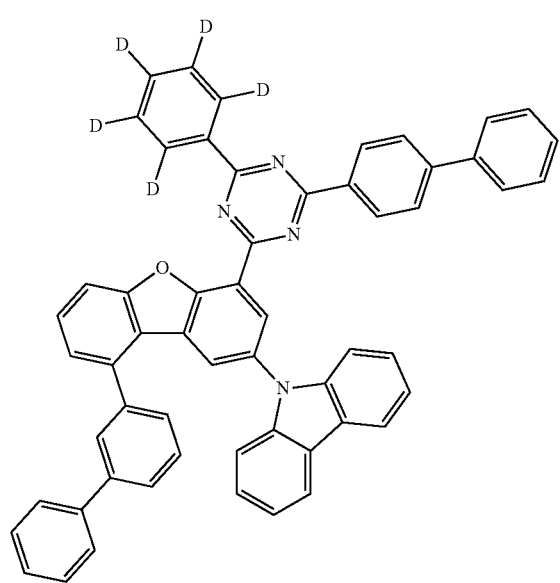
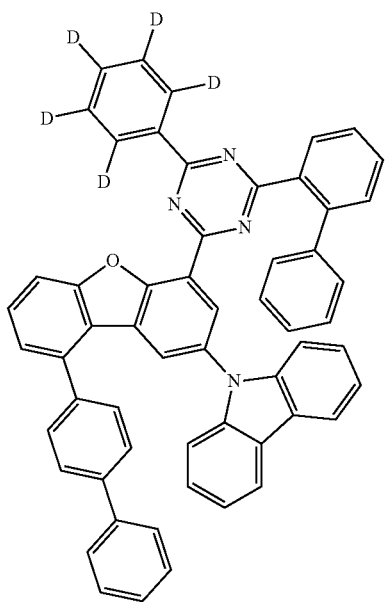

553
-continued
554
-continued
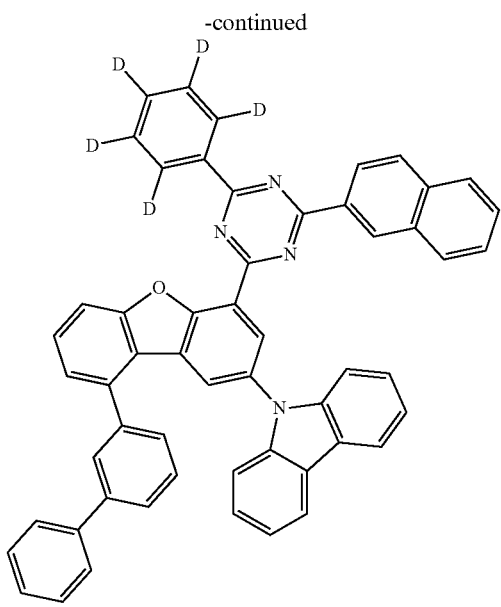
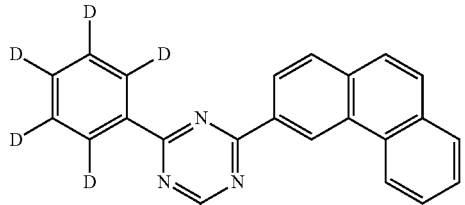
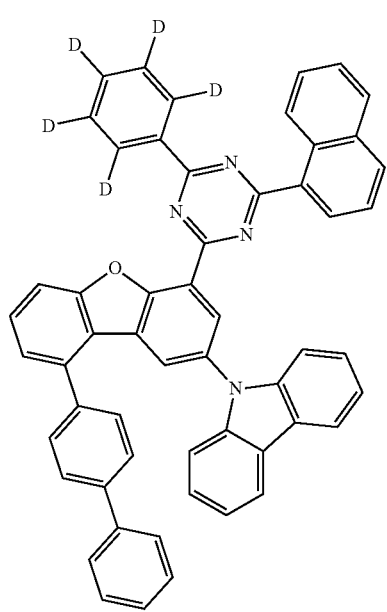

555
-continued
556
-continued
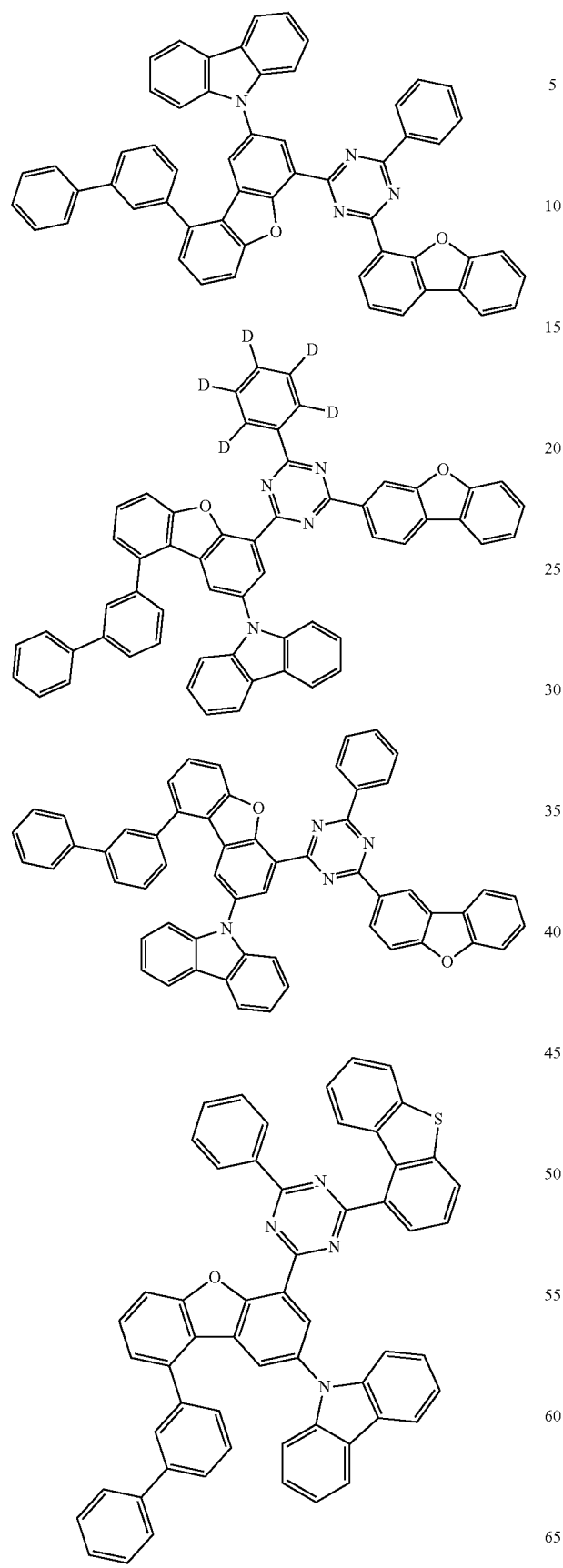
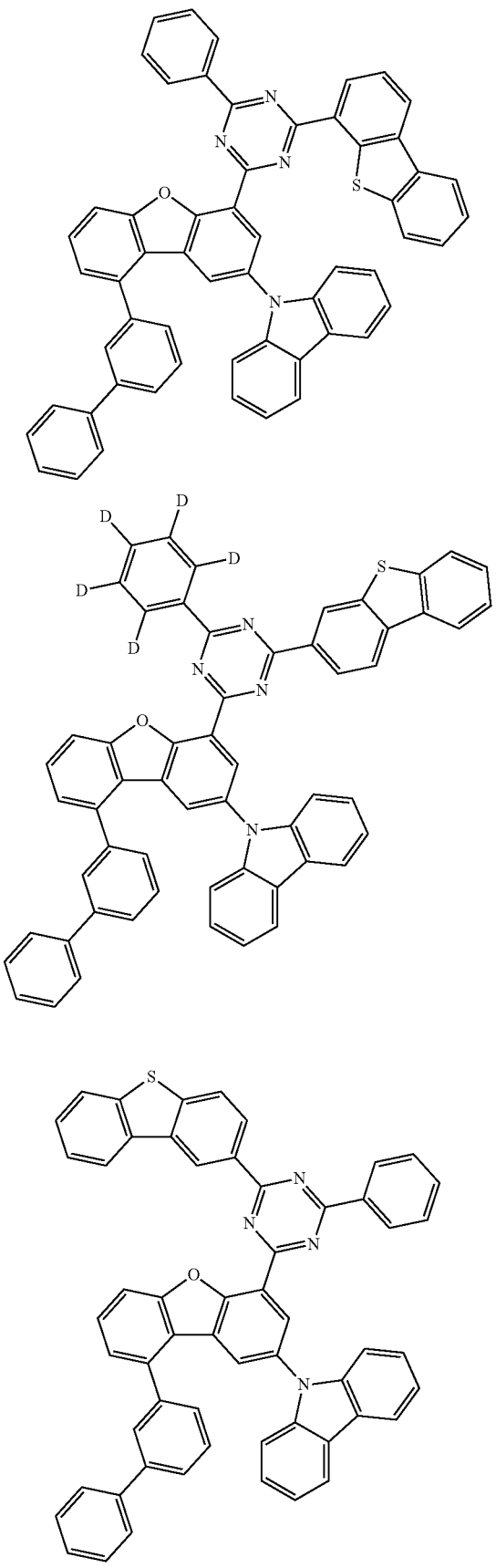

557
-continued
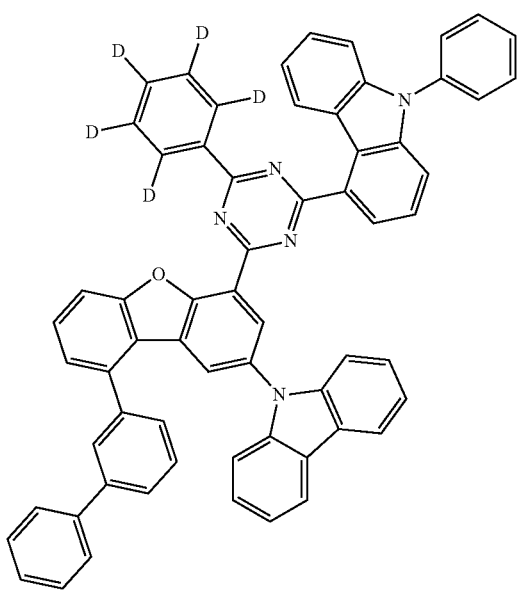
558
-continued
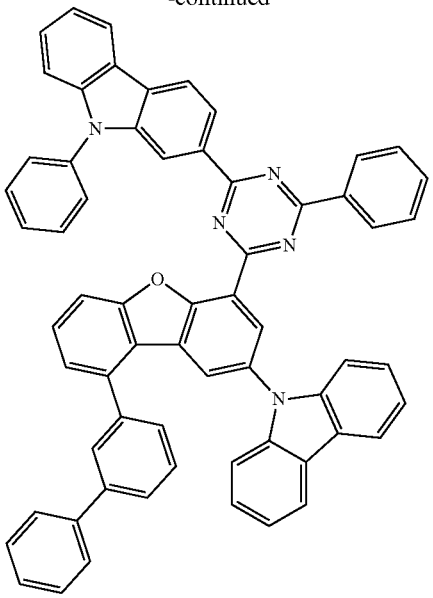
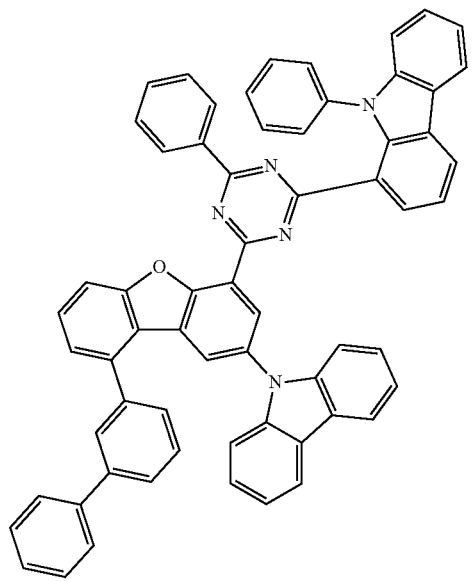
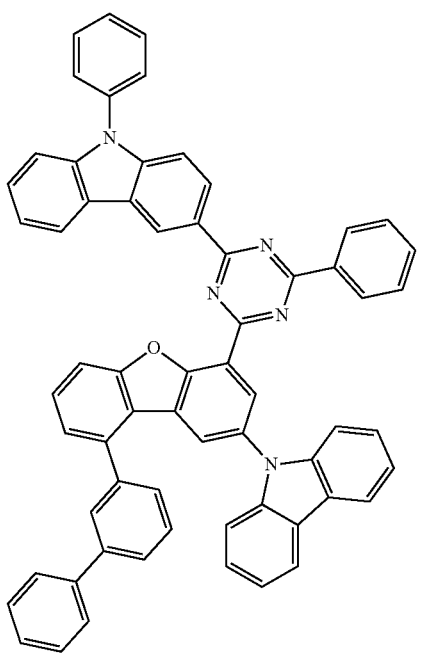

559
-continued
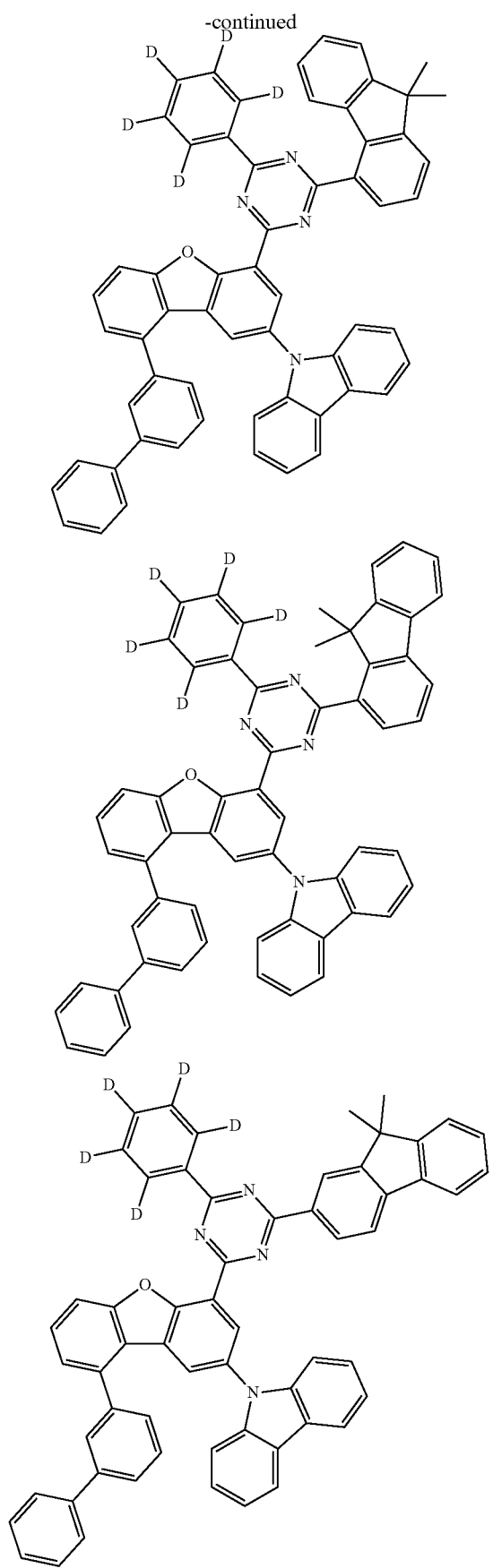
560
-continued
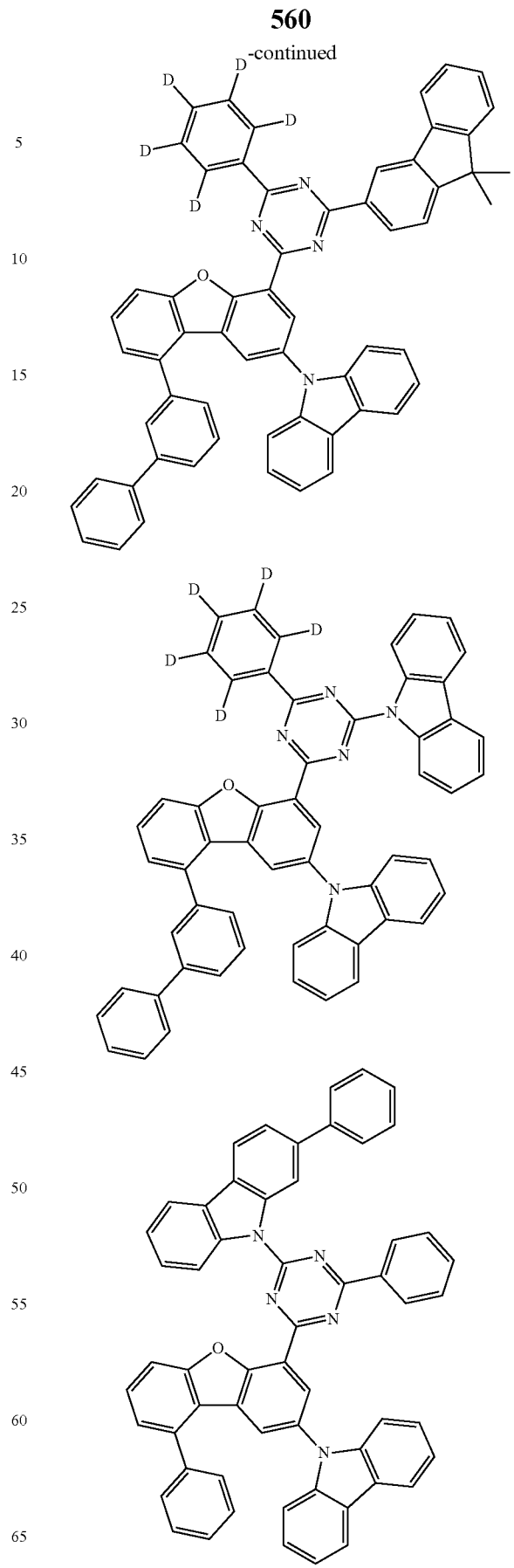

561
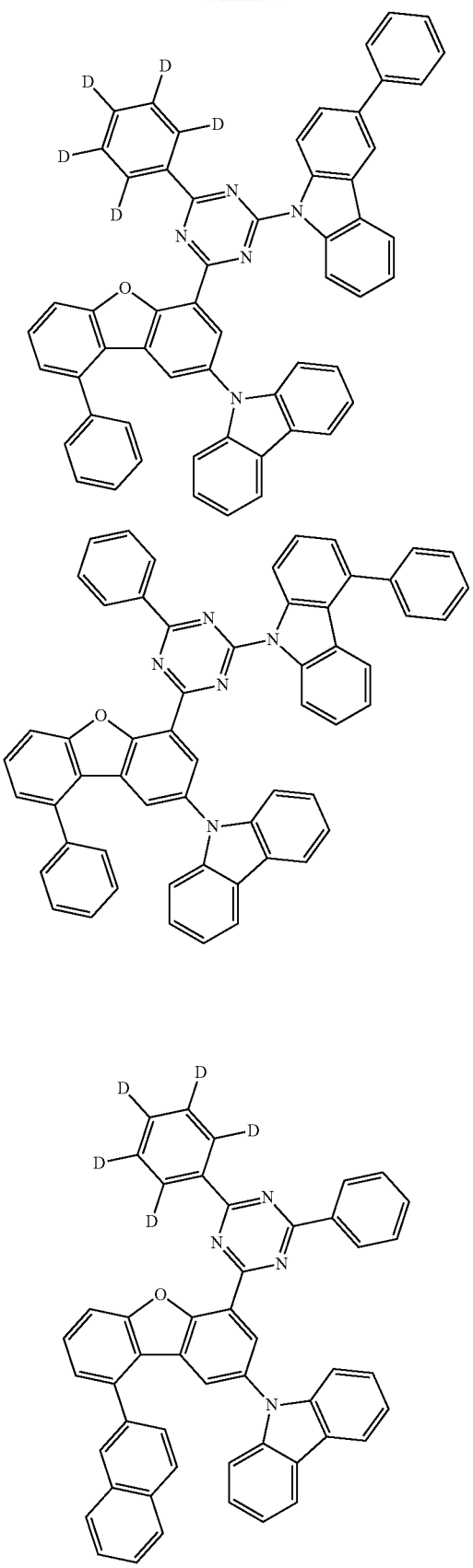
562
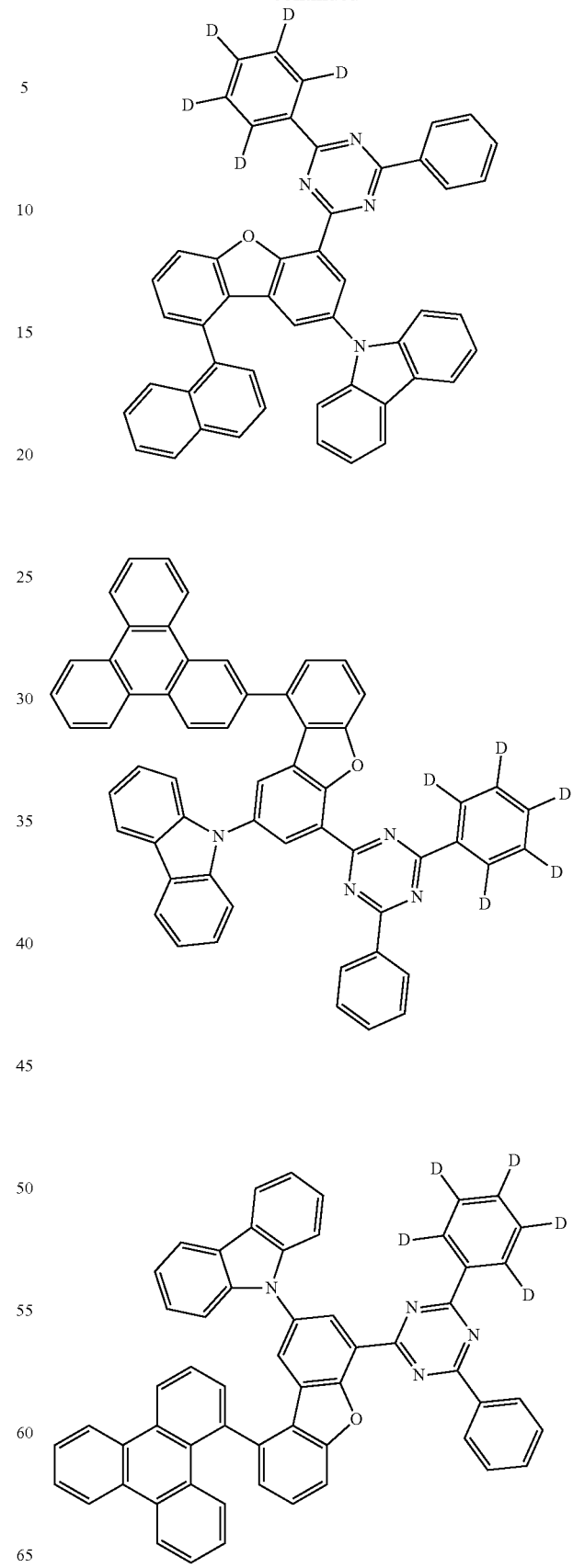

563
-continued
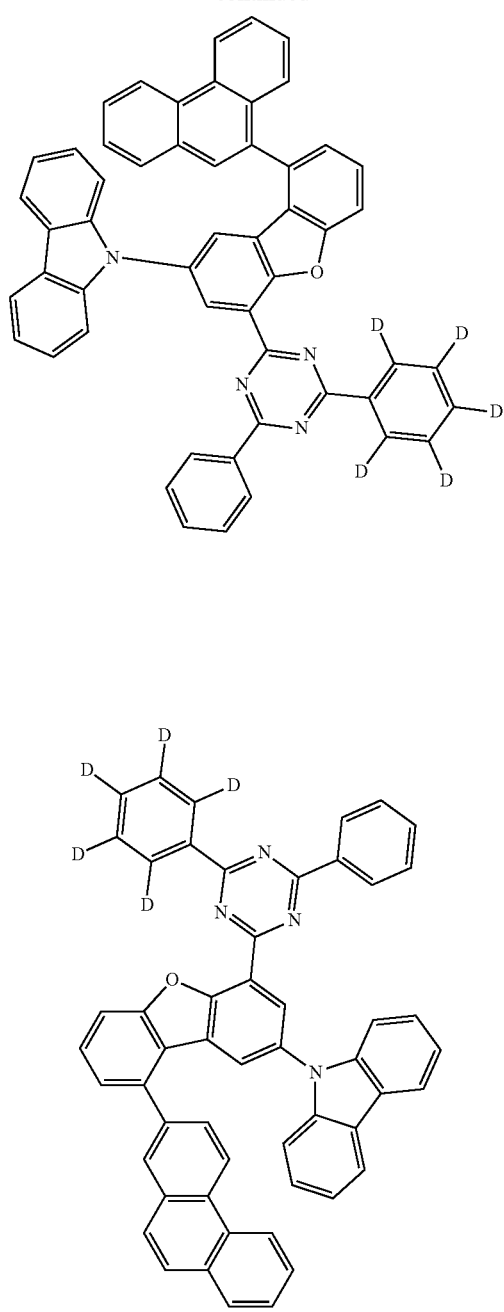
564
-continued
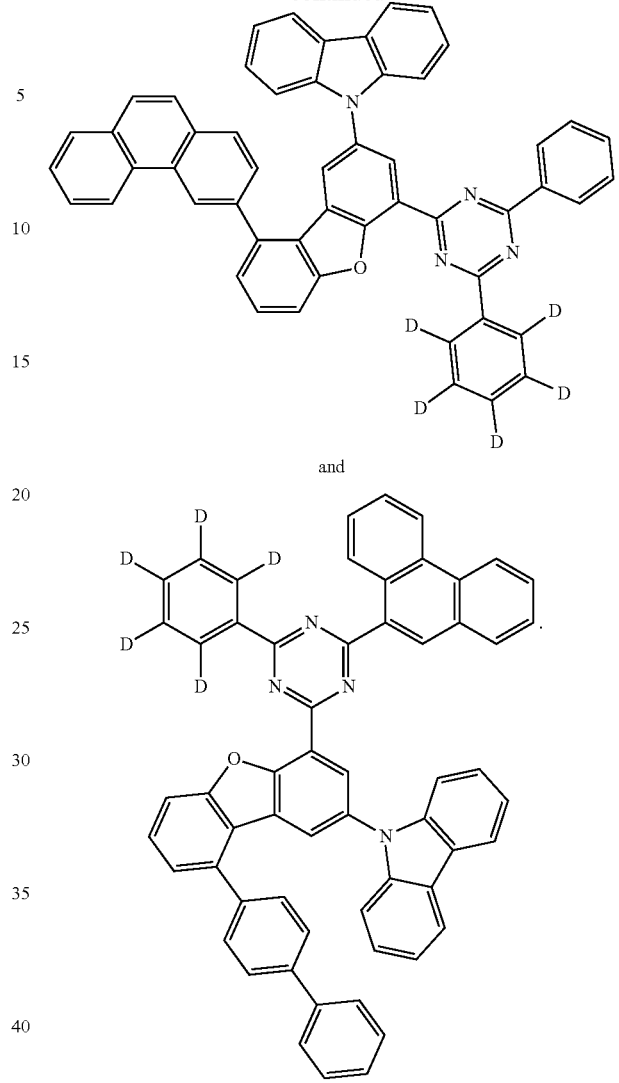
and
8. An organic light emitting device, comprising
a first electrode;
a second electrode that is provided opposite to the first electrode; and
one or more organic material layers that are provided between the first electrode and the second electrode, wherein one or more layers of the organic material layers include the compound of claim 1.
* * * * *